United States Patent
Satterfield et al.

(10) Patent No.: US 11,589,583 B2
(45) Date of Patent: *Feb. 28, 2023

(54) PYRROLIDINONES HERBICIDES

(71) Applicant: FMC CORPORATION, Philadelphia, PA (US)

(72) Inventors: Andrew Duncan Satterfield, Furlong, PA (US); Thomas Paul Selby, Hockessin, DE (US); David Andrew Travis, North East, MD (US); Kanu Maganbhai Patel, Sugarland, TX (US); Andrew Edmund Taggi, New Hope, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/415,241

(22) Filed: May 17, 2019

(65) Prior Publication Data

US 2020/0367494 A1 Nov. 26, 2020
US 2022/0030863 A9 Feb. 3, 2022

Related U.S. Application Data

(63) Continuation of application No. 15/101,615, filed as application No. PCT/US2014/068073 on Dec. 2, 2014, now Pat. No. 10,294,202.

(60) Provisional application No. 61/911,324, filed on Dec. 3, 2013.

(51) Int. Cl.
*A01N 43/36* (2006.01)
*C07D 207/22* (2006.01)
*C07D 207/277* (2006.01)

(52) U.S. Cl.
CPC ........... *A01N 43/36* (2013.01); *C07D 207/22* (2013.01); *C07D 207/277* (2013.01)

(58) Field of Classification Search
CPC ... A01N 43/36; C07D 207/22; C07D 207/277
See application file for complete search history.

(56) References Cited

U.S. PATENT DOCUMENTS

| | | | |
|---|---|---|---|
| 3,741,989 A | 6/1973 | Zaugg | |
| 3,959,481 A | 5/1976 | Davis et al. | |
| 4,594,094 A | 6/1986 | Kollmeyer | |
| 4,874,422 A | 10/1989 | Woolard | |
| 5,196,534 A | 3/1993 | Whitehead et al. | |
| 5,856,273 A | 1/1999 | Kay et al. | |
| 6,455,472 B1 * | 9/2002 | Fischer | C07C 323/62 548/566 |
| 7,205,318 B2 | 4/2007 | Qiao et al. | |
| 7,355,053 B2 | 4/2008 | Reinhard et al. | |
| 7,375,232 B2 | 5/2008 | Clark et al. | |
| 8,293,926 B2 | 10/2012 | Yasuoka et al. | |
| 8,461,202 B2 | 6/2013 | Sancho Sanz et al. | |
| 8,575,154 B2 | 11/2013 | Kori et al. | |
| 8,946,216 B2 | 2/2015 | Deng et al. | |
| 9,119,397 B2 | 9/2015 | Yerkes et al. | |
| 9,446,995 B2 | 9/2016 | Chong | |
| 9,737,073 B2 | 8/2017 | Gifford et al. | |
| 9,944,602 B2 | 4/2018 | Satterfield et al. | |
| 9,969,728 B2 | 5/2018 | Defays et al. | |
| 10,227,286 B2 * | 3/2019 | Satterfield | C07C 233/07 |
| 10,294,202 B2 * | 5/2019 | Satterfield | A01N 43/54 |
| 10,405,547 B2 * | 9/2019 | Satterfield | A01N 43/36 |
| 10,442,807 B2 | 10/2019 | Campbell et al. | |
| 10,654,804 B2 * | 5/2020 | Satterfield | C07D 409/12 |
| 10,875,838 B2 | 12/2020 | Chen et al. | |
| 2004/0242671 A1 | 12/2004 | Grimee et al. | |

(Continued)

FOREIGN PATENT DOCUMENTS

| | | |
|---|---|---|
| CN | 102531918 | 10/2013 |
| DE | 1262277 | 3/1968 |
| EP | 2336104 | 6/2011 |
| IN | 1462DEL08 | 6/2008 |
| JP | 51131870 | 11/1976 |
| JP | 52156859 | 12/1977 |
| JP | 53-056288 | 5/1978 |
| JP | 54-088114 | 7/1979 |
| JP | H0770037 | 3/1995 |
| JP | 08-269145 | 10/1996 |

(Continued)

OTHER PUBLICATIONS

Kaushik et al. Pest Manag Sci 62:1092-1097, 2006 (Year: 2006).*
Murata et al.; "Oxidation of N-Acyl-Pyrrolidines and -Piperidines with Iron(II)-Hydrogen Peroxide and an Iron Complex-Molecular Oxygen"; J. Chem. Soc. Perkin Trans.; 1987; 1259-1262. (XP055297105).

(Continued)

*Primary Examiner* — Mina Haghighatian
*Assistant Examiner* — Janice Y Silverman
(74) *Attorney, Agent, or Firm* — Armstrong Teasdale LLP

(57) ABSTRACT

Disclosed are compounds of Formula 1, including all stereoisomers, N-oxides, and salts thereof:

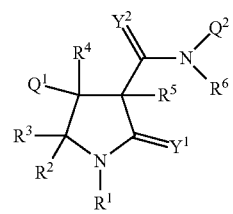

wherein $R^1$, $R^2$, $R^3$, $R^4$, $R^5$, $R^6$, $Q^1$, $Q^2$, $Y^1$, and $Y^2$ are as defined in the disclosure.
Also disclosed are compositions containing the compounds of Formula 1 and methods for controlling undesired vegetation comprising contacting the undesired vegetation or its environment with an effective amount of a compound or a composition of the invention.

6 Claims, No Drawings

(56) References Cited

U.S. PATENT DOCUMENTS

| | | |
|---|---|---|
| 2007/0123508 A1 | 5/2007 | Olsson et al. |
| 2009/0062366 A1 | 3/2009 | Hachiya et al. |
| 2009/0203694 A1 | 8/2009 | Hurley et al. |
| 2011/0218199 A1 | 9/2011 | Georges et al. |
| 2015/0173371 A1 | 6/2015 | Mann et al. |
| 2016/0137639 A1 | 5/2016 | Kotoku et al. |
| 2018/0049437 A1 | 2/2018 | Satterfield et al. |
| 2018/0057442 A1 | 3/2018 | Satterfield |
| 2018/0077931 A1 | 3/2018 | Stevenson et al. |
| 2018/0099935 A1 | 4/2018 | Satterfield et al. |
| 2018/0141904 A1 | 5/2018 | Campbell et al. |
| 2018/0213788 A1 | 8/2018 | Satterfield et al. |
| 2020/0095202 A1 | 3/2020 | Puri |
| 2020/0115337 A1 | 4/2020 | Campbell |
| 2020/0120931 A1 | 4/2020 | Campbell |
| 2020/0154709 A1 | 5/2020 | Mcmahon |

FOREIGN PATENT DOCUMENTS

| | | | | |
|---|---|---|---|---|
| KR | 20130142477 | 12/2013 | | |
| RU | 2555370 | 7/2015 | | |
| WO | 200009481 | 2/2000 | | |
| WO | 2002/006512 | 1/2002 | | |
| WO | 2003/024222 | 3/2003 | | |
| WO | 2004046081 | 6/2004 | | |
| WO | 2006081562 | 8/2006 | | |
| WO | 2006/127396 | 11/2006 | | |
| WO | 2009062371 | 5/2009 | | |
| WO | 20120034957 | 3/2012 | | |
| WO | WO-2015084796 A1 | * | 6/2015 | ............ A01N 47/38 |
| WO | 2016003997 | 1/2016 | | |
| WO | 2016094117 | 6/2016 | | |
| WO | WO-2016094117 A1 | * | 6/2016 | ............ C07B 31/00 |
| WO | WO-2018175226 A1 | * | 8/2016 | ............ A01N 43/46 |
| WO | 2016164201 | 10/2016 | | |
| WO | WO-2016164201 A1 | * | 10/2016 | .......... C07D 405/12 |
| WO | 2016176082 | 11/2016 | | |
| WO | 2016182780 | 11/2016 | | |
| WO | 2016196019 | 12/2016 | | |
| WO | 2016196593 | 12/2016 | | |
| WO | WO-2016196593 A1 | * | 12/2016 | .......... C07D 401/04 |
| WO | 20170023515 | 2/2017 | | |
| WO | 2017/075559 | 5/2017 | | |
| WO | WO-2017075559 A1 | * | 5/2017 | ............ A01N 43/36 |
| WO | 2018/065311 | 4/2018 | | |
| WO | 20180118384 | 6/2018 | | |
| WO | 2018/175226 | 9/2018 | | |
| WO | 20180175231 | 9/2018 | | |
| WO | 2018/222646 | 12/2018 | | |
| WO | 2018/222647 | 12/2018 | | |

OTHER PUBLICATIONS

Banerjee et al., "A Stereoselective Cyclization Strategy for the Preparation of gamma-Lactams and Their Use in the Synthesis of alpha-Methyl-beta-Proline", J. Org. Chem. 2012, vol. 77, pp. 10925-10930.

Campaigne et el.; Synthesis of Some Ureidodihydrofurans and Related Pyrimidones as Potential Antimalarials; J. Med. Chem.; 1969; 339-342. (XP002278920).

Cauliez et al.; "Studies on Pyrrolidinones. On the Carbamoylation of Some Pyroglutamic Derivatives"; J. Het. Chem.; 33; 1996; 1233-1237. (XP055297107).

Hajra et al., "Organocatalytic enantioselective conjugate addition of nitromethane to alkylidenemalonates: asymmetric synthesis of pyrrolidine-3-carboxylic acid derivatives", RSC Advances, vol. 3, No. 26, Jan. 1, 2013, pp. 10185-10188 (XP055665141).

Hwang et al.; "Diastereoselective Synthesis of Oxazolidinone Derivatives and Their Antifungal Activities"; Korean J of Med. Chem.; vol. 4, No. 1; 1994; 52-56. (XP009191451).

IPCOM000241978D; Jun. 11, 2015.

PubChem Entry CID 29937915 (4S)-4-[3-(trifluoromethyl)phenyl]pyrrolidin-2-one: May 28, 2009.

Wang et al., "Asymmetric Cyanation of Activated Olefins with Ethyl Cyanoformate Catalyzed by a Modular Titanium Catalyst", Org. Lett., 2010, vol. 12(6), pp. 1280-1283.

XP002734980; Jan. 20, 2002.

XP002734981; WO0009481; Feb. 24, 2000.

XP002759805; Jan. 20, 2002.

XP002759806; Mar. 23, 2009.

V. G. Belikov, Pharmaceutical Chemistry, Chapter 2.6, "The relationship between chemical structure, properties of substances and their effect on the body", M.: MEDpress-inform, 2007, p. 27-29.

CN Decision, "Invalidation Request Examination Decision," in CN Appln. No. 201480074726.8, dated Apr. 20, 2021, 23 pages.

CN Opposition, "Request for Invalitation of a Patent Right," in CN Appln. No 201480074726.8, dated Sep. 9, 2020, 49 pages (English Translation).

CN Support, "Declaration of Aman Chandi," in CN Appln. No 201480074726.8, dated Dec. 18, 2020, 9 pages.

CN Support, "Declaration of Steven Gutteridge," in CN Appln. No. 201480074726.8, dated Dec. 18, 2020, 5 pages.

CN Support, "Declaration of Steven Gutteridge," in CN Appln. No. 201480074726.8, dated Feb. 10, 2021, 5 pages.

EP Opposition Response, "Auxiliary Request 1—marked up," in EP Appln No. 14815174.9, from response dated Jun. 25, 2021, 10 pages.

EP Opposition Response, "Auxiliary Request 1," in EP Appln No. 14815174.9, from response dated Jun. 25, 2021, 10 pages.

EP Opposition Response, "Auxiliary Request 2—marked up," in EP Appln No. 14815174.9, from response dated Jun. 25, 2021, 10 pages.

EP Opposition Response, "Auxiliary Request 2," in EP Appln No. 14815174.9, from response dated Jun. 25, 2021, 10 pages.

EP Opposition Response, "Auxiliary Request 3—marked up," in EP Appln No. 14815174.9, from response dated Jun. 25, 2021, 10 pages.

EP Opposition Response, "Auxiliary Request 3," in EP Appln No. 14815174.9, from response dated Jun. 25, 2021, 9 pages.

EP Opposition Response, "Auxiliary Request 4—marked up," in EP Appln No. 14815174.9, from response dated Jun. 25, 2021, 10 pages.

EP Opposition Response, "Auxiliary Request 4," in EP Appln No. 14815174.9, from response dated Jun. 25, 2021, 9 pages.

EP Opposition Response, "Auxiliary Request 5—marked up," in EP Appln No. 14815174.9, from response dated Jun. 25, 2021, 11 pages.

EP Opposition Response, "Auxiliary Request 5," in EP Appln No. 14815174.9, from response dated Jun. 25, 2021, 7 pages.

EP Opposition Response, "Data testing herbicidal activity of compounds IC1*, IC3* andIC6 against plants," Exhibit D16 in EP Appln No. 14815174.9, from response dated Jun. 25, 2021, 5 pages.

EP Opposition Response, "Experimental data for further compounds," Exhibit D19 in EP Appln. No. 14815174.9, from response dated Jun. 25, 2021, 9 pages.

EP Opposition Response, "HRAC Mode of Action Classification 2021," Exhibit D21 in EP Appln. No. 14815174 9, from response dated Jun. 25, 2021, 2 pages.

EP Opposition Response, "Press Release—Novel herbicide tetflupyrolimet from FMC Corporation granted a new mode of action classification," Exhibit D20 in EP Appln. No 14815174 9, dated Apr. 8, 2021, 3 pages.

EP Opposition Response, "Submission In Opposition Proceedings—FMC," in EP Appln. No. 14815174.9, dated Jun. 25, 2021, 43 pages.

EP Opposition, "Cudney—Why Herbicides Are Selective," Exhibit D22 in EP Appln. No. 14815174.9, 1996 Symposium Proceedings, 3 pages.

EP Opposition, "Notice of Opposition to a European Patent," in EP Appln. No. 14815174.9, dated Aug. 31, 2020, 55 pages.

EP Opposition, "English translation of the second amendments based on granted claims in CNIPA Decision," Exhibit D28 in EP Appln. No 14815174.9, dated Apr. 15, 2021, 3 pages.

EP Opposition, "Smith—Organic Chemistry, An Acid-Base Approach," Exhibit D25 in EP Appln. No. 14815174.9, CRC Press, Taylor & Francis Group, LLC, 2011, pp. 24-32, 23 pages.

EP Opposition, "Submission In Opposition Proceedings—Syngenta," in EP Appln. No. 14815174.9, dated Nov. 5, 2020, 68 pages.

(56) References Cited

OTHER PUBLICATIONS

EP Opposition, "Summons to Attend Oral Proceedings Pursuant to Rule 115(1) EPC," in EP Appln. No 14815174.9, dated Jul. 16, 2021, 14 pages.
EP Opposition, "TechLine Invasive Plant News—Factors Affecting Herbicide Performance," Exhibit D23 in EP Appln. No 14815174.9, dated Jun. 2019, 9 pages.
EP Opposition, "US-PTAB Decision in relation to U.S. Pat. No. 10,294,202 B2," Exhibit D30 in EP Appln. No. 14815174.9, dated Aug. 31, 2021, 66 pages.
EP Opposition, "Walsh—Enzymatic Reaction Mechanisms," Exhibit D26 in EP Appln. No. 14815174.9, W. H. Freeman and Company, 1979, Chapter 2, pp. 24-48, 27 pages.
EP Opposition, "Williams—Opportunities for Chiral Agrochemicals," Exhibit D24 in EP Appln. No. 14815174.9, Pestic Sci., 1996, 46:3-9.
EP Opposition, "Written Submission," in EP Appln. No. 14815174.9, dated Dec. 14, 2021, 3 pages.
EP Opposition, "Written Submission," in EP Appln. No. 14815174.9, dated Dec. 7, 2021, 2 pages.
EP Opposition, "Written Submission," in EP Appln. No. 14815174.9, dated Nov. 25, 2021, 32 pages.
EP Opposition, "Written Submission," in EP Appln. No. 14815174.9, dated Nov. 30, 2021, 6 pages.
IN Opposition, "Declaration of Dhaval Dayabhai Diyora," in IN Appln. No. 201617018886, dated Jun. 1, 2016, 60 pages.
International Search Report in International Appln. No. PCT/US2014/068073, dated Feb. 10, 2015, 10 pages.
International Preliminary Report on Patentability in International Appln. No. PCT/US2014/068073, dated Nov. 10, 2016, 15 pages.

\* cited by examiner

PYRROLIDINONES HERBICIDES

FIELD OF THE INVENTION

This invention relates to certain pyrrolidinones, their N-oxides and salts, and compositions and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all stereoisomers), including N-oxides and salts thereof agricultural compositions containing them and their use as herbicides:

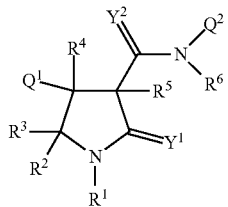

1 wherein
- $Q^1$ is a phenyl ring or a naphthalenyl ring system, each ring or ring system optionally substituted with up to 5 substituents independently selected from $R^7$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members;
- $Q^2$ is a phenyl ring or a naphthalenyl ring system, each ring or ring system optionally substituted with up to 5 substituents independently selected from $R^{10}$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members;
- $Y^1$ and $Y^2$ are each independently O, S or $NR^{12}$;
- $R^1$ is H, hydroxy, amino, $C_1$-$C_6$ alkyl, $C_1$-$C_6$ haloalkyl, $C_2$-$C_6$ alkenyl, $C_3$-$C_6$ alkynyl, $C_4$-$C_5$ cycloalkylalkyl, $C_2$-$C_8$ alkoxyalkyl, $C_2$-$C_8$ haloalkoxyalkyl, $C_2$-$C_8$ alkylthioalkyl, $C_2$-$C_5$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulonyl, $C_1$-$C_6$ alkylaminosulfonyl, $C_2$-$C_8$ dialkylaminosulfonyl, $C_3$-$C_{10}$ trialkylsilyl or $G^1$;
- $R^2$ and $R^3$ are each independently H, halogen or $C_1$-$C_4$ alkyl; or
- $R^2$ and $R^3$ are taken together with the carbon atom to which they are bonded to form a $C_3$-$C_7$ cycloalkyl ring;
- $R^4$ and $R^5$ are each independently H, halogen or $C_1$-$C_4$ alkyl;
- $R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl. $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;
- each $R^7$ and $R^{10}$ is independently halogen, cyano, nitro, $C_1$-$C_8$ alkyl, $C_1$-$C_8$ haloalkyl, $C_1$-$C_8$ nitroalkyl, $C_2$-$C_5$ alkenyl, $C_2$-$C_5$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_5$ halocycloalkyl, $C_4$-$C_{10}$ alkylcycloalkyl. $C_6$-$C_{12}$ cycloalkylcycloalkyl, $C_3$-$C_8$ cycloalkenyl, $C_3$-$C_8$ halocycloalkenyl, $C_2$-$C_5$ alkoxyalkyl, $C_2$-$C_5$ haloalkoxyalkyl, $C_3$-$C_8$ haloalkoxyalkoxy, $C_3$-$C_8$ alkoxyalkoxy, $C_4$-$C_{10}$ cycloalkoxyalkyl, $C_3$-$C_{10}$ alkoxyalkoxyalkyl. $C_2$-$C_8$ alkylthioalkyl, $C_2$-$C_8$ alkylsulfinylalkyl, $C_2$-$C_8$ alkylsulfonylalkyl, $C_2$-$C_5$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_5$ haloalkylcarbonyl, $C_4$-$C_{10}$ cycloalkylcarbonyl, —C(=O)OH. $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_5$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_2$-$C_8$ alkoxycarbonylamino, $C_1$-$C_6$ alkylsulfonylamino, $C_1$-$C_6$ haloalkylsulfonylamino, —$SF_5$, —SCN, $SO_2NH_2$, $C_3$-$C_{12}$ trialkylsilyl. $C_4$-$C_{12}$ trialkylsilylalkyl, $C_4$-$C_{12}$ trialkylsilylalkoxy or $G^2$;

each $R^8$ is independently H, cyano, $C_2$-$C_3$ alkylcarbonyl or $C_2$-$C_3$ haloalkylcarbonyl;

each $R^9$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl $C_1$43 alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, $C_1$-$C_4$ alkyl, $C_1$-$C_4$ haloalkyl, —(C=O)$CH_3$ or —(C=O)$CF_3$;

each $G^1$ is independently phenyl, phenylmethyl (i.e. benzyl), pyridinylmethyl, phenylcarbonyl (i.e. benzoyl), phenoxy, phenylethynyl, phenylsulfonyl or a 5- or 6-membered heteroaromatic ring, each optionally substituted on ring members with up to 5 substituents independently selected from $R^{13}$;

each $G^2$ is independently phenyl, phenylmethyl (i.e. benzyl), pyridinylmethyl, phenylcarbonyl (i.e. benzoyl), phenoxy, phenylethynyl, phenylsulfonyl or a 5- or 6-membered heteroaromatic ring, each optionally substituted on ring members with up to 5 substituents independently selected from $R^{14}$;

each $R^{13}$ and $R^{14}$ is independently halogen, cyano, hydroxy, amino, nitro, —CHO, —C(=O)OH, —C(=O)$NH_2$, —$SO_2NH_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_5$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy. $C_1$-$C_6$ haloalkoxy, $C_2$-$C_5$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl; and each u and v are independently 0, 1 or 2 in each instance of $S(=O)_u(=NR^8)$, provided that the sum of u and v is 0, 1 or 2;

provided that (a) the compound of Formula 1 is other than N—H-benzotriazol-1-yl-2-oxo-4-phenyl-3-pyrrolidinecarboxamide;

(b) when $Q^1$ comprises a 3-furanyl or 3-pyridinyl ring directly bonded to the remainder of Formula 1, then said ring is substituted with at least one substituent selected from $R^7$;

(c) when $Q^1$ is an unsubstituted phenyl ring, and $Q^2$ comprises a phenyl ring directly bonded to the remainder of Formula 1, then said $Q^2$ ring is substituted with $R^{10}$ other than optionally substituted phenoxy or F at a 2-position, cyano or —$CF_3$ at the 4-position and $R^5$ is H or halogen;

(d) when $Q^1$ is unsubstituted phenyl, and $Q^2$ comprises a pyridinyl ring directly bonded to the remainder of Formula 1, then said pyridinyl ring is substituted with at least one substituent selected from $R^{10}$;

(e) when $Q^1$ is a phenyl ring substituted with 4-phenyl or 4-phenoxy, said $Q^1$ ring is further substituted with and $R^7$ substituent;

(f) when $Q^1$ comprises a phenyl ring directly bonded to the remainder of Formula 1 and said ring is substituted with $R^7$ at both ortho positions (relative to the bond to the remainder of Formula 1), then said ring is also independently substituted with $R^7$ on at least one additional position;

(g) when $Q^1$ is other than unsubstituted 1-naphthalenyl, then $Q^2$ is other than 2,3-difluorophenyl or 2-$CF_3$-phenyl;

(h) $Q^2$ is other than optionally substituted 1H-pyrazol-5-yl; and (i) when $Q^2$ comprises a H-pyrazol-3-yl ring directly bonded to the remainder of Formula 1, said ring is substituted at the 1-position with $R^9$.

More particularly, this invention pertains to a compound of Formula 1 (including all stereoisomers), an N-oxide or a salt thereof, his invention also relates to a herbicidal composition comprising a compound of the invention (i.e. in a herbicidally effective amount) and at least one component selected from the group consisting of surfactants, solid diluents and liquid diluents, the composition optionally further comprising at least one additional active ingredient selected from the group consisting of other herbicides and herbicide safeners. This invention further relates to a method for controlling the growth of undesired vegetation comprising contacting the vegetation or its environment with a herbicidally effective amount of a compound of the invention (e.g., as a composition described herein).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3CH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxyalkyl" denotes at least alkoxy substitution on the alkoxy moiety of alkoxyalkyl moiety. Examples of "alkoxyalkoxyalkyl" include $CH_3OCH_2OCH_2$—, $CH_3CH_2O(CH_3)CHOCH_2$— and $(CH_3O)_2CHOCH_2$—. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$. $(CH_3)_2C=CHCH_2$, $(CH_3)CH=CHCH_2$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC≡CCH_2O$, $CH_3C≡CCH_2O$ and $CH_3C≡CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinylalkyl" denotes alkylsulfinyl substitution on alkyl. Examples of "alkylsulfinylalkyl" include $CH_3S(=O)CH_2$, $CH_3S(=O)CH_2CH_2$, $CH_3CH_2S(=O)CH_2$ and $CH_3CH_2S(=O)CH_2CH_2$. "Alkylsulfonylalkyl" denotes alkylsulfinyl substitution on alkyl. Examples of "alkylsulfinylalkyl" include $CH_3S(=O)_2CH_2$, $CH_3S(=O)_2CH_2CH_2$, $CH_3CH_2S(=O)_2CH_2$ and $CH_3CH_2S(=O)_2CH_2CH_2$. "Alkylamino", "dialkylamino", and the like, are defined analogously to the above examples. Examples of "alkylaminoalkyl" include $CH_3NHCH_2$—, $(CH_3)_2CHNHCH_2$— and $CH_3NHCH(CH_3)$—. Examples of "dialkylaminoalkyl" include $(CH_3)_2NCH_2$—, $(CH_3)_2NC(CH_3)H$— and $(CH_3)(CH_3)NCH_2$—. Examples of "dialkylaminocarbonyl" include $(CH_3)_2NC(O)$—. Examples of "dialkylaminosulfonyl" include $(CH_3)_2NS(O)_2$—. The term "alkoxycarbonylamino" denotes a straight-chain or branched alkoxy moieties bonded to a C(=O) moiety of carbonylamino group. Examples of "alkoxycarbonylamino" include $CH_3OC(=O)NH$— and $CH_3CH_2OC(=O)NH$—.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalky", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "halocycloalkyl", "haloalkoxy", "haloalkylthio", "haloalkenyl", "haloalkynyl", "haloalkenyloxy", "haloalkylcarbonylamino", "haloalkylsulfonylamino", "haloalkylsulfonyloxy", "haloalkoxyalkyl", "haloalkylcarbonyloxy", "haloalkylaminoalkyl" and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include CCl$_3$S—, CF$_3$S—, CCl$_3$CH$_2$S— and ClCH$_2$CH$_2$CH$_2$S—. Examples of "haloalkylsulfinyl" include CF$_3$S(O)—, CCl$_3$S(O)—, CF$_3$CH$_2$S(O)— and CF$_3$CF$_2$S(O)—. Examples of "haloalkylsulfonyl" include CF$_3$S(O)$_2$—, CCl$_3$S(O)$_2$—, CF$_3$CH$_2$S(O)$_2$— and CF$_3$CF$_2$S(O)$_2$—. Examples of "haloalkenyl" include (Cl)$_2$C=CHCH$_2$— and CF$_3$CH$_2$CH=CHCH$_2$—. Examples of "haloalkenyloxy" include (Cl)$_2$C=CHCH$_2$O— and CF$_3$CH$_2$CH=CHCH$_2$O—. Examples of "haloalkynyl" include HC≡CCHCl—, CF$_3$C≡C—, CCl$_3$C≡C— and FCH$_2$C≡ClCH$_2$—. Examples of "haloalkoxyalkyl" include CF$_3$OCH$_2$—, ClCH$_2$CH$_2$OCH$_2$CH$_2$—, C$_{13}$ClCH$_2$OCH$_2$— as well as branched alkyl derivatives. Examples of "haloalkoxycarbonyl" include CF$_3$C(O)—, ClCH$_2$CH$_2$OCH$_2$CH$_2$—, C$_{13}$ClCH$_2$CH$_2$C(O)— as well as branched alkyl derivatives.

"Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$C(=O)—, (CH$_3$)$_2$CHOC(=O)— and the different butoxy- or pentoxycarbonyl isomers. "Cycloalkylalkoxycarbonyl" denotes a cycloalkylalkyl moieties bonded to an oxygen atom of alkoxycarbonyl moiety. Examples of "cycloalkylalkoxycarbonyl" include cyclopropyl-CH$_2$OC(=O)—, cyclopropyl-CH(CH$_3$)OC(=O)— and cyclopentyl-CH$_2$OC(=O)—.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates CH$_3$OCH$_2$—; $C_3$ alkoxyalkyl designates, for example, CH$_3$CH(OCH$_3$)—, CH$_3$OCH$_2$CH$_2$— or CH$_3$CH$_2$OCH$_2$—; and $C_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., [R$^7$)$_n$], n is 1, 2, 3, 4 or 5). Further, when the subscript indicates a range, e.g. (R)$_{i-j}$, then the number of substituents may be selected from the integers between i and j inclusive. When a group contains a substituent which can be hydrogen, for example R$^1$ or R$^2$, then when this substituent is taken as hydrogen, it is recognized that this is equivalent to said group being unsubstituted. When a variable group is shown to be optionally attached to a position, for example [R$^{(7)}{}_n$] wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hükel's rule then it can also be described as aromatic.

Unless otherwise indicated, a "ring" or "ring system" as a component of Formula 1 (e.g., substituent Q$^1$) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. A "bridged bicyclic ring system" is formed by bonding a segment of one or more atoms to nonadjacent ring members of a ring. The term "ring member" refers to an atom or other moiety (e.g., C(=O), C(=S), S(O) or S(O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) a electrons, where n is a positive integer, are associated with the ring to comply with Hackel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When $Q^1$ or $Q^2$ is 5- or 6-membered nitrogen-containing heterocyclic ring, it may be attached to the remainder of Formula 1 though any available carbon or nitrogen ring atom, unless otherwise described. As noted above, $Q^1$ and $Q^2$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein, for example, R is $R^7$ as defined in the Summary of the Invention for $Q^1$, or $R^v$ is $R^{10}$ as defined in the Summary of the Invention for $Q^2$, and r is an integer (from 0 to 5).

As noted above, $Q^1$ and $Q^2$ can be (among others) a 5- or 6-membered fully unsaturated heterocyclic ring, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for $Q^1$ and $Q^2$, and r is an integer from 0 to 4, limited by the number of available positions on each U group. As U-29, U-30, U-36, U-37, U-38, U-39, U40, U41, U-42 and U43 have only one available position, for these U groups r is limited to the integers 0 or 1, and r being 0 means that the U group is unsubstituted and a hydrogen is present at the position indicated by $(R^v)_r$.

Exhibit 1

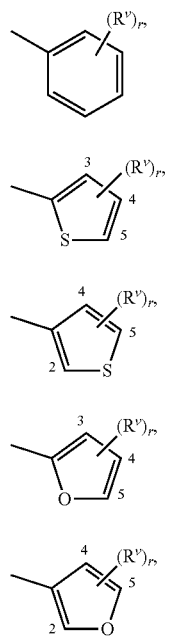

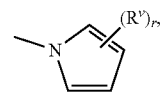

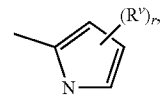

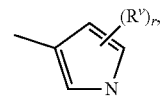

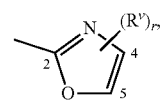

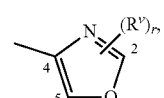

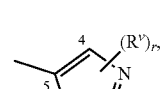

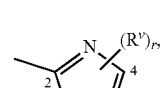

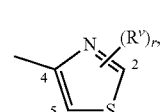

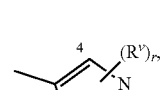

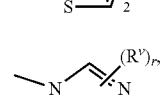

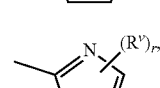

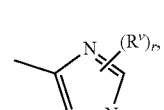

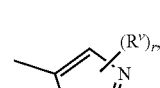

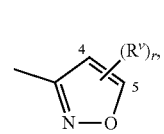

| | | | |
|---|---|---|---|
| 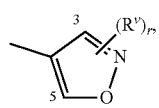 | U-20 | 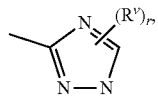 | U-33 |
| 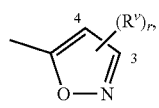 | U-21 | 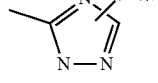 | U-34 |
| 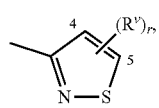 | U-22 | 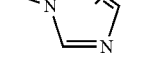 | U-35 |
| 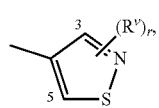 | U-23 | 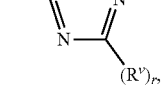 | U-36 |
| 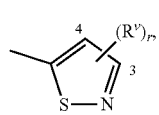 | U-24 | 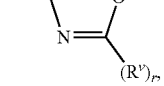 | U-37 |
| 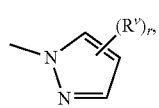 | U-25 | 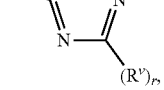 | U-38 |
| 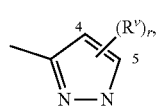 | U-26 | 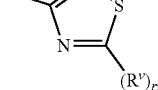 | U-39 |
| 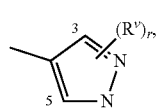 | U-27 | 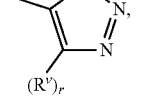 | U-40 |
| 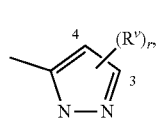 | U-28 | 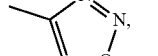 | U-41 |
| 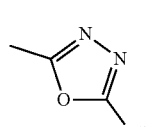 | U-29 | 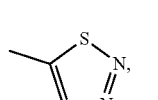 | |
| 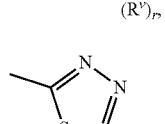 | U-30 | 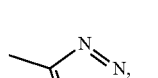 | U-42 |
| 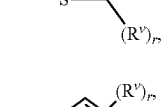 | U-31 | 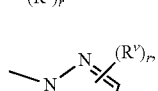 | U-43 |
| 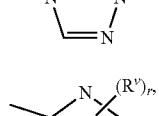 | U-32 |  | U-44 |

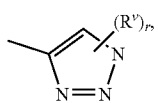 U-45

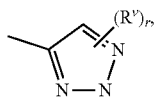 U-46

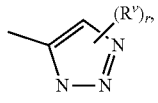 U-47

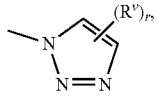 U-48

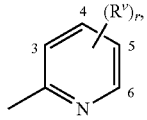 U-49

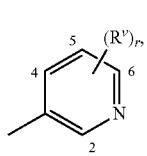 U-50

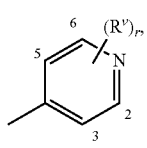 U-51

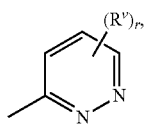 U-52

 U-53

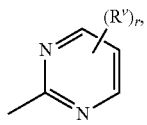 U-54

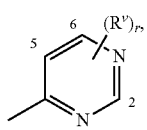 U-55

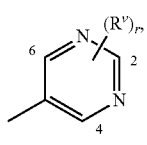 U-56

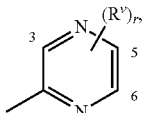 U-57

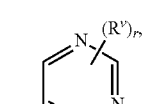 U-58

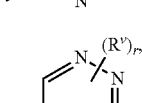 U-59

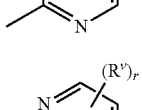 U-60

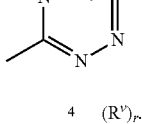 and

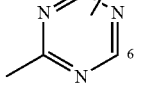 U-61

As noted above, $Q^1$ and $Q^2$ can be (among others) an 8-, 9- or 10-membered heteroaromatic bicyclic ring system optionally substituted with one or more substitutes selected from a group of substituents as defined in the Summary of the Invention for $Q^1$ and $Q^2$. Examples of 8-, 9- or 10-membered heteroaromatic bicyclic ring system optionally substituted with from one or more substituents include the rings U-62 through U-00 illustrated in Exhibit 2 wherein $R^v$ is any substituent as defined in the Summary of the Invention for $Q^1$ or $Q^2$, and r is typically an integer from 0 to 4.

Exhibit 2

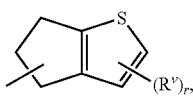 U-62

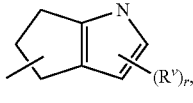 U-63

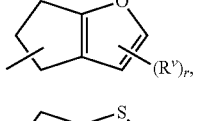 U-64

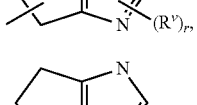 U-65

 U-66

| | |
|---|---|
| 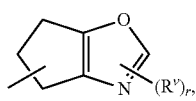 | U-67 |
| 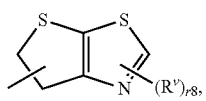 | U-68 |
| 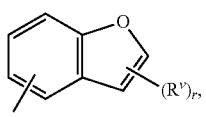 | U-69 |
| 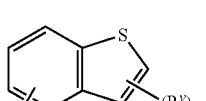 | U-70 |
| 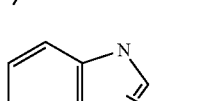 | U-71 |
| 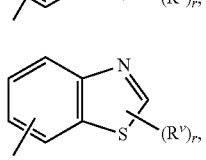 | U-72 |
| 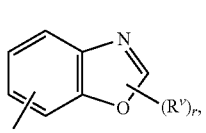 | U-73 |
| 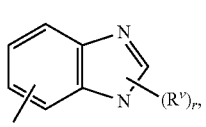 | U-74 |
| 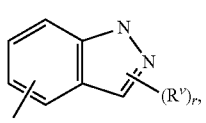 | U-75 |
| 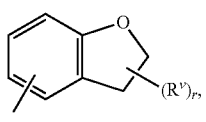 | U-76 |
| 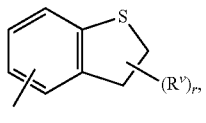 | U-77 |
| 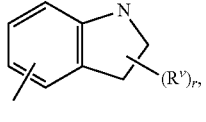 | U-78 |
| 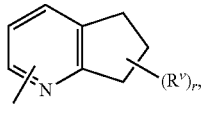 | U-79 |
| 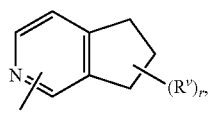 | U-80 |
| 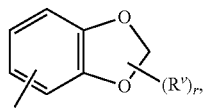 | U-81 |
| 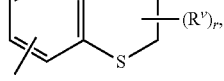 | U-82 |
| 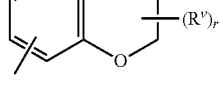 | U-83 |
| 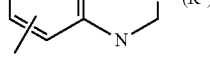 | U-84 |
| 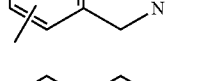 | U-85 |
|  | U-86 |
| 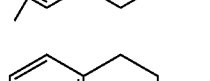 | U-87 |
| 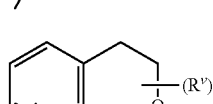 | U-88 |
| 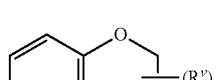 | U-89 |
| 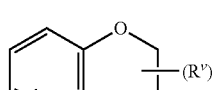 | U-90 |
| 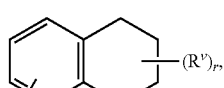 | U-91 |
|  | U-92 |

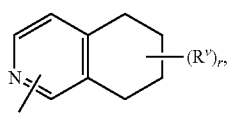 U-93

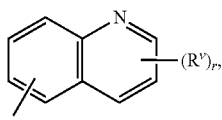 U-94

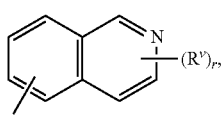 U-95

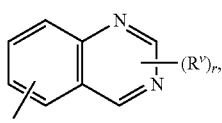 U-96

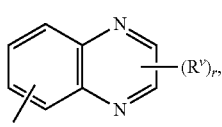 U-97

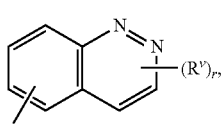 U-98

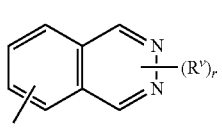 U-99 and

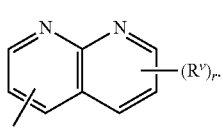 U-100

Although $R^v$ groups are shown in the structures U-1 through U-100, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Preferably for greatest herbicidal activity, the U group is attached to the remainder of Formula 1 through an available carbon or nitrogen on a fully unsaturated ring of the U group. Note that some U groups can only be substituted with less than 4 $R^v$ groups (e.g., U-2 through U-5, U-7 through U-48, and U-52 through U-61).

In the present disclosure and claims, the term "pyrrolidinone" and related terms such as "pyrrolidinone ring" refer to 2-oxo-pyrrolidine derivatives according to the Chemical Abstracts system of nomenclature, including derivatives in which the oxygen atom of the 2-oxo moiety is replaced by S or $NR^{12}$ as $Y^1$, unless limited to oxygen by particular context.

A wide variety of synthetic methods are known in the art to enable preparation of aromatic and nonaromatic heterocyclic rings and ring systems; for extensive reviews see the eight volume set of *Comprehensive Heterocyclic Chemistry*, A R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. Particularly when $R^4$ and $R^5$ are each H, the $C(O)N(Q^2)(R^6)$ and Qt substituents are typically mostly in the thermodynamically preferred trans configuration on the pyrrolidinone ring.

For example the $C(O)N(Q^2)(R^6)$ moiety (bonded to the carbon at the 3-position of the pyrrolidinone ring) and $Q^1$ (bonded to the carbon at the 4-position of the pyrrolidinone ring) are generally found in the trans configuration. These two carbon atoms (i.e. at the 3- and 4-positions each possess the pyrroldinone ring of Formula 1) both possess a chiral center. The two most prevelant pairs of enantiomers are depicted as Formula 1' and Formula 1" where the chiral centers are identified (i.e. as 3R,4S or as 3S,4R) wherein $R^1$ is hydrogen. While this invention pertains to all stereoisomers, the preferred enantiomeric pair for biological operability is identified as Formula 1' (i.e. the 3R,4S configuration) wherein $R^1$ is hydrogen. For a comprehensive discussion of all aspects of stereoisomerism, see Ernest L. Eliel and Samuel H. Wilen, *Stereochemistry of Organic Compounds*, John Wiley & Sons, 1994.

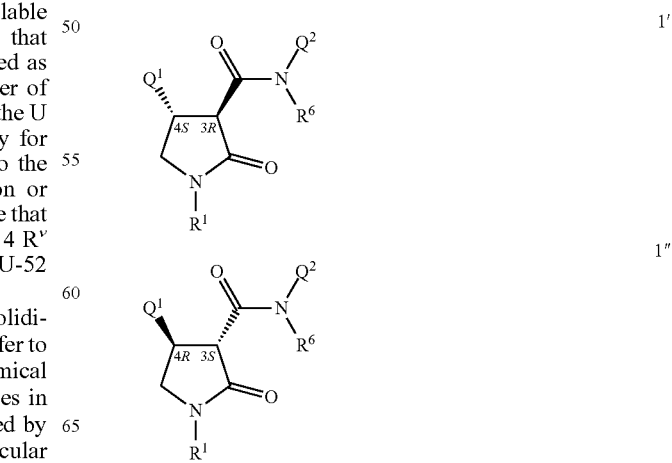

The skilled artisan will also recognize that the carbon atom at the 5-position of the pyrrolidinone ring (i.e. the carbon atom to which both R$^2$ and R$^3$ are bonded) also contains a stereocenter indicated by a (*) as shown in Formula 1'''. This invention pertains to all stereoisomers, and therefore, when either R$^2$ or R$^3$ are other than the same substituent, then a mixture of diastereomers is possible.

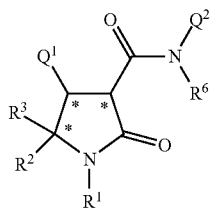

1'''

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention also comprises racemic mixtures, for example, equal amounts of the enantiomers of Formulae 1' and 1" (and optionally 1'''). In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enentiomeric ratio (ER) expressed as the relative area % of the two entantiomers determined by chiral high-performance liquid chromatography.

Preferably the compositions of this invention have at least a 50% ER; more preferably at least a 75% ER, still more preferably at least a 90% ER; and the most preferably at least a 94% ER of the more active isomer. Of particular note are enantiomerically pure embodiments of the more active isomer.

Compounds of Formula 1 can comprise additional chiral centers. For example, substituents and other molecular constituents such as R$^2$, R$^3$ and R$^6$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond C(O)N(Q$^2$)(R$^6$) in Formula 1. This invention comprises mixtures of conformational isomers. In addition, this invention includes compounds that are enriched in one conformer relative to others. Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 wherein when $Q^1$ is an 8- to 10-membered heteroaromatic bicyclic ring system optionally substituted with $R^7$ and $R^9$, the remainder of Formula 1 is bonded to a fully unsaturated ring of said bicyclic ring system.

Embodiment 2

A compound of Formula 1 or Embodiment 1 wherein $Q^1$ is a phenyl ring optionally substituted with up to 5 substituents independently selected from $R^7$.

Embodiment 3

A compound of Embodiment 2 wherein $Q^1$ is a phenyl ring substituted with 1 to 3 substituents independently selected from $R^7$.

Embodiment 4

A compound of Embodiment 3 wherein $Q^1$ is a phenyl ring substituted with 1 to 2 substituents independently selected from $R^7$.

Embodiment 5

A compound of Formula 1 or any one of Embodiments 1 through 4 wherein $Q^1$ is a phenyl ring having a substituent selected from $R^7$ at the para (4-) position (and optionally other substituents).

Embodiment 6

A compound of Formula 1 or any one of Embodiments 1 through 5 wherein when $Q^1$ is a phenyl ring substituted with at least two substituents selected from $R^1$, then one substituent is at the para (4-) position and at least one other substituent is at a meta position (of the phenyl ring).

Embodiment 7

A compound of Formula 1 or any one of Embodiments 1 through 6 wherein when $Q^2$ is an 8- to 10-membered heteroaromatic bicyclic ring system optionally substituted with $R^{10}$ and $R^{11}$, the remainder of Formula 1 is bonded to a fully unsaturated ring of said bicyclic ring system.

Embodiment 8

A compound of Formula 1 or any one of Embodiments 1 through 7 wherein $Q^2$ is a phenyl ring substituted with up to 5 substituents independently selected from $R^{10}$.

Embodiment 9

A compound of Embodiment 8 wherein $Q^2$ is a phenyl ring substituted with 1 to 3 substituents independently selected from $R^{10}$.

Embodiment 10

A compound of Embodiment 9 wherein $Q^2$ is a phenyl ring substituted with 1 to 2 substituents independently selected from $R^1$.

Embodiment 11

A compound of Formula 1 or any one of Embodiments 1 through 10 wherein $Q^2$ is a phenyl ring having at least one substituent selected from $R^{10}$ at an ortho (e.g., 2-) position (and optionally other substituents).

Embodiment 12

A compound of Formula 1 or any one of Embodiments 1 through 11 wherein when $Q^2$ is a phenyl ring substituted with at least two substituents selected from $R^{10}$, then at least one substituent is at an ortho (e.g., 2-) position and at least one substituent is at an adjacent meta (e.g., 3-) position (of the phenyl ring).

Embodiment 13

A compound of Formula 1 or any one of Embodiments 1 through 12 wherein, independently, each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy.

Embodiment 14

A compound of Embodiment 13 wherein each $R^7$ is independently halogen, cyano, $C_1$-$C_2$ alkyl, $C_1$-$C_3$ haloalkyl or $C_1$-$C_3$ alkylsulfonyl.

Embodiment 15

A compound of Embodiment 14 wherein each $R^7$ is independently halogen or $C_1$-$C_2$ haloalkyl.

Embodiment 16

A compound of Embodiment 15 wherein each $R^7$ is independently halogen or $C_1$ haloalkyl.

Embodiment 17

A compound of Embodiment 16 wherein each $R^7$ is independently halogen or $C_1$ fluoroalkyl.

Embodiment 18

A compound of Embodiment 17 wherein each $R^7$ is independently halogen or $CF_3$.

Embodiment 19

A compound of Embodiment 18 wherein each $R^7$ is independently F, Cl, Br or $CF_3$.

Embodiment 20

A compound of Embodiment 19 wherein each $R^7$ is independently F or $CF_3$.

Embodiment 21

A compound of Embodiment 19 or 20 wherein at most only one $CF_3$ substituent is present and is at the para position of the $Q^1$ phenyl ring.

Embodiment 22

A compound of any one of Embodiments 13 through 21 wherein each $R^{10}$ is independently halogen, cyano, nitro, $C_1$-$C_2$ alkyl, $C_1$-$C_3$ haloalkyl or $C_1$-$C_3$ alkylsulfonyl.

Embodiment 23

A compound of Embodiment 22 wherein each $R^{10}$ is independently halogen or $C_1$-$C_2$ haloalkyl.

Embodiment 24

A compound of Embodiment 23 wherein each $R^{10}$ is independently halogen or $C_1$ haloalkyl.

Embodiment 25

A compound of Embodiment 24 wherein each $R^{10}$ is independently halogen or $C_1$ fluoroalkyl.

Embodiment 26

A compound of Embodiment 25 wherein each $R^{10}$ is independently halogen or $CF_3$.

Embodiment 27

A compound of Embodiment 26 wherein each $R^{10}$ is independently F. Cl, Br or $CF_3$-Embodiment 28. A compound of Embodiment 27 wherein each $R^{10}$ is independently F or $CF_3$.

Embodiment 29

A compound of Embodiment 28 wherein each $R^{10}$ is F.

Embodiment 30

A compound of Formula 1 or any one of Embodiments 1 through 29 wherein, independently, each $R^9$ and $R^{11}$ is independently H or $C_1$-$C_2$ alkyl.

Embodiment 31

A compound of Embodiment 28 wherein, independently, each $R^9$ and $R^{11}$ is $CH_3$.

Embodiment 32

A compound of Formula 1 or any one of Embodiments 1 through 31 wherein $Y^1$ is O.

Embodiment 33

A compound of Formula 1 or any one of Embodiments 1 through 32 wherein $Y^2$ is O.

Embodiment 33a

A compound of Formula 1 or any one of Embodiments 1 through 33 wherein $R^1$ is H, $C_1$-$C_6$ alkyl. $C_1$-$C_6$ haloalkyl or $C_4$-$C_8$ cycloalkylalkyl.

Embodiment 33b

A compound of Formula 1 or any one of Embodiments 1 through 33a wherein $R^1$ is H, $C_1$-$C_6$ alkyl or $C_1$-$C_6$ haloalkyl.

Embodiment 33c

A compound of Formula 1 or any one of Embodiments 1 through 33b wherein $R^1$ is H, Me, Et or $CHF_2$.

Embodiment 33d

A compound of Formula 1 or any one of Embodiments 1 through 33c wherein $R^1$ is H, Me or Et.

Embodiment 34

A compound of Formula 1 or any one of Embodiments 1 through 33 wherein $R^1$ is H or $CH_3$.

Embodiment 34a

A compound of Formula 1 or any one of Embodiments 1 through 34 wherein $R^1$ is $CH_3$.

Embodiment 35

A compound of Embodiment 34 wherein $R^1$ is H.

Embodiment 36

A compound of Formula 1 or any one of Embodiments 1 through 35 wherein $R^2$ is H or $CH_3$.

Embodiment 37

A compound of Embodiment 36 wherein $R^2$ is H.

Embodiment 38

A compound of Formula 1 or any one of Embodiments 1 through 37 wherein $R^3$ is H or $CH_3$.

Embodiment 39

A compound of Embodiment 38 wherein $R^3$ is H.

Embodiment 40

A compound of Formula 1 or any one of Embodiments 1 through 39 wherein $R^4$ is H or $CH_3$.

Embodiment 41

A compound of Embodiment 40 wherein $R^4$ is H.

Embodiment 42

A compound of Formula 1 or any one of Embodiments 1 through 41 wherein $R^5$ is H or $CH_3$.

Embodiment 43

A compound of Embodiment 42 wherein $R^5$ is H.

Embodiment 44

A compound of Formula 1 or any one of Embodiments 1 through 43 wherein $R^6$ is H or $CH_3$.

Embodiment 45

A compound of Embodiment 44 wherein $R^6$ is H.

Embodiment 46

A compound of Formula 1 or any one of Embodiments 1 through 45 wherein $Q^2$ is other than 1H-indazol-5-yl optionally substituted at the 3-position.

Embodiment 47

A compound of Embodiment 46 wherein $Q^2$ is other than 1H-indazol-5-yl optionally substituted at the 1- and 3-positions.

Embodiment 48

A compound of Embodiment 47 wherein $Q^2$ is other than optionally substituted 1H-indazol-5-yl.

Embodiment 49

A compound of any one of Embodiments 1 through 48 wherein $Q^1$ is other than unsubstituted phenyl.

Embodiment 50

A compound of any one of Embodiments 1 through 49 wherein $Q^2$ is other than unsubstituted pyridinyl.

Embodiment 51

A compound of any one of Embodiments 1 through 50 wherein $Q^1$ is other than optionally substituted naphthalenyl.

Embodiment 52

A compound of any one of Embodiments 1 through 51 wherein $G^2$ is other than optionally substituted phenyl.

Embodiment 53

A compound of any one of Embodiments 1 through 51 wherein $G^2$ is other then optionally substituted phenyl at the 4 position (of $Q^1$).

Embodiment 54

A compound of any one of Embodiments 1 through 52 wherein $G^2$ is other than optionally substituted phenoxy

Embodiment 55

A compound of any one of Embodiments 1 through 54 wherein $G^2$ is other than optionally substituted phenoxy at the 4-position (of $Q^1$).

Embodiment 56

A compound of Formula 1 or any one of Embodiments 1 through 55 wherein the stereochemistry is (3R,4S) or (3S,4R).

Embodiment 57

A compound of Embodiment 54 wherein the stereochemistry is (3R,4S)

Embodiment 58

A compound of Embodiment 54 wherein the stereochemistry is (3S,4R).

Embodiments of this invention, including Embodiments 1-58 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-58 above as well as any other embodiments described herein, and any combination thereof, pertain to the compositions and methods of the present invention.

Combinations of Embodiments 1-58 are illustrated by:

Embodiment A

A compound of Formula 1 wherein
each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_4$ trialkylsilyl, trimethylsilylmethyl or trimethylsilylmethoxy; and each $R^9$ and $R^1$ is independently H or $C_1$-$C_2$ alkyl.

Embodiment B

A compound of Embodiment A wherein
$Y^1$ and $Y^2$ are each O; and
$R^1$, $R^2$, $R^3$, $R^4$, $R^5$ and $R^6$ are each H.

Embodiment C

A compound of Embodiment B wherein
$Q^1$ is a phenyl ring substituted with 1 to 3 substituents independently selected from $R^7$; and
$Q^2$ is a phenyl ring substituted with 1 to 3 substituents independently selected from $R^{10}$.

Embodiment D

A compound of Embodiment C wherein
each $R^7$ is independently halogen, cyano, $C_1$-$C_2$ alkyl, $C_1$-$C_3$ haloalkyl or $C_1$-$C_3$ alkylsulfonyl; and
each $R^1$ is independently halogen, cyano, nitro, $C_1$-$C_2$ alkyl, $C_1$-$C_3$ haloalkyl or $C_1$-$C_3$ alkylsulfonyl.

Embodiment E

A compound of Embodiment D wherein
$Q^1$ is a phenyl ring substituted with 1 substituent selected from $R^7$ at the para position or substituted with 2 substituents independently selected from $R^7$ wherein one substituent is at the para position and the other substituent is at a meta position; and
$Q^2$ is a phenyl ring substituted with 1 substituent selected from $R^{10}$ at an ortho position or substituted with 2 substituents independently selected from $R^{10}$ wherein one substituent is at an ortho position and the other substituent is at the adjacent meta position.

Embodiment F

A compound of Embodiment E wherein
each $R^7$ is independently F or $CF_3$; and
each $R^{10}$ is F.

Specific embodiments include compounds of Formula 1 selected from the group consisting of
N-(2,3-difluorophenyl)-4-(3,4-difluorophenyl)-2-oxo-3-pyrrolidinecarboxamide (Compound 17);
N-(2-fluorophenyl)-2-oxo-4-[4-(trifluoromethyl)phenyl]-3-pyrrolidinecarboxamide (Compound 79):
N-(2,3-difluorophenyl)-2-oxo-4-[4-(trifluoromethyl)phenyl]-3-pyrrolidinecarboxamide (Compound 80);
N-(3,4-difluorophenyl)-N-(2-fluorophenyl)-2-oxo-3-pyrrolidinecarboxamide (Compound 5); and
(3R,4S)—N-(2-fluorophenyl)-2-oxo-4-[3-(trifluoromethyl)phenyl]-3-pyrrolidinecarboxamide (Compound 204).

Specific Embodiments include a compound of Formula 1 selected from the group consisting of Compound Numbers (where the Compound Number refers to the compound in Index Tables A, B or C): 80, 202, 204, 206, 232, 263, 304, 306, 315 and 319; or 202, 206, 232, 304 and 306; or 202, 232 and 306.

Specific Embodiments include a compound of Formula 1 selected from the group consisting of Compound Numbers (where the Compound Number refers to the compound in Index Tables A, B or C): 3, 5, 17, 101, 103, 156, 204, 271, 323 and 351; or 3, 17, 103, 156, and 204; or 103, 204 and 351.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, acetohydroxy acid synthase (AHAS) inhibitors, acetyl-CoA carboxylase (ACCase) inhibitors, auxin mimics, (b5) 5-enol-pyruvylshikimate-3-phosphate (EPSP) synthase inhibitors, photosystem I electron diverters, protoporphyrinogen oxidase (PPO) inhibitors, glutamine synthetase (GS) inhibitors, very long chain fatty acid (VLCFA) elongase inhibitors, auxin transport inhibitors, phytoene desaturase (PDS) inhibitors, (b12) 4-hydroxyphenyl-pyruvate dioxygenase (HPPD) inhibitors, homogentisate solenesyl-transererase (HST) inhibitors, cellulose biosynthesis inhibitors, other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazone, nitriles such as bromoxynil and phenyl-pyridazines such as pyridate. Examples of photosystem 11 inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol pyridate, siduron, simazine, simetryn, tebuthiuron, terbacil, terbumeton, terbuthylazine, terbutryn and trietazine.

"AHAS inhibitors" are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]-benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP (5-enol-pyruvylshikimate-3-phosphate) synthase inhibitors" are chemical compounds that inhibit the enzyme, 5-enol-pyruvylshikimate-3-phosphate synthase, which is involved in the synthesis of aromatic amino acids such as trosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, tiafenacil (methyl N-[2-[[2-chloro-5-[3,6-dihydro-3-methyl-2,6-dioxo-4-(trifluoromethyl)-(2H)-pyrimidinyl]-4-fluorophenyl]thio]-1-oxopropyl]-β-alaninate) and 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione.

"GS (glutamine synthase) inhibitors" (8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts, such as glufosinate-ammonium and other phosphinothricin derivatives, glufosinate-P ((2S)-2-amino-4-(hydroxymethylphosphinyl)butanoic acid) and bilanaphos.

"VLCFA (very long chain fatty acid) elongase inhibitors" are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS (phytoene desaturase inhibitors) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD (4-hydroxyphenyl-pyruvate dioxygenase) inhibitors" are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl] carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, topramezone, 5-chloro-3-[(2-hydroxy-6-oxo-1-cyclohexen-1-yl) carbonyl]-1-(4-methoxyphenyl)-2(1H)-quinoxalinone, 4-(2, 6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H, 4H)-dione, 5-[(2-hydroxy-6-oxo-1-cyclohexen-1-yl) carbonyl]-2-(3-methoxyphenyl)-3-(3-methoxy-propyl)-4 (3H)-pyrimidinone, 2-methyl-N-(4-methyl-1,2,5-oxadiazol-3-yl)-3-(methyl-sulfinyl)-4-(trifluoromethyl)benzamide and 2-methyl-3-(methylsulfonyl)-N-(1-methyl-1H-tetrazol-5-yl)-4-(trifluoromethyl)benzamide.

HST (homogentisate solenesyltransererase) inhibitors disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(H)-one, 7-(3,5-dichloro-4-pyridinyl)-5-(2,2-difluoroethyl)-8-hydroxypyrido[2,3-b] pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

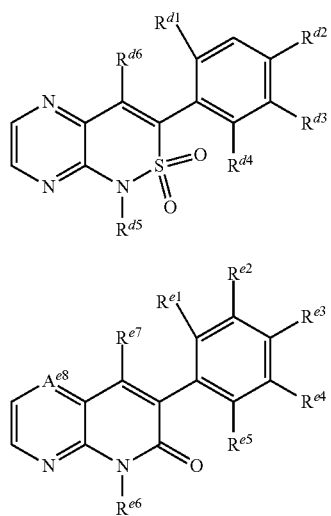

A

B wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H. $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=)Et, —OC(=O)-i-Pr or —OC(=O)-t-Bu; and $A^{e8}$ is N or CH.

Cellulose biosynthesis inhibitors inhibit the biosynthesis of cellulose in certain plants. They are most effective when using a pre-application or early post-application on young or rapidly growing plants. Examples of cellulose biosynthesis inhibitors include chlorthiamid, dichlobenil, flupoxam, indaziflam ($N^2$—[(R,2S)-2,3-dihydro-2,6-dimethyl-1H-inden-1-yl]-6-(1-fluoroethyl)-1,3,5-triazine-2,4-diamine), isoxaben and triaziflam.

Other herbicides include herbicides that act through a variety of different modes of action such as mitotic disruptors (e.g., flamprop-M-methyl and flamprop-M-isopropyl) organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl) methoxy]methyl]-4,5-dihydro-5-methyl-3-(3-methyl-2-thienyl)isoxazole.

"Herbicide safeners" are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG191), 4-(dichloroacetyl)-1-oxa-4-azospiro-[4.5]decane (MON 4660).

The compounds of Formula 1 can be prepared by general methods known in the art of synthetic organic chemistry. Of note are the following methods described in Schemes 1-15 and variations thereof. The definitions of $R^1$, $R^2$, $R^3$, $R^4$, $R^5$, $R^6$, $Q^1$, $Q^2$, $Y^1$, and $Y^2$ in the compounds of Formulae 1 through 19 below are as defined above in the Summary of the Invention unless otherwise noted. Formulae 1a-1h and 5a and 10a are various subsets of a compound of Formulae 1, 5 and 10 respectively. Substituents for each subset formula are as defined for its parent formula unless otherwise noted.

As shown in Scheme 1 compounds of Formula 1a (i.e. Formula 1 wherein $R^1$, $R^4$ and $R^5$ are H. and $Y^1$ and $Y^2$ are O) can be prepared by reaction of acids of Formula 2 with amines of Formula 3 in the presence of a dehydrative coupling reagent such as propylphosphonic anhydride, dicyclohexylcarbodiimide, N-(3-dimethylaminopropyl)-M-ethylcarbodiimide, N,N-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0-60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride. The method of Scheme 1 utilizing propylphosphonic anhydride is illustrated by Step E of Synthesis Example 1. Substituents in the 3- and 4-positions of the pyrrolidinone ring of compounds of Formula 1a, i.e. C(O)N($Q^2$)($R^6$) and $Q^1$, respectively, are predominantly in the trans configuration. In some instances, the presence of minor amounts of the cis isomer can be detected by NMR.

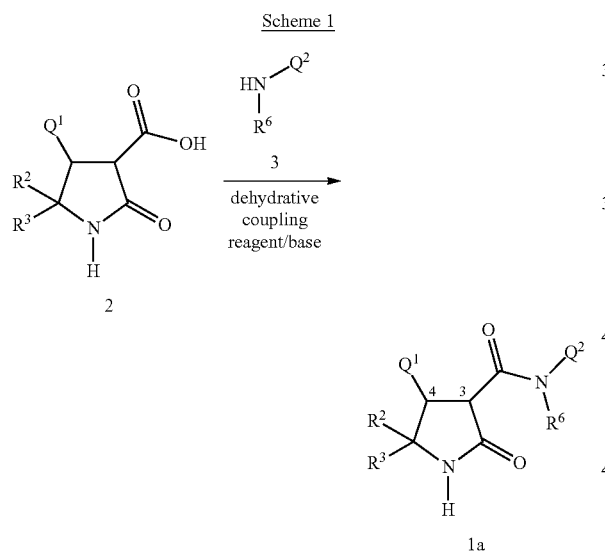

Scheme 1

As shown in Scheme 2 compounds of Formula 2 can be prepared by hydrolysis of esters of Formula 4 by methods well known to those skilled in the art. Hydrolysis is carried out with aqueous base or aqueous acid, typically in the presence of a co-solvent. Suitable bases for the reaction include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. to the boiling point of the solvent, and typically from 0 to 100° C. The method of Scheme 2 is illustrated by Step D of Synthesis Example 1.

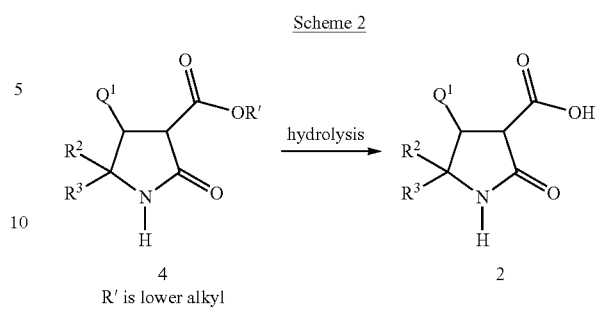

Scheme 2

R' is lower alkyl

As shown in Scheme 3, compounds of Formula 4 can be obtained by reduction of compounds of Formula 5 and subsequent in situ cyclization of the resulting intermediate amine. A wide variety of methods for reduction of the aliphatic nitro group in compounds of Formula 5 are known in the literature. Methods well known to those skilled in the art include catalytic hydrogenation in the presence of palladium on carbon or Raney nickel, iron or zinc metal in acidic medium (see, for example, *Berichte der Deutschen Chemischen Gesellschaft* 1904, 37, 3520-3525), and lithium aluminum hydride. Reduction can also be achieved with samarium(II) iodide in the presence of a proton source such as methanol (see for example, *Tetrahedron Letters* 1991, 32 (14), 1699-1702). Alternatively sodium borohydride in the presence of a nickel catalyst such as nickel(II) acetate or nickel(II) chloride can be used (see for example, *Tetrahedron Letters* 1985, 26 (52), 6413-6416). The method of Scheme 3 utilizing sodium borohydride in the presence of nickel(11) acetate is illustrated by Step C of Synthesis Example 1. Specific examples of a compound of Formula 4 that is useful in the preparation of a compound of Formula 1 can be found in Tables I through IV.

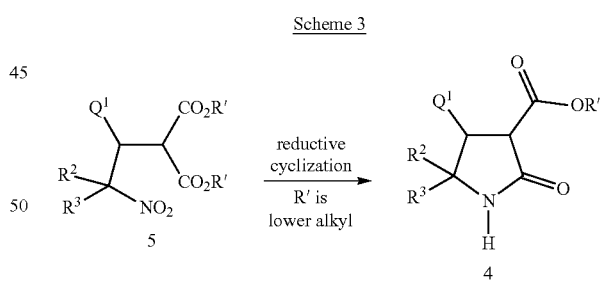

Scheme 3

As shown in Scheme 4, compounds of Formula 5 can be prepared by reacting diesters of Formula 6 with nitroalkanes of Formula 7, typically in the presence of a base. Suitable bases for the reaction include alkali metal lower alkoxides such as sodium methoxide in methanol or sodium ethoxide in ethanol. The method of Scheme 4 is illustrated by Step B of Synthesis Example 1. Compounds of Formula 6 can readily be prepared by methods known to those skilled in the art, e.g., by Knoevenagel condensation of aldehydes and malonates (see for example G. Jones, *Organic Reactions* Volume 15, John Wiley and Sons, 1967).

Scheme 4

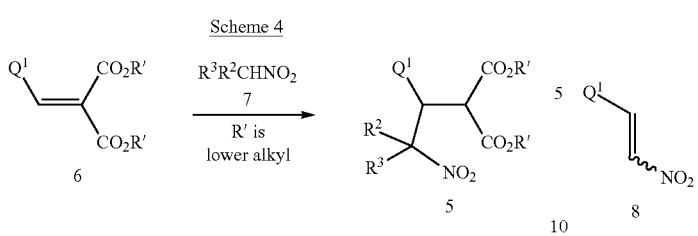

Compounds of Formula 5a (i.e. Formula 5 wherein $R^2$ and $R^3$ are H) can be prepared by reacting nitroalkenes of Formula 8 with malonates of Formula 9 in the presence of a base as shown in Scheme 5. Suitable bases for this reaction include, but are not limited to, alkali metal lower alkoxides such as sodium methoxide in methanol or sodium ethoxide in ethanol, or bases such as lithium bis(trimethylsilyl)amide, sodium bis(trimethylsilyl)amide and lithium diisopropylamide in solvents such as tetrahydrofuran. Typically, the reaction is carried out in the range of from −78° C. to 23° C. See *Synthesis* 2005, 2239-2245 for conditions for effecting this transformation. Conditions for effecting this transformation in refluxing water in the absence of a catalyst have been reported in *Synthetic Communications* 2013, 43, 744-748. Nitroalkenes of Formula 8 can readily be prepared from aldehydes and nitromethane by methods known to those skilled in the art.

Scheme 5

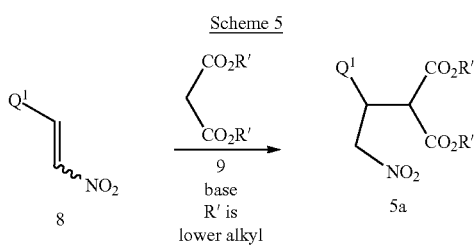

Compounds of Formula 5a' and 5a" can be prepared stereoselectively by reacting nitroalkenes of Formula 8 with malonates of Formula 9 in the presence of a chiral catalyst and optionally in the presence of a suitable base as shown in Scheme 5A. Suitable catalysts include, but are not limited to Ni(II) with vicinal diamine ligands such as Ni(II) Bis[(R, R)—N,N'-dibenzylcyclohexane-1,2-diamine]dibromide, Ni(II) Bis[(S,S)—N,R'-dibenzylcyclohexane-1,2-diamine] dibromide or nickel(II) bromide with chiral 1,1'-bi(tetrahydroisoquinoline) type diamines. Suitable organic bases for this reaction include, but are not limited to, piperidine, morpholine, triethylamine, 4-methylmorpholine or N,N-diisopropylethylamine. This transformation can be accomplished neat or in solvents such as tetrahydrofuran, toluene or dichloromethane. Typically, the reaction is carried out in the range of from −78° C. to 80° C. using 0 to 1 equivalent of catalyst and optionally 0 to 1 equivalent of a base. Conditions for effecting this transformation have been reported in *J. Am. Chem. Soc.* 2005, 9958-9959 or *Eur. J. Org. Chem.* 2011, 5441-5446 for conditions. Nitroalkenes of Formula 8 can readily be prepared from aldehydes and nitromethane by methods known to those skilled in the art.

Scheme 5A

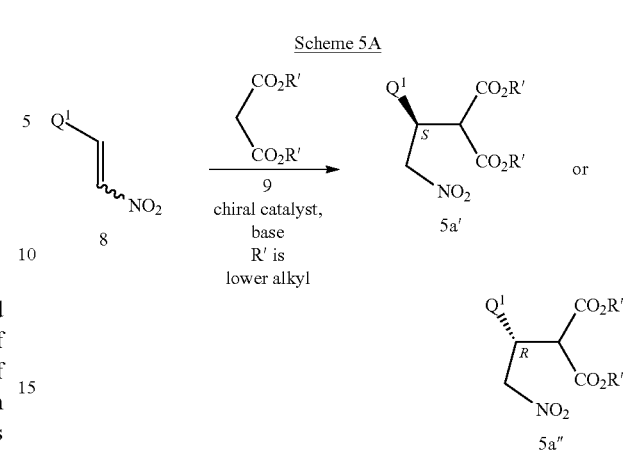

As shown in Scheme 6, compounds of Formula 1a can also be prepared by reductive cyclization of compounds of Formula 10 analogous to the method of Scheme 3. As also shown in Scheme 6, compounds of Formula 1b (i.e. Formula 1 wherein $R^1$ is OH, $R^4$ and $R^5$ are H, and $Y^1$ and $Y^2$ are O) can be prepared from compounds of Formula 10 by catalytic transfer hydrogenation with ammonium formate in the presence of palladium on carbon, and subsequent in situ cyclization of the intermediate hydroxylamine. See *J Med. Chem.* 1993, 36, 1041-1047 for catalytic transfer hydrogenation/cyclization conditions to produce N-hydroxypyrrolidinones. The method of Scheme 6 for preparing N-hydroxypyrrolidinones is illustrated by Step D of Synthesis Example 3.

Scheme 6

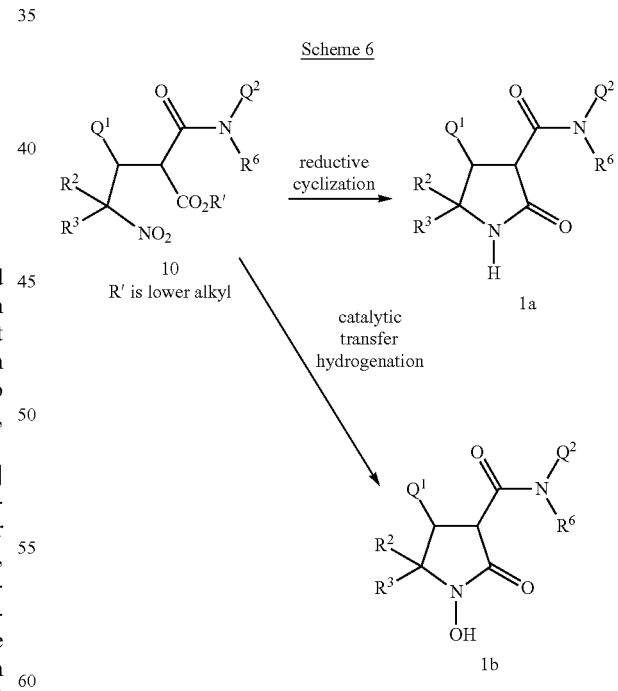

As shown in Scheme 7, compounds of Formula 10 can be prepared by reacting compounds of Formula 11 with nitroalkanes of Formula 7 in a solvent, in the presence of a base analogous to the method described in Scheme 4. The method of Scheme 7 is illustrated by Step C of Synthesis Example 3.

Scheme 7

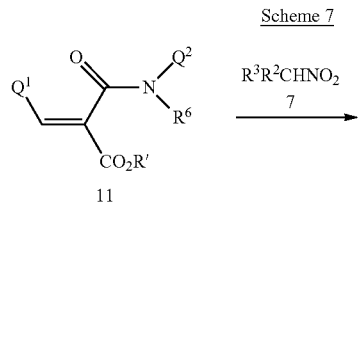

As shown in Scheme 8, compounds of Formula 10a (i.e. Formula 10 wherein $R^2$ and $R^3$ are H) can be prepared, analogous to the method of Scheme 5, by reacting nitroalkenes of Formula 8 with malonates of Formula 12.

Scheme 8

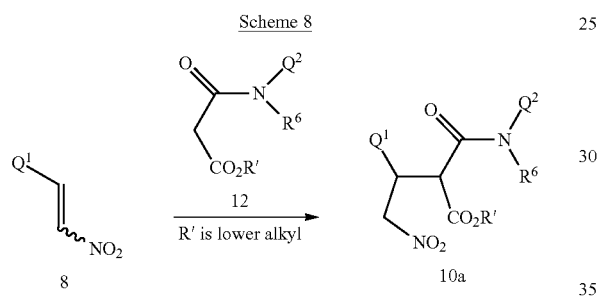

As shown in Scheme 9, compounds of Formula 11 can be prepared by reaction of malonic amide Formula 12 with aldehydes of Formula 14 by methods known to those skilled in the art. As also shown in Scheme 9, malonates of Formula 12 can readily be prepared from lower alkyl malonyl chlorides of Formula 13 such as methyl malonyl chloride and amines of Formula 3 by methods known to those skilled in the art. The method of Scheme 9 is illustrated by Steps A and B of Synthesis Example 3.

Scheme 9

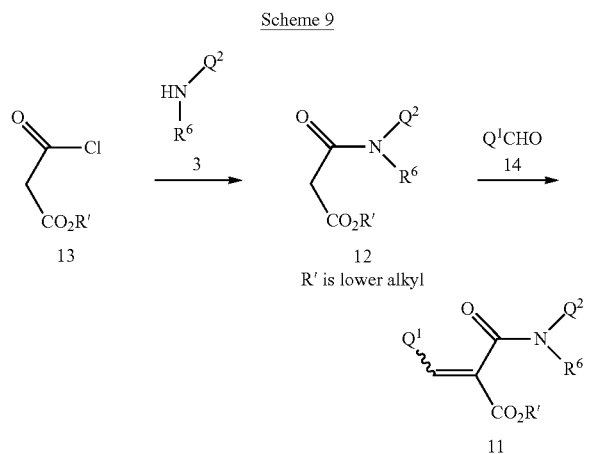

As shown in Scheme 10, mixtures of compounds of Formula 1c (i.e. Formula 1 wherein $R^1$ and $R^5$ are H, $R^4$ is halogen and $Y^1$ and $Y^2$ are O) and Formula 1d (i.e. Formula 1 wherein $R^1$ and $R^4$ are H, $R^5$ is halogen and $Y^1$ and $Y^2$ are O) can be prepared by reacting compounds of Formula 1a with a halogen source in a solvent, in the presence or absence of an initiator. Separation of the regioisomers produced in this reaction can be achieved by standard methods such as chromatography or fractional crystallization. Suitable halogen sources for this reaction include bromine, chlorine, N-chlorosuccinimide, N-bromosuccinimide and N-iodosuccinimide. Suitable initiators for this reaction include 2,2'-azobisisobutyronitrile (AIBN) and benzoyl peroxide. Typically, the reaction is carried out in solvents such as dichloromethane in the range of from 0° C. to the boiling point of the solvent. The method of Scheme 10 is illustrated by Synthesis Example 2.

Scheme 10

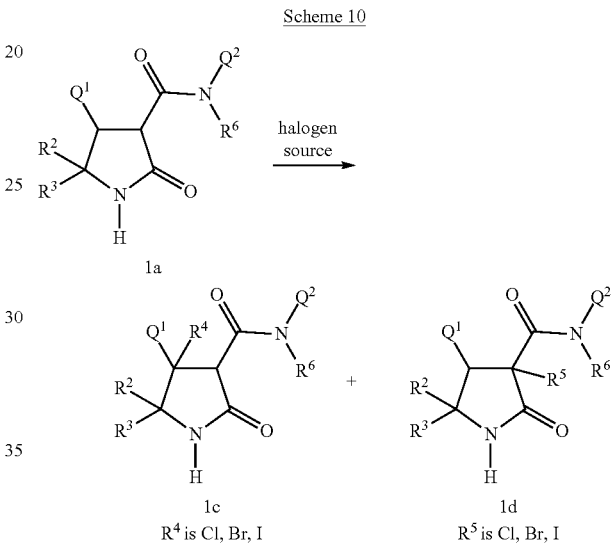

As shown in Scheme 11, compounds of Formula 1e (i.e. Formula 1 wherein $R^1$ is $NH_2$, $R^4$ and $R^5$ are H and $Y^1$ and $Y^2$ are O) can be prepared by reacting compounds of Formula 1a with an aminating reagent such as O-(diphenylphosphinyl)hydroxylamine and hydroxylamino-O-sulphonic acid. For procedures, conditions and reagents see *Bioorganic & Medicinal Chemistry Letters* 2009, 19, 5924-5926 and *Journal of Organic Chemistry* 2002, 67, 6236-6239.

Scheme 11

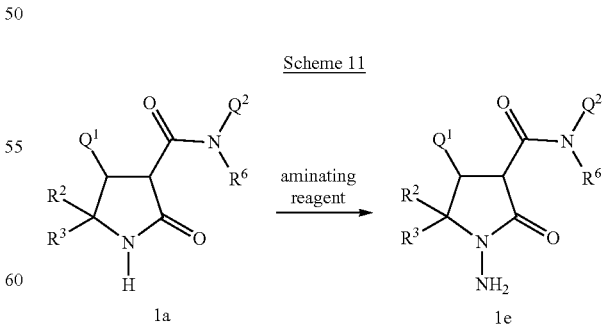

As shown in Scheme 12, compounds of Formula 1f (i.e. Formula 1 wherein $R^4$, $R^5$ and $R^6$ are H and $Y^1$ is O) can be produced by reaction of compounds of Formula 15 with isocyanates (i.e. Formula 16 wherein $Y^2$ is O) or isothiocyanates (i.e. Formula 16 wherein $Y^2$ is S) in the presence of base. Examples of the base which can be used for the present process include those listed for the method of Scheme 4. The reaction temperature can be selected from the range of from −78° C. to the boiling point of an inert solvent used. Typically, the reaction is carried out at temperatures ranging from −78° C. to 100° C. in solvents such as toluene.

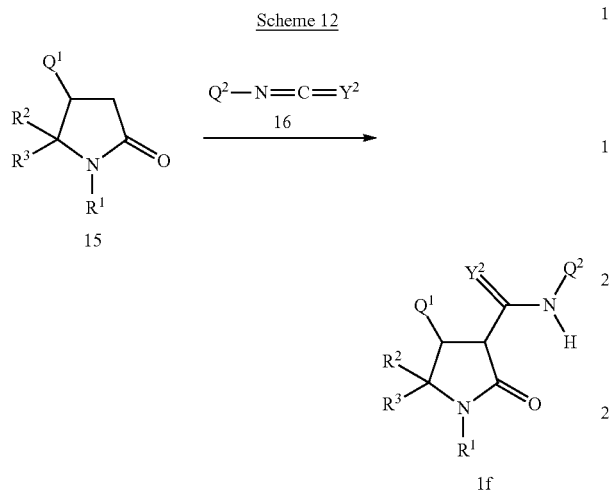

As shown in Scheme 13, compounds of Formula 15 can be prepared by reaction of compounds of Formula 17 with corresponding electrophiles of Formula 18 in the presence of base. In Formula 18, G denotes a leaving group, i.e. a nucleofuge. Depending upon selection of $R^1$, suitable electrophiles for the reaction can include alkyl halides such as chlorides, bromides and iodides, alkylsulfonates, acid anhydrides such as tert-butoxycarbonyl anhydride and acetic anhydride, and haloalkylsilanes such as chlorotrimethylsilane. Suitable bases for the reaction include inorganic bases such as alkali or alkaline earth metal (e.g., lithium, sodium, potassium and cesium) hydroxides, alkoxides, carbonates, and phosphates, and organic bases such as triethylamine, N,N-diisopropylethylamine and 1,8-diazabicyclo[5.4.0]undec-7-ene. A wide variety of solvents are suitable for the reaction including, for example but not limited to, tetrahydrofuran, dichloromethane, N,N-dimethylformamide. N,N-dimethylacetamide, N-methylpyrrolidinone, acetonitrile, $C_2$-$C_6$ alcohols and acetone as well as mixtures of these solvents. This reaction is conducted at temperatures ranging from −20 to 200° C., and typically between 0 and 50° C.

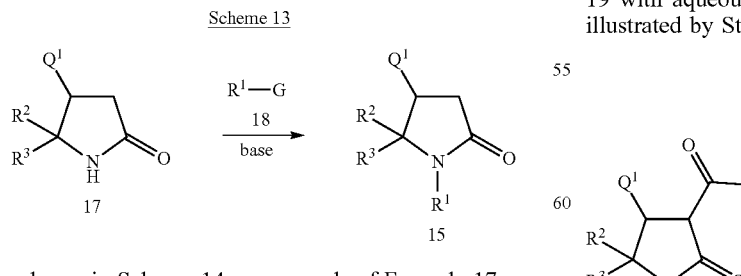

As shown in Scheme 14, compounds of Formula 17 can be prepared by decarboxylation of acids of Formula 2 by methods well known to those skilled in the art. Decarboxylation is carried by heating compounds of Formula 2 in a solvent, typically in the presence of an acid. Suitable acids for the reaction include, but are not limited to, p-toluenesulfonic acid. A wide variety of co-solvents are suitable for the reaction including, but not limited to, toluene, isopropanol acetate and isobutyl methylketone. The reaction is conducted at temperatures ranging from −20° C. and to the boiling point of the solvent, and typically from 0 to 150° C. The method of Scheme 14 is illustrated by Step A of Synthesis Example 6.

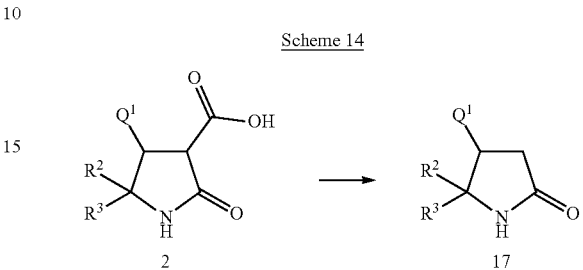

As shown in Scheme 15, compounds of Formula 1g (i.e. Formula 1 wherein $R^1$ is H $R^4$ and $R^5$ are H. and $Y^1$ and $Y^2$ are S) can be prepared by reacting compounds of Formula 1a with at least two equivalents of a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C. One skilled in the art recognizes that using less than two equivalents of the thionating reagent can provide mixtures comprising Formula 1 products wherein $Y^1$ is O and $Y^2$ is S. or Y is S and $Y^2$ is O, which can be separated by conventional methods such as chromatography and crystallization.

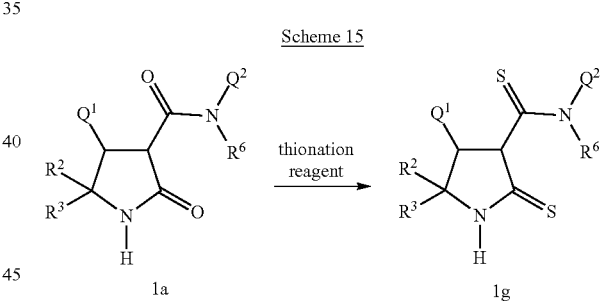

As shown in Scheme 16, compounds of Formula 1h (i.e. Formula 1 wherein $R^1$, $R^4$, $R^5$ are H, $Y^2$ is O and $Y^1$ is NH) can be prepared by alkylation of compounds of Formula 1a triethyloxonium tetrafluoroborate (Meerwein's reagent) followed by treatment of the resulting imino ether of Formula 19 with aqueous ammonia. The method of Scheme 16 is illustrated by Steps A and B of Synthesis Example 4

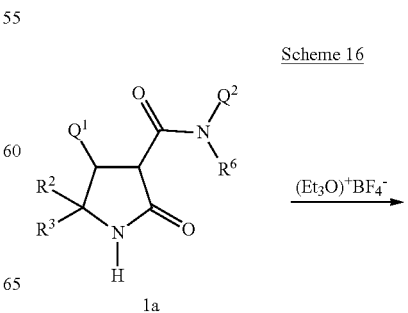

-continued

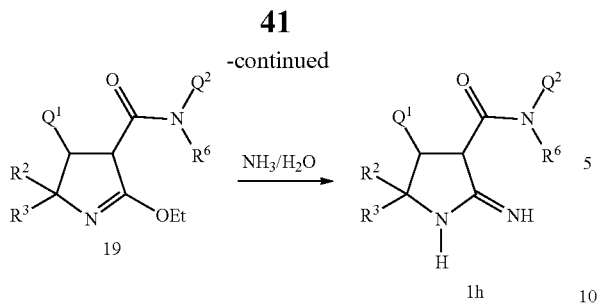

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*. 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ solution unless indicated otherwise; "s" means singlet, "d" means doublet, "t" means triplet, "q" means quartet, "m" means multiplet and "br s" means broad singlet. $^{19}$F NMR spectra are reported in ppm downfield from CFCl$_3$ in CDCl$_3$ unless indicated otherwise. The enentiomeric ratio (ER) was determined by chiral high performance liquid chromatography analysis using a Chiralpak AD-RH column and eluting with a 50:50 isopropanol/water mixture at 40° C. at 0.3 mL/min.

Synthesis Example 1

Preparation of 4-(3-chloro-4-fluorophenyl)-2-oxo-N-[2-(trifluoromethyl)phenyl]-3-pyrrolidinecarboxamide (Compound 74)

Step A: Preparation of 1,3-diethyl 2-(3-chloro-4-fluorophenyl)methylenepropanedioate A mixture of 3-chloro-4-fluorobenzaldehyde (3 g, 18.9 mmol), diethyl malonate (3.16 mL, 20.8 mmol), piperidine (0.37 mL, 3.8 mmol) and toluene (40 mL) was refluxed for 18 h with continuous removal of water (Dean-Stark trap). The cooled reaction mixture was concentrated under reduced pressure, and the residue was chromatographed on silica gel, eluted with 0% to 10% ethyl acetate in hexanes, to afford the title compound as a yellow oil (5 g).

$^1$H NMR δ 7.61 (m, 1H), 7.61 (m, 1H), 7.53 (m, 1H), 7.35 (m, 1H), 7.15 (m, 1H), 4.33 (m, 4H), 1.33 (m, 6H).

Step B: Preparation 1,3-diethyl 2-[1-(3-chloro-4-fluorophenyl)-2-nitroethyl]-propanedioate A mixture of 1,3-diethyl 2-(3-chloro-4-fluorophenyl)methylenepropanedioate (i.e. the product of Step A, 5 g, 16.7 mmol), nitromethane (8.9 mL, 166 mmol) and a methanol solution of sodium methoxide (25 wt %, 0.36 g, 1.67 mmol) in ethanol (60 mL) was stirred at 23° C. for 18 h. The reaction mixture was then concentrated under reduced pressure to afford a thick oil, which was diluted with 25% ethyl acetate in hexanes and filtered through a pad of Celite® diatomaceous filter aid to remove insoluble particulates. The filtrate was concentrated under reduced pressure to afford the title compound as a yellow oil (5.3 g).

$^1$H NMR δ 7.32 (m, 1H), 7.15 (m, 1H), 7.10 (m, 1H), 4.87 (m, 2H), 4.22 (m, 3H), 4.07 (m, 2H), 3.76 (d, 1H), 1.27 (m, 3H), 1.12 (m, 3H).

Step C: Preparation of ethyl 4-(3-chloro-4-fluorophenyl)-2-oxo-3-pyrrolidinecarboxylate A stirred mixture of 1,3-diethyl 2-[1-(3-chloro-4-fluorophenyl)-2-nitroethyl]-propanedioate (i.e. the product of Step B, 5.3 g, 14.7 mmol), nickel(II) acetate tetrahydrate (18.3 g, 73.4 mmol) and ethanol (120 mL) was cooled in an ice bath and treated with sodium borohydride (2.8 g, 73.4 mmol) in 0.5 g portions added over 5 minutes. The resulting mixture was stirred at 26° C. for 18 h. Saturated ammonium chloride solution (120 mL) and ethyl acetate (120 mL) were then added, the mixture was stirred for 1 h and then filtered through a pad of Celite® diatomaceous filter aid to remove insoluble particulates. The layers of the filtrate were separated, and the aqueous layer was extracted with ethyl acetate (2×100 mL). The combined organic extracts were washed with saturated ammonium chloride solution (100 mL), brine (100 mL), dried (MgSO$_4$) and concentrated under reduced pressure to afford the title compound as a yellow-orange solid (4.73 g) which was used without purification.

¹H NMR δ 7.31 (m, 1H), 7.12 (m, 2H), 6.93 (br s, 1H), 4.24 (m, 2H), 4.06 (m, 1H), 3.82 (m, 1H), 3.49 (d, 1H), 3.39 (m, 1H), 1.29 (m, 3H).

Step D: Preparation of 4-(3-chloro-4-fluorophenyl)-2-oxo-3-pyrrolidinecarboxylic acid A mixture of ethyl 4-(3-chloro-4-fluorophenyl)-2-oxo-3-pyrrolidinecarboxylate (i.e. the product of Step C, 4.73 g, 16.5 mmol) and aqueous sodium hydroxide (50 wt %, 1.98 g, 49.5 mmol) in ethanol (50 mL) was stirred at 26° C. for 18 h. The reaction mixture was then diluted with water (50 mL) and extracted with diethyl ether (2×50 mL). The aqueous phase was acidified with concentrated hydrochloric acid to pH 2 and extracted with dichloromethane (3×50 mL). The combined dichloromethane extracts were washed with brine, dried (MgSO₄), and concentrated under reduced pressure to afford the title compound as a white solid (2.37 g).
¹H NMR (acetone-d₆) δ 7.63 (m, 1H), 7.46 (m, 1H), 7.31 (m, 1H), 4.05 (m, 1H), 3.82 (m, 1H), 3.70 (d, 1H), 3.45 (m, 1H).

Step E: Preparation of 4-(3-chloro-4-fluorophenyl)-2-oxo-N-[2-(trifluoromethyl)-phenyl]-3-pyrrolidinecarboxamide A mixture of 4-(3-chloro-4-fluorophenyl)-2-oxo-3-pyrrolidinecarboxylic acid (i.e. the product of Step D, 0.3 g, 1.17 mmol), triethylamine (0.49 mL, 3.5 mmol) and 2-(trifluoromethyl)aniline (0.16 mL, 1.28 mmol) in dichloromethane (8 mL) was stirred at ambient temperature for 30 minutes, and then treated with propylphosphonic anhydride in ethyl acetate (50%, 1.26 g, 1.98 mmol). The resulting mixture was stirred at ambient temperature for 18 h. The reaction mixture was then concentrated under reduced pressure, and the residue was chromatographed on silica gel, eluted with 0-30% ethyl acetate in hexanes, to afford a solid residue which on trituration with 1-chlorobutane afforded the title product, a compound of the present invention, as a light pink solid (0.2 g).
¹H NMR δ 9.85 (s, 1H), 8.15 (m, 1H), 7.62 (m, 1H), 7.52 (m, 1H), 7.43 (m, 1H), 7.27 (m, 1H), 7.22 (m, 1H), 7.14 (m, 1H), 6.93 (s, 1H), 4.15 (m, 1H), 3.82 (m, 1H), 3.55 (d, 1H), 3.44 (m, 1H).

Synthesis Example 2

Preparation of 4-bromo-N-(2-fluorophenyl)-2-oxo-4-phenyl-3-pyrrolidinecarboxamide and 3-bromo-N-(2-fluorophenyl)-2-oxo-4-phenyl-3-pyrrolidinecarboxamide (Compounds 92 and 93)

A mixture of 4-phenyl-2-oxo-N-(2-fluorophenyl)-3-pyrrolidinecarboxamide (prepared by the method of Example 1, 0.75 g, 2.5 mmol) in dichloromethane (25 mL) at room temperature was treated with bromine (0.16 mL, 3.0 mmol), and the resulting mixture was stirred for 18 h. The reaction mixture was then concentrated under reduced pressure, and the residue was chromatographed on silica gel, eluted with 0-2% methanol in dichloromethane, to give as the faster eluting product, 4-bromo-N-(2-fluorophenyl)-2-oxo-4-phenyl-3-pyrrolidinecarboxamide, a compound of the present invention, as a white solid (90 mg):
¹H NMR δ 10.2 (br s, 1H), 8.00 (m, 1H), 7.28 (m, 5H), 7.02 (m, 3H), 6.45 (br s, 1H), 4.15 (d, 1H), 4.05 (m, 1H), 3.55 (d, 1H);

and the slower eluting product, 3-bromo-N-(2-fluorophenyl)-2-oxo-4-phenyl-3-pyrrolidinecarboxamide, a compound of the present invention, as a clear yellow oil (0.31 g):
¹H NMR δ 9.55 (br s, 1H), 8.25 (t, 1H), 7.48 (d, 2H), 7.38 (m, 3H), 7.11 (m, 3H), 6.85 (br s, 1H), 4.45 (m, 1H), 3.77 (m, 1H), 3.65 (m, 1H).

Synthesis Example 3

Preparation of 4-(3,4-difluorophenyl)-N-(2-fluorophenyl)-1-hydroxy-2-oxo-3-pyrrolidinecarboxamide (Compound 44)

Step A: Preparation of ethyl 3-[(2-fluorophenyl)amino]-3-oxopropanote

To a stirred solution of 2-fluoroaniline (10 g, 90.0 mmol) and triethylamine (9.1 g, 90.0 mmol) in dichloromethane (50 mL) at 0° C. was added dropwise over 10 minutes a solution of ethyl malonyl chloride (15.5 g, 90.0 mmol) in dichloromethane (30 mL). The resulting mixture was stirred at room temperature for 24 h. The reaction mixture was then poured into water (100 mL), and the organic layer was separated, washed with water (50 mL) and brine (50 mL), dried (MgSO₄) and concentrated under reduced pressure to provide the title compound as an amber oil (19.0 g).
¹H NMR δ 9.46 (br s, 1H), 8.28 (m, 1H), 7.1 (m, 2H), 4.26 (m, 2H), 3.51 (s, 2H), 1.32 (t, 3H).

Step B: Preparation of ethyl 3-(3,4-difluorophenyl)-2-[[(2-fluorophenyl)amino]-carbonyl]-2-propenoate A solution of ethyl 3-[(2-fluorophenyl)amino]-3-oxopropanote (i.e. the product of Step A, 20.27 g, 90.0 mmol), 3,4-difluorobenzaldehyde (16.62 g, 117 mmol), acetic acid (2.6 mL, mmol) and piperidine (0.89 mL, 9.0 mmol) in toluene (150 mL) was refluxed for 10 h with continuous removal of water (Dean-Stark trap). The reaction mixture was then cooled to room temperature and poured into water (100 mL). The organic layer was separated, and the water layer was extracted with ethyl acetate (3×50 mL). The combined organic extracts were washed with aqueous hydrochloric acid (1 N, 100 mL), dried (MgSO₄) and concentrated under reduced pressure to give a solid residue. Recrystallization of the solid from diethyl ether (100 mL) afforded the title compound as a white solid (10.5 g).
¹H NMR δ 8.26-8.48 (m, 1H), 8.15 (m, 1H), 7.74 (s, 1H), 7.51 (m, 1H), 7.35 (m, 1H), 7.11 (m, 4H), 4.35 (m, 2H), 1.36 (t, 3H).

Step C: Preparation of ethyl 3,4-difluoro-α-[[(2-fluorophenyl)amino]carbonyl]-β-(nitromethyl)benzenepropanoate To a stirred suspension of ethyl 3-(3,4-difluorophenyl)-2-[[(2-fluorophenyl)amino]-carbonyl]-2-propenoate (i.e. the product of Step B, 4.42 g, 12.7 mmol) and nitromethane (17 mL, 317.5 mmol) at −20° C. was added 1,1,3,3-tetramethylguanidine (0.288 mL, 2.3 mmol). The mixture was stirred at −20° C. for 30 minutes, and then allowed to come to room temperature and stirred for an additional 2 h. The reaction mixture was diluted with dichloromethane (50 mL) and extracted with water (3×25 mL). The organic layer was dried (MgSO₄) and concentrated under reduced pressure to provide a solid residue. The solid was chromatographed on silica gel, eluted with 0-100% ethyl acetate in hexane, to provide the title compound as a white solid (4.42 g).

¹H NMR δ 8.6 (br s, 1H), 8.00-8.30 (m, 3H), 7.23 (m, 4H), 5.41 (m, 1H), 4.6 (m, 1H), 4.35 (m, 2H), 3.77-4.00 (m, 2H) 1.45 (m, 3H).

Step D: Preparation of 4-(3,4-difluorophenyl)-N-(2-fluorophenyl)-1-hydroxy-2-oxo-3-pyrrolidinecarboxamide A mixture of ethyl 3,4-difluoro-α-[[(2-fluorophenyl)amino]carbonyl]-β-(nitromethyl)-benzenepropanoate (i.e. the product of Step C, 0.50 g, 1.22 mmol), 5% palladium on carbon (0.25 g) and methanol-ethyl acetate (1:1 by volume, 10 mL) was stirred at room temperature for 30 minutes, then cooled to at 0° C. and treated with ammonium formate (0.5 g). The resulting mixture was stirred for 1 h at room temperature. Additional 5% palladium on carbon (0.25 g) and ammonium formate (0.5 g) were added, and stirring at room temperature was continued for an additional 4 h. The reaction mixture was then filtered, and the filtrate was concentrated under reduced pressure to provide a residue, which was suspended in water (10 mL) and extracted with ethyl acetate (3×20 mL). The combined organic extracts were dried (MgSO₄) and concentrated under reduced pressure to provide an oil, which on recrystallization from dichloromethane afforded the title product, a compound of the present invention, as a white solid (0.1 g).
¹H NMR (DMSO-d₆) δ 10.11 (br s, 2H), 8.00 (m, 1H), 7.71 (m, 1H), 7.42 (m, 1H), 7.33 (m, 3H), 7.1 (m, 1H), 4.25-3.61 (m, 4H).

Synthesis Example 4

Preparation of 2-amino-4-(3,4-difluorophenyl)-N-(2-fluorophenyl)dihydro-3H-pyrrole-3-carboxamide (Compound 95)

Step A: Preparation of 4-(3,4-difluorophenyl)-N-(2-fluorophenyl)-2-oxo-3-pyrrolidinecarboxamide To a stirred mixture of ethyl 3,4-difluoro-α-[[(2-fluorophenyl)amino]carbonyl]-0-(nitromethyl)benzenepropanoate (i.e. the product of Example 3 Step C, 3.346 g, 8.16 mmol) and nickel(II) acetate tetrahydrate (10.15 g, 40.8 mmol) in ethanol (50 mL) at 0° C., was added portionwise sodium borohydride (1.54 g, 40.8 mmol), and the resulting mixture was stirred at room temperature for 24 h. The reaction mixture was concentrated under reduced pressure, dissolved in ethyl acetate (100 mL) and washed successively with saturated ammonium chloride solution (50 mL), water (2×25 mL) and saturated sodium chloride (20 mL). The organic layer was dried (MgSO₄) and concentrated under reduced pressure to provide a solid residue. The residue was chromatographed on silica gel, eluted with 0-100% ethyl acetate in hexane, to provide the title compound as a white solid (0.746 g).
¹H NMR δ 9.67 (br s, 1H), 8.21 (m, 1H), 7.09 (m, 6H), 4.75 (br s, 1H), 4.21 (m, 1H), 3.82 (m, 1H) 3.52 (m, 1H), 3.43 (m, 1H).

Step B: Preparation of 4-(3,4-difluorophenyl)-N-(2-fluorophenyl)dihydro-2-methoxy-3H-pyrrole-3-carboxamide A mixture of 4-(3,4-difluorophenyl)-N-(2-fluorophenyl)-2-oxo-3-pyrrolidinecarboxamide (i.e. the product of Step A, 0.187 g, 0.56 mmol) and trimethyloxonium tetrafluoroborate (0.083 g, 0.56 mmol) in dichloromethane (5 mL) was stirred under an atmosphere of nitrogen for 2 days. The reaction mixture was then treated with 1 N aqueous sodium hydroxide until basic (pH 10) and extracted with dichloromethane (3×5 mL). The organic layer was dried (MgSO₄) and concentrated under reduced pressure to provide title compound as light yellow oil (0.138 g).
¹H NMR δ 9.7 (br s, 1H), 8.62 (m, 1H), 8.25 (s, 1H), 7.26 (m, 4H), 7.00 (m, 1H), 4.26 (m, 2H), 4.00 (s, 3H), 3.42 (m, 2H).

Step C: Preparation of 2-amino-4-(3,4-difluorophenyl)-N-(2-fluorophenyl)dihydro-3H-pyrrole-3-carboxamide A mixture of 4-(3,4-difluorophenyl)-N-(2-fluorophenyl)dihydro-2-methoxy-3H-pyrrole-3-carboxamide (i.e. the product Step B, 0.10 g, 0.287 mmol) and aqueous ammonium hydroxide (50%, 0.5 mL) in ethanol (2 mL) was heated in microwave apparatus for 10 minutes. The reaction mixture was concentrated under reduced pressure and the residue chromatographed on silica gel, eluted with 0-100% ethyl acetate/hexane, to afford the title product, a compound of the present invention, as a solid (0.016 g).
¹H NMR δ 9.67 (br s, 1H), 8.21 (m, 1H), 7.27-7.01 (m, 6H), 6.50 (br s, 1H), 5.00 (br s, 1H), 4.26 (m, 1H), 3.82 (m, 1H), 3.55 (m, 1H), 3.43 (m, 1H).

Synthesis Example 5

Preparation of (3R,4S)—N-(2-fluorophenyl)-2-oxo-4-[3-(trifluoromethyl)phenyl]-3-pyrrolidinecarboxamide (Compound 204)

Step A: Preparation of 1-[(E)-2-nitroethenyl]-3-(trifluoromethyl)benzene

To a stirred solution of 3-(trifluoromethyl)benzaldehyde (12.2 g, 70.1 mmol) in methanol (50 mL) was added nitromethane (4.34 g, 71.1 mmol). The mixture was cooled to 2° C. and sodium hydroxide (5.65 g, 70.6 mmol) was added as a 50% solution in 24.3 mL of water dropwise over 15 min. An exotherm was noted and additional ice was added to maintain the temperature below R10 C. while stirring for an additional 1 h. The reaction mixture was poured into 75 mL (75 mmol) of 1 N hydrochloric acid, rinsing the flask with 10 mL of methanol/water. The quenched reaction mixture was transferred to a separatory funnel and extracted with 150 mL of toluene. The aqueous layer was separated and concentrated under vacuum to yield 15.84 g of a yellow oil.

The intermediate thus obtained (15.84 g, 67.3 mmol) was taken up in 160 mL dichloromethane. The solution was cooled to 3° C. and methanesulfonyl chloride (8.03 g, 71.1 mmol) was added via pipette as a solution in 50 mL of dichloromethane. A solution of triethylamine (14.2 g, 140 mmol) in 50 mL of dichloromethane was then added dropwise over 50 min, and the resulting solution was stirred for 2 h. The reaction mixture was poured into 150 mL (150 mmol) of 1 N hydrochloric acid and transferred to a separatory funnel. The layers were separated and the organic layer was washed with 150 mL water and then filtered. The organic layer was concentrated under reduced pressure and the crude solid was tritrated with hexanes to yield 12.09 g of product as a yellow solid.
¹H NMR (500 MHz) δ 7.54-7.66 (m, 2H) 7.69-7.84 (m, 3H) 7.96-8.08 (m, 1H).

Step B: Preparation of 1,3-diethyl 2-[(1S)-2-nitro-1-[3-(trifluoromethyl)phenyl]ethyl]propanedioate To a stirred mixture of 1-[(E)-2-nitroethenyl]-3-(trifluoromethyl)benzene (i.e. the product of Step A, 3 g, 13.8 mmol) and diethyl malonate (3.319 g, 20.7 mmol) in toluene (1.5 mL) was added Ni(II) bis[(R,R)—N,N-dibenzylcyclohexane-1,2-diamine]bromide (prepared as described in J. Am. Chem. Soc. 2005, 127, 9958-9959; 0.111 g, 0.1 mmol). The resulting solution was stirred at 55° C. for 16 h. The solution was diluted with dichloromethane (20 mL) and concentrated under reduced pressure onto silica gel and purified by chromatography eluting with a gradient of ethyl acetate in hexanes (0 to 50%) to give 3.6 g of a light yellow oil. ER 94:6 (major eluting at 26.5 min, minor eluting at 20.3 min).
$^1$H NMR (500 MHz) δ 7.54-7.60 (m, 1H), 7.43-7.48 (m, 2H), 7.51 (s, 1H), 4.83-5.00 (m, 2H), 4.17-4.35 (m, 3H), 3.98-4.06 (m, 2H), 3.77-3.85 (m, 1H), 1.20-1.29 (m, 3H), 0.99-1.10 (m, 3H). $^{19}$F NMR (471 MHz) δ −62.78 (s, 3F). ES [M−1] 376.3.

Step C: Preparation of ethyl (3R,4S)-2-oxo-4-[3-(trifluoromethyl)phenyl]-3-pyrrolidinecarboxylate A stirred mixture of 1,3-diethyl 2-[(1S)-2-nitro-1-[3-(trifluoromethyl)phenyl]ethyl]propanedioate (i.e. the product of Step B, 3.24 g, 8.48 mmol), nickel(II) chloride hexahydrate (2.01 g, 8.48 mmol) and ethanol (60 mL) was cooled in an ice bath and treated with sodium borohydride (0.97 g, 25.8 mmol) in 0.5 g portions added over 5 min. The resulting mixture was stirred at 26° C. for 18 h. Saturated ammonium chloride solution (120 mL) and ethyl acetate (120 mL) were then added, the mixture was stirred for 1 h and then filtered through a pad of Celite® diatomaceous filter aid to remove insoluble particulates. The layers of the filtrate were separated, and the aqueous layer was extracted with ethyl acetate (2-100 mL). The combined organic extracts were washed with saturated ammonium chloride solution (100 mL), brine (100 mL), dried (MgSO$_4$) and concentrated under reduced pressure to afford the title compound as a thick yellow oil (2.66 g) which was used without purification.
$^1$H NMR (500 MHz) δ 7.38-7.62 (m, 4H), 6.50 (br s, 1H), 4.21-4.31 (m, 2H), 4.15-4.21 (m, 1H), 3.82-3.92 (m, 1H), 3.51-3.58 (m, 1H), 3.37-3.50 (m, 1H), 1.27-1.34 (m, 3H). $^{19}$F NMR (471 MHz) δ −62.70 (s, 3F). ESI; [M+1]=302.0.

Step D: Preparation of (3R,4S)-2-oxo-4-[3-(trifluoromethyl)phenyl]-3-pyrrolidinecarboxylic acid A mixture of ethyl (3R,4S)-2-oxo-4-[3-(trifluoromethyl)phenyl]-3-pyrrolidinecarboxylate (i.e. the product of Step C, 2.66 g, 8.8 mmol) and aqueous sodium hydroxide (50 wt %, 2.12 g, 26.5 mmol) in ethanol (30 mL) was stirred at 26° C. for 18 h. The reaction mixture was then diluted with water (50 mL) and extracted with diethyl ether (2 10×50 mL). The aqueous phase was acidified with concentrated hydrochloric acid to pH 2 and extracted with dichloromethane (3×50 mL). The combined dichloromethane extracts were washed with brine, dried (MgSO$_4$), and concentrated under reduced pressure to afford the title compound as a white solid (2.05 g).
$^1$H NMR (500 MHz, acetone-d$_6$) δ 11.50 (br s, 1H), 7.70-7.89 (m, 2H), 7.56-7.68 (m, 2H), 7.45 (br s, 1H), 4.09-4.21 (m, 1H), 3.83-3.92 (m, 1H), 3.73-3.81 (m, 1H), 3.42-3.55 (m, 1H). $^{19}$F NMR (471 MHz, acetone-d$_6$) δ −63.03 (s, 3F). ES [M+1] 274.0.

Step E: Preparation of (3R,4S)—N-(2-fluorophenyl)-2-oxo-4-[3-(trifluoromethyl)phenyl]-3-pyrrolidinecarboxamide A mixture of (3R,4S)-2-oxo-4-[3-(trifluoromethyl)phenyl]-3-pyrrolidinecarboxylic acid (i.e. the product of Step D, 2.0 g, 7.32 mmol), triethylamine (3.06 mL, 21.96 mmol) and 2-fluoroaniline (0.85 mL, 8.78 mmol) in dichloromethane (50 mL) was stirred at ambient temperature for 30 min, and then treated with propylphosphonic anhydride in ethyl acetate (50%, 7.92 g, 12.44 mmol). The resulting mixture was stirred at ambient temperature for 18 h. The reaction mixture was then concentrated under reduced pressure, and the residue was chromatographed on silica gel, eluted with 0-100% ethyl acetate in hexanes, to afford a solid residue which on trituration with 1-chlorobutane afforded the title product, a compound of the present invention, as a white solid (1.9 g). ER 88:12 (major eluting at 25.86 min, minor eluting at 17.66 min). Specific Rotation +74.71 at 23.4° C. at 589 nm, as a 1% solution (1 g/100 mL) in CHCl$_3$.
$^1$H NMR (500 MHz, acetone-d$_6$) δ 10.05 (br s, 1H), 8.21-8.35 (m, 1H), 7.77-7.91 (m, 2H), 7.58-7.66 (m, 2H), 7.51 (br s, 1H), 7.02-7.22 (m, 3H), 4.18-4.30 (m, 1H), 3.94-4.04 (m, 1H), 3.84-3.93 (m, 1H), 3.42-3.53 (m, 1H). $^{19}$F NMR (471 MHz, acetone-d$_6$) δ −62.93 (s, 3F), −131.13--131.02 (m, 1F).

Synthesis Example 6

Preparation of (3S,4S)—N-(2-fluorophenyl)-1-methyl-2-oxo-4-[3-(trifluoromethyl)phenyl]-3-pyrrolidinecarboxamide (Compound 351)

Step A Preparation of (4S)-4-[3-(trifluoromethyl)phenyl]-2-pyrrolidinone

A mixture of (3R,4S)-2-oxo-4-[3-(trifluoromethyl)phenyl]-3-pyrrolidinecarboxylic acid (i.e. the product of Example 5, Step D, 1.5 g, 5.5 mmol) and toluene-4-sulfonic acid (0.010 g, 0.055 mmol) in toluene (12 mL) was stirred at 90° C. overnight. The reaction mixture was then concentrated under reduced pressure to afford a clear oil (1.29 g). The crude product was used without further purification.
$^1$H NMR (500 MHz) δ 7.36-7.59 (m, 4H), 6.84 (br s, 1H), 3.70-3.88 (m, 2H), 3.35-3.50 (m, 1H), 2.72-2.87 (n, 1H), 2.44-2.58 (m, 1H). $^{19}$F NMR (471 MHz) δ −62.66 (s, 3F).

Step B: Preparation of (4S)-1-methyl-4-[3-(trifluoromethyl)phenyl]-2-pyrrolidinone To a solution of (4S)-4-[3-(trifluoromethyl)phenyl]-2-pyrrolidinone (i.e. the product of Step A, 1.29 g, 5.6 mmol) in N,N-dimethylformamide (7 mL) was added sodium hydride (60% dispersion in mineral oil, 0.25 g, 6.2 mmol) in portions. The mixture was stirred for 10 min and then iodomethane (0.88 mL, 14.1 mmol) was added. The solution was stirred overnight at ambient temperature. The reaction mixture was diluted with water and extracted with diethyl ether (2×50 mL). The organic layer was washed with water, brine and then dried (MgSO$_4$), filtered and concentrated under reduced pressure. The crude residue was chromatographed on silica gel, eluted with 0-20% ethyl acetate in dichloromethane, to afford a light brown oil (0.775 g).
$^1$H NMR (500 MHz) δ 7.38-7.57 (m, 4H), 3.75-3.83 (m, 1H), 3.59-3.70 (m, 1H), 3.38-3.45 (m, 1H), 2.90-2.94 (m, 3H), 2.80-2.89 (m, 1H), 2.48-2.58 (m, 1H). $^{19}$F NMR (471 MHz) δ −62.67 (s, 3F).

Step C Preparation of (3S,4S)—N-(2-fluorophenyl)-1-methyl-2-oxo-4-[3-(trifluoromethyl)phenyl]-3-pyrrolidinecarboxamide A solution of (4S)-1-methyl-4-[3-(trifluoromethyl)phenyl]-2-pyrrolidinone (i.e. the product of Step B, 0.350 g, 1.44 mmol) in tetrahydrofuran (5 mL) was cooled to −78° C. To this mixture lithium bis(trimethylsilyl)amide (1.6 mL, 1.6 mmol as a 1 M solution in tetrahydrofuran) was added dropwise and the resulting solution was stirred for 30 min. Then 1-fluoro-2-isocyanatobenzene (0.17 mL, 1.44 mmol) was added dropwise and the solution was stirred for 2 h at −78° C. The reaction mixture was quenched with saturated aqueous ammonium chloride (10 mL), warmed to ambient temperature and the aqueous layer was extracted with ethyl acetate (3×25 mL). The organic layers were combined, washed with brine and then dried (MgSO$_4$), filtered and concentrated under reduced pressure onto silica gel. The crude residue was chromatographed on silica gel, eluting with 0 to 40% ethyl acetate in hexanes, to afford a light pink solid (0.223 g).

$^1$H NMR (500 MHz) δ 9.93 (br s, 1H), 8.15-8.27 (m, 1H), 7.38-7.65 (m, 4H), 6.93-7.15 (m, 3H) 4.10-4.23 (m, 1H), 3.72-3.88 (m, 1H) 3.56-3.68 (m, 1H), 3.39-3.53 (m, 1H) 0.2.90-3.06 (m, 3H). $^{19}$F NMR (471 MHz) δ −62.55 (s, 3F), −129.83−−129.50 (m, 1F). ESI [M+1] 381.0.

Synthesis Example 7

Preparation of 1,3-diethyl 2-[(S)-1-(3,4-difluorophenyl)-2-nitro-ethyl]propanedioate (Intermediate to Prepare Compound 103)

Step A: Preparation of 1,3-diethyl 2-[(1S)-1-(3,4-difluorophenyl)-2-nitro-ethyl]propanedioate To a stirred mixture of 1-[(E)-2-nitroethenyl]-3,4-difluorobenzene (prepared as described generally in WO2008/39882 A1, 1.67 g, 9.0 mmol) and diethyl malonate (1.73 g, 10.8 mmol) in toluene (10 mL) was added Ni(II) bis[(R,R)—N,N-dibenzylcyclohexane-1,2-diamine]bromide (prepared as described in *J. Am. Chem. Soc.* 2005, 127, 9958-9959; 0.072 g, 0.1 mmol). The resulting solution was stirred at ambient temperature for 72 h. The solution was diluted with dichloromethane (20 mL) and concentrated under reduced pressure onto silica gel and purified by silica gel chromatography eluting with a gradient of ethyl acetate in hexanes (0 to 50%) to provide 2.18 g of a light yellow waxy solid. ER 96:4 (major eluting at 37.05 min, minor eluting at 27.09 min).

$^1$H NMR (500 MHz) δ 7.06-7.16 (m, 2H), 6.95-7.03 (m, 1H), 4.73-4.94 (m, 2H), 4.16-4.29 (m, 3H), 4.01-4.10 (m, 2H), 3.71-3.79 (m, 1H), 1.22-1.30 (m, 3H), 1.07-1.15 (m, 3H). $^{19}$F NMR (471 MHz) δ −137.66−−137.47 (m, 1F) −136.10−−135.87 (m, 1F). ESI [M+1]; 346.4

By the procedures described herein together with methods known in the art, the following compounds of Tables 1 to 6800 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, c-Pr cyclopropyl, t-Bu means tertiary butyl, c-Bu means cyclobutyl. Ph means phenyl. OMe means methoxy, OEt means ethoxy, SMe means methylthio, NHMe means methylamino, CN means cyano. NO$_2$ means nitro, TMS means trimethylsilyl, SOMe means methylsulfinyl, C$_2$F$_5$ means CF$_2$CF$_3$ and SO$_2$Me means methylsulfonyl.

TABLE 1

Y$^1$ is O; Y$^2$ is O; R$^2$ is H; R$^4$ is H; R$^5$ is H; Q$^2$ is Ph(2-F); and Q$^1$ is

| Q$^1$ | Q$^1$ | Q$^1$ |
|---|---|---|
| Ph(3-Cl) | Ph(3-NO$_2$) | 2-Thienyl(4-F) |
| Ph(3-F) | Ph(3-Ph) | 2-Thienyl(4-Cl) |
| Ph(3-Br) | Ph(3-COMe) | 2-Thienyl(4-CF$_3$) |
| Ph(3-Me) | Ph(3-OCOMe) | 2-Thienyl(5-F) |
| Ph(3-Et) | Ph(3-CO$_2$Me) | 2-Thienyl(5-Cl) |
| Ph(3-t-Bu) | Ph(3-OCO$_2$Me) | 2-Thienyl(5-CF$_3$) |
| Ph(3-i-Pr) | Ph(3-TMS) | Ph(4-Cl) |
| Ph(3-c-Pr) | Ph(3-SF$_5$) | Ph(4-F) |
| Ph(3-cyclohexyl) | Ph[3-(1H-pyrazol-1-yl)] | Ph(4-Br) |
| Ph(3-CH=CH$_2$) | Ph[3-(2H-1,2,3-triazol-2-yl)] | Ph(4-Me) |
| Ph(3-CF$_3$) | Ph[3-(1H-imidazol-1-yl)] | Ph(4-Et) |
| Ph(3-CH$_2$CF$_3$) | Ph[3-(3-pyridinyl)] | Ph(4-t-Bu) |
| Ph(3-CHF$_2$) | Ph[3-(4-pyridinyl)] | Ph(4-i-Pr) |
| Ph(3-CH$_2$F) | Ph[3-(2-pyridinyl)] | Ph(4-c-Pr) |
| Ph(3-OCF$_3$) | 4-Pyridinyl(2-CF$_3$) | Ph(4-cyclohexyl) |
| Ph(3-OCH$_2$F) | 4-Pyridinyl(2-Cl) | Ph(4-CH=CH$_2$) |
| Ph(3-SCF$_3$) | 4-Pyridinyl(2-F) | Ph(4-CF$_3$) |
| Ph(3-SMe) | 4-Pyridinyl(2-OCF$_3$) | Ph(4-CH$_2$CF$_3$) |
| Ph(3-SOMe) | 4-Pyridinyl(2-Me) | Ph(4-CHF$_2$) |
| 3-SO$_2$Me | 4-Pyridinyl(2-Br) | Ph(4-CH$_2$F) |
| Ph(3-OSO$_2$Me) | 4-Pyridinyl | Ph(4-OCF$_3$) |
| Ph(3-C≡CH) | 1H-Pyrazol-4-yl(1-Me) | Ph(4-OCH$_2$F) |

TABLE 1-continued

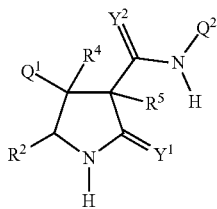

Y¹ is O; Y² is O; R² is H; R⁴ is H; R⁵ is H; Q² is Ph(2-F); and Q¹ is

| Q¹ | Q¹ | Q¹ |
|---|---|---|
| Ph(3-OMe) | 1H-Pyrazol-4-yl(1-CH₂CF₃) | Ph(4-SCF₃) |
| Ph(3-OEt) | 1H-Imidazol-2-yl(1-Me) | Ph(4-SMe) |
| Ph(3-NHCO₂-t-Bu) | 1H-Imidazol-2-yl(1-CH₂CF₃) | Ph(4-SOMe) |
| Ph(3-NHCOMe) | 1H-Imidazol-2-yl(1-Me,5-Cl) | Ph(4-SO₂Me) |
| Ph(3-NHCOCF₃) | 1H-Imidazol-2-yl(1-Me,5-F) | Ph(4-OSO₂Me) |
| Ph(3-CN) | 2-Thienyl | Ph(4-C≡CH) |
| Ph(4-OMe) | 3-Thienyl(5-Cl) | Ph(3-Br,4-OCHF₂) |
| Ph(4-OEt) | 3-Thienyl(5-CF₃) | Ph(3-Br,4-SO₂Me) |
| Ph(4-NHCO₂-t-Bu) | Ph(3,4-di-Cl) | Ph(3-Br,4-TMS) |
| Ph(4-NHCOMe) | Ph(3-Cl,4-F) | Ph(3-Br,4-CN) |
| Ph(4-NHCOCF₃) | Ph(3-Cl,4-Br) | Ph(3-Me,4-Cl) |
| Ph(4-CN) | Ph(3-Cl,4-Me) | Ph(3-Me,4-F) |
| Ph(4-NO₂) | Ph(3-Cl,4-t-Bu) | Ph(3-Me,4-Br) |
| Ph(4-Ph) | Ph(3-Cl,4-c-Pr) | Ph(3,4-di-Me) |
| Ph(4-COMe) | Ph(3-Cl,4-CF₃) | Ph(3-Me,4-t-Bu) |
| Ph(4-OCOMe) | Ph(3-Cl,4-CHF₂) | Ph(3-Me,4-c-Pr) |
| Ph(4-CO₂Me) | Ph(3-Cl,4-OCF₃) | Ph(3-Me,4-CF₃) |
| Ph(4-OCO₂Me) | Ph(3-Cl,4-OCHF₂) | Ph(3-Me,4-OCF₃) |
| Ph(4-TMS) | Ph(3-Cl,4-SO₂Me) | Ph(3-Me,4-OCHF₂) |
| Ph(4-SF₅) | Ph(3-Cl,4-TMS) | Ph(3-Me,4-SO₂Me) |
| Ph(1H-pyrazol-1-yl) | Ph(3-Cl,4-CN) | Ph(3-Me,4-TMS) |
| Ph(2H-1,2,3-triazol-2-yl) | Ph(3-F,4-Cl) | Ph(3-Me,4-CN) |
| Ph(1H-imidazol-1-yl) | Ph(3,4-di-F)* | Ph(3-t-Bu,4-Cl) |
| Ph[4-(3-pyridinyl)] | Ph(3-F,4-Br) | Ph(3-t-Bu,4-F) |
| Ph[4-(4-pyridinyl)] | Ph(3-F,4-Me) | Ph(3-t-Bu,4-Br) |
| Ph[4-(2-pyridinyl)] | Ph(3-F,4-t-Bu) | Ph(3-t-Bu,4-Me) |
| 3-Pyridinyl(5-CF₃) | Ph(3-F,4-c-Pr) | Ph(3,4-di-t-Bu) |
| 3-Pyridinyl(5-Cl) | Ph(3-F,4-CF₃) | Ph(3-t-Bu,4-c-Pr) |
| 3-Pyridinyl(5-F) | Ph(3-F,4-CHF₂) | Ph(3-t-Bu,4-CF₃) |
| 3-Pyridinyl(5-OCF₃) | Ph(3-F,4-OCF₃) | Ph(3-t-Bu,4-CHF₂) |
| 3-Pyridinyl(5-Me) | Ph(3-F,4-OCHF₂) | Ph(3-t-Bu,4-OCF₃) |
| 3-Pyridinyl(5-Br) | Ph(3-F,4-SO₂Me) | Ph(3-t-Bu,4-OCHF₂) |
| 3-Pyridinyl | Ph(3-F,4-TMS) | Ph(3-t-Bu,4-SO₂Me) |
| 1H-Pyrazol-3-yl(1-Me) | Ph(3-F,4-CN) | Ph(3-t-Bu,4-TMS) |
| 1H-Pyrazol-3-yl(1-CH₂CF₃) | Ph(3-F,4-SF₅) | Ph(3-t-Bu,4-CN) |
| 1H-Pyrazol-3-yl(1-Me,4-F) | Ph(3-Br,4-Cl) | Ph(3-c-Pr,4-Cl) |
| 1H-Pyrazol-3-yl(1-Me,4-Cl) | Ph(3-Br,4-F) | Ph(3-c-Pr,4-F) |
| 1H-Imidazol-5-yl(1-Me) | Ph(3,4-di-Br) | Ph(3-c-Pr,4-Br) |
| 1H-Imidazol-5-yl(1-CH₂CF₃) | Ph(3-Br,4-Me) | Ph(3-c-Pr,4-Me) |
| 1H-Imidazol-4-yl(1-Me) | Ph(3-Br,4-c-Pr) | Ph(3-c-Pr,4-t-Bu) |
| 1H-Imidazol-4-yl(1-CH₂CF₃) | Ph(3-Br,4-CF₃) | Ph(3,4-di-c-Pr) |
| 3-Thienyl | Ph(3-Br,4-CHF₂) | Ph(3-c-Pr,4-CF₃) |
| 3-Thienyl(5-F) | Ph(3-Br,4-OCF₃) | Ph(3-c-Pr,4-CHF₂) |
| Ph(3-c-Pr,4-OCF₃) | Ph(3-SO₂Me,4-CF₃) | Ph(2-F,3-Cl,4-Me) |
| Ph(3-c-Pr,4-OCHF₂) | Ph(3-SO₂Me,4-CHF₂) | Ph(2-F,3-Cl,4-t-Bu) |
| Ph(3-c-Pr,4-SO₂Me) | Ph(3-SO₂Me,4-OCF₃) | Ph(2-F,3-Cl,4-c-Pr) |
| Ph(3-c-Pr,4-TMS) | Ph(3-SO₂Me,4-OCHF₂) | Ph(2-F,3-Cl,4-CF₃) |
| Ph(3-c-Pr,4-CN) | Ph(3,4-di-SO₂Me) | Ph(2-F,3-Cl,4-CHF₂) |
| Ph(3-CF₃,4-Cl) | Ph(3-SO₂Me,4-TMS) | Ph(2-F,3-Cl,4-OCF₃) |
| Ph(3-CF₃,4-F) | Ph(3-SO₂Me,4-CN) | Ph(2-F,3-Cl,4-OCHF₂) |
| Ph(3-CF₃,4-Br) | Ph(3-CHF₂,4-Cl) | Ph(2-F,3-Cl,4-SO₂Me) |
| Ph(3-CF₃,4-Me) | Ph(3-CHF₂,4-F) | Ph(2-F,3-Cl,4-TMS) |
| Ph(3-CF₃,4-t-Bu) | Ph(3-CHF₂,4-Br) | Ph(2-F,3-Cl,4-CN) |
| Ph(3-CF₃,4-c-Pr) | Ph(3-CHF₂,4-Me) | Ph(2-F,3-F,4-Cl) |
| Ph(3,4-di-CF₃) | Ph(3-CHF₂,4-t-Bu) | Ph(2-F,3-F,4-F) |
| Ph(3-CF₃,4-CHF₂) | Ph(3-CHF₂,4-c-Pr) | Ph(2-F,3-F,4-Br) |
| Ph(3-CF₃,4-OCF₃) | Ph(3-CHF₂,4-CF₃) | Ph(2-F,3-F,4-Me) |
| Ph(3-CF₃,4-OCHF₂) | Ph(3-CHF₂,4-CHF₂) | Ph(2-F,3-F,4-t-Bu) |
| Ph(3-CF₃,4-SO₂Me) | Ph(3-CHF₂,4-OCF₃) | Ph(2-F,3-F,4-c-Pr) |
| Ph(3-CF₃,4-TMS) | Ph(3-CHF₂,4-OCHF₂) | Ph(2-F,3-F,4-CF₃) |
| Ph(3-CF₃,4-CN) | Ph(3-CHF₂,4-SO₂Me) | Ph(2-F,3-F,4-CHF₂) |
| Ph(3-OCF₃,4-Cl) | Ph(3-CHF₂,4-TMS) | Ph(2-F,3-F,4-OCF₃) |
| Ph(3-OCF₃,4-F) | Ph(3-CHF₂,4-CN) | Ph(2-F,3-F,4-OCHF₂) |
| Ph(3-OCF₃,4-Br) | Ph(3-CN,4-Cl) | Ph(2-F,3-F,4-SO₂Me) |
| Ph(3-OCF₃,4-Me) | Ph(3-CN,4-F) | Ph(2-F,3-F,4-TMS) |
| Ph(3-OCF₃,4-t-Bu) | Ph(3-CN,4-Br) | Ph(2-F,3-F,4-CN) |

TABLE 1-continued

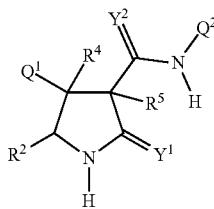

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(3-OCF$_3$,4-c-Pr) | Ph(3-CN,4-Me) | Ph(2-F,3-Br,4-Cl) |
| Ph(3-OCF$_3$-4-CF$_3$) | Ph(3-CN,4-t-Bu) | Ph(2-F,3-Br,4-F) |
| Ph(3-OCF$_3$,4-CHF$_2$) | Ph(3-CN,4-c-Pr) | Ph(2-F,3-Br,4-Br) |
| Ph(3,4-di-OCF$_3$) | Ph(3-CN,4-CF$_3$) | Ph(2-F,3-Br,4-Me) |
| Ph(3-OCF$_3$,4-OCHF$_2$) | Ph(3-CN,4-CHF$_2$) | Ph(2-F,3-Br,4-t-Bu) |
| Ph(3-OCF$_3$,4-SO$_2$Me) | Ph(3-CN,4-OCF$_3$) | Ph(2-F,3-Br,4-c-Pr) |
| Ph(3-OCF$_3$,4-TMS) | Ph(3-CN,4-OCHF$_2$) | Ph(2-F,3-Br,4-CF$_3$) |
| Ph(3-OCF$_3$,4-CN) | Ph(3-CN,4-SO$_2$Me) | Ph(2-F,3-Br,4-CHF$_2$) |
| Ph(3-SO$_2$Me,4-Cl) | Ph(3-CN,4-TMS) | Ph(2-F,3-Br,4-OCF$_3$) |
| Ph(3-SO$_2$Me,4-F) | Ph(3,4-di-CN) | Ph(2-F,3-Br,4-OCHF$_2$) |
| Ph(3-SO$_2$Me,4-Br) | Ph(3-SF$_5$,4-F) | Ph(2-F,3-Br,4-SO$_2$Me) |
| Ph(3-SO$_2$Me,4-Me) | Ph(2-F,3-Cl,4-Cl) | Ph(2-F,3-Br,4-TMS) |
| Ph(3-SO$_2$Me,4-t-Bu) | Ph(2-F,3-Cl,4-F) | Ph(2-F,3-Br,4-CN) |
| Ph(3-SO$_2$Me,4-c-Pr) | Ph(2-F,3-Cl,4-Br) | Ph(2-F,3-Me,4-Cl) |
| Ph(2-F,3-Me,4-F) | Ph(2-F,3-CF$_3$,4-Cl) | Ph(2-F,3-SO$_2$Me,4-TMS) |
| Ph(2-F,3-Me,4-Br) | Ph(2-F,3-CF$_3$,4-F) | Ph(2-F,3-SO$_2$Me,4-CN) |
| Ph(2-F,3-Me,4-Me) | Ph(2-F,3-CF$_3$,4-Br) | Ph(2-F,3-CHF$_2$,4-Cl) |
| Ph(2-F,3-Me,4-t-Bu) | Ph(2-F,3-CF$_3$,4-Me) | Ph(2-F,3-CHF$_2$,4-F) |
| Ph(2-F,3-Me,4-CF$_3$) | Ph(2-F,3-CF$_3$,4-t-Bu) | Ph(2-F,3-CHF$_2$,4-Br) |
| Ph(2-F,3-Me,4-CHF$_2$) | Ph(2-F,3-CF$_3$,4-c-Pr) | Ph(2-F,3-CHF$_2$,4-Me) |
| Ph(2-F,3-Me,4-OCF$_3$) | Ph(2-F,CF$_3$,4-CF$_3$) | Ph(2-F,3-CHF$_2$,4-t-Bu) |
| Ph(2-F,3-Me,4-OCHF$_2$) | Ph(2-F,3-CF$_3$,4-CHF$_2$) | Ph(2-F,3-CHF$_2$,4-c-Pr) |
| Ph(2-F,3-Me,4-SO$_2$Me) | Ph(2-F,3-CF$_3$,4-OCF$_3$) | Ph(2-F,3-CHF$_2$,4-CF$_3$) |
| Ph(2-F,3-Me,4-TMS) | Ph(2-F,3-CF$_3$,4-OCHF$_2$) | Ph(2-F,3-CHF$_2$,4-CHF$_2$) |
| Ph(2-F,3-Me,4-CN) | Ph(2-F,3-CF$_3$,4-SO$_2$Me) | Ph(2-F,3-CHF$_2$,4-OCF$_3$) |
| Ph(2-F,3-t-Bu,4-Cl) | Ph(2-F,3-CF$_3$,4-TMS) | Ph(2-F,3-CHF$_2$,4-OCHF$_2$) |
| Ph(2-F,3-t-Bu,4-F) | Ph(2-F,3-CF$_3$,4-CN) | Ph(2-F,3-CHF$_2$,4-SO$_2$Me) |
| Ph(2-F,3-t-Bu,4-Br) | Ph(2-F,3-OCF$_3$,4-Cl) | Ph(2-F,3-CHF$_2$,4-TMS) |
| Ph(2-F,3-t-Bu,4-Me) | Ph(2-F,3-OCF$_3$,4-F) | Ph(2-F,3-CHF$_2$,4-CN) |
| Ph(2-F,3-t-Bu,4-t-Bu) | Ph(2-F,3-OCF$_3$,4-Br) | Ph(2-F,3-CN,4-Cl) |
| Ph(2-F,3-t-Bu,4-c-Pr) | Ph(2-F,3-OCF$_3$,4-Me) | Ph(2-F,3-CN,4-F) |
| Ph(2-F,3-t-Bu,4-CF$_3$) | Ph(2-F,3-OCF$_3$,4-t-Bu) | Ph(2-F,3-CN,4-Br) |
| Ph(2-F,3-t-Bu,4-CHF$_2$) | Ph(2-F,3-OCF$_3$,4-c-Pr) | Ph(2-F,3-CN,4-Me) |
| Ph(2-F,3-t-Bu,4-OCF$_3$) | Ph(2-F,3-OCF$_3$,4-CF$_3$) | Ph(2-F,3-CN,4-t-Bu) |
| Ph(2-F,3-t-Bu,4-OCHF$_2$) | Ph(2-F,3-OCF$_3$,4-CHF$_2$) | Ph(2-F,3-CN,4-c-Pr) |
| Ph(2-F,3-t-Bu,4-SO$_2$Me) | Ph(2-F,3-OCF$_3$,4-OCF$_3$) | Ph(2-F,3-CN,4-CF$_3$) |
| Ph(2-F,3-t-Bu,4-TMS) | Ph(2-F,3-OCF$_3$,4-OCHF$_2$) | Ph(2-F,3-CN,4-CHF$_2$) |
| Ph(2-F,3-t-Bu,4-CN) | Ph(2-F,3-OCF$_3$,4-SO$_2$Me) | Ph(2-F,3-CN,4-OCF$_3$) |
| Ph(2-F,3-c-Pr,4-Cl) | Ph(2-F,3-OCF$_3$,4-TMS) | Ph(2-F,3-CN,4-OCHF$_2$) |
| Ph(2-F,3-c-Pr,4-F) | Ph(2-F,3-OCF$_3$,4-CN) | Ph(2-F,3-CN,4-SO$_2$Me) |
| Ph(2-F,3-c-Pr,4-Br) | Ph(2-F,3-SO$_2$Me,4-Cl) | Ph(2-F,3-CN,4-TMS) |
| Ph(2-F,3-c-Pr,4-Me) | Ph(2-F,3-SO$_2$Me,4-F) | Ph(2-F,3-CN,4-CN) |
| Ph(2-F,3-c-Pr,4-t-Bu) | Ph(2-F,3-SO$_2$Me,4-Br) | Ph(2-F,4-Cl) |
| Ph(2-F,3,4-di-c-Pr) | Ph(2-F,3-SO$_2$Me,4-Me) | Ph(2-F,4-F) |
| Ph(2-F,3-c-Pr,4-CF$_3$) | Ph(2-F,3-SO$_2$Me,4-t-Bu) | Ph(2-F,4-Br) |
| Ph(2-F,3-c-Pr,4-CHF$_2$) | Ph(2-F,3-SO$_2$Me,4-c-Pr) | Ph(2-F,4-Me) |
| Ph(2-F,3-c-Pr,4-OCF$_3$) | Ph(2-F,3-SO$_2$Me,4-CF$_3$) | Ph(2-F,4-t-Bu) |
| Ph(2-F,3-c-Pr,4-OCHF$_2$) | Ph(2-F,3-SO$_2$Me,4-CHF$_2$) | Ph(2-F,4-c-Pr) |
| Ph(2-F,3-c-Pr,4-SO$_2$Me) | Ph(2-F,3-SO$_2$Me,4-OCF$_3$) | Ph(2-F,4-CF$_3$) |
| Ph(2-F,3-c-Pr,4-TMS) | Ph(2-F,3-SO$_2$Me,4-OCHF$_2$) | Ph(2-F,4-CHF$_2$) |
| Ph(2-F,3-c-Pr,4-CN) | Ph(2-F,3,4-di-SO$_2$Me) | Ph(2-F,4-OCF$_3$) |
| Ph(2-F,4-OCHF$_2$) | Ph(2-SMe) | Ph(2-OPh) |
| Ph(2-F,4-SO$_2$Me) | Ph(2-SOMe) | Ph(2-C≡CCF$_3$) |
| Ph(2-F,4-TMS) | Ph(2-SO$_2$Me) | Ph(2-CH=CF$_2$) |
| Ph(2-F,4-CN) | Ph(2-OSO$_2$Me) | Ph(2-CH=CCl$_2$) |
| Ph(2-F,3-Cl) | Ph(2-C≡CH) | Ph(2-CH=CBr$_2$) |
| Ph(2-F,3F) | Ph(2-OMe) | Ph(2-OCH=CH$_2$) |
| Ph(2-F,3-Br) | Ph(2-OEt) | Ph(2-OCH=CF$_2$) |
| Ph(2-F,3-Me) | Ph(2-NHCO$_2$-t-Bu) | Ph(2-OCH=CCl$_2$) |
| Ph(2-F,3-t-Bu) | Ph(2-NHCOMe) | Ph(2-OCH=CBr$_2$) |
| Ph(2-F,3-c-Pr) | Ph(2-NHCOCF$_3$) | Ph(2-CH$_2$CH=CH$_2$) |
| Ph(2-F,3-CF$_3$) | Ph(2-CN) | Ph(2-CH$_2$CH=CF$_2$) |
| Ph(2-F,3-CHF$_2$) | Ph(2-NO$_2$) | Ph(2-CH$_2$CH=CCl$_2$) |
| Ph(2-F,3-OCF$_3$) | Ph(2-Ph) | Ph(2-CH$_2$CH=CBr$_2$) |
| Ph(2-F,3-OCHF$_2$) | Ph(2-COMe) | Ph(2-OCH$_2$CH=CH$_2$) |
| Ph(2-F,3-SO$_2$Me) | Ph(2-OCOMe) | Ph(2-OCH$_2$CH=CF$_2$) |

TABLE 1-continued

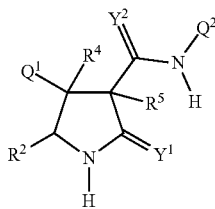

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-F,3-TMS) | Ph(2-CO₂Me) | Ph(2-OCH₂CH=CCl₂) |
| Ph(2-F,3-CN) | Ph(2-OCO₂Me) | Ph(2-OCH₂CH=CBr₂) |
| Ph(2-Cl) | Ph(2-TMS) | Ph(2-SCF₂H) |
| Ph(2-F) | Ph[2-(1H-pyrazol-1yl)] | Ph(2-SCF₂CF₂H) |
| Ph(2-Br) | Ph[2-(2H-1,2,3-triazol-2-yl)] | Ph(3-I) |
| Ph(2-I) | Ph[2-(1H-imidazol-1-yl)] | Ph(3-n-Pr) |
| Ph(2-Me) | Ph[2-(3-pyridinyl)] | Ph(3-CF₂H) |
| Ph(2-Et) | Ph[2-(4-pyridinyl)] | Ph(3-OCF₂H) |
| Ph(2-n-Pr) | Ph[2-(2-pyridinyl)] | Ph(3-SO₂Me) |
| Ph(2-t-Bu) | Ph(2-C₂F₅) | Ph(3-C₂F₅) |
| Ph(2-i-Pr) | Ph(2-CF₂CF₂H) | Ph(3-CF₂CF₂H) |
| Ph(2-c-Pr) | Ph(2-OCF₂CF₂H) | Ph(3-OCF₂CF₂H) |
| Ph(2-cyclohexyl) | Ph(2-OC₂F₅) | Ph(3-OC₂F₅) |
| Ph(2-CH=CH₂) | Ph(2-OCH₂CF₃) | Ph(3-OCH₂CF₃) |
| Ph(2-CF₃) | Ph(2-OCH₂C≡CH) | Ph(3-OCH₂C≡CH) |
| Ph(2-CH₂CF₃) | Ph(2-OCH₂C≡CCF₃) | Ph(3-OCH₂C≡CCF₃) |
| Ph(2-CF₂H) | Ph(2-OCH₂C≡CCF₂H) | Ph(3-OCH₂C≡CCF₂H) |
| Ph(2-CH₂F) | Ph(2-OCH₂C≡CCH₃) | Ph(3-OCH₂C≡CCH₃) |
| Ph(2-OCF₃) | Ph(2-OCH₂C≡C-c-Pr) | Ph(3-OCH₂C≡C-c-Pr) |
| Ph(2-OCH₂F) | Ph(2-C≡CCF₂H) | Ph(3-C≡CCF₂H) |
| Ph(2-OCF₂H) | Ph(2-C≡CCH₃) | Ph(3-C≡CCH₃) |
| Ph(2-SCF₃) | Ph(2-C≡C-c-Pr) | Ph(3-C≡C-c-Pr) |
| Ph(3-OPh) | Ph(2-Cl,3-OCF₂H) | Ph(2-Cl,3-C≡CCH₃) |
| Ph(3-C≡CCF₃) | Ph(2-Cl,3-SCF₃) | Ph(2-Cl,3-C≡C-c-Pr) |
| Ph(3-CH=CF₂) | Ph(2-Cl,3-SMe) | Ph(2-Cl,3-OPh) |
| Ph(3-CH=CCl₂) | Ph(2-Cl,3-SOMe) | Ph(2-Cl,3-C≡CCF₃) |
| Ph(3-CH=CBr₂) | Ph(2-Cl,3-SO₂Me) | Ph(2-Cl,3-CH=CF₂) |
| Ph(3-OCH=CH₂) | Ph(2-Cl,3-OSO₂Me) | Ph(2-Cl,3-CH=CCl₂) |
| Ph(3-OCH=CF₂) | Ph(2-Cl,3-C≡CH) | Ph(2-Cl,3-CH=CBr₂) |
| Ph(3-OCH=CCl₂) | Ph(2-Cl,3-OMe) | Ph(2-Cl,3-OCH=CH₂) |
| Ph(3-OCH=CBr₂) | Ph(2-Cl,3-OEt) | Ph(2-Cl,3-OCH=CF₂) |
| Ph(3-CH₂CH=CH₂) | Ph(2-Cl,3-NHCO₂-t-Bu) | Ph(2-Cl,3-OCH=CCl₂) |
| Ph(3-CH₂CH=CF₂) | Ph(2-Cl,3-NHCOMe) | Ph(2-Cl,3-OCH=CBr₂) |
| Ph(3-CH₂CH=CCl₂) | Ph(2-Cl,3-NHCOCF₃) | Ph(2-Cl,3-CH₂CH=CH₂) |
| Ph(3-CH₂CH=CBr₂) | Ph(2-Cl,3-CN) | Ph(2-Cl,3-CH₂CH=CF₂) |
| Ph(3-OCH₂CH=CH₂) | Ph(2-Cl,3-NO₂) | Ph(2-Cl,3-CH₂CH=CCl₂) |
| Ph(3-OCH₂CH=CF₂) | Ph(2-Cl,3-Ph) | Ph(2-Cl,3-CH₂CH=CBr₂) |
| Ph(3-OCH₂CH=CCl₂) | Ph(2-Cl,3-COMe) | Ph(2-Cl,3-OCH₂CH=CH₂) |
| Ph(3-OCH₂CH=CBr₂) | Ph(2-Cl,3-OCOMe) | Ph(2-Cl,3-OCH₂CH=CF₂) |
| Ph(3-SCF₂H) | Ph(2-Cl,3-CO₂Me) | Ph(2-Cl,3-OCH₂CH=CCl₂) |
| Ph(3-SCF₂CF₂H) | Ph(2-Cl,3-OCO₂Me) | Ph(2-Cl,3-OCH₂CH=CBr₂) |
| Ph(2-Cl,3-Cl) | Ph(2-Cl,3-TMS) | Ph(2-Cl,3-SCF₂H) |
| Ph(2-Cl,3-F) | Ph[3-(2-Cl,1H-pyrazol-1-yl)] | Ph(2-Cl,3-SCF₂CF₂H) |
| Ph(2-Cl,3-Br) | Ph[3-(2-Cl,2H-1,2,3-triazol-2-yl)] | Ph(2-F,3-F) |
| Ph(2-Cl,3-I) | Ph[3-(2-Cl,1H-imidazol-1-yl)] | Ph(2-F,3-Br) |
| Ph(2-Cl,3-Me) | Ph[3-(2-Cl,3-pyridinyl)] | Ph(2-F,3-I) |
| Ph(2-Cl,3-Et) | Ph[3-(2-Cl,4-pyridinyl)] | Ph(2-F,3-Me) |
| Ph(2-Cl,3-n-Pr) | Ph[3-(2-Cl,2-pyridinyl)] | Ph(2-F,3-Et) |
| Ph(2-Cl,3-t-Bu) | Ph(2-Cl,3-C₂F₅) | Ph(2-F,3-n-Pr) |
| Ph(2-Cl,3-i-Pr) | Ph(2-Cl,3-CF₂CF₂H) | Ph(2-F,3-t-Bu) |
| Ph(2-Cl,3-c-Pr) | Ph(2-Cl,3-OCF₂CF₂H) | Ph(2-F,3-i-Pr) |
| Ph(2-Cl,3-cyclohexyl) | Ph(2-Cl,3-OC₂F₅) | Ph(2-F,3-cyclohexyl) |
| Ph(2-Cl,3-CH=CH₂) | Ph(2-Cl,3-OCH₂CF₃) | Ph(2-F,3-CH=CH₂) |
| Ph(2-Cl,3-CF₃) | Ph(2-Cl,3-OCH₂C≡CH) | Ph(2-F,3-CF₃) |
| Ph(2-Cl,3-CH₂CF₃) | Ph(2-Cl,3-OCH₂C≡CCF₃) | Ph(2-F,3-CH₂CF₃) |
| Ph(2-Cl,3-CF₂H) | Ph(2-Cl,3-OCH₂C≡CCF₂H) | Ph(2-F,3-CF₂H) |
| Ph(2-Cl,3-CH₂F) | Ph(2-Cl,3-OCH₂C≡CCH₃) | Ph(2-F,3-CH₂F) |
| Ph(2-Cl,3-OCF₃) | Ph(2-Cl,3-OCH₂C≡C-c-Pr) | Ph(2-F,3-OCH₂F) |
| Ph(2-Cl,3-OCH₂F) | Ph(2-Cl,3-C≡CCF₂H) | Ph(2-F,3-OCF₂H) |
| Ph(2-F,3-SCF₃) | Ph(2-F,3-CH=CCl₂) | 2-Furanyl(4-CF₃) |
| Ph(2-F,3-SMe) | Ph(2-F,3-CH=CBr₂) | 2-Furanyl(5-F) |
| Ph(2-F,3-SOMe) | Ph(2-F,3-OCH=CH₂) | 2-Furanyl(5-Cl) |
| Ph(2-F,3-SO₂Me) | Ph(2-F,3-OCH=CF₂) | 2-Furanyl(5-CF₃) |
| Ph(2-F,3-OSO₂Me) | Ph(2-F,3-OCH=CCl₂) | 2-Furanyl(4-Me) |
| Ph(2-F,3-C≡CH) | Ph(2-F,3-OCH=CBr₂) | 2-Furanyl(4-Et) |
| Ph(2-F,3-OMe) | Ph(2-F,3-CH₂CH=CH₂) | 2-Furanyl(4-i-Pr) |

TABLE 1-continued

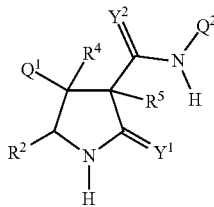

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-F,3-OEt) | Ph(2-F,3-CH₂CH=CF₂) | 2-Furanyl(4-c-Pr) |
| Ph(2-F,3-NHCO₂-t-Bu) | Ph(2-F,3-CH₂CH=CCl₂) | 2-Furanyl(4-CF₂H) |
| Ph(2-F,3-NHCOMe) | Ph(2-F,3-CH₂CH=CBr₂) | 2-Furanyl(4-OCF₂H) |
| Ph(2-F,3-NHCOCF₃) | Ph(2-F,3-OCH₂CH=CH₂) | 2-Furanyl(4-OCF₂CF₂H) |
| Ph(2-F,3-NO₂) | Ph(2-F,3-OCH₂CH=CF₂) | 2-Furanyl(5-Me) |
| Ph(2-F,3-Ph) | Ph(2-F,3-OCH₂CH=CCl₂) | 2-Furanyl(5-Et) |
| Ph(2-F,3-COMe) | Ph(2-F,3-OCH₂CH=CBr₂) | 2-Furanyl(5-i-Pr) |
| Ph(2-F,3-OCOMe) | Ph(2-F,3-SCF₂H) | 2-Furanyl(5-c-Pr) |
| Ph(2-F,3-CO₂Me) | Ph(2-F,3-SCF₂CF₂H) | 2-Furanyl(5-CF₂H) |
| Ph(2-F,3-OCO₂Me) | Ph(2-F,3-SF₅) | 2-Furanyl(5-OCF₂H) |
| Ph[3-(2-F,1H-imidazol-1-yl)] | 4-Pyridinyl(5-OCF₂H) | 2-Furanyl(5-OCF₂CF₂H) |
| Ph[3-(2-F,3-pyridinyl)] | 4-Pyridinyl(5-CF₂H) | 2-Furanyl(5-OC₂F₅) |
| Ph[3-(2-F,4-pyridinyl)] | 4-Pyridinyl(5-OCF₂CF₂H) | Ph(4-I) |
| Ph[3-(2-F,2-pyridinyl)] | 2-Thienyl(4-Me) | Ph(4-n-Pr) |
| Ph(2-F,3-C₂F₅) | 2-Thienyl(4-Et) | Ph(4-OCHF₂) |
| Ph(2-F,3-CF₂CF₂H) | 2-Thienyl(4-i-Pr) | Ph(4-C₂F₅) |
| Ph(2-F,3-OCF₂CF₂H) | 2-Thienyl(4-c-Pr) | Ph(4-CF₂CF₂H) |
| Ph(2-F,3-OC₂F₅) | 2-Thienyl(4-CF₂H) | Ph(4-OCF₂CF₂H) |
| Ph(2-F,3-OCH₂CF₃) | 2-Thienyl(4-OCF₂H) | Ph(4-OC₂F₅) |
| Ph(2-F,3-OCH₂C≡CH) | 2-Thienyl(4-OCF₂CF₂H) | Ph(4-OCH₂CF₃) |
| Ph(2-F,3-OCH₂C≡CCF₃) | 2-Thienyl(5-Me) | Ph(4-OCH₂C≡CH) |
| Ph(2-F,3-OCH₂C≡CCF₂H) | 2-Thienyl(5-Et) | Ph(4-OCH₂C≡CCF₃) |
| Ph(2-F,3-OCH₂C≡CCH₃) | 2-Thienyl(5-i-Pr) | Ph(4-OCH₂C≡CCF₂H) |
| Ph(2-F,3-OCH₂C≡C-c-Pr) | 2-Thienyl(5-c-Pr) | Ph(4-OCH₂C≡CCH₃) |
| Ph(2-F,3-C≡CCF₂H) | 2-Thienyl(5-CF₂H) | Ph(4-OCH₂C≡C-c-Pr) |
| Ph(2-F,3-C≡CCH₃) | 2-Thienyl(5-OCF₂H) | Ph(4-C≡CCF₂H) |
| Ph(2-F,3-C≡C-c-Pr) | 2-Thienyl(5-OCF₂CF₂H) | Ph(4-C≡CCH₃) |
| Ph(2-F,3-OPh) | 2-Thienyl(5-OC₂F₅) | Ph(4-C≡C-c-Pr) |
| Ph(2-F,3-C≡CCF₃) | 2-Furanyl(4-F) | Ph(4-OPh) |
| Ph(2-F,3-CH=CF₂) | 2-Furanyl(4-Cl) | Ph(4-C≡CCF₃) |
| Ph(4-CH=CF₂) | 2-Furanyl(4-SMe) | Ph(2-Cl,4-OCH=CF₂) |
| Ph(4-CH=CCl₂) | 2-Cl,4-SOMe) | Ph(2-Cl,4-OCH=CCl₂) |
| Ph(4-CH=CBr₂) | Ph(2-Cl,4-SO₂Me) | Ph(2-Cl,4-OCH=CBr₂) |
| Ph(4-OCH=CH₂) | Ph(2-Cl,4-OSO₂Me) | Ph(2-Cl,4-CH₂CH=CH₂) |
| Ph(4-OCH=CF₂) | Ph(2-Cl,4-C≡CH) | Ph(2-Cl,4-CH₂CH=CF₂) |
| Ph(4-OCH=CCl₂) | Ph(2-Cl,4-OMe) | Ph(2-Cl,4-CH₂CH=CCl₂) |
| Ph(4-OCH=CBr₂) | Ph(2-Cl,4-OEt) | Ph(2-Cl,4-CH₂CH=CBr₂) |
| Ph(4-CH₂CH=CH) | Ph(2-Cl,4-NHCO₂-t-Bu) | Ph(2-Cl,4-OCH₂CH=CH₂) |
| Ph(4-CH₂CH=CF₂) | Ph(2-Cl,4-NHCOMe) | Ph(2-Cl,4-OCH₂CH=CF₂) |
| Ph(4-CH₂CH=CCl₂) | Ph(2-Cl,4-NHCOCF₃) | Ph(2-Cl,4-OCH₂CH=CCl₂) |
| Ph(4-CH₂CH=CBr₂) | Ph(2-Cl,4-CN) | Ph(2-Cl,4-OCH₂CH=CBr₂) |
| Ph(4-OCH₂CH=CH₂) | Ph(2-Cl,4-NO₂) | Ph(2-Cl,4-SCF₂H) |
| Ph(4-OCH₂CH=CF₂) | Ph(2-Cl,4-Ph) | Ph(2-Cl,4-SCF₂CF₂H) |
| Ph(4-OCH₂CH=CCl₂) | Ph(2-Cl,4-COMe) | Ph(2,4-di-F) |
| Ph(4-OCH₂CH=CBr₂) | Ph(2-Cl,4-OCOMe) | Ph(2,4-di-F) |
| Ph(4-SCF₂H) | Ph(2-Cl,4-CO₂Me) | Ph(2-F,4-Br) |
| Ph(4-SCF₂CF₂H) | Ph(2-Cl,4-OCO₂Me) | Ph(2-F,4-I) |
| Ph(2,4-di-Cl) | Ph(2-Cl,4-TMS) | Ph(2-F,4-Me) |
| Ph(2-Cl,4-F) | Ph(2-Cl,4-C₂F₅) | Ph(2-F,4-Et) |
| Ph(2-Cl,4-Br) | Ph(2-Cl,4-CF₂CF₂H) | Ph(2-F,4-n-Pr) |
| Ph(2-Cl,4-I) | Ph(2-Cl,4-OCF₂CF₂H) | Ph(2-F,4-t-Bu) |
| Ph(2-Cl,4-Me) | Ph(2-Cl,4-OC₂F₅) | Ph(2-F,4-i-Pr) |
| Ph(2-Cl,4-Et) | Ph(2-Cl,4-OCH₂CF₃) | Ph(2-F,4-cyclohexyl) |
| Ph(2-Cl,4-n-Pr) | Ph(2-Cl,4-OCH₂C≡CH) | Ph(2-F,4-CH=CH₂) |
| Ph(2-Cl,4-t-Bu) | Ph(2-Cl,4-OCH₂C≡CCF₃) | Ph(2-F,4-CF₃) |
| Ph(2-Cl,4-i-Pr) | Ph(2-Cl,4-OCH₂C≡CCF₂H) | Ph(2-F,4-CH₂CF₃) |
| Ph(2-Cl,4-c-Pr) | Ph(2-Cl,4-OCH₂C≡CCH₃) | Ph(2-F,4-CHF₂) |
| Ph(2-Cl,4-cyclohexyl) | Ph(2-Cl,4-OCH₂C≡C-c-Pr) | Ph(2-F,4-CH₂F) |
| Ph(2-Cl,4-CH=CH₂) | Ph(2-Cl,4-C≡CCF₂H) | Ph(2-F,4-OCF₃) |
| Ph(2-Cl,4-CF₃) | Ph(2-Cl,4-C≡CCH₃) | Ph(2-F,4-OCH₂F) |
| Ph(2-Cl,4-CH₂CF₃) | Ph(2-Cl,4-C≡C-c-Pr) | Ph(2-F,4-OCHF₂) |
| Ph(2-Cl,4-CHF₂) | Ph(2-Cl,4-OPh) | Ph(2-F,4-SCF₃) |
| Ph(2-Cl,4-CH₂F) | Ph(2-Cl,4-C≡CCF₃) | Ph(2-F,4-SMe) |
| Ph(2-Cl,4-OCF₃) | Ph(2-Cl,4-CH=CF₂) | Ph(2-F,4-SOMe) |
| Ph(2-Cl,4-OCH₂F) | Ph(2-Cl,4-CH=CCl₂) | Ph(2-F,4-SO₂Me) |
| Ph(2-Cl,4-OCHF₂) | Ph(2-Cl,4-CH=CBr₂) | Ph(2-F,4-OSO₂Me) |

TABLE 1-continued

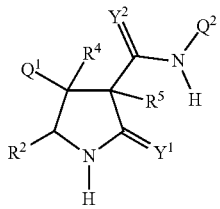

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(2-Cl,4-SCF₃) | Ph(2-Cl,4-OCH=CH₂) | Ph(2-F,4-C≡CH) |
| Ph(2-F,4-OMe) | Ph(2-F,4-CH₂CH=CBr₂) | Ph(3-Cl,4-OMe) |
| Ph(2-F,4-OEt) | Ph(2-F,4-OCH₂CH=CH₂) | Ph(3-Cl,4-OCF₂CF₂H) |
| Ph(2-F,4-NHCO₂-t-Bu) | Ph(2-F,4-OCH₂CH=CF₂) | Ph(3-Cl,4-OC₂F₅) |
| Ph(2-F,4-NHCOMe) | Ph(2-F,4-OCH₂CH=CCl₂) | Ph(3,4-di-F) |
| Ph(2-F,4-NHCOCF₃) | Ph(2-F,4-OCH₂CH=CBr₂) | Ph(3-F,4-I) |
| Ph(2-F,4-CN) | Ph(2-F,4-SCF₂H) | Ph(3-F,4-Et) |
| Ph(2-F,4-NO₂) | Ph(2-F,4-SCF₂CF₂H) | Ph(3-F,4-n-Pr) |
| Ph(2-F,4-Ph) | Ph(2-F,4-SF₅) | Ph(3-F,4-i-Pr) |
| Ph(2-F,4-COMe) | 3-Pyridinyl(5-OCF₂H) | Ph(3-F,4-C₂F₅) |
| Ph(2-F,4-OCOMe) | 3-Pyridinyl(5-CF₂H) | Ph(3-F,4-CF₂CF₂H) |
| Ph(2-F,4-CO₂Me) | 3-Pyridinyl(5-OCF₂CF₂H) | Ph(3-F,4-CF₂H) |
| Ph(2-F,4-OCO₂Me) | 3-Thienyl(4-Me) | Ph(3-F,4-OMe) |
| Ph(2-F,4-C₂F₅) | 3-Thienyl(4-Et) | Ph(3-F,4-OCF₂CF₂H) |
| Ph(2-F,4-CF₂CF₂H) | 3-Thienyl(4-i-Pr) | Ph(3-F,4-OC₂F₅) |
| Ph(2-F,4-OCF₂CF₂H) | 3-Thienyl(4-c-Pr) | Ph(3-Br,4-I) |
| Ph(2-F,4-OC₂F₅) | 3-Thienyl(4-CF₂H) | Ph(3-Br,4-Et) |
| Ph(2-F,4-OCH₂CF₃) | 3-Thienyl(4-OCF₂H) | Ph(3-Br,4-n-Pr) |
| Ph(2-F,4-OCH₂C≡CH) | 3-Thienyl(4-OCF₂CF₂H) | Ph(3-Br,4-t-Bu) |
| Ph(2-F,4-OCH₂C≡CCF₃) | 3-Thienyl(4-OC₂F₅) | Ph(3-Br,4-i-Pr) |
| Ph(2-F,4-OCH₂C≡CCF₂H) | 3-Furanyl(5-F) | Ph(3-Br,4-C₂F₅) |
| Ph(2-F,4-OCH₂C≡CCH₃) | 3-Furanyl(5-Cl) | Ph(3-Br,4-CF₂CF₂H) |
| Ph(2-F,4-OCH₂C≡C-c-Pr) | 3-Furanyl(5-CF₃) | Ph(3-Br,4-CF₂H) |
| Ph(2-F,4-C≡CCF₂H) | 3-Furanyl(4-Me) | Ph(3-Br,4-OMe) |
| Ph(2-F,4-C≡CCH₃) | 3-Furanyl(4-Et) | Ph(3-Br,4-OCF₂CF₂H) |
| Ph(2-F,4-C≡C-c-Pr) | 3-Furanyl(4-i-Pr) | Ph(3-Br,4-OC₂F₅) |
| Ph(2-F,4-OPh) | 3-Furanyl(4-c-Pr) | Ph(3-I,4-Cl) |
| Ph(2-F,4-C≡CCF₃) | 3-Furanyl(4-CF₂H) | Ph(3-I,4-F) |
| Ph(2-F,4-CH=CF₂) | 3-Furanyl(4-OCF₂H) | Ph(3-I,4-Br) |
| Ph(2-F,4-CH=CCl₂) | 3-Furanyl(4-OCF₂CF₂H) | Ph(3,4-di-I) |
| Ph(2-F,4-CH=CBr₂) | 3-Furanyl(4-OC₂F₅) | Ph(3-I,4-Me) |
| Ph(2-F,4-OCH=CH₂) | Ph(3-Cl,4-I) | Ph(3-I,4-Et) |
| Ph(2-F,4-OCH=CF₂) | Ph(3-Cl,4-Et) | Ph(3-I,4-n-Pr) |
| Ph(2-F,4-OCH=CCl₂) | Ph(3-Cl,4-n-Pr) | Ph(3-I,4-t-Bu) |
| Ph(2-F,4-OCH=CBr₂) | Ph(3-Cl,4-i-Pr) | Ph(3-I,4-i-Pr) |
| Ph(2-F,4-CH₂CH=CH₂) | Ph(3-Cl,4-C₂F₅) | Ph(3-I,4-c-Pr) |
| Ph(2-F,4-CH₂CH=CF₂) | Ph(3-Cl,4-CF₂CF₂H) | Ph(3-I,4-CF₃) |
| Ph(2-F,4-CH₂CH=CCl₂) | Ph(3-Cl,4-CF₂H) | Ph(3-I,4-C₂F₅) |
| Ph(3-I,4-CF₂CF₂H) | Ph(3-Et,4-OCF₂CF₂H) | Ph(3-i-Pr,4-Cl) |
| Ph(3-I,4-CF₂H) | Ph(3-Et,4-OC₂F₅) | Ph(3-i-Pr,4-F) |
| Ph(3-I,4-OMe) | Ph(3-Et,4-SO₂Me) | Ph(3-i-Pr,4-Br) |
| Ph(3-I,4-OCF₃) | Ph(3-Et,4-TMS) | Ph(3-i-Pr,4-I) |
| Ph(3-I,4-OCHF₂) | Ph(3-Et,4-CN) | Ph(3-i-Pr,4-Me) |
| Ph(3-I,4-OCF₂CF₂H) | Ph(3-n-Pr,4-Cl) | Ph(3-i-Pr,4-Et) |
| Ph(3-I,4-OC₂F₅) | Ph(3-n-Pr,4-F) | Ph(3-i-Pr,4-n-Pr) |
| Ph(3-I,4-SO₂Me) | Ph(3-n-Pr,4-Br) | Ph(3-i-Pr,4-t-Bu) |
| Ph(3-I,4-TMS) | Ph(3-n-Pr,4-I) | Ph(3,4,-di-i-Pr) |
| Ph(3-I,4-CN) | Ph(3-n-Pr,4-Me) | Ph(3-i-Pr,4-c-Pr) |
| Ph(3-Me,4-I) | Ph(3-n-Pr,4-Et) | Ph(3-i-Pr,CF₃) |
| Ph(3-Me,4-Et) | Ph(3,4-di-n-Pr) | Ph(3-i-Pr,4-C₂F₅) |
| Ph(3-Me,4-n-Pr) | Ph(3-n-Pr,4-t-Bu) | Ph(3-i-Pr,4-CF₂CF₂H) |
| Ph(3-Me,4-i-Pr) | Ph(3-n-Pr,4-i-Pr) | Ph(3-i-Pr,4-CF₂H) |
| Ph(3-Me,4-C₂F₅) | Ph(3-n-Pr,4-c-Pr) | Ph(3-i-Pr,4-OMe) |
| Ph(3-Me,4-CF₂CF₂H) | Ph(3-n-Pr,4-CF₃) | Ph(3-i-Pr,4-OCF₃) |
| Ph(3-Me,4-CF₂H) | Ph(3-n-Pr,4-C₂F₅) | Ph(3-i-Pr,4-OCHF₂) |
| Ph(3-Me,4-OMe) | Ph(3-n-Pr,4-CF₂CF₂H) | Ph(3-i-Pr,4-OCF₂CF₂H) |
| Ph(3-Me,4-OCF₂CF₂H) | Ph(3-n-Pr,4-CF₂H) | Ph(3-i-Pr,4-OC₂F₅) |
| Ph(3-Me,4-OC₂F₅) | Ph(3-n-Pr,4-OMe) | Ph(3-i-Pr,4-SO₂Me) |
| Ph(3-Et,4-Cl) | Ph(3-n-Pr,4-OCF₃) | Ph(3-i-Pr,4-TMS) |
| Ph(3-Et,4-F) | Ph(3-n-Pr,4-OCHF₂) | Ph(3-i-Pr,4-CN) |
| Ph(3-Et,4-Br) | Ph(3-n-Pr,4-OCF₂CF₂H) | Ph(3-c-Pr,4-I) |
| Ph(3-Et,4-I) | Ph(3-n-Pr,4-OC₂F₅) | Ph(3-c-Pr,4-Et) |
| Ph(3-Et,4-Me) | Ph(3-n-Pr,4-SO₂Me) | Ph(3-c-Pr,4-n-Pr) |
| Ph(3,4-di-Et) | Ph(3-n-Pr,4-TMS) | Ph(3-c-Pr,4-i-Pr) |
| Ph(3-Et,4-n-Pr) | Ph(3-n-Pr,4-CN) | Ph(3-c-Pr,4-C₂F₅) |
| Ph(3-Et,4-t-Bu) | Ph(3-t-Bu,4-I) | Ph(3-c-Pr,4-CF₂CF₂H) |

TABLE 1-continued

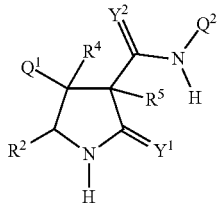

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(3-Et,4-i-Pr) | Ph(3-t-Bu,4-Et) | Ph(3-c-Pr,4-$CF_2$H) |
| Ph(3-Et,4-c-Pr) | Ph(3-t-Bu,4-n-Pr) | Ph(3-c-Pr,4-OMe) |
| Ph(3-Et,4-$CF_3$) | Ph(3-t-Bu,4-i-Pr) | Ph(3-c-Pr,4-$OCF_2CF_2H$) |
| Ph(3-Et,4-$C_2F_5$) | Ph(3-t-Bu,4-$C_2F_5$) | Ph(3-c-Pr,4-$OC_2F_5$) |
| Ph(3-Et,4-$CF_2CF_2H$) | Ph(3-t-Bu,4-$CF_2CF_2H$) | Ph(3-$CF_3$,4-I) |
| Ph(3-Et,4-$CF_2H$) | Ph(3-t-Bu,4-$CF_2H$) | Ph(3-$CF_3$,4-Et) |
| Ph(3-Et,4-OMe) | Ph(3-t-Bu,4-OMe) | Ph(3-$CF_3$,4-n-Pr) |
| Ph(3-Et,4-$OCF_3$) | Ph(3-t-Bu,4-$OCF_2CF_2H$) | Ph(3-$CF_3$,4-i-Pr) |
| Ph(3-Et,4-$OCHF_2$) | Ph(3-t-Bu,4-$OC_2F_5$) | Ph(3-$CF_3$,4-$C_2F_5$) |
| Ph(3-$CF_3$,4-$CF_2CF_2H$) | Ph(3-$CF_2CF_2H$,4-c-Pr) | Ph(3-OMe,4-Br) |
| Ph(3-$CF_3$,4-$CF_2H$) | Ph(3-$CF_2CF_2H$,4-$CF_3$) | Ph(3-OMe,4-I) |
| Ph(3-$CF_3$,4-OMe) | Ph(3-$CF_2CF_2H$,4-$C_2F_5$) | Ph(3-OMe,4-Me) |
| Ph(3-$CF_3$,4-$OCF_2CF_2H$) | Ph(3,4-di-$CF_2CF_2H$) | Ph(3-OMe,4-Et) |
| Ph(3-$CF_3$,4-$OC_2F_5$) | Ph(3-$CF_2CF_2H$,4-$CF_2H$) | Ph(3-OMe,4-n-Pr) |
| Ph(3-$CF_3$,4-TMS) | Ph(3-$CF_2CF_2H$,4-OMe) | Ph(3-OMe,4-t-Bu) |
| Ph(3-$C_2F_5$,4-Cl) | Ph(3-$CF_2CF_2H$,4-$OCF_3$) | Ph(3-OMe,4-i-Pr) |
| Ph(3-$C_2F_5$,4-F) | Ph(3-$CF_2CF_2H$,4-$OCHF_2$) | Ph(3-OMe,4-c-Pr) |
| Ph(3-$C_2F_5$,4-Br) | Ph93-$CF_2CF_2H$,4-$OCF_2CF_2H$) | Ph(3-OMe,4-$CF_3$) |
| Ph(3-$C_2F_5$,4-I) | Ph(3-$CF_2CF_2H$,4-$OC_2F_5$) | Ph(3-OMe,4-$C_2F_5$) |
| Ph(3-$C_2F_5$,4-Me) | Ph(3-$CF_2CF_2H$,4-$SO_2Me$) | Ph(3-OMe,4-$CF_2CF_2H$) |
| Ph(3-$C_2F_5$,4-Et) | Ph(3-$CF_2CF_2H$,4-TMS) | Ph(3-OMe,4-$CF_2H$) |
| Ph(3-$C_2F_5$,4-n-Pr) | Ph(3-$CF_2CF_2H$,4-CN) | Ph(3,4-di-OMe) |
| Ph(3-$C_2F_5$,4-t-Bu) | Ph(3-$CF_2H$,4-Cl) | Ph(3-OMe,4-$OCF_3$) |
| Ph(3-$C_2F_5$,4-i-Pr) | Ph(3-$CF_2H$,4-F) | Ph(3-OMe,4-$OCHF_2$) |
| Ph(3-$C_2F_5$,4-c-Pr) | Ph(3-$CF_2H$,4-Br) | Ph(3-OMe,4-$OCF_2CF_2H$) |
| Ph(3-$C_2F_5CF_3$,4-$CF_3$) | Ph(3-$CF_2H$,4-I) | Ph(3-OMe,4-$OC_2F_5$) |
| Ph(3,4-di-$C_2F_5$) | Ph(3-$CF_2H$,4-Me) | Ph(3-OMe,4-$SO_2Me$) |
| Ph(3-$C_2F_5$,4-$CF_2CF_2H$) | Ph(3-$CF_2H$,4-Et) | Ph(3-OMe,4-TMS) |
| Ph(3-$C_2F_5$,4-$CF_2H$) | Ph(3-$CF_2H$,4-n-Pr) | Ph(3-OMe,4-CN) |
| Ph(3-$C_2F_5$,4-OMe) | Ph(3-$CF_2H$,4-t-Bu) | Ph(3-$OCF_3$,4-I) |
| Ph(3-$C_2F_5$,4-$OCF_3$) | Ph(3-$CF_2H$,4-i-Pr) | Ph(3-$OCF_3$,4-Et) |
| Ph(3-$C_2F_5$,4-$OCHF_2$) | Ph(3-$CF_2H$,4-c-Pr) | Ph(3-$OCF_3$,4-n-Pr) |
| Ph(3-$C_2F_5$,4-$OCF_2CF_2H$) | Ph(3-$CF_2H$,4-$CF_3$) | Ph(3-$OCF_3$,4-i-Pr) |
| Ph(3-$C_2F_5$,4-$OC_2F_5$) | Ph(3-$CF_2H$,4-$C_2F_5$) | Ph(3-$OCF_3$,4-$CF_3$) |
| Ph(3-$C_2F_5$,4-$SO_2Me$) | Ph(3-$CF_2H$,4-$CF_2CF_2H$) | Ph(3-$OCF_3$,4-$C_2F_5$) |
| Ph(3-$C_2F_5$,4-TMS) | Ph(3,4-di-$CF_2H$) | Ph(3-$OCF_3$,4-$CF_2CF_2H$) |
| Ph(3-$C_2F_5$,4-CN) | Ph(3-$CF_2H$,4-OMe) | Ph(3-$OCF_3$,4-$CF_2H$) |
| Ph(3-$CF_2CF_2H$,4-Cl) | Ph(3-$CF_2H$,4-$OCF_3$) | Ph(3-$OCF_3$,4-OMe) |
| Ph(3-$CF_2CF_2H$,4-F) | Ph(3-$CF_2H$,4-$OCHF_2$) | Ph(3-$OCF_3$,4-$OCF_2CF_2H$) |
| Ph(3-$CF_2CF_2H$,4-Br) | Ph(3-$CF_2H$,4-$OCF_2CF_2H$) | Ph(3-$OCF_3$,4-$OC_2F_5$) |
| Ph(3-$CF_2CF_2H$,4-I) | Ph(3-$CF_2H$,4-$OC_2F_5$) | Ph(3-$OCHF_2$,4-Cl) |
| Ph(3-$CF_2CF_2H$,4-Me) | Ph(3-$CF_2H$,4-$SO_2Me$) | Ph(3-$OCHF_2$,4-F) |
| Ph(3-$CF_2CF_2H$,4-Et) | Ph(3-$CF_2H$,4-TMS) | Ph(3-$OCHF_2$,4-Br) |
| Ph(3-$CF_2CF_2H$,4-n-Pr) | Ph(3-$CF_2H$,4-CN) | Ph(3-$OCHF_2$,4-I) |
| Ph(3-$CF_2CF_2H$,4-t-Bu) | Ph(3-OMe,4-Cl) | Ph(3-$OCHF_2$,4-Me) |
| Ph(3-$CF_2CF_2H$,4-i-Pr) | Ph(3-OMe,4-F) | Ph(3-$OCHF_2$,4-Et) |
| Ph(3-$OCHF_2$,4-n-Pr) | Ph(3-$OCF_2CF_2H$,4-CN) | Ph(3-TMS,4-Me) |
| Ph(3-$OCHF_2$,4-t-Bu) | Ph(3-$OC_2F_5$,4-Cl) | Ph(3-TMS,4-Et) |
| Ph(3-$OCHF_2$,4-i-Pr) | Ph(3-$OC_2F_5$,4-F) | Ph(3-TMS,4-n-Pr) |
| Ph(3-$OCHF_2$,4-c-Pr) | Ph(3-$OC_2F_5$,4-Br) | Ph(3-TMS,4-t-Bu) |
| Ph(3-$OCHF_2CF_3$,4-$CF_3$) | Ph(3-$OC_2F_5$,4-I) | Ph(3-TMS,4-i-Pr) |
| Ph(3-$OCHF_2$,4-$C_2F_5$) | Ph(3-$OC_2F_5$,4-Me) | Ph(3-TMS,4-c-Pr) |
| Ph(3-$OCHF_2$,4-$CF_2CF_2H$) | Ph(3-$OC_2F_5$,4-Et) | Ph(3-TMS,4-$CF_3$) |
| Ph(3-$OCHF_2$,4-$CF_2H$) | Ph(3-$OC_2F_5$,4-n-Pr) | Ph(3-TMS,4-$C_2F_5$) |
| Ph(3-$OCHF_2$,4-OMe) | Ph(3-$OC_2F_5$,4-t-Bu) | Ph(3-TMS,4-$CF_2CF_2H$) |
| Ph(3-$OCHF_2$,4-$OCF_3$) | Ph(3-$OC_2F_5$,4-i-Pr) | Ph(3-TMS,4-$CF_2H$) |
| Ph(3,4-di-$OCHF_2$) | Ph(3-$OC_2F_5$,4-c-Pr) | Ph(3-TMS,4-OMe) |
| Ph(3-$OCHF_2$,4-$OCF_2CF_2H$) | Ph(3-$OC_2F_5CF_3$,4-$CF_3$) | Ph(3-TMS,4-$OCF_3$) |
| Ph(3-$OCHF_2$,4-$OC_2F_5$) | Ph(3-$OC_2F_5$,4-$CF_2CF_2H$) | Ph(3-TMS,4-$OCHF_2$) |
| Ph(3-$OCHF_2$,4-$SO_2Me$) | Ph(3-$OC_2F_5$,4-$CF_2H$) | Ph(3-TMS,4-$OCF_2CF_2H$) |
| Ph(3-$OCHF_2$,4-TMS) | Ph(3-$OC_2F_5$,4-OMe) | Ph(3-TMS,4-$OC_2F_5$) |
| Ph(3-$OCHF_2$,4-CN) | Ph(3-$OC_2F_5$,4-$OCF_3$) | Ph(3-TMS,4-$SO_2Me$) |
| Ph(3-$OCF_2CF_2H$,4-Cl) | Ph(3-$OC_2F_5$,4-$OCHF_2$) | Ph(3,4-di-TMS) |
| Ph(3-$OCF_2CF_2H$,4-F) | Ph(3-$OC_2F_5$,4-$OCF_2CF_2H$) | Ph(3-TMS,4-CN) |
| Ph(3-$OCF_2CF_2H$,4-Br) | Ph(3,4-di-$OC_2F_5$) | Ph(3-CN,4-I) |
| Ph(3-$OCF_2CF_2H$,4-I) | Ph(3-$OC_2F_5$,4-$SO_2Me$) | Ph(3-CN,4-Et) |

TABLE 1-continued

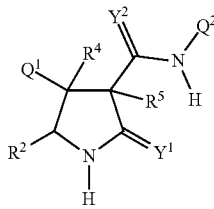

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(3-OCF$_2$CF$_2$H,4-Me) | Ph(3-OC$_2$F$_5$,4-TMS) | Ph(3-CN,4-n-Pr) |
| Ph(3-OCF$_2$CF$_2$H,4-Et) | Ph(3-OC$_2$F$_5$,4-CN) | Ph(3-CN,4-i-Pr) |
| Ph(3-OCF$_2$CF$_2$H,4-n-Pr) | Ph(3-SO$_2$Me,4-I) | Ph(3-CN,4-C$_2$F$_5$) |
| Ph(3-OCF$_2$CF$_2$H,4-t-Bu) | Ph(3-SO$_2$Me,4-Et) | Ph(3-CN,4-CF$_2$CF$_2$H) |
| Ph(3-OCF$_2$CF$_2$H,4-i-Pr) | Ph(3-SO$_2$Me,4-n-Pr) | Ph(3-CN,4-CF$_2$H) |
| Ph(3-OCF$_2$CF$_2$H,4-c-Pr) | Ph(3-SO$_2$Me,4-i-Pr) | Ph(3-CN,4-OMe) |
| Ph(3-OCF$_2$CF$_2$H,4-CF$_3$) | Ph(3-SO$_2$MeCF$_3$,4-CF$_3$) | Ph(3-CN,4-OCF$_2$CF$_2$H) |
| Ph(3-OCF$_2$CF$_2$H,4-C$_2$F$_5$) | Ph(3-SO$_2$Me,4-C$_2$F$_5$) | Ph(3-CN,4-OC$_2$F$_5$) |
| Ph(3-OCF$_2$CF$_2$H,4-CF$_2$CF$_2$H) | Ph(3-SO$_2$Me,4-CF$_2$CF$_2$H) | Ph(3,5-di-Cl) |
| Ph(3-OCF$_2$CF$_2$H,4-CF$_2$H) | Ph(3-SO$_2$Me,4-CF$_2$H) | Ph(3-Cl,5-F) |
| Ph(3-OCF$_2$CF$_2$H,4-OMe) | Ph(3-SO$_2$Me,4-OMe) | Ph(3-Cl,5-Br) |
| Ph(3-OCF$_2$CF$_2$H,4-OCF$_3$) | Ph(3-SO$_2$Me,4-OCF$_2$CF$_2$H) | Ph(3-Cl,5-I) |
| Ph(3-OCF$_2$CF$_2$H,4-OCHF$_2$) | Ph(3-SO$_2$Me,4-OC$_2$F$_5$) | Ph(3-Cl,5-Me) |
| Ph(3,4-di-OCF$_2$CF$_2$H) | Ph(3-TMS,4-Cl) | Ph(3-Cl,5-Et) |
| Ph(3-OCF$_2$CF$_2$H,4-OC$_2$F$_5$) | Ph(3-TMS,4-F) | Ph(3-Cl,5-n-Pr) |
| Ph(3-OCF$_2$CF$_2$H,4-SO$_2$Me) | Ph(3-TMS,4-Br) | Ph(3-Cl,5-t-Bu) |
| Ph(3-OCF$_2$CF$_2$H,4-TMS) | Ph(3-TMS,4-I) | Ph(3-Cl,5-i-Pr) |
| Ph(3-Cl,5-c-Pr) | Ph(3,5-di-Br) | Ph(3-I,5-OCF$_2$CF$_2$H) |
| Ph(3-Cl,5-CF$_3$) | Ph(3-Br,5-I) | Ph(3-I,5-OC$_2$F$_5$) |
| Ph(3-Cl,5-C$_2$F$_5$) | Ph(3-Br,5-Me) | Ph(3-I,5-SO$_2$Me) |
| Ph(3-Cl,5-CF$_2$CF$_2$H) | Ph(3-Br,5-Et) | Ph(3-I,5-TMS) |
| Ph(3-Cl,5-CF$_2$H) | Ph(3-Br,5-n-Pr) | Ph(3-I,5-CN) |
| Ph(3-Cl,5-OMe) | Ph(3-Br,5-t-Bu) | Ph(3-Me,5-Cl) |
| Ph(3-Cl,5-OCF$_3$) | Ph(3-Br,5-i-Pr) | Ph(3-Me,5-F) |
| Ph(3-Cl,5-OCHF$_2$) | Ph(3-Br,5-c-Pr) | Ph(3-Me,5-Br) |
| Ph(3-Cl,5-OCF$_2$CF$_2$H) | Ph(3-Br,5-CF$_3$) | Ph(3-Me,5-I) |
| Ph(3-Cl,5-OC$_2$F$_5$) | Ph(3-Br,5-C$_2$F$_5$) | Ph(3,5-di-Me) |
| Ph(3-Cl,5-SO$_2$Me) | Ph(3-Br,5-CF$_2$CF$_2$H) | Ph(3-Me,5-Et) |
| Ph(3-Cl,5-TMS) | Ph(3-Br,5-CF$_2$H) | Ph(3-Me,5-n-Pr) |
| Ph(3-Cl,5-CN) | Ph(3-Br,5-OMe) | Ph(3-Me,5-t-Bu) |
| Ph(3-F,5-Cl) | Ph(3-Br,5-OCF$_3$) | Ph(3-Me,5-i-Pr) |
| Ph(3,5-di-F) | Ph(3-Br,5-OCHF$_2$) | Ph(3-Me,5-c-Pr) |
| Ph(3-F,5-Br) | Ph(3-Br,5-OCF$_2$CF$_2$H) | Ph(3-Me,5-CF$_3$) |
| Ph(3-F,5-I) | Ph(3-Br,5-C$_2$F$_5$) | Ph(3-Me,5-C$_2$F$_5$) |
| Ph(3-F,5-Me) | Ph(3-Br,5-SO$_2$Me) | Ph(3-Me,5-CF$_2$CF$_2$H) |
| Ph(3-F,5-Et) | Ph(3-Br,5-TMS) | Ph(3-Me,5-CF$_2$H) |
| Ph(3-F,5-n-Pr) | Ph(3-Br,5-CN) | Ph(3-Me,5-OMe) |
| Ph(3-F,5-t-Bu) | Ph(3-I,5-Cl) | Ph(3-Me,5-OCF$_3$) |
| Ph(3-F,5-i-Pr) | Ph(3-I,5-F) | Ph(3-Me,5-OCHF$_2$) |
| Ph(3-F,5-c-Pr) | Ph(3-I,5-Br) | Ph(3-Me,5-OCF$_2$CF$_2$H) |
| Ph(3-F,5-CF$_3$) | Ph(3,5-di-I) | Ph(3-Me,5-OC$_2$F$_5$) |
| Ph(3-F,5-C$_2$F$_5$) | Ph(3-I,5-Me) | Ph(3-Me,5-SO$_2$Me) |
| Ph(3-F,5-CF$_2$CF$_2$H) | Ph(3-I,5-Et) | Ph(3-Me,5-TMS) |
| Ph(3-F,5-CF$_2$H) | Ph(3-I,5-n-Pr) | Ph(3-Me,5-CN) |
| Ph(3-F,5-OMe) | Ph(3-I,5-t-Bu) | Ph(3-Et,5-Cl) |
| Ph(3-F,5-OCF$_3$) | Ph(3-I,5-i-Pr) | Ph(3-Et,5-F) |
| Ph(3-F,5-OCHF$_2$) | Ph(3-I,5-c-Pr) | Ph(3-Et,5-Br) |
| Ph(3-F,5-OCF$_2$CF$_2$H) | Ph(3-I,5-CF$_3$) | Ph(3-Et,5-I) |
| Ph(3-F,5-OC$_2$F$_5$) | Ph(3-I,5-C$_2$F$_5$) | Ph(3-Et,5-Me) |
| Ph(3-F,5-SO$_2$Me) | Ph(3-I,5-CF$_2$CF$_2$H) | Ph(3,5-di-Et) |
| Ph(3-F,5-TMS) | Ph(3-I,5-CF$_2$H) | Ph(3-Et,5-n-Pr) |
| Ph(3-F,5-CN) | Ph(3-I,5-OMe) | Ph(3-Et,5-t-Bu) |
| Ph(3-Br,5-Cl) | Ph(3-I,5-OCF$_3$) | Ph(3-Et,5-i-Pr) |
| Ph(3-Br,5-F) | Ph(3-I,5-OCHF$_2$) | Ph(3-Et,5-c-Pr) |
| Ph(3-Et,5-CF$_3$) | Ph(3-t-Bu,5-I) | Ph(3-i-Pr,5-OC$_2$F$_5$) |
| Ph(3-Et,5-C$_2$F$_5$) | Ph(3-t-Bu,5-Me) | Ph(3-i-Pr,5-SO$_2$Me) |
| Ph(3-Et,5-CF$_2$CF$_2$H) | Ph(3-t-Bu,5-Et) | Ph(3-i-Pr,5-TMS) |
| Ph(3-Et,5-CF$_2$H) | Ph(3-t-Bu,5-n-Pr) | Ph(3-i-Pr,5-CN) |
| Ph(3-Et,5-OMe) | Ph(3,5-di-t-Bu) | Ph(3-c-Pr,5-Cl) |
| Ph(3-Et,5-OCF$_3$) | Ph(3-t-Bu,5-i-Pr) | Ph(3-c-Pr,5-F) |
| Ph(3-Et,5-OCHF$_2$) | Ph(3-t-Bu,5-c-Pr) | Ph(3-c-Pr,5-Br) |
| Ph(3-Et,5-OCF$_2$CF$_2$H) | Ph(3-t-Bu,5-CF$_3$) | Ph(3-c-Pr,5-I) |
| Ph(3-Et,5-OC$_2$F$_5$) | Ph(3-t-Bu,5-C$_2$F$_5$) | Ph(3-c-Pr,5-Me) |
| Ph(3-Et,5-SO$_2$Me) | Ph(3-t-Bu,5-CF$_2$CF$_2$H) | Ph(3-c-Pr,5-Et) |
| Ph(3-Et,5-TMS) | Ph(3-t-Bu,5-CF$_2$H) | Ph(3-c-Pr,5-n-Pr) |
| Ph(3-Et,5-CN) | Ph(3-t-Bu,5-OMe) | Ph(3-c-Pr,5-t-Bu) |

TABLE 1-continued

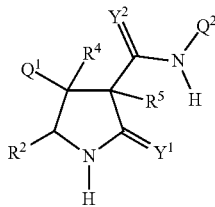

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(3-n-Pr,5-Cl) | Ph(3-t-Bu,5-OCF$_3$) | Ph(3-c-Pr,5-i-Pr) |
| Ph(3-n-Pr,5-F) | Ph(3-t-Bu,5-OCHF$_2$) | Ph(3,5-di-c-Pr) |
| Ph(3-n-Pr,5-Br) | Ph(3-t-Bu,5-OCF$_2$CF$_2$H) | Ph(3-c-Pr,5-CF$_3$) |
| Ph(3-n-Pr,5-I) | Ph(3-t-Bu,5-OC$_2$F$_5$) | Ph(3-c-Pr,5-C$_2$F$_5$) |
| Ph(3-n-Pr,5-Me) | Ph(3-t-Bu,5-SO$_2$Me) | Ph(3-c-Pr,5-CF$_2$CF$_2$H) |
| Ph(3-n-Pr,5-Et) | Ph(3-t-Bu,5-TMS) | Ph(3-c-Pr,5-CF$_2$H) |
| Ph(3,5-di-n-Pr) | Ph(3-t-Bu,5-CN) | Ph(3-c-Pr,5-OMe) |
| Ph(3-n-Pr,5-t-Bu) | Ph(3-i-Pr,5-Cl) | Ph(3-c-Pr,5-OCF$_3$) |
| Ph(3-n-Pr,5-i-Pr) | Ph(3-i-Pr,5-F) | Ph(3-c-Pr,5-OCHF$_2$) |
| Ph(3-n-Pr,5-c-Pr) | Ph(3-i-Pr,5-Br) | Ph(3-c-Pr,5-OCF$_2$CF$_2$H) |
| Ph(3-n-Pr,5-CF$_3$) | Ph(3-i-Pr,5-I) | Ph(3-c-Pr,5-OC$_2$F$_5$) |
| Ph(3-n-Pr,5-C$_2$F$_5$) | Ph(3-i-Pr,5-Me) | Ph(3-c-Pr,5-SO$_2$Me) |
| Ph(3-n-Pr,5-CF$_2$CF$_2$H) | Ph(3-i-Pr,5-Et) | Ph(3-c-Pr,5-TMS) |
| Ph(3-n-Pr,5-CF$_2$H) | Ph(3-i-Pr,5-n-Pr) | Ph(3-c-Pr,5-CN) |
| Ph(3-n-Pr,5-OMe) | Ph(3-i-Pr,5-t-Bu) | Ph(3-CF$_3$,5-Cl) |
| Ph(3-n-Pr,5-OCF$_3$) | Ph(3,5-di-i-Pr) | Ph(3-CF$_3$,5-F) |
| Ph(3-n-Pr,5-OCHF$_2$) | Ph(3-i-Pr,5-c-Pr) | Ph(3-CF$_3$,5-Br) |
| Ph(3-n-Pr,5-OCF$_2$CF$_2$H) | Ph(3-i-Pr,5-CF$_3$) | Ph(3-CF$_3$,5-I) |
| Ph(3-n-Pr,5-OC$_2$F$_5$) | Ph(3-i-Pr,5-C$_2$F$_5$) | Ph(3-CF$_3$,5-Me) |
| Ph(3-n-Pr,5-SO$_2$Me) | Ph(3-i-Pr,5-CF$_2$CF$_2$H) | Ph(3-CF$_3$,5-Et) |
| Ph(3-n-Pr,5-TMS) | Ph(3-i-Pr,5-CF$_2$H) | Ph(3-CF$_3$,5-n-Pr) |
| Ph(3-n-Pr,5-CN) | Ph(3-i-Pr,5-OMe) | Ph(3-CF$_3$,5-t-Bu) |
| Ph(3-t-Bu,5-Cl) | Ph(3-i-Pr,5-OCF$_3$) | Ph(3-CF$_3$,5-i-Pr) |
| Ph(3-t-Bu,5-F) | Ph(3-i-Pr,5-OCHF$_2$) | Ph(3-CF$_3$,5-c-Pr) |
| Ph(3-t-Bu,5-Br) | Ph(3-i-Pr,5-OCF$_2$CF$_2$H) | Ph(3,5-di-CF$_3$) |
| Ph(3-CF$_3$,5-C$_2$F$_5$) | Ph(3-CF$_2$CF$_2$H,5-Me) | Ph(3-CF$_2$H,5-SO$_2$Me) |
| Ph(3-CF$_3$,5-CF$_2$CF$_2$H) | Ph(3-CF$_2$CF$_2$H,5-Et) | Ph(3-CF$_2$H,5-TMS) |
| Ph(3-CF$_3$,5-CF$_2$H) | Ph(3-CF$_2$CF$_2$H,5-n-Pr) | Ph(3-CF$_2$H,5-CN) |
| Ph(3-CF$_3$,5-OMe) | Ph(3-CF$_2$CF$_2$H,5-t-Bu) | Ph(3-OMe,5-Cl) |
| Ph(3-CF$_3$,5-OCF$_3$) | Ph(3-CF$_2$CF$_2$H,5-i-Pr) | Ph(3-OMe,5-F) |
| Ph(3-CF$_3$,5-OCHF$_2$) | Ph(3-CF$_2$CF$_2$H,5-c-Pr) | Ph(3-OMe,5-Br) |
| Ph(3-CF$_3$,5-OCF$_2$CF$_2$H) | Ph(3-CF$_2$CF$_2$H,5-CF$_3$) | Ph(3-OMe,5-I) |
| Ph(3-CF$_3$,5-OC$_2$F$_5$) | Ph(3-CF$_2$CF$_2$H,5-C$_2$F$_5$) | Ph(3-OMe,5-Me) |
| Ph(3-CF$_3$,5-SO$_2$Me) | Ph(3,5-di-CF$_2$CF$_2$H) | Ph(3-OMe,5-Et) |
| Ph(3-CF$_3$,5-TMS) | Ph(3-CF$_2$CF$_2$H,5-CF$_2$H) | Ph(3-OMe,5-n-Pr) |
| Ph(3-CF$_3$,5-CN) | Ph(3-CF$_2$CF$_2$H,5-OMe) | Ph(3-OMe,5-t-Bu) |
| Ph(3-C$_2$F$_5$,5-Cl) | Ph(3-CF$_2$CF$_2$H,5-OCF$_3$) | Ph(3-OMe,5-i-Pr) |
| Ph(3-C$_2$F$_5$,5-F) | Ph(3-CF$_2$CF$_2$H,5-OCHF$_2$) | Ph(3-OMe,5-c-Pr) |
| Ph(3-C$_2$F$_5$,5-Br) | Ph(3-CF$_2$CF$_2$H,5-OCF$_2$CF$_2$H | Ph(3-OMeCF$_3$,5-CF$_3$) |
| Ph(3-C$_2$F$_5$,5-I) | Ph(3-CF$_2$CF$_2$H,5-OC$_2$F$_5$) | Ph(3-OMe,5-C$_2$F$_5$) |
| Ph(3-C$_2$F$_5$,5-Me) | Ph(3-CF$_2$CF$_2$H,5-SO$_2$Me) | Ph(3-OMe,5-CF$_2$CF$_2$H) |
| Ph(3-C$_2$F$_5$,5-Et) | Ph(3-CF$_2$CF$_2$H,5-TMS) | Ph(3-OMe,5-CF$_2$H) |
| Ph(3-C$_2$F$_5$,5-n-Pr) | Ph(3-CF$_2$CF$_2$H,5-CN) | Ph(3,5-di-OMe) |
| Ph(3-C$_2$F$_5$,5-t-Bu) | Ph(3-CF$_2$H,5-Cl) | Ph(3-OMe,5-OCF$_3$) |
| Ph(3-C$_2$F$_5$,5-i-Pr) | Ph(3-CF$_2$H,5-F) | Ph(3-OMe,5-OCHF$_2$) |
| Ph(3-C$_2$F$_5$,5-c-Pr) | Ph(3-CF$_2$H,5-Br) | Ph(3-OMe,5-OCF$_2$CF$_2$H) |
| Ph(3-C$_2$F$_5$CF$_3$,5-CF$_3$) | Ph(3-CF$_2$H,5-I) | Ph(3-OMe,5-OC$_2$F$_5$) |
| Ph(3,5-di-C$_2$F$_5$) | Ph(3-CF$_2$H,5-Me) | Ph(3-OMe,5-SO$_2$Me) |
| Ph(3-C$_2$F$_5$,5-CF$_2$CF$_2$H) | Ph(3-CF$_2$H,5-Et) | Ph(3-OMe,5-TMS) |
| Ph(3-C$_2$F$_5$,5-CF$_2$H) | Ph(3-CF$_2$H,5-n-Pr) | Ph(3-OMe,5-CN) |
| Ph(3-C$_2$F$_5$,5-OMe) | Ph(3-CF$_2$H,5-t-Bu) | Ph(3-OCF$_3$,5-Cl) |
| Ph(3-C$_2$F$_5$,5-OCF$_3$) | Ph(3-CF$_2$H,5-i-Pr) | Ph(3-OCF$_3$,5-F) |
| Ph(3-C$_2$F$_5$,5-OCHF$_2$) | Ph(3-CF$_2$H,5-c-Pr) | Ph(3-OCF$_3$,5-Br) |
| Ph(3-C$_2$F$_5$,5-OCF$_2$CF$_2$H) | Ph(3-CF$_2$H,5-CF$_3$) | Ph(3-OCF$_3$,5-I) |
| Ph(3-C$_2$F$_5$,5-OC$_2$F$_5$) | Ph(3-CF$_2$H,5-C$_2$F$_5$) | Ph(3-OCF$_3$,5-Me) |
| Ph(3-C$_2$F$_5$,5-SO$_2$Me) | Ph(3-CF$_2$H,5-CF$_2$CF$_2$H) | Ph(3-OCF$_3$,5-Et) |
| Ph(3-C$_2$F$_5$,5-TMS) | Ph(3,5-di-CF$_2$H) | Ph(3-OCF$_3$,5-n-Pr) |
| Ph(3-C$_2$F$_5$,5-CN) | Ph(3-CF$_2$H,5-OMe) | Ph(3-OCF$_3$,5-t-Bu) |
| Ph(3-CF$_2$CF$_2$H,5-Cl) | Ph(3-CF$_2$H,5-OCF$_3$) | Ph(3-OCF$_3$,5-i-Pr) |
| Ph(3-CF$_2$CF$_2$H,5-F) | Ph(3-CF$_2$H,5-OCHF$_2$) | Ph(3-OCF$_3$,5-c-Pr) |
| Ph(3-CF$_2$CF$_2$H,5-Br) | Ph(3-CF$_2$H,5-OCF$_2$CF$_2$H) | Ph(3-OCF$_3$,5-CF$_3$) |
| Ph(3-CF$_2$CF$_2$H,5-I) | Ph(3-CF$_2$H,5-OC$_2$F$_5$) | Ph(3-OCF$_3$,5-C$_2$F$_5$) |
| Ph(3-OCF$_3$,5-CF$_2$CF$_2$H) | Ph(3-OCF$_2$CF$_2$H,5-Et) | Ph(3-OC$_2$F$_5$,5-CN) |
| Ph(3-OCF$_3$,5-CF$_2$H) | Ph(3-OCF$_2$CF$_2$H,5-n-Pr) | Ph(3-SO$_2$Me,5-Cl) |
| Ph(3-OCF$_3$,5-OMe) | Ph(3-OCF$_2$CF$_2$H,5-t-Bu) | Ph(3-SO$_2$Me,5-F) |
| Ph(3,5-di-OCF$_3$) | Ph(3-OCF$_2$CF$_2$H,5-i-Pr) | Ph(3-SO$_2$Me,5-Br) |

TABLE 1-continued

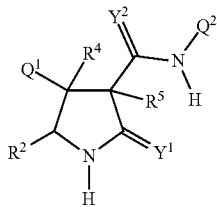

Y¹ is O; Y² is O; R² is H; R⁴ is H; R⁵ is H; Q² is Ph(2-F); and Q¹ is

| Q¹ | Q¹ | Q¹ |
|---|---|---|
| Ph(3-OCF₃,5-OCHF₂) | Ph(3-OCF₂CF₂H,5-c-Pr) | Ph(3-SO₂Me,5-I) |
| Ph(3-OCF₃,5-OCF₂CF₂H) | Ph(3-OCF₂CF₂H,5-CF₃) | Ph(3-SO₂Me,5-Me) |
| Ph(3-OCF₃,5-OC₂F₅) | Ph(3-OCF₂CF₂H,5-C₂F₅) | Ph(3-SO₂Me,5-Et) |
| Ph(3-OCF₃,5-SO₂Me) | Ph(3-OCF₂CF₂H,5-CF₂CF₂H) | Ph(3-SO₂Me,5-n-Pr) |
| Ph(3-OCF₃,5-TMS) | Ph(3-OCF₂CF₂H,5-CF₂H) | Ph(3-SO₂Me,5-t-Bu) |
| Ph(3-OCF₃,5-CN) | Ph(3-OCF₂CF₂H,5-OMe) | Ph(3-SO₂Me,5-i-Pr) |
| Ph(3-OCHF₂,5-Cl) | Ph(3-OCF₂CF₂H,5-OCF₃) | Ph(3-SO₂Me,5-c-Pr) |
| Ph(3-OCHF₂,5-F) | Ph(3-OCF₂CF₂H,5-OCHF₂) | Ph(3-SO₂MeCF₃,5-CF₃) |
| Ph(3-OCHF₂,5-Br) | Ph(3,5-di-OCF₂CF₂H) | Ph(3-SO₂Me,5-C₂F₅) |
| Ph(3-OCHF₂,5-I) | Ph(3-OCF₂CF₂H,5-OC₂F₅) | Ph(3-SO₂Me,5-CF₂CF₂H) |
| Ph(3-OCHF₂,5-Me) | Ph(3-OCF₂CF₂H,5-SO₂Me) | Ph(3-SO₂Me,5-CF₂H) |
| Ph(3-OCHF₂,5-Et) | Ph(3-OCF₂CF₂H,5-TMS) | Ph(3-SO₂Me,5-OMe) |
| Ph(3-OCHF₂,5-n-Pr) | Ph(3-OCF₂CF₂H,5-CN) | Ph(3-SO₂Me,5-OCF₃) |
| Ph(3-OCHF₂,5-t-Bu) | Ph(3-OC₂F₅,5-Cl) | Ph(3-SO₂Me,5-OCHF₂) |
| Ph(3-OCHF₂,5-i-Pr) | Ph(3-OC₂F₅,5-F) | Ph(3-SO₂Me,5-OCF₂CF₂H) |
| Ph(3-OCHF₂,5-c-Pr) | Ph(3-OC₂F₅,5-Br) | Ph(3-SO₂Me,5-OC₂F₅) |
| Ph(3-OCHF₂CF₃,5-CF₃) | Ph(3-OC₂F₅,5-I) | Ph(3,5-di-SO₂Me) |
| Ph(3-OC₂F₅,5-C₂F₅) | Ph(3-OC₂F₅,5-Me) | Ph(3-SO₂Me,5-TMS) |
| Ph(3-OCHF₂,5-CF₂CF₂H) | Ph(3-OC₂F₅,5-Et) | Ph(3-SO₂Me,5-CN) |
| Ph(3-OCHF₂,5-CF₂H) | Ph(3-OC₂F₅,5-n-Pr) | Ph(3-TMS,5-Cl) |
| Ph(3-OCHF₂,5-OMe) | Ph(3-OC₂F₅,5-t-Bu) | Ph(3-TMS,5-F) |
| Ph(3-OCHF₂,5-OCF₃) | Ph(3-OC₂F₅,5-i-Pr) | Ph(3-TMS,5-Br) |
| Ph(3,5-di-OCHF₂) | Ph(3-OC₂F₅,5-c-Pr) | Ph(3-TMS,5-I) |
| Ph(3-OCHF₂,5-OCF₂CF₂H) | Ph(3-OC₂F₅CF₃,5-CF₃) | Ph(3-TMS,5-Me) |
| Ph(3-OCHF₂,5-OC₂F₅) | Ph(3-OC₂F₅,5-CF₂CF₂H) | Ph(3-TMS,5-Et) |
| Ph(3-OCHF₂,5-SO₂Me) | Ph(3-OC₂F₅,5-CF₂H) | Ph(3-TMS,5-n-Pr) |
| Ph(3-OCHF₂,5-TMS) | Ph(3-OC₂F₅,5-OMe) | Ph(3-TMS,5-t-Bu) |
| Ph(3-OCHF₂,5-CN) | Ph(3-OC₂F₅,5-OCF₃) | Ph(3-TMS,5-i-Pr) |
| Ph(3-OCF₂CF₂H,5-Cl) | Ph(3-OC₂F₅,5-OCHF₂) | Ph(3-TMS,5-c-Pr) |
| Ph(3-OCF₂CF₂H,5-F) | Ph(3,5-di-OC₂F₅) | Ph(3-TMS,5-CF₃) |
| Ph(3-OCF₂CF₂H,5-Br) | Ph(3,5-di-OC₂F₅) | Ph(t-TMS,5-C₂F₅) |
| Ph(3-OCF₂CF₂H,5-I) | Ph(3-OC₂F₅,5-SO₂Me) | Ph(3-TMS,5-CF₂CF₂H) |
| Ph(3-OCF₂CF₂H,5-Me) | Ph(3-OC₂F₅,5-TMS) | Ph(3-TMS,5-CF₂H) |
| Ph(3-TMS,5-OMe) | Ph(2-Cl,3-Cl,4-t-Bu) | Ph(2-Cl,3-Br,4-Cl) |
| Ph(3-TMS,5-OCF₃) | Ph(2-Cl,3-Cl,4-i-Pr) | Ph(2-Cl,3-Br,4-F) |
| Ph(3-TMS,OCHF₂) | Ph(2-Cl,3-Cl,4-c-Pr) | Ph(2-Cl,3,4-di-Br) |
| Ph(3-TMS,5-OCF₂CF₂H) | Ph(2-Cl,3-Cl,4-CF₃) | Ph(2-Cl,3-Br,4-I) |
| Ph(3-TMS,5-OC₂F₅) | Ph(2-Cl,3-Cl,4-C₂F₅) | Ph(2-Cl,3-Br,4-Me) |
| Ph(3-TMS,5-SO₂Me) | Ph(2-Cl,3-Cl,4-CF₂CF₂H) | Ph(2-Cl,3-Br,4-Et) |
| Ph(3,5-di-TMS) | Ph(2-Cl,3-Cl,4-CF₂H) | Ph(2-Cl,3-Br,4-n-Pr) |
| Ph(3-TMS,5-CN) | Ph(2-Cl,3-Cl,4-OMe) | Ph(2-Cl,3-Br,4-t-Bu) |
| Ph(3-CN,5-Cl) | Ph(2-Cl,3-Cl,4-OCF₃) | Ph(2-Cl,3-Br,4-i-Pr) |
| Ph(3-CN,5-F) | Ph(2-Cl,3-Cl,4-OCHF₂) | Ph(2-Cl,3-Br,4-c-Pr) |
| Ph(3-CN,5-Br) | Ph(2-Cl,3-Cl,4-OCF₂CF₂H) | Ph(2-Cl,3-Br,4-CF₃) |
| Ph(3-CN,5-I) | Ph(2-Cl,3-Cl,4-OC₂F₅) | Ph(2-Cl,3-Br,4-C₂F₅) |
| Ph(3-CN,5-Me) | Ph(2-Cl,3-Cl,4-SO₂Me) | Ph(2-Cl,3-Br,4-CF₂CF₂H) |
| Ph(3-CN,5-Et) | Ph(2-Cl,3-Cl,4-TMS) | Ph(2-Cl,3-Br,4-CF₂H) |
| Ph(3-CN,5-n-Pr) | Ph(2-Cl,3-Cl,4-CN) | Ph(2-Cl,3-Br,4-OMe) |
| Ph(3-CN,5-t-Bu) | Ph(2-Cl,3-F,4-Cl) | Ph(2-Cl,3-Br,4-OCF₃) |
| Ph(3-CN,5-i-Pr) | Ph(2-Cl,3,4-di-F) | Ph(2-Cl,3-Br,4-OCHF₂) |
| Ph(3-CN,5-c-Pr) | Ph(2-Cl,3-F,4-Br) | Ph(2-Cl,3-Br,4-OCF₂CF₂H) |
| Ph(3-CN,5-CF₃) | Ph(2-Cl,3-F,4-I) | Ph(2-Cl,3-Br,4-OC₂F₅) |
| Ph(3-CN,5-C₂F₅) | Ph(2-Cl,3-F,4-Me) | Ph(2-Cl,3-Br,4-SO₂Me) |
| Ph(3-CN,5-CF₂CF₂H) | Ph(2-Cl,3-F,4-Et) | Ph(2-Cl,3-Br,4-TMS) |
| Ph(3-CN,5-CF₂H) | Ph(2-Cl,3-F,4-n-Pr) | Ph(2-Cl,3-Br,4-CN) |
| Ph(3-CN,5-OMe) | Ph(2-Cl,3-F,4-t-Bu) | Ph(2-Cl,3-I,4-Cl) |
| Ph(3-CN,5-OCF₃) | Ph(2-Cl,3-F,4-i-Pr) | Ph(2-Cl,3-I,4-F) |
| Ph(3-CN,5-OCHF₂) | Ph(2-Cl,3-F,4-c-Pr) | Ph(2-Cl,3-I,4-Br) |
| Ph(3-CN,5-OCF₂CF₂H) | Ph(2-Cl,3-F,4-CF₃) | Ph(2-Cl,3,4-di-I) |
| Ph(3-CN,5-OC₂F₅) | Ph(2-Cl,3-F,4-C₂F₅) | Ph(2-Cl,3-I,4-Me) |
| Ph(3-CN,5-SO₂Me) | Ph(2-Cl,3-F,4-CF₂CF₂H) | Ph(2-Cl,3-I,4-Et) |
| Ph(3-CN,5-TMS) | Ph(2-Cl,3-F,4-CF₂H) | Ph(2-Cl,3-I,4-n-Pr) |
| Ph(3,5-di-CN) | Ph(2-Cl,3-F,4-OMe) | Ph(2-Cl,3-I,4-t-Bu) |
| Ph(2,3,4-tri-Cl) | Ph(2-Cl,3-F,4-OCF₃) | Ph(2-Cl,3-I,4-i-Pr) |
| Ph(2-Cl,3-Cl,4-F) | Ph(2-Cl,3-F,4-OCHF₂) | Ph(2-Cl,3-I,4-c-Pr) |
| Ph(2-Cl,3-Cl,4-Br) | Ph(2-Cl,3-F,4-OCF₂CF₂H) | Ph(2-Cl,3-I,4-CF₃) |

TABLE 1-continued

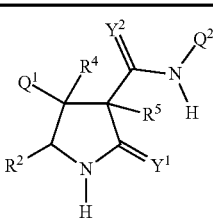

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-Cl,3-Cl,4-I) | Ph(2-Cl,3-F,4-OC$_2$F$_5$) | Ph(2-Cl,3-I,4-C$_2$F$_5$) |
| Ph(2-Cl,3-Cl,4-Me) | Ph(2-Cl,3-F,4-SO$_2$Me) | Ph(2-Cl,3-I,4-CF$_2$CF$_2$H) |
| Ph(2-Cl,3-Cl,4-Et) | Ph(2-Cl,3-F,4-TMS) | Ph(2-Cl,3-I,4-CF$_2$H) |
| Ph(2-Cl,3-Cl,4-n-Pr) | Ph(2-Cl,3-F,4-CN) | Ph(2-Cl,3-I,4-OMe) |
| Ph(2-Cl,3-I,4-OCF$_3$) | Ph(2-Cl,3-Et,4-i-Pr) | Ph(2-Cl,3-t-Bu,4-F) |
| Ph(2-Cl,3-I,4-OCHF$_2$) | Ph(2-Cl,3-Et,4-c-Pr) | Ph(2-Cl,3-t-Bu,4-Br) |
| Ph(2-Cl,3-I,4-OCF$_2$CF$_2$H) | Ph(2-Cl,3-Et,4-CF$_3$) | Ph(2-Cl,3-t-Bu,4-I) |
| Ph(2-Cl,3-I,4-OC$_2$F$_5$) | Ph(2-Cl,3-Et,4-C$_2$F$_5$) | Ph(2-Cl,3-t-Bu,4-Me) |
| Ph(2-Cl,3-I,4-SO$_2$Me) | Ph(2-Cl,3Et,4-CF$_2$CF$_2$H) | Ph(2-Cl,3-t-Bu,4-Et) |
| Ph(2-Cl,3-I,4-TMS) | Ph(2-Cl,3-Et,4-CF$_2$H) | Ph(2-Cl,3-t-Bu,4-n-Pr) |
| Ph(2-Cl,3-I,4-CN) | Ph(2-Cl,3-Et,4-OMe) | Ph(2-Cl,3,4-di-t-Bu) |
| Ph(2-Cl,3-Me,4-Cl) | Ph(2-Cl,3-Et,4-OCF$_3$) | Ph(2-Cl,3-t-Bu,4-i-Pr) |
| Ph(2-Cl,3-Me,4-F) | Ph(2-Cl,3-Et,4-OCHF$_2$) | Ph(2-Cl,3-t-Bu,4-c-Pr) |
| Ph(2-Cl,3-Me,4-Br) | Ph(2-Cl,3-Et,4-OCF$_2$CF$_2$H) | Ph(2-Cl,3-t-Bu,4-CF$_3$) |
| Ph(2-Cl,3-Me,4-I) | Ph(2-Cl,3-Et,4-OC$_2$F$_5$) | Ph(2-Cl,3-t-Bu,4-C$_2$F$_5$) |
| Ph(2-Cl,3,4-di-Me) | Ph(2-Cl,3-Et,4-SO$_2$Me) | Ph(2-Cl,3-t-Bu,4-CF$_2$CF$_2$H) |
| Ph(2-Cl,3-Me,4-Et) | Ph(2-Cl,3-Et,4-TMS) | Ph(2-Cl,3-t-Bu,4-CF$_2$H) |
| Ph(2-Cl,3-Me,4-n-Pr) | Ph(2-Cl,3-Et,4-CN) | Ph(2-Cl,3-t-Bu,4-OMe) |
| Ph(2-Cl,3-Me,4-t-Bu) | Ph(2-Cl,3-n-Pr,4-Cl) | Ph(2-Cl,3-t-Bu,4-OCF$_3$) |
| Ph(2-Cl,3-Me,4-i-Pr) | Ph(2-Cl,3-n-Pr,4-F) | Ph(2-Cl,3-t-Bu,4-OCHF$_2$) |
| Ph(2-Cl,3-Me,4-c-Pr) | Ph(2-Cl,3-n-Pr,4-Br) | Ph(2-Cl,3-t-Bu,4-OCF$_2$CF$_2$H) |
| Ph(2-Cl,3-Me,4-CF$_3$) | Ph(2-Cl,3-n-Pr,4-I) | Ph(2-Cl,3-t-Bu,4-OC$_2$F$_5$) |
| Ph(2-Cl,3-Me,4-C$_2$F$_5$) | Ph(2-Cl,3-n-Pr,4-Me) | Ph(2-Cl,3-t-Bu,4-SO$_2$Me) |
| Ph(2-Cl,3-Me,4-CF$_2$CF$_2$H) | Ph(2-Cl,3-n-Pr,4-Et) | Ph(2-Cl,3-t-Bu,4-TMS) |
| Ph(2-Cl,3-Me,4-CF$_2$H) | Ph(2-Cl,3,4-di-n-Pr) | Ph(2-Cl,3-t-Bu,4-CN) |
| Ph(2-Cl,3-Me,4-OMe) | Ph(2-Cl,3-n-Pr,4-t-Bu) | Ph(2-Cl,3-i-Pr,4-Cl) |
| Ph(2-Cl,3-Me,4-OCF$_3$) | Ph(2-Cl,3-n-Pr,4-i-Pr) | Ph(2-Cl,3-i-Pr,4-F) |
| Ph(2-Cl,3-Me,4-OCHF$_2$) | Ph(2-Cl,3-n-Pr,4-c-Pr) | Ph(2-Cl,3-i-Pr,4-Br) |
| Ph(2-Cl,3-Me,4-OCF$_2$CF$_2$H) | Ph(2-Cl,3-n-Pr,4-CF$_3$) | Ph(2-Cl,3-i-Pr,4-I) |
| Ph(2-Cl,3-Me,4-OC$_2$F$_5$) | Ph(2-Cl,3-n-Pr,4-C$_2$F$_5$) | Ph(2-Cl,3-i-Pr,4-Me) |
| Ph(2-Cl,3-Me,4-SO$_2$Me) | Ph(2-Cl,3-n-Pr,4-CF$_2$CF$_2$H) | Ph(2-Cl,3-i-Pr,4-Et) |
| Ph(2-Cl,3-Me,4-TMS) | Ph(2-Cl,3-n-Pr,4-CF$_2$H) | Ph(2-Cl,3-i-Pr,4-n-Pr) |
| Ph(2-Cl,3-Me,4-CN) | Ph(2-Cl,3-n-Pr,4-OMe) | Ph(2-Cl,3-i-Pr,4-t-Bu) |
| Ph(2-Cl,3-Et,4-Cl) | Ph(2-Cl,3-n-Pr,4-OCF$_3$) | Ph(2-Cl,3,4-di-i-Pr) |
| Ph(2-Cl,3-Et,4-F) | Ph(2-Cl,3-n-Pr,4-OCHF$_2$) | Ph(2-Cl,3-i-Pr,4-c-Pr) |
| Ph(2-Cl,3-Et,4-Br) | Ph(2-Cl,3-n-Pr,4-OCF$_2$CF$_2$H) | Ph(2-Cl,3-i-Pr,4-CF$_3$) |
| Ph(2-Cl,3-Et,4-I) | Ph(2-Cl,3-n-Pr,4-OC$_2$F$_5$) | Ph(2-Cl,3-i-Pr,4-C$_2$F$_5$) |
| Ph(2-Cl,3-Et,4-Me) | Ph(2-Cl,3-n-Pr,4-SO$_2$Me) | Ph(2-Cl,3-i-Pr,4-CF$_2$CF$_2$H) |
| Ph(2-Cl,3,4-di-Et) | Ph(2-Cl,3-n-Pr,4-TMS) | Ph(2-Cl,3-i-Pr,4-CF$_2$H) |
| Ph(2-Cl,3-Et,4-n-Pr) | Ph(2-Cl,3-n-Pr,4-CN) | Ph(2-Cl,3-i-Pr,4-OMe) |
| Ph(2-Cl,3-Et,4-t-Bu) | Ph(2-Cl,3-t-Bu,4-Cl) | Ph(2-Cl,3-i-Pr,4-OCF$_3$) |
| Ph(2-Cl,3-i-Pr,4-OCHF$_2$) | Ph(2-Cl,3-CF$_3$,4-c-Pr) | Ph(2-Cl,3-CF$_2$CF$_2$H),4-Br) |
| Ph(2-Cl,3-i-Pr,4-OCF$_2$CF$_2$H) | Ph(2-Cl,3,4-di-CF$_3$) | Ph(2-Cl,3-CF$_2$CF$_2$H,4-I) |
| Ph(2-Cl,3-i-Pr,4-OC$_2$F$_5$) | Ph(2-Cl,3-CF$_3$,4-C$_2$F$_5$) | Ph(2-Cl,3-CF$_2$CF$_2$H,4-Me) |
| Ph(2-Cl,3-i-Pr,4-SO$_2$Me) | Ph(2-Cl,3-CF$_3$,4-CF$_2$CF$_2$H) | Ph(2-Cl,3-CF$_2$CF$_2$H,4-Et) |
| Ph(2-Cl,3-i-Pr,4-TMS) | Ph(2-Cl,3-CF$_3$,4-CF$_2$H) | Ph(2-Cl,3-CF$_2$CF$_2$H,4-n-Pr) |
| Ph(2-Cl,3-i-Pr,4-CN) | Ph(2-Cl,3-CF$_3$,4-OMe) | Ph(2-Cl,3-CF$_2$CF$_2$H,4-t-Bu) |
| Ph(2-Cl,3-c-Pr,4-Cl) | Ph(2-Cl,3-CF$_3$,4-OCF$_3$) | Ph(2-Cl,3-CF$_2$CF$_2$H,4-i-Pr) |
| Ph(2-Cl,3-c-Pr,4-F) | Ph(2-Cl,3-CF$_3$,4-OCHF$_2$) | Ph(2-Cl,3-CF$_2$CF$_2$H,4-c-Pr) |
| Ph(2-Cl,3-c-Pr,4-Br) | Ph(2-Cl,3-CF$_3$,4-OCF$_2$CF$_2$H) | Ph(2-Cl,3-CF$_2$CF$_2$H,4-CF$_3$) |
| Ph(2-Cl,3-c-Pr,4-I) | Ph(2-Cl,3-CF$_3$,4-OC$_2$F$_5$) | Ph(2-Cl,3-CF$_2$CF$_2$H,4-C$_2$F$_5$) |
| Ph(2-Cl,3-c-Pr,4-Me) | Ph(2-Cl,3-CF$_3$,4-SO$_2$Me) | Ph(2-Cl,3,4-di-CF$_2$CF$_2$H) |
| Ph(2-Cl,3-c-Pr,4-Et) | Ph(2-Cl,3-CF$_3$,4-TMS) | Ph(2-Cl,3-CF$_2$CF$_2$H,4-CF$_2$H) |
| Ph(2-Cl,3-c-Pr,4-n-Pr) | Ph(2-Cl,3-CF$_3$,4-CN) | Ph(2-Cl,3-CF$_2$CF$_2$H,4-OMe) |
| Ph(2-Cl,3-c-Pr,4,-t-Bu) | Ph(2-Cl,3-C$_2$F$_5$,4-Cl) | Ph(2-Cl,3-CF$_2$CF$_2$H,4-OCF$_3$) |
| Ph(2-Cl,3-c-Pr,4-i-Pr) | Ph(2-Cl,3-C$_2$F$_5$,4-F) | Ph(2-Cl,3-CF$_2$CF$_2$H,4-OCHF$_2$) |
| Ph(2-Cl,3,4-di-c-Pr) | Ph(2-Cl,3-C$_2$F$_5$,4-Br) | Ph(2-Cl,3-CF$_2$CF$_2$H,4-OCF$_2$CF$_2$H) |
| Ph(2-Cl,3-c-Pr,4-CF$_3$) | Ph(2-Cl,3-C$_2$F$_5$,4-I) | |
| Ph(2-Cl,3-c-Pr,4-C$_2$F$_5$) | Ph(2-Cl,3-C$_2$F$_5$,4-Me) | Ph(2-Cl,3-CF$_2$CF$_2$H,4-OC$_2$F$_5$) |
| Ph(2-Cl,3-c-Pr,4-CF$_2$CF$_2$H) | Ph(2-Cl,3-C$_2$F$_5$,4-Et) | Ph(2-Cl,3-CF$_2$CF$_2$H,4-SO$_2$Me) |
| Ph(2-Cl,3-c-Pr,4-CF$_2$H) | Ph(2-Cl,3-C$_2$F$_5$,4-n-Pr) | Ph(2-Cl,3-CF$_2$CF$_2$H,4-TMS) |
| Ph(2-Cl,3-c-Pr,4-OMe) | Ph(2-Cl,3-C$_2$F$_5$,4-i-Bu) | Ph(2-Cl,3-CF$_2$CF$_2$H,4-CN) |
| Ph(2-Cl,3-c-Pr,4-OCF$_3$) | Ph(2-Cl,3-C$_2$F$_5$,4-i-Pr) | Ph(2-Cl,3-CF$_2$H,4-Cl) |
| Ph(2-Cl,3-c-Pr,4-OCHF$_2$) | Ph(2-Cl,3-C$_2$F$_5$,4-c-Pr) | Ph(2-Cl,3-CF$_2$H,4-F) |
| Ph(2-Cl,3-c-Pr,4-OCF$_2$CF$_2$H) | Ph(2-Cl,3-C$_2$F$_5$CF$_3$,4-CF$_3$) | Ph(2-Cl,3-CF$_2$H,4-Br) |
| Ph(2-Cl,3-c-Pr,4-OC$_2$F$_5$) | Ph(2-Cl,3,4-di-C$_2$F$_5$) | Ph(2-Cl,3-CF$_2$H,4-I) |

TABLE 1-continued

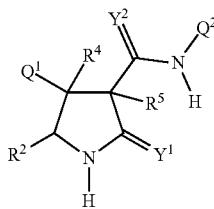

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(2-Cl,3-c-Pr,4-SO$_2$Me) | Ph(2-Cl,3-C$_2$F$_5$,4-CF$_2$CF$_2$H) | Ph(2-Cl,3-CF$_2$H,4-Me) |
| Ph(2-Cl,3-c-Pr,4-TMS) | Ph(2-Cl,3-C$_2$F$_5$,4-CF$_2$H) | Ph(2-Cl,3-CF$_2$H,4-Et) |
| Ph(2-Cl,3-c-Pr,4-CN) | Ph(2-Cl,3-C$_2$F$_5$,4-OMe) | Ph(2-Cl,3-CF$_2$H,4-n-Pr) |
| Ph(2-Cl,3-CF$_3$,4-Cl) | Ph(2-Cl,3-C$_2$F$_5$,4-OCF$_3$) | Ph(2-Cl,3-CF$_2$H,4-t-Bu) |
| Ph(2-Cl,3-CF$_3$,4-F) | Ph(2-Cl,3-C$_2$F$_5$,4-OCHF$_2$) | Ph(2-Cl,3-CF$_2$H,4-i-Pr) |
| Ph(2-Cl,3-CF$_3$,4-Br) | Ph(2-Cl,3-C$_2$F$_5$,4-OCF$_2$CF$_2$H) | Ph(2-Cl,3-CF$_2$H,4-c-Pr) |
| Ph(2-Cl,3-CF$_3$,4-I) | Ph(2-Cl,3-C$_2$F$_5$,4-OC$_2$F$_5$) | Ph(2-Cl,3-CF$_2$H,4-CF$_3$) |
| Ph(2-Cl,3-CF$_3$,4-Me) | Ph(2-Cl,3-C$_2$F$_5$,4-SO$_2$Me) | Ph(2-Cl,3-CF$_2$H,4-C$_2$F$_5$) |
| Ph(2-Cl,3-CF$_3$,4-Et) | Ph(2-Cl,3-C$_2$F$_5$,4-TMS) | Ph(2-Cl,3-CF$_2$H,4-CF$_2$CF$_2$H) |
| Ph(2-Cl,3-CF$_3$-4-n-Pr) | Ph(2-Cl,3-C$_2$F$_5$,4-CN) | Ph(2-Cl,3,4-di-CF$_2$H) |
| Ph(2-Cl,3-CF$_3$,4-t-Bu) | Ph(2-Cl,3-CF$_2$CF$_2$H,4-Cl) | Ph(2-Cl,3-CF$_2$H,4-OMe) |
| Ph(2-Cl,3-CF$_3$,4-i-Pr) | Ph(2-Cl,3-CF$_2$CF$_2$H,4-F) | Ph(2-Cl,3-CF$_2$H,4-OCF$_3$) |
| Ph(2-Cl,3-CF$_2$H,4-OCHF$_2$) | Ph(2-Cl,3-OCF$_3$,4-c-Pr) | Ph(2-Cl,3-OCF$_2$CF$_2$H,4-Br) |
| Ph(2-Cl,3-CF$_2$H,4-OCF$_2$CF$_2$H) | Ph(2-Cl,3-OCF$_3$,4-CF$_3$) | Ph(2-Cl,3-OCF$_2$CF$_2$H,4-I) |
| Ph(2-Cl,3-CF$_2$H,4-OC$_2$F$_5$) | Ph(2-Cl,3-OCF$_3$,4-C$_2$F$_5$) | Ph(2-Cl,3-OCF$_2$CF$_2$H,4-Me) |
| Ph(2-Cl,3-CF$_2$H,4-SO$_2$Me) | Ph(2-Cl,3-OCF$_3$,4-CF$_2$CF$_2$H) | Ph(2-Cl,3-OCF$_2$CF$_2$H,4-Et) |
| Ph(2-Cl,3-CF$_2$H,4-TMS) | Ph(2-Cl,3-OCF$_3$,4-CF$_2$H) | Ph(2-Cl,3-OCF$_2$CF$_2$H,4-n-Pr) |
| Ph(2-Cl,3-CF$_2$H,4-CN) | Ph(2-Cl,3-OCF$_3$,4-OMe) | Ph(2-Cl,3-OCF$_2$CF$_2$H,4-t-Bu) |
| Ph(2-Cl,3-OMe,4-Cl) | Ph(2-Cl,3,4-di-OCF$_3$) | Ph(2-Cl,3-OCF$_2$CF$_2$H,4-i-Pr) |
| Ph(2-Cl,3-OMe,4-F) | Ph(2-Cl,3-OCF$_3$,4-OCHF$_2$) | Ph(2-Cl,3-OCF$_2$CF$_2$H,4-c-Pr) |
| Ph(2-Cl,3-OMe,4-Br) | Ph(2-Cl,3-OCF$_3$,4-OCF$_2$CF$_2$H) | Ph(2-Cl,3-OCF$_2$CF$_2$H,4-CF$_3$) |
| Ph(2-Cl,3-OMe,4-I) | Ph(2-Cl,3-OCF$_3$,4-OC$_2$F$_5$) | Ph(2-Cl,3-OCF$_2$CF$_2$H,4-C$_2$F$_5$) |
| Ph(2-Cl,3-OMe,4-Me) | Ph(2-Cl,3-OCF$_3$,4-SO$_2$Me) | Ph(2-Cl,3-OCF$_2$CF$_2$H,4-CF$_2$CF$_2$H) |
| Ph(2-Cl,3-OMe,4-Et) | Ph(2-Cl,3-OCF$_3$,4-TMS) | Ph(2-Cl,3-OCF$_2$CF$_2$H,4-CF$_2$H) |
| Ph(2-Cl,3-OMe,4-n-Pr) | Ph(2-Cl,3-OCF$_3$,4-CN) | Ph(2-Cl,3-OCF$_2$CF$_2$H,4-OMe) |
| Ph(2-Cl,3-OMe,4-t-Bu) | Ph(2-Cl,3-OCHF$_2$,4-Cl) | Ph(2-Cl,3-OCF$_2$CF$_2$H,4-OCF$_3$) |
| Ph(2-Cl,3-OMe,4-i-Pr) | Ph(2-Cl,3-OCHF$_2$,4-F) | Ph(2-Cl,3-OCF$_2$CF$_2$H,4-OCHF$_2$) |
| Ph(2-Cl,3-OMe,4-c-Pr) | Ph(2-Cl,3-OCHF$_2$,4-Br) | Ph(2-Cl,3,4-di-OCF$_2$CF$_2$H) |
| Ph(2-Cl,3-OMe,4-CF$_3$) | Ph(2-Cl,3-OCHF$_2$,4-I) | Ph(2-Cl,3-OCF$_2$CF$_2$H,4-OC$_2$F$_5$) |
| Ph(2-Cl,3-OMe,4-C$_2$F$_5$) | Ph(2-Cl,3-OCHF$_2$,4-Me) | Ph(2-Cl,3-OCF$_2$CF$_2$H,4-SO$_2$Me) |
| Ph(2-Cl,3-OMe,4-CF$_2$CF$_2$H) | Ph(2-Cl,3-OCHF$_2$,4-Et) | Ph(2-Cl,3-OCF$_2$CF$_2$H,4-TMS) |
| Ph(2-Cl,3-OMe,4-CF$_2$H) | Ph(2-Cl,3-OCHF$_2$,4-n-Pr) | Ph(2-Cl,3-OCF$_2$CF$_2$H,4-CN) |
| Ph(2-Cl,3,4-di-OMe) | Ph(2-Cl,3-OCHF$_2$,4-t-Bu) | Ph(2-Cl,3-OC$_2$F$_5$,4-Cl) |
| Ph(2-Cl,3-OMe,4-OCF$_3$) | Ph(2-Cl,3-OCHF$_2$,4-i-Pr) | Ph(2-Cl,3-OC$_2$F$_5$,4-F) |
| Ph(2-Cl,3-OMe,4-OCHF$_2$) | Ph(2-Cl,3-OCHF$_2$,4-c-Pr) | Ph(2-Cl,3-OC$_2$F$_5$,4-Br) |
| Ph(2-Cl,3-OMe,4-OCF$_2$CF$_2$H) | Ph(2-Cl,3-OCHF$_2$CF$_3$,4-CF$_3$) | Ph(2-Cl,3-OC$_2$F$_5$,4-I) |
| Ph(2-Cl,3-OMe,4-OC$_2$F$_5$) | Ph(2-Cl,3-OC$_2$F$_5$,4-C$_2$F$_5$) | Ph(2-Cl,3-OC$_2$F$_5$,4-Me) |
| Ph(2-Cl,3-OMe,4-SO$_2$Me) | Ph(2-Cl,3-OCHF$_2$,4-CF$_2$CF$_2$H) | Ph(2-Cl,3-OC$_2$F$_5$,4-Et) |
| Ph(2-Cl,3-OMe,4-TMS) | Ph(2-Cl,3-OCHF$_2$,4-CF$_2$H) | Ph(2-Cl,3-OC$_2$F$_5$,4-n-Pr) |
| Ph(2-Cl,3-OMe,4-CN) | Ph(2-Cl,3-OCHF$_2$,4-OMe) | Ph(2-Cl,3-OC$_2$F$_5$,4-t-Bu) |
| Ph(2-Cl,3-OCF$_3$,4-Cl) | Ph(2-Cl,3-OCHF$_2$,4-OCF$_3$) | Ph(2-Cl,3-OC$_2$F$_5$,4-i-Pr) |
| Ph(2-Cl,3-OCF$_3$,4-F) | Ph(2-Cl,3,4-di-OCHF$_2$) | Ph(2-Cl,3-OC$_2$F$_5$,4-c-Pr) |
| Ph(2-Cl,3-OCF$_3$,4-Br) | Ph(2-Cl,3-OCHF$_2$,4-OCF$_2$CF$_2$H) | Ph(2-Cl,3-OC$_2$F$_5$CF$_3$,4-CF$_3$) |
| Ph(2-Cl,3-OCF$_3$,4-I) | Ph(2-Cl,3-OCHF$_2$,4-OC$_2$F$_5$) | Ph(2-Cl,3-OC$_2$F$_5$,4-CF$_2$CF$_2$H) |
| Ph(2-Cl,3-OCF$_3$,4-Me) | Ph(2-Cl,3-OCHF$_2$,4-SO$_2$Me) | Ph(2-Cl,3-OC$_2$F$_5$,4-CF$_2$H) |
| Ph(2-Cl,3-OCF$_3$,4-Et) | Ph(2-Cl,3-OCHF$_2$,4-TMS) | Ph(2-Cl,3-OC$_2$F$_5$,4-OMe) |
| Ph(2-Cl,3-OCF$_3$,4-n-Pr) | Ph(2-Cl,3-OCHF$_2$,4-CN) | Ph(2-Cl,3-OC$_2$F$_5$,4-OCF$_3$) |
| Ph(2-Cl,3-OCF$_3$,4-t-Bu) | Ph(2-Cl,3-OCF$_2$CF$_2$H,4-Cl) | Ph(2-Cl,3-OC$_2$F$_5$,4-OCHF$_2$) |
| Ph(2-Cl,3-OCF$_3$,4-i-Pr) | Ph(2-Cl,3-OCF$_2$CF$_2$H,4-F) | Ph(2-Cl,3-Cl,5-I) |
| Ph(2-Cl,3-OC$_2$F$_5$,4-OCF$_2$CF$_2$H) | Ph(2-Cl,3-TMS,4-CF$_3$) | Ph(2-Cl,3-Cl,5-Me) |
| Ph(2-Cl,3,4-di-OC$_2$F$_5$) | Ph(2-Cl,3-TMS,4-C$_2$F$_5$) | Ph(2-Cl,3-Cl,5-Et) |
| Ph(2-Cl,3-OC$_2$F$_5$,4-SO$_2$Me) | Ph(2-Cl,3-TMS,4-CF$_2$CF$_2$H) | Ph(2-Cl,3-Cl,5-n-Pr) |
| Ph(2-Cl,3-OC$_2$F$_5$,4-TMS) | Ph(2-Cl,3-TMS,4-CF$_2$H) | Ph(2-Cl,3-Cl,5-t-Bu) |
| Ph(2-Cl,3-OC$_2$F$_5$,4-CN) | Ph(2-Cl,3-TMS,4-OMe) | Ph(2-Cl,3-Cl,5-i-Pr) |
| Ph(2-Cl,3-SO$_2$Me,4-Cl) | Ph(2-Cl,3-TMS,4-OCF$_3$) | Ph(2-Cl,3-Cl,5-c-Pr) |
| Ph(2-Cl,3-SO$_2$Me,4-F) | Ph(2-Cl,3-TMS,4-OCHF$_2$) | Ph(2-Cl,3-Cl,5-CF$_3$) |
| Ph(2-Cl,3-SO$_2$Me,4-Br) | Ph(2-Cl,3-TMS,4-OCF$_2$CF$_2$H) | Ph(2-Cl,3-Cl,5-C$_2$F$_5$) |
| Ph(2-Cl,3-SO$_2$Me,4-I) | Ph(2-Cl,3-TMS,4-OC$_2$F$_5$) | Ph(2-Cl,3-Cl,5-CF$_2$CF$_2$H) |
| Ph(2-Cl,3-SO$_2$Me,4-Me) | Ph(2-Cl,3-TMS,4-SO$_2$Me) | Ph(2-Cl,3-Cl,5-CF$_2$H) |
| Ph(2-Cl,3-SO$_2$Me,4-Et) | Ph92-Cl,3,4-di-TMS) | Ph(2-Cl,3-Cl,5-OMe) |
| Ph(2-Cl,3-SO$_2$Me,4-n-Pr) | Ph(2-Cl,3-TMS,4-CN) | Ph(2-Cl,3-Cl,5-OCF$_3$) |
| Ph(2-Cl,3-SO$_2$Me,4-t-Bu) | Ph(2-Cl,3-CN,4-Cl) | Ph(2-Cl,3-Cl,5-OCHF$_2$) |
| Ph(2-Cl,3-SO$_2$Me,4-i-Pr) | Ph(2-Cl,3-CN,4-F) | Ph(2-Cl,3-Cl,5-OCF$_2$CF$_2$H) |
| Ph(2-Cl,3-SO$_2$Me,4-c-Pr) | Ph(2-Cl,3-CN,4-Br) | Ph(2-Cl,3-Cl,5-OC$_2$F$_5$) |
| Ph(2-Cl,3-SO$_2$MeCF$_3$,4-CF$_3$) | Ph(2-Cl,3-CN,4-I) | Ph(2-Cl,3-Cl,5-SO$_2$Me) |
| Ph(2-Cl,3-SO$_2$Me,4-C$_2$F$_5$) | Ph(2-Cl,3-CN,4-Me) | |

TABLE 1-continued

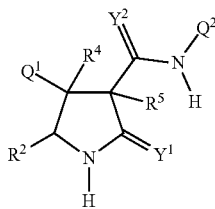

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-Cl,3-SO₂Me,4-CF₂CF₂H) | Ph(2-Cl,3-CN,4-Et) | Ph(2-Cl,3-Cl,5-TMS) |
| Ph(2-Cl,3-SO₂Me,4-CF₂H) | Ph(2-Cl,3-CN,4-n-Pr) | Ph(2-Cl,3-Cl,5-CN) |
| Ph(2-Cl,3-SO₂Me,4-OMe) | Ph(2-Cl,3-CN,4-t-Bu) | Ph(2-Cl,3-F,5-Cl) |
| Ph(2-Cl,3-SO₂Me,4-OCF₃) | Ph(2-Cl,3-CN,4-i-Pr) | Ph(2-Cl,3,5-di-F) |
| Ph(2-Cl,3-SO₂Me,4-OCHF₂) | Ph(2-Cl,3-CN,4-c-Pr) | Ph(2-Cl,3-F,5-Br) |
| Ph(2-Cl,3-SO₂Me,4-OCF₂CF₂H) | Ph(2-Cl,3-CN,4-CF₃) | Ph(2-Cl,3-F,5-I) |
| Ph(2-Cl,3-SO₂Me,4-OC₂F₅) | Ph(2-Cl,3-CN,4-C₂F₅) | Ph(2-Cl,3-F,5-Me) |
| Ph(2-Cl,3,4-di-SO₂Me) | Ph(2-Cl,3-CN,4-CF₂CF₂H) | Ph(2-Cl,3-F,5-Et) |
| Ph(2-Cl,3-SO₂Me,4-TMS) | Ph(2-Cl,3-CN,4-CF₂H) | Ph(2-Cl,3-F,5-n-Pr) |
| Ph(2-Cl,3-SO₂Me,4-CN) | Ph(2-Cl,3-CN,4-OMe) | Ph(2-Cl,3-F,5,t-Bu) |
| Ph(2-Cl,3-TMS,4-Cl) | Ph(2-Cl,3-CN,4-OCF₃) | Ph(2-Cl,3-F,5-i-Pr) |
| Ph(2-Cl,3-TMS,4-F) | Ph(2-Cl,3-CN,4-OCHF₂) | Ph(2-Cl,3-F,5-c-Pr) |
| Ph(2-Cl,3-TMS,4-Br) | Ph(2-Cl,3-CN,4-OCF₂CF₂H) | Ph(2-Cl,3-F,5-CF₃) |
| Ph(2-Cl,3-TMS,4-I) | Ph(2-Cl,3-CN,4-OC₂F₅) | Ph(2-Cl,3-F,5-C₂F₅) |
| Ph(2-Cl,3-TMS,4-Me) | Ph(2-Cl,3-CN,4-SO₂Me) | Ph(2-Cl,3-F,5-CF₂CF₂H) |
| Ph(2-Cl,3-TMS,4-Et) | Ph(2-Cl,3-CN,4-TMS) | Ph(2-Cl,3-F,5-CF₂H) |
| Ph(2-Cl,3-TMS,4-n-Pr) | Ph(2-Cl,3,4-di-CN) | Ph(2-Cl,3-F,5-OMe) |
| Ph(2-Cl,3-TMS,4-t-Bu) | Ph(2,3,5-tri-Cl) | Ph(2-Cl,3-F,5-OCF₃) |
| Ph(2-Cl,3-TMS,4-i-Pr) | Ph(2-Cl,3-Cl,5-F) | Ph(2-Cl,3-F,5-OCHF₂) |
| Ph(2-Cl,3-TMS,4-c-Pr) | Ph(2-Cl,3-Cl,5-Br) | Ph(2-Cl,3-F,5-OCF₂CF₂H) |
| Ph(2-Cl,3-F,5-OC₂F₅) | Ph(2-Cl,3-I,5-C₂F₅) | Ph(2-Cl,3-Et,5-Me) |
| Ph(2-Cl,3-F,5-SO₂Me) | Ph(2-Cl,3-I,5-CF₂CF₂H) | Ph(2-Cl,3,5-di-Et) |
| Ph(2-Cl,3-F,5-TMS) | Ph(2-Cl,3-I,5-CF₂H) | Ph(2-Cl,3-Et,5-n-Pr) |
| Ph(2-Cl,3-F,5-CN) | Ph(2-Cl,3-I,5-OMe) | Ph(2-Cl,3-Et,5-t-Bu) |
| Ph(2-Cl,3-Br,5-Cl) | Ph(2-Cl,3-I,5-OCF₃) | Ph(2-Cl,3-Et,5-i-Pr) |
| Ph(2-Cl,3-Br,5-F) | Ph(2-Cl,3-I,5-OCHF₂) | Ph(2-Cl,3-Et,5-c-Pr) |
| Ph(2-Cl,3,5-di-Br) | Ph(2-Cl,3-I,5-OCF₂CF₂H) | Ph(2-Cl,3-Et,5-CF₃) |
| Ph(2-Cl,3-Br,5-I) | Ph(2-Cl,3-I,5-OC₂F₅) | Ph(2-Cl,3-Et,5-C₂F₅) |
| Ph(2-Cl,3-Br,5-Me) | Ph(2-Cl,3-I,5-SO₂Me) | Ph(2-Cl,3-Et,5-CF₂CF₂H) |
| Ph(2-Cl,3-Br,5-Et) | Ph(2-Cl,3-I,5-TMS) | Ph(2-Cl,3-Et,5-CF₂H) |
| Ph(2-Cl,3-Br,5-n-Pr) | Ph(2-Cl,3-I,5-CN) | Ph(2-Cl,3-Et,5-OMe) |
| Ph(2-Cl,3-Br,5-t-Bu) | Ph(2-Cl,3-Me,5-Cl) | Ph(2-Cl,3-Et,5-OCF₃) |
| Ph(2-Cl,3-Br,5-i-Pr) | Ph(2-Cl,3-Me,5-F) | Ph(2-Cl,3-Et,5-OCHF₂) |
| Ph(2-Cl,3-Br,5-c-Pr) | Ph(2-Cl,3-Me,5-Br) | Ph(2-Cl,3-Et,5-OCF₂CF₂H) |
| Ph(2-Cl,3-Br,5-CF₃) | Ph(2-Cl,3-Me,5-I) | Ph(2-Cl,3-Et,5-OC₂F₅) |
| Ph(2-Cl,3-Br,5-C₂F₅) | Ph(2-Cl,3,5-di-Me) | Ph(2-Cl,3-Et,5-SO₂Me) |
| Ph(2-Cl,3-Br,5-CF₂CF₂H) | Ph(2-Cl,3-Me,5-Et) | Ph(2-Cl,3-Et,5-TMS) |
| Ph(2-Cl,3-Br,5-CF₂H) | Ph(2-Cl,3-Me,5-n-Pr) | Ph(2-Cl,3-Et,5-CN) |
| Ph(2-Cl,3-Br,5-OMe) | Ph(2-Cl,3-Me,5-t-Bu) | Ph(2-Cl,3-n-Pr,5-Cl) |
| Ph(2-Cl,3-Br,5-OCF₃) | Ph(2-Cl,3-Me,5-i-Pr) | Ph(2-Cl,3-n-Pr,5-F) |
| Ph(2-Cl,3-Br,5-OCHF₂) | Ph(2-Cl,3-Me,5-c-Pr) | Ph(2-Cl,3-n-Pr,5-Br) |
| Ph(2-Cl,3-Br,5-OCF₂CF₂H) | Ph(2-Cl,3-Me,5-CF₃) | Ph(2-Cl,3-n-Pr,5-I) |
| Ph(2-Cl,3-Br,5-OC₂F₅) | Ph(2-Cl,3-Me,5-C₂F₅) | Ph(2-Cl,3-n-Pr,5-Me) |
| Ph(2-Cl,3-Br,5-SO₂Me) | Ph(2-Cl,3-Me,5-CF₂CF₂H) | Ph(2-Cl,3-n-Pr,5-Et) |
| Ph(2-Cl,3-Br,5-TMS) | Ph(2-Cl,3-Me,5-CF₂H) | Ph(2-Cl,3,5-di-n-Pr) |
| Ph(2-Cl,3-Br,5-CN) | Ph(2-Cl,3-Me,5-OMe) | Ph(2-Cl,3-n-Pr,5,t,Bu) |
| Ph(2-Cl,3-I,5-Cl) | Ph(2-Cl,3-Me,5-OCF₃) | Ph(2-Cl,3-n-Pr,5-i-Pr) |
| Ph(2-Cl,3-I,5-F) | Ph(2-Cl,3-Me,5-OCHF₂) | Ph(2-Cl,3-n-Pr,5-c-Pr) |
| Ph(2-Cl,3-I,5-Br) | Ph(2-Cl,3-Me,5-OCF₂CF₂H) | Ph(2-Cl,3-n-Pr,5-CF₃) |
| Ph(2-Cl,3,5-di-I) | Ph(2-Cl,3-Me,5-OC₂F₅) | Ph(2-Cl,3-n-Pr,5-C₂F₅) |
| Ph(2-Cl,3-I,5-Me) | Ph(2-Cl,3-Me,5-SO₂Me) | Ph(2-Cl,3-n-Pr,5-CF₂CF₂H) |
| Ph(2-Cl,3-I,5-Et) | Ph(2-Cl,3-Me,5-TMS) | Ph(2-Cl,3-n-Pr,5-CF₂H) |
| Ph(2-Cl,3-I,5-n-Pr) | Ph(2-Cl,3-Me,5-CN) | Ph(2-Cl,3-n-Pr,5-OMe) |
| Ph(2-Cl,3-I,5-t-Bu) | Ph(2-Cl,3-Et,5-Cl) | Ph(2-Cl,3-n-Pr,5-OCF₃) |
| Ph(2-Cl,3-I,5-i-Pr) | Ph(2-Cl,3-Et,5-F) | Ph(2-Cl,3-n-Pr,5-OCHF₂) |
| Ph(2-Cl,3-I,5-c-Pr) | Ph(2-Cl,3-Et,5-Br) | Ph(2-Cl,3-n-Pr,5-OCF₂CF₂H) |
| Ph(2-Cl,3-I,5-CF₃) | Ph(2-Cl,3-Et,5-I) | Ph(2-Cl,3-n-Pr,5-OC₂F₅) |
| Ph(2-Cl,3-n-Pr,5-SO₂Me) | Ph(2-Cl,3-i-Pr,5-CF₂CF₂H) | Ph(2-Cl,3-CF₃,5-Et) |
| Ph(2-Cl,3-n-Pr,5-TMS) | Ph(2-Cl,3-i-Pr,5-CF₂H) | Ph(2-Cl,3-CF₃,5-n-Pr) |
| Ph(2-Cl,3-n-Pr,5-CN) | Ph(2-Cl,3-i-Pr,5-OMe) | Ph(2-Cl,3-CF₃,5-t-Bu) |
| Ph(2-Cl,3-t-Bu,5-Cl) | Ph(2-Cl,3-i-Pr,5-OCF₃) | Ph(2-Cl,3-CF₃,5-i-Pr) |
| Ph(2-Cl,3-t-But,5-F) | Ph(2-Cl,3-i-Pr,5-OCHF₂) | Ph(2-Cl,3-CF₃,5-c-Pr) |
| Ph(2-Cl,3-t-Bu,5-Br) | Ph(2-Cl,3-i-Pr,5-OCF₂CF₂H) | Ph(2-Cl,3,5-di-CF₃) |
| Ph(2-Cl,3-t-Bu,5-I) | Ph(2-Cl,3-i-Pr,5-OC₂F₅) | Ph(2-Cl,3-CF₃,5-C₂F₅) |
| Ph(2-Cl,3-t-Bu,5-Me) | Ph(2-Cl,3-i-Pr,5-SO₂Me) | Ph(2-Cl,3-CF₃,5-CF₂CF₂H) |
| Ph(2-Cl,3-t-Bu,5-Et) | Ph(2-Cl,3-i-Pr,5-TMS) | Ph(2-Cl,3-CF₃,5-CF₂H) |

TABLE 1-continued

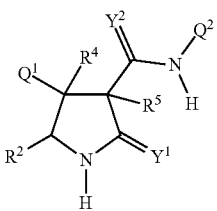

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(2-Cl,3-t-Bu,5-n-Pr) | Ph(2-Cl,3-i-Pr,5-CN) | Ph(2-Cl,3-CF$_3$,5-OMe) |
| Ph(2-Cl,3,5-di-t-Bu) | Ph(2-Cl,3-c-Pr,5-Cl) | Ph(2-Cl,3-CF$_3$,5-OCF$_3$) |
| Ph(2-Cl,3-t-Bu,5-i-Pr) | Ph(2-Cl,3-c-Pr,5-F) | Ph(2-Cl,3-CF$_3$,5-OCHF$_2$) |
| Ph(2-Cl,3-t-Bu,5-c-Pr) | Ph(2-Cl,3-c-Pr,5-Br) | Ph(2-Cl,3-CF$_3$,5-OCF$_2$CF$_2$H) |
| Ph(2-Cl,3-t-Bu,5-CF$_3$) | Ph(2-Cl,3-c-Pr,5-I) | Ph(2-Cl,3-CF$_3$,5-OC$_2$F$_5$) |
| Ph(2-Cl,3-t-Bu,5-C$_2$F$_5$) | Ph(2-Cl,3-c-Pr,5-Me) | Ph(2-Cl,3-CF$_3$,5-SO$_2$Me) |
| Ph(2-Cl,3-t-Bu,5-CF$_2$CF$_2$H) | Ph(2-Cl,3-c-Pr,5-Et) | Ph(2-Cl,3-CF$_3$,5-TMS) |
| Ph(2-Cl,3-t-Bu,5-CF$_2$H) | Ph(2-Cl,3-c-Pr,5-n-Pr) | Ph(2-Cl,3-CF$_3$,5-CN) |
| Ph(2-Cl,3-t-Bu,5-OMe) | Ph(2-Cl,3-c-Pr,5-t-Bu) | Ph(2-Cl,3-C$_2$F$_5$,5-Cl) |
| Ph(2-Cl,3-t-Bu,5-OCF$_3$) | Ph(2-Cl,3-c-Pr,5-i-Pr) | Ph(2-Cl,3-C$_2$F$_5$,5-F) |
| Ph(2-Cl,3-t-Bu,5-OCHF$_2$) | Ph(2-Cl,3,5-di-c-Pr) | Ph(2-Cl,3-C$_2$F$_5$,5-Br) |
| Ph(2-Cl,3-t-Bu,5-OCF$_2$CF$_2$H) | Ph(2-Cl,3-c-Pr,5-CF$_3$) | Ph(2-Cl,3-C$_2$F$_5$,5-I) |
| Ph(2-Cl,3-t-Bu,5-OC$_2$F$_5$) | Ph(2-Cl,3-c-Pr,5-C$_2$F$_5$) | Ph(2-Cl,3-C$_2$F$_5$,5-Me) |
| Ph(2-Cl,3-t-Bu,5-SO$_2$Me) | Ph(2-Cl,3-c-Pr,5-CF$_2$CF$_2$H) | Ph(2-Cl,3-C$_2$F$_5$,5-Et) |
| Ph(2-Cl,3-t-Bu,5-TMS) | Ph(2-Cl,3-c-Pr,5-CF$_2$H) | Ph(2-Cl,3-C$_2$F$_5$,5-n-Pr) |
| Ph(2-Cl,3-t-Bu,5-CN) | Ph(2-Cl,3-c-Pr,5-OMe) | Ph92-Cl,3-C$_2$F$_5$,5-t-Bu) |
| Ph(2-Cl,3-i-Pr,5-Cl) | Ph(2-Cl,3-c-Pr,5-OCF$_3$) | Ph(2-Cl,3-C$_2$F$_5$,5-i-Pr) |
| Ph(2-Cl,3-i-Pr,5-F) | Ph(2-Cl,3-c-Pr,5-OCFH2) | Ph(2-Cl,3-C$_2$F$_5$,5-c-Pr) |
| Ph(2-Cl,3-i-Pr,5-Br) | Ph(2-Cl,3-c-Pr,5-OCF$_2$CF$_2$H) | Ph(2-Cl,3-C$_2$F$_5$CF$_3$,5-CF$_3$) |
| Ph(2-Cl,3-i-Pr,5-I) | Ph(2-Cl,3-c-Pr,5-OC$_2$F$_5$) | Ph(2-Cl,3,5-di-C$_2$F$_5$) |
| Ph(2-Cl,3-i-Pr,5-Me) | Ph(2-Cl,3-c-Pr,5-SO$_2$Me) | Ph(2-Cl,3-C$_2$F$_5$,5-CF$_2$CF$_2$H) |
| Ph(2-Cl,3-i-Pr,5-Et) | Ph(2-Cl,3-c-Pr,5-TMS) | Ph(2-Cl,3-C$_2$F$_5$,5-CF$_2$H) |
| Ph(2-Cl,3-i-Pr,5-n-Pr) | Ph(2-Cl,3-c-Pr,5-CN) | Ph(2-Cl,3-C$_2$F$_5$,5-OMe) |
| Ph(2-Cl,3-i-Pr,5-t-Bu) | Ph(2-Cl,3-CF$_3$,5-Cl) | Ph(2-Cl,3-C$_2$F$_5$,5-OCF$_3$) |
| Ph(2-Cl,3,5-di-i-Pr) | Ph(2-Cl,3-CF$_3$,5-F) | Ph(2-Cl,3-C$_2$F$_5$,5-OCHF$_2$) |
| Ph(2-Cl,3-i-Pr,5-c-Pr) | Ph(2-Cl,3-CF$_3$,5-Br) | Ph(2-Cl,3-C$_2$F$_5$,5-OCF$_2$CF$_2$H) |
| Ph(2-Cl,3-i-Pr,5-CF$_3$) | Ph(2-Cl,3-CF$_3$,5-I) | Ph(2-Cl,3-C$_2$F$_5$,5-OC$_2$F$_5$) |
| Ph(2-Cl,3-i-Pr,5-C$_2$F$_5$) | Ph(2-Cl,3-CF$_3$,5-Me) | Ph(2-Cl,3-C$_2$F$_5$,5-SO$_2$Me) |
| Ph(2-Cl,3-C$_2$F$_5$,5-TMS) | Ph(2-Cl,3-CF$_2$H,5-CF$_2$CF$_2$H) | Ph(2-Cl,3-OCF$_3$,5-Et) |
| Ph(2-Cl,3-C$_2$F$_5$,5-CN) | Ph(2-Cl,3,5-di-CF$_2$H) | Ph(2-Cl,3-OCF$_3$,5-n-Pr) |
| Ph(2-Cl,3-CF$_2$CF$_2$H,5-Cl) | Ph(2-Cl,3-CF$_2$H,5-OMe) | Ph(2-Cl,3-OCF$_3$,5-t-Bu) |
| Ph(2-Cl,3-CF$_2$CF$_2$H,5-F) | Ph(2-Cl,3-CF$_2$H,5-OCF$_3$) | Ph(2-Cl,3-OCF$_3$,5-i-Pr) |
| Ph(2-Cl,3-CF$_2$CF$_2$H,5-Br) | Ph(2-Cl,3-CF$_2$H,5-OCHF$_2$) | Ph(2-Cl,3-OCF$_3$,5-c-Pr) |
| Ph(2-Cl,3-CF$_2$CF$_2$H,5-I) | Ph(2-Cl,3-CF$_2$H,5-OCF$_2$CF$_2$H) | Ph(2-Cl,3-OCF$_3$,5-CF$_3$) |
| Ph(2-Cl,3-CF$_2$CF$_2$H,5-Me) | Ph(2-Cl,3-CF$_2$H,5-OC$_2$F$_5$) | Ph(2-Cl,3-OCF$_3$,5-C$_2$F$_5$) |
| Ph(2-Cl,3-CF$_2$CF$_2$H,5-Et) | Ph(2-Cl,3-CF$_2$H,5-SO$_2$Me) | Ph(2-Cl,3-OCF$_3$,5-CF$_2$CF$_2$H) |
| Ph(2-Cl,3-CF$_2$CF$_2$H,5-n-Pr) | Ph(2-Cl,3-CF$_2$H,5-TMS) | Ph(2-Cl,3-OCF$_3$,5-CF$_2$H) |
| Ph(2-Cl,3-CF$_2$CF$_2$H,5-t-Bu) | Ph(2-Cl,3-CF$_2$H,5-CN) | Ph(2-Cl,3-OCF$_3$,5-OMe) |
| Ph(2-Cl,3-CF$_2$CF$_2$H,5-i-Pr) | Ph(2-Cl,3-OMe,5-Cl) | Ph(2-Cl,3,5-di-OCF$_3$) |
| Ph(2-Cl,3-CF$_2$CF$_2$H,5-c-Pr) | Ph(2-Cl,3-OMe,5-F) | Ph(2-Cl,3-OCF$_3$,5-OCHF$_2$) |
| Ph(2-Cl,3-CF$_2$CF$_2$H,5-CF$_3$) | Ph(2-Cl,3-OMe,5-Br) | Ph(2-Cl,3-OCF$_3$,5-OCF$_2$CF$_2$H) |
| Ph(2-Cl,3-CF$_2$CF$_2$H,5-C$_2$F$_5$) | Ph(2-Cl,3-OMe,5-I) | Ph(2-Cl,3-OCF$_3$,-5-OC$_2$F$_5$) |
| Ph(2-Cl,3,5-di-CF$_2$CF$_2$H) | Ph(2-Cl,3-OMe,5-Me) | Ph(2-Cl,3-OCF$_3$,5-SO$_2$Me) |
| Ph(2-Cl,3-CF$_2$CF$_2$H,5-CF$_2$H) | Ph(2-Cl,3-OMe,5-Et) | Ph(2-Cl,3-OCF$_3$,5-TMS) |
| Ph(2-Cl,3-CF$_2$CF$_2$H,5-OMe) | Ph(2-Cl,3-OMe,5-n-Pr) | Ph(2-Cl,3-OCF$_3$,5-CN) |
| Ph(2-Cl,3-CF$_2$CF$_2$H,5-OCF$_3$) | Ph(2-Cl,3-OMe,5-t-Bu) | Ph(2-Cl,3-OCHF$_2$,5-Cl) |
| Ph(2-Cl,3-CF$_2$CF$_2$H,5-OCHF$_2$) | Ph(2-Cl,3-OMe,5-i-Pr) | Ph(2-Cl,3-OCHF$_2$,-F) |
| Ph(2-Cl3-CF$_2$CF$_2$H,5-OCF$_2$CF$_2$H) | Ph(2-Cl,3-OMe,5-c-Pr) | Ph(2-Cl,3-OCHF$_2$,5-F) |
| Ph(2-Cl,3-CF$_2$CF$_2$H,5-OC$_2$F$_5$) | Ph(2-Cl,3-OMe,5-CF$_3$) | Ph(23-Cl,3-OCHF$_2$,5-I) |
| Ph(2-Cl,3-CF$_2$CF$_2$H,5-SO$_2$Me) | Ph(2-Cl,3-OMe,5-C$_2$F$_5$) | Ph(2-Cl,3-OCHF$_2$,5-Me) |
| Ph(2-Cl,3-CF$_2$CF$_2$H,5-TMS) | Ph(2-Cl,3-OMe,5-CF$_2$CF$_2$H) | Ph(2-Cl,3-OCHF$_2$,5-Et) |
| Ph(2-Cl,3-CF$_2$CF$_2$H,5-CN) | Ph(2-Cl,3-OMe,5-CF$_2$H) | Ph(2-Cl,3-OCHF$_2$,5-n-Pr) |
| Ph(2-Cl,3-CF$_2$H,5-Cl) | Ph(2-Cl,3,5-di-OMe) | Ph(2-Cl,3-OCHF$_2$,5-t-Bu) |
| Ph(2-Cl,3-CF$_2$H,5-F) | Ph(2-Cl,3-OMe,5-OCF$_3$) | Ph(2-Cl,3-OCHF$_2$,5-i-Pr) |
| Ph(2-Cl,3-CF$_2$H,5-Br) | Ph(2-Cl,3-OMe,5-OCHF$_2$) | Ph(2-Cl,3-OCHF$_2$,5-c-Pr) |
| Ph(2-Cl,3-CF$_2$H,5-I) | Ph(2-Cl,3-OMe,5-OCF$_2$CF$_2$H) | Ph(2-Cl,3-OCHF$_2$CF$_3$,5-CF$_3$) |
| Ph(2-Cl,3-CF$_2$H,5-Me) | Ph(2-Cl,3-OMe,5-OC$_2$F$_5$) | Ph(2-Cl,3-OC$_2$F$_5$,5-C$_2$F$_5$) |
| Ph(2-Cl,3-CF$_2$H,5-Et) | Ph(2-Cl,3-OMe,5-SO$_2$Me) | Ph(2-Cl,3-OCHF$_2$,5-CF$_2$CF$_2$H) |
| Ph(2-Cl,3-CF$_2$H,5-n-Pr) | Ph(2-Cl,3-OMe,5-TMS) | Ph(2-Cl,3-OCHF$_2$,5-CF$_2$H) |
| Ph(2-Cl,3-CF$_2$H,5-t-Bu) | Ph(2-Cl,3-OMe,5-CN) | Ph(2-Cl,3-OCHF$_2$,5-OMe) |
| Ph(2-Cl,3-CF$_2$H,5-i-Pr) | Ph(2-Cl,3-OCF$_3$,5-Cl) | Ph(2-Cl,3-OCHF$_2$,5-OCF$_3$) |
| Ph(2-Cl,3-CF$_2$H,5-c-Pr) | Ph(2-Cl,3-OCF$_3$,5-F) | Ph(2-Cl,3,5-di-OCHF$_2$) |
| Ph(2-Cl,3-CF$_2$H,5-CF$_3$) | Ph(2-Cl,3-OCF$_3$,5-Br) | Ph(2-Cl,3-OCHF$_2$,5-OCF$_2$CF$_2$H) |
| Ph(2-Cl,3-CF$_2$H,5-C$_2$F$_5$) | Ph(2-Cl,3-OCF$_3$,5-I) | Ph(2-Cl,3-OCHF$_2$,5-OC$_2$F$_5$) |
| Ph(2-Cl,3-OCHF$_2$,5-TMS) | Ph(2-Cl,3-OCF$_3$,5-Me) | Ph(2-Cl,3-OCHF$_2$,5-SO$_2$Me) |
| | Ph(2-Cl,3-OC$_2$F$_5$,5-CF$_2$H) | Ph(2-Cl,3-TMS,5-n-Pr) |

TABLE 1-continued

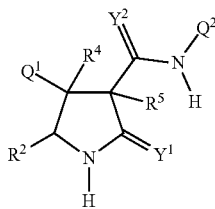

Y$^1$ is O; Y$^2$ is O; R$^2$ is H; R$^4$ is H; R$^5$ is H; Q$^2$ is Ph(2-F); and Q$^1$ is

| Q$^1$ | Q$^1$ | Q$^1$ |
|---|---|---|
| Ph(2-Cl,3-OCHF$_2$,5-CN) | Ph(2-Cl,3-OC$_2$F$_5$,5-OMe) | Ph(2-Cl,3-TMS,5-t-Bu) |
| Ph(2-Cl,3-OCF$_2$CF$_2$H,5-Cl) | Ph(2-Cl,3-OC$_2$F$_5$,5-OCF$_3$) | Ph(2-Cl,3-TMS,5-i-Pr) |
| Ph(2-Cl,3-OCF$_2$CF$_2$H,5-F) | Ph(2-Cl,3-OC$_2$F$_5$,5-OCHF$_2$) | Ph(2-Cl,3-TMS,5-c-Pr) |
| Ph(2-Cl,3-OCF$_2$CF$_2$H,5-Br) | Ph(2-Cl,3-OC$_2$F$_5$,5-OCF$_2$CF$_2$H) | Ph(2-Cl,3-TMS,5-CF$_3$) |
| Ph(2-Cl,3-OCF$_2$CF$_2$H,5-I) | Ph(2-Cl,3,5-di-OC$_2$F$_5$) | Ph(2-Cl,3-TMS,5-C$_2$F$_5$) |
| Ph(2-Cl,3-OCF$_2$CF$_2$H,5-Me) | Ph(2-Cl,3-OC$_2$F$_5$,5-SO$_2$Me) | Ph(2-Cl,3-TMS,5-CF$_2$CF$_2$H) |
| Ph(2-Cl,3-OCF$_2$CF$_2$H,5-Et) | Ph(2-Cl,3-OC$_2$F$_5$,5-TMS) | Ph(2-Cl,3-TMS,5-CF$_2$H) |
| Ph(2-Cl,3-OCF$_2$CF$_2$H,5-n-Pr) | Ph(2-Cl,3-OC$_2$F$_5$,5-CN) | Ph(2-Cl,3-TMS,5-OMe) |
| Ph(2-Cl,3-OCF$_2$CF$_2$H,5-t-Bu) | Ph(2-Cl,3-SO$_2$Me,5-Cl) | Ph(2-Cl,3-TMS,5-OCF$_3$) |
| Ph(2-Cl,3-OCF$_2$CF$_2$H,5-i-Pr) | Ph(2-Cl,3-SO$_2$Me,5-F) | Ph(2-Cl,3-TMS,5-OCHF$_2$) |
| Ph(2-Cl,3-OCF$_2$CF$_2$H,5-c-Pr) | Ph(2-Cl,3-SO$_2$Me,5-Br) | Ph(2-Cl,3-TMS,5-OCF$_2$CF$_2$H) |
| Ph(2-Cl,3-OCF$_2$CF$_2$H,5-CF$_3$) | Ph(2-Cl,3-SO$_2$Me,5-I) | Ph(2-Cl,3-TMS,5-OC$_2$F$_5$) |
| Ph(2-Cl,3-OCF$_2$CF$_2$H,5-C$_2$F$_5$) | Ph(2-Cl,3-SO$_2$Me,5-Me) | Ph(2-Cl,3-TMS,5-SO$_2$Me) |
| Ph(2-Cl,3-OCF$_2$CF$_2$H,5-CF$_2$CF$_2$H) | Ph(2-Cl,3-S2Me,5-Et) | Ph(2-Cl,3,5-di-TMS) |
| Ph(2-Cl,3-OCF$_2$CF$_2$H,5-CF$_2$H) | Ph(2-Cl,3-SO$_2$Me,5-n-Pr) | Ph(2-Cl,3-TMS,5-CN) |
| Ph(2-Cl,3-OCF$_2$CF$_2$H,5-OMe) | Ph(23-Cl,3-SO$_2$Me,5-t-Bu) | Ph(2-Cl,3-CN,5-Cl) |
| Ph(2-Cl,3-OCF$_2$CF$_2$H,5-OCF$_3$) | Ph(2-Cl,3-SO$_2$Me,5-i-Pr) | Ph(2-Cl,3-CN,5-F) |
| Ph(2-Cl,3-OCF$_2$CF$_2$H,5-OCHF$_2$) | Ph(2-Cl,3-SO$_2$Me,5-c-Pr) | Ph(2-Cl,3-CN,5-Br) |
| Ph(2-Cl,3,5-di-OCF$_2$CF$_2$H) | Ph(2-Cl,3-SO$_2$MeCF$_3$,5-CF$_3$) | Ph(2-Cl,3-CN,5-I) |
| Ph(2-Cl,3-OCF$_2$CF$_2$H,5-OC$_2$F$_5$) | Ph(2-Cl,3-SO$_2$Me,5-C$_2$F$_5$) | Ph(2-Cl,3-CN,5-Me) |
| Ph(2-Cl,3-OCF$_2$CF$_2$H,5-SO$_2$Me) | Ph(2-Cl,3-SO$_2$Me,5-CF$_2$CF$_2$H) | Ph(2-Cl,3-CN,5-Et) |
| Ph(2-Cl,3-OCF$_2$CF$_2$H,5-TMS) | Ph(2-Cl,3-SO$_2$Me,5-CF$_2$H) | Ph(2-Cl,3-CN,5-n-Pr) |
| Ph(2-Cl,3-OCF$_2$CF$_2$H,5-CN) | Ph(2-Cl,3-SO$_2$Me,5-OMe) | Ph(2-Cl,3-CN,5-t-Bu) |
| Ph(2-Cl,3-OC$_2$F$_5$,5-Cl) | Ph(2-Cl,3-SO$_2$Me,5-OCF$_3$) | Ph(2-Cl,3-CN,5-i-Pr) |
| Ph(2-Cl,3-OC$_2$F$_5$,5-F) | Ph(2-Cl,3-SO$_2$Me,5-OCHF$_2$) | Ph(2-Cl,3-CN,5-c-Pr) |
| Ph(2-Cl,3-OC$_2$F$_5$,5-Br) | Ph(2-Cl,3-SO$_2$Me,5-OCF$_2$CF$_2$H) | Ph(2-Cl,3-CN,5-CF$_3$) |
| Ph(2-Cl,3-OC$_2$F$_5$,5-I) | Ph(2-Cl,3-SO$_2$Me,5-OC$_2$F$_5$) | Ph(2-Cl,3-CN,5-C$_2$F$_5$) |
| Ph(2-Cl,3-OC$_2$F$_5$,5-Me) | Ph(2-Cl,3,5-di-SO$_2$Me) | Ph(2-Cl,3-CN,5-CF$_2$CF$_2$H) |
| Ph(2-Cl,3-OC$_2$F$_5$,5-Et) | Ph(2-Cl,3-SO$_2$Me,5-TMS) | Ph(2-Cl,3-CN,5-CF$_2$H) |
| Ph(2-Cl,3-OC$_2$F$_5$,5-n-Pr) | Ph(2-Cl,3-SO$_2$Me,5-CN) | Ph(2-Cl,3-CN,5-OMe) |
| Ph(2-Cl,3-OC$_2$F$_5$,5-t-Bu) | Ph(2-Cl,3-TMS,5-Cl) | Ph(2-Cl,3-CN,5-OCF$_3$) |
| Ph(2-Cl,3-OC$_2$F$_5$,5-i-Pr) | Ph(2-Cl,3-TMS,5-F) | Ph(2-Cl,3-CN,5-OCHF$_2$) |
| Ph(2-Cl,3-OC$_2$F$_5$,5-c-Pr) | Ph(2-Cl,3-TMS,5-Br) | Ph(2-Cl,3-CN,5-OCF$_2$CF$_2$H) |
| Ph(2-Cl,3-OC$_2$F$_5$CF$_3$,5-CF$_3$) | Ph(2-Cl,3-TMS,5-I) | Ph(2-Cl,3-CN,5-OC$_2$F$_5$) |
| Ph(2-Cl,3-OC$_2$F$_5$,5-CF$_2$CF$_2$H) | Ph(2-Cl,3-TMS,5-Me) | Ph(2-Cl,3-CN,5-SO$_2$Me) |
| Ph(2-Cl,3,5-di-CN) | Ph(2-Cl,3-TMS,5-Et) | Ph(2-Cl,3-CN,5-TMS) |
| Ph(2,4,5-tri-Cl) | Ph(2-Cl,4-F,5-OMe) | Ph(2-Cl,4-I,5-t-Bu) |
| Ph(2-Cl,4-Cl,5-F) | Ph(2-Cl,4-F,5-OCF$_3$) | Ph(2-Cl,4-I,5-i-Pr) |
| Ph(2-Cl,4-Cl,5-Br) | Ph(2-Cl,4-F,5-OCHF$_2$) | Ph(2-Cl,4-I,5-c-Pr) |
| Ph(2-Cl,4-Cl,5-I) | Ph(2-Cl,4-F,5-OCF$_2$CF$_2$H) | Ph(2-Cl,4-I,5-CF$_3$) |
| Ph(2-Cl,4-Cl,5-Me) | Ph(2-Cl,4-F,5-OC$_2$F$_5$) | Ph(2-Cl,4-I,5-C$_2$F$_5$) |
| Ph(2-Cl,4-C,5-Et) | Ph(2-Cl,4-F,5-SO$_2$Me) | Ph(2-Cl,4-I,5-CF$_2$CF$_2$H) |
| Ph(2-Cl,4-Cl,5-n-Pr) | Ph(2-Cl,4-F,5-TMS) | Ph(2-Cl,4-I,5-CF$_2$H) |
| Ph(2-Cl,4-Cl,5-t-Bu) | Ph(2-Cl,4-F,5-CN) | Ph(2-Cl,4-I,5-OMe) |
| Ph(2-Cl,4-Cl,5-i-Pr) | Ph(2-Cl,4-Br,5-Cl) | Ph(2-Cl,4-I,5-OCF$_3$) |
| Ph(2-Cl,4-Cl,5-c-Pr) | Ph(2-Cl,4-Br,5-F) | Ph(2-Cl,4-I,5-OCHF$_2$) |
| Ph(2-Cl,4-Cl,5-CF$_3$) | Ph(2-Cl,4,5-di-Br) | Ph(2-Cl,4-I,5-OCF$_2$CF$_2$H) |
| Ph(2-Cl,4-Cl,5-C$_2$F$_5$) | Ph(2-Cl,4-Br,5-I) | Ph(2-Cl,4-I,5-OC$_2$F$_5$) |
| Ph(2-Cl,4-Cl,5-CF$_2$CF$_2$H) | Ph(2-Cl,4-Br,5-Me) | Ph(2-Cl,4-I,5-SO$_2$Me) |
| Ph(2-Cl,4-Cl,5-CF$_2$H) | Ph(2-Cl,4-Br,5-Et) | Ph(2-Cl,4-I,5-TMS) |
| Ph(2-Cl,4-Cl,5-OMe) | Ph(2-Cl,4-Br,5-n-Pr) | Ph(2-Cl,4-I,5-CN) |
| Ph(2-Cl,4-Cl,5-OCF$_3$) | Ph(2-Cl,4-Br,5-t-Bu) | Ph(2-Cl,4-Me,5-Cl) |
| Ph(2-Cl,4-Cl,5-OCHF$_2$) | Ph(2-Cl,4-Br,5-i-Pr) | Ph(2-Cl,4-Me,5-F) |
| Ph(2-Cl,4-Cl,5-OCF$_2$CF$_2$H) | Ph(2-Cl,4-Br,5-c-Pr) | Ph(2-Cl,4-Me,5-Br) |
| Ph(2-Cl,4-Cl,5-OC$_2$F$_5$) | Ph(2-Cl,4-Br,5-CF$_3$) | Ph(2-Cl,4-Me,5-I) |
| Ph(2-Cl,4-Cl,5-SO$_2$Me) | Ph(2-Cl,4-Br,5-C$_2$F$_5$) | Ph(2-Cl,4,5-di-Me) |
| Ph(2-Cl,4-Cl,5-TMS) | Ph(2-Cl,4-Br,5-CF$_2$CF$_2$H) | Ph(2-Cl,4-Me,5-Et) |
| Ph(2-Cl,4-Cl,5-CN) | Ph(2-Cl,4-Br,5-CF$_2$H) | Ph(2-Cl,4-Me,5-n-Pr) |
| Ph(2-Cl,4-F,5-Cl) | Ph(2-Cl,4-Br,5-OMe) | Ph(2-Cl,4-Me,5-t-Bu) |
| Ph(2-Cl,4,5-di-F) | Ph(2-Cl,4-Br,5-OCF$_3$) | Ph(2-Cl,4-Me,5-i-Pr) |
| Ph(2-Cl,4-F,5-Br) | Ph(2-Cl,4-Br,5-OCHF$_2$) | Ph(2-Cl,4-Me,5-c-Pr) |
| Ph(2-Cl,4-F,5-I) | Ph(2-Cl,4-Br,5-OCF$_2$CF$_2$H) | Ph(2-Cl,4-Me,5-CF$_3$) |
| Ph(2-Cl,4-F,5-Me) | Ph(2-Cl,4-Br,5-OC$_2$F$_5$) | Ph(2-Cl,4-Me,5-C$_2$F$_5$) |
| Ph(2-Cl,4-F,5-Et) | Ph(2-Cl,4-Br,5-SO$_2$Me) | Ph(2-Cl,4-Me,5-CF$_2$CF$_2$H) |
| Ph(2-Cl,4-F,5-n-Pr) | Ph(2-Cl,4-Br,5-TMS) | Ph(2-Cl,4-Me,5-CF$_2$H) |
| | Ph(2-Cl,4-Br,5-CN) | Ph(2-Cl,4-Me,5-OMe) |

TABLE 1-continued

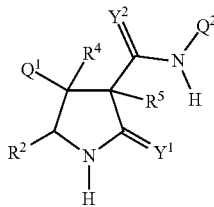

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(2-Cl,4-F,5-t-Bu) | Ph(2-Cl,4-I,5-Cl) | Ph(2-Cl,4-Me,5-OCF$_3$) |
| Ph(2-Cl,4-F,5-i-Pr) | Ph(2-Cl,4-I,5-F) | Ph(2-Cl,4-Me,5-OCHF$_2$) |
| Ph(2-Cl,4-F,5-c-Pr) | Ph(2-Cl,4-I,5-Br) | Ph(2-Cl,4-Me,5-OCF$_2$CF$_2$H) |
| Ph(2-Cl,4-F,5-CF$_3$) | Ph(2-Cl,4,5-di-I) | Ph(2-Cl,4-Me,5-OC$_2$F$_5$) |
| Ph(2-Cl,4-F,5-C$_2$F$_5$) | Ph(2-Cl,4-I,5-Me) | Ph(2-Cl,4-Me,5-SO$_2$Me) |
| Ph(2-Cl,4-F,5-CF$_2$CF$_2$H) | Ph(2-Cl,4-I,5-Et) | Ph(2-Cl,4-Me,5-TMS) |
| Ph(2-Cl,4-F,5-CF$_2$H) | Ph(2-Cl,4-I,5-n-Pr) | Ph(2-Cl,4-Me,5-CN) |
| Ph(2-Cl,4-Et,5-Cl) | Ph(2-Cl,4-n-Pr,5-OCF$_3$) | Ph(2-Cl,4,5-di-i-Pr) |
| Ph(2-Cl,4-Et,5-F) | Ph(2-Cl,4-n-Pr,5-OCHF$_2$) | Ph(2-Cl,4-i-Pr,5-c-Pr) |
| Ph(2-Cl,4-Et,5-Br) | Ph(2-Cl,4-n-Pr,5-OCF$_2$CF$_2$H) | Ph(2-Cl,4-i-Pr,5-CF$_3$) |
| Ph(2-Cl,4-Et,5-I) | Ph(2-Cl,4-n-Pr,5-OC$_2$F$_5$) | Ph(2-Cl,4-i-Pr,5-C$_2$F$_5$) |
| Ph(2-Cl,4-Et,5-Me) | Ph(2-Cl,4-n-Pr,5-SO$_2$Me) | Ph(2-Cl,4-i-Pr,5-CF$_2$CF$_2$H) |
| Ph(2-Cl,4,5-di-Et) | Ph(2-Cl,4-n-Pr,5-TMS) | Ph(2-Cl,4-i-Pr,5-CF$_2$H) |
| Ph(2-Cl,4-Et,5-n-Pr) | Ph(2-Cl,4-n-Pr,5-CN) | Ph(2-Cl,4-i-Pr,5-OMe) |
| Ph(2-Cl,4-Et,5-t-Bu) | Ph(2-Cl,4-t-Bu,5-Cl) | Ph(2-Cl,4-i-Pr,5-OCF$_3$) |
| Ph(2-Cl,4-Et,5-i-Pr) | Ph(2-Cl,4-t-Bu,5-F) | Ph(2-Cl,4-i-Pr,5-OCHF$_2$) |
| Ph(2-Cl,4-Et,5-c-Pr) | Ph(2-Cl,4-t-Bu,5-Br) | Ph(2-Cl,4-i-Pr,5-OCF$_2$CF$_2$H) |
| Ph(2-Cl,4-Et,5-CF$_3$) | Ph(2-Cl,4-t-Bu,5-I) | Ph(2-Cl,4-i-Pr,5-OC$_2$F$_5$) |
| Ph(2-Cl,4-Et,5-C$_2$F$_5$) | Ph(2-Cl,4-t-Bu,5-Me) | Ph(2-Cl,4-i-Pr,5-SO$_2$Me) |
| Ph(2-Cl,4-Et,5-CF$_2$CF$_2$H) | Ph(2-Cl,4-t-Bu,5-Et) | Ph(2-Cl,4-i-Pr,5-TMS) |
| Ph(2-Cl,4-Et,5-CF$_2$H) | Ph(2-Cl,4-t-Bu,5-n-Pr) | Ph(2-Cl,4-i-Pr,5-CN) |
| Ph(2-Cl,4-Et,5-OMe) | Ph(2-Cl,4-5-di-t-Bu) | Ph(2-Cl,4-c-Pr,5-Cl) |
| Ph(2-Cl,4-Et,5-OCF$_3$) | Ph(2-Cl,4-t-Bu,5-i-Pr) | Ph(2-Cl,4-c-Pr,5-F) |
| Ph(2-Cl,4-Et,5-OCHF$_2$) | Ph(2-Cl,4-t-Bu,5-c-Pr) | Ph(2-Cl,-4-c-Pr,5-Br) |
| Ph(2-Cl,4-Et,5-OCF$_2$CF$_2$H) | Ph(2-Cl,4-t-Bu,5-CF$_3$) | Ph(2-Cl,4-c-Pr,5-I) |
| Ph(2-Cl,4-Et,5-OC$_2$F$_5$) | Ph(2-Cl,4-t-Bu,5-C$_2$F$_5$) | Ph(2-Cl,4-c-Pr,5-Me) |
| Ph(2-Cl,4-Et,5-SO$_2$Me) | Ph(2-Cl,4-t-Bu,5-CF$_2$CF$_2$H) | Ph(2-Cl,4-c-Pr,5-Et) |
| Ph(2-Cl,4-Et,5-TMS) | Ph(2-Cl,4-t-Bu,5-CF$_2$H) | Ph(2-Cl,4-c-Pr,5-n-Pr) |
| Ph(2-Cl,4-Et,5-CN) | Ph(2-Cl,4-t-Bu,5-OMe) | Ph(2-Cl,4-c-Pr,5-t-Bu) |
| Ph(2-Cl,4-n-Pr,5-Cl) | Ph(2-Cl,4-t-Bu,5-OCF$_3$) | Ph(2-Cl,4-c-Pr,5-i-Pr) |
| Ph(2-Cl,4-n-Pr,5-F) | Ph(2-Cl,4-t-Bu,5-OCHF$_2$) | Ph(2-Cl,4,5-di-c-Pr) |
| Ph(2-Cl,4-n-Pr,5-Br) | Ph(2-Cl,4-t-Bu,5-OCF$_2$CF$_2$H) | Ph(2-Cl,4-c-Pr,5-CF$_3$) |
| Ph(2-Cl,4-n-Pr,5-I) | Ph(2-Cl,4-t-Bu,5-OC$_2$F$_5$) | Ph(2-Cl,4-c-Pr,5-C$_2$F$_5$) |
| Ph(2-Cl,4-n-Pr,5-Me) | Ph(2-Cl,4-t-Bu,5-SO$_2$Me) | Ph(2-Cl,4-c-Pr,5-CF$_2$CF$_2$H) |
| Ph(2-Cl,4-n-Pr,5-Et) | Ph(2-Cl,4-t-Bu,5-TMS) | Ph(2-Cl,4-c-Pr,5-CF$_2$H) |
| Ph(2-Cl,4,5-di-n-Pr) | Ph(2-Cl,4-t-Bu,5-CN) | Ph(2-Cl,4-c-Pr,5-OMe) |
| Ph(2-Cl,4-n-Pr,5-t-Bu) | Ph(2-Cl,4-i-Pr,5-Cl) | Ph(2-Cl,4-c-Pr,5-OCF$_3$) |
| Ph(2-Cl,4-n-Pr,5-i-Pr) | Ph(2-Cl,4-i-Pr,5-F) | Ph(-Cl,4-c-Pr,5-OCHF$_2$) |
| Ph(2-Cl,4-n-Pr,5-c-Pr) | Ph(2-Cl,4-i-Pr,5-Br) | Ph(2-Cl,4-c-Pr,5-OCF$_2$CF$_2$H) |
| Ph(2-Cl,4-n-Pr,5-CF$_3$) | Ph(2-Cl,4-i-Pr,5-I) | Ph(2-Cl,4-c-Pr,5-OC$_2$F$_5$) |
| Ph(2-Cl,4-n-Pr,5-C$_2$F$_5$) | Ph(2-Cl,4-i-Pr,5-Me) | Ph(2-Cl,4-c-Pr,5-SO$_2$Me) |
| Ph(2-Cl,4-n-Pr,5-CF$_2$CF$_2$H) | Ph(2-Cl,4-i-Pr,5-Et) | Ph(2-Cl,4-c-Pr,5-TMS) |
| Ph(2-Cl,4-n-Pr,5-CF$_2$H) | Ph(2-Cl,4-i-Pr,5-n-Pr) | Ph(2-Cl,4-c-Pr,5-CN) |
| Ph(2-Cl,4-n-Pr,5-OMe) | Ph(2-Cl,4-i-Pr,5-t-Bu) | Ph(2-Cl,4-CF$_3$,5-Cl) |
| Ph(2-Cl,4-CF$_3$,5-F) | Ph(2-Cl,4-CF$_2$CF$_3$,5-OCHF$_2$) | Ph(2-Cl,4-CF$_2$H,5-t-Bu) |
| Ph(2-Cl,4-CF$_3$,5-Br) | Ph(2-Cl,4-CF$_2$CF$_3$,5-OCF$_2$CF$_2$H) | Ph(2-Cl,4-CF$_2$H,5-i-Pr) |
| Ph(2-Cl,4-CF$_3$,5-I) | | Ph(2-Cl,4-CF$_2$H,5-c-Pr) |
| Ph(2-Cl,4-CF$_3$,5-Me) | Ph(2-Cl,4-CF$_2$CF$_3$,5-OC$_2$F$_5$) | Ph(2-Cl,4-CF$_2$H,5-CF$_3$) |
| Ph(2-Cl,4-CF$_3$,5-Et) | Ph(2-Cl,4-CF$_2$CF$_3$,5-SO$_2$Me) | Ph(2-Cl,4-CF$_2$H,5-C$_2$F$_5$) |
| Ph(2-Cl,4-CF$_3$,5-n-Pr) | Ph(2-Cl,4-CF$_2$CF$_3$,5-TMS) | Ph(2-Cl,4-CF$_2$H,5-CF$_2$CF$_2$H) |
| Ph(2-Cl,4-CF$_3$,5-t-Bu) | Ph(2-Cl,4-CF$_2$CF$_3$,5-CN) | Ph(2-Cl,4,5-di-CF$_2$H) |
| Ph(2-Cl,4-CF$_3$,5-i-Pr) | Ph(2-Cl,4-CF$_2$CF$_2$H,5-Cl) | Ph(2-Cl,4-CF$_2$H,5-OMe) |
| Ph(2-Cl,4-CF$_3$,5-c-Pr) | Ph(2-Cl,4-CF$_2$CF$_2$H,5-F) | Ph(2-Cl,4-CF$_2$H,5-OCF$_3$) |
| Ph(2-Cl,4,5-di-CF$_3$) | Ph(2-Cl,4-CF$_2$CF$_2$H,5-Br) | Ph(2-Cl,4-CF$_2$H,5-OCHF$_2$) |
| Ph(2-Cl,4-CF$_3$,5-C$_2$F$_5$) | Ph(2-Cl,4-CF$_2$CF$_2$H,5-I) | Ph(2-Cl,4-CF$_2$H,5-OCF$_2$CF$_2$H) |
| Ph(2-Cl,4-CF$_3$,5-CF$_2$CF$_2$H) | Ph(2-Cl,4-CF$_2$CF$_2$H,5-Me) | Ph(2-Cl,4-CF$_2$H,5-OC$_2$F$_5$) |
| Ph(2-Cl,4-CF$_3$,5-CF$_2$H) | Ph(2-Cl,4-CF$_2$CF$_2$H,5-Et) | Ph(2-Cl,4-CF$_2$H,5-SO$_2$Me) |
| Ph(2-Cl,4-CF$_3$,5-OMe) | Ph(2-Cl,4-CF$_2$CF$_2$H,5-n-Pr) | Ph(2-Cl,4-CF$_2$H,5-TMS) |
| Ph(2-Cl,4-CF$_3$,5-OCF$_3$) | Ph(23-Cl,4-CF$_2$CF$_2$H,5-t-Bu) | Ph(2-Cl,4-CF$_2$H,5-CN) |
| Ph(2-Cl,4-CF$_3$,5-OCHF$_2$) | Ph(2-Cl,4-CF$_2$CF$_2$H,5-i-Pr) | Ph(2-Cl,4-OMe,5-Cl) |
| Ph(2-Cl,4-CF$_3$,5-OCF$_2$CF$_2$H) | Ph(2-Cl,4-CF$_2$CF$_2$H,5-c-Pr) | Ph(2-Cl,4-OMe,5-F) |
| Ph(2-Cl,4-CF$_3$,5-OC$_2$F$_5$) | Ph(2-Cl,4-CF$_2$CF$_2$CF$_3$H,5-CF$_3$) | Ph(2-Cl,4-OMe,5-Br) |
| Ph(2-Cl,4-CF$_3$,5-SO$_2$Me) | Ph(2-Cl,4-CF$_2$CF$_2$H,5-C$_2$F$_5$) | Ph(2-Cl,4-OMe,5-I) |
| Ph(2-Cl,4-CF$_3$,5-TMS) | Ph(2-Cl,4,5-di-CF$_2$CF$_2$H) | Ph(2-Cl,4-OMe,5-Me) |
| Ph(2-Cl,4-CF$_3$,5-CN) | Ph(2-Cl,4-CF$_2$CF$_2$H,5-CF$_2$H) | Ph(2-Cl,4-OMe,5-Et) |
| Ph(2-Cl,4-CF$_2$CF$_3$,5-Cl) | Ph(2-Cl,4-CF$_2$CF$_2$H,5-OMe), | Ph(2-Cl,4-OMe,5-n-Pr) |

TABLE 1-continued

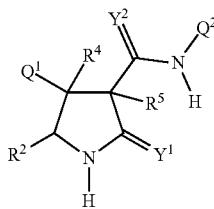

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-Cl,4-CF$_2$CF$_3$,5-F) | Ph(2-Cl,4-CF$_2$CF$_2$H,5-OCF$_3$) | Ph(2-Cl,4-OMe,5-t-Bu) |
| Ph(2-Cl,4-CF$_2$CF$_3$,5-Br) | Ph(2-Cl,4-CF$_2$CF$_2$H,5-OCHF$_2$) | Ph(2-Cl,4-OMe,5-i-Pr) |
| Ph(2-Cl,4-CF$_2$CF$_3$,5-I) | Ph(2-Cl,4-CF$_2$CF$_2$H,5-OCF$_2$CF$_2$H) | Ph(2-Cl,4-OMe,5-c-Pr) |
| Ph(2-Cl,4-CF$_2$CF$_3$,5-Me) | | Ph(2-Cl,4-OMeCF$_3$,5-CF$_3$) |
| Ph(2-Cl,4-CF$_2$CF$_3$,5-Et) | Ph(2-Cl,4-CF$_2$CF$_2$H,5-OC$_2$F$_5$) | Ph(2-Cl,4-OMe,5-C$_2$F$_5$) |
| Ph(2-Cl,4-CF$_2$CF$_3$,5-n-Pr) | Ph(2-Cl,4-CF$_2$CF$_2$H,5-SO$_2$Me) | Ph(2-Cl,4-OMe,5-CF$_2$CF$_2$H) |
| Ph(2-Cl,4-CF$_2$CF$_3$,5-t-Bu) | Ph(2-Cl,4-CF$_2$CF$_2$H,5-TMS) | Ph(2-Cl,4-OMe,5-CF$_2$H) |
| Ph(2-Cl,4-CF$_2$CF$_3$,5-i-Pr) | Ph(2-Cl,4-CF$_2$CF$_2$H,5-CN) | Ph(2-Cl,4,5-di-OMe) |
| Ph(2-Cl,4-CF$_2$CF$_3$,5-c-Pr) | Ph(2-Cl,4-CF$_2$H,5-Cl) | Ph(2-Cl,4-OMe,5-OCF$_3$) |
| Ph(2-Cl,4-C$_2$F$_5$CF$_3$,5-CF$_3$) | Ph(2-Cl,4-CF$_2$H,5-F) | Ph(2-Cl,4-OMe,5-OCHF$_2$) |
| Ph(2-Cl,4,5-di-C$_2$F$_5$) | Ph(2-Cl,4-CF$_2$H,5-Br) | Ph(2-Cl,4-OMe,5-OCF$_2$CF$_2$H) |
| Ph(2-Cl,4-CF$_2$CF$_3$,5-CF$_2$CF$_2$H) | Ph(2-Cl,4-CF$_2$H,5-I) | Ph(2-Cl,4-Me,5-OC$_2$F$_5$) |
| Ph(2-Cl,4-CF$_2$CF$_3$,5-CF$_2$H) | Ph(2-Cl,4-CF$_2$H,5-Me) | Ph(2-Cl,4-OMe,5-SO$_2$Me) |
| Ph(2-Cl,4-CF$_2$CF$_3$,5-OMe) | Ph(2-Cl,4-CF$_2$H,5-Et) | Ph(2-Cl,4-OMe,5-TMS) |
| Ph(2-Cl,4-CF$_2$CF$_3$,5-OCF$_3$) | Ph(2-Cl,4-CF$_2$H,5-n-Pr) | Ph(2-Cl,4-OMe,5-CN) |
| Ph(2-Cl,4-OCF$_3$,5-Cl) | Ph(2-Cl,4-OCHF$_2$,5-OCF$_3$) | Ph(2-Cl,4-OCF$_2$CF$_3$,5-n-Pr) |
| Ph(2-Cl,4-OCF$_3$,5-F) | Ph(2-Cl,4,5-di-OCHF$_2$) | Ph(2-Cl,4-OCF$_2$CF$_3$,5-t-Bu) |
| Ph(2-Cl,4-OCF$_3$,5-Br) | Ph(2-Cl,4-OCHF$_2$,5-OCF$_2$CF$_2$H) | Ph(2-Cl,4-OCF$_2$CF$_3$,5-i-Pr) |
| Ph(2-Cl,4-OCF$_3$,5-I) | Ph(2-Cl,4-OCHF$_2$,5-OC$_2$F$_5$) | Ph(2-Cl,4-OCF$_2$CF$_3$,5-c-Pr) |
| Ph(2-Cl,4-OCF$_3$,5-Me) | Ph(2-Cl,4-OCHF$_2$,5-SO$_2$Me) | Ph(2-Cl,4-OC$_2$F$_5$CF$_3$,5-CF$_3$) |
| Ph(2-Cl,4-OCF$_3$,5-Et) | Ph(2-Cl,4-OCHF$_2$,5-TMS) | Ph(2-Cl,4-OCF$_2$CF$_3$,5-CF$_2$CF$_2$H) |
| Ph(2-Cl,4-OCF$_3$,5-n-Pr) | Ph(2-Cl,4-OCHF$_2$,5-CN) | |
| Ph(2-Cl,4-OCF$_3$,5-t-Bu) | Ph(2-Cl,4-OCF$_2$CF$_2$H,5-Cl) | Ph(2-Cl,4-OCF$_2$CF$_3$,5-CF$_2$H) |
| Ph(2-Cl,4-OCF$_3$,5-i-Pr) | Ph(2-Cl,4-OCF$_2$CF$_2$H,5-F) | Ph(2-Cl,4-OCF$_2$CF$_3$,5-OMe) |
| Ph(2-Cl,4-OCF$_3$,5-c-Pr) | Ph(2-Cl,4-OCF$_2$CF$_2$H,5-Br) | Ph(2-Cl,4-OCF$_2$CF$_3$,5-OCF$_3$) |
| Ph(2-Cl,4-OCF$_3$,5-CF$_3$) | Ph(2-Cl,4-OCF$_2$CF$_2$H,5-I) | Ph(2-Cl,4-OCF$_2$CF$_3$,5-OCHF$_2$) |
| Ph(2-Cl,4-OCF$_3$,5-C$_2$F$_5$) | Ph(2-Cl,4-OCF$_2$CF$_2$H,5-Me) | Ph(2-Cl,4-OCF$_2$CF$_3$,5-OCF$_2$CF$_2$H) |
| Ph(2-Cl,4-OCF$_3$,5-CF$_2$CF$_2$H) | Ph(2-Cl,4-OCF$_2$CF$_2$H,5-Et) | |
| Ph(2-Cl,4-OCF$_3$,5-CF$_2$H) | Ph(2-Cl,4-OCF$_2$CF$_2$H,5-n-Pr) | Ph(2-Cl,4,5-di-OC$_2$F$_5$) |
| Ph(2-Cl,4-OCF$_3$,5-OMe) | Ph(2-Cl,4-OCF$_2$CF$_2$H,5-t-Bu) | Ph(2-Cl,4-OCF$_2$CF$_3$,5-SO$_2$Me) |
| Ph(2-Cl,4,5-di-OCF$_3$) | Ph(2-Cl,4-OCF$_2$CF$_2$H,5-i-Pr) | Ph(2-Cl,4-OCF$_2$CF$_3$,5-TMS) |
| Ph(2-Cl,4-OCF$_3$,5-OCHF$_2$) | Ph(2-Cl,4-OCF$_2$CF$_2$H,5-c-Pr) | Ph(2-Cl,4-OCF$_2$CF$_3$,5-CN) |
| Ph(2-Cl,4-OCF$_3$,5-OCF$_2$CF$_2$H) | Ph(2-Cl,4-OCF$_2$CF$_2$CF$_2$H,5-CF$_3$) | Ph(2-Cl,4-SO$_2$Me,5-Cl) |
| Ph(2-Cl,4-OCF$_3$,5-OC$_2$F$_5$) | | Ph(2-Cl,4-SO$_2$Me,5-F) |
| Ph(2-Cl,4-OCF$_3$,5-SO$_2$Me) | Ph(2-Cl,4-OCF$_2$CF$_2$H,5-C$_2$F$_5$) | Ph(2-Cl,4-SO$_2$Me,5-Br) |
| Ph(2-Cl,4-OCF$_3$,5-TMS) | Ph(2-Cl,4-OCF$_2$CF$_2$H,5-CF$_2$CF$_2$H) | Ph(2-Cl,4-SO$_2$Me,5-I) |
| Ph(2-Cl,4-OCF$_3$,5-CN) | | Ph(2-Cl,4-SO$_2$Me,5-Me) |
| Ph(2-Cl,4-OCHF$_2$,5-Cl) | Ph(2-Cl,4-OCF$_2$CF$_2$H,5-CF$_2$H) | Ph(2-Cl,4-SO$_2$Me,5-Et) |
| Ph(2-Cl,4-OCHF$_2$,5-F) | Ph(2-Cl,4-OCF$_2$CF$_2$H,5-OMe) | Ph(2-Cl,4-SO$_2$Me,5-n-Pr) |
| Ph(2-Cl,4-OCHF$_2$,5-Br) | Ph(2-Cl,4-OCF$_2$CF$_2$H,5-OCF$_3$) | Ph(2-Cl,4-SO$_2$Me,5-t-Bu) |
| Ph(2-Cl,4-OCHF$_2$,5-I) | Ph(2-Cl,4-OCF$_2$CF$_2$H,5-OCHF$_2$) | Ph(2-Cl,4-SO$_2$Me,5-i-Pr) |
| Ph(2-Cl,4-OCHF$_2$,5-Me) | Ph(2-Cl,4,5-di-OCF$_2$CF$_2$H) | Ph(2-Cl,4-SO$_2$Me,5-c-Pr) |
| Ph(2-Cl,4-OCHF$_2$,5-Et) | Ph(2-Cl,4-OCF$_2$CF$_2$H,5-OC$_2$F$_5$) | Ph(2-Cl,4-SO$_2$MeCF$_3$,5-CF$_3$) |
| Ph(2-Cl,4-OCHF$_2$,5-n-Pr) | Ph(2-Cl,4-OCF$_2$CF$_2$H,5-SO$_2$Me) | Ph(2-Cl,4-SO$_2$Me,5-C$_2$F$_5$) |
| Ph(2-Cl,4-OCHF$_2$,5-t-Bu) | Ph(2-Cl,4-OCF$_2$CF$_2$H,5-TMS) | Ph(2-Cl,4-SO$_2$Me,5-CF$_2$CF$_2$H) |
| Ph(2-Cl,4-OCHF$_2$,5-i-Pr) | Ph(2-Cl,4-OCF$_2$CF$_2$H,5-CN) | Ph(2-Cl,4-SO$_2$Me,5-CF$_2$H) |
| Ph(2-Cl,4-OCHF$_2$,5-c-Pr) | Ph(2-Cl,4-OCF$_2$CF$_3$,5-Cl) | Ph(2-Cl,4-SO$_2$Me,5-OMe) |
| Ph(2-Cl,4-OCHF$_2$CF$_3$,5-CF$_3$) | Ph(2-Cl,4-OCF$_2$CF$_3$,5-F) | Ph(2-Cl,4-SO$_2$Me,5-OCF$_3$) |
| Ph(2-Cl,4-OCF$_2$CF$_3$,5-C$_2$F$_5$) | Ph(2-Cl,4-OCF$_2$CF$_3$,5-Br) | Ph92-Cl,4-SO$_2$me,5-OCHF$_2$) |
| Ph(2-Cl,4-OCHF$_2$,5-CF$_2$CF$_2$H) | Ph(2-Cl,4-OCF$_2$CF$_3$,5-I) | Ph(2-Cl,4-SO$_2$Me,5-OCF$_2$CF$_2$H) |
| Ph(2-Cl,4-OCHF$_2$,5-CF$_2$H) | Ph(2-Cl,4-OCF$_2$CF$_3$,5-Me) | Ph(2-Cl,4-SO$_2$Me,5-OC$_2$F$_5$) |
| Ph(2-Cl,4-OCHF$_2$,5-OMe) | Ph(2-Cl,4-OCF$_2$CF$_3$,5-Et) | Ph(2-Cl,4,5-di-SO$_2$Me) |
| Ph(2-Cl,4-SO$_2$Me,5-TMS) | Ph(2-Cl,4-CN,5-CF$_2$H) | Ph(2-F,3-F,4-OC$_2$F$_5$) |
| Ph(2-Cl,4-SO$_2$Me,5-CN) | Ph(2-Cl,4-CN,5-OMe) | Ph(2-F,3-Br,5-Cl) |
| Ph(2-Cl,4-TMS,5-Cl) | Ph(2-Cl,4-CN,5-OCF$_3$) | Ph(2-F,3,4-di-Br) |
| Ph(2-Cl,4-TMS,5-F) | Ph(2-Cl,4-CN,5-OCHF$_2$) | Ph(2-F,3-Br,4-I) |
| Ph(2-Cl,4-TMS,5-Br) | Ph(2-Cl,4-CN,5-OCF$_2$CF$_2$H) | Ph(2-F,3-Br,4-Me) |
| Ph(2-Cl,4-TMS,5-I) | Ph(2-Cl,4-CN,5-OC$_2$F$_5$) | Ph(2-F,3-Br,4-Et) |
| Ph(2-Cl,4-TMS,5-Me) | Ph(2-Cl,4-CN,5-SO$_2$Me) | Ph(2-F,3-Br,4-n-Pr) |
| Ph(2-Cl,4-TMS,5-Et) | Ph(2-Cl,4-CN,5-TMS) | Ph(2-F,3-Br,4-t-Bu) |
| Ph(2-Cl,4-TMS,5-n-Pr) | Ph(2-Cl,4,5-di-CN) | Ph(2-F,3-Br,4-i-Pr) |
| Ph(2-Cl,4-TMS,5-t-Bu) | Ph(2-F,3,4-di-Cl) | Ph(2-F,3-Br,4-CF$_3$) |
| Ph(2-Cl,4-TMS,5-i-Pr) | Ph(2-F,3-Cl,4-I) | Ph(2-F,3-Br,4-C$_2$F$_5$) |
| Ph(2-Cl,4-TMS,5-c-Pr) | Ph(2-F,3-Cl,4-Me) | Ph(2-F,3-Br,4-CF$_2$CF$_2$H) |
| Ph(2-Cl,4-TMS,5-CF$_3$) | Ph(2-F,3-Cl,4-Et) | Ph(2-F,3-Br,4-CF$_2$H) |
| Ph(2-Cl,4-TMS,5-C$_2$F$_5$) | Ph(2-F,3-Cl,4-n-Pr) | Ph(2-F,3-Br,4-OMe) |

TABLE 1-continued

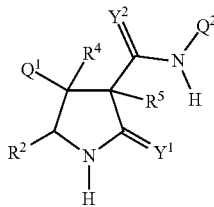

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-Cl,4-TMS,5-CF$_2$CF$_2$H) | Ph(2-F,3-Cl,4-i-Pr) | Ph(2-F,3-Br,4-OCF$_2$CF$_2$H) |
| Ph(2-Cl,4-TMS,5-CF$_2$H) | Ph(2-F,3-Cl,4-CF$_3$) | Ph(2-F,3-Br,4-OC$_2$F$_5$) |
| Ph(2-Cl,4-TMS,5-OMe) | Ph(2-F,3-Cl,4-C$_2$F$_5$) | Ph(2-F,3-I,4-Cl) |
| Ph(2-Cl,4-TMS,5-OCF$_3$) | Ph(2-F,3-Cl,4-CF$_2$CF$_2$H) | Ph(2-F,3-I,4-F) |
| Ph(2-Cl,4-TMS,5-OCHF$_2$) | Ph(2-F,3-Cl,4-CF$_2$H) | Ph(2-F,3-I,4-Br) |
| Ph(2-Cl,4-TMS,5-OCF$_2$CF$_2$H) | Ph(2-F,3-Cl,4-OMe) | Ph(2-F,3,4-di-I) |
| Ph(2-Cl,4-TMS,5-OC$_2$F$_5$) | Ph(2-F,3-Cl,4-OCHF$_2$) | Ph(2-F,3-I,4-Me) |
| Ph(2-Cl,4-TMS,5-SO$_2$Me) | Ph(2-F,3-Cl,4-OCF$_2$CF$_2$H) | Ph(2-F,3-I,4-Et) |
| Ph(2-Cl,4,5-di-TMS) | Ph(2-F,3-Cl,4-OC$_2$F$_5$) | Ph(2-F,3-I,4-n-Pr) |
| Ph(2-Cl,4-TMS,5-CN) | Ph(2,3,4-tri-F) | Ph(2-F,3-I,4-t-Bu) |
| Ph(2-Cl,4-CN,5-Cl) | Ph(2-F,3-F,4-Br) | Ph(2-F,3-I,4-i-Pr) |
| Ph(2-Cl,4-CN,5-F) | Ph(2-F,3-F,4-I) | Ph(2-F,3-I,4-c-Pr) |
| Ph(2-Cl,4-CN,5-Br) | Ph(2-F,3-F,4-Et) | Ph(2-F,3-I,4-CF$_3$) |
| Ph(2-Cl,4-CN,5-I) | Ph(2-F,3-F,4-n-Pr) | Ph(2-F,3-I,4-C$_2$F$_5$) |
| Ph(2-Cl,4-CN,5-Me) | Ph(2-F,3-F,4-t-Bu) | Ph(2-F,3-I,4-CF$_2$CF$_2$H) |
| Ph(2-Cl,4-CN,5-Et) | Ph(2-F,3-F,4-i-Pr) | Ph(2-F,3-I,4-CF$_2$H) |
| Ph(2-Cl,4-CN,5-n-Pr) | Ph(2-F,3-F,4-CF$_3$) | Ph(2-F,3-I,4-OMe) |
| Ph(2-Cl,4-CN,5-t-Bu) | Ph(2-F,3-F,4-C$_2$F$_5$) | Ph(2-F,3-I,4-OCF$_3$) |
| Ph(2-Cl,4-CN,5-i-Pr) | Ph(2-F,3-F,4-CF$_2$CF$_2$H) | Ph(2-F,3-I,4-OCHF$_2$) |
| Ph(2-Cl,4-CN,5-c-Pr) | Ph(2-F,3-F,4-CF$_2$H) | Ph(2-F,3-I,4-OCF$_2$CF$_2$H) |
| Ph(2-Cl,4-CN,5-CF$_3$) | Ph(2-F,3-F,4-OMe) | Ph(2-F,3-I,4-OC$_2$F$_5$) |
| Ph(2-Cl,4-CN,5-C$_2$F$_5$) | Ph(2-F,3-F,4-OCHF$_2$) | Ph(2-F,3-I,4-SO$_2$Me) |
| Ph(2-Cl,4-CN,5-CF$_2$CF$_2$H) | Ph(2-F,3-F,4-OCF$_2$CF$_2$H) | Ph(2-F,3-I,4-TMS) |
| Ph(2-F,3-I,4-CN) | Ph(2-F,3-n-Pr,4-Br) | Ph(2-F,3-i-Pr,4-n-Pr) |
| Ph(2-F,3-Me,4-I) | Ph(2-F,3-n-Pr,4-I) | Ph(2-F,3-i-Pr,4-t-Bu) |
| Ph(2-F,3,4-di-Me) | Ph(2-F,3-n-Pr,4-Me) | Ph(2-F,3,4-di-i-Pr) |
| Ph(2-F,3-Me,4-Et) | Ph(2-F,3-n-Pr,4-Et) | Ph(2-F,3-i-Pr,4-c-Pr) |
| Ph(2-F,3-Me,4-n-Pr) | Ph(2-F,3,4-di-n-Pr) | Ph(2-F,3-i-Pr,4-CF$_3$) |
| Ph(2-F,3-Me,4-i-Pr) | Ph(2-F,3-n-Pr,4-t-Bu) | Ph(2-F,3-i-Pr,4-C$_2$F$_5$) |
| Ph(2-F,3-Me,4-c-Pr) | Ph(2-F,3-n-Pr,4-i-Pr) | Ph(2-F,3-i-Pr,4-CF$_2$CF$_2$H) |
| Ph(2-F,3-Me,4-C$_2$F$_5$) | Ph(2-F,3-n-Pr,4-c-Pr) | Ph(2-F,3-i-Pr,4-CF$_2$H) |
| Ph(2-F,3-Me,4-CF$_2$CF$_2$H) | Ph(2-F,3-n-Pr,4-CF$_3$) | Ph(2-F,3-i-Pr,4-OMe) |
| Ph(2-F,3-Me,4-CF$_2$H) | Ph(2-F,3-n-Pr,4-C$_2$F$_5$) | Ph(2-F,3-i-Pr,4-OCF$_3$) |
| Ph(2-F,3-Me,4-OMe) | Ph(2-F,3-n-Pr,4-CF$_2$CF$_2$H) | Ph(2-F,3-i-Pr,4-OCHF$_2$) |
| Ph(2-F,3-Me,4-OCF$_2$CF$_2$H) | Ph(2-F,3-n-Pr,4-CF$_2$H) | Ph(2-F,3-i-Pr,4-OCF$_2$CF$_2$H) |
| Ph(2-F,3-Me,4-OC$_2$F$_5$) | Ph(2-F,3-n-Pr,4-OMe) | Ph(2-F,3-i-Pr,4-OC$_2$F$_5$) |
| Ph(2-F,3-Et,4-Cl) | Ph(2-F,3-n-Pr,4-OCF$_3$) | Ph(2-F,3-i-Pr,4-SO$_2$Me) |
| Ph(2-F,3-Et,4-F) | Ph(2-F,3-n-Pr,4-OCHF$_2$) | Ph(2-F,3-i-Pr,4-TMS) |
| Ph(2-F,3-Et,4-Br) | Ph(2-F,3-n-Pr,4-OCF$_2$CF$_2$H) | Ph(2-F,3-i-Pr,4-CN) |
| Ph(2-F,3-Et,4-I) | Ph(2-F,3-n-Pr,4-OC$_2$F$_5$) | Ph(2-F,3-c-Pr,4-I) |
| Ph(2-F,3-Et,4-Me) | Ph(2-F,3-n-Pr,4-SO$_2$Me) | Ph(2-F,3-c-Pr,4-Et) |
| Ph(2-F,3,4-di-Et) | Ph(2-F,3-n-Pr,4-TMS) | Ph(2-F,3-c-Pr,4-n-Pr) |
| Ph(2-F,3-Et,4-n-Pr) | Ph(2-F,3-n-Pr,4-CN) | Ph(2-F,3-c-Pr,4-i-Pr) |
| Ph(2-F,3-Et,4-t-Bu) | Ph(2-F,3-t-Bu,4-I) | Ph(2-F,3-c-Pr,4-C$_2$F$_5$) |
| Ph(2-F,3-Et,4-i-Pr) | Ph(2-F,3-t-Bu,4-Et) | Ph(2-F,3-c-Pr,4-CF$_2$CF$_2$H) |
| Ph(2-F,3-Et,4-c-Pr) | Ph(2-F,3-t-Bu,4-n-Pr) | Ph(2-F,3-c-Pr,4-CF$_2$H) |
| Ph(2-F,3-Et,4-CF$_3$) | Ph(2-F,3,4-di-t-Bu) | Ph(2-F,3-c-Pr,4-OMe) |
| Ph(2-F,3-Et,4-C$_2$F$_5$) | Ph(2-F,3-t-Bu,4-i-Pr) | Ph(2-F,3-c-Pr,4-OCF$_2$CF$_2$H) |
| Ph(2-F,3-Et,4-CF$_2$CF$_2$H) | Ph(2-F,3-t-Bu,4-C$_2$F$_5$) | Ph(2-F,3-c-Pr,4-OC$_2$F$_5$) |
| Ph(2-F,3-Et,4-CF$_2$H) | Ph(2-F,3-t-Bu,4-CF$_2$CF$_2$H) | Ph(2-F,3-CF$_3$,4-I) |
| Ph(2-F,3-Et,4-OMe) | Ph(2-F,3-t-Bu,4-CF$_2$H) | Ph(2-F,3-CF$_3$,4-Et) |
| Ph(2-F,3-Et,4-OCF$_3$) | Ph(2-F,3-t-Bu,4-OMe) | Ph(2-F,3-CF$_3$,4-n-Pr) |
| Ph(2-F,3-Et,4-OCHF$_2$) | Ph(2-F,3-t-Bu,4-OCF$_2$CF$_2$H) | Ph(2-F,3-CF$_3$,4-i-Pr) |
| Ph(2-F,3-Et,4-OCF$_2$CF$_2$H) | Ph(2-F,3-t-Bu,4-OC$_2$F$_5$) | Ph(2-F,3,4-di-CF$_3$) |
| Ph(2-F,3-Et,4-OC$_2$F$_5$) | Ph(2-F,3-i-Pr,4-Cl) | Ph(2-F,3-CF$_3$,4-C$_2$F$_5$) |
| Ph(2-F,3-Et,4-SO$_2$Me) | Ph(2-F,3-i-Pr,4-F) | Ph(2-F,3-CF$_3$,4-CF$_2$CF$_2$H) |
| Ph(2-F,3-Et,4-TMS) | Ph(2-F,3-i-Pr,4-Br) | Ph(2-F,3-CF$_3$,4-CF$_2$H) |
| Ph(2-F,3-Et,4-CN) | Ph(2-F,3-i-Pr,4-I) | Ph(2-F,3-CF$_3$,4-OMe) |
| Ph(2-F,3-n-Pr,4-Cl) | Ph(2-F,3-i-Pr,4-Me) | Ph(2-F,3-CF$_3$,4-OCF$_3$) |
| Ph(2-F,3-n-Pr,4-F) | Ph(2-F,3-i-Pr,4-Et) | Ph(2-F,3-CF$_3$,4-OCHF$_2$) |
| Ph(2-F,3-CF$_3$,4-OCF$_2$CF$_2$H) | Ph(2-F,3-CF$_2$CF$_2$H,4-C$_2$F$_5$) | Ph(2-F,3-OMe,4-I) |
| Ph(2-F,3-CF$_3$,4-OC$_2$F$_5$) | Ph(2-F,3,4-di-CF$_2$CF$_2$H) | Ph(2-F,3-OMe,4-Me) |
| Ph(2-F,3-CF$_3$,4-TMS) | Ph(2-F,3-CF$_2$CF$_2$H,4-CF$_2$H) | Ph(2-F,3-OMe,4-Et) |
| Ph(2-F,3-CF$_3$,4-CN) | Ph(2-F,3-CF$_2$CF$_2$H,4-OMe) | Ph(2-F,3-OMe,4-n-Pr) |
| Ph(2-F,3-C$_2$F$_5$,4-Cl) | Ph(2-F,3-CF$_2$CF$_2$H,4-OCF$_3$) | Ph(2-F,3-OMe,4-t-Bu) |
| Ph(2-F,3-C$_2$F$_5$,4-F) | Ph(2-F,3-CF$_2$CF$_2$H,4-OCHF$_2$) | Ph(2-F,3-OMe,4-i-Pr) |

TABLE 1-continued

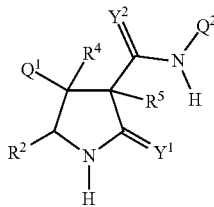

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(2-F,3-C$_2$F$_5$,4-Br) | Ph(2-F,3-CF$_2$CF$_2$H,4-OCF$_2$CF$_2$H) | Ph(2-F,3-OMe,4-c-Pr) |
| Ph(2-F,3-C$_2$F$_5$,4-I) | Ph(2-F,3-CF$_2$CF$_2$H,4-OC$_2$F$_5$) | Ph(2-F,3-OMe,4-CF$_3$) |
| Ph(2-F,3-C$_2$F$_5$,4-Me) | Ph(2-F,3-CF$_2$CF$_2$H,4-SO$_2$Me) | Ph(2-F,3-OMe,4-C$_2$F$_5$) |
| Ph(2-F,3-C$_2$F$_5$,4-Et) | Ph(2-F,3-CF$_2$CF$_2$H,4-TMS) | Ph(2-F,3-OMe,4-CF$_2$CF$_2$H) |
| Ph(2-F,3-C$_2$F$_5$,4-n-Pr) | Ph(2-F,3-CF$_2$CF$_2$H,4-CN) | Ph(2-F,3-OMe,4-CF$_2$H) |
| Ph(2-F,3-C$_2$F$_5$,4-t-Bu) | Ph(2-F,3-CF$_2$H,4-Cl) | Ph(2-F,3,4-di-OMe) |
| Ph(2-F,3-C$_2$F$_5$,4-i-Pr) | Ph(2-F,3-CF$_2$H,4-F) | Ph(2-F,3-OMe,4-OCF$_3$) |
| Ph(2-F,3-C$_2$F$_5$,4-c-Pr) | Ph(2-F,3-CF$_2$H,4-Br) | Ph(2-F,3-OMe,4-OCHF$_2$) |
| Ph(2-F,3-C$_2$F$_5$CF$_3$,4-CF$_3$) | Ph(2-F,3-CF$_2$H,4-I) | Ph(2-F,3-OMe,4-OCF$_2$CF$_2$H) |
| Ph(2-F,3,4-di-C$_2$F$_5$) | Ph(2-F,3-CF$_2$H,4-Me) | Ph(2-F,3-OMe,4-OC$_2$F$_5$) |
| Ph(2-F,3-C$_2$F$_5$,4-CF$_2$CF$_2$H) | Ph(2-F,3-CF$_2$H,4-Et) | Ph(2-F,3-OMe,4-SO$_2$Me) |
| Ph(2-F,3-C$_2$F$_5$,4-CF$_2$H) | Ph(2-F,3-CF$_2$H,4-n-Pr) | Ph(2-F,3-OMe,4-TMS) |
| Ph(2-F,3-C$_2$F$_5$,4-OMe) | Ph(2-F,3-CF$_2$H,4-t-Bu) | Ph(2-F,3-OMe,4-CN) |
| Ph(2-F,3-C$_2$F$_5$,4-OCF$_3$) | Ph(2-F,3-CF$_2$H,4-i-Pr) | Ph(2-F,3-OCF$_3$,4-Cl) |
| Ph(2-F,3-C$_2$F$_5$,4-OCHF$_2$) | Ph(2-F,3-CF$_2$H,4-c-Pr) | Ph(2-F,3-OCF$_3$,4-F) |
| Ph(2-F,3-C$_2$F$_5$,4-OCF$_2$CF$_2$H) | Ph(2-F,3-CF$_2$H,4-CF$_3$) | Ph(2-F,3-OCF$_3$,4-Br) |
| Ph(2-F,3-C$_2$F$_5$,4-OC$_2$F$_5$) | Ph(2-F,3-CF$_2$H,4-C$_2$F$_5$) | Ph(2-F,3-OCF$_3$,4-I) |
| Ph(2-F,3-C$_2$F$_5$,4-SO$_2$Me) | Ph(2-F,3-CF$_2$H,4-CF$_2$CF$_2$H) | Ph(2-F,3-OCF$_3$,4-Me) |
| Ph(2-F,3-C$_2$F$_5$,4-TMS) | Ph(2-F,3,4-di-CF$_2$H) | Ph(2-F,3-OCF$_3$,4-Et) |
| Ph(2-F,3-C$_2$F$_5$,4-CN) | Ph(2-F,3-CF$_2$H,4-OMe) | Ph(2-F,3-OCF$_3$,4-n-Pr) |
| Ph(2-F,3-CF$_2$CF$_2$H,4-Cl) | Ph(2-F,3-CF$_2$H,4-OCF$_3$) | Ph(2-F,3-OCF$_3$,4-t-Bu) |
| Ph(2-F,3-CF$_2$CF$_2$H,4-F) | Ph(2-F,3-CF$_2$H,4-OCHF$_2$) | Ph(2-F,3-OCF$_3$,4-i-Pr) |
| Ph(2-F,3-CF$_2$CF$_2$H,4-Br) | Ph(2-F,3-CF$_2$H,4-OCF$_2$CF$_2$H) | Ph(2-F,3-OCF$_3$,4-CF$_3$) |
| Ph(2-F,3-CF$_2$CF$_2$H,4-I) | Ph(2-F,3-CF$_2$H,4-OC$_2$F$_5$) | Ph(2-F,3-OCF$_3$,4-C$_2$F$_5$) |
| Ph(2-F,3-CF$_2$CF$_2$H,4-Me) | Ph(2-F,3-CF$_2$H,4-SO$_2$Me) | Ph(2-F,3-OCF$_3$,4-CF$_2$CF$_2$H) |
| Ph(2-F,3-CF$_2$CF$_2$H,4-Et) | Ph(2-F,3-CF$_2$H,4-TMS) | Ph(2-F,3-OCF$_3$,4-CF$_2$H) |
| Ph(2-F,3-CF$_2$CF$_2$H,4-n-Pr) | Ph(2-F,3-CF$_2$H,4-CN) | Ph(2-F,3-OCF$_3$,4-OMe) |
| Ph(2-F,3-CF$_2$CF$_2$H,4-t-Bu) | Ph(2-F,3-OMe,4-Cl) | Ph(2-F,3,4-di-OCF$_3$) |
| Ph(2-F,3-CF$_2$CF$_2$H,4-i-Pr) | Ph(2-F,3-OMe,4-F) | Ph(2-F,3-OCF$_3$,4-OCHF$_2$) |
| Ph(2-F,3-CF$_2$CF$_2$H,4-c-Pr) | Ph(2-F,3-OMe,4-Br) | Ph(2-F,3-OCF$_3$,4-OCF$_2$CF$_2$H) |
| Ph(2-F,3-CF$_2$CF$_2$H,4-CF$_3$) | Ph(2-F,3-OCF$_2$CF$_2$H,4-OCF$_3$) | Ph(2-F,3-OCF$_3$,4-OC$_2$F$_5$) |
| Ph(2-F,3-OCHF$_2$,4-F) | Ph(2-F,3-OCF$_2$CF$_2$H),4-OCHF$_2$) | Ph(2-F,3-OCHF$_2$,4-Cl) |
| Ph(2-F,3-OCHF$_2$,4-Br) | Ph(2-F,3,4-di-OCF$_2$CF$_2$H) | Ph(2-F,3-SO$_2$Me,4-C$_2$F$_5$) |
| Ph(2-F,3-OCHF$_2$,4-I) | Ph(2-F,3-OCF$_2$CF$_2$H,4-OC$_2$F$_5$) | Ph(2-F,3-SO$_2$Me,4-CF$_2$CF$_2$H) |
| Ph(2-F,3-OCHF$_2$,4-Me) | Ph(2-F,3-OCF$_2$CF$_2$H,4-SO$_2$Me) | Ph(2-F,3-SO$_2$Me,4-CF$_2$H) |
| Ph(2-F,3-OCHF$_2$,4-Et) | Ph(2-F,3-OCF$_2$CF$_2$H,4-TMS) | Ph(2-F,3-SO$_2$Me,4-OMe) |
| Ph(2-F,3-OCHF$_2$,4-n-Pr) | Ph(2-F,3-OCF$_2$CF$_2$H,4-CN) | Ph(2-F,3-SO$_2$Me,4-OCHF$_2$) |
| Ph(2-F,3-OCHF$_2$,4-t-Bu) | Ph(2-F,3-OC$_2$F$_5$,4-Cl) | Ph(2-F,3-SO$_2$Me,4-OCF$_2$CF$_2$H) |
| Ph(2-F,3-OCHF$_2$,4-i-Pr) | Ph(2-F,3-OC$_2$F$_5$,4-F) | Ph(2-F,3-SO$_2$Me,4-OC$_2$F$_5$) |
| Ph(2-F,3-OCHF$_2$,4-c-Pr) | Ph(2-F,3-OC$_2$F$_5$,4-Br) | Ph(2-F,3-TMS,4-Cl) |
| Ph(2-F,3-OCHF$_2$CF$_3$,4-CF$_3$) | Ph(2-F,3-OC$_2$F$_5$,4-I) | Ph(2-F,3-TMS,4-F) |
| Ph(2-F,3-OC$_2$F$_5$,4-C$_2$F$_5$) | Ph(2-F,3-OC$_2$F$_5$,4-Me) | Ph(2-F,3-TMS,4-Br) |
| Ph(2-F,3-OCHF$_2$,4-CF$_2$CF$_2$H) | Ph(2-F,3-OC$_2$F$_5$,4-Et) | Ph(2-F,3-TMS,4-I) |
| Ph(2-F,3-OCHF$_2$,4-CF$_2$H) | Ph(2-F,3-OC$_2$F$_5$,4-n-Pr) | Ph(2-F,3-TMS,4-Me) |
| Ph(2-F,3-OCHF$_2$,4-OMe) | Ph(2-F,3-OC$_2$F$_5$,4-t-Bu) | Ph(2-F,3-TMS,4-Et) |
| Ph(2-F,3-OCHF$_2$,4-OCF$_3$) | Ph(2-F,3-OC$_2$F$_5$,4-i-Pr) | Ph(2-F,3-TMS,4-n-Pr) |
| Ph(2-F,3,4-di-OCHF$_2$) | Ph(2-F,3-OC$_2$F$_5$,4-c-Pr) | Ph(2-F,3-TMS,4-t-Bu) |
| Ph(2-F,3-OCHF$_2$,4-OCF$_2$CF$_2$H) | Ph(2-F,3-OC$_2$F$_5$CF$_3$,4-CF$_3$) | Ph(2-F,3-TMS,4-i-Pr) |
| Ph(2-F,3-OCHF$_2$,4-OC$_2$F$_5$) | Ph(2-F,3-OC$_2$F$_5$,4-CF$_2$CF$_2$H) | Ph(2-F,3-TMS,4-c-Pr) |
| Ph(2-F,3-OCHF$_2$,4-SO$_2$Me) | Ph(2-F,3-OC$_2$F$_5$,4-CF$_2$H) | Ph(2-F,3-TMS,4-CF$_3$) |
| Ph(2-F,3-OCHF$_2$,4-TMS) | Ph(2-F,3-OC$_2$F$_5$,4-OMe) | Ph(2-F,3-TMS,4-C$_2$F$_5$) |
| Ph(2-F,3-OCHF$_2$,4-CN) | Ph(2-F,3-OC$_2$F$_5$,4-OCF$_3$) | Ph(2-F,3-TMS,4-CF$_2$CF$_2$H) |
| Ph(2-F,3-OCF$_2$CF$_2$H,4-Cl) | Ph(2-F,3-OC$_2$F$_5$,4-OCHF$_2$) | Ph(2-F,3-TMS,4-CF$_2$H) |
| Ph(2-F,3-OCF$_2$CF$_2$H,4-F) | Ph(2-F,3-OC$_2$F$_5$,4-OCF$_2$CF$_2$H) | Ph(2-F,3-TMS,4-OMe) |
| Ph(2-F,3-OCF$_2$CF$_2$H,4-Br) | Ph(2-F,3,4-di-OC$_2$F$_5$) | Ph(2-F,3-TMS,4-OCF$_3$) |
| Ph(2-F,3-OCF$_2$CF$_2$H,4-I) | Ph(2-F,3-OC$_2$F$_5$,4-SO$_2$Me) | Ph(2-F,3-TMS,4-OCHF$_2$) |
| Ph(2-F,3-OCF$_2$CF$_2$H,4-Me) | Ph(2-F,3-OC$_2$F$_5$,4-TMS) | Ph(2-F,3-TMS,4-OCF$_2$CF$_2$H) |
| Ph(2-F,3-OCF$_2$CF$_2$H,4-Et) | Ph(2-F,3-OC$_2$F$_5$,4-CN) | Ph(2-F,3-TMS,4-OC$_2$F$_5$) |
| Ph(2-F,3-OCF$_2$CF$_2$H,4-n-Pr) | Ph(2-F,3-SO$_2$Me,4-Cl) | Ph(2-F,3-TMS,4-SO$_2$Me) |
| Ph(2-F,3-OCF$_2$CF$_2$H,4-t-Bu) | Ph(2-F,3-SO$_2$Me,4-Br) | Ph(2-F,3,4,-di-TMS) |
| Ph(2-F,3-OCF$_2$CF$_2$H,4-i-Pr) | Ph(2-F,3-SO$_2$Me,4-I) | Ph(2-F,3-TMS,4-CN) |
| Ph(2-F,3-OCF$_2$CF$_2$H,4-c-Pr) | Ph(2-F,3-SO$_2$Me,4-Me) | Ph(2-F,3-CN,4-F) |
| Ph(2-F,3-OCF$_2$CF$_2$H,4-CF$_3$) | Ph(2-F,3-SO$_2$Me,4-Et) | Ph(2-F,3-CN,4-Br) |
| Ph(2-F,3-OCF$_2$CF$_2$H,4-C$_2$F$_5$) | Ph(2-F,3-SO$_2$Me,4-n-Pr) | Ph(2-F,3-CN,4-I) |
| Ph(2-F,3-OCF$_2$CF$_2$H,4-CF$_2$CF$_2$H) | Ph(2-F,3-SO$_2$Me,4-t-Bu) | Ph(2-F,3-CN,4-Me) |
| | | Ph(2-F,3-CN,4-Et) |
| | | Ph(2-F,3-CN,4-n-Pr) |

TABLE 1-continued

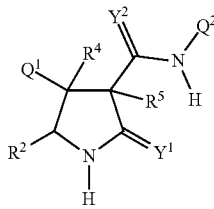

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-F,3-OCF₂CF₂H,4-CF₂H) | Ph(2-F,3-SO₂Me,4-i-Pr) | Ph(2-F,3-CN,4-t-Bu) |
| Ph(2-F,3-OCF₂CF₂H,4-OMe) | Ph(2-F,3-SO₂MeCF₃,4-CF₃) | Ph(2-F,3-CN,4-i-Pr) |
| Ph(2-F,3-CN,4-c-Pr) | Ph(2-F,3-F,5-I) | Ph(2-F,3-Br,5-OC₂F₅) |
| Ph(2-F,3-CN,4-CF₃) | Ph(2-F,3-F,5-Me) | Ph(2-F,3-Br,5-SO₂Me) |
| Ph(2-F,3-CN,4-C₂F₅) | Ph(2-F,3-F,5-Et) | Ph(2-F,3-Br,5-TMS) |
| Ph(2-F,3-CN,4-CF₂CF₂H) | Ph(2-F,3-F,5-n-Pr) | Ph(2-F,3-Br,5-CN) |
| Ph(2-F,3-CN,4-CF₂H) | Ph(2-F,3-F,5-t-Bu) | Ph(2-F,3-I,5-Cl) |
| Ph(2-F,3-CN,4-OMe) | Ph(2-F,3-F,5-i-Pr) | Ph(2-F,3-I,5-F) |
| Ph(2-F,3-CN,4-OCF₃) | Ph(2-F,3-F,5-c-Pr) | Ph(2-F,3-I,5-Br) |
| Ph(2-F,3-CN,4-OCHF₂) | Ph(2-F,3-F,5-CF₃) | Ph(2-F,3,5-di-I) |
| Ph(2-F,3-CN,4-OCF₂CF₂H) | Ph(2-F,3-F,5-C₂F₅) | Ph(2-F,3-I,5-Me) |
| Ph(2-F,3-CN,4-OC₂F₅) | Ph(2-F,3-F,5-CF₂CF₂H) | Ph(2-F,3-I,5-Et) |
| Ph(2-F,3-CN,4-TMS) | Ph(2-F,3-F,5-CF₂H) | Ph(2-F,3-I,5-n-Pr) |
| Ph(2-F,3,4-di-CN) | Ph(2-F,3-F,5-OMe) | Ph(2-F,3-I,5-t-Bu) |
| Ph(2-F,3,5-di-Cl) | Ph(2-F,3-F,5-OCF₃) | Ph(2-F,3-I,5-i-Pr) |
| Ph(2-F,3-Cl,5-F) | Ph(2-F,3-F,5-OCHF₂) | Ph(2-F,3-I,5-c-Pr) |
| Ph(2-F,3-Cl,5-Br) | Ph(2-F,3-F,5-OCF₂CF₂H) | Ph(2-F,3-I,5-CF₃) |
| Ph(2-F,3-Cl,5-I) | Ph(2-F,3-F,5-OC₂F₅) | Ph(2-F,3-I,5-C₂F₅) |
| Ph(2-F,3-Cl,5-Me) | Ph(2-F,3-F,5-SO₂Me) | Ph(2-F,3-I,5-CF₂CF₂H) |
| Ph(2-F,3-Cl,5-Et) | Ph(2-F,3-F,5-TMS) | Ph(2-F,3-I,5-CF₂H) |
| Ph(2-F,3-Cl,5-n-Pr) | Ph(2-F,3-F,5-CN) | Ph(2-F,3-I,5-OMe) |
| Ph(2-F,3-Cl,5-t-Bu) | Ph(2-F,3-Br,5-Cl) | Ph(2-F,3-I,5-OCF₃) |
| Ph(2-F,3-Cl,5-i-Pr) | Ph(2-F,3-Br,5-F) | Ph(2-F,3-I,5-OCHF₂) |
| Ph(2-F,3-Cl,5-c-Pr) | Ph(2-F,3,5-di-Br) | Ph(2-F,3-I,5-OCF₂CF₂H) |
| Ph(2-F,3-Cl,5-CF₃) | Ph(2-F,3-Br,5-I) | Ph(2-F,3-I,5-OC₂F₅) |
| Ph(2-F,3-Cl,5-C₂F₅) | Ph(2-F,3-Br,5-Me) | Ph(2-F,3-I,5-SO₂Me) |
| Ph(2-F,3-Cl,5-CF₂CF₂H) | Ph(2-F,3-Br,5-Et) | Ph(2-F,3-I,5-TMS) |
| Ph(2-F,3-Cl,5-CF₂H) | Ph(2-F,3-Br,5-n-Pr) | Ph(2-F,3-I,5-CN) |
| Ph(2-F,3-Cl,5-OMe) | Ph(2-F,3-Br,5-t-Bu) | Ph(2-F,3-Me,5-Cl) |
| Ph(2-F,3-Cl,5-OCF₃) | Ph(2-F,3-Br,5-i-Pr) | Ph(2-F,3-Me,5-F) |
| Ph(2-F,3-Cl,5-OCHF₂) | Ph(2-F,3-Br,5-c-Pr) | Ph(2-F,3-Me,5-Br) |
| Ph(2-F,3-Cl,5-OCF₂CF₂H) | Ph(2-F,3-Br,5-CF₃) | Ph(2-F,3-Me,5-I) |
| Ph(2-F,3-Cl,5-OC₂F₅) | Ph(2-F,3-Br,5-C₂F₅) | Ph(2-F,3,5,-di-Me) |
| Ph(2-F,3-Cl,5-SO₂Me) | Ph(2-F,3-Br,5-CF₂CF₂H) | Ph(2-F,3-Me,5-Et) |
| Ph(2-F,3-Cl,5-TMS) | Ph(2-F,3-Br,5-CF₂H) | Ph(2-F,3-Me,5-n-Pr) |
| Ph(2-F,3-Cl,5-CN) | Ph(2-F,3-Br,5-OMe) | Ph(2-F,3-Me,5-t-Bu) |
| Ph(2-F,3-F,5-Cl) | Ph(2-F,3-Br,5-OCF₃) | Ph(2-F,3-Me,5-i-Pr) |
| Ph(2,3,5-tri-F) | Ph(2-F,3-Br,5-OCHF₂) | Ph(2-F,3-Me,5-c-Pr) |
| Ph(2-F,3-F,5-Br) | Ph(2-F,3-Br,5-OCF₂CF₂H) | Ph(2-F,3-Me,5-CF₃) |
| Ph(2-F,3-Me,5-C₂F₅) | Ph(2-F,3-n-Pr,5-Me) | Ph(2-F,3-t-Bu,5-SO₂Me) |
| Ph(2-F,3-Me,5-CF₂CF₂H) | Ph(2-F,3-n-Pr,5-Et) | Ph(2-F,3-t-Bu,5-TMS) |
| Ph(2-F,3-Me,5-CF₂H) | Ph(2-F,3,5-di-n-Pr) | Ph(2-F,3-t-Bu,5-CN) |
| Ph(2-F,3-Me,5-OMe) | Ph(2-F,3-n-Pr,5-t-Bu) | Ph(2-F,3-i-Pr,5-Cl) |
| Ph(2-F,3-Me,5-OCF₃) | Ph(2-F,3-n-Pr,5-i-Pr) | Ph(2-F,3-i-Pr,5-F) |
| Ph(2-F,3-Me,5-OCHF₂) | Ph(2-F,3-n-Pr,5-c-Pr) | Ph(2-F,3-i-Pr,5-Br) |
| Ph(2-F,3-Me,5-OCF₂CF₂H) | Ph(2-F,3-n-Pr,5-CF₃) | Ph(2-F,3-i-Pr,5-I) |
| Ph(2-F,3-Me,5-OC₂F₅) | Ph(2-F,3-n-Pr,5-C₂F₅) | Ph(2-F,3-i-Pr,5-Me) |
| Ph(2-F,3-Me,5-SO₂Me) | Ph(2-F,3-n-Pr,5-CF₂CF₂H) | Ph(2-F,3-i-Pr,5-Et) |
| Ph(2-F,3-Me,5-TMS) | Ph(2-F,3-n-Pr,5-CF₂H) | Ph(2-F,3-i-Pr,5-n-Pr) |
| Ph(2-F,3-Me,5-CN) | Ph(2-F,3-n-Pr,5-OMe) | Ph(2-F,3-i-Pr,5-t-Bu) |
| Ph(2-F,3-Et,5-Cl) | Ph(2-F,3-n-Pr,5-OCF₃) | Ph(2-F,3,5-di-i-Pr) |
| Ph(2-F,3-Et,5-F) | Ph(2-F,3-n-Pr,5-OCHF₂) | Ph(2-F,3-i-Pr,5-c-Pr) |
| Ph(2-F,3-Et,5-Br) | Ph(2-F,3-n-Pr,5-OCF₂CF₂H) | Ph(2-F,3-i-Pr,5-CF₃) |
| Ph(2-F,3-Et,5-I) | Ph(2-F,3-n-Pr,5-OC₂F₅) | Ph(2-F,3-i-Pr,5-C₂F₅) |
| Ph(2-F,3-Et,5-Me) | Ph(2-F,3-n-Pr,5-SO₂Me) | Ph(2-F,3-i-Pr,5-CF₂CF₂H) |
| Ph(2-F,3,5-di-Et) | Ph(2-F,3-n-Pr,5-TMS) | Ph(2-F,3-i-Pr,5-CF₂H) |
| Ph(2-F,3-Et,5-n-Pr) | Ph(2-F,3-n-Pr,5-CN) | Ph(2-F,3-i-Pr,5-OMe) |
| Ph(2-F,3-Et,5-t-Bu) | Ph(2-F,3-t-Bu,5-Cl) | Ph(2-F,3-i-Pr,5-OCF₃) |
| Ph(2-F,3-Et,5-i-Pr) | Ph(2-F,3-t-Bu,5-F) | Ph(2-F,3-i-Pr,5-OCFH2) |
| Ph(2-F,3-Et,5-c-Pr) | Ph(2-F,3-t-Bu,5-Br) | Ph(2-F,3-i-Pr,5-OCF₂CF₂H) |
| Ph(2-F,3-Et,5-CF₃) | Ph(2-F,3-t-Bu,5-I) | Ph(2-F,3-i-Pr,5-OC₂F₅) |
| Ph(2-F,3-Et,5-C₂F₅) | Ph(2-F,3-t-Bu,5-Me) | Ph(2-F,3-i-Pr,5-SO₂Me) |
| Ph(2-F,3-Et,5-CF₂CF₂H) | Ph(2-F,3-t-Bu,5-Et) | Ph(2-F,3-i-Pr,5-TMS) |
| Ph(2-F,3-Et,5-CF₂H) | Ph(2-F,3-i-Bu,5-n-Pr) | Ph(2-F,3-i-Pr,5-CN) |
| Ph(2-F,3-Et,5-OMe) | Ph(2-F,3,5-di-t-Bu) | Ph(2-F,3-c-Pr,5-Cl) |
| Ph(2-F,3-Et,5-OCF₃) | Ph(2-F,3-t-Bu,5-i-Pr) | Ph(2-F,3-c-Pr,5-F) |

TABLE 1-continued

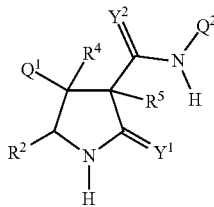

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(2-F,3-Et,5-OCHF$_2$) | Ph(2-F,3-t-Bu,5-c-Pr) | Ph(2-F,3-c-Pr,5-Br) |
| Ph(2-F,3-Et,5-OCF$_2$CF$_2$H) | Ph(2-F,3-t-Bu,5-CF$_3$) | Ph(2-F,3-c-Pr,5-I) |
| Ph(2-F,3-Et,5-OC$_2$F$_5$) | Ph(2-F,3-t-Bu,,5-C$_2$F$_5$) | Ph(2-F,3-c-Pr,5-Me) |
| Ph(2-F,3-Et,5-SO$_2$Me) | Ph(2-F,3-t-Bu,5-CF$_2$CF$_2$H) | Ph(2-F,3-c-Pr,5-Et) |
| Ph(2-F,3-Et,5-TMS) | Ph(2-F,3-t-Bu,5-CF$_2$H) | Ph(2-F,3-c-Pr,5-n-Pr) |
| Ph(2-F,3-Et,5-CN) | Ph(2-F,3-t-Bu,5-OMe) | Ph(2-F,3-c-Pr,5-t-Bu) |
| Ph(2-F,3-n-Pr,5-Cl) | Ph(2-F,3-t-Bu,5-OCF$_3$) | Ph(2-F,3-c-Pr,5-i-Pr) |
| Ph(2-F,3-n-Pr,5-F) | Ph(2-F,3-t-Bu,5-OCHF$_2$) | Ph(2-F,3,5-di-c-Pr) |
| Ph(2-F,3-n-Pr,5-Br) | Ph(2-F,3-t-Bu,5-OCF$_2$CF$_2$H) | Ph(2-F,3-c-Pr,5-CF$_3$) |
| Ph(2-F,3-n-Pr,5-I) | Ph(2-F,3-t-Bu,5-OC$_2$F$_5$) | Ph(2-F,3-c-Pr,5-C$_2$F$_5$) |
| Ph(2-F,3-c-Pr,5-CF$_2$CF$_2$H) | Ph(2-F,3-C$_2$F$_5$,5-Et) | Ph(2-F,3-CF$_2$CF$_2$H,5-SO$_2$Me) |
| Ph(2-F,3-c-Pr,5-CF$_2$H) | Ph(2-F,3-C$_2$F$_5$,5-n-Pr) | Ph(2-F,3-CF$_2$CF$_2$H,5-TMS) |
| Ph(2-F,3-c-Pr,5-OMe) | Ph(2-F,3-C$_2$F$_5$,5-t-Bu) | Ph(2-F,3-CF$_2$CF$_2$H,5-CN) |
| Ph(2-F,3-c-Pr,5-OCF$_3$) | Ph(2-F,3-C$_2$F$_5$,t-i-Pr) | Ph(2-F,3-CF$_2$H,5-Cl) |
| Ph(2-F,3-c-Pr,5-OCHF$_2$) | Ph(2-F,3-C$_2$F$_5$,5-c-Pr) | Ph(2-F,3-CF$_2$H,5-F) |
| Ph(2-F,3-c-Pr,5-OCF$_2$CF$_2$H) | Ph(2-F,3-C$_2$F$_5$CF$_3$,5-CF$_3$) | Ph(2-F,3-CF$_2$H,5-Br) |
| Ph(2-F,3-c-Pr,5-OC$_2$F$_5$) | Ph(2-F,3,5-di-C$_2$F$_5$) | Ph(2-F,3-CF$_2$H,5-I) |
| Ph(2-F,3-c-Pr,5-SO$_2$Me) | Ph(2-F,3-C$_2$F$_5$,5-CF$_2$CF$_2$H) | Ph(2-F,3-CF$_2$H,5-Me) |
| Ph(2-F,3-c-Pr,5-TMS) | Ph(2-F,3-C$_2$F$_5$,5-CF$_2$H) | Ph(2-F,3-CF$_2$H,5-Et) |
| Ph(2-F,3-c-Pr,5-CN) | Ph(2-F,3-C$_2$F$_5$,5-OMe) | Ph(2-F,3-CF$_2$H,5-n-Pr) |
| Ph(2-F,3-CF$_3$,5-Cl) | Ph(2-F,3-C$_2$F$_5$,5-OCF$_3$) | Ph(2-F,3-CF$_2$H,5-t-Bu) |
| Ph(2-F,3-CF$_3$,5-F) | Ph(2-F,3-C$_2$F$_5$,5-OCHF$_2$) | Ph(2-F,3-CF$_2$H,5-i-Pr) |
| Ph(2-F,3-CF$_3$,5-Br) | Ph(2-F,3-C$_2$F$_5$,5-OCF$_2$CF$_2$H) | Ph(2-F,3-CF$_2$H,5-c-Pr) |
| Ph(2-F,3-CF$_3$,5-I) | Ph(2-F,3-C$_2$F$_5$,5-OC$_2$F$_5$) | Ph(2-F,3-CF$_2$H,5-CF$_3$) |
| Ph(2-F,3-CF$_3$,5-Me) | Ph(2-F,3-C$_2$F$_5$,5-SO$_2$Me) | Ph(2-F,3-CF$_2$H,5-C$_2$F$_5$) |
| Ph(2-F,3-CF$_3$,5-Et) | Ph(2-F,3-C$_2$F$_5$,5-TMS) | Ph(2-F,3-CF$_2$H,5-CF$_2$CF$_2$H) |
| Ph92-F,3-CF$_3$,5-n-Pr) | Ph(2-F,3-C$_2$F$_5$,5-CN) | Ph(2-F,3,5-di-CF$_2$H) |
| Ph(2-F,3-CF$_3$,5-t-Bu) | Ph(2-F,3-CF$_2$CF$_2$H,5-Cl) | Ph(2-F,3-CF$_2$H,5-OMe) |
| Ph(2-F,3-CF$_3$,5-i-Pr) | Ph(2-F,3-CF$_2$CF$_2$H,5-F) | Ph(2-F,3-CF$_2$H,5-OCF$_3$) |
| Ph(2-F,3-CF$_3$,5-c-Pr) | Ph(2-F,3-CF$_2$CF$_2$H,5-Br) | Ph(2-F,3-CF$_2$H,5-OCHF$_2$) |
| Ph(2-F,3,5-di-CF$_3$) | Ph(2-F,3-CF$_2$CF$_2$H,5-I) | Ph(2-F,3-CF$_2$H,5-OCF$_2$CF$_2$H) |
| Ph(2-F,3-CF$_3$,5-C$_2$F$_5$) | Ph(2-F,3-CF$_2$CF$_2$H,5-Me) | Ph(2-F,3-CF$_2$H,5-OC$_2$F$_5$) |
| Ph(2-F,3-CF$_3$,5-CF$_2$CF$_2$H) | Ph(2-F,3-CF$_2$CF$_2$H,5-Et) | Ph(2-F,3-CF$_2$H,5-SO$_2$Me) |
| Ph(2-F,3-CF$_3$,5-CF$_2$H) | Ph(2-F,3-CF$_2$CF$_2$H,5-n-Pr) | Ph(2-F,3-CF$_2$H,5-TMS) |
| Ph(2-F,3-CF$_3$,5-OMe) | Ph(2-F,3-CF$_2$CF$_2$H,5-t-Bu) | Ph(2-F,3-CF$_2$H,5-CN) |
| Ph(2-F,3-CF$_3$,5-OCF$_3$) | Ph(2-F,3-CF$_2$CF$_2$H,5-i-Pr) | Ph(2-F,3-OMe,5-Cl) |
| Ph(2-F,3-CF$_3$,5-OCHF$_2$) | Ph(2-F,3-CF$_2$CF$_2$H,5-c-Pr) | Ph(2-F,3-OMe,5-F) |
| Ph(2-F,3-CF$_3$,5-OCF$_2$CF$_2$H) | Ph(2-F,3-CF$_2$CF$_2$H,5-CF$_3$) | Ph(2-F,3-OMe,5-Br) |
| Ph(2-F,3-CF$_3$,5-OC$_2$F$_5$) | Ph(2-F,3-CF$_2$CF$_2$H,5-C$_2$F$_5$) | Ph(2-F,3-OMe,5-I) |
| Ph(2-F,3-CF$_3$,5-SO$_2$Me) | Ph(2-F,3,5-di-CF$_2$CF$_2$H) | Ph(2-F,3-OMe,5-Me) |
| Ph(2-F,3-CF$_3$,5-TMS) | Ph(2-F,3-CF$_2$CF$_2$H,5-CF$_2$H) | Ph(2-F,3-OMe,5-Et) |
| Ph(2-F,3-CF$_3$,5-CN) | Ph(2-F,3-CF$_2$CF$_2$H,5-OMe) | Ph(2-F,3-OMe,5-n-Pr) |
| Ph(2-F,3-C$_2$F$_5$,5-Cl) | Ph(2-F,3-CF$_2$CF$_2$H,5-OCF$_3$) | Ph(2-F,3-OMe,5-t-Bu) |
| Ph(2-F,3-C$_2$F$_5$,5-F) | Ph(2-F,3-CF$_2$CF$_2$H,5-OCHF$_2$) | Ph(2-F,3-OMe,5-i-Pr) |
| Ph(2-F,3-C$_2$F$_5$,5-Br) | Ph(2-F,3-CF$_2$CF$_2$H,5-OCF$_2$CF$_2$H) | Ph(2F,3-OMe,5-c-Pr) |
| Ph(2-F,3-C$_2$F$_5$,5-I) | Ph(2-F,3-CF$_2$CF$_2$H,5-OC$_2$F$_5$) | Ph(2-F,3-OMe,5-CF$_3$) |
| Ph(2-F,3-C$_2$F$_5$,5-Me) | Ph(2-F,3-OCHF$_2$,5-Et) | Ph(2-F,3-OMe,5-C$_2$F$_5$) |
| Ph(2-F,3-OMe,5-CF$_2$CF$_2$H) | Ph(2-F,3-OCHF$_2$,5-n-Pr) | Ph(2-F,3-OCF$_2$CF$_2$H,5-SO$_2$Me) |
| Ph(2-F,3-OMe,5-CF$_2$H) | Ph(2-F,3-OCHF2,5-t-Bu) | Ph(2-F,3-OCF$_2$CF$_2$H,5-TMS) |
| Ph(2-F,3,5-di-OMe) | Ph(2-F,3-OCHF$_2$,5-i-Pr) | Ph(2-F,3-OCF$_2$CF$_2$H,5-CN) |
| Ph(2-F,3-OMe,5-OCF$_3$) | Ph(2-F,3-OCHF$_2$,5-c-Pr) | Ph(2-F,3-OC$_2$F$_5$,5-Cl) |
| Ph(2-F,3-OMe,5-OCHF$_2$) | Ph(2-F,3-OCHF$_2$CF$_3$,5-CF$_3$) | Ph(2-F,3-OC$_2$F$_5$,5-F) |
| Ph(2-F,3-OMe,5-OCF$_2$CF$_2$H) | Ph(2-F,3-OC$_2$F$_5$,5-C$_2$F$_5$) | Ph(2-F,3-OC$_2$F$_5$,5-Br) |
| Ph(2-F,3-OMe,5-OC$_2$F$_5$) | Ph(2-F,3-OCHF$_2$,5-CF$_2$CF$_2$H) | Ph(2-F,3-OC$_2$F$_5$,5-I) |
| Ph(2-F,3-OMe,5-SO$_2$Me) | Ph(2-F,3-OCHF$_2$,5-CF$_2$H) | Ph(2-F,3-OC$_2$F$_5$,5-Me) |
| Ph(2-F,3-OMe,5-TMS) | Ph(2-F,3-OCHF$_2$,5-OMe) | Ph(2-F,3-OC$_2$F$_5$,5-Et) |
| Ph(2-F,3-OMe,5-CN) | Ph(2-F,3-OCHF$_2$,5-OCF$_3$) | Ph(2-F,3-OC$_2$F$_5$,5-n-Pr) |
| Ph(2-F,3-OCF$_3$,5-Cl) | Ph(2-F,3,5-di-OCHF$_2$) | Ph(2-F,3-OC$_2$F$_5$,5-t-Bu) |
| Ph(2-F,3-OCF$_3$,5-F) | Ph(2-F,3-OCHF$_2$,5-OCF$_2$CF$_2$H) | Ph(2-F,3-OC$_2$F$_5$,5-i-Pr) |
| Ph(2-F,3-OCF$_3$,5-Br) | Ph(2-F,3-OCHF$_2$,5-OC$_2$F$_5$) | Ph(2-F,3-OC$_2$F$_5$,5-c-Pr) |
| Ph(2-F,3-OCF$_3$,5-I) | Ph(2-F,3-OCHF$_2$,5-SO$_2$Me) | Ph(2-F,3-OC$_2$F$_5$CF$_3$,5-CF$_3$) |
| Ph(2-F,3-OCF$_3$,5-Me) | Ph(2-F,3-OCHF$_2$,5-TMS) | Ph(2-F,3-OC$_2$F$_5$,5-CF$_2$CF$_2$H) |
| Ph(2-F,3-OCF$_3$,5-Et) | Ph(2-F,3-OCHF$_2$,5-CN) | Ph(2-F,3-OC$_2$F$_5$,5-CF$_2$H) |
| Ph(2-F,3-OCF$_3$,5-n-Pr) | Ph(2-F,3-OCF$_2$CF$_2$H,5-Cl) | Ph(2-F,3-OC$_2$F$_5$,5-OMe) |
| Ph(2-F,3-OCF$_3$,5-t-Bu) | Ph(2-F,3-OCF$_2$CF$_2$H,5-Cl) | Ph(2-F,3-OC$_2$F$_5$,5-OCF$_3$) |
| Ph(2-F,3-OCF$_3$,5-i-Pr) | Ph(2-F,3-OCF$_2$CF$_2$H,5-F) | Ph(2-F,3-OC$_2$F$_5$,5-OCHF$_2$) |

TABLE 1-continued

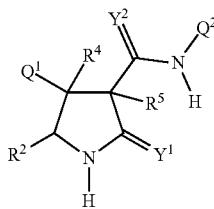

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-F,3-OCF$_3$,5-c-Pr) | Ph(2-F,3-OCF$_2$CF$_2$H,5-Br) | Ph(2-F,3-OC$_2$F$_5$,5-OCF$_2$CF$_2$H) |
| Ph(2-F,3-OCF$_3$,5-CF$_3$) | Ph(2-F,3-OCF$_2$CF$_2$H,5-I) | Ph(2-F,3,5-di-OC$_2$F$_5$) |
| Ph(2-F,3-OCF$_3$,5-C$_2$F$_5$) | Ph(2-F,3-OCF$_2$CF$_2$H,5-Me) | Ph(2-F,3-OC$_2$F$_5$,5-SO$_2$Me) |
| Ph(2-F,3-OCF$_3$,5-CF$_2$CF$_2$H) | Ph(2-F,3-OCF$_2$CF$_2$H,5-Et) | Ph(2-F,3-OC$_2$F$_5$,5-TMS) |
| Ph(2-F,3-OCF$_3$,5-CF$_2$H) | Ph(2-F,3-OCF$_2$CF$_2$H,5-n-Pr) | Ph(2-F,3-OC$_2$F$_5$,5-CN) |
| Ph(2-F,3-OCF$_3$,5-OMe) | Ph(2-F,3-OCF$_2$CF$_2$H,5-t-Bu) | Ph(2-F,3-SO$_2$Me,5-Cl) |
| Ph(2-F,3,5-di-OCF$_3$) | Ph(2-F,3-OCF$_2$CF$_2$H,5-i-Pr) | Ph(2-F,3-SO$_2$Me,5-F) |
| Ph(2-F,3-OCF$_3$,5-OCHF$_2$) | Ph(2-F,3-OCF$_2$CF$_2$H,5-c-Pr) | Ph(2-F,3-SO$_2$Me,5-Br) |
| Ph(2-F,3-OCF$_3$,5-OCF$_2$CF$_2$H) | Ph(2-F,3-OCF$_2$CF$_2$H,5-CF$_3$) | Ph(2-F,3-SO$_2$Me,5-I) |
| Ph(2-F,3-OCF$_3$,5-OC$_2$F$_5$) | Ph(2-F,3-OCF$_2$CF$_2$H,5-C$_2$F$_5$) | Ph(2-F,3-SO$_2$Me,5-Me) |
| Ph(2-F,3-OCF$_3$,5-SO$_2$Me) | Ph(2-F,3-OCF$_2$CF$_2$H,5-CF$_2$CF$_2$H) | Ph(2-F,3-SO$_2$Me,5-Et) |
| Ph(2-F,3-OCF$_3$,5-TMS) | Ph(2-F,3-OCF$_2$CF$_2$H,5-CF$_2$H) | Ph(2-F,3-SO$_2$Me,5-n-Pr) |
| Ph(2-F,3-OCF$_3$,5-CN) | Ph(2-F,3-OCF$_2$CF$_2$H,5-OMe) | Ph(2-F,3-SO$_2$Me,5-t-Bu) |
| Ph(2-F,3-OCHF$_2$,5-Cl) | Ph(2-F,3-OCF$_2$CF$_2$H,5-OCF$_3$) | Ph(2-F,3-SO$_2$Me,5-i-Pr) |
| Ph(2-F,3-OCHF$_2$,5-F) | Ph(2-F,3-OCF$_2$CF$_2$H,5-OCHF$_2$) | Ph(2-F,3-SO$_2$Me,5-c-Pr) |
| Ph(2-F,3-OCHF$_2$,5-Br) | Ph(2-F,3,5-di-OCF$_2$CF$_2$H) | Ph(2-F,3-SO$_2$MeCF$_3$,5-CF$_3$) |
| Ph(2-F,3-OCHF$_2$,5-I) | Ph(2-F,3-OCF$_2$CF$_2$H,5-OC$_2$F$_5$) | Ph(2-F,3-SO$_2$Me,5-C$_2$F$_5$) |
| Ph(2-F,3-OCHF$_2$,5-Me) | Ph(2-F,4-Cl,5-n-Pr) | Ph(2-F,3-SO$_2$Me,5-CF$_2$CF$_2$H) |
| Ph(2-F,3-SO$_2$Me,5-CF$_2$H) | Ph(2-F,3-CN,5-t-Bu) | Ph(2-F,4-Cl,5-CN) |
| Ph(2-F,3-SO$_2$Me,5-OMe) | Ph(2-F,3-CN,5-i-Pr) | Ph(2-F,4-F,5-Cl) |
| Ph(2-F,3-SO$_2$Me,5-OCF$_3$) | Ph(2-F,3-CN,5-c-Pr) | Ph(2,4,5-tri-F) |
| Ph(2-F,3-SO$_2$Me,5-OCHF$_2$) | Ph(2-F,3-CN,5-CF$_3$) | Ph(2-F,4-F,5-Br) |
| Ph(2-F,3-SO$_2$Me,5-OCF$_2$CF$_2$H) | Ph(2-F,3-CN,5-C$_2$F$_5$) | Ph(2-F,4-F,5-I) |
| Ph(2-F,3-SO$_2$Me,5-OC$_2$F$_5$) | Ph(2-F,3-CN,5-CF$_2$CF$_2$H) | Ph(2-F,4-F,5-Me) |
| Ph(2-F,3,5-di-SO$_2$Me) | Ph(2-F,3-CN,5-CF$_2$H) | Ph(2-F,4-F,5-Et) |
| Ph(2-F,3-SO$_2$Me,5-TMS) | Ph(2-F,3-CN,5-OMe) | Ph(2-F,4-F,5-n-Pr) |
| Ph(2-F,3-SO$_2$Me,5-CN) | Ph(2-F,3-CN,5-OCF$_3$) | Ph(2-F,4-F,5-t-Bu) |
| Ph(2-F,3-TMS,5-Cl) | Ph(2-F,3-CN,5-OCHF$_2$) | Ph(2-F,4-F,5-i-Pr) |
| Ph(2-F,3-TMS,5-F) | Ph(2-F,3-CN,5-OCF$_2$CF$_2$H) | Ph(2-F,4-F,5-c-Pr) |
| Ph(2-F,3-TMS,5-Br) | Ph(2-F,3-CN,5-OC$_2$F$_5$) | Ph(2-F,4-F,5-CF$_3$) |
| Ph(2-F,3-TMS,5-I) | Ph(2-F,3-CN,5-SO$_2$Me) | Ph(2-F,4-F,5-C$_2$F$_5$) |
| Ph(2-F,3-TMS,5-Me) | Ph(2-F,3-CN,5-TMS) | Ph(2-F,4-F,5-CF$_2$CF$_2$H) |
| Ph(2-F,3-TMS,5-Et) | Ph(2-F,3,5-di-CN) | Ph(2-F,4-F,5-CF$_2$H) |
| Ph(2-F,3-TMS,5-n-Pr) | Ph(2-F,4,5-di-Cl) | Ph(2-F,4-F,5-OMe) |
| Ph(2-F,3-TMS,5-t-Bu) | Ph(2-F,4-Cl,5-F) | Ph(2-F,4-F,5-OCF$_3$) |
| Ph(2-F,3-TMS,5-i-Pr) | Ph(2-F,4-Cl,5-Br) | Ph(2-F,4-F,5-OCHF$_2$) |
| Ph(2-F,3-TMS,5-c-Pr) | Ph(2-F,4-Cl,5-I) | Ph(2-F,4-F,5-OCF$_2$CF$_2$H) |
| Ph(2-F,3-TMS,5-CF$_3$) | Ph(2-F,4-Cl,5-Me) | Ph(2-F,4-F,5-OC$_2$F$_5$) |
| Ph(2-F,3-TMS,5-C$_2$F$_5$) | Ph(2-F,4-Cl,5-Et) | Ph(2-F,4-F,5-SO$_2$Me) |
| Ph(2-F,3-TMS,5-CF$_2$CF$_2$H) | Ph(2-F,4-Cl,5-n-Pr) | Ph(2-F,4-F,5-TMS) |
| Ph(2-F,3-TMS,5-CF$_2$H) | Ph(2-F,4-Cl,5-t-Bu) | Ph(2-F,4-F,5-CN) |
| Ph(2-F,3-TMS,5-OMe) | Ph(2-F,4-Cl,5-i-Pr) | Ph(2-F,4-Br,5-Cl) |
| Ph(2-F,3-TMS,5-OCF$_3$) | Ph(2-F,4-Cl,5-c-Pr) | Ph(2-F,4-Br,5-F) |
| Ph(2-F,3-TMS,5-OCHF$_2$) | Ph(2-F,4-Cl,5-CF$_3$) | Ph(2-F,4,5-di-Br) |
| Ph(2-F,3-TMS,5-OCF$_2$CF$_2$H) | Ph(2-F,4-Cl,5-C$_2$F$_5$) | Ph(2-F,4-Br,5-I) |
| Ph(2-F,3-TMS,5-OC$_2$F$_5$) | Ph(2-F,4-Cl,5-CF$_2$CF$_2$H) | Ph(2-F,4-Br,5-Me) |
| Ph(2-F,3-TMS,5-SO$_2$Me) | Ph(2-F,4-Cl,5-CF$_2$H) | Ph(2-F,4-Br,5-Et) |
| Ph(2-F,3,5-di-TMS) | Ph(2-F,4-Cl,5-OMe) | Ph(2-F,4-Br,5-n-Pr) |
| Ph(2-F,3-TMS,5-CN) | Ph(2-F,4-Cl,5-OCF$_3$) | Ph(2-F,4-Br,5-t-Bu) |
| Ph(2-F,3-CN,5-Cl) | Ph(2-F,4-Cl,5-OCHF$_2$) | Ph(2-F,4-Br,5-i-Pr) |
| Ph(2-F,3-CN,5-F) | Ph(2-F,4-Cl,5-OCF$_2$CF$_2$H) | Ph(2-F,4-Br,5-c-Pr) |
| Ph(2-F,3-CN,5-Br) | Ph(2-F,4-Cl,5-OC$_2$F$_5$) | Ph(2-F,4-Br,5-CF$_3$) |
| Ph(2-F,3-CN,5-I) | Ph(2-F,4-Cl,5-SO$_2$Me) | Ph(2-F,4-Br,5-C$_2$F$_5$) |
| Ph(2-F,3-CN,5-Me) | Ph(2-F,4-Cl,5-TMS) | Ph(2-F,4-Br,5-CF$_2$CF$_2$H) |
| Ph(2-F,3-CN,5-Et) | Ph(2-F,4-Me,5-t-Bu) | Ph(2-F,4-Br,5-CF$_2$H) |
| Ph(2-F,4-Br,5-OMe) | Ph(2-F,4-Me,5-i-Pr) | Ph(2-F,4-n-Pr,5-Cl) |
| Ph(2-F,4-Br,5-OCF$_3$) | Ph(2-F,4-Me,5-c-Pr) | Ph(2-F,4-n-Pr,5-F) |
| Ph(2-F,4-Br,5-OCHF$_2$) | Ph(2-F,4-Me,5-CF$_3$) | Ph(2-F,4-n-Pr,5-Br) |
| Ph(2-F,4-Br,5-OCF$_2$CF$_2$H) | Ph(2-F,4-Me,5-C$_2$F$_5$) | Ph(2-F,4-n-Pr,5-I) |
| Ph(2-F,4-Br,5-OC$_2$F$_5$) | Ph(2-F,4-Me,5-CF$_2$CF$_2$H) | Ph(2-F,4-n-Pr,5-Me) |
| Ph(2-F,4-Br,5-SO$_2$Me) | Ph(2-F,4-Me,5-CF$_2$H) | Ph(2-F,4-n-Pr,5-Et) |
| Ph(2-F,4-Br,5-TMS) | Ph(2-F,4-Me,5-OMe) | Ph(2-F,4,5-di-n-Pr) |
| Ph(2-F,4-Br,5-CN) | Ph(2-F,4-Me,5-OCF$_3$) | Ph(2-F,4-n-Pr,5-t-Bu) |
| Ph(2-F,4-I,5-Cl) | Ph(2-F,4-Me,5-OCHF$_2$) | Ph(2-F,4-n-Pr,,5-i-Pr) |
| Ph(2-F,4-I,5-F) | Ph(2-F,4-Me,5-OCF$_2$CF$_2$H) | Ph(2-F,4-n-Pr,5-c-Pr) |
| Ph(2-F,4-I,5-Br) | Ph(2-F,4-Me,5-OCF$_2$CF$_2$H) | Ph(2-F,4-n-Pr,5-CF$_3$) |

TABLE 1-continued

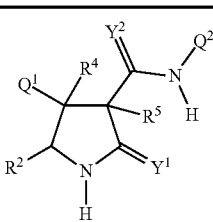

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-F,4,5-di-I) | Ph(2-F,4-Me,5-OC₂F₅) | Ph(2-F,4-n-Pr,5-C₂F₅) |
| Ph(2-F,4-I,5-Me) | Ph(2-F,4-Me,5-SO₂Me) | Ph(2-F,4-n-Pr,5-CF₂CF₂H) |
| Ph(2-F,4-I,5-Et) | Ph(2-F,4-Me,5-TMS) | Ph(2-F,4-n-Pr,5-CF₂H) |
| Ph(2-F,4-I,5-n-Pr) | Ph(2-F,4-Me,5-CN) | Ph(2-F,4-n-Pr,5-OMe) |
| Ph(2-F,4-I,5-t-Bu) | Ph(2-F,4-Et,5-Cl) | Ph(2-F,4-n-Pr,5-OCF₃) |
| Ph(2-F,4-I,5-i-Pr) | Ph(2-F,4-Et,5-F) | Ph(2-F,4-n-Pr,5-OCHF₂) |
| Ph(2-F,4-I,5-c-Pr) | Ph(2-F,4-Et,5-Br) | Ph(2-F,4-n-Pr,5-OCF₂CF₂H) |
| Ph(2-F,4-I,5-CF₃) | Ph(2-F,4-Et,5-I) | Ph(2-F,4-n-Pr,5-OC₂F₅) |
| Ph(2-F,4-I,5-C₂F₅) | Ph(2-F,4-Et,5-Me) | Ph(2-F,4-n-Pr,5-SO₂Me) |
| Ph(2-F,4-I,5-CF₂CF₂H) | Ph(2-F,4,5-di-Et) | Ph(2-F,4-n-Pr,5-TMS) |
| Ph(2-F,4-I,5-CF₂H) | Ph(2-F,4-Et,5-n-Pr) | Ph(2-F,4-n-Pr,5-CN) |
| Ph(2-F,4-I,5-OMe) | Ph(2-F,4-Et,5-t-Bu) | Ph(2-F,4-t-Bu,5-Cl) |
| Ph(2-F,4-I,5-OCF₃) | Ph(2-F,4-Et,5-i-Pr) | Ph(2-F,4-t-Bu,5-F) |
| Ph(2-F,4-I,5-OCHF₂) | Ph(2-F,4-Et,5-c-Pr) | Ph(2-F,4-t-Bu,5-Br) |
| Ph(2-F,4-I,5-OCF₂CF₂H) | Ph(2-F,4-Et,5-CF₃) | Ph(2-F,4-t-Bu,5-I) |
| Ph(2-F,4-I,5-OC₂F₅) | Ph(2-F,4-Et,5-C₂F₅) | Ph(2-F,4-t-Bu,5-Me) |
| Ph(2-F,4-I,5-SO₂Me) | Ph(2-F,4-Et,5-CF₂CF₂H) | Ph(2-F,4-t-Bu,5-Et) |
| Ph(2-F,4-I,5-TMS) | Ph(2-F,4-Et,5-CF₂H) | Ph(2-F,4-t-Bu,5-n-Pr) |
| Ph(2-F,4-I,5-CN) | Ph(2-F,4-Et,5-OMe) | Ph(2-F,4,5-di-t-Bu) |
| Ph(2-F,4-Me,5-Cl) | Ph(2-F,4-Et,5-OCF₃) | Ph(2-F,4-t-Bu,5-i-Pr) |
| Ph(2-F,4-Me,5-F) | Ph(2-F,4-Et,5-OCHF₂) | Ph(2-F,4-t-Bu,5-c-Pr) |
| Ph(2-F,4-Me,5-Br) | Ph(2-F,4-Et,5-OCF₂CF₂H) | Ph(2-F,4-t-Bu,5-CF₃) |
| Ph(2-F,4-Me,5-I) | Ph(2-F,4-Et,5-OC₂F₅) | Ph(2-F,4-t-Bu,5-C₂F₅) |
| Ph(2-F,4,5-di-Me) | Ph(2-F,4-Et,5-SO₂Me) | Ph(2-F,4-t-Bu,5-CF₂CF₂H) |
| Ph(2-F,4-Me,5-Et) | Ph(2-F,4-Et,5-TMS) | Ph(2-F,4-t-Bu,5-CF₂H) |
| Ph(2-F,4-Me,5-n-Pr) | Ph(2-F,4-Et,5-CN) | Ph(2-F,4-t-Bu,5-OMe) |
| Ph(2-F,4-t-Bu,5-OCF₃) | Ph(2-F,4-c-Pr,5-i-Pr) | Ph(2-F,4-CF₂CF₃,5-F) |
| Ph(2-F,4-t-Bu,5-OCHF₂) | Ph(2-F,4,5-di-c-Pr) | Ph(2-F,4-CF₂CF₃,5-Br) |
| Ph(2-F,4-t-Bu,5-OCF₂CF₂H) | Ph(2-F,4-c-Pr,5-CF₃) | Ph(2-F,4-CF₂CF₃,5-I) |
| Ph(2-F,4-t-Bu,5-OC₂F₅) | Ph(2-F,4-c-Pr,5-C₂F₅) | Ph(2-F,4-CF₂CF₃,5-Me) |
| Ph(2-F,4-t-Bu,5-SO₂Me) | Ph(2-F,4-c-Pr,5-CF₂CF₂H) | Ph(2-F,4-CF₂CF₃,5-Et) |
| Ph(2-F,4-t-Bu,5-TMS) | Ph(2-F,4-c-Pr,5-CF₂H) | Ph(2-F,4-CF₂CF₃,5-n-Pr) |
| Ph(2-F,4-t-Bu,5-CN) | Ph(2-F,4-c-Pr,5-OMe) | Ph(2-F,4-CF₂CF₃,5-t-Bu) |
| Ph(2-F,4-i-Pr,5-Cl) | Ph(2-F,4-c-Pr,5-OCF₃) | Ph(2-F,4-CF₂CF₃,5-i-Pr) |
| Ph(2-F,4-i-Pr,5-F) | Ph(2-F,4-c-Pr,5-OCHF₂) | Ph(2-F,4-CF₂CF₃,5-c-Pr) |
| Ph(2-F,4-i-Pr,5-Br) | Ph(2-F,4-c-Pr,5-OCF₂CF₂H) | Ph(2-F,4-C₂F₅CF₃,5-CF₃) |
| Ph(2-F,4-i-Pr,5-I) | Ph(2-F,4-c-Pr,5-OC₂F₅) | Ph(2-F,4,5-di-C₂F₅) |
| Ph(2-F,4-i-Pr,5-Me) | Ph(2-F,4-c-Pr,5-SO₂Me) | Ph(2-F,4-CF₂CF₃,5-CF₂CF₂H) |
| Ph(2-F,4-i-Pr,5-Et) | Ph(2-F,4-c-Pr,5-TMS) | Ph(2-F,4-CF₂CF₃,5-CF₂H) |
| Ph(2-F,4-i-Pr,5-n-Pr) | Ph(2-F,4-c-Pr,5-CN) | Ph(2-F,4-CF₂CF₃,5-OMe) |
| Ph(2-F,4-i-Pr,5-t-Bu) | Ph(2-F,4-CF₃,5-Cl) | Ph(2-F,4-CF₂CF₃,5-OCF₃) |
| Ph(2-F,4,5-di-i-Pr) | Ph(2-F,4-CF₃,5-F) | Ph(2-F,4-CF₂CF₃,5-OCHF₂) |
| Ph(2-F,4-i-Pr,5-c-Pr) | Ph(2-F,4-CF₃,5-Br) | Ph(2-F,4-CF₂CF₃,5-OCF₂CF₂H) |
| Ph(2-F,4-i-Pr,5-CF₃) | Ph(2-F,4-CF₃,5-I) | Ph(2-F,4-CF₂CF₃,5-OC₂F₅) |
| Ph(2-F,4-i-Pr,5-C₂F₅) | Ph(2-F,4-CF₃,5-Me) | Ph(2-F,4-CF₂CF₃,5-SO₂Me) |
| Ph(2-F,4-i-Pr,5-CF₂CF₂H) | Ph(2-F,4-CF₃,5-Et) | Ph(2-F,4-CF₂CF₃,5-TMS) |
| Ph(2-F,4-i-Pr,5-CF₂H) | Ph(2-F,4-CF₃,5-n-Pr) | Ph(2-F,4-CF₂CF₃,5-CN) |
| Ph(2-F,4-i-Pr,5-OMe) | Ph(2-F,4-CF₃,5-t-Bu) | Ph(2-F,4-CF₂CF₂H,5-Cl) |
| Ph(2-F,4-i-Pr,5-OCF₃) | Ph(2-F,4-CF₃,5-i-Pr) | Ph(2-F,4-CF₂CF₂H,5-F) |
| Ph(2-F,4-i-Pr,5-OCHF₂) | Ph(2-F,4-CF₃,5-c-Pr) | Ph(2-F,4-CF₂CF₂H,5-Br) |
| Ph(2-F,4-i-Pr,5-OCF₂CF₂H) | Ph(2-F,4,5-di-CF₃) | Ph(2-F,4-CF₂CF₂H,5-I) |
| Ph(2-F,4-i-Pr,5-OC₂F₅) | Ph(2-F,4-CF₃,5-C₂F₅) | Ph(2-F,4-CF₂CF₂H,5-Me) |
| Ph(2-F,4-i-Pr,5-SO₂Me) | Ph(2-F,4-CF₃,5-CF₂CF₂H) | Ph(2-F,4-CF₂CF₂H,5-Et) |
| Ph(2-F,4-i-Pr,5-TMS) | Ph(2-F,4-CF₃,5-CF₂H) | Ph(2-F,4-CF₂CF₂H,5-n-Pr) |
| Ph(2-F,4-i-Pr,5-CN) | Ph(2-F,4-CF₃,5-OMe) | Ph(2-F,4-CF₂CF₂H,5-t-Bu) |
| Ph(2-F,4-c-Pr,5-Cl) | Ph(2-F,4-CF₃,5-OCF₃) | Ph(2-F,4-CF₂CF₂H,5-i-Pr) |
| Ph(2-F,4-c-Pr,5-F) | Ph(2-F,4-CF₃,5-OCHF₂) | Ph(2-F,4-CF₂CF₂H,5-c-Pr) |
| Ph(2-F,4-c-Pr,5-Br) | Ph(2-F,4-CF₃,5-OCF₂CF₂H) | Ph(2-F,4-CF₂CF₂H,5-CF₃) |
| Ph(2-F,4-c-Pr,5-I) | Ph(2-F,4-CF₃,5-OC₂F₅) | Ph(2-F,4-CF₂CF₂H,5-C₂F₅) |
| Ph(2-F,4-c-Pr,5-Me) | Ph(2-F,4-CF₃,5-SO₂Me) | Ph(2-F,4,5-di-CF₂CF₂H) |
| Ph(2-F,4-c-Pr,5-Et) | Ph(2-F,4-CF₃,5-TMS) | Ph(2-F,4-CF₂CF₂H,5-CF₂H) |
| Ph(2-F,4-c-Pr,5-n-Pr) | Ph(2-F,4-CF₃,5-CN) | Ph(2-F,4-CF₂CF₂H,5-OMe) |
| Ph(2-F,4-c-Pr,5-t-Bu) | Ph(2-F,4-CF₂CF₃,5-Cl) | Ph(2-F,4-CF₂CF₂H,5-OCF₃) |
| Ph(2-F,4-CF₂CF₂H,5-OCHF₂) | Ph(2-F,4-OMe,5-i-Pr) | Ph(2-F,4-OCHF₂,5-F) |
| Ph(2-F,4-CF₂CF₂H,5-OCF₂CF₂H) | Ph(2-F,4-OMe,5-c-Pr) | Ph(2-F,4-OCHF₂,5-Br) |
| | Ph(2-F,4-OMe,5-CF₃) | Ph(2-F,4-OCHF₂,5-I) |

TABLE 1-continued

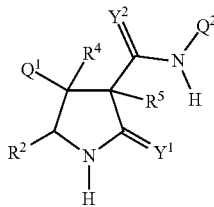

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-F,4-CF₂CF₂H,5-OC₂F₅) | Ph(2-F,4-OMe,5-C₂F₅) | Ph(2-F,4-OCHF₂,5-Me) |
| Ph(2-F,4-CF₂CF₂H,5-SO₂Me) | Ph(2-F,4-OMe,5-CF₂CF₂H) | Ph(2-F,4-OCHF₂,5-Et) |
| Ph(2-F,4-CF₂CF₂H,5-TMS) | Ph(2-F,4-OMe,5-CF₂H) | Ph(2-F,4-OCHF₂,5-n-Pr) |
| Ph(2-F,4-CF₂CF₂H,5-CN) | Ph(2-F,4,5-di-OMe) | Ph(2-F,4-OCHF₂,5-t-Bu) |
| Ph(2-F,4-CF₂H,5-Cl) | Ph(2-F,4-OMe,5-OCF₃) | Ph(2-F,4-OCHF₂,5-i-Pr) |
| Ph(2-F,4-CF₂H,5-F) | Ph(2-F,4-OMe,5-OCHF₂) | Ph(2-F,4-OCHF₂,5-c-Pr) |
| Ph(2-F,4-CF₂H,5-Br) | Ph(2-F,4-OMe,5-OCF₂CF₂H) | Ph(2-F,4-OCHF₂CF₃,5-CF₃) |
| Ph(2-F,4-CF₂H,5-I) | Ph(2-F,4-OMe,5-OC₂F₅) | Ph(2-F,4-OCF₂CF₃,5-C₂F₅) |
| Ph(2-F,4-CF₂H,5-Me) | Ph(2-F,4-OMe,5-SO₂Me) | Ph(2-F,4-OCHF₂,5-CF₂CF₂H) |
| Ph(2-F,4-CF₂H,5-Et) | Ph(2-F,4-OMe,5-TMS) | Ph(2-F,4-OCHF₂,5-CF₂H) |
| Ph(2-F,4-CF₂H,5-n-Pr) | Ph(2-F,4-OMe,5-CN) | Ph(2-F,4-OCHF₂,5-OMe) |
| Ph(2-F,4-CF₂H,5-t-Bu) | Ph(2-F,4-OCF₃,5-Cl) | Ph(2-F,4-OCHF₂,5-OCF₃) |
| Ph(2-F,4-CF₂H,5-i-Pr) | Ph(2-F,4-OCF₃,5-F) | Ph(2-F,4,5-di-OCHF₂) |
| Ph(2-F,4-CF₂H,5-c-Pr) | Ph(2-F,4-OCF₃,5-Br) | Ph(2-F,4-OCHF₂,5-OCF₂CF₂H) |
| Ph(2-F,4-CF₂H,5-CF₃) | Ph(2-F,4-OCF₃,5-I) | Ph(2-F,4-OCHF₂,5-OC₂F₅) |
| Ph(2-F,4-CF₂H,5-C₂F₅) | Ph(2-F,4-OCF₃,5-Me) | Ph(2-F,4-OCHF₂,5-SO₂Me) |
| Ph(2-F,4-CF₂H,5-CF₂CF₂H) | Ph(2-F,4-OCF₃,5-Et) | Ph(2-F,4-OCHF₂,5-TMS) |
| Ph(2-F,4,5-di-CF₂H) | Ph(2-F,4-OCF₃,5-n-Pr) | Ph(2-F,4-OCHF₂,5-CN) |
| Ph(2-F,4-CF₂H,5-OMe) | Ph(2-F,4-OCF₃,5-t-Bu) | Ph(2-F,4-OCF₂CF₂H,5-Cl) |
| Ph(2-F,4-CF₂H,5-OCF₃) | Ph(2-F,4-OCF₃,5-i-Pr) | Ph(2-F,4-OCF₂CF₂H,5-F) |
| Ph(2-F,4-CF₂H,5-OCHF₂) | Ph(2-F,4-OCF₃,5-c-Pr) | Ph(2-F,4-OCF₂CF₂H,5-Br) |
| Ph(2-F,4-CF₂H,5-OCF₂CF₂H) | Ph(2-F,4-OCF₃,5-CF₃) | Ph(2-F,4-OCF₂CF₂H,5-I) |
| Ph(2-F,4-CF₂H,5-OC₂F₅) | Ph(2-F,4-OCF₃,5-C₂F₅) | Ph(2-F,4-OCF₂CF₂H,5-Me) |
| Ph(2-F,4-CF₂H,5-SO₂Me) | Ph(2-F,4-OCF₃,5-CF₂CF₂H) | Ph(2-F,4-OCF₂CF₂H,5-Et) |
| Ph(2-F,4-CF₂H,5-TMS) | Ph(2-F,4-OCF₃,5-CF₂H) | Ph(2-F,4-OCF₂CF₂H,5-n-Pr) |
| Ph(2-F,4-CF₂H,5-CN) | Ph(2-F,4-OCF₃,5-OMe) | Ph(2-F,4-OCF₂CF₂H,5-t-Bu) |
| Ph(2-F,4-OMe,5-Cl) | Ph(2-F,4,5-di-OCF₃) | Ph(2-F,4-OCF₂CF₂H,5-i-Pr) |
| Ph(2-F,4-OMe,5-F) | Ph(2-F,4-OCF₃,5-OCHF₂) | Ph(2-F,4-OCF₂CF₂H,5-c-Pr) |
| Ph(2-F,4-OMe,5-Br) | Ph(2-F,4-OCF₃,5-OCF₂CF₂H) | Ph(2-F,4-OCF₂CF₂CF₂H,5-CF₃) |
| Ph(2-F,4-OMe,5-I) | Ph(2-F,4-OCF₃,5-OC₂F₅) | Ph(2-F,4-OCF₂CF₂H,5-C₂F₅) |
| Ph(2-F,4-OMe,5-Me) | Ph(2-F,4-OCF₃,5-SO₂Me) | Ph(2-F,4-OCF₂CF₂H,5-CF₂CF₂H) |
| Ph(2-F,4-OMe,5-Et) | Ph(2-F,4-OCF₃,5-TMS) | |
| Ph(2-F,4-OMe,5-n-Pr) | Ph(2-F,4-OCF₃,5-CN) | Ph(2-F,4-OCF₂CF₂H,5-CF₂H) |
| Ph(2-F,4-OMe,5-t-Bu) | Ph(2-F,4-OCHF₂,5-Cl) | Ph(2-F,4-OCF₂CF₂H,5-OMe) |
| Ph(2-F,4-OCF₂CF₂H,5-OCF₃) | Ph(2-F,SO₂Me,5-i-Pr) | Ph(2-F,4-CN,5-F) |
| Ph(2-F,4-OCF₂CF₂H,5-OCHF₂) | Ph(2-F,4-SO₂Me,5-c-Pr) | Ph(2-F,4-CN,5-Br) |
| Ph(2-F,4,5-di-OCF₂CF₂H) | Ph(2-F,4-SO₂MeCF₃,5-CF₃) | Ph(-F,4-CN,5-I) |
| Ph(2-F,4-OCF₂CF₂H,5-OC₂F₅) | Ph(2-F,4-SO₂Me,5-C₂F₅) | Ph(2-F,4-CN,5-Me) |
| Ph(2-F,4-OCF₂CF₂H,5-SO₂Me) | Ph(2-F,4-SO₂Me,5-CF₂CF₂H) | Ph(2-F,4-CN,5-Et) |
| Ph(2-F,4-OCF₂CF₂H,5-TMS) | Ph(2-F,4-SO₂Me,5-CF₂H) | Ph(2-F,4-CN,5-n-Pr) |
| Ph(2-F,4-OCF₂CF₂H,5-CN) | Ph(2-F,4-SO₂Me,5-OMe) | Ph(2-F,4-CN,5-t-Bu) |
| Ph(2-F,4-OCF₂CF₃,5-Cl) | Ph(2-F,4-SO₂Me,5-OCF₃) | Ph(2-F,4-CN,5-i-Pr) |
| Ph(2-F,4-OCF₂CF₃,5-F) | Ph(2-F,4-SO₂Me,5-OCHF₂) | Ph(2-F,4-CN,5-c-Pr) |
| Ph(2-F,4-OCF₂CF₃,5-Br) | Ph(2-F,4-SO₂Me,5-OCF₂CF₂H) | Ph(2-F,4-CN,5-CF₃) |
| Ph(2-F,4-OCF₂CF₃,5-I) | Ph(2-F,4-SO₂Me,5-OC₂F₅) | Ph(2-F,4-CN,5-C₂F₅) |
| Ph(2-F,4-OCF₂CF₃,5-Me) | Ph(2-F,4,5-di-SO₂Me) | Ph(2-F,4-CN,5-CF₂CF₂H) |
| Ph(2-F,4-OCF₂CF₃,5-Et) | Ph(2-F,4-SO₂Me,5-TMS) | Ph(2-F,4-CN,5-CF₂H) |
| Ph(2-F,4-OCF₂CF₃,5-n-Pr) | Ph(2-F,4-SO₂Me,5-CN) | Ph(2-F,4-CN,5-OMe) |
| Ph(2-F,4-OCF₂CF₃,5-t-Bu) | Ph(2-F,4-TMS,5-Cl) | Ph(2-F,4-CN,5-OCF₃) |
| Ph(2-F,4-OCF₂CF₃,5-i-Pr) | Ph(2-F,4-TMS,5-F) | Ph(2-F,4-CN,5-OCHF₂) |
| Ph(2-F,4-OCF₂CF₃,5-c-Pr) | Ph(2-F,4-TMS,5-Br) | Ph(2-F,4-CN,5-OCF₂CF₂H) |
| Ph(2-F,4-OC₂F₅CF₃,5-CF₃) | Ph(2-F,4-TMS,5-I) | Ph(2-F,4-CN,5-OC₂F₅) |
| Ph(2-F,4-OCF₂CF₃,5-CF₂CF₂H) | Ph(2-F,4-TMS,5-Me) | Ph(2-F,4-CN,5-SO₂Me) |
| Ph(2-F,4-OCF₂CF₃,5-CF₂H) | Ph(2-F,4-TMS,5-Et) | Ph(2-F,4-CN,5-TMS) |
| Ph(2-F,4-OCF₂CF₃,5-OMe) | Ph(2-F,4-TMS,5-n-Pr) | Ph(2-F,4,5-di-CN) |
| Ph(2-F,4-OCF₂CF₃,5-t-Bu) | Ph(2-F,4-TMS,5-t-Bu) | Ph(3,4,5-tri-Cl) |
| Ph(2-F,4-OCF₂CF₃,5-OCHF₂) | Ph(2-F,4-TMS,5-i-Pr) | Ph(3-Cl,4-F,5-Cl) |
| Ph(2-F,4-OCF₂CF₃,5-OCF₂CF₂H) | Ph(2-F,4-TMS,5-c-Pr) | Ph(3-Cl,4-Br,5-Cl) |
| Ph(2-F,4-OCF₂CF₃,5-CF₃) | Ph(2-F,4-TMS,5-C₂F₅) | Ph(3-Cl,4-I,5-Cl) |
| Ph(2-F,4,5-di-OC₂F₅) | Ph(2-F,4-TMS,5-CF₂CF₂H) | Ph(3-Cl,4-Me,5-Cl) |
| Ph(2-F,4-OCF₃,5-SO₂Me) | Ph(2-F,4-TMS,5-CF₂H) | Ph(3-Cl,4-Et,5-Cl) |
| Ph(2-F,4-OCF₂CF₃,5-TMS) | Ph(2-F,4-TMS,5-OMe) | Ph(3-Cl,4-n-Pr,5-Cl) |
| Ph(2-F,4-OCF₂CF₃,5-CN) | Ph(2-F,4-TMS,5-OCF₃) | Ph(3-Cl,4-t-Bu,5-Cl) |
| Ph(2-F,4-SO₂Me,5-Cl) | Ph(2-F,5-TMS,5-OCHF₂) | Ph(3-Cl,4-i-Pr,5-Cl) |
| Ph(2-F,4-SO₂Me,5-F) | Ph(2-F,4-TMS,5-OCF₂CF₂H) | Ph(3-Cl,4-c-Pr,5-Cl) |
| Ph(2-F,4-SO₂Me,5-Br) | | Ph(3-Cl,4-CF₃,5-Cl) |

TABLE 1-continued

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-F,4-SO₂Me,5-I) | Ph(2-F,4-TMS,5-OC₂F₅) | Ph(3-Cl,4-C₂F₅,5-Cl) |
| Ph(2-F,4-SO₂Me,5-Me) | Ph(2-F,4-TMS,5-SO₂Me) | Ph(3-Cl,4-CF₂CF₂H,5-Cl) |
| Ph(2-F,4-SO₂Me,5-Et) | Ph(2-F,4,5-di-TMS) | Ph(3-Cl,4-CF₂H,5-Cl) |
| Ph(2-F,4-SO₂Me,5-n-Pr) | Ph(2-F,4-TMS,5-CN) | Ph(3-Cl,4-OMe,5-Cl) |
| Ph(2-F,4-SO₂Me,5-t-Bu) | Ph(2-F,4-CN,5-Cl) | Ph(3-Cl,4-OCF₃,5-Cl) |
| Ph(3-Cl,4-OCHF₂,5-Cl) | Ph(3-Br,4-c-Pr,5-Br) | Ph(3-CF₃,4-Br,5-CF₃) |
| Ph(3-Cl,4-OCF₂CF₂H,5-Cl) | Ph(3-Br,4-CF₃,5-Br) | Ph(3-CF₃,4-I,5-CF₃) |
| Ph(3-Cl,4-OC₂F₅,5-Cl) | Ph(3-Br,4-C₂F₅,5-Br) | Ph(3-CF₃,4-Me,5-CF₃) |
| Ph(3-Cl,4-SO₂Me,5-Cl) | Ph(3-Br,4-CF₂CF₂H,5-Br) | Ph(3-CF₃,4-Et,5-CF₃) |
| Ph(3-Cl,4-TMS,5-Cl) | Ph(3-Br,4-CF₂H,5-Br) | Ph(3-CF₃,4-n-Pr,5-CF₃) |
| Ph(3-Cl,4-CN,5-Cl) | Ph(3-Br,4-OMe,5-Br) | Ph(3-CF₃,4-t-Bu,5-CF₃) |
| Ph(3-F,4-Cl,5-F) | Ph(3-Br,4-OCF₃,5-Br) | Ph(3-CF₃,4-i-Pr,5-CF₃) |
| Ph(3,4,5-tri-F) | Ph(3-Br,4-OCHF₂,5-Br) | Ph(3-CF₃,4-c-Pr,5-CF₃) |
| Ph(3-F,4-Br,5-F) | Ph(3-Br,4-OCF₂CF₂H,5-Br) | Ph(3,4,5-tri-CF₃) |
| Ph(3-F,4-I,5-F) | Ph(3-Br,4-OC₂F₅,5-Br) | Ph(3-CF₃,4-C₂F₅,5-CF₃) |
| Ph(3-F,4-Me,5-F) | Ph(3-Br,4-SO₂Me,5-Br) | Ph(3-CF₃,4-CF₂CF₂H,5-CF₃) |
| Ph(3-F,4-Et,5-F) | Ph(3-Br,4-TMS,5-Br) | Ph(3-CF₃,4-CF₂H,5-CF₃) |
| Ph(3-F,4-n-Pr,5-F) | Ph(3-Br,4-CN,5-Br) | Ph(3-CF₃,4-OMe,5-CF₃) |
| Ph(3-F,4-t-Bu,5-F) | Ph(3-Me,4-Cl,5-Me) | Ph(3-CF₃,4-OCF₃,5-CF₃) |
| Ph(3-F,4-i-Pr,5-F) | Ph(3-Me,4-F,5-Me) | Ph(3-CF₃,4-OCHF₂,5-CF₃) |
| Ph(3-F,4-c-Pr,5-F) | Ph(3-Me,4-Br,5-Me) | Ph(3-CF₃,4-OCF₂CF₂H,5-CF₃) |
| Ph(3-F,4-CF₃,5-F) | Ph(3-Me,4-I,5-Me) | Ph(3,5-di-CF₃,4-OC₂F₅) |
| Ph(3-F,4-C₂F₅,5-F) | Ph(3,4-tri-Me) | Ph(3-CF₃,4-SO₂Me,5-CF₃) |
| Ph(3-F,4-CF₂CF₂H,5-F) | Ph(3-Me,4-Et,5-Me) | Ph(3-CF₃,4-TMS,4-CF₃) |
| Ph(3-F,4-CF₂H,5-F) | Ph(3-Me,4-n-Pr,5-Me) | Ph(3-CF₃,4-CN,5-CF₃) |
| Ph(3-F,4-OMe,5-F) | Ph(3-Me,4-t-Bu,5-Me) | Ph(3-OCHF₂,4-Cl,5-OCHF₂) |
| Ph(3-F,4-OCF₃,5-F) | Ph(3-Me,4-i-Pr,5-Me) | Ph(3-OCHF₂,4-F,5-OCHF₂) |
| Ph(3-F,4-OCHF₂,5-F) | Ph(3-Me,4-c-Pr,5-Me) | Ph(3-OCHF₂,4-Br,5-OCHF₂) |
| Ph(3-F,4-OCF₂CF₂H,5-F) | Ph(3-Me,4-CF₃,5-Me) | Ph(3-OCHF₂,4-I,5-OCFH2) |
| Ph(3-F,4-OC₂F₅,5-F) | Ph(3-Me,4-C₂F₅,5-Me) | Ph(3-OCHF₂,4-Me,5-OCHF₂) |
| Ph(3-F,4-SO₂Me,5-F) | Ph(3-Me,4-CF₂CF₂H,5-Me) | Ph(3-OCHF₂,4-Et,5-OCHF₂) |
| Ph(3-F,4-TMS,5-F) | Ph(3-Me,4-CF₂H,5-Me) | Ph(3-OCHF₂,4-n-Pr,5-OCHF₂) |
| Ph(3-F,4-CN,5-F) | Ph(3-Me,4-OMe,5-Me) | Ph(3-OCHF₂,4-t-Bu,5-OCHF₂) |
| Ph(3-Br,4-Cl,5-Br) | Ph(3-Me,4-OCF₃,5-Me) | Ph(3-OCHF₂,4-i-Pr,5-OCHF₂) |
| Ph(3-Br,4-F,5-Br) | Ph(3-Me,4-OCHF₂,5-Me) | Ph(3-OCHF₂,4-c-Pr,5-OCHF₂) |
| Ph(3,4,5-tri-Br) | Ph(3-Me,4-OCF₂CF₂H,5-Me) | Ph(3,5-di-OCHF₂CF₃,4-CF₃,) |
| Ph(3-Br,4-I,5-Br) | Ph(3-Me,4-OC₂F₅,5-Me) | Ph(3-OC₂F₅,4-C₂F₅,5-OCHF₂) |
| Ph(3-Br,4-Me,5-Br) | Ph(3-Me,4-SO₂Me,5-Me) | Ph(3,5-di-OCHF₂,4-CF₂CF₂H) |
| Ph(3-Br,4-Et,5-Br) | Ph(3-Me,4-TMS,5-Me) | Ph(3-OCHF₂,4-CF₂H,5-OCHF₂) |
| Ph(3-Br,4-n-Pr,5-Br) | Ph(3-Me,4-CN,5-Me) | Ph(3-OCHF₂,4-OMe,5-OCHF₂) |
| Ph(3-Br,4-t-Bu,5-Br) | Ph(3-CF₃,4-Cl,5-CF₃) | Ph(3-OCHF₂,4-OCF₃,5-OCHF₂) |
| Ph(3-Br,4-i-Pr,5-Br) | Ph(3-CF₃,4-F,5-CF₃) | Ph(3,4,5-tri-OCHF₂) |
| Ph(3,5-di-OCHF₂,4-OCF₂CF₂H) | Ph(2-Cl,4-F,4-CF₃,5-F) | Ph(2-Cl,3-Me,4-I,5-Me) |
| Ph(3,5-di-OCHF₂,4-OC₂F₅) | Ph(2-Cl,3-F,4-C₂F₅,5-F) | Ph(2-Cl,3,4-tri-Me) |
| Ph(3,5-di-OCHF₂,4-SO₂Me) | Ph(2-Cl,3-F,4-CF₂CF₂H,5-F) | Ph(2-Cl,3-Me,4-Et,5-Me) |
| Ph(3-OCHF₂,4-TMS,5-OCHF₂) | Ph(2-Cl,3-F,4-CF₂H,5-F) | Ph(2-Cl,3-Me,4-n-Pr,5-Me) |
| Ph(3-OCHF₂,4-CN,5-OCHF₂) | Ph(2-Cl,3-F,4-OMe,5-F) | Ph(2-Cl,3-Me,4-t-Bu,5-Me) |
| Ph(2,3,4,5-tetra-Cl) | Ph(2-Cl,3-F,4-OCF₃,5-F) | Ph(2-Cl,3-Me,4-i-Pr,5-Me) |
| Ph(2-Cl,3-Cl,4-F,5-Cl) | Ph(2-Cl,3-F,4-OCHF₂,5-F) | Ph(2-Cl,3-Me,4-c-Pr,5-Me) |
| Ph(2-Cl,3-Cl,4-Br,5-Cl) | Ph(2-Cl,3-F,4-OCF₂CF₂H,5-F) | Ph(2-Cl,3-Me,4-CF₃,5-Me) |
| Ph(2-Cl,3-Cl,4-I,5-Cl) | Ph(2-Cl,3,5-di-F,4-OC₂F₅,) | Ph(2-Cl,3,5-di-Me,4-C₂F₅) |
| Ph(2-Cl,3-Cl,4-Me,5-Cl) | Ph(2-Cl,3-F,4-SO₂Me,5-F) | Ph(2-Cl,3-Me,4-CF₂CF₂H,5-Me) |
| Ph(2-Cl,3-Cl,4-Et,5-Cl) | Ph(2-Cl,3-F,4-TMS,5-F) | Ph(2-Cl,3-Me,4-CF₂H,5-Me) |
| Ph(2-Cl,3-Cl,4-n-Pr,5-Cl) | Ph(2-Cl,3-F,4-CN,5-F) | Ph(2-Cl,3-Me,4-OMe,5-Me) |
| Ph(2-Cl,3-Cl,4-t-Bu,5-Cl) | Ph(2-Cl,3-Br,4-Cl,5-Br) | Ph(2-Cl,3-Me,4-OCF₃,5-Me) |
| Ph(2-Cl,3-Cl,4-i-Pr,5-Cl) | Ph(2-Cl,3-Br,4-F,5-Br) | Ph(2-Cl,3-Me,4-OCHF₂,5-Me) |
| Ph(2-Cl,3-Cl,4-c-Pr,5-Cl) | Ph(2-Cl,3,4,5-tri-Br) | Ph(2-Cl,3,5-di-Me,4-OCF₂CF₂H) |
| Ph(2-Cl,3-Cl,4-CF₃,5-Cl) | Ph(2-Cl,3-Br,4-I,5-Br) | Ph(2-Cl,3-Me,4-OC₂F₅,5-Me) |
| Ph(2-Cl,3,5-di-Cl,4-C₂F₅) | Ph(2-Cl,3-br,4-Me,5-Br) | Ph(2-Cl,3,5-di-Me,4-SO₂Me) |
| Ph(2-Cl,3-Cl,4-CF₂CF₂H,5-Cl) | Ph(2-Cl,3-Br,4-Et,5-Br) | Ph(2-Cl,3-Me,4-TMS,5-Me) |
| Ph(2-Cl,3-Cl,4-CF₂H,5-Cl) | Ph(2-Cl,3-Br,4-n-Pr,5-Br) | Ph(2-Cl,3-Me,4-CN,5-Me) |
| Ph(2-Cl,3-Cl,4-OMe,5-Cl) | Ph(2-Cl,3-Br,4-t-Bu,5-Br) | Ph(2-Cl,3-CF₃,4-Cl,5-CF₃) |
| Ph(2-Cl,3-Cl,4-OCF₃,5-Cl) | Ph(2-Cl,3-Br,4-i-Pr,5-Br) | Ph(2-Cl,3-CF₃,4-F,5-CF₃) |
| Ph(2-Cl,3-Cl,4-OCHF₂,5-Cl) | Ph(2-Cl,3-Br,4-c-Pr,5-Br) | Ph(2-Cl,3-CF₃,4-Br,5-CF₃) |
| Ph(2-Cl,3-Cl,4-OCF₂CF₂H,5-Cl) | Ph(2-Cl,3-Br,4-CF₃,5-Br) | Ph(2-Cl,3-CF₃,4-I,5-CF₃) |
| Ph(2-Cl,3,5-di-Cl,4-OC₂F₅) | Ph(2-Cl,3,5-di-Br,4-C₂F₅) | Ph(2-Cl,3-CF₃,4-Me,5-CF₃) |

TABLE 1-continued

Y¹ is O; Y² is O; R² is H; R⁴ is H; R⁵ is H; Q² is Ph(2-F); and Q¹ is

| Q¹ | Q¹ | Q¹ |
|---|---|---|
| Ph(2-Cl,3-Cl,4-SO₂Me,5-Cl) | Ph(2-Cl,3-Br,4-CF₂CF₂H,5-Br) | Ph(2-Cl,3-CF₃,4-Et,5-CF₃) |
| Ph(2-Cl,3-Cl,4-TMS,5-Cl) | Ph(2-Cl,3-Br,4-CF₂H,5-Br) | Ph(2-Cl,3-CF₃,4-n-Pr,5-CF₃) |
| Ph(2-Cl,3-Cl,4-CN,5-Cl) | Ph(2-Cl,3-Br,4-OMe,5-Br) | Ph(2-Cl,3-CF₃,4-t-Bu,5-CF₃) |
| Ph(2-Cl,3-F,4-Cl,5-F) | Ph(2-Cl,3-Br,4-OCF₃,5-Br) | Ph(2-Cl,3-CF₃,4-i-Pr,5-CF₃) |
| Ph(2-Cl,3,4,5-tri-F) | Ph(2-Cl,3-Br,4-OCHF₂,5-Br) | Ph(2-Cl,3-CF₃,4-c-Pr,5-CF₃) |
| Ph(2-Cl,3-F,4-Br,5-F) | Ph(2-Cl,3-Br,4-OCF₂CF₂H,5-Br) | Ph(2-Cl,3,4,5-tri-CF₃) |
| Ph(2-Cl,3-F,4-I,5-F) | Ph(2-Cl,3,5-di-Br,4-OC₂F₅) | Ph(2-Cl,3,5-di-CF₃,4-C₂F₅) |
| Ph(2-Cl,3-F,4-Me,5-F) | Ph(2-Cl,3-Br,4-SO₂Me,5-Br) | Ph(2-Cl,3,5-di-CF₃,4-CF₂CF₂H) |
| Ph(2-Cl,3-F,4-Et,5-F) | Ph(2-Cl,3-Br,4-TMS,5-Br) | Ph(2-Cl,3-CF₃,4-CF₂H,5-CF₃) |
| Ph(2-Cl,3-F,4-n-Pr,5-F) | Ph(2-Cl,3-Br,4-CN,5-Br) | Ph(2-Cl,3-CF₃,4-OMe,5-CF₃) |
| Ph(2-Cl,3-F,4-t-Bu,5-F) | Ph(2-Cl,3-Me,4-Cl,5-Me) | Ph(2-Cl,3-CF₃,4-OCF₃,5-CF₃) |
| Ph(2-Cl,3-F,4-i-Pr,5-F) | Ph(2-Cl,3-Me,4-F,5-Me) | Ph(2-Cl,3-CF₃,4-OCHF₂,5-CF₃) |
| Ph(2-Cl,3-F,4-c-Pr,5-F) | Ph(2-Cl,3-Me,4-Br,5-Me) | Ph(2-Cl,3,5-di-CF₃,4-OCF₂CF₂H—) |
| Ph(2-Cl,3,5-di-CF₃,4-OC₂F₅) | Ph(2-F,3-Cl,4-Me,5-Cl) | Ph(2-F,3-F,4-SO₂Me,5-F) |
| Ph(2-Cl,3,5-di-CF₃,4-SO₂Me) | Ph(2-F,3-Cl,4-Et,5-Cl) | Ph(2-F,3-F,4-TMS,5-F) |
| Ph(2-Cl,3,5-di-CF₃,4-TMS) | Ph(2-F,3-Cl,4-n-Pr,5-Cl) | Ph(2-F,3-F,4-CN,5-F) |
| Ph(2-Cl,3-CF₃,4-CN,5-CF₃) | Ph(2-F,3-Cl,4-t-Bu,5-Cl) | Ph(2-F,3-Br,4-Cl,5-Br) |
| Ph(2-Cl,3,5-di-OCHF₂,4-Cl) | Ph(2-F,3-Cl,4-i-Pr,5-Cl) | Ph(2-F,3-Br,4-F,5-Br) |
| Ph(2-Cl,3-OCHF₂,4-F,5-OCHF₂) | Ph(2-F,3-Cl,4-c-Pr,5-Cl) | Ph(2-F,3,4,5-tri-Br) |
| Ph(2-Cl,3,5-di-OCHF₂,4-Br) | Ph(2-F,3-Cl,4-CF₃,5-Cl) | Ph(2-F,3-Br,4-I,5-Br) |
| Ph(2-Cl,3-OCHF₂,4-I,5-OCHF₂) | Ph(2-F,3-Cl,4-C₂F₅,5-Cl) | Ph(2-F,3-Br,4-Me,5-Br) |
| Ph(2-Cl,3,5-di-OCHF₂,4-Me) | Ph(2-F,3-Cl,4-CF₂CF₂H,5-Cl) | Ph(2-F,3-Br,4-Et,5-Br) |
| Ph(2-Cl,3,5-di-OCHF₂,4-Et) | Ph(2-F,3-Cl,4-CF₂H,5-Cl) | Ph(2-F,3-Br,4-n-Pr,5-Br) |
| Ph(2-Cl,3,5-di-OCHF₂,4-n-Pr) | Ph(2-F,3-Cl,4-OMe,5-Cl) | Ph(2-F,3-Br,4-t-Bu,5-Br) |
| Ph(2-Cl,3,5-di-OCHF₂,4-t-Bu) | Ph(2-F,3-Cl,4-OCF₃,5-Cl) | Ph(2-F,3-Br,4-i-Pr,5-Br) |
| Ph(2-Cl,3,5-di-OCHF₂,4-i-Pr) | Ph(2-F,3-Cl,4-OCHF₂,5-Cl) | Ph(2-F,3-Br,4-c-Pr,5-Br) |
| Ph(2-Cl,3,5-di-OCHF₂,4-c-Pr) | Ph(2-F,3-Cl,4-OCF₂CF₂H,5-Cl) | Ph(2-F,3-Br,4-CF₃,5-Br) |
| Ph(2-Cl,3,5-di-OCHF₂CF₃,4-CF₃) | Ph(2-F,3,5-di-Cl,4-OC₂F₅) | Ph(2-F,3,5-di-Br,4-C₂F₅) |
| Ph(2-Cl,3-OC₂F₅,4-C₂F₅,5-OCHF₂) | Ph(2-F,3-Cl,4-SO₂Me,5-Cl) | Ph(2-F,3-B,4-CF₂CF₂H,5-Br) |
| Ph(2-Cl,3,5-di-OCHF₂,4-CF₂CF₂H) | Ph(2-F,3-Cl,4-TMS,5-Cl) | Ph(2-F,3-Br,4-CF₂H,5-Br) |
| Ph(2-Cl,3-OCHF₂,4-CF₂H,5-OCHF₂) | Ph(2-F,3-Cl,4-CN,5-Cl) | Ph(2-F,3-Br,4-OMe,5-Br) |
| Ph(2-Cl,3,5-di OCHF₂,4-OMe) | Ph(2-F,3-F,4-Cl,5-F) | Ph(2-F,3-Br,4-OCF₃,5-Br) |
| Ph(2-Cl,3,5-di-OCHF₂,4-OCF₃) | Ph(2,3,4,5-tetra-F) | Ph(2-F,3-Br,4-OCHF₂,5-Br) |
| Ph(2-Cl,3,4,5-tri-OCHF₂) | Ph(2-F,3-F,4-Br,5-F) | Ph(2-F,3-Br,4-OCF₂CF₂H,5-Br) |
| Ph(2-Cl,3-OCHF₂,4-OCF₂CF₂H,5-OCHF₂) | Ph(2-F,3-F,4-I,5-F) | Ph(2-F,3-Br,4-OC₂F₅,5-Br) |
| Ph(2-Cl,3-OCHF₂,4-OC₂F₅,5-OCHF₂) | Ph(2-F,3-F,4-Me,5-F) | Ph(2-F,3-Br,4-SO₂Me,5-Br) |
| Ph(2-Cl,3,5-di-OCHF₂,4-SO₂Me) | Ph(2-F,3-F,4-Et,5-F) | Ph(2-F,3-Br,4-TMS,5-Br) |
| Ph(2-Cl,3,5-di-OCHF₂,4-TMS) | Ph(2-F,3-F,4-n-Pr,5-F) | Ph(2-F,3-Br,4-CN,5-Br) |
| Ph(2-Cl,3,5-di-OCHF₂,4-CN) | Ph(2-F,3-F,4-t-Bu,5-F) | Ph(2-F,3-Me,4-Cl,5-Me) |
| Ph(2-F,3,4,5-tri-Cl) | Ph(2-F,3-F,4-i-Pr,5-F) | Ph(2-F,3-Me,4-Br,5-Me) |
| Ph(2-F,3-Cl,4-F,5-Cl) | Ph(2-F,3-F,4-c-Pr,5-F) | Ph(2-F,3-Me,4-I,5-Me) |
| Ph(2-F,3-Cl,4-Br,5-Cl) | Ph(2-F,3-F,4-CF₃,5-F) | Ph(2-F,3,4-tri-Me) |
| Ph(2-F,3-Cl,4-I,5-Cl) | Ph(2-F,3-F,4-C₂F₅,5-F) | Ph(2-F,3-Me,4-Et,5-Me) |
| Ph(2-F,3-Me,4-CF₂CF₂H,5-Me) | Ph(2-F,3-F,4-CF₂CF₂H,5-F) | Ph(2-F,3-Me,4-n-Pr,5-Me) |
| Ph(2-F,3-Me,4-CF₂H,5-Me) | Ph(2-F,3-F,4-CF₂H,5-F) | Ph(2-F,3-Me,4-t-Bu,5-Me) |
| Ph(2-F,3-Me,4-OMe,5-Me) | Ph(2-F,3-F,4-OMe,5-F) | Ph(2-F,3-Me,4-i-Pr,5-Me) |
| Ph(2-F,3-Me,4-OCF₃,5-Me) | Ph(2-F,3-F,4-OCF₃,5-F) | Ph(2-F,3-Me,4-c-Pr,5-Me) |
| Ph(2-F,3-Me,4-OCHF₂,5-Me) | Ph(2-F,3-F,4-OCHF₂,5-F) | Ph(2-F,3-Me,4-CF₃,5-Me) |
| Ph(2-F,3-Me,4-OCF₂CF₂H,5-Me) | Ph(2-F,3-F,4-OCF₂CF₂H,5-F) | Ph(2-F,3-Me,4-C₂F₅,5-Me) |
| Ph(2-F,3-Me,4-OC₂F₅,5-Me) | Ph(2-F,3-F,4-OC₂F₅,5-F) | Ph(2-F,3-OCHF₂,4-TMS,5-OCHF₂) |
| Ph(2-F,3-Me,4-SO₂Me,5-Me) | Ph(2-F,3-OCHF₂,4-Cl,5-OCHF₂) | Ph(2-F,3-OCHF₂,4-CN,5-OCHF₂) |
| Ph(2-F,3-Me,4-TMS,5-Me) | Ph(2-F,3-OCHF₂,4-F,5-OCHF₂) | 1H-Imidazol-2-yl(1-CF₂CF₂H,5-Cl) |
| Ph(2-F,3-Me,4-CN,5-Me) | Ph(2-F,3-OCHF₂,4-Br,5-OCHF₂) | 1H-Imidazol-2-yl(1-CF₂CF₂H,5-F) |
| Ph(2-F,3-CF₃,4-Cl,5-CF₃) | Ph(2-F,3-OCHF₂,4-I,5-OCHF₂) | 1H-Imidazol-2-yl(1-CH₂CF₃,5-Cl) |
| Ph(2-F,3-CF₃,4-F,5-CF₃) | Ph(2-F,3-OCHF₂,4-Me,5-OCHF₂) | 1H-Imidazol-2-yl(1-CH₂CF₃,5-F) |
| Ph(2-F,3-CF₃,4-Br,5-CF₃) | Ph(2-F,3-OCHF₂,4-Et,5-OCHF₂) | 1H-Imidazol-2-yl(1-Me,5-CF₂H) |
| Ph(2-F,3-CF₃,4-I,5-CF₃) | Ph(2-F,3-OCHF₂,4-n-Pr,5-OCHF₂) | 1H-Imidazol-2-yl(1-CF₂CF₂H,5-CF₂H) |
| Ph(2-F,3-CF₃,4-Me,5-CF₃) | Ph(2-F,3-OCHF₂,4-t-Bu,5-OCHF₂) | 1H-Imidazol-2-yl(1-CH₂CF₃,5-CF₂H) |
| Ph(2-F,3-CF₃,4-Et,5-CF₃) | Ph(2-F,3-OCHF₂,4-i-Pr,5-OCHF₂) | |
| | Ph(2-F,3,5-di-OCHF₂,4-c-Pr) | |
| | Ph(2-F,3-OCHF₂CF₃,4-CF₃,5-OCHF₂) | |

TABLE 1-continued

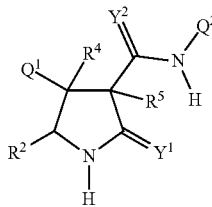

$Y^1$ is O; $Y^2$ is O; $R^2$ is H; $R^4$ is H; $R^5$ is H; $Q^2$ is Ph(2-F); and $Q^1$ is

| $Q^1$ | $Q^1$ | $Q^1$ |
|---|---|---|
| Ph(2-F,3-CF$_3$,4-n-Pr,5-CF$_3$) | Ph(2-F,3-OC$_2$F$_5$,4-C$_2$F$_5$,5-OCHF$_2$) | 1H-Imidazol-2-yl(1-Me,5-CF$_3$) |
| Ph(2-F,3-CF$_3$,4-t-Bu,5-CF$_3$) | Ph(2-F,3,5-di-OCHF$_2$,4-CF$_2$CF$_2$H) | 1H-Imidazol-2-yl(1-CF$_2$CF$_2$H,5-CF$_3$) |
| Ph(2-F,3-CF$_3$,4-i-Pr,5-CF$_3$) | Ph(2-F,3-OCHF$_2$,4-CF$_2$H,5-OCHF$_2$) | 1H-Imidazol-2-yl(1-CH$_2$CF$_3$,5-CF$_3$) |
| Ph(2-F,3-CF$_3$,4-c-Pr,5-CF$_3$) | Ph(2-F,3-OCHF$_2$,4-OMe,5-OCHF$_2$) | 1,3-Benzodioxol-4-yl |
| Ph(2-F,3,4,5-tri-CF$_3$) | Ph(2-F,3-OCHF$_2$,4-OCF$_3$,5-OCHF$_2$) | 1,3-Benzodioxol-4-yl(2,2-di-Me) |
| Ph(2-F,3-CF$_3$,4-C$_2$F$_5$,5-CF$_3$) | Ph(2-F,3,4,5-tri-OCHF$_2$) | 1,4-Benzodioxol-4-yl(2,3-dihydro) |
| Ph(2-F,3-CF$_3$,4-CF$_2$CF$_2$H,5-CF$_3$) | Ph(2-F,3-OCHF$_2$,4-OCF$_2$CF$_2$H,5-OCHF$_2$) | 1,4-Benzodioxol-4-yl(2,2,3,3-tetrafluoro) |
| Ph(2-F,3-CF$_3$,4-CF$_2$H,5-CF$_3$) | Ph(2-F,3-OCHF$_2$,4-OC$_2$F$_5$,5-OCHF$_2$) | 1H-Pyrazol-3-yl(1-CH$_2$CF$_3$,4-F) |
| Ph(2-F,3-CF$_3$,4-OMe,5-CF$_3$) | Ph(2-F,3-OCHF$_2$,4-SO$_2$Me,5-OCHF$_2$) | 1H-Pyrazol-3-yl(1-CH$_2$CF$_3$,4-Cl) |
| Ph(2-F,3-CF$_3$,4-OCF$_3$,5-CF$_3$) | | 1H-Pyrazol-3-yl(1-CF$_2$CF$_2$H,4-F) |
| Ph(2-F,3-CF$_3$,4-OCHF$_2$,5-CF$_3$) | | 1H-Pyrazol-3-yl(1-CF$_2$CF$_2$H,4-Cl) |
| Ph(2-F,3-CF$_3$,4-OCF$_2$CF$_2$H,5-CF$_3$) | | 1,3-Benzodioxol-4-yl(2,2-di-F) |
| Ph(2-F,3-CF$_3$,4-OC$_2$F$_5$,5-CF$_3$) | | |
| Ph(2-F,3-CF$_3$,4-SO$_2$Me,5-CF$_3$) | | |
| Ph(2-F,3-CF$_3$,4-TMS,5-CF$_3$) | | |
| Ph(2-F,3-CF$_3$,4-CN,5-CF$_3$) | | |

Table 2 is constructed in the same manner except that the Row Heading "$Y^1$ is O; $Y^2$ is O $R^2$ is H; $R^4$ is H; $R^5$ is H; $Q^2$ is Ph(2-F); and Q is" is replaced with the Row Heading listed for Table 2 below (i.e. "$Y^1$ is O; $Y^1$ is O; $R^2$ is H; $R^4$ is H; $R^5$ is H; $Q^2$ is Ph(2,3-F); and $Q^1$ is"). Therefore the first entry in Table 2 is a compound of Formula 1 wherein $Y^1$ is O, $R^2$ is H, $R^4$ is H, $R^5$ is H, $Q^2$ is Ph(2,3-F); and $Q^1$ is Ph(3-Cl) (i.e. 3-chlorophenyl). Tables 3 through 1699 are constructed similarly.

| Table | Row Heading |
|---|---|
| 2 | $Y^1$ is O; $Y^2$ is O; $R^2$ is H; $R^4$ is H; $R^5$ is H; $Q^2$ is Ph(2,3-di-F); and $Q^1$ is |
| 3 | $Y^1$ is O; $Y^2$ is O; $R^2$ is H; $R^4$ is H; $R^5$ is H; $Q^2$ is Ph(2,4-di-F); and $Q^1$ is |
| 4 | $Y^1$ is O; $Y^2$ is O; $R^2$ is H; $R^4$ is H; $R^5$ is H; $Q^2$ is Ph(2,5-di-F); and $Q^1$ is |
| 5 | $Y^1$ is O; $Y^2$ is O; $R^2$ is H; $R^4$ is H; $R^5$ is H; $Q^2$ is Ph(2,3,4-tri-F); and $Q^1$ is |
| 6 | $Y^1$ is O; $Y^2$ is O; $R^2$ is H; $R^4$ is H; $R^5$ is H; $Q^2$ is Ph(2,3,5-tri-F); and $Q^1$ is |
| 7 | $Y^1$ is O; $Y^2$ is O; $R^2$ is H; $R^4$ is H; $R^5$ is H; $Q^2$ is Ph(2,3,4,5-tetra-F); and $Q^1$ is |
| 8 | $Y^1$ is O; $Y^2$ is O; $R^2$ is H; $R^4$ is H; $R^5$ is H; $Q^2$ is Ph(2-F,3-Cl,4-Br); and $Q^1$ is |
| 9 | $Y^1$ is O; $Y^2$ is O; $R^2$ is H; $R^4$ is H; $R^5$ is H; $Q^2$ is Ph(2-F,3-Cl,4-F); and $Q^1$ is |
| 10 | $Y^1$ is O; $Y^2$ is O; $R^2$ is H; $R^4$ is H; $R^5$ is H; $Q^2$ is Ph(2-F,3-Br,4-F); and $Q^1$ is |
| 11 | $Y^1$ is O; $Y^2$ is O; $R^2$ is H; $R^4$ is H; $R^5$ is H; $Q^2$ is Ph(2-F,3-Me); and $Q^1$ is |
| 12 | $Y^1$ is O; $Y^2$ is O; $R^2$ is H; $R^4$ is H; $R^5$ is H; $Q^2$ is Ph(2-F,3-Me,4-F); and $Q^1$ is |
| 13 | $Y^1$ is O; $Y^2$ is O; $R^2$ is H; $R^4$ is H; $R^5$ is H; $Q^2$ is Ph(2-F,3-Me,4-Cl); and $Q^1$ is |
| 14 | $Y^1$ is O; $Y^2$ is O; $R^2$ is H; $R^4$ is H; $R^5$ is H; $Q^2$ is Ph(2-F,3-Cl); and $Q^1$ is |
| 15 | $Y^1$ is O; $Y^2$ is O; $R^2$ is H; $R^4$ is H; $R^5$ is H; $Q^2$ is Ph(2-F,4-Cl); and $Q^1$ is |
| 16 | $Y^1$ is O; $Y^2$ is O; $R^2$ is H; $R^4$ is H; $R^5$ is H; $Q^2$ is Ph(2-F,3,4-di-Cl); and $Q^1$ is |
| 17 | $Y^1$ is O; $Y^2$ is O; $R^2$ is H; $R^4$ is H; $R^5$ is H; $Q^2$ is Ph(2-F,4-Br); and $Q^1$ is |
| 18 | $Y^1$ is O; $Y^2$ is O; $R^2$ is H; $R^4$ is H; $R^5$ is H; $Q^2$ is Ph(2-F,3-OMe); and $Q^1$ is |
| 19 | $Y^1$ is O; $Y^2$ is O; $R^2$ is H; $R^4$ is H; $R^5$ is H; $Q^2$ is Ph(2-F,3-OMe,4-F); and $Q^1$ is |
| 20 | $Y^1$ is O; $Y^2$ is O; $R^2$ is H; $R^4$ is H; $R^5$ is H; $Q^2$ is Ph(2-F,3-OMe,4-Cl); and $Q^1$ is |
| 21 | $Y^1$ is O; $Y^2$ is O; $R^2$ is H; $R^4$ is H; $R^5$ is H; $Q^2$ is Ph(2-F,3-CF$_2$H); and $Q^1$ is |
| 22 | $Y^1$ is O; $Y^2$ is O; $R^2$ is H; $R^4$ is H; $R^5$ is H; $Q^2$ is Ph(2-F,3-CF$_3$); and $Q^1$ is |
| 23 | $Y^1$ is O; $Y^2$ is O; $R^2$ is H; $R^4$ is H; $R^5$ is H; $Q^2$ is Ph(2-F,3-CF$_3$,4-F); and $Q^1$ is |
| 24 | $Y^1$ is O; $Y^2$ is O; $R^2$ is H; $R^4$ is H; $R^5$ is H; $Q^2$ is Ph(2-F,3-NO$_2$); and $Q^1$ is |
| 25 | $Y^1$ is O; $Y^2$ is O; $R^2$ is H; $R^4$ is H; $R^5$ is H; $Q^2$ is Ph(2-F,3-NO$_2$,4-F); and $Q^1$ is |
| 26 | $Y^1$ is O; $Y^2$ is O; $R^2$ is H; $R^4$ is H; $R^5$ is H; $Q^2$ is Ph(2-F,3-SO$_2$Me); and $Q^1$ is |
| 27 | $Y^1$ is O; $Y^2$ is O; $R^2$ is H; $R^4$ is H; $R^5$ is H; $Q^2$ is Ph(2-F,3-SO$_2$Me,4-F); and $Q^1$ is |
| 28 | $Y^1$ is O; $Y^2$ is O; $R^2$ is H; $R^4$ is H; $R^5$ is H; $Q^2$ is Ph(2-CF$_3$); and $Q^1$ is |
| 29 | $Y^1$ is O; $Y^2$ is O; $R^2$ is H; $R^4$ is H; $R^5$ is H; $Q^2$ is Ph(2-CF$_3$,3-F); and $Q^1$ is |
| 30 | $Y^1$ is O; $Y^2$ is O; $R^2$ is H; $R^4$ is H; $R^5$ is H; $Q^2$ is Ph(2-CF$_3$,3-Me); and $Q^1$ is |
| 31 | $Y^1$ is O; $Y^2$ is O; $R^2$ is H; $R^4$ is H; $R^5$ is H; $Q^2$ is Ph(2-CF$_3$,4-F); and $Q^1$ is |
| 32 | $Y^1$ is O; $Y^2$ is O; $R^2$ is H; $R^4$ is H; $R^5$ is H; $Q^2$ is Ph(2-CF$_3$,3-Cl); and $Q^1$ is |
| 33 | $Y^1$ is O; $Y^2$ is O; $R^2$ is H; $R^4$ is H; $R^5$ is H; $Q^2$ is Ph(2-CF$_3$,4-Cl); and $Q^1$ is |
| 34 | $Y^1$ is O; $Y^2$ is O; $R^2$ is H; $R^4$ is H; $R^5$ is H; $Q^2$ is Ph(2-CF$_3$,3,4-di-F); and $Q^1$ is |
| 35 | $Y^1$ is O; $Y^2$ is O; $R^2$ is H; $R^4$ is H; $R^5$ is H; $Q^2$ is Ph(2-CF$_2$H); and $Q^1$ is |
| 36 | $Y^1$ is O; $Y^2$ is O; $R^2$ is H; $R^4$ is H; $R^5$ is H; $Q^2$ is Ph(2-CF$_2$H,3-F); and $Q^1$ is |
| 37 | $Y^1$ is O; $Y^2$ is O; $R^2$ is H; $R^4$ is H; $R^5$ is H; $Q^2$ is Ph(2-CF$_2$H,3-Me); and $Q^1$ is |

-continued

| Table Row Heading |
|---|
| 38 $Y^1$ is O; $Y^2$ is O; $R^2$ is H; $R^4$ is H; $R^5$ is H; $Q^2$ is Ph(2-CF$_2$H,4-F); and $Q^1$ is
| 39 $Y^1$ is O; $Y^2$ is O; $R^2$ is H; $R^4$ is H; $R^5$ is H; $Q^2$ is Ph(2-CF$_2$H,3-Cl); and $Q^1$ is
| 40 $Y^1$ is O; $Y^2$ is O; $R^2$ is H; $R^4$ is H; $R^5$ is H; $Q^2$ is Ph(2-CF$_2$H,4-Cl); and $Q^1$ is
| 41 $Y^1$ is O; $Y^2$ is O; $R^2$ is H; $R^4$ is H; $R^5$ is H; $Q^2$ is Ph(2-CF$_2$H,3,4-di-F); and $Q^1$ is
| 42 $Y^1$ is O; $Y^2$ is O; $R^2$ is H; $R^4$ is H; $R^5$ is H; $Q^2$ is Ph(2-Me); and $Q^1$ is
| 43 $Y^1$ is O; $Y^2$ is O; $R^2$ is H; $R^4$ is H; $R^5$ is H; $Q^2$ is Ph(2,3-di-Me); and $Q^1$ is
| 44 $Y^1$ is O; $Y^2$ is O; $R^2$ is H; $R^4$ is H; $R^5$ is H; $Q^2$ is Ph(2-Me,3-F); and $Q^1$ is
| 45 $Y^1$ is O; $Y^2$ is O; $R^2$ is H; $R^4$ is H; $R^5$ is H; $Q^2$ is Ph(2-Me,3-Cl); and $Q^1$ is
| 46 $Y^1$ is O; $Y^2$ is O; $R^2$ is H; $R^4$ is H; $R^5$ is H; $Q^2$ is Ph(2-Me,3-CF$_3$); and $Q^1$ is
| 47 $Y^1$ is O; $Y^2$ is O; $R^2$ is H; $R^4$ is H; $R^5$ is H; $Q^2$ is Ph(2-Me,3,4-di-Cl); and $Q^1$ is
| 48 $Y^1$ is O; $Y^2$ is O; $R^2$ is H; $R^4$ is H; $R^5$ is H; $Q^2$ is Ph(2-Me,3-Cl,4-F); and $Q^1$ is
| 49 $Y^1$ is O; $Y^2$ is O; $R^2$ is H; $R^4$ is H; $R^5$ is H; $Q^2$ is Ph(2-Me,4-Cl); and $Q^1$ is
| 50 $Y^1$ is O; $Y^2$ is O; $R^2$ is H; $R^4$ is H; $R^5$ is H; $Q^2$ is Ph(2-Me,4-F); and $Q^1$ is
| 51 $Y^1$ is O; $Y^2$ is O; $R^2$ is H; $R^4$ is H; $R^5$ is H; $Q^2$ is Ph(2-Me,5-F); and $Q^1$ is
| 52 $Y^1$ is O; $Y^2$ is O; $R^2$ is H; $R^4$ is H; $R^5$ is H; $Q^2$ is Ph(2-Me,3,4-di-F); and $Q^1$ is
| 53 $Y^1$ is O; $Y^2$ is O; $R^2$ is H; $R^4$ is H; $R^5$ is H; $Q^2$ is Ph(2-Me,3,5-di-F); and $Q^1$ is
| 54 $Y^1$ is O; $Y^2$ is O; $R^2$ is H; $R^4$ is H; $R^5$ is H; $Q^2$ is Ph(2-Et); and $Q^1$ is
| 55 $Y^1$ is O; $Y^2$ is O; $R^2$ is H; $R^4$ is H; $R^5$ is H; $Q^2$ is Ph(2-Et,3-F); and $Q^1$ is
| 56 $Y^1$ is O; $Y^2$ is O; $R^2$ is H; $R^4$ is H; $R^5$ is H; $Q^2$ is Ph(2-Et,3-Cl); and $Q^1$ is
| 57 $Y^1$ is O; $Y^2$ is O; $R^2$ is H; $R^4$ is H; $R^5$ is H; $Q^2$ is Ph(2-Et,4-F); and $Q^1$ is
| 58 $Y^1$ is O; $Y^2$ is O; $R^2$ is H; $R^4$ is H; $R^5$ is H; $Q^2$ is Ph(2-Et,3,4-di-F); and $Q^1$ is
| 59 $Y^1$ is O; $Y^2$ is O; $R^2$ is H; $R^4$ is H; $R^5$ is H; $Q^2$ is Ph(2-i-Pr); and $Q^1$ is
| 60 $Y^1$ is O; $Y^2$ is O; $R^2$ is H; $R^4$ is H; $R^5$ is H; $Q^2$ is Ph(2-i-Pr,3-F); and $Q^1$ is
| 61 $Y^1$ is O; $Y^2$ is O; $R^2$ is H; $R^4$ is H; $R^5$ is H; $Q^2$ is Ph(2-i-Pr,3-Cl); and $Q^1$ is
| 62 $Y^1$ is O; $Y^2$ is O; $R^2$ is H; $R^4$ is H; $R^5$ is H; $Q^2$ is Ph(2-i-Pr,4-F); and $Q^1$ is
| 63 $Y^1$ is O; $Y^2$ is O; $R^2$ is H; $R^4$ is H; $R^5$ is H; $Q^2$ is Ph(2-i-Pr,3,4-di-F); and $Q^1$ is
| 64 $Y^1$ is O; $Y^2$ is O; $R^2$ is H; $R^4$ is H; $R^5$ is H; $Q^2$ is Ph(2-c-Pr); and $Q^1$ is
| 65 $Y^1$ is O; $Y^2$ is O; $R^2$ is H; $R^4$ is H; $R^5$ is H; $Q^2$ is Ph(2-c-Pr,3-F); and $Q^1$ is
| 66 $Y^1$ is O; $Y^2$ is O; $R^2$ is H; $R^4$ is H; $R^5$ is H; $Q^2$ is Ph(2-c-Pr,3-Cl); and $Q^1$ is
| 67 $Y^1$ is O; $Y^2$ is O; $R^2$ is H; $R^4$ is H; $R^5$ is H; $Q^2$ is Ph(2-c-Pr,4-F); and $Q^1$ is
| 68 $Y^1$ is O; $Y^2$ is O; $R^2$ is H; $R^4$ is H; $R^5$ is H; $Q^2$ is Ph(2-c-Pr,3,4-di-F); and $Q^1$ is
| 69 $Y^1$ is O; $Y^2$ is O; $R^2$ is H; $R^4$ is H; $R^5$ is H; $Q^2$ is Ph(2-NO$_2$); and $Q^1$ is
| 70 $Y^1$ is O; $Y^2$ is O; $R^2$ is H; $R^4$ is H; $R^5$ is H; $Q^2$ is Ph(2-NO$_2$,3-F); and $Q^1$ is
| 71 $Y^1$ is O; $Y^2$ is O; $R^2$ is H; $R^4$ is H; $R^5$ is H; $Q^2$ is Ph(2-NO$_2$,3-Cl); and $Q^1$ is
| 72 $Y^1$ is O; $Y^2$ is O; $R^2$ is H; $R^4$ is H; $R^5$ is H; $Q^2$ is Ph(2-NO$_2$,4-F); and $Q^1$ is
| 73 $Y^1$ is O; $Y^2$ is O; $R^2$ is H; $R^4$ is H; $R^5$ is H; $Q^2$ is Ph(2-NO$_2$,3,4-di-F); and $Q^1$ is
| 74 $Y^1$ is O; $Y^2$ is O; $R^2$ is H; $R^4$ is H; $R^5$ is H; $Q^2$ is Ph(2-OCF$_3$); and $Q^1$ is
| 75 $Y^1$ is O; $Y^2$ is O; $R^2$ is H; $R^4$ is H; $R^5$ is H; $Q^2$ is Ph(2-OCF$_3$,3-F); and $Q^1$ is
| 76 $Y^1$ is O; $Y^2$ is O; $R^2$ is H; $R^4$ is H; $R^5$ is H; $Q^2$ is Ph(2-OCF$_3$,4-F); and $Q^1$ is
| 77 $Y^1$ is O; $Y^2$ is O; $R^2$ is H; $R^4$ is H; $R^5$ is H; $Q^2$ is Ph(2-Cl); and $Q^1$ is
| 78 $Y^1$ is O; $Y^2$ is O; $R^2$ is H; $R^4$ is H; $R^5$ is H; $Q^2$ is Ph(2-Cl,3-Me); and $Q^1$ is
| 79 $Y^1$ is O; $Y^2$ is O; $R^2$ is H; $R^4$ is H; $R^5$ is H; $Q^2$ is Ph(2-Cl,3-Me,4-F); and $Q^1$ is
| 80 $Y^1$ is O; $Y^2$ is O; $R^2$ is H; $R^4$ is H; $R^5$ is H; $Q^2$ is Ph(2,3-di-Cl); and $Q^1$ is
| 81 $Y^1$ is O; $Y^2$ is O; $R^2$ is H; $R^4$ is H; $R^5$ is H; $Q^2$ is Ph(2,4-di-Cl); and $Q^1$ is
| 82 $Y^1$ is O; $Y^2$ is O; $R^2$ is H; $R^4$ is H; $R^5$ is H; $Q^2$ is Ph(2-Cl,3-F); and $Q^1$ is
| 83 $Y^1$ is O; $Y^2$ is O; $R^2$ is H; $R^4$ is H; $R^5$ is H; $Q^2$ is Ph(2-Cl,4-F); and $Q^1$ is
| 84 $Y^1$ is O; $Y^2$ is O; $R^2$ is H; $R^4$ is H; $R^5$ is H; $Q^2$ is Ph(2-Cl,5-F); and $Q^1$ is
| 85 $Y^1$ is O; $Y^2$ is O; $R^2$ is H; $R^4$ is H; $R^5$ is H; $Q^2$ is Ph(2-Cl,3,4-di-F); and $Q^1$ is
| 86 $Y^1$ is O; $Y^2$ is O; $R^2$ is H; $R^4$ is H; $R^5$ is H; $Q^2$ is Ph(2-Cl,3,5-di-F); and $Q^1$ is
| 87 $Y^1$ is O; $Y^2$ is O; $R^2$ is H; $R^4$ is H; $R^5$ is H; $Q^2$ is Ph(2-OCF$_2$H); and $Q^1$ is
| 88 $Y^1$ is O; $Y^2$ is O; $R^2$ is H; $R^4$ is H; $R^5$ is H; $Q^2$ is Ph(2-OCF$_2$H,3-Me); and $Q^1$ is
| 89 $Y^1$ is O; $Y^2$ is O; $R^2$ is H; $R^4$ is H; $R^5$ is H; $Q^2$ is Ph(2-OCF$_2$H,3-Cl); and $Q^1$ is
| 90 $Y^1$ is O; $Y^2$ is O; $R^2$ is H; $R^4$ is H; $R^5$ is H; $Q^2$ is Ph(2-OCF$_2$H,3-F); and $Q^1$ is
| 91 $Y^1$ is O; $Y^2$ is O; $R^2$ is H; $R^4$ is H; $R^5$ is H; $Q^2$ is Ph(2-OCF$_2$H,4-F); and $Q^1$ is
| 92 $Y^1$ is O; $Y^2$ is O; $R^2$ is H; $R^4$ is H; $R^5$ is H; $Q^2$ is Ph(2-OCF$_2$CF$_2$H); and $Q^1$ is
| 93 $Y^1$ is O; $Y^2$ is O; $R^2$ is H; $R^4$ is H; $R^5$ is H; $Q^2$ is Ph(2-OCF$_2$CF$_2$H,3-F); and $Q^1$ is
| 94 $Y^1$ is O; $Y^2$ is O; $R^2$ is H; $R^4$ is H; $R^5$ is H; $Q^2$ is Ph(2-OCF$_2$CF$_2$H,4-F); and $Q^1$ is
| 95 $Y^1$ is O; $Y^2$ is O; $R^2$ is H; $R^4$ is H; $R^5$ is H; $Q^2$ is Ph(2-Br); and $Q^1$ is
| 96 $Y^1$ is O; $Y^2$ is O; $R^2$ is H; $R^4$ is H; $R^5$ is H; $Q^2$ is Ph(2-Br,3-F); and $Q^1$ is
| 97 $Y^1$ is O; $Y^2$ is O; $R^2$ is H; $R^4$ is H; $R^5$ is H; $Q^2$ is Ph(2-Br,4-F); and $Q^1$ is
| 98 $Y^1$ is O; $Y^2$ is O; $R^2$ is H; $R^4$ is H; $R^5$ is H; $Q^2$ is Ph(2-Br,3,4-di-F); and $Q^1$ is
| 99 $Y^1$ is O; $Y^2$ is O; $R^2$ is H; $R^4$ is H; $R^5$ is H; $Q^2$ is Ph(2-I); and $Q^1$ is
| 100 $Y^1$ is O; $Y^2$ is O; $R^2$ is H; $R^4$ is H; $R^5$ is H; $Q^2$ is Ph(2-I,3-F); and $Q^1$ is
| 101 $Y^1$ is O; $Y^2$ is O; $R^2$ is H; $R^4$ is H; $R^5$ is H; $Q^2$ is Ph(2-I,4-F); and $Q^1$ is
| 102 $Y^1$ is O; $Y^2$ is O; $R^2$ is H; $R^4$ is H; $R^5$ is H; $Q^2$ is Ph(2-I,3,4-di-F); and $Q^1$ is
| 103 $Y^1$ is O; $Y^2$ is O; $R^2$ is H; $R^4$ is H; $R^5$ is H; $Q^2$ is Ph(2-CN); and $Q^1$ is
| 104 $Y^1$ is O; $Y^2$ is O; $R^2$ is H; $R^4$ is H; $R^5$ is H; $Q^2$ is Ph(2-CN,3-Me); and $Q^1$ is
| 105 $Y^1$ is O; $Y^2$ is O; $R^2$ is H; $R^4$ is H; $R^5$ is H; $Q^2$ is Ph(2-CN,3-F); and $Q^1$ is
| 106 $Y^1$ is O; $Y^2$ is O; $R^2$ is H; $R^4$ is H; $R^5$ is H; $Q^2$ is Ph(2-CN,4-F); and $Q^1$ is
| 107 $Y^1$ is O; $Y^2$ is O; $R^2$ is H; $R^4$ is H; $R^5$ is H; $Q^2$ is Ph(2-CN,3-Cl); and $Q^1$ is
| 108 $Y^1$ is O; $Y^2$ is O; $R^2$ is H; $R^4$ is H; $R^5$ is H; $Q^2$ is Ph(2-CN,4-Cl); and $Q^1$ is
| 109 $Y^1$ is O; $Y^2$ is O; $R^2$ is H; $R^4$ is H; $R^5$ is H; $Q^2$ is Ph(2-CN,3,4-di-F); and $Q^1$ is
| 110 $Y^1$ is O; $Y^2$ is O; $R^2$ is H; $R^4$ is H; $R^5$ is H; $Q^2$ is 2-Pyridinyl; and $Q^1$ is
| 111 $Y^1$ is O; $Y^2$ is O; $R^2$ is H; $R^4$ is H; $R^5$ is H; $Q^2$ is 2-Pyridinyl,3-F; and $Q^1$ is
| 112 $Y^1$ is O; $Y^2$ is O; $R^2$ is H; $R^4$ is H; $R^5$ is H; $Q^2$ is 2-Pyridinyl,4-F; and $Q^1$ is
| 113 $Y^1$ is O; $Y^2$ is O; $R^2$ is H; $R^4$ is H; $R^5$ is H; $Q^2$ is 2-Pyridinyl,3,4-di-F; and $Q^1$ is
| 114 $Y^1$ is O; $Y^2$ is O; $R^2$ is H; $R^4$ is H; $R^5$ is H; $Q^2$ is 2-Pyridinyl,3-Cl; and $Q^1$ is -continued

| Table Row Heading |
|---|
| 115  $Y^1$ is O; $Y^2$ is O; $R^2$ is H; $R^4$ is H; $R^5$ is H; $Q^2$ is 2-Pyridinyl,4-Cl; and $Q^1$ is |
| 116  $Y^1$ is O; $Y^2$ is O; $R^2$ is H; $R^4$ is H; $R^5$ is H; $Q^2$ is 2-Pyridinyl,3-Cl,4-F; and $Q^1$ is |
| 117  $Y^1$ is O; $Y^2$ is O; $R^2$ is H; $R^4$ is H; $R^5$ is H; $Q^2$ is Ph(2-SO$_2$Me); and $Q^1$ is |
| 118  $Y^1$ is O; $Y^2$ is O; $R^2$ is H; $R^4$ is H; $R^5$ is H; $Q^2$ is Ph(2-SO$_2$Me, 3-F); and $Q^1$ is |
| 119  $Y^1$ is O; $Y^2$ is O; $R^2$ is H; $R^4$ is H; $R^5$ is H; $Q^2$ is Ph(2-SO$_2$Me, 3-Me); and $Q^1$ is |
| 120  $Y^1$ is O; $Y^2$ is O; $R^2$ is H; $R^4$ is H; $R^5$ is H; $Q^2$ is Ph(2-SO$_2$Me, 4-F); and $Q^1$ is |
| 121  $Y^1$ is O; $Y^2$ is O; $R^2$ is H; $R^4$ is H; $R^5$ is H; $Q^2$ is Ph(2-SO$_2$Me, 5-F); and $Q^1$ is |
| 122  $Y^1$ is O; $Y^2$ is O; $R^2$ is H; $R^4$ is H; $R^5$ is H; $Q^2$ is Ph(2-SO$_2$Me,3,4-di-F); and $Q^1$ is |
| 123  $Y^1$ is O; $Y^2$ is O; $R^2$ is H; $R^4$ is H; $R^5$ is H; $Q^2$ is Ph(2-SO$_2$Me, 3-Cl); and $Q^1$ is |
| 124  $Y^1$ is O; $Y^2$ is O; $R^2$ is H; $R^4$ is H; $R^5$ is H; $Q^2$ is Ph(2-SO$_2$Me, 4-Cl); and $Q^1$ is |
| 125  $Y^1$ is O; $Y^2$ is O; $R^2$ is H; $R^4$ is H; $R^5$ is H; $Q^2$ is Ph(2-SO$_2$Me,3-Cl,4-F); and $Q^1$ is |
| 126  $Y^1$ is O; $Y^2$ is O; $R^2$ is H; $R^4$ is H; $R^5$ is H; $Q^2$ is Ph(2-SO$_2$NH$_2$); and $Q^1$ is |
| 127  $Y^1$ is O; $Y^2$ is O; $R^2$ is H; $R^4$ is H; $R^5$ is H; $Q^2$ is Ph(2-SO$_2$NH$_2$, 3-F); and $Q^1$ is |
| 128  $Y^1$ is O; $Y^2$ is O; $R^2$ is H; $R^4$ is H; $R^5$ is H; $Q^2$ is Ph(2-SO$_2$NH$_2$, 3-Cl); and $Q^1$ is |
| 129  $Y^1$ is O; $Y^2$ is O; $R^2$ is H; $R^4$ is H; $R^5$ is H; $Q^2$ is Ph(2-SO$_2$NH$_2$, 4-F); and $Q^1$ is |
| 130  $Y^1$ is O; $Y^2$ is O; $R^2$ is H; $R^4$ is H; $R^5$ is H; $Q^2$ is Ph(2-SO$_2$NH$_2$, 5-F); and $Q^1$ is |
| 131  $Y^1$ is O; $Y^2$ is O; $R^2$ is H; $R^4$ is H; $R^5$ is H; $Q^2$ is Ph(2-SO$_2$NH$_2$,3,4-di-F); and $Q^1$ is |
| 132  $Y^1$ is O; $Y^2$ is O; $R^2$ is H; $R^4$ is H; $R^5$ is H; $Q^2$ is Ph(3-F); and $Q^1$ is |
| 133  $Y^1$ is O; $Y^2$ is O; $R^2$ is H; $R^4$ is H; $R^5$ is H; $Q^2$ is Ph(3,4-di-F); and $Q^1$ is |
| 134  $Y^1$ is O; $Y^2$ is O; $R^2$ is H; $R^4$ is H; $R^5$ is H; $Q^2$ is Ph(3,5-di-F); and $Q^1$ is |
| 135  $Y^1$ is O; $Y^2$ is O; $R^2$ is H; $R^4$ is H; $R^5$ is H; $Q^2$ is Ph(3,4,5-tri-F); and $Q^1$ is |
| 136  $Y^1$ is O; $Y^2$ is O; $R^2$ is H; $R^4$ is H; $R^5$ is H; $Q^2$ is Ph(3-F,4-Cl); and $Q^1$ is |
| 137  $Y^1$ is O; $Y^2$ is O; $R^2$ is H; $R^4$ is H; $R^5$ is H; $Q^2$ is Ph(3-CF$_3$); and $Q^1$ is |
| 138  $Y^1$ is O; $Y^2$ is O; $R^2$ is H; $R^4$ is H; $R^5$ is H; $Q^2$ is Ph(3-CF$_3$,4-F); and $Q^1$ is |
| 139  $Y^1$ is O; $Y^2$ is O; $R^2$ is H; $R^4$ is H; $R^5$ is H; $Q^2$ is Ph(3-CF$_3$,4-Cl); and $Q^1$ is |
| 140  $Y^1$ is O; $Y^2$ is O; $R^2$ is H; $R^4$ is H; $R^5$ is H; $Q^2$ is Ph(3-CF$_3$,5-F); and $Q^1$ is |
| 141  $Y^1$ is O; $Y^2$ is O; $R^2$ is H; $R^4$ is H; $R^5$ is H; $Q^2$ is Ph(3-CF$_3$,4,5-di-F); and $Q^1$ is |
| 142  $Y^1$ is O; $Y^2$ is O; $R^2$ is H; $R^4$ is H; $R^5$ is H; $Q^2$ is Ph(3-SO$_2$Me); and $Q^1$ is |
| 143  $Y^1$ is O; $Y^2$ is O; $R^2$ is H; $R^4$ is H; $R^5$ is H; $Q^2$ is Ph(3-SO$_2$Me,4-Cl); and $Q^1$ is |
| 144  $Y^1$ is O; $Y^2$ is O; $R^2$ is H; $R^4$ is H; $R^5$ is H; $Q^2$ is Ph(3-SO$_2$Me,4-F); and $Q^1$ is |
| 145  $Y^1$ is O; $Y^2$ is O; $R^2$ is H; $R^4$ is H; $R^5$ is H; $Q^2$ is Ph(3-SO$_2$Me,4,5-di-F); and $Q^1$ is |
| 146  $Y^1$ is O; $Y^2$ is O; $R^2$ is H; $R^4$ is H; $R^5$ is H; $Q^2$ is Ph(3-SO$_2$Me,5-F); and $Q^1$ is |
| 147  $Y^1$ is O; $Y^2$ is O; $R^2$ is H; $R^4$ is H; $R^5$ is H; $Q^2$ is Ph(3-SO$_2$NH$_2$); and $Q^1$ is |
| 148  $Y^1$ is O; $Y^2$ is O; $R^2$ is H; $R^4$ is H; $R^5$ is H; $Q^2$ is Ph(3-SO$_2$NH$_2$,4-F); and $Q^1$ is |
| 149  $Y^1$ is O; $Y^2$ is O; $R^2$ is H; $R^4$ is H; $R^5$ is H; $Q^2$ is Ph(3-SO$_2$NH$_2$,4,5-di-F); and $Q^1$ is |
| 150  $Y^1$ is O; $Y^2$ is O; $R^2$ is H; $R^4$ is H; $R^5$ is H; $Q^2$ is Ph(3-SO$_2$NH$_2$,4-Cl); and $Q^1$ is |
| 151  $Y^1$ is O; $Y^2$ is O; $R^2$ is H; $R^4$ is H; $R^5$ is H; $Q^2$ is Ph(3-SO$_2$NH$_2$,5-F); and $Q^1$ is |
| 152  $Y^1$ is O; $Y^2$ is O; $R^2$ is H; $R^4$ is H; $R^5$ is H; $Q^2$ is Ph(3-Me); and $Q^1$ is |
| 153  $Y^1$ is O; $Y^2$ is O; $R^2$ is H; $R^4$ is H; $R^5$ is H; $Q^2$ is Ph(3-Me,4-F); and $Q^1$ is |
| 154  $Y^1$ is O; $Y^2$ is O; $R^2$ is H; $R^4$ is H; $R^5$ is H; $Q^2$ is Ph(3-Me,4-Cl); and $Q^1$ is |
| 155  $Y^1$ is O; $Y^2$ is O; $R^2$ is H; $R^4$ is H; $R^5$ is H; $Q^2$ is Ph(3-Me,5-F); and $Q^1$ is |
| 156  $Y^1$ is O; $Y^2$ is O; $R^2$ is H; $R^4$ is H; $R^5$ is H; $Q^2$ is Ph(3-Me,4,5-di-F); and $Q^1$ is |
| 157  $Y^1$ is O; $Y^2$ is O; $R^2$ is H; $R^4$ is H; $R^5$ is H; $Q^2$ is Ph(3-Cl); and $Q^1$ is |
| 158  $Y^1$ is O; $Y^2$ is O; $R^2$ is H; $R^4$ is H; $R^5$ is H; $Q^2$ is Ph(3-Cl,4-F); and $Q^1$ is |
| 159  $Y^1$ is O; $Y^2$ is O; $R^2$ is H; $R^4$ is H; $R^5$ is H; $Q^2$ is Ph(3,4-di-Cl); and $Q^1$ is |
| 160  $Y^1$ is O; $Y^2$ is O; $R^2$ is H; $R^4$ is H; $R^5$ is H; $Q^2$ is Ph(3-Cl,5-F); and $Q^1$ is |
| 161  $Y^1$ is O; $Y^2$ is O; $R^2$ is H; $R^4$ is H; $R^5$ is H; $Q^2$ is Ph(3-Cl,4,5-di-F); and $Q^1$ is |
| 162  $Y^1$ is O; $Y^2$ is O; $R^2$ is H; $R^4$ is H; $R^5$ is H; $Q^2$ is Ph(3,5-di-Cl); and $Q^1$ is |
| 163  $Y^1$ is O; $Y^2$ is O; $R^2$ is H; $R^4$ is H; $R^5$ is H; $Q^2$ is Ph(4-F); and $Q^1$ is |
| 164  $Y^1$ is O; $Y^2$ is O; $R^2$ is H; $R^4$ is H; $R^5$ is H; $Q^2$ is Ph(4-Cl); and $Q^1$ is |
| 165  $Y^1$ is O; $Y^2$ is O; $R^2$ is H; $R^4$ is H; $R^5$ is H; $Q^2$ is 2,2-di-F-1,3-benzodioxol-4-yl; and $Q^1$ is |
| 166  $Y^1$ is O; $Y^2$ is O; $R^2$ is H; $R^4$ is H; $R^5$ is H; $Q^2$ is 2,2-di-F-1,3-benzodioxol-5-yl; and $Q^1$ is |
| 167  $Y^1$ is O; $Y^2$ is O; $R^2$ is H; $R^4$ is H; $R^5$ is H; $Q^2$ is 2,2-di-Me-1,3-benzodioxol-4-yl; and $Q^1$ is |
| 168  $Y^1$ is O; $Y^2$ is O; $R^2$ is H; $R^4$ is H; $R^5$ is H; $Q^2$ is 2,2-di-Me-1,3-benzodioxol-5-yl; and $Q^1$ is |
| 169  $Y^1$ is O; $Y^2$ is O; $R^2$ is H; $R^4$ is H; $R^5$ is H; $Q^2$ is 1,3-benzodioxol-4-yl; and $Q^1$ is |
| 170  $Y^1$ is O; $Y^2$ is O; $R^2$ is H; $R^4$ is H; $R^5$ is H; $Q^2$ is 1,3-benzodioxol-5-yl; and $Q^1$ is |
| 171  $Y^1$ is S; $Y^2$ is O; $R^2$ is H; $R^4$ is H; $R^5$ is H; $Q^2$ is Ph(2-F); and $Q^1$ is |
| 172  $Y^1$ is S; $Y^2$ is O; $R^2$ is H; $R^4$ is H; $R^5$ is H; $Q^2$ is Ph(2,3-di-F); and $Q^1$ is |
| 173  $Y^1$ is S; $Y^2$ is O; $R^2$ is H; $R^4$ is H; $R^5$ is H; $Q^2$ is Ph(2,4-di-F); and $Q^1$ is |
| 174  $Y^1$ is S; $Y^2$ is O; $R^2$ is H; $R^4$ is H; $R^5$ is H; $Q^2$ is Ph(2,5-di-F); and $Q^1$ is |
| 175  $Y^1$ is S; $Y^2$ is O; $R^2$ is H; $R^4$ is H; $R^5$ is H; $Q^2$ is Ph(2,3,4-tri-F); and $Q^1$ is |
| 176  $Y^1$ is S; $Y^2$ is O; $R^2$ is H; $R^4$ is H; $R^5$ is H; $Q^2$ is Ph(2,3,5-tri-F); and $Q^1$ is |
| 177  $Y^1$ is S; $Y^2$ is O; $R^2$ is H; $R^4$ is H; $R^5$ is H; $Q^2$ is Ph(2,3,4,5-tetra-F); and $Q^1$ is |
| 178  $Y^1$ is S; $Y^2$ is O; $R^2$ is H; $R^4$ is H; $R^5$ is H; $Q^2$ is Ph(2-F,3-Cl,4-Br); and $Q^1$ is |
| 179  $Y^1$ is S; $Y^2$ is O; $R^2$ is H; $R^4$ is H; $R^5$ is H; $Q^2$ is Ph(2-F,3-Cl,4-F); and $Q^1$ is |
| 180  $Y^1$ is S; $Y^2$ is O; $R^2$ is H; $R^4$ is H; $R^5$ is H; $Q^2$ is Ph(2-F,3-Br,4-F); and $Q^1$ is |
| 181  $Y^1$ is S; $Y^2$ is O; $R^2$ is H; $R^4$ is H; $R^5$ is H; $Q^2$ is Ph(2-F,3-Me); and $Q^1$ is |
| 182  $Y^1$ is S; $Y^2$ is O; $R^2$ is H; $R^4$ is H; $R^5$ is H; $Q^2$ is Ph(2-F,3-Me,4-F); and $Q^1$ is |
| 183  $Y^1$ is S; $Y^2$ is O; $R^2$ is H; $R^4$ is H; $R^5$ is H; $Q^2$ is Ph(2-F,3-Me,4-Cl); and $Q^1$ is |
| 184  $Y^1$ is S; $Y^2$ is O; $R^2$ is H; $R^4$ is H; $R^5$ is H; $Q^2$ is Ph(2-F,3-Cl); and $Q^1$ is |
| 185  $Y^1$ is S; $Y^2$ is O; $R^2$ is H; $R^4$ is H; $R^5$ is H; $Q^2$ is Ph(2-F,4-Cl); and $Q^1$ is |
| 186  $Y^1$ is S; $Y^2$ is O; $R^2$ is H; $R^4$ is H; $R^5$ is H; $Q^2$ is Ph(2-F,3,4-di-Cl); and $Q^1$ is |
| 187  $Y^1$ is S; $Y^2$ is O; $R^2$ is H; $R^4$ is H; $R^5$ is H; $Q^2$ is Ph(2-F,4-Br); and $Q^1$ is |
| 188  $Y^1$ is S; $Y^2$ is O; $R^2$ is H; $R^4$ is H; $R^5$ is H; $Q^2$ is Ph(2-F,3-OMe); and $Q^1$ is |
| 189  $Y^1$ is S; $Y^2$ is O; $R^2$ is H; $R^4$ is H; $R^5$ is H; $Q^2$ is Ph(2-F,3-OMe,4-F); and $Q^1$ is |
| 190  $Y^1$ is S; $Y^2$ is O; $R^2$ is H; $R^4$ is H; $R^5$ is H; $Q^2$ is Ph(2-F,3-OMe,4-Cl); and $Q^1$ is |
| 191  $Y^1$ is S; $Y^2$ is O; $R^2$ is H; $R^4$ is H; $R^5$ is H; $Q^2$ is Ph(2-F,3-CF$_2$H); and $Q^1$ is |

-continued

| Table Row Heading |
|---|
| 192 $Y^1$ is S; $Y^2$ is O; $R^2$ is H; $R^4$ is H; $R^5$ is H; $Q^2$ is Ph(2-F,3-CF$_3$); and $Q^1$ is |
| 193 $Y^1$ is S; $Y^2$ is O; $R^2$ is H; $R^4$ is H; $R^5$ is H; $Q^2$ is Ph(2-F,3-CF$_3$,4-F); and $Q^1$ is |
| 194 $Y^1$ is S; $Y^2$ is O; $R^2$ is H; $R^4$ is H; $R^5$ is H; $Q^2$ is Ph(2-F,3-NO$_2$); and $Q^1$ is |
| 195 $Y^1$ is S; $Y^2$ is O; $R^2$ is H; $R^4$ is H; $R^5$ is H; $Q^2$ is Ph(2-F,3-NO$_2$,4-F); and $Q^1$ is |
| 196 $Y^1$ is S; $Y^2$ is O; $R^2$ is H; $R^4$ is H; $R^5$ is H; $Q^2$ is Ph(2-F,3-SO$_2$Me); and $Q^1$ is |
| 197 $Y^1$ is S; $Y^2$ is O; $R^2$ is H; $R^4$ is H; $R^5$ is H; $Q^2$ is Ph(2-F,3-SO$_2$Me,4-F); and $Q^1$ is |
| 198 $Y^1$ is S; $Y^2$ is O; $R^2$ is H; $R^4$ is H; $R^5$ is H; $Q^2$ is Ph(2-CF$_3$); and $Q^1$ is |
| 199 $Y^1$ is S; $Y^2$ is O; $R^2$ is H; $R^4$ is H; $R^5$ is H; $Q^2$ is Ph(2-CF$_3$,3-F); and $Q^1$ is |
| 200 $Y^1$ is S; $Y^2$ is O; $R^2$ is H; $R^4$ is H; $R^5$ is H; $Q^2$ is Ph(2-CF$_3$,3-Me); and $Q^1$ is |
| 201 $Y^1$ is S; $Y^2$ is O; $R^2$ is H; $R^4$ is H; $R^5$ is H; $Q^2$ is Ph(2-CF$_3$,4-F); and $Q^1$ is |
| 202 $Y^1$ is S; $Y^2$ is O; $R^2$ is H; $R^4$ is H; $R^5$ is H; $Q^2$ is Ph(2-CF$_3$,3-Cl); and $Q^1$ is |
| 203 $Y^1$ is S; $Y^2$ is O; $R^2$ is H; $R^4$ is H; $R^5$ is H; $Q^2$ is Ph(2-CF$_3$,4-Cl); and $Q^1$ is |
| 204 $Y^1$ is S; $Y^2$ is O; $R^2$ is H; $R^4$ is H; $R^5$ is H; $Q^2$ is Ph(2-CF$_3$,3,4-di-F); and $Q^1$ is |
| 205 $Y^1$ is S; $Y^2$ is O; $R^2$ is H; $R^4$ is H; $R^5$ is H; $Q^2$ is Ph(2-CF$_2$H); and $Q^1$ is |
| 206 $Y^1$ is S; $Y^2$ is O; $R^2$ is H; $R^4$ is H; $R^5$ is H; $Q^2$ is Ph(2-CF$_2$H,3-F); and $Q^1$ is |
| 207 $Y^1$ is S; $Y^2$ is O; $R^2$ is H; $R^4$ is H; $R^5$ is H; $Q^2$ is Ph(2-CF$_2$H,3-Me); and $Q^1$ is |
| 208 $Y^1$ is S; $Y^2$ is O; $R^2$ is H; $R^4$ is H; $R^5$ is H; $Q^2$ is Ph(2-CF$_2$H,4-F); and $Q^1$ is |
| 209 $Y^1$ is S; $Y^2$ is O; $R^2$ is H; $R^4$ is H; $R^5$ is H; $Q^2$ is Ph(2-CF$_2$H,3-Cl); and $Q^1$ is |
| 210 $Y^1$ is S; $Y^2$ is O; $R^2$ is H; $R^4$ is H; $R^5$ is H; $Q^2$ is Ph(2-CF$_2$H,4-Cl); and $Q^1$ is |
| 211 $Y^1$ is S; $Y^2$ is O; $R^2$ is H; $R^4$ is H; $R^5$ is H; $Q^2$ is Ph(2-CF$_2$H,3,4-di-F); and $Q^1$ is |
| 212 $Y^1$ is S; $Y^2$ is O; $R^2$ is H; $R^4$ is H; $R^5$ is H; $Q^2$ is Ph(2-Me); and $Q^1$ is |
| 213 $Y^1$ is S; $Y^2$ is O; $R^2$ is H; $R^4$ is H; $R^5$ is H; $Q^2$ is Ph(2,3-di-Me); and $Q^1$ is |
| 214 $Y^1$ is S; $Y^2$ is O; $R^2$ is H; $R^4$ is H; $R^5$ is H; $Q^2$ is Ph(2-Me,3-F); and $Q^1$ is |
| 215 $Y^1$ is S; $Y^2$ is O; $R^2$ is H; $R^4$ is H; $R^5$ is H; $Q^2$ is Ph(2-Me,3-Cl); and $Q^1$ is |
| 216 $Y^1$ is S; $Y^2$ is O; $R^2$ is H; $R^4$ is H; $R^5$ is H; $Q^2$ is Ph(2-Me,3-CF$_3$); and $Q^1$ is |
| 217 $Y^1$ is S; $Y^2$ is O; $R^2$ is H; $R^4$ is H; $R^5$ is H; $Q^2$ is Ph(2-Me,3,4-di-Cl); and $Q^1$ is |
| 218 $Y^1$ is S; $Y^2$ is O; $R^2$ is H; $R^4$ is H; $R^5$ is H; $Q^2$ is Ph(2-Me,3-Cl,4-F); and $Q^1$ is |
| 219 $Y^1$ is S; $Y^2$ is O; $R^2$ is H; $R^4$ is H; $R^5$ is H; $Q^2$ is Ph(2-Me,4-Cl); and $Q^1$ is |
| 220 $Y^1$ is S; $Y^2$ is O; $R^2$ is H; $R^4$ is H; $R^5$ is H; $Q^2$ is Ph(2-Me,4-F); and $Q^1$ is |
| 221 $Y^1$ is S; $Y^2$ is O; $R^2$ is H; $R^4$ is H; $R^5$ is H; $Q^2$ is Ph(2-Me,5-F); and $Q^1$ is |
| 222 $Y^1$ is S; $Y^2$ is O; $R^2$ is H; $R^4$ is H; $R^5$ is H; $Q^2$ is Ph(2-Me,3,4-di-F); and $Q^1$ is |
| 223 $Y^1$ is S; $Y^2$ is O; $R^2$ is H; $R^4$ is H; $R^5$ is H; $Q^2$ is Ph(2-Me,3,5-di-F); and $Q^1$ is |
| 224 $Y^1$ is S; $Y^2$ is O; $R^2$ is H; $R^4$ is H; $R^5$ is H; $Q^2$ is Ph(2-Et); and $Q^1$ is |
| 225 $Y^1$ is S; $Y^2$ is O; $R^2$ is H; $R^4$ is H; $R^5$ is H; $Q^2$ is Ph(2-Et,3-F); and $Q^1$ is |
| 226 $Y^1$ is S; $Y^2$ is O; $R^2$ is H; $R^4$ is H; $R^5$ is H; $Q^2$ is Ph(2-Et,3-Cl); and $Q^1$ is |
| 227 $Y^1$ is S; $Y^2$ is O; $R^2$ is H; $R^4$ is H; $R^5$ is H; $Q^2$ is Ph(2-Et,4-F); and $Q^1$ is |
| 228 $Y^1$ is S; $Y^2$ is O; $R^2$ is H; $R^4$ is H; $R^5$ is H; $Q^2$ is Ph(2-Et,3,4-di-F); and $Q^1$ is |
| 229 $Y^1$ is S; $Y^2$ is O; $R^2$ is H; $R^4$ is H; $R^5$ is H; $Q^2$ is Ph(2-i-Pr); and $Q^1$ is |
| 230 $Y^1$ is S; $Y^2$ is O; $R^2$ is H; $R^4$ is H; $R^5$ is H; $Q^2$ is Ph(2-i-Pr,3-F); and $Q^1$ is |
| 231 $Y^1$ is S; $Y^2$ is O; $R^2$ is H; $R^4$ is H; $R^5$ is H; $Q^2$ is Ph(2-i-Pr,3-Cl); and $Q^1$ is |
| 232 $Y^1$ is S; $Y^2$ is O; $R^2$ is H; $R^4$ is H; $R^5$ is H; $Q^2$ is Ph(2-i-Pr,4-F); and $Q^1$ is |
| 233 $Y^1$ is S; $Y^2$ is O; $R^2$ is H; $R^4$ is H; $R^5$ is H; $Q^2$ is Ph(2-i-Pr,3,4-di-F); and $Q^1$ is |
| 234 $Y^1$ is S; $Y^2$ is O; $R^2$ is H; $R^4$ is H; $R^5$ is H; $Q^2$ is Ph(2-c-Pr); and $Q^1$ is |
| 235 $Y^1$ is S; $Y^2$ is O; $R^2$ is H; $R^4$ is H; $R^5$ is H; $Q^2$ is Ph(2-c-Pr,3-F); and $Q^1$ is |
| 236 $Y^1$ is S; $Y^2$ is O; $R^2$ is H; $R^4$ is H; $R^5$ is H; $Q^2$ is Ph(2-c-Pr,3-Cl); and $Q^1$ is |
| 237 $Y^1$ is S; $Y^2$ is O; $R^2$ is H; $R^4$ is H; $R^5$ is H; $Q^2$ is Ph(2-c-Pr,4-F); and $Q^1$ is |
| 238 $Y^1$ is S; $Y^2$ is O; $R^2$ is H; $R^4$ is H; $R^5$ is H; $Q^2$ is Ph(2-c-Pr,3,4-di-F); and $Q^1$ is |
| 239 $Y^1$ is S; $Y^2$ is O; $R^2$ is H; $R^4$ is H; $R^5$ is H; $Q^2$ is Ph(2-NO$_2$); and $Q^1$ is |
| 240 $Y^1$ is S; $Y^2$ is O; $R^2$ is H; $R^4$ is H; $R^5$ is H; $Q^2$ is Ph(2-NO$_2$,3-F); and $Q^1$ is |
| 241 $Y^1$ is S; $Y^2$ is O; $R^2$ is H; $R^4$ is H; $R^5$ is H; $Q^2$ is Ph(2-NO$_2$,3-Cl); and $Q^1$ is |
| 242 $Y^1$ is S; $Y^2$ is O; $R^2$ is H; $R^4$ is H; $R^5$ is H; $Q^2$ is Ph(2-NO$_2$,4-F); and $Q^1$ is |
| 243 $Y^1$ is S; $Y^2$ is O; $R^2$ is H; $R^4$ is H; $R^5$ is H; $Q^2$ is Ph(2-NO$_2$,3,4-di-F); and $Q^1$ is |
| 244 $Y^1$ is S; $Y^2$ is O; $R^2$ is H; $R^4$ is H; $R^5$ is H; $Q^2$ is Ph(2-OCF$_3$); and $Q^1$ is |
| 245 $Y^1$ is S; $Y^2$ is O; $R^2$ is H; $R^4$ is H; $R^5$ is H; $Q^2$ is Ph(2-OCF$_3$,3-F); and $Q^1$ is |
| 246 $Y^1$ is S; $Y^2$ is O; $R^2$ is H; $R^4$ is H; $R^5$ is H; $Q^2$ is Ph(2-OCF$_3$,4-F); and $Q^1$ is |
| 247 $Y^1$ is S; $Y^2$ is O; $R^2$ is H; $R^4$ is H; $R^5$ is H; $Q^2$ is Ph(2-Cl); and $Q^1$ is |
| 248 $Y^1$ is S; $Y^2$ is O; $R^2$ is H; $R^4$ is H; $R^5$ is H; $Q^2$ is Ph(2-Cl,3-Me); and $Q^1$ is |
| 249 $Y^1$ is S; $Y^2$ is O; $R^2$ is H; $R^4$ is H; $R^5$ is H; $Q^2$ is Ph(2-Cl,3-Me,4-F); and $Q^1$ is |
| 250 $Y^1$ is S; $Y^2$ is O; $R^2$ is H; $R^4$ is H; $R^5$ is H; $Q^2$ is Ph(2,3-di-Cl); and $Q^1$ is |
| 251 $Y^1$ is S; $Y^2$ is O; $R^2$ is H; $R^4$ is H; $R^5$ is H; $Q^2$ is Ph(2,4-di-Cl); and $Q^1$ is |
| 252 $Y^1$ is S; $Y^2$ is O; $R^2$ is H; $R^4$ is H; $R^5$ is H; $Q^2$ is Ph(2-Cl,3-F); and $Q^1$ is |
| 253 $Y^1$ is S; $Y^2$ is O; $R^2$ is H; $R^4$ is H; $R^5$ is H; $Q^2$ is Ph(2-Cl,4-F); and $Q^1$ is |
| 254 $Y^1$ is S; $Y^2$ is O; $R^2$ is H; $R^4$ is H; $R^5$ is H; $Q^2$ is Ph(2-Cl,5-F); and $Q^1$ is |
| 255 $Y^1$ is S; $Y^2$ is O; $R^2$ is H; $R^4$ is H; $R^5$ is H; $Q^2$ is Ph(2-Cl,3,4-di-F); and $Q^1$ is |
| 256 $Y^1$ is S; $Y^2$ is O; $R^2$ is H; $R^4$ is H; $R^5$ is H; $Q^2$ is Ph(2-Cl,3,5-di-F); and $Q^1$ is |
| 257 $Y^1$ is S; $Y^2$ is O; $R^2$ is H; $R^4$ is H; $R^5$ is H; $Q^2$ is Ph(2-OCF$_2$H); and $Q^1$ is |
| 258 $Y^1$ is S; $Y^2$ is O; $R^2$ is H; $R^4$ is H; $R^5$ is H; $Q^2$ is Ph(2-OCF$_2$H,3-Me); and $Q^1$ is |
| 259 $Y^1$ is S; $Y^2$ is O; $R^2$ is H; $R^4$ is H; $R^5$ is H; $Q^2$ is Ph(2-OCF$_2$H,3-Cl); and $Q^1$ is |
| 260 $Y^1$ is S; $Y^2$ is O; $R^2$ is H; $R^4$ is H; $R^5$ is H; $Q^2$ is Ph(2-OCF$_2$H,3-F); and $Q^1$ is |
| 261 $Y^1$ is S; $Y^2$ is O; $R^2$ is H; $R^4$ is H; $R^5$ is H; $Q^2$ is Ph(2-OCF$_2$H,4-F); and $Q^1$ is |
| 262 $Y^1$ is S; $Y^2$ is O; $R^2$ is H; $R^4$ is H; $R^5$ is H; $Q^2$ is Ph(2-OCF$_2$CF$_2$H); and $Q^1$ is |
| 263 $Y^1$ is S; $Y^2$ is O; $R^2$ is H; $R^4$ is H; $R^5$ is H; $Q^2$ is Ph(2-OCF$_2$CF$_2$H,3-F); and $Q^1$ is |
| 264 $Y^1$ is S; $Y^2$ is O; $R^2$ is H; $R^4$ is H; $R^5$ is H; $Q^2$ is Ph(2-OCF$_2$CF$_2$H,4-F); and $Q^1$ is |
| 265 $Y^1$ is S; $Y^2$ is O; $R^2$ is H; $R^4$ is H; $R^5$ is H; $Q^2$ is Ph(2-Br); and $Q^1$ is |
| 266 $Y^1$ is S; $Y^2$ is O; $R^2$ is H; $R^4$ is H; $R^5$ is H; $Q^2$ is Ph(2-Br,3-F); and $Q^1$ is |
| 267 $Y^1$ is S; $Y^2$ is O; $R^2$ is H; $R^4$ is H; $R^5$ is H; $Q^2$ is Ph(2-Br,4-F); and $Q^1$ is |
| 268 $Y^1$ is S; $Y^2$ is O; $R^2$ is H; $R^4$ is H; $R^5$ is H; $Q^2$ is Ph(2-Br,3,4-di-F); and $Q^1$ is |

| Table Row Heading |
|---|
| 269 $Y^1$ is S; $Y^2$ is O; $R^2$ is H; $R^4$ is H; $R^5$ is H; $Q^2$ is Ph(2-I); and $Q^1$ is |
| 270 $Y^1$ is S; $Y^2$ is O; $R^2$ is H; $R^4$ is H; $R^5$ is H; $Q^2$ is Ph(2-I,3-F); and $Q^1$ is |
| 271 $Y^1$ is S; $Y^2$ is O; $R^2$ is H; $R^4$ is H; $R^5$ is H; $Q^2$ is Ph(2-I,4-F); and $Q^1$ is |
| 272 $Y^1$ is S; $Y^2$ is O; $R^2$ is H; $R^4$ is H; $R^5$ is H; $Q^2$ is Ph(2-I,3,4-di-F); and $Q^1$ is |
| 273 $Y^1$ is S; $Y^2$ is O; $R^2$ is H; $R^4$ is H; $R^5$ is H; $Q^2$ is Ph(2-CN); and $Q^1$ is |
| 274 $Y^1$ is S; $Y^2$ is O; $R^2$ is H; $R^4$ is H; $R^5$ is H; $Q^2$ is Ph(2-CN,3-Me); and $Q^1$ is |
| 275 $Y^1$ is S; $Y^2$ is O; $R^2$ is H; $R^4$ is H; $R^5$ is H; $Q^2$ is Ph(2-CN,3-F); and $Q^1$ is |
| 276 $Y^1$ is S; $Y^2$ is O; $R^2$ is H; $R^4$ is H; $R^5$ is H; $Q^2$ is Ph(2-CN,4-F); and $Q^1$ is |
| 277 $Y^1$ is S; $Y^2$ is O; $R^2$ is H; $R^4$ is H; $R^5$ is H; $Q^2$ is Ph(2-CN,3-Cl); and $Q^1$ is |
| 278 $Y^1$ is S; $Y^2$ is O; $R^2$ is H; $R^4$ is H; $R^5$ is H; $Q^2$ is Ph(2-CN,4-Cl); and $Q^1$ is |
| 279 $Y^1$ is S; $Y^2$ is O; $R^2$ is H; $R^4$ is H; $R^5$ is H; $Q^2$ is Ph(2-CN,3,4-di-F); and $Q^1$ is |
| 280 $Y^1$ is S; $Y^2$ is O; $R^2$ is H; $R^4$ is H; $R^5$ is H; $Q^2$ is 2-Pyridinyl; and $Q^1$ is |
| 281 $Y^1$ is S; $Y^2$ is O; $R^2$ is H; $R^4$ is H; $R^5$ is H; $Q^2$ is 2-Pyridinyl,3-F; and $Q^1$ is |
| 282 $Y^1$ is S; $Y^2$ is O; $R^2$ is H; $R^4$ is H; $R^5$ is H; $Q^2$ is 2-Pyridinyl,4-F; and $Q^1$ is |
| 283 $Y^1$ is S; $Y^2$ is O; $R^2$ is H; $R^4$ is H; $R^5$ is H; $Q^2$ is 2-Pyridinyl,3,4-di-F; and $Q^1$ is |
| 284 $Y^1$ is S; $Y^2$ is O; $R^2$ is H; $R^4$ is H; $R^5$ is H; $Q^2$ is 2-Pyridinyl,3-Cl; and $Q^1$ is |
| 285 $Y^1$ is S; $Y^2$ is O; $R^2$ is H; $R^4$ is H; $R^5$ is H; $Q^2$ is 2-Pyridinyl,4-Cl; and $Q^1$ is |
| 286 $Y^1$ is S; $Y^2$ is O; $R^2$ is H; $R^4$ is H; $R^5$ is H; $Q^2$ is 2-Pyridinyl,3-Cl,4-F; and $Q^1$ is |
| 287 $Y^1$ is S; $Y^2$ is O; $R^2$ is H; $R^4$ is H; $R^5$ is H; $Q^2$ is Ph(2-SO$_2$Me); and $Q^1$ is |
| 288 $Y^1$ is S; $Y^2$ is O; $R^2$ is H; $R^4$ is H; $R^5$ is H; $Q^2$ is Ph(2-SO$_2$Me, 3-F); and $Q^1$ is |
| 289 $Y^1$ is S; $Y^2$ is O; $R^2$ is H; $R^4$ is H; $R^5$ is H; $Q^2$ is Ph(2-SO$_2$Me, 3-Me); and $Q^1$ is |
| 290 $Y^1$ is S; $Y^2$ is O; $R^2$ is H; $R^4$ is H; $R^5$ is H; $Q^2$ is Ph(2-SO$_2$Me, 4-F); and $Q^1$ is |
| 291 $Y^1$ is S; $Y^2$ is O; $R^2$ is H; $R^4$ is H; $R^5$ is H; $Q^2$ is Ph(2-SO$_2$Me, 5-F); and $Q^1$ is |
| 292 $Y^1$ is S; $Y^2$ is O; $R^2$ is H; $R^4$ is H; $R^5$ is H; $Q^2$ is Ph(2-SO$_2$Me,3,4-di-F); and $Q^1$ is |
| 293 $Y^1$ is S; $Y^2$ is O; $R^2$ is H; $R^4$ is H; $R^5$ is H; $Q^2$ is Ph(2-SO$_2$Me, 3-Cl); and $Q^1$ is |
| 294 $Y^1$ is S; $Y^2$ is O; $R^2$ is H; $R^4$ is H; $R^5$ is H; $Q^2$ is Ph(2-SO$_2$Me, 4-Cl); and $Q^1$ is |
| 295 $Y^1$ is S; $Y^2$ is O; $R^2$ is H; $R^4$ is H; $R^5$ is H; $Q^2$ is Ph(2-SO$_2$Me,3-Cl,4-F); and $Q^1$ is |
| 296 $Y^1$ is S; $Y^2$ is O; $R^2$ is H; $R^4$ is H; $R^5$ is H; $Q^2$ is Ph(2-SO$_2$NH$_2$); and $Q^1$ is |
| 297 $Y^1$ is S; $Y^2$ is O; $R^2$ is H; $R^4$ is H; $R^5$ is H; $Q^2$ is Ph(2-SO$_2$NH$_2$, 3-F); and $Q^1$ is |
| 298 $Y^1$ is S; $Y^2$ is O; $R^2$ is H; $R^4$ is H; $R^5$ is H; $Q^2$ is Ph(2-SO$_2$NH$_2$, 3-Cl); and $Q^1$ is |
| 299 $Y^1$ is S; $Y^2$ is O; $R^2$ is H; $R^4$ is H; $R^5$ is H; $Q^2$ is Ph(2-SO$_2$NH$_2$, 4-F); and $Q^1$ is |
| 300 $Y^1$ is S; $Y^2$ is O; $R^2$ is H; $R^4$ is H; $R^5$ is H; $Q^2$ is Ph(2-SO$_2$NH$_2$, 5-F); and $Q^1$ is |
| 301 $Y^1$ is S; $Y^2$ is O; $R^2$ is H; $R^4$ is H; $R^5$ is H; $Q^2$ is Ph(2-SO$_2$NH$_2$,3,4-di-F); and $Q^1$ is |
| 302 $Y^1$ is S; $Y^2$ is O; $R^2$ is H; $R^4$ is H; $R^5$ is H; $Q^2$ is Ph(3-F); and $Q^1$ is |
| 303 $Y^1$ is S; $Y^2$ is O; $R^2$ is H; $R^4$ is H; $R^5$ is H; $Q^2$ is Ph(3,4-di-F); and $Q^1$ is |
| 304 $Y^1$ is S; $Y^2$ is O; $R^2$ is H; $R^4$ is H; $R^5$ is H; $Q^2$ is Ph(3,5-di-F); and $Q^1$ is |
| 305 $Y^1$ is S; $Y^2$ is O; $R^2$ is H; $R^4$ is H; $R^5$ is H; $Q^2$ is Ph(3,4,5-tri-F); and $Q^1$ is |
| 306 $Y^1$ is S; $Y^2$ is O; $R^2$ is H; $R^4$ is H; $R^5$ is H; $Q^2$ is Ph(3-F,4-Cl); and $Q^1$ is |
| 307 $Y^1$ is S; $Y^2$ is O; $R^2$ is H; $R^4$ is H; $R^5$ is H; $Q^2$ is Ph(3-CF$_3$); and $Q^1$ is |
| 308 $Y^1$ is S; $Y^2$ is O; $R^2$ is H; $R^4$ is H; $R^5$ is H; $Q^2$ is Ph(3-CF$_3$,4-F); and $Q^1$ is |
| 309 $Y^1$ is S; $Y^2$ is O; $R^2$ is H; $R^4$ is H; $R^5$ is H; $Q^2$ is Ph(3-CF$_3$,4-Cl); and $Q^1$ is |
| 310 $Y^1$ is S; $Y^2$ is O; $R^2$ is H; $R^4$ is H; $R^5$ is H; $Q^2$ is Ph(3-CF$_3$,5-F); and $Q^1$ is |
| 311 $Y^1$ is S; $Y^2$ is O; $R^2$ is H; $R^4$ is H; $R^5$ is H; $Q^2$ is Ph(3-CF$_3$,4,5-di-F); and $Q^1$ is |
| 312 $Y^1$ is S; $Y^2$ is O; $R^2$ is H; $R^4$ is H; $R^5$ is H; $Q^2$ is Ph(3-SO$_2$Me); and $Q^1$ is |
| 313 $Y^1$ is S; $Y^2$ is O; $R^2$ is H; $R^4$ is H; $R^5$ is H; $Q^2$ is Ph(3-SO$_2$Me,4-Cl); and $Q^1$ is |
| 314 $Y^1$ is S; $Y^2$ is O; $R^2$ is H; $R^4$ is H; $R^5$ is H; $Q^2$ is Ph(3-SO$_2$Me,4-F); and $Q^1$ is |
| 315 $Y^1$ is S; $Y^2$ is O; $R^2$ is H; $R^4$ is H; $R^5$ is H; $Q^2$ is Ph(3-SO$_2$Me,4,5-di-F); and $Q^1$ is |
| 316 $Y^1$ is S; $Y^2$ is O; $R^2$ is H; $R^4$ is H; $R^5$ is H; $Q^2$ is Ph(3-SO$_2$Me,5-F); and $Q^1$ is |
| 317 $Y^1$ is S; $Y^2$ is O; $R^2$ is H; $R^4$ is H; $R^5$ is H; $Q^2$ is Ph(3-SO$_2$NH$_2$); and $Q^1$ is |
| 318 $Y^1$ is S; $Y^2$ is O; $R^2$ is H; $R^4$ is H; $R^5$ is H; $Q^2$ is Ph(3-SO$_2$NH$_2$,4-F); and $Q^1$ is |
| 319 $Y^1$ is S; $Y^2$ is O; $R^2$ is H; $R^4$ is H; $R^5$ is H; $Q^2$ is Ph(3-SO$_2$NH$_2$,4,5-di-F); and $Q^1$ is |
| 320 $Y^1$ is S; $Y^2$ is O; $R^2$ is H; $R^4$ is H; $R^5$ is H; $Q^2$ is Ph(3-SO$_2$NH$_2$,4-Cl); and $Q^1$ is |
| 321 $Y^1$ is S; $Y^2$ is O; $R^2$ is H; $R^4$ is H; $R^5$ is H; $Q^2$ is Ph(3-SO$_2$NH$_2$,5-F); and $Q^1$ is |
| 322 $Y^1$ is S; $Y^2$ is O; $R^2$ is H; $R^4$ is H; $R^5$ is H; $Q^2$ is Ph(3-Me); and $Q^1$ is |
| 323 $Y^1$ is S; $Y^2$ is O; $R^2$ is H; $R^4$ is H; $R^5$ is H; $Q^2$ is Ph(3-Me,4-F); and $Q^1$ is |
| 324 $Y^1$ is S; $Y^2$ is O; $R^2$ is H; $R^4$ is H; $R^5$ is H; $Q^2$ is Ph(3-Me,4-Cl); and $Q^1$ is |
| 325 $Y^1$ is S; $Y^2$ is O; $R^2$ is H; $R^4$ is H; $R^5$ is H; $Q^2$ is Ph(3-Me,5-F); and $Q^1$ is |
| 326 $Y^1$ is S; $Y^2$ is O; $R^2$ is H; $R^4$ is H; $R^5$ is H; $Q^2$ is Ph(3-Me,4,5-di-F); and $Q^1$ is |
| 327 $Y^1$ is S; $Y^2$ is O; $R^2$ is H; $R^4$ is H; $R^5$ is H; $Q^2$ is Ph(3-Cl); and $Q^1$ is |
| 328 $Y^1$ is S; $Y^2$ is O; $R^2$ is H; $R^4$ is H; $R^5$ is H; $Q^2$ is Ph(3-Cl,4-F); and $Q^1$ is |
| 329 $Y^1$ is S; $Y^2$ is O; $R^2$ is H; $R^4$ is H; $R^5$ is H; $Q^2$ is Ph(3,4-di-Cl); and $Q^1$ is |
| 330 $Y^1$ is S; $Y^2$ is O; $R^2$ is H; $R^4$ is H; $R^5$ is H; $Q^2$ is Ph(3-Cl,5-F); and $Q^1$ is |
| 331 $Y^1$ is S; $Y^2$ is O; $R^2$ is H; $R^4$ is H; $R^5$ is H; $Q^2$ is Ph(3-Cl,4,5-di-F); and $Q^1$ is |
| 332 $Y^1$ is S; $Y^2$ is O; $R^2$ is H; $R^4$ is H; $R^5$ is H; $Q^2$ is Ph(3,5-di-Cl); and $Q^1$ is |
| 333 $Y^1$ is S; $Y^2$ is O; $R^2$ is H; $R^4$ is H; $R^5$ is H; $Q^2$ is Ph(4-F); and $Q^1$ is |
| 334 $Y^1$ is S; $Y^2$ is O; $R^2$ is H; $R^4$ is H; $R^5$ is H; $Q^2$ is Ph(4-Cl); and $Q^1$ is |
| 335 $Y^1$ is S; $Y^2$ is O; $R^2$ is H; $R^4$ is H; $R^5$ is H; $Q^2$ is 2,2-di-F-1,3-benzodioxol-4-yl; and $Q^1$ is |
| 336 $Y^1$ is S; $Y^2$ is O; $R^2$ is H; $R^4$ is H; $R^5$ is H; $Q^2$ is 2,2-di-F-1,3-benzodioxol-5-yl; and $Q^1$ is |
| 337 $Y^1$ is S; $Y^2$ is O; $R^2$ is H; $R^4$ is H; $R^5$ is H; $Q^2$ is 2,2-di-Me-1,3-benzodioxol-4-yl; and $Q^1$ is |
| 338 $Y^1$ is S; $Y^2$ is O; $R^2$ is H; $R^4$ is H; $R^5$ is H; $Q^2$ is 2,2-di-Me-1,3-benzodioxol-5-yl; and $Q^1$ is |
| 339 $Y^1$ is S; $Y^2$ is O; $R^2$ is H; $R^4$ is H; $R^5$ is H; $Q^2$ is 1,3-benzodioxol-4-yl; and $Q^1$ is |
| 340 $Y^1$ is S; $Y^2$ is O; $R^2$ is H; $R^4$ is H; $R^5$ is H; $Q^2$ is 1,3-benzodioxol-5-yl; and $Q^1$ is |
| 341 $Y^1$ is O; $Y^2$ is S; $R^2$ is H; $R^4$ is H; $R^5$ is H; $Q^2$ is Ph(2-F); and $Q^1$ is |
| 342 $Y^1$ is O; $Y^2$ is S; $R^2$ is H; $R^4$ is H; $R^5$ is H; $Q^2$ is Ph(2,3-di-F); and $Q^1$ is |
| 343 $Y^1$ is O; $Y^2$ is S; $R^2$ is H; $R^4$ is H; $R^5$ is H; $Q^2$ is Ph(2,4-di-F); and $Q^1$ is |
| 344 $Y^1$ is O; $Y^2$ is S; $R^2$ is H; $R^4$ is H; $R^5$ is H; $Q^2$ is Ph(2,5-di-F); and $Q^1$ is |
| 345 $Y^1$ is O; $Y^2$ is S; $R^2$ is H; $R^4$ is H; $R^5$ is H; $Q^2$ is Ph(2,3,4-tri-F); and $Q^1$ is |

-continued

| Table Row Heading |
|---|
| 346 $Y^1$ is O; $Y^2$ is S; $R^2$ is H; $R^4$ is H; $R^5$ is H; $Q^2$ is Ph(2,3,5-tri-F); and $Q^1$ is |
| 347 $Y^1$ is O; $Y^2$ is S; $R^2$ is H; $R^4$ is H; $R^5$ is H; $Q^2$ is Ph(2,3,4,5-tetra-F); and $Q^1$ is |
| 348 $Y^1$ is O; $Y^2$ is S; $R^2$ is H; $R^4$ is H; $R^5$ is H; $Q^2$ is Ph(2-F,3-Cl,4-Br); and $Q^1$ is |
| 349 $Y^1$ is O; $Y^2$ is S; $R^2$ is H; $R^4$ is H; $R^5$ is H; $Q^2$ is Ph(2-F,3-Cl,4-F); and $Q^1$ is |
| 350 $Y^1$ is O; $Y^2$ is S; $R^2$ is H; $R^4$ is H; $R^5$ is H; $Q^2$ is Ph(2-F,3-Br,4-F); and $Q^1$ is |
| 351 $Y^1$ is O; $Y^2$ is S; $R^2$ is H; $R^4$ is H; $R^5$ is H; $Q^2$ is Ph(2-F,3-Me); and $Q^1$ is |
| 352 $Y^1$ is O; $Y^2$ is S; $R^2$ is H; $R^4$ is H; $R^5$ is H; $Q^2$ is Ph(2-F,3-Me,4-F); and $Q^1$ is |
| 353 $Y^1$ is O; $Y^2$ is S; $R^2$ is H; $R^4$ is H; $R^5$ is H; $Q^2$ is Ph(2-F,3-Me,4-Cl); and $Q^1$ is |
| 354 $Y^1$ is O; $Y^2$ is S; $R^2$ is H; $R^4$ is H; $R^5$ is H; $Q^2$ is Ph(2-F,3-Cl); and $Q^1$ is |
| 355 $Y^1$ is O; $Y^2$ is S; $R^2$ is H; $R^4$ is H; $R^5$ is H; $Q^2$ is Ph(2-F,4-Cl); and $Q^1$ is |
| 356 $Y^1$ is O; $Y^2$ is S; $R^2$ is H; $R^4$ is H; $R^5$ is H; $Q^2$ is Ph(2-F,3,4-di-Cl); and $Q^1$ is |
| 357 $Y^1$ is O; $Y^2$ is S; $R^2$ is H; $R^4$ is H; $R^5$ is H; $Q^2$ is Ph(2-F,4-Br); and $Q^1$ is |
| 358 $Y^1$ is O; $Y^2$ is S; $R^2$ is H; $R^4$ is H; $R^5$ is H; $Q^2$ is Ph(2-F,3-OMe); and $Q^1$ is |
| 359 $Y^1$ is O; $Y^2$ is S; $R^2$ is H; $R^4$ is H; $R^5$ is H; $Q^2$ is Ph(2-F,3-OMe,4-F); and $Q^1$ is |
| 360 $Y^1$ is O; $Y^2$ is S; $R^2$ is H; $R^4$ is H; $R^5$ is H; $Q^2$ is Ph(2-F,3-OMe,4-Cl); and $Q^1$ is |
| 361 $Y^1$ is O; $Y^2$ is S; $R^2$ is H; $R^4$ is H; $R^5$ is H; $Q^2$ is Ph(2-F,3-CF$_2$H); and $Q^1$ is |
| 362 $Y^1$ is O; $Y^2$ is S; $R^2$ is H; $R^4$ is H; $R^5$ is H; $Q^2$ is Ph(2-F,3-CF$_3$); and $Q^1$ is |
| 363 $Y^1$ is O; $Y^2$ is S; $R^2$ is H; $R^4$ is H; $R^5$ is H; $Q^2$ is Ph(2-F,3-CF$_3$,4-F); and $Q^1$ is |
| 364 $Y^1$ is O; $Y^2$ is S; $R^2$ is H; $R^4$ is H; $R^5$ is H; $Q^2$ is Ph(2-F,3-NO$_2$); and $Q^1$ is |
| 365 $Y^1$ is O; $Y^2$ is S; $R^2$ is H; $R^4$ is H; $R^5$ is H; $Q^2$ is Ph(2-F,3-NO$_2$,4-F); and $Q^1$ is |
| 366 $Y^1$ is O; $Y^2$ is S; $R^2$ is H; $R^4$ is H; $R^5$ is H; $Q^2$ is Ph(2-F,3-SO$_2$Me); and $Q^1$ is |
| 367 $Y^1$ is O; $Y^2$ is S; $R^2$ is H; $R^4$ is H; $R^5$ is H; $Q^2$ is Ph(2-F,3-SO$_2$Me,4-F); and $Q^1$ is |
| 368 $Y^1$ is O; $Y^2$ is S; $R^2$ is H; $R^4$ is H; $R^5$ is H; $Q^2$ is Ph(2-CF$_3$); and $Q^1$ is |
| 369 $Y^1$ is O; $Y^2$ is S; $R^2$ is H; $R^4$ is H; $R^5$ is H; $Q^2$ is Ph(2-CF$_3$,3-F); and $Q^1$ is |
| 370 $Y^1$ is O; $Y^2$ is S; $R^2$ is H; $R^4$ is H; $R^5$ is H; $Q^2$ is Ph(2-CF$_3$,3-Me); and $Q^1$ is |
| 371 $Y^1$ is O; $Y^2$ is S; $R^2$ is H; $R^4$ is H; $R^5$ is H; $Q^2$ is Ph(2-CF$_3$,4-F); and $Q^1$ is |
| 372 $Y^1$ is O; $Y^2$ is S; $R^2$ is H; $R^4$ is H; $R^5$ is H; $Q^2$ is Ph(2-CF$_3$,3-Cl); and $Q^1$ is |
| 373 $Y^1$ is O; $Y^2$ is S; $R^2$ is H; $R^4$ is H; $R^5$ is H; $Q^2$ is Ph(2-CF$_3$,4-Cl); and $Q^1$ is |
| 374 $Y^1$ is O; $Y^2$ is S; $R^2$ is H; $R^4$ is H; $R^5$ is H; $Q^2$ is Ph(2-CF$_3$,3,4-di-F); and $Q^1$ is |
| 375 $Y^1$ is O; $Y^2$ is S; $R^2$ is H; $R^4$ is H; $R^5$ is H; $Q^2$ is Ph(2-CF$_2$H); and $Q^1$ is |
| 376 $Y^1$ is O; $Y^2$ is S; $R^2$ is H; $R^4$ is H; $R^5$ is H; $Q^2$ is Ph(2-CF$_2$H,3-F); and $Q^1$ is |
| 377 $Y^1$ is O; $Y^2$ is S; $R^2$ is H; $R^4$ is H; $R^5$ is H; $Q^2$ is Ph(2-CF$_2$H,3-Me); and $Q^1$ is |
| 378 $Y^1$ is O; $Y^2$ is S; $R^2$ is H; $R^4$ is H; $R^5$ is H; $Q^2$ is Ph(2-CF$_2$H,4-F); and $Q^1$ is |
| 379 $Y^1$ is O; $Y^2$ is S; $R^2$ is H; $R^4$ is H; $R^5$ is H; $Q^2$ is Ph(2-CF$_2$H,3-Cl); and $Q^1$ is |
| 380 $Y^1$ is O; $Y^2$ is S; $R^2$ is H; $R^4$ is H; $R^5$ is H; $Q^2$ is Ph(2-CF$_2$H,4-Cl); and $Q^1$ is |
| 381 $Y^1$ is O; $Y^2$ is S; $R^2$ is H; $R^4$ is H; $R^5$ is H; $Q^2$ is Ph(2-CF$_2$H,3,4-di-F); and $Q^1$ is |
| 382 $Y^1$ is O; $Y^2$ is S; $R^2$ is H; $R^4$ is H; $R^5$ is H; $Q^2$ is Ph(2-Me); and $Q^1$ is |
| 383 $Y^1$ is O; $Y^2$ is S; $R^2$ is H; $R^4$ is H; $R^5$ is H; $Q^2$ is Ph(2,3-di-Me); and $Q^1$ is |
| 384 $Y^1$ is O; $Y^2$ is S; $R^2$ is H; $R^4$ is H; $R^5$ is H; $Q^2$ is Ph(2-Me,3-F); and $Q^1$ is |
| 385 $Y^1$ is O; $Y^2$ is S; $R^2$ is H; $R^4$ is H; $R^5$ is H; $Q^2$ is Ph(2-Me,3-Cl); and $Q^1$ is |
| 386 $Y^1$ is O; $Y^2$ is S; $R^2$ is H; $R^4$ is H; $R^5$ is H; $Q^2$ is Ph(2-Me,3-CF$_3$); and $Q^1$ is |
| 387 $Y^1$ is O; $Y^2$ is S; $R^2$ is H; $R^4$ is H; $R^5$ is H; $Q^2$ is Ph(2-Me,3,4-di-Cl); and $Q^1$ is |
| 388 $Y^1$ is O; $Y^2$ is S; $R^2$ is H; $R^4$ is H; $R^5$ is H; $Q^2$ is Ph(2-Me,3-Cl,4-F); and $Q^1$ is |
| 389 $Y^1$ is O; $Y^2$ is S; $R^2$ is H; $R^4$ is H; $R^5$ is H; $Q^2$ is Ph(2-Me,4-Cl); and $Q^1$ is |
| 390 $Y^1$ is O; $Y^2$ is S; $R^2$ is H; $R^4$ is H; $R^5$ is H; $Q^2$ is Ph(2-Me,4-F); and $Q^1$ is |
| 391 $Y^1$ is O; $Y^2$ is S; $R^2$ is H; $R^4$ is H; $R^5$ is H; $Q^2$ is Ph(2-Me,5-F); and $Q^1$ is |
| 392 $Y^1$ is O; $Y^2$ is S; $R^2$ is H; $R^4$ is H; $R^5$ is H; $Q^2$ is Ph(2-Me,3,4-di-F); and $Q^1$ is |
| 393 $Y^1$ is O; $Y^2$ is S; $R^2$ is H; $R^4$ is H; $R^5$ is H; $Q^2$ is Ph(2-Me,3,5-di-F); and $Q^1$ is |
| 394 $Y^1$ is O; $Y^2$ is S; $R^2$ is H; $R^4$ is H; $R^5$ is H; $Q^2$ is Ph(2-Et); and $Q^1$ is |
| 395 $Y^1$ is O; $Y^2$ is S; $R^2$ is H; $R^4$ is H; $R^5$ is H; $Q^2$ is Ph(2-Et,3-F); and $Q^1$ is |
| 396 $Y^1$ is O; $Y^2$ is S; $R^2$ is H; $R^4$ is H; $R^5$ is H; $Q^2$ is Ph(2-Et,3-Cl); and $Q^1$ is |
| 397 $Y^1$ is O; $Y^2$ is S; $R^2$ is H; $R^4$ is H; $R^5$ is H; $Q^2$ is Ph(2-Et,4-F); and $Q^1$ is |
| 398 $Y^1$ is O; $Y^2$ is S; $R^2$ is H; $R^4$ is H; $R^5$ is H; $Q^2$ is Ph(2-Et,3,4-di-F); and $Q^1$ is |
| 399 $Y^1$ is O; $Y^2$ is S; $R^2$ is H; $R^4$ is H; $R^5$ is H; $Q^2$ is Ph(2-i-Pr); and $Q^1$ is |
| 400 $Y^1$ is O; $Y^2$ is S; $R^2$ is H; $R^4$ is H; $R^5$ is H; $Q^2$ is Ph(2-i-Pr,3-F); and $Q^1$ is |
| 401 $Y^1$ is O; $Y^2$ is S; $R^2$ is H; $R^4$ is H; $R^5$ is H; $Q^2$ is Ph(2-i-Pr,3-Cl); and $Q^1$ is |
| 402 $Y^1$ is O; $Y^2$ is S; $R^2$ is H; $R^4$ is H; $R^5$ is H; $Q^2$ is Ph(2-i-Pr,4-F); and $Q^1$ is |
| 403 $Y^1$ is O; $Y^2$ is S; $R^2$ is H; $R^4$ is H; $R^5$ is H; $Q^2$ is Ph(2-i-Pr,3,4-di-F); and $Q^1$ is |
| 404 $Y^1$ is O; $Y^2$ is S; $R^2$ is H; $R^4$ is H; $R^5$ is H; $Q^2$ is Ph(2-c-Pr); and $Q^1$ is |
| 405 $Y^1$ is O; $Y^2$ is S; $R^2$ is H; $R^4$ is H; $R^5$ is H; $Q^2$ is Ph(2-c-Pr,3-F); and $Q^1$ is |
| 406 $Y^1$ is O; $Y^2$ is S; $R^2$ is H; $R^4$ is H; $R^5$ is H; $Q^2$ is Ph(2-c-Pr,3-Cl); and $Q^1$ is |
| 407 $Y^1$ is O; $Y^2$ is S; $R^2$ is H; $R^4$ is H; $R^5$ is H; $Q^2$ is Ph(2-c-Pr,4-F); and $Q^1$ is |
| 408 $Y^1$ is O; $Y^2$ is S; $R^2$ is H; $R^4$ is H; $R^5$ is H; $Q^2$ is Ph(2-c-Pr,3,4-di-F); and $Q^1$ is |
| 409 $Y^1$ is O; $Y^2$ is S; $R^2$ is H; $R^4$ is H; $R^5$ is H; $Q^2$ is Ph(2-NO$_2$); and $Q^1$ is |
| 410 $Y^1$ is O; $Y^2$ is S; $R^2$ is H; $R^4$ is H; $R^5$ is H; $Q^2$ is Ph(2-NO$_2$,3-F); and $Q^1$ is |
| 411 $Y^1$ is O; $Y^2$ is S; $R^2$ is H; $R^4$ is H; $R^5$ is H; $Q^2$ is Ph(2-NO$_2$,3-Cl); and $Q^1$ is |
| 412 $Y^1$ is O; $Y^2$ is S; $R^2$ is H; $R^4$ is H; $R^5$ is H; $Q^2$ is Ph(2-NO$_2$,4-F); and $Q^1$ is |
| 413 $Y^1$ is O; $Y^2$ is S; $R^2$ is H; $R^4$ is H; $R^5$ is H; $Q^2$ is Ph(2-NO$_2$,3,4-di-F); and $Q^1$ is |
| 414 $Y^1$ is O; $Y^2$ is S; $R^2$ is H; $R^4$ is H; $R^5$ is H; $Q^2$ is Ph(2-OCF$_3$); and $Q^1$ is |
| 415 $Y^1$ is O; $Y^2$ is S; $R^2$ is H; $R^4$ is H; $R^5$ is H; $Q^2$ is Ph(2-OCF$_3$,3-F); and $Q^1$ is |
| 416 $Y^1$ is O; $Y^2$ is S; $R^2$ is H; $R^4$ is H; $R^5$ is H; $Q^2$ is Ph(2-OCF$_3$,4-F); and $Q^1$ is |
| 417 $Y^1$ is O; $Y^2$ is S; $R^2$ is H; $R^4$ is H; $R^5$ is H; $Q^2$ is Ph(2-Cl); and $Q^1$ is |
| 418 $Y^1$ is O; $Y^2$ is S; $R^2$ is H; $R^4$ is H; $R^5$ is H; $Q^2$ is Ph(2-Cl,3-Me); and $Q^1$ is |
| 419 $Y^1$ is O; $Y^2$ is S; $R^2$ is H; $R^4$ is H; $R^5$ is H; $Q^2$ is Ph(2-Cl,3-Me,4-F); and $Q^1$ is |
| 420 $Y^1$ is O; $Y^2$ is S; $R^2$ is H; $R^4$ is H; $R^5$ is H; $Q^2$ is Ph(2,3-di-Cl); and $Q^1$ is |
| 421 $Y^1$ is O; $Y^2$ is S; $R^2$ is H; $R^4$ is H; $R^5$ is H; $Q^2$ is Ph(2,4-di-Cl); and $Q^1$ is |
| 422 $Y^1$ is O; $Y^2$ is S; $R^2$ is H; $R^4$ is H; $R^5$ is H; $Q^2$ is Ph(2-Cl,3-F); and $Q^1$ is |

-continued

| Table Row Heading |
|---|
| 423 $Y^1$ is O; $Y^2$ is S; $R^2$ is H; $R^4$ is H; $R^5$ is H; $Q^2$ is Ph(2-Cl,4-F); and $Q^1$ is |
| 424 $Y^1$ is O; $Y^2$ is S; $R^2$ is H; $R^4$ is H; $R^5$ is H; $Q^2$ is Ph(2-Cl,5-F); and $Q^1$ is |
| 425 $Y^1$ is O; $Y^2$ is S; $R^2$ is H; $R^4$ is H; $R^5$ is H; $Q^2$ is Ph(2-Cl,3,4-di-F); and $Q^1$ is |
| 426 $Y^1$ is O; $Y^2$ is S; $R^2$ is H; $R^4$ is H; $R^5$ is H; $Q^2$ is Ph(2-Cl,3,5-di-F); and $Q^1$ is |
| 427 $Y^1$ is O; $Y^2$ is S; $R^2$ is H; $R^4$ is H; $R^5$ is H; $Q^2$ is Ph(2-OCF$_2$H); and $Q^1$ is |
| 428 $Y^1$ is O; $Y^2$ is S; $R^2$ is H; $R^4$ is H; $R^5$ is H; $Q^2$ is Ph(2-OCF$_2$H,3-Me); and $Q^1$ is |
| 429 $Y^1$ is O; $Y^2$ is S; $R^2$ is H; $R^4$ is H; $R^5$ is H; $Q^2$ is Ph(2-OCF$_2$H,3-Cl); and $Q^1$ is |
| 430 $Y^1$ is O; $Y^2$ is S; $R^2$ is H; $R^4$ is H; $R^5$ is H; $Q^2$ is Ph(2-OCF$_2$H,3-F); and $Q^1$ is |
| 431 $Y^1$ is O; $Y^2$ is S; $R^2$ is H; $R^4$ is H; $R^5$ is H; $Q^2$ is Ph(2-OCF$_2$H,4-F); and $Q^1$ is |
| 432 $Y^1$ is O; $Y^2$ is S; $R^2$ is H; $R^4$ is H; $R^5$ is H; $Q^2$ is Ph(2-OCF$_2$CF$_2$H); and $Q^1$ is |
| 433 $Y^1$ is O; $Y^2$ is S; $R^2$ is H; $R^4$ is H; $R^5$ is H; $Q^2$ is Ph(2-OCF$_2$CF$_2$H,3-F); and $Q^1$ is |
| 434 $Y^1$ is O; $Y^2$ is S; $R^2$ is H; $R^4$ is H; $R^5$ is H; $Q^2$ is Ph(2-OCF$_2$CF$_2$H,4-F); and $Q^1$ is |
| 435 $Y^1$ is O; $Y^2$ is S; $R^2$ is H; $R^4$ is H; $R^5$ is H; $Q^2$ is Ph(2-Br); and $Q^1$ is |
| 436 $Y^1$ is O; $Y^2$ is S; $R^2$ is H; $R^4$ is H; $R^5$ is H; $Q^2$ is Ph(2-Br,3-F); and $Q^1$ is |
| 437 $Y^1$ is O; $Y^2$ is S; $R^2$ is H; $R^4$ is H; $R^5$ is H; $Q^2$ is Ph(2-Br,4-F); and $Q^1$ is |
| 438 $Y^1$ is O; $Y^2$ is S; $R^2$ is H; $R^4$ is H; $R^5$ is H; $Q^2$ is Ph(2-Br,3,4-di-F); and $Q^1$ is |
| 439 $Y^1$ is O; $Y^2$ is S; $R^2$ is H; $R^4$ is H; $R^5$ is H; $Q^2$ is Ph(2-I); and $Q^1$ is |
| 440 $Y^1$ is O; $Y^2$ is S; $R^2$ is H; $R^4$ is H; $R^5$ is H; $Q^2$ is Ph(2-I,3-F); and $Q^1$ is |
| 441 $Y^1$ is O; $Y^2$ is S; $R^2$ is H; $R^4$ is H; $R^5$ is H; $Q^2$ is Ph(2-I,4-F); and $Q^1$ is |
| 442 $Y^1$ is O; $Y^2$ is S; $R^2$ is H; $R^4$ is H; $R^5$ is H; $Q^2$ is Ph(2-I,3,4-di-F); and $Q^1$ is |
| 443 $Y^1$ is O; $Y^2$ is S; $R^2$ is H; $R^4$ is H; $R^5$ is H; $Q^2$ is Ph(2-CN); and $Q^1$ is |
| 444 $Y^1$ is O; $Y^2$ is S; $R^2$ is H; $R^4$ is H; $R^5$ is H; $Q^2$ is Ph(2-CN,3-Me); and $Q^1$ is |
| 445 $Y^1$ is O; $Y^2$ is S; $R^2$ is H; $R^4$ is H; $R^5$ is H; $Q^2$ is Ph(2-CN,3-F); and $Q^1$ is |
| 446 $Y^1$ is O; $Y^2$ is S; $R^2$ is H; $R^4$ is H; $R^5$ is H; $Q^2$ is Ph(2-CN,4-F); and $Q^1$ is |
| 447 $Y^1$ is O; $Y^2$ is S; $R^2$ is H; $R^4$ is H; $R^5$ is H; $Q^2$ is Ph(2-CN,3-Cl); and $Q^1$ is |
| 448 $Y^1$ is O; $Y^2$ is S; $R^2$ is H; $R^4$ is H; $R^5$ is H; $Q^2$ is Ph(2-CN,4-Cl); and $Q^1$ is |
| 449 $Y^1$ is O; $Y^2$ is S; $R^2$ is H; $R^4$ is H; $R^5$ is H; $Q^2$ is Ph(2-CN,3,4-di-F); and $Q^1$ is |
| 450 $Y^1$ is O; $Y^2$ is S; $R^2$ is H; $R^4$ is H; $R^5$ is H; $Q^2$ is 2-Pyridinyl; and $Q^1$ is |
| 451 $Y^1$ is O; $Y^2$ is S; $R^2$ is H; $R^4$ is H; $R^5$ is H; $Q^2$ is 2-Pyridinyl,3-F; and $Q^1$ is |
| 452 $Y^1$ is O; $Y^2$ is S; $R^2$ is H; $R^4$ is H; $R^5$ is H; $Q^2$ is 2-Pyridinyl,4-F; and $Q^1$ is |
| 453 $Y^1$ is O; $Y^2$ is S; $R^2$ is H; $R^4$ is H; $R^5$ is H; $Q^2$ is 2-Pyridinyl,3,4-di-F; and $Q^1$ is |
| 454 $Y^1$ is O; $Y^2$ is S; $R^2$ is H; $R^4$ is H; $R^5$ is H; $Q^2$ is 2-Pyridinyl,3-Cl; and $Q^1$ is |
| 455 $Y^1$ is O; $Y^2$ is S; $R^2$ is H; $R^4$ is H; $R^5$ is H; $Q^2$ is 2-Pyridinyl,4-Cl; and $Q^1$ is |
| 456 $Y^1$ is O; $Y^2$ is S; $R^2$ is H; $R^4$ is H; $R^5$ is H; $Q^2$ is 2-Pyridinyl,3-Cl,4-F; and $Q^1$ is |
| 457 $Y^1$ is O; $Y^2$ is S; $R^2$ is H; $R^4$ is H; $R^5$ is H; $Q^2$ is Ph(2-SO$_2$Me); and $Q^1$ is |
| 458 $Y^1$ is O; $Y^2$ is S; $R^2$ is H; $R^4$ is H; $R^5$ is H; $Q^2$ is Ph(2-SO$_2$Me, 3-F); and $Q^1$ is |
| 459 $Y^1$ is O; $Y^2$ is S; $R^2$ is H; $R^4$ is H; $R^5$ is H; $Q^2$ is Ph(2-SO$_2$Me, 3-Me); and $Q^1$ is |
| 460 $Y^1$ is O; $Y^2$ is S; $R^2$ is H; $R^4$ is H; $R^5$ is H; $Q^2$ is Ph(2-SO$_2$Me, 4-F); and $Q^1$ is |
| 461 $Y^1$ is O; $Y^2$ is S; $R^2$ is H; $R^4$ is H; $R^5$ is H; $Q^2$ is Ph(2-SO$_2$Me, 5-F); and $Q^1$ is |
| 462 $Y^1$ is O; $Y^2$ is S; $R^2$ is H; $R^4$ is H; $R^5$ is H; $Q^2$ is Ph(2-SO$_2$Me,3,4-di-F); and $Q^1$ is |
| 463 $Y^1$ is O; $Y^2$ is S; $R^2$ is H; $R^4$ is H; $R^5$ is H; $Q^2$ is Ph(2-SO$_2$Me, 3-Cl); and $Q^1$ is |
| 464 $Y^1$ is O; $Y^2$ is S; $R^2$ is H; $R^4$ is H; $R^5$ is H; $Q^2$ is Ph(2-SO$_2$Me, 4-Cl); and $Q^1$ is |
| 465 $Y^1$ is O; $Y^2$ is S; $R^2$ is H; $R^4$ is H; $R^5$ is H; $Q^2$ is Ph(2-SO$_2$Me,3-Cl,4-F); and $Q^1$ is |
| 466 $Y^1$ is O; $Y^2$ is S; $R^2$ is H; $R^4$ is H; $R^5$ is H; $Q^2$ is Ph(2-SO$_2$NH$_2$); and $Q^1$ is |
| 467 $Y^1$ is O; $Y^2$ is S; $R^2$ is H; $R^4$ is H; $R^5$ is H; $Q^2$ is Ph(2-SO$_2$NH$_2$, 3-F); and $Q^1$ is |
| 468 $Y^1$ is O; $Y^2$ is S; $R^2$ is H; $R^4$ is H; $R^5$ is H; $Q^2$ is Ph(2-SO$_2$NH$_2$, 3-Cl); and $Q^1$ is |
| 469 $Y^1$ is O; $Y^2$ is S; $R^2$ is H; $R^4$ is H; $R^5$ is H; $Q^2$ is Ph(2-SO$_2$NH$_2$, 4-F); and $Q^1$ is |
| 470 $Y^1$ is O; $Y^2$ is S; $R^2$ is H; $R^4$ is H; $R^5$ is H; $Q^2$ is Ph(2-SO$_2$NH$_2$, 5-F); and $Q^1$ is |
| 471 $Y^1$ is O; $Y^2$ is S; $R^2$ is H; $R^4$ is H; $R^5$ is H; $Q^2$ is Ph(2-SO$_2$NH$_2$,3,4-di-F); and $Q^1$ is |
| 472 $Y^1$ is O; $Y^2$ is S; $R^2$ is H; $R^4$ is H; $R^5$ is H; $Q^2$ is Ph(3-F); and $Q^1$ is |
| 473 $Y^1$ is O; $Y^2$ is S; $R^2$ is H; $R^4$ is H; $R^5$ is H; $Q^2$ is Ph(3,4-di-F); and $Q^1$ is |
| 474 $Y^1$ is O; $Y^2$ is S; $R^2$ is H; $R^4$ is H; $R^5$ is H; $Q^2$ is Ph(3,5-di-F); and $Q^1$ is |
| 475 $Y^1$ is O; $Y^2$ is S; $R^2$ is H; $R^4$ is H; $R^5$ is H; $Q^2$ is Ph(3,4,5-tri-F); and $Q^1$ is |
| 476 $Y^1$ is O; $Y^2$ is S; $R^2$ is H; $R^4$ is H; $R^5$ is H; $Q^2$ is Ph(3-F,4-Cl); and $Q^1$ is |
| 477 $Y^1$ is O; $Y^2$ is S; $R^2$ is H; $R^4$ is H; $R^5$ is H; $Q^2$ is Ph(3-CF$_3$); and $Q^1$ is |
| 478 $Y^1$ is O; $Y^2$ is S; $R^2$ is H; $R^4$ is H; $R^5$ is H; $Q^2$ is Ph(3-CF$_3$,4-F); and $Q^1$ is |
| 479 $Y^1$ is O; $Y^2$ is S; $R^2$ is H; $R^4$ is H; $R^5$ is H; $Q^2$ is Ph(3-CF$_3$,4-Cl); and $Q^1$ is |
| 480 $Y^1$ is O; $Y^2$ is S; $R^2$ is H; $R^4$ is H; $R^5$ is H; $Q^2$ is Ph(3-CF$_3$,5-F); and $Q^1$ is |
| 481 $Y^1$ is O; $Y^2$ is S; $R^2$ is H; $R^4$ is H; $R^5$ is H; $Q^2$ is Ph(3-CF$_3$,4,5-di-F); and $Q^1$ is |
| 482 $Y^1$ is O; $Y^2$ is S; $R^2$ is H; $R^4$ is H; $R^5$ is H; $Q^2$ is Ph(3-SO$_2$Me); and $Q^1$ is |
| 483 $Y^1$ is O; $Y^2$ is S; $R^2$ is H; $R^4$ is H; $R^5$ is H; $Q^2$ is Ph(3-SO$_2$Me,4-Cl); and $Q^1$ is |
| 484 $Y^1$ is O; $Y^2$ is S; $R^2$ is H; $R^4$ is H; $R^5$ is H; $Q^2$ is Ph(3-SO$_2$Me,4-F); and $Q^1$ is |
| 485 $Y^1$ is O; $Y^2$ is S; $R^2$ is H; $R^4$ is H; $R^5$ is H; $Q^2$ is Ph(3-SO$_2$Me,4,5-di-F); and $Q^1$ is |
| 486 $Y^1$ is O; $Y^2$ is S; $R^2$ is H; $R^4$ is H; $R^5$ is H; $Q^2$ is Ph(3-SO$_2$Me,5-F); and $Q^1$ is |
| 487 $Y^1$ is O; $Y^2$ is S; $R^2$ is H; $R^4$ is H; $R^5$ is H; $Q^2$ is Ph(3-SO$_2$NH$_2$); and $Q^1$ is |
| 488 $Y^1$ is O; $Y^2$ is S; $R^2$ is H; $R^4$ is H; $R^5$ is H; $Q^2$ is Ph(3-SO$_2$NH$_2$,4-F); and $Q^1$ is |
| 489 $Y^1$ is O; $Y^2$ is S; $R^2$ is H; $R^4$ is H; $R^5$ is H; $Q^2$ is Ph(3-SO$_2$NH$_2$,4,5-di-F); and $Q^1$ is |
| 490 $Y^1$ is O; $Y^2$ is S; $R^2$ is H; $R^4$ is H; $R^5$ is H; $Q^2$ is Ph(3-SO$_2$NH$_2$,4-Cl); and $Q^1$ is |
| 491 $Y^1$ is O; $Y^2$ is S; $R^2$ is H; $R^4$ is H; $R^5$ is H; $Q^2$ is Ph(3-SO$_2$NH$_2$,5-F); and $Q^1$ is |
| 492 $Y^1$ is O; $Y^2$ is S; $R^2$ is H; $R^4$ is H; $R^5$ is H; $Q^2$ is Ph(3-Me); and $Q^1$ is |
| 493 $Y^1$ is O; $Y^2$ is S; $R^2$ is H; $R^4$ is H; $R^5$ is H; $Q^2$ is Ph(3-Me,4-F); and $Q^1$ is |
| 494 $Y^1$ is O; $Y^2$ is S; $R^2$ is H; $R^4$ is H; $R^5$ is H; $Q^2$ is Ph(3-Me,4-Cl); and $Q^1$ is |
| 495 $Y^1$ is O; $Y^2$ is S; $R^2$ is H; $R^4$ is H; $R^5$ is H; $Q^2$ is Ph(3-Me,5-F); and $Q^1$ is |
| 496 $Y^1$ is O; $Y^2$ is S; $R^2$ is H; $R^4$ is H; $R^5$ is H; $Q^2$ is Ph(3-Me,4,5-di-F); and $Q^1$ is |
| 497 $Y^1$ is O; $Y^2$ is S; $R^2$ is H; $R^4$ is H; $R^5$ is H; $Q^2$ is Ph(3-Cl); and $Q^1$ is |
| 498 $Y^1$ is O; $Y^2$ is S; $R^2$ is H; $R^4$ is H; $R^5$ is H; $Q^2$ is Ph(3-Cl,4-F); and $Q^1$ is |
| 499 $Y^1$ is O; $Y^2$ is S; $R^2$ is H; $R^4$ is H; $R^5$ is H; $Q^2$ is Ph(3,4-di-Cl); and $Q^1$ is |

-continued

| Table Row Heading |
|---|
| 500 $Y^1$ is O; $Y^2$ is S; $R^2$ is H; $R^4$ is H; $R^5$ is H; $Q^2$ is Ph(3-Cl,5-F); and $Q^1$ is |
| 501 $Y^1$ is O; $Y^2$ is S; $R^2$ is H; $R^4$ is H; $R^5$ is H; $Q^2$ is Ph(3-Cl,4,5-di-F); and $Q^1$ is |
| 502 $Y^1$ is O; $Y^2$ is S; $R^2$ is H; $R^4$ is H; $R^5$ is H; $Q^2$ is Ph(3,5-di-Cl); and $Q^1$ is |
| 503 $Y^1$ is O; $Y^2$ is S; $R^2$ is H; $R^4$ is H; $R^5$ is H; $Q^2$ is Ph(4-F); and $Q^1$ is |
| 504 $Y^1$ is O; $Y^2$ is S; $R^2$ is H; $R^4$ is H; $R^5$ is H; $Q^2$ is Ph(4-Cl); and $Q^1$ is |
| 505 $Y^1$ is O; $Y^2$ is S; $R^2$ is H; $R^4$ is H; $R^5$ is H; $Q^2$ is 2,2-di-F-1,3-benzodioxol-4-yl; and $Q^1$ is |
| 506 $Y^1$ is O; $Y^2$ is S; $R^2$ is H; $R^4$ is H; $R^5$ is H; $Q^2$ is 2,2-di-F-1,3-benzodioxol-5-yl; and $Q^1$ is |
| 507 $Y^1$ is O; $Y^2$ is S; $R^2$ is H; $R^4$ is H; $R^5$ is H; $Q^2$ is 2,2-di-Me-1,3-benzodioxol-4-yl; and $Q^1$ is |
| 508 $Y^1$ is O; $Y^2$ is S; $R^2$ is H; $R^4$ is H; $R^5$ is H; $Q^2$ is 2,2-di-Me-1,3-benzodioxol-5-yl; and $Q^1$ is |
| 509 $Y^1$ is O; $Y^2$ is S; $R^2$ is H; $R^4$ is H; $R^5$ is H; $Q^2$ is 1,3-benzodioxol-4-yl; and $Q^1$ is |
| 510 $Y^1$ is O; $Y^2$ is S; $R^2$ is H; $R^4$ is H; $R^5$ is H; $Q^2$ is 1,3-benzodioxol-5-yl; and $Q^1$ is |
| 511 $Y^1$ is S; $Y^2$ is S; $R^2$ is H; $R^4$ is H; $R^5$ is H; $Q^2$ is Ph(2-F); and $Q^1$ is |
| 512 $Y^1$ is S; $Y^2$ is S; $R^2$ is H; $R^4$ is H; $R^5$ is H; $Q^2$ is Ph(2,3-di-F); and $Q^1$ is |
| 513 $Y^1$ is S; $Y^2$ is S; $R^2$ is H; $R^4$ is H; $R^5$ is H; $Q^2$ is Ph(2,4-di-F); and $Q^1$ is |
| 514 $Y^1$ is S; $Y^2$ is S; $R^2$ is H; $R^4$ is H; $R^5$ is H; $Q^2$ is Ph(2,5-di-F); and $Q^1$ is |
| 515 $Y^1$ is S; $Y^2$ is S; $R^2$ is H; $R^4$ is H; $R^5$ is H; $Q^2$ is Ph(2,3,4-tri-F); and $Q^1$ is |
| 516 $Y^1$ is S; $Y^2$ is S; $R^2$ is H; $R^4$ is H; $R^5$ is H; $Q^2$ is Ph(2,3,5-tri-F); and $Q^1$ is |
| 517 $Y^1$ is S; $Y^2$ is S; $R^2$ is H; $R^4$ is H; $R^5$ is H; $Q^2$ is Ph(2,3,4,5-tetra-F); and $Q^1$ is |
| 518 $Y^1$ is S; $Y^2$ is S; $R^2$ is H; $R^4$ is H; $R^5$ is H; $Q^2$ is Ph(2-F,3-Cl,4-Br); and $Q^1$ is |
| 519 $Y^1$ is S; $Y^2$ is S; $R^2$ is H; $R^4$ is H; $R^5$ is H; $Q^2$ is Ph(2-F,3-Cl,4-F); and $Q^1$ is |
| 520 $Y^1$ is S; $Y^2$ is S; $R^2$ is H; $R^4$ is H; $R^5$ is H; $Q^2$ is Ph(2-F,3-Br,4-F); and $Q^1$ is |
| 521 $Y^1$ is S; $Y^2$ is S; $R^2$ is H; $R^4$ is H; $R^5$ is H; $Q^2$ is Ph(2-F,3-Me); and $Q^1$ is |
| 522 $Y^1$ is S; $Y^2$ is S; $R^2$ is H; $R^4$ is H; $R^5$ is H; $Q^2$ is Ph(2-F,3-Me,4-F); and $Q^1$ is |
| 523 $Y^1$ is S; $Y^2$ is S; $R^2$ is H; $R^4$ is H; $R^5$ is H; $Q^2$ is Ph(2-F,3-Me,4-Cl); and $Q^1$ is |
| 524 $Y^1$ is S; $Y^2$ is S; $R^2$ is H; $R^4$ is H; $R^5$ is H; $Q^2$ is Ph(2-F,3-Cl); and $Q^1$ is |
| 525 $Y^1$ is S; $Y^2$ is S; $R^2$ is H; $R^4$ is H; $R^5$ is H; $Q^2$ is Ph(2-F,4-Cl); and $Q^1$ is |
| 526 $Y^1$ is S; $Y^2$ is S; $R^2$ is H; $R^4$ is H; $R^5$ is H; $Q^2$ is Ph(2-F,3,4-di-Cl); and $Q^1$ is |
| 527 $Y^1$ is S; $Y^2$ is S; $R^2$ is H; $R^4$ is H; $R^5$ is H; $Q^2$ is Ph(2-F,4-Br); and $Q^1$ is |
| 528 $Y^1$ is S; $Y^2$ is S; $R^2$ is H; $R^4$ is H; $R^5$ is H; $Q^2$ is Ph(2-F,3-OMe); and $Q^1$ is |
| 529 $Y^1$ is S; $Y^2$ is S; $R^2$ is H; $R^4$ is H; $R^5$ is H; $Q^2$ is Ph(2-F,3-OMe,4-F); and $Q^1$ is |
| 530 $Y^1$ is S; $Y^2$ is S; $R^2$ is H; $R^4$ is H; $R^5$ is H; $Q^2$ is Ph(2-F,3-OMe,4-Cl); and $Q^1$ is |
| 531 $Y^1$ is S; $Y^2$ is S; $R^2$ is H; $R^4$ is H; $R^5$ is H; $Q^2$ is Ph(2-F,3-CF$_2$H); and $Q^1$ is |
| 532 $Y^1$ is S; $Y^2$ is S; $R^2$ is H; $R^4$ is H; $R^5$ is H; $Q^2$ is Ph(2-F,3-CF$_3$); and $Q^1$ is |
| 533 $Y^1$ is S; $Y^2$ is S; $R^2$ is H; $R^4$ is H; $R^5$ is H; $Q^2$ is Ph(2-F,3-CF$_3$,4-F); and $Q^1$ is |
| 534 $Y^1$ is S; $Y^2$ is S; $R^2$ is H; $R^4$ is H; $R^5$ is H; $Q^2$ is Ph(2-F,3-NO$_2$); and $Q^1$ is |
| 535 $Y^1$ is S; $Y^2$ is S; $R^2$ is H; $R^4$ is H; $R^5$ is H; $Q^2$ is Ph(2-F,3-NO$_2$,4-F); and $Q^1$ is |
| 536 $Y^1$ is S; $Y^2$ is S; $R^2$ is H; $R^4$ is H; $R^5$ is H; $Q^2$ is Ph(2-F,3-SO$_2$Me); and $Q^1$ is |
| 537 $Y^1$ is S; $Y^2$ is S; $R^2$ is H; $R^4$ is H; $R^5$ is H; $Q^2$ is Ph(2-F,3-SO$_2$Me,4-F); and $Q^1$ is |
| 538 $Y^1$ is S; $Y^2$ is S; $R^2$ is H; $R^4$ is H; $R^5$ is H; $Q^2$ is Ph(2-CF$_3$); and $Q^1$ is |
| 539 $Y^1$ is S; $Y^2$ is S; $R^2$ is H; $R^4$ is H; $R^5$ is H; $Q^2$ is Ph(2-CF$_3$,3-F); and $Q^1$ is |
| 540 $Y^1$ is S; $Y^2$ is S; $R^2$ is H; $R^4$ is H; $R^5$ is H; $Q^2$ is Ph(2-CF$_3$,3-Me); and $Q^1$ is |
| 541 $Y^1$ is S; $Y^2$ is S; $R^2$ is H; $R^4$ is H; $R^5$ is H; $Q^2$ is Ph(2-CF$_3$,4-F); and $Q^1$ is |
| 542 $Y^1$ is S; $Y^2$ is S; $R^2$ is H; $R^4$ is H; $R^5$ is H; $Q^2$ is Ph(2-CF$_3$,3-Cl); and $Q^1$ is |
| 543 $Y^1$ is S; $Y^2$ is S; $R^2$ is H; $R^4$ is H; $R^5$ is H; $Q^2$ is Ph(2-CF$_3$,4-Cl); and $Q^1$ is |
| 544 $Y^1$ is S; $Y^2$ is S; $R^2$ is H; $R^4$ is H; $R^5$ is H; $Q^2$ is Ph(2-CF$_3$,3,4-di-F); and $Q^1$ is |
| 545 $Y^1$ is S; $Y^2$ is S; $R^2$ is H; $R^4$ is H; $R^5$ is H; $Q^2$ is Ph(2-CF$_2$H); and $Q^1$ is |
| 546 $Y^1$ is S; $Y^2$ is S; $R^2$ is H; $R^4$ is H; $R^5$ is H; $Q^2$ is Ph(2-CF$_2$H,3-F); and $Q^1$ is |
| 547 $Y^1$ is S; $Y^2$ is S; $R^2$ is H; $R^4$ is H; $R^5$ is H; $Q^2$ is Ph(2-CF$_2$H,3-Me); and $Q^1$ is |
| 548 $Y^1$ is S; $Y^2$ is S; $R^2$ is H; $R^4$ is H; $R^5$ is H; $Q^2$ is Ph(2-CF$_2$H,4-F); and $Q^1$ is |
| 549 $Y^1$ is S; $Y^2$ is S; $R^2$ is H; $R^4$ is H; $R^5$ is H; $Q^2$ is Ph(2-CF$_2$H,3-Cl); and $Q^1$ is |
| 550 $Y^1$ is S; $Y^2$ is S; $R^2$ is H; $R^4$ is H; $R^5$ is H; $Q^2$ is Ph(2-CF$_2$H,4-Cl); and $Q^1$ is |
| 551 $Y^1$ is S; $Y^2$ is S; $R^2$ is H; $R^4$ is H; $R^5$ is H; $Q^2$ is Ph(2-CF$_2$H,3,4-di-F); and $Q^1$ is |
| 552 $Y^1$ is S; $Y^2$ is S; $R^2$ is H; $R^4$ is H; $R^5$ is H; $Q^2$ is Ph(2-Me); and $Q^1$ is |
| 553 $Y^1$ is S; $Y^2$ is S; $R^2$ is H; $R^4$ is H; $R^5$ is H; $Q^2$ is Ph(2,3-di-Me); and $Q^1$ is |
| 554 $Y^1$ is S; $Y^2$ is S; $R^2$ is H; $R^4$ is H; $R^5$ is H; $Q^2$ is Ph(2-Me,3-F); and $Q^1$ is |
| 555 $Y^1$ is S; $Y^2$ is S; $R^2$ is H; $R^4$ is H; $R^5$ is H; $Q^2$ is Ph(2-Me,3-Cl); and $Q^1$ is |
| 556 $Y^1$ is S; $Y^2$ is S; $R^2$ is H; $R^4$ is H; $R^5$ is H; $Q^2$ is Ph(2-Me,3-CF$_3$); and $Q^1$ is |
| 557 $Y^1$ is S; $Y^2$ is S; $R^2$ is H; $R^4$ is H; $R^5$ is H; $Q^2$ is Ph(2-Me,3,4-di-Cl); and $Q^1$ is |
| 558 $Y^1$ is S; $Y^2$ is S; $R^2$ is H; $R^4$ is H; $R^5$ is H; $Q^2$ is Ph(2-Me,3-Cl,4-F); and $Q^1$ is |
| 559 $Y^1$ is S; $Y^2$ is S; $R^2$ is H; $R^4$ is H; $R^5$ is H; $Q^2$ is Ph(2-Me,4-Cl); and $Q^1$ is |
| 560 $Y^1$ is S; $Y^2$ is S; $R^2$ is H; $R^4$ is H; $R^5$ is H; $Q^2$ is Ph(2-Me,4-F); and $Q^1$ is |
| 561 $Y^1$ is S; $Y^2$ is S; $R^2$ is H; $R^4$ is H; $R^5$ is H; $Q^2$ is Ph(2-Me,5-F); and $Q^1$ is |
| 562 $Y^1$ is S; $Y^2$ is S; $R^2$ is H; $R^4$ is H; $R^5$ is H; $Q^2$ is Ph(2-Me,3,4-di-F); and $Q^1$ is |
| 563 $Y^1$ is S; $Y^2$ is S; $R^2$ is H; $R^4$ is H; $R^5$ is H; $Q^2$ is Ph(2-Me,3,5-di-F); and $Q^1$ is |
| 564 $Y^1$ is S; $Y^2$ is S; $R^2$ is H; $R^4$ is H; $R^5$ is H; $Q^2$ is Ph(2-Et); and $Q^1$ is |
| 565 $Y^1$ is S; $Y^2$ is S; $R^2$ is H; $R^4$ is H; $R^5$ is H; $Q^2$ is Ph(2-Et,3-F); and $Q^1$ is |
| 566 $Y^1$ is S; $Y^2$ is S; $R^2$ is H; $R^4$ is H; $R^5$ is H; $Q^2$ is Ph(2-Et,3-Cl); and $Q^1$ is |
| 567 $Y^1$ is S; $Y^2$ is S; $R^2$ is H; $R^4$ is H; $R^5$ is H; $Q^2$ is Ph(2-Et,4-F); and $Q^1$ is |
| 568 $Y^1$ is S; $Y^2$ is S; $R^2$ is H; $R^4$ is H; $R^5$ is H; $Q^2$ is Ph(2-Et,3,4-di-F); and $Q^1$ is |
| 569 $Y^1$ is S; $Y^2$ is S; $R^2$ is H; $R^4$ is H; $R^5$ is H; $Q^2$ is Ph(2-i-Pr); and $Q^1$ is |
| 570 $Y^1$ is S; $Y^2$ is S; $R^2$ is H; $R^4$ is H; $R^5$ is H; $Q^2$ is Ph(2-i-Pr,3-F); and $Q^1$ is |
| 571 $Y^1$ is S; $Y^2$ is S; $R^2$ is H; $R^4$ is H; $R^5$ is H; $Q^2$ is Ph(2-i-Pr,3-Cl); and $Q^1$ is |
| 572 $Y^1$ is S; $Y^2$ is S; $R^2$ is H; $R^4$ is H; $R^5$ is H; $Q^2$ is Ph(2-i-Pr,4-F); and $Q^1$ is |
| 573 $Y^1$ is S; $Y^2$ is S; $R^2$ is H; $R^4$ is H; $R^5$ is H; $Q^2$ is Ph(2-i-Pr,3,4-di-F); and $Q^1$ is |
| 574 $Y^1$ is S; $Y^2$ is S; $R^2$ is H; $R^4$ is H; $R^5$ is H; $Q^2$ is Ph(2-c-Pr); and $Q^1$ is |
| 575 $Y^1$ is S; $Y^2$ is S; $R^2$ is H; $R^4$ is H; $R^5$ is H; $Q^2$ is Ph(2-c-Pr,3-F); and $Q^1$ is |
| 576 $Y^1$ is S; $Y^2$ is S; $R^2$ is H; $R^4$ is H; $R^5$ is H; $Q^2$ is Ph(2-c-Pr,3-Cl); and $Q^1$ is |

-continued

| Table Row Heading |
|---|
| 577 $Y^1$ is S; $Y^2$ is S; $R^2$ is H; $R^4$ is H; $R^5$ is H; $Q^2$ is Ph(2-c-Pr,4-F); and $Q^1$ is |
| 578 $Y^1$ is S; $Y^2$ is S; $R^2$ is H; $R^4$ is H; $R^5$ is H; $Q^2$ is Ph(2-c-Pr,3,4-di-F); and $Q^1$ is |
| 579 $Y^1$ is S; $Y^2$ is S; $R^2$ is H; $R^4$ is H; $R^5$ is H; $Q^2$ is Ph(2-NO$_2$); and $Q^1$ is |
| 580 $Y^1$ is S; $Y^2$ is S; $R^2$ is H; $R^4$ is H; $R^5$ is H; $Q^2$ is Ph(2-NO$_2$,3-F); and $Q^1$ is |
| 581 $Y^1$ is S; $Y^2$ is S; $R^2$ is H; $R^4$ is H; $R^5$ is H; $Q^2$ is Ph(2-NO$_2$,3-Cl); and $Q^1$ is |
| 582 $Y^1$ is S; $Y^2$ is S; $R^2$ is H; $R^4$ is H; $R^5$ is H; $Q^2$ is Ph(2-NO$_2$,4-F); and $Q^1$ is |
| 583 $Y^1$ is S; $Y^2$ is S; $R^2$ is H; $R^4$ is H; $R^5$ is H; $Q^2$ is Ph(2-NO$_2$,3,4-di-F); and $Q^1$ is |
| 584 $Y^1$ is S; $Y^2$ is S; $R^2$ is H; $R^4$ is H; $R^5$ is H; $Q^2$ is Ph(2-OCF$_3$); and $Q^1$ is |
| 585 $Y^1$ is S; $Y^2$ is S; $R^2$ is H; $R^4$ is H; $R^5$ is H; $Q^2$ is Ph(2-OCF$_3$,3-F); and $Q^1$ is |
| 586 $Y^1$ is S; $Y^2$ is S; $R^2$ is H; $R^4$ is H; $R^5$ is H; $Q^2$ is Ph(2-OCF$_3$,4-F); and $Q^1$ is |
| 587 $Y^1$ is S; $Y^2$ is S; $R^2$ is H; $R^4$ is H; $R^5$ is H; $Q^2$ is Ph(2-Cl); and $Q^1$ is |
| 588 $Y^1$ is S; $Y^2$ is S; $R^2$ is H; $R^4$ is H; $R^5$ is H; $Q^2$ is Ph(2-Cl,3-Me); and $Q^1$ is |
| 589 $Y^1$ is S; $Y^2$ is S; $R^2$ is H; $R^4$ is H; $R^5$ is H; $Q^2$ is Ph(2-Cl,3-Me,4-F); and $Q^1$ is |
| 590 $Y^1$ is S; $Y^2$ is S; $R^2$ is H; $R^4$ is H; $R^5$ is H; $Q^2$ is Ph(2,3-di-Cl); and $Q^1$ is |
| 591 $Y^1$ is S; $Y^2$ is S; $R^2$ is H; $R^4$ is H; $R^5$ is H; $Q^2$ is Ph(2,4-di-Cl); and $Q^1$ is |
| 592 $Y^1$ is S; $Y^2$ is S; $R^2$ is H; $R^4$ is H; $R^5$ is H; $Q^2$ is Ph(2-Cl,3-F); and $Q^1$ is |
| 593 $Y^1$ is S; $Y^2$ is S; $R^2$ is H; $R^4$ is H; $R^5$ is H; $Q^2$ is Ph(2-Cl,4-F); and $Q^1$ is |
| 594 $Y^1$ is S; $Y^2$ is S; $R^2$ is H; $R^4$ is H; $R^5$ is H; $Q^2$ is Ph(2-Cl,5-F); and $Q^1$ is |
| 595 $Y^1$ is S; $Y^2$ is S; $R^2$ is H; $R^4$ is H; $R^5$ is H; $Q^2$ is Ph(2-Cl,3,4-di-F); and $Q^1$ is |
| 596 $Y^1$ is S; $Y^2$ is S; $R^2$ is H; $R^4$ is H; $R^5$ is H; $Q^2$ is Ph(2-Cl,3,5-di-F); and $Q^1$ is |
| 597 $Y^1$ is S; $Y^2$ is S; $R^2$ is H; $R^4$ is H; $R^5$ is H; $Q^2$ is Ph(2-OCF$_2$H); and $Q^1$ is |
| 598 $Y^1$ is S; $Y^2$ is S; $R^2$ is H; $R^4$ is H; $R^5$ is H; $Q^2$ is Ph(2-OCF$_2$H,3-Me); and $Q^1$ is |
| 599 $Y^1$ is S; $Y^2$ is S; $R^2$ is H; $R^4$ is H; $R^5$ is H; $Q^2$ is Ph(2-OCF$_2$H,3-Cl); and $Q^1$ is |
| 600 $Y^1$ is S; $Y^2$ is S; $R^2$ is H; $R^4$ is H; $R^5$ is H; $Q^2$ is Ph(2-OCF$_2$H,3-F); and $Q^1$ is |
| 601 $Y^1$ is S; $Y^2$ is S; $R^2$ is H; $R^4$ is H; $R^5$ is H; $Q^2$ is Ph(2-OCF$_2$H,4-F); and $Q^1$ is |
| 602 $Y^1$ is S; $Y^2$ is S; $R^2$ is H; $R^4$ is H; $R^5$ is H; $Q^2$ is Ph(2-OCF$_2$CF$_2$H); and $Q^1$ is |
| 603 $Y^1$ is S; $Y^2$ is S; $R^2$ is H; $R^4$ is H; $R^5$ is H; $Q^2$ is Ph(2-OCF$_2$CF$_2$H,3-F); and $Q^1$ is |
| 604 $Y^1$ is S; $Y^2$ is S; $R^2$ is H; $R^4$ is H; $R^5$ is H; $Q^2$ is Ph(2-OCF$_2$CF$_2$H,4-F); and $Q^1$ is |
| 605 $Y^1$ is S; $Y^2$ is S; $R^2$ is H; $R^4$ is H; $R^5$ is H; $Q^2$ is Ph(2-Br); and $Q^1$ is |
| 606 $Y^1$ is S; $Y^2$ is S; $R^2$ is H; $R^4$ is H; $R^5$ is H; $Q^2$ is Ph(2-Br,3-F); and $Q^1$ is |
| 607 $Y^1$ is S; $Y^2$ is S; $R^2$ is H; $R^4$ is H; $R^5$ is H; $Q^2$ is Ph(2-Br,4-F); and $Q^1$ is |
| 608 $Y^1$ is S; $Y^2$ is S; $R^2$ is H; $R^4$ is H; $R^5$ is H; $Q^2$ is Ph(2-Br,3,4-di-F); and $Q^1$ is |
| 609 $Y^1$ is S; $Y^2$ is S; $R^2$ is H; $R^4$ is H; $R^5$ is H; $Q^2$ is Ph(2-I); and $Q^1$ is |
| 610 $Y^1$ is S; $Y^2$ is S; $R^2$ is H; $R^4$ is H; $R^5$ is H; $Q^2$ is Ph(2-I,3-F); and $Q^1$ is |
| 611 $Y^1$ is S; $Y^2$ is S; $R^2$ is H; $R^4$ is H; $R^5$ is H; $Q^2$ is Ph(2-I,4-F); and $Q^1$ is |
| 612 $Y^1$ is S; $Y^2$ is S; $R^2$ is H; $R^4$ is H; $R^5$ is H; $Q^2$ is Ph(2-I,3,4-di-F); and $Q^1$ is |
| 613 $Y^1$ is S; $Y^2$ is S; $R^2$ is H; $R^4$ is H; $R^5$ is H; $Q^2$ is Ph(2-CN); and $Q^1$ is |
| 614 $Y^1$ is S; $Y^2$ is S; $R^2$ is H; $R^4$ is H; $R^5$ is H; $Q^2$ is Ph(2-CN,3-Me); and $Q^1$ is |
| 615 $Y^1$ is S; $Y^2$ is S; $R^2$ is H; $R^4$ is H; $R^5$ is H; $Q^2$ is Ph(2-CN,3-F); and $Q^1$ is |
| 616 $Y^1$ is S; $Y^2$ is S; $R^2$ is H; $R^4$ is H; $R^5$ is H; $Q^2$ is Ph(2-CN,4-F); and $Q^1$ is |
| 617 $Y^1$ is S; $Y^2$ is S; $R^2$ is H; $R^4$ is H; $R^5$ is H; $Q^2$ is Ph(2-CN,3-Cl); and $Q^1$ is |
| 618 $Y^1$ is S; $Y^2$ is S; $R^2$ is H; $R^4$ is H; $R^5$ is H; $Q^2$ is Ph(2-CN,4-Cl); and $Q^1$ is |
| 619 $Y^1$ is S; $Y^2$ is S; $R^2$ is H; $R^4$ is H; $R^5$ is H; $Q^2$ is Ph(2-CN,3,4-di-F); and $Q^1$ is |
| 620 $Y^1$ is S; $Y^2$ is S; $R^2$ is H; $R^4$ is H; $R^5$ is H; $Q^2$ is 2-Pyridinyl; and $Q^1$ is |
| 621 $Y^1$ is S; $Y^2$ is S; $R^2$ is H; $R^4$ is H; $R^5$ is H; $Q^2$ is 2-Pyridinyl,3-F; and $Q^1$ is |
| 622 $Y^1$ is S; $Y^2$ is S; $R^2$ is H; $R^4$ is H; $R^5$ is H; $Q^2$ is 2-Pyridinyl,4-F; and $Q^1$ is |
| 623 $Y^1$ is S; $Y^2$ is S; $R^2$ is H; $R^4$ is H; $R^5$ is H; $Q^2$ is 2-Pyridinyl,3,4-di-F; and $Q^1$ is |
| 624 $Y^1$ is S; $Y^2$ is S; $R^2$ is H; $R^4$ is H; $R^5$ is H; $Q^2$ is 2-Pyridinyl,3-Cl; and $Q^1$ is |
| 625 $Y^1$ is S; $Y^2$ is S; $R^2$ is H; $R^4$ is H; $R^5$ is H; $Q^2$ is 2-Pyridinyl,4-Cl; and $Q^1$ is |
| 626 $Y^1$ is S; $Y^2$ is S; $R^2$ is H; $R^4$ is H; $R^5$ is H; $Q^2$ is 2-Pyridinyl,3-Cl,4-F; and $Q^1$ is |
| 627 $Y^1$ is S; $Y^2$ is S; $R^2$ is H; $R^4$ is H; $R^5$ is H; $Q^2$ is Ph(2-SO$_2$Me); and $Q^1$ is |
| 628 $Y^1$ is S; $Y^2$ is S; $R^2$ is H; $R^4$ is H; $R^5$ is H; $Q^2$ is Ph(2-SO$_2$Me, 3-F); and $Q^1$ is |
| 629 $Y^1$ is S; $Y^2$ is S; $R^2$ is H; $R^4$ is H; $R^5$ is H; $Q^2$ is Ph(2-SO$_2$Me, 3-Me); and $Q^1$ is |
| 630 $Y^1$ is S; $Y^2$ is S; $R^2$ is H; $R^4$ is H; $R^5$ is H; $Q^2$ is Ph(2-SO$_2$Me, 4-F); and $Q^1$ is |
| 631 $Y^1$ is S; $Y^2$ is S; $R^2$ is H; $R^4$ is H; $R^5$ is H; $Q^2$ is Ph(2-SO$_2$Me, 5-F); and $Q^1$ is |
| 632 $Y^1$ is S; $Y^2$ is S; $R^2$ is H; $R^4$ is H; $R^5$ is H; $Q^2$ is Ph(2-SO$_2$Me,3,4-di-F); and $Q^1$ is |
| 633 $Y^1$ is S; $Y^2$ is S; $R^2$ is H; $R^4$ is H; $R^5$ is H; $Q^2$ is Ph(2-SO$_2$Me, 3-Cl); and $Q^1$ is |
| 634 $Y^1$ is S; $Y^2$ is S; $R^2$ is H; $R^4$ is H; $R^5$ is H; $Q^2$ is Ph(2-SO$_2$Me, 4-Cl); and $Q^1$ is |
| 635 $Y^1$ is S; $Y^2$ is S; $R^2$ is H; $R^4$ is H; $R^5$ is H; $Q^2$ is Ph(2-SO$_2$Me,3-Cl,4-F); and $Q^1$ is |
| 636 $Y^1$ is S; $Y^2$ is S; $R^2$ is H; $R^4$ is H; $R^5$ is H; $Q^2$ is Ph(2-SO$_2$NH$_2$); and $Q^1$ is |
| 637 $Y^1$ is S; $Y^2$ is S; $R^2$ is H; $R^4$ is H; $R^5$ is H; $Q^2$ is Ph(2-SO$_2$NH$_2$, 3-F); and $Q^1$ is |
| 638 $Y^1$ is S; $Y^2$ is S; $R^2$ is H; $R^4$ is H; $R^5$ is H; $Q^2$ is Ph(2-SO$_2$NH$_2$, 3-Cl); and $Q^1$ is |
| 639 $Y^1$ is S; $Y^2$ is S; $R^2$ is H; $R^4$ is H; $R^5$ is H; $Q^2$ is Ph(2-SO$_2$NH$_2$, 4-F); and $Q^1$ is |
| 640 $Y^1$ is S; $Y^2$ is S; $R^2$ is H; $R^4$ is H; $R^5$ is H; $Q^2$ is Ph(2-SO$_2$NH$_2$, 5-F); and $Q^1$ is |
| 641 $Y^1$ is S; $Y^2$ is S; $R^2$ is H; $R^4$ is H; $R^5$ is H; $Q^2$ is Ph(2-SO$_2$NH$_2$,3,4-di-F); and $Q^1$ is |
| 642 $Y^1$ is S; $Y^2$ is S; $R^2$ is H; $R^4$ is H; $R^5$ is H; $Q^2$ is Ph(3-F); and $Q^1$ is |
| 643 $Y^1$ is S; $Y^2$ is S; $R^2$ is H; $R^4$ is H; $R^5$ is H; $Q^2$ is Ph(3,4-di-F); and $Q^1$ is |
| 644 $Y^1$ is S; $Y^2$ is S; $R^2$ is H; $R^4$ is H; $R^5$ is H; $Q^2$ is Ph(3,5-di-F); and $Q^1$ is |
| 645 $Y^1$ is S; $Y^2$ is S; $R^2$ is H; $R^4$ is H; $R^5$ is H; $Q^2$ is Ph(3,4,5-tri-F); and $Q^1$ is |
| 646 $Y^1$ is S; $Y^2$ is S; $R^2$ is H; $R^4$ is H; $R^5$ is H; $Q^2$ is Ph(3-F,4-Cl); and $Q^1$ is |
| 647 $Y^1$ is S; $Y^2$ is S; $R^2$ is H; $R^4$ is H; $R^5$ is H; $Q^2$ is Ph(3-CF$_3$); and $Q^1$ is |
| 648 $Y^1$ is S; $Y^2$ is S; $R^2$ is H; $R^4$ is H; $R^5$ is H; $Q^2$ is Ph(3-CF$_3$,4-F); and $Q^1$ is |
| 649 $Y^1$ is S; $Y^2$ is S; $R^2$ is H; $R^4$ is H; $R^5$ is H; $Q^2$ is Ph(3-CF$_3$,4-Cl); and $Q^1$ is |
| 650 $Y^1$ is S; $Y^2$ is S; $R^2$ is H; $R^4$ is H; $R^5$ is H; $Q^2$ is Ph(3-CF$_3$,5-F); and $Q^1$ is |
| 651 $Y^1$ is S; $Y^2$ is S; $R^2$ is H; $R^4$ is H; $R^5$ is H; $Q^2$ is Ph(3-CF$_3$,4,5-di-F); and $Q^1$ is |
| 652 $Y^1$ is S; $Y^2$ is S; $R^2$ is H; $R^4$ is H; $R^5$ is H; $Q^2$ is Ph(3-SO$_2$Me); and $Q^1$ is |
| 653 $Y^1$ is S; $Y^2$ is S; $R^2$ is H; $R^4$ is H; $R^5$ is H; $Q^2$ is Ph(3-SO$_2$Me,4-Cl); and $Q^1$ is |

-continued

| Table Row Heading |
|---|
| 654 $Y^1$ is S; $Y^2$ is S; $R^2$ is H; $R^4$ is H; $R^5$ is H; $Q^2$ is Ph(3-SO$_2$Me,4-F); and $Q^1$ is |
| 655 $Y^1$ is S; $Y^2$ is S; $R^2$ is H; $R^4$ is H; $R^5$ is H; $Q^2$ is Ph(3-SO$_2$Me,4,5-di-F); and $Q^1$ is |
| 656 $Y^1$ is S; $Y^2$ is S; $R^2$ is H; $R^4$ is H; $R^5$ is H; $Q^2$ is Ph(3-SO$_2$Me,5-F); and $Q^1$ is |
| 657 $Y^1$ is S; $Y^2$ is S; $R^2$ is H; $R^4$ is H; $R^5$ is H; $Q^2$ is Ph(3-SO$_2$NH$_2$); and $Q^1$ is |
| 658 $Y^1$ is S; $Y^2$ is S; $R^2$ is H; $R^4$ is H; $R^5$ is H; $Q^2$ is Ph(3-SO$_2$NH$_2$,4-F); and $Q^1$ is |
| 659 $Y^1$ is S; $Y^2$ is S; $R^2$ is H; $R^4$ is H; $R^5$ is H; $Q^2$ is Ph(3-SO$_2$NH$_2$,4,5-di-F); and $Q^1$ is |
| 660 $Y^1$ is S; $Y^2$ is S; $R^2$ is H; $R^4$ is H; $R^5$ is H; $Q^2$ is Ph(3-SO$_2$NH$_2$,4-Cl); and $Q^1$ is |
| 661 $Y^1$ is S; $Y^2$ is S; $R^2$ is H; $R^4$ is H; $R^5$ is H; $Q^2$ is Ph(3-SO$_2$NH$_2$,5-F); and $Q^1$ is |
| 662 $Y^1$ is S; $Y^2$ is S; $R^2$ is H; $R^4$ is H; $R^5$ is H; $Q^2$ is Ph(3-Me); and $Q^1$ is |
| 663 $Y^1$ is S; $Y^2$ is S; $R^2$ is H; $R^4$ is H; $R^5$ is H; $Q^2$ is Ph(3-Me,4-F); and $Q^1$ is |
| 664 $Y^1$ is S; $Y^2$ is S; $R^2$ is H; $R^4$ is H; $R^5$ is H; $Q^2$ is Ph(3-Me,4-Cl); and $Q^1$ is |
| 665 $Y^1$ is S; $Y^2$ is S; $R^2$ is H; $R^4$ is H; $R^5$ is H; $Q^2$ is Ph(3-Me,5-F); and $Q^1$ is |
| 666 $Y^1$ is S; $Y^2$ is S; $R^2$ is H; $R^4$ is H; $R^5$ is H; $Q^2$ is Ph(3-Me,4,5-di-F); and $Q^1$ is |
| 667 $Y^1$ is S; $Y^2$ is S; $R^2$ is H; $R^4$ is H; $R^5$ is H; $Q^2$ is Ph(3-Cl); and $Q^1$ is |
| 668 $Y^1$ is S; $Y^2$ is S; $R^2$ is H; $R^4$ is H; $R^5$ is H; $Q^2$ is Ph(3-Cl,4-F); and $Q^1$ is |
| 669 $Y^1$ is S; $Y^2$ is S; $R^2$ is H; $R^4$ is H; $R^5$ is H; $Q^2$ is Ph(3,4-di-Cl); and $Q^1$ is |
| 670 $Y^1$ is S; $Y^2$ is S; $R^2$ is H; $R^4$ is H; $R^5$ is H; $Q^2$ is Ph(3-Cl,5-F); and $Q^1$ is |
| 671 $Y^1$ is S; $Y^2$ is S; $R^2$ is H; $R^4$ is H; $R^5$ is H; $Q^2$ is Ph(3-Cl,4,5-di-F); and $Q^1$ is |
| 672 $Y^1$ is S; $Y^2$ is S; $R^2$ is H; $R^4$ is H; $R^5$ is H; $Q^2$ is Ph(3,5-di-Cl); and $Q^1$ is |
| 673 $Y^1$ is S; $Y^2$ is S; $R^2$ is H; $R^4$ is H; $R^5$ is H; $Q^2$ is Ph(4-F); and $Q^1$ is |
| 674 $Y^1$ is S; $Y^2$ is S; $R^2$ is H; $R^4$ is H; $R^5$ is H; $Q^2$ is Ph(4-Cl); and $Q^1$ is |
| 675 $Y^1$ is S; $Y^2$ is S; $R^2$ is H; $R^4$ is H; $R^5$ is H; $Q^2$ is 2,2-di-F-1,3-benzodioxol-4-yl; and $Q^1$ is |
| 676 $Y^1$ is S; $Y^2$ is S; $R^2$ is H; $R^4$ is H; $R^5$ is H; $Q^2$ is 2,2-di-F-1,3-benzodioxol-5-yl; and $Q^1$ is |
| 677 $Y^1$ is S; $Y^2$ is S; $R^2$ is H; $R^4$ is H; $R^5$ is H; $Q^2$ is 2,2-di-Me-1,3-benzodioxol-4-yl; and $Q^1$ is |
| 678 $Y^1$ is S; $Y^2$ is S; $R^2$ is H; $R^4$ is H; $R^5$ is H; $Q^2$ is 2,2-di-Me-1,3-benzodioxol-5-yl; and $Q^1$ is |
| 679 $Y^1$ is S; $Y^2$ is S; $R^2$ is H; $R^4$ is H; $R^5$ is H; $Q^2$ is 1,3-benzodioxol-4-yl; and $Q^1$ is |
| 680 $Y^1$ is S; $Y^2$ is S; $R^2$ is H; $R^4$ is H; $R^5$ is H; $Q^2$ is 1,3-benzodioxol-5-yl; and $Q^1$ is |
| 681 $Y^1$ is NH; $Y^2$ is O; $R^2$ is H; $R^4$ is H; $R^5$ is H; $Q^2$ is Ph(2-F); and $Q^1$ is |
| 682 $Y^1$ is NH; $Y^2$ is O; $R^2$ is H; $R^4$ is H; $R^5$ is H; $Q^2$ is Ph(2,3-di-F); and $Q^1$ is |
| 683 $Y^1$ is NH; $Y^2$ is O; $R^2$ is H; $R^4$ is H; $R^5$ is H; $Q^2$ is Ph(2,4-di-F); and $Q^1$ is |
| 684 $Y^1$ is NH; $Y^2$ is O; $R^2$ is H; $R^4$ is H; $R^5$ is H; $Q^2$ is Ph(2,5-di-F); and $Q^1$ is |
| 685 $Y^1$ is NH; $Y^2$ is O; $R^2$ is H; $R^4$ is H; $R^5$ is H; $Q^2$ is Ph(2,3,4-tri-F); and $Q^1$ is |
| 686 $Y^1$ is NH; $Y^2$ is O; $R^2$ is H; $R^4$ is H; $R^5$ is H; $Q^2$ is Ph(2,3,5-tri-F); and $Q^1$ is |
| 687 $Y^1$ is NH; $Y^2$ is O; $R^2$ is H; $R^4$ is H; $R^5$ is H; $Q^2$ is Ph(2,3,4,5-tetra-F); and $Q^1$ is |
| 688 $Y^1$ is NH; $Y^2$ is O; $R^2$ is H; $R^4$ is H; $R^5$ is H; $Q^2$ is Ph(2-F,3-Cl,4-Br); and $Q^1$ is |
| 689 $Y^1$ is NH; $Y^2$ is O; $R^2$ is H; $R^4$ is H; $R^5$ is H; $Q^2$ is Ph(2-F,3-Cl,4-F); and $Q^1$ is |
| 690 $Y^1$ is NH; $Y^2$ is O; $R^2$ is H; $R^4$ is H; $R^5$ is H; $Q^2$ is Ph(2-F,3-Br,4-F); and $Q^1$ is |
| 691 $Y^1$ is NH; $Y^2$ is O; $R^2$ is H; $R^4$ is H; $R^5$ is H; $Q^2$ is Ph(2-F,3-Me); and $Q^1$ is |
| 692 $Y^1$ is NH; $Y^2$ is O; $R^2$ is H; $R^4$ is H; $R^5$ is H; $Q^2$ is Ph(2-F,3-Me,4-F); and $Q^1$ is |
| 693 $Y^1$ is NH; $Y^2$ is O; $R^2$ is H; $R^4$ is H; $R^5$ is H; $Q^2$ is Ph(2-F,3-Me,4-Cl); and $Q^1$ is |
| 694 $Y^1$ is NH; $Y^2$ is O; $R^2$ is H; $R^4$ is H; $R^5$ is H; $Q^2$ is Ph(2-F,3-Cl); and $Q^1$ is |
| 695 $Y^1$ is NH; $Y^2$ is O; $R^2$ is H; $R^4$ is H; $R^5$ is H; $Q^2$ is Ph(2-F,4-Cl); and $Q^1$ is |
| 696 $Y^1$ is NH; $Y^2$ is O; $R^2$ is H; $R^4$ is H; $R^5$ is H; $Q^2$ is Ph(2-F,3,4-di-Cl); and $Q^1$ is |
| 697 $Y^1$ is NH; $Y^2$ is O; $R^2$ is H; $R^4$ is H; $R^5$ is H; $Q^2$ is Ph(2-F,4-Br); and $Q^1$ is |
| 698 $Y^1$ is NH; $Y^2$ is O; $R^2$ is H; $R^4$ is H; $R^5$ is H; $Q^2$ is Ph(2-F,3-OMe); and $Q^1$ is |
| 699 $Y^1$ is NH; $Y^2$ is O; $R^2$ is H; $R^4$ is H; $R^5$ is H; $Q^2$ is Ph(2-F,3-OMe,4-F); and $Q^1$ is |
| 700 $Y^1$ is NH; $Y^2$ is O; $R^2$ is H; $R^4$ is H; $R^5$ is H; $Q^2$ is Ph(2-F,3-OMe,4-Cl); and $Q^1$ is |
| 701 $Y^1$ is NH; $Y^2$ is O; $R^2$ is H; $R^4$ is H; $R^5$ is H; $Q^2$ is Ph(2-F,3-CF$_2$H); and $Q^1$ is |
| 702 $Y^1$ is NH; $Y^2$ is O; $R^2$ is H; $R^4$ is H; $R^5$ is H; $Q^2$ is Ph(2-F,3-CF$_3$); and $Q^1$ is |
| 703 $Y^1$ is NH; $Y^2$ is O; $R^2$ is H; $R^4$ is H; $R^5$ is H; $Q^2$ is Ph(2-F,3-CF$_3$,4-F); and $Q^1$ is |
| 704 $Y^1$ is NH; $Y^2$ is O; $R^2$ is H; $R^4$ is H; $R^5$ is H; $Q^2$ is Ph(2-F,3-NO$_2$); and $Q^1$ is |
| 705 $Y^1$ is NH; $Y^2$ is O; $R^2$ is H; $R^4$ is H; $R^5$ is H; $Q^2$ is Ph(2-F,3-NO$_2$,4-F); and $Q^1$ is |
| 706 $Y^1$ is NH; $Y^2$ is O; $R^2$ is H; $R^4$ is H; $R^5$ is H; $Q^2$ is Ph(2-F,3-SO$_2$Me); and $Q^1$ is |
| 707 $Y^1$ is NH; $Y^2$ is O; $R^2$ is H; $R^4$ is H; $R^5$ is H; $Q^2$ is Ph(2-F,3-SO$_2$Me,4-F); and $Q^1$ is |
| 708 $Y^1$ is NH; $Y^2$ is O; $R^2$ is H; $R^4$ is H; $R^5$ is H; $Q^2$ is Ph(2-CF$_3$); and $Q^1$ is |
| 709 $Y^1$ is NH; $Y^2$ is O; $R^2$ is H; $R^4$ is H; $R^5$ is H; $Q^2$ is Ph(2-CF$_3$,3-F); and $Q^1$ is |
| 710 $Y^1$ is NH; $Y^2$ is O; $R^2$ is H; $R^4$ is H; $R^5$ is H; $Q^2$ is Ph(2-CF$_3$,3-Me); and $Q^1$ is |
| 711 $Y^1$ is NH; $Y^2$ is O; $R^2$ is H; $R^4$ is H; $R^5$ is H; $Q^2$ is Ph(2-CF$_3$,4-F); and $Q^1$ is |
| 712 $Y^1$ is NH; $Y^2$ is O; $R^2$ is H; $R^4$ is H; $R^5$ is H; $Q^2$ is Ph(2-CF$_3$,3-Cl); and $Q^1$ is |
| 713 $Y^1$ is NH; $Y^2$ is O; $R^2$ is H; $R^4$ is H; $R^5$ is H; $Q^2$ is Ph(2-CF$_3$,4-Cl); and $Q^1$ is |
| 714 $Y^1$ is NH; $Y^2$ is O; $R^2$ is H; $R^4$ is H; $R^5$ is H; $Q^2$ is Ph(2-CF$_3$,3,4-di-F); and $Q^1$ is |
| 715 $Y^1$ is NH; $Y^2$ is O; $R^2$ is H; $R^4$ is H; $R^5$ is H; $Q^2$ is Ph(2-CF$_2$H); and $Q^1$ is |
| 716 $Y^1$ is NH; $Y^2$ is O; $R^2$ is H; $R^4$ is H; $R^5$ is H; $Q^2$ is Ph(2-CF$_2$H,3-F); and $Q^1$ is |
| 717 $Y^1$ is NH; $Y^2$ is O; $R^2$ is H; $R^4$ is H; $R^5$ is H; $Q^2$ is Ph(2-CF$_2$H,3-Me); and $Q^1$ is |
| 718 $Y^1$ is NH; $Y^2$ is O; $R^2$ is H; $R^4$ is H; $R^5$ is H; $Q^2$ is Ph(2-CF$_2$H,4-F); and $Q^1$ is |
| 719 $Y^1$ is NH; $Y^2$ is O; $R^2$ is H; $R^4$ is H; $R^5$ is H; $Q^2$ is Ph(2-CF$_2$H,3-Cl); and $Q^1$ is |
| 720 $Y^1$ is NH; $Y^2$ is O; $R^2$ is H; $R^4$ is H; $R^5$ is H; $Q^2$ is Ph(2-CF$_2$H,4-Cl); and $Q^1$ is |
| 721 $Y^1$ is NH; $Y^2$ is O; $R^2$ is H; $R^4$ is H; $R^5$ is H; $Q^2$ is Ph(2-CF$_2$H,3,4-di-F); and $Q^1$ is |
| 722 $Y^1$ is NH; $Y^2$ is O; $R^2$ is H; $R^4$ is H; $R^5$ is H; $Q^2$ is Ph(2-Me); and $Q^1$ is |
| 723 $Y^1$ is NH; $Y^2$ is O; $R^2$ is H; $R^4$ is H; $R^5$ is H; $Q^2$ is Ph(2,3-di-Me); and $Q^1$ is |
| 724 $Y^1$ is NH; $Y^2$ is O; $R^2$ is H; $R^4$ is H; $R^5$ is H; $Q^2$ is Ph(2-Me,3-F); and $Q^1$ is |
| 725 $Y^1$ is NH; $Y^2$ is O; $R^2$ is H; $R^4$ is H; $R^5$ is H; $Q^2$ is Ph(2-Me,3-Cl); and $Q^1$ is |
| 726 $Y^1$ is NH; $Y^2$ is O; $R^2$ is H; $R^4$ is H; $R^5$ is H; $Q^2$ is Ph(2-Me,3-CF$_3$); and $Q^1$ is |
| 727 $Y^1$ is NH; $Y^2$ is O; $R^2$ is H; $R^4$ is H; $R^5$ is H; $Q^2$ is Ph(2-Me,3,4-di-Cl); and $Q^1$ is |
| 728 $Y^1$ is NH; $Y^2$ is O; $R^2$ is H; $R^4$ is H; $R^5$ is H; $Q^2$ is Ph(2-Me,3-Cl,4-F); and $Q^1$ is |
| 729 $Y^1$ is NH; $Y^2$ is O; $R^2$ is H; $R^4$ is H; $R^5$ is H; $Q^2$ is Ph(2-Me,4-Cl); and $Q^1$ is |
| 730 $Y^1$ is NH; $Y^2$ is O; $R^2$ is H; $R^4$ is H; $R^5$ is H; $Q^2$ is Ph(2-Me,4-F); and $Q^1$ is |

-continued

| Table Row Heading |
|---|
| 731 $Y^1$ is NH; $Y^2$ is O; $R^2$ is H; $R^4$ is H; $R^5$ is H; $Q^2$ is Ph(2-Me,5-F); and $Q^1$ is |
| 732 $Y^1$ is NH; $Y^2$ is O; $R^2$ is H; $R^4$ is H; $R^5$ is H; $Q^2$ is Ph(2-Me,3,4-di-F); and $Q^1$ is |
| 733 $Y^1$ is NH; $Y^2$ is O; $R^2$ is H; $R^4$ is H; $R^5$ is H; $Q^2$ is Ph(2-Me,3,5-di-F); and $Q^1$ is |
| 734 $Y^1$ is NH; $Y^2$ is O; $R^2$ is H; $R^4$ is H; $R^5$ is H; $Q^2$ is Ph(2-Et); and $Q^1$ is |
| 735 $Y^1$ is NH; $Y^2$ is O; $R^2$ is H; $R^4$ is H; $R^5$ is H; $Q^2$ is Ph(2-Et,3-F); and $Q^1$ is |
| 736 $Y^1$ is NH; $Y^2$ is O; $R^2$ is H; $R^4$ is H; $R^5$ is H; $Q^2$ is Ph(2-Et,3-Cl); and $Q^1$ is |
| 737 $Y^1$ is NH; $Y^2$ is O; $R^2$ is H; $R^4$ is H; $R^5$ is H; $Q^2$ is Ph(2-Et,4-F); and $Q^1$ is |
| 738 $Y^1$ is NH; $Y^2$ is O; $R^2$ is H; $R^4$ is H; $R^5$ is H; $Q^2$ is Ph(2-Et,3,4-di-F); and $Q^1$ is |
| 739 $Y^1$ is NH; $Y^2$ is O; $R^2$ is H; $R^4$ is H; $R^5$ is H; $Q^2$ is Ph(2-i-Pr); and $Q^1$ is |
| 740 $Y^1$ is NH; $Y^2$ is O; $R^2$ is H; $R^4$ is H; $R^5$ is H; $Q^2$ is Ph(2-i-Pr,3-F); and $Q^1$ is |
| 741 $Y^1$ is NH; $Y^2$ is O; $R^2$ is H; $R^4$ is H; $R^5$ is H; $Q^2$ is Ph(2-i-Pr,3-Cl); and $Q^1$ is |
| 742 $Y^1$ is NH; $Y^2$ is O; $R^2$ is H; $R^4$ is H; $R^5$ is H; $Q^2$ is Ph(2-i-Pr,4-F); and $Q^1$ is |
| 743 $Y^1$ is NH; $Y^2$ is O; $R^2$ is H; $R^4$ is H; $R^5$ is H; $Q^2$ is Ph(2-i-Pr,3,4-di-F); and $Q^1$ is |
| 744 $Y^1$ is NH; $Y^2$ is O; $R^2$ is H; $R^4$ is H; $R^5$ is H; $Q^2$ is Ph(2-c-Pr); and $Q^1$ is |
| 745 $Y^1$ is NH; $Y^2$ is O; $R^2$ is H; $R^4$ is H; $R^5$ is H; $Q^2$ is Ph(2-c-Pr,3-F); and $Q^1$ is |
| 746 $Y^1$ is NH; $Y^2$ is O; $R^2$ is H; $R^4$ is H; $R^5$ is H; $Q^2$ is Ph(2-c-Pr,3-Cl); and $Q^1$ is |
| 747 $Y^1$ is NH; $Y^2$ is O; $R^2$ is H; $R^4$ is H; $R^5$ is H; $Q^2$ is Ph(2-c-Pr,4-F); and $Q^1$ is |
| 748 $Y^1$ is NH; $Y^2$ is O; $R^2$ is H; $R^4$ is H; $R^5$ is H; $Q^2$ is Ph(2-c-Pr,3,4-di-F); and $Q^1$ is |
| 749 $Y^1$ is NH; $Y^2$ is O; $R^2$ is H; $R^4$ is H; $R^5$ is H; $Q^2$ is Ph(2-$NO_2$); and $Q^1$ is |
| 750 $Y^1$ is NH; $Y^2$ is O; $R^2$ is H; $R^4$ is H; $R^5$ is H; $Q^2$ is Ph(2-$NO_2$,3-F); and $Q^1$ is |
| 751 $Y^1$ is NH; $Y^2$ is O; $R^2$ is H; $R^4$ is H; $R^5$ is H; $Q^2$ is Ph(2-$NO_2$,3-Cl); and $Q^1$ is |
| 752 $Y^1$ is NH; $Y^2$ is O; $R^2$ is H; $R^4$ is H; $R^5$ is H; $Q^2$ is Ph(2-$NO_2$,4-F); and $Q^1$ is |
| 753 $Y^1$ is NH; $Y^2$ is O; $R^2$ is H; $R^4$ is H; $R^5$ is H; $Q^2$ is Ph(2-$NO_2$,3,4-di-F); and $Q^1$ is |
| 754 $Y^1$ is NH; $Y^2$ is O; $R^2$ is H; $R^4$ is H; $R^5$ is H; $Q^2$ is Ph(2-$OCF_3$); and $Q^1$ is |
| 755 $Y^1$ is NH; $Y^2$ is O; $R^2$ is H; $R^4$ is H; $R^5$ is H; $Q^2$ is Ph(2-$OCF_3$,3-F); and $Q^1$ is |
| 756 $Y^1$ is NH; $Y^2$ is O; $R^2$ is H; $R^4$ is H; $R^5$ is H; $Q^2$ is Ph(2-$OCF_3$,4-F); and $Q^1$ is |
| 757 $Y^1$ is NH; $Y^2$ is O; $R^2$ is H; $R^4$ is H; $R^5$ is H; $Q^2$ is Ph(2-Cl); and $Q^1$ is |
| 758 $Y^1$ is NH; $Y^2$ is O; $R^2$ is H; $R^4$ is H; $R^5$ is H; $Q^2$ is Ph(2-Cl,3-Me); and $Q^1$ is |
| 759 $Y^1$ is NH; $Y^2$ is O; $R^2$ is H; $R^4$ is H; $R^5$ is H; $Q^2$ is Ph(2-Cl,3-Me,4-F); and $Q^1$ is |
| 760 $Y^1$ is NH; $Y^2$ is O; $R^2$ is H; $R^4$ is H; $R^5$ is H; $Q^2$ is Ph(2,3-di-Cl); and $Q^1$ is |
| 761 $Y^1$ is NH; $Y^2$ is O; $R^2$ is H; $R^4$ is H; $R^5$ is H; $Q^2$ is Ph(2,4-di-Cl); and $Q^1$ is |
| 762 $Y^1$ is NH; $Y^2$ is O; $R^2$ is H; $R^4$ is H; $R^5$ is H; $Q^2$ is Ph(2-Cl,3-F); and $Q^1$ is |
| 763 $Y^1$ is NH; $Y^2$ is O; $R^2$ is H; $R^4$ is H; $R^5$ is H; $Q^2$ is Ph(2-Cl,4-F); and $Q^1$ is |
| 764 $Y^1$ is NH; $Y^2$ is O; $R^2$ is H; $R^4$ is H; $R^5$ is H; $Q^2$ is Ph(2-Cl,5-F); and $Q^1$ is |
| 765 $Y^1$ is NH; $Y^2$ is O; $R^2$ is H; $R^4$ is H; $R^5$ is H; $Q^2$ is Ph(2-Cl,3,4-di-F); and $Q^1$ is |
| 766 $Y^1$ is NH; $Y^2$ is O; $R^2$ is H; $R^4$ is H; $R^5$ is H; $Q^2$ is Ph(2-Cl,3,5-di-F); and $Q^1$ is |
| 767 $Y^1$ is NH; $Y^2$ is O; $R^2$ is H; $R^4$ is H; $R^5$ is H; $Q^2$ is Ph(2-$OCF_2H$); and $Q^1$ is |
| 768 $Y^1$ is NH; $Y^2$ is O; $R^2$ is H; $R^4$ is H; $R^5$ is H; $Q^2$ is Ph(2-$OCF_2H$,3-Me); and $Q^1$ is |
| 769 $Y^1$ is NH; $Y^2$ is O; $R^2$ is H; $R^4$ is H; $R^5$ is H; $Q^2$ is Ph(2-$OCF_2H$,3-Cl); and $Q^1$ is |
| 770 $Y^1$ is NH; $Y^2$ is O; $R^2$ is H; $R^4$ is H; $R^5$ is H; $Q^2$ is Ph(2-$OCF_2H$,3-F); and $Q^1$ is |
| 771 $Y^1$ is NH; $Y^2$ is O; $R^2$ is H; $R^4$ is H; $R^5$ is H; $Q^2$ is Ph(2-$OCF_2H$,4-F); and $Q^1$ is |
| 772 $Y^1$ is NH; $Y^2$ is O; $R^2$ is H; $R^4$ is H; $R^5$ is H; $Q^2$ is Ph(2-$OCF_2CF_2H$); and $Q^1$ is |
| 773 $Y^1$ is NH; $Y^2$ is O; $R^2$ is H; $R^4$ is H; $R^5$ is H; $Q^2$ is Ph(2-$OCF_2CF_2H$,3-F); and $Q^1$ is |
| 774 $Y^1$ is NH; $Y^2$ is O; $R^2$ is H; $R^4$ is H; $R^5$ is H; $Q^2$ is Ph(2-$OCF_2CF_2H$,4-F); and $Q^1$ is |
| 775 $Y^1$ is NH; $Y^2$ is O; $R^2$ is H; $R^4$ is H; $R^5$ is H; $Q^2$ is Ph(2-Br); and $Q^1$ is |
| 776 $Y^1$ is NH; $Y^2$ is O; $R^2$ is H; $R^4$ is H; $R^5$ is H; $Q^2$ is Ph(2-Br,3-F); and $Q^1$ is |
| 777 $Y^1$ is NH; $Y^2$ is O; $R^2$ is H; $R^4$ is H; $R^5$ is H; $Q^2$ is Ph(2-Br,4-F); and $Q^1$ is |
| 778 $Y^1$ is NH; $Y^2$ is O; $R^2$ is H; $R^4$ is H; $R^5$ is H; $Q^2$ is Ph(2-Br,3,4-di-F); and $Q^1$ is |
| 779 $Y^1$ is NH; $Y^2$ is O; $R^2$ is H; $R^4$ is H; $R^5$ is H; $Q^2$ is Ph(2-I); and $Q^1$ is |
| 780 $Y^1$ is NH; $Y^2$ is O; $R^2$ is H; $R^4$ is H; $R^5$ is H; $Q^2$ is Ph(2-I,3-F); and $Q^1$ is |
| 781 $Y^1$ is NH; $Y^2$ is O; $R^2$ is H; $R^4$ is H; $R^5$ is H; $Q^2$ is Ph(2-I,4-F); and $Q^1$ is |
| 782 $Y^1$ is NH; $Y^2$ is O; $R^2$ is H; $R^4$ is H; $R^5$ is H; $Q^2$ is Ph(2-I,3,4-di-F); and $Q^1$ is |
| 783 $Y^1$ is NH; $Y^2$ is O; $R^2$ is H; $R^4$ is H; $R^5$ is H; $Q^2$ is Ph(2-CN); and $Q^1$ is |
| 784 $Y^1$ is NH; $Y^2$ is O; $R^2$ is H; $R^4$ is H; $R^5$ is H; $Q^2$ is Ph(2-CN,3-Me); and $Q^1$ is |
| 785 $Y^1$ is NH; $Y^2$ is O; $R^2$ is H; $R^4$ is H; $R^5$ is H; $Q^2$ is Ph(2-CN,3-F); and $Q^1$ is |
| 786 $Y^1$ is NH; $Y^2$ is O; $R^2$ is H; $R^4$ is H; $R^5$ is H; $Q^2$ is Ph(2-CN,4-F); and $Q^1$ is |
| 787 $Y^1$ is NH; $Y^2$ is O; $R^2$ is H; $R^4$ is H; $R^5$ is H; $Q^2$ is Ph(2-CN,3-Cl); and $Q^1$ is |
| 788 $Y^1$ is NH; $Y^2$ is O; $R^2$ is H; $R^4$ is H; $R^5$ is H; $Q^2$ is Ph(2-CN,4-Cl); and $Q^1$ is |
| 789 $Y^1$ is NH; $Y^2$ is O; $R^2$ is H; $R^4$ is H; $R^5$ is H; $Q^2$ is Ph(2-CN,3,4-di-F); and $Q^1$ is |
| 790 $Y^1$ is NH; $Y^2$ is O; $R^2$ is H; $R^4$ is H; $R^5$ is H; $Q^2$ is 2-Pyridinyl; and $Q^1$ is |
| 791 $Y^1$ is NH; $Y^2$ is O; $R^2$ is H; $R^4$ is H; $R^5$ is H; $Q^2$ is 2-Pyridinyl,3-F; and $Q^1$ is |
| 792 $Y^1$ is NH; $Y^2$ is O; $R^2$ is H; $R^4$ is H; $R^5$ is H; $Q^2$ is 2-Pyridinyl,4-F; and $Q^1$ is |
| 793 $Y^1$ is NH; $Y^2$ is O; $R^2$ is H; $R^4$ is H; $R^5$ is H; $Q^2$ is 2-Pyridinyl,3,4-di-F; and $Q^1$ is |
| 794 $Y^1$ is NH; $Y^2$ is O; $R^2$ is H; $R^4$ is H; $R^5$ is H; $Q^2$ is 2-Pyridinyl,3-Cl; and $Q^1$ is |
| 795 $Y^1$ is NH; $Y^2$ is O; $R^2$ is H; $R^4$ is H; $R^5$ is H; $Q^2$ is 2-Pyridinyl,4-Cl; and $Q^1$ is |
| 796 $Y^1$ is NH; $Y^2$ is O; $R^2$ is H; $R^4$ is H; $R^5$ is H; $Q^2$ is 2-Pyridinyl,3-Cl,4-F; and $Q^1$ is |
| 797 $Y^1$ is NH; $Y^2$ is O; $R^2$ is H; $R^4$ is H; $R^5$ is H; $Q^2$ is Ph(2-$SO_2$Me); and $Q^1$ is |
| 798 $Y^1$ is NH; $Y^2$ is O; $R^2$ is H; $R^4$ is H; $R^5$ is H; $Q^2$ is Ph(2-$SO_2$Me, 3-F); and $Q^1$ is |
| 799 $Y^1$ is NH; $Y^2$ is O; $R^2$ is H; $R^4$ is H; $R^5$ is H; $Q^2$ is Ph(2-$SO_2$Me, 3-Me); and $Q^1$ is |
| 800 $Y^1$ is NH; $Y^2$ is O; $R^2$ is H; $R^4$ is H; $R^5$ is H; $Q^2$ is Ph(2-$SO_2$Me, 4-F); and $Q^1$ is |
| 801 $Y^1$ is NH; $Y^2$ is O; $R^2$ is H; $R^4$ is H; $R^5$ is H; $Q^2$ is Ph(2-$SO_2$Me, 5-F); and $Q^1$ is |
| 802 $Y^1$ is NH; $Y^2$ is O; $R^2$ is H; $R^4$ is H; $R^5$ is H; $Q^2$ is Ph(2-$SO_2$Me,3,4-di-F); and $Q^1$ is |
| 803 $Y^1$ is NH; $Y^2$ is O; $R^2$ is H; $R^4$ is H; $R^5$ is H; $Q^2$ is Ph(2-$SO_2$Me, 3-Cl); and $Q^1$ is |
| 804 $Y^1$ is NH; $Y^2$ is O; $R^2$ is H; $R^4$ is H; $R^5$ is H; $Q^2$ is Ph(2-$SO_2$Me, 4-Cl); and $Q^1$ is |
| 805 $Y^1$ is NH; $Y^2$ is O; $R^2$ is H; $R^4$ is H; $R^5$ is H; $Q^2$ is Ph(2-$SO_2$Me,3-Cl,4-F); and $Q^1$ is |
| 806 $Y^1$ is NH; $Y^2$ is O; $R^2$ is H; $R^4$ is H; $R^5$ is H; $Q^2$ is Ph(2-$SO_2NH_2$); and $Q^1$ is |
| 807 $Y^1$ is NH; $Y^2$ is O; $R^2$ is H; $R^4$ is H; $R^5$ is H; $Q^2$ is Ph(2-$SO_2NH_2$, 3-F); and $Q^1$ is |

-continued

| Table Row Heading |
|---|
| 808 $Y^1$ is NH; $Y^2$ is O; $R^2$ is H; $R^4$ is H; $R^5$ is H; $Q^2$ is Ph(2-SO$_2$NH$_2$, 3-Cl); and $Q^1$ is |
| 809 $Y^1$ is NH; $Y^2$ is O; $R^2$ is H; $R^4$ is H; $R^5$ is H; $Q^2$ is Ph(2-SO$_2$NH$_2$, 4-F); and $Q^1$ is |
| 810 $Y^1$ is NH; $Y^2$ is O; $R^2$ is H; $R^4$ is H; $R^5$ is H; $Q^2$ is Ph(2-SO$_2$NH$_2$, 5-F); and $Q^1$ is |
| 811 $Y^1$ is NH; $Y^2$ is O; $R^2$ is H; $R^4$ is H; $R^5$ is H; $Q^2$ is Ph(2-SO$_2$NH$_2$,3,4-di-F); and $Q^1$ is |
| 812 $Y^1$ is NH; $Y^2$ is O; $R^2$ is H; $R^4$ is H; $R^5$ is H; $Q^2$ is Ph(3-F); and $Q^1$ is |
| 813 $Y^1$ is NH; $Y^2$ is O; $R^2$ is H; $R^4$ is H; $R^5$ is H; $Q^2$ is Ph(3,4-di-F); and $Q^1$ is |
| 814 $Y^1$ is NH; $Y^2$ is O; $R^2$ is H; $R^4$ is H; $R^5$ is H; $Q^2$ is Ph(3,5-di-F); and $Q^1$ is |
| 815 $Y^1$ is NH; $Y^2$ is O; $R^2$ is H; $R^4$ is H; $R^5$ is H; $Q^2$ is Ph(3,4,5-tri-F); and $Q^1$ is |
| 816 $Y^1$ is NH; $Y^2$ is O; $R^2$ is H; $R^4$ is H; $R^5$ is H; $Q^2$ is Ph(3-F,4-Cl); and $Q^1$ is |
| 817 $Y^1$ is NH; $Y^2$ is O; $R^2$ is H; $R^4$ is H; $R^5$ is H; $Q^2$ is Ph(3-CF$_3$); and $Q^1$ is |
| 818 $Y^1$ is NH; $Y^2$ is O; $R^2$ is H; $R^4$ is H; $R^5$ is H; $Q^2$ is Ph(3-CF$_3$,4-F); and $Q^1$ is |
| 819 $Y^1$ is NH; $Y^2$ is O; $R^2$ is H; $R^4$ is H; $R^5$ is H; $Q^2$ is Ph(3-CF$_3$,4-Cl); and $Q^1$ is |
| 820 $Y^1$ is NH; $Y^2$ is O; $R^2$ is H; $R^4$ is H; $R^5$ is H; $Q^2$ is Ph(3-CF$_3$,5-F); and $Q^1$ is |
| 821 $Y^1$ is NH; $Y^2$ is O; $R^2$ is H; $R^4$ is H; $R^5$ is H; $Q^2$ is Ph(3-CF$_3$,4,5-di-F); and $Q^1$ is |
| 822 $Y^1$ is NH; $Y^2$ is O; $R^2$ is H; $R^4$ is H; $R^5$ is H; $Q^2$ is Ph(3-SO$_2$Me); and $Q^1$ is |
| 823 $Y^1$ is NH; $Y^2$ is O; $R^2$ is H; $R^4$ is H; $R^5$ is H; $Q^2$ is Ph(3-SO$_2$Me,4-Cl); and $Q^1$ is |
| 824 $Y^1$ is NH; $Y^2$ is O; $R^2$ is H; $R^4$ is H; $R^5$ is H; $Q^2$ is Ph(3-SO$_2$Me,4-F); and $Q^1$ is |
| 825 $Y^1$ is NH; $Y^2$ is O; $R^2$ is H; $R^4$ is H; $R^5$ is H; $Q^2$ is Ph(3-SO$_2$Me,4,5-di-F); and $Q^1$ is |
| 826 $Y^1$ is NH; $Y^2$ is O; $R^2$ is H; $R^4$ is H; $R^5$ is H; $Q^2$ is Ph(3-SO$_2$Me,5-F); and $Q^1$ is |
| 827 $Y^1$ is NH; $Y^2$ is O; $R^2$ is H; $R^4$ is H; $R^5$ is H; $Q^2$ is Ph(3-SO$_2$NH$_2$); and $Q^1$ is |
| 828 $Y^1$ is NH; $Y^2$ is O; $R^2$ is H; $R^4$ is H; $R^5$ is H; $Q^2$ is Ph(3-SO$_2$NH$_2$,4-F); and $Q^1$ is |
| 829 $Y^1$ is NH; $Y^2$ is O; $R^2$ is H; $R^4$ is H; $R^5$ is H; $Q^2$ is Ph(3-SO$_2$NH$_2$,4,5-di-F); and $Q^1$ is |
| 830 $Y^1$ is NH; $Y^2$ is O; $R^2$ is H; $R^4$ is H; $R^5$ is H; $Q^2$ is Ph(3-SO$_2$NH$_2$,4-Cl); and $Q^1$ is |
| 831 $Y^1$ is NH; $Y^2$ is O; $R^2$ is H; $R^4$ is H; $R^5$ is H; $Q^2$ is Ph(3-SO$_2$NH$_2$,5-F); and $Q^1$ is |
| 832 $Y^1$ is NH; $Y^2$ is O; $R^2$ is H; $R^4$ is H; $R^5$ is H; $Q^2$ is Ph(3-Me); and $Q^1$ is |
| 833 $Y^1$ is NH; $Y^2$ is O; $R^2$ is H; $R^4$ is H; $R^5$ is H; $Q^2$ is Ph(3-Me,4-F); and $Q^1$ is |
| 834 $Y^1$ is NH; $Y^2$ is O; $R^2$ is H; $R^4$ is H; $R^5$ is H; $Q^2$ is Ph(3-Me,4-Cl); and $Q^1$ is |
| 835 $Y^1$ is NH; $Y^2$ is O; $R^2$ is H; $R^4$ is H; $R^5$ is H; $Q^2$ is Ph(3-Me,5-F); and $Q^1$ is |
| 836 $Y^1$ is NH; $Y^2$ is O; $R^2$ is H; $R^4$ is H; $R^5$ is H; $Q^2$ is Ph(3-Me,4,5-di-F); and $Q^1$ is |
| 837 $Y^1$ is NH; $Y^2$ is O; $R^2$ is H; $R^4$ is H; $R^5$ is H; $Q^2$ is Ph(3-Cl); and $Q^1$ is |
| 838 $Y^1$ is NH; $Y^2$ is O; $R^2$ is H; $R^4$ is H; $R^5$ is H; $Q^2$ is Ph(3-Cl,4-F); and $Q^1$ is |
| 839 $Y^1$ is NH; $Y^2$ is O; $R^2$ is H; $R^4$ is H; $R^5$ is H; $Q^2$ is Ph(3,4-di-Cl); and $Q^1$ is |
| 840 $Y^1$ is NH; $Y^2$ is O; $R^2$ is H; $R^4$ is H; $R^5$ is H; $Q^2$ is Ph(3-Cl,5-F); and $Q^1$ is |
| 841 $Y^1$ is NH; $Y^2$ is O; $R^2$ is H; $R^4$ is H; $R^5$ is H; $Q^2$ is Ph(3-Cl,4,5-di-F); and $Q^1$ is |
| 842 $Y^1$ is NH; $Y^2$ is O; $R^2$ is H; $R^4$ is H; $R^5$ is H; $Q^2$ is Ph(3,5-di-Cl); and $Q^1$ is |
| 843 $Y^1$ is NH; $Y^2$ is O; $R^2$ is H; $R^4$ is H; $R^5$ is H; $Q^2$ is Ph(4-F); and $Q^1$ is |
| 844 $Y^1$ is NH; $Y^2$ is O; $R^2$ is H; $R^4$ is H; $R^5$ is H; $Q^2$ is Ph(4-Cl); and $Q^1$ is |
| 845 $Y^1$ is NH; $Y^2$ is O; $R^2$ is H; $R^4$ is H; $R^5$ is H; $Q^2$ is 2,2-di-F-1,3-benzodioxol-4-yl; and $Q^1$ is |
| 846 $Y^1$ is NH; $Y^2$ is O; $R^2$ is H; $R^4$ is H; $R^5$ is H; $Q^2$ is 2,2-di-F-1,3-benzodioxol-5-yl; and $Q^1$ is |
| 847 $Y^1$ is NH; $Y^2$ is O; $R^2$ is H; $R^4$ is H; $R^5$ is H; $Q^2$ is 2,2-di-Me-1,3-benzodioxol-4-yl; and $Q^1$ is |
| 848 $Y^1$ is NH; $Y^2$ is O; $R^2$ is H; $R^4$ is H; $R^5$ is H; $Q^2$ is 2,2-di-Me-1,3-benzodioxol-5-yl; and $Q^1$ is |
| 849 $Y^1$ is NH; $Y^2$ is O; $R^2$ is H; $R^4$ is H; $R^5$ is H; $Q^2$ is 1,3-benzodioxol-4-yl; and $Q^1$ is |
| 850 $Y^1$ is NH; $Y^2$ is O; $R^2$ is H; $R^4$ is H; $R^5$ is H; $Q^2$ is 1,3-benzodioxol-5-yl; and $Q^1$ is |
| 851 $Y^1$ is O; $Y^2$ is O; $R^2$ is Me; $R^4$ is H; $R^5$ is H; $Q^2$ is Ph(2-F); and $Q^1$ is |
| 852 $Y^1$ is O; $Y^2$ is O; $R^2$ is Me; $R^4$ is H; $R^5$ is H; $Q^2$ is Ph(2,3-di-F); and $Q^1$ is |
| 853 $Y^1$ is O; $Y^2$ is O; $R^2$ is Me; $R^4$ is H; $R^5$ is H; $Q^2$ is Ph(2,4-di-F); and $Q^1$ is |
| 854 $Y^1$ is O; $Y^2$ is O; $R^2$ is Me; $R^4$ is H; $R^5$ is H; $Q^2$ is Ph(2,5-di-F); and $Q^1$ is |
| 855 $Y^1$ is O; $Y^2$ is O; $R^2$ is Me; $R^4$ is H; $R^5$ is H; $Q^2$ is Ph(2,3,4-tri-F); and $Q^1$ is |
| 856 $Y^1$ is O; $Y^2$ is O; $R^2$ is Me; $R^4$ is H; $R^5$ is H; $Q^2$ is Ph(2,3,5-tri-F); and $Q^1$ is |
| 857 $Y^1$ is O; $Y^2$ is O; $R^2$ is Me; $R^4$ is H; $R^5$ is H; $Q^2$ is Ph(2,3,4,5-tetra-F); and $Q^1$ is |
| 858 $Y^1$ is O; $Y^2$ is O; $R^2$ is Me; $R^4$ is H; $R^5$ is H; $Q^2$ is Ph(2-F,3-Cl,4-Br); and $Q^1$ is |
| 859 $Y^1$ is O; $Y^2$ is O; $R^2$ is Me; $R^4$ is H; $R^5$ is H; $Q^2$ is Ph(2-F,3-Cl,4-F); and $Q^1$ is |
| 860 $Y^1$ is O; $Y^2$ is O; $R^2$ is Me; $R^4$ is H; $R^5$ is H; $Q^2$ is Ph(2-F,3-Br,4-F); and $Q^1$ is |
| 861 $Y^1$ is O; $Y^2$ is O; $R^2$ is Me; $R^4$ is H; $R^5$ is H; $Q^2$ is Ph(2-F,3-Me); and $Q^1$ is |
| 862 $Y^1$ is O; $Y^2$ is O; $R^2$ is Me; $R^4$ is H; $R^5$ is H; $Q^2$ is Ph(2-F,3-Me,4-F); and $Q^1$ is |
| 863 $Y^1$ is O; $Y^2$ is O; $R^2$ is Me; $R^4$ is H; $R^5$ is H; $Q^2$ is Ph(2-F,3-Me,4-Cl); and $Q^1$ is |
| 864 $Y^1$ is O; $Y^2$ is O; $R^2$ is Me; $R^4$ is H; $R^5$ is H; $Q^2$ is Ph(2-F,3-Cl); and $Q^1$ is |
| 865 $Y^1$ is O; $Y^2$ is O; $R^2$ is Me; $R^4$ is H; $R^5$ is H; $Q^2$ is Ph(2-F,4-Cl); and $Q^1$ is |
| 866 $Y^1$ is O; $Y^2$ is O; $R^2$ is Me; $R^4$ is H; $R^5$ is H; $Q^2$ is Ph(2-F,3,4-di-Cl); and $Q^1$ is |
| 867 $Y^1$ is O; $Y^2$ is O; $R^2$ is Me; $R^4$ is H; $R^5$ is H; $Q^2$ is Ph(2-F,4-Br); and $Q^1$ is |
| 868 $Y^1$ is O; $Y^2$ is O; $R^2$ is Me; $R^4$ is H; $R^5$ is H; $Q^2$ is Ph(2-F,3-OMe); and $Q^1$ is |
| 869 $Y^1$ is O; $Y^2$ is O; $R^2$ is Me; $R^4$ is H; $R^5$ is H; $Q^2$ is Ph(2-F,3-OMe,4-F); and $Q^1$ is |
| 870 $Y^1$ is O; $Y^2$ is O; $R^2$ is Me; $R^4$ is H; $R^5$ is H; $Q^2$ is Ph(2-F,3-OMe,4-Cl); and $Q^1$ is |
| 871 $Y^1$ is O; $Y^2$ is O; $R^2$ is Me; $R^4$ is H; $R^5$ is H; $Q^2$ is Ph(2-F,3-CF$_2$H); and $Q^1$ is |
| 872 $Y^1$ is O; $Y^2$ is O; $R^2$ is Me; $R^4$ is H; $R^5$ is H; $Q^2$ is Ph(2-F,3-CF$_3$); and $Q^1$ is |
| 873 $Y^1$ is O; $Y^2$ is O; $R^2$ is Me; $R^4$ is H; $R^5$ is H; $Q^2$ is Ph(2-F,3-CF$_3$,4-F); and $Q^1$ is |
| 874 $Y^1$ is O; $Y^2$ is O; $R^2$ is Me; $R^4$ is H; $R^5$ is H; $Q^2$ is Ph(2-F,3-NO$_2$); and $Q^1$ is |
| 875 $Y^1$ is O; $Y^2$ is O; $R^2$ is Me; $R^4$ is H; $R^5$ is H; $Q^2$ is Ph(2-F,3-NO$_2$,4-F); and $Q^1$ is |
| 876 $Y^1$ is O; $Y^2$ is O; $R^2$ is Me; $R^4$ is H; $R^5$ is H; $Q^2$ is Ph(2-F,3-SO$_2$Me); and $Q^1$ is |
| 877 $Y^1$ is O; $Y^2$ is O; $R^2$ is Me; $R^4$ is H; $R^5$ is H; $Q^2$ is Ph(2-F,3-SO$_2$Me,4-F); and $Q^1$ is |
| 878 $Y^1$ is O; $Y^2$ is O; $R^2$ is Me; $R^4$ is H; $R^5$ is H; $Q^2$ is Ph(2-CF$_3$); and $Q^1$ is |
| 879 $Y^1$ is O; $Y^2$ is O; $R^2$ is Me; $R^4$ is H; $R^5$ is H; $Q^2$ is Ph(2-CF$_3$,3-F); and $Q^1$ is |
| 880 $Y^1$ is O; $Y^2$ is O; $R^2$ is Me; $R^4$ is H; $R^5$ is H; $Q^2$ is Ph(2-CF$_3$,3-Me); and $Q^1$ is |
| 881 $Y^1$ is O; $Y^2$ is O; $R^2$ is Me; $R^4$ is H; $R^5$ is H; $Q^2$ is Ph(2-CF$_3$,4-F); and $Q^1$ is |
| 882 $Y^1$ is O; $Y^2$ is O; $R^2$ is Me; $R^4$ is H; $R^5$ is H; $Q^2$ is Ph(2-CF$_3$,3-Cl); and $Q^1$ is |
| 883 $Y^1$ is O; $Y^2$ is O; $R^2$ is Me; $R^4$ is H; $R^5$ is H; $Q^2$ is Ph(2-CF$_3$,4-Cl); and $Q^1$ is |
| 884 $Y^1$ is O; $Y^2$ is O; $R^2$ is Me; $R^4$ is H; $R^5$ is H; $Q^2$ is Ph(2-CF$_3$,3,4-di-F); and $Q^1$ is |

-continued

| Table Row Heading |
|---|
| 885  $Y^1$ is O; $Y^2$ is O; $R^2$ is Me; $R^4$ is H; $R^5$ is H; $Q^2$ is Ph(2-CF$_2$H); and $Q^1$ is
| 886  $Y^1$ is O; $Y^2$ is O; $R^2$ is Me; $R^4$ is H; $R^5$ is H; $Q^2$ is Ph(2-CF$_2$H,3-F); and $Q^1$ is
| 887  $Y^1$ is O; $Y^2$ is O; $R^2$ is Me; $R^4$ is H; $R^5$ is H; $Q^2$ is Ph(2-CF$_2$H,3-Me); and $Q^1$ is
| 888  $Y^1$ is O; $Y^2$ is O; $R^2$ is Me; $R^4$ is H; $R^5$ is H; $Q^2$ is Ph(2-CF$_2$H,4-F); and $Q^1$ is
| 889  $Y^1$ is O; $Y^2$ is O; $R^2$ is Me; $R^4$ is H; $R^5$ is H; $Q^2$ is Ph(2-CF$_2$H,3-Cl); and $Q^1$ is
| 890  $Y^1$ is O; $Y^2$ is O; $R^2$ is Me; $R^4$ is H; $R^5$ is H; $Q^2$ is Ph(2-CF$_2$H,4-Cl); and $Q^1$ is
| 891  $Y^1$ is O; $Y^2$ is O; $R^2$ is Me; $R^4$ is H; $R^5$ is H; $Q^2$ is Ph(2-CF$_2$H,3,4-di-F); and $Q^1$ is
| 892  $Y^1$ is O; $Y^2$ is O; $R^2$ is Me; $R^4$ is H; $R^5$ is H; $Q^2$ is Ph(2-Me); and $Q^1$ is
| 893  $Y^1$ is O; $Y^2$ is O; $R^2$ is Me; $R^4$ is H; $R^5$ is H; $Q^2$ is Ph(2,3-di-Me); and $Q^1$ is
| 894  $Y^1$ is O; $Y^2$ is O; $R^2$ is Me; $R^4$ is H; $R^5$ is H; $Q^2$ is Ph(2-Me,3-F); and $Q^1$ is
| 895  $Y^1$ is O; $Y^2$ is O; $R^2$ is Me; $R^4$ is H; $R^5$ is H; $Q^2$ is Ph(2-Me,3-Cl); and $Q^1$ is
| 896  $Y^1$ is O; $Y^2$ is O; $R^2$ is Me; $R^4$ is H; $R^5$ is H; $Q^2$ is Ph(2-Me,3-CF$_3$); and $Q^1$ is
| 897  $Y^1$ is O; $Y^2$ is O; $R^2$ is Me; $R^4$ is H; $R^5$ is H; $Q^2$ is Ph(2-Me,3,4-di-Cl); and $Q^1$ is
| 898  $Y^1$ is O; $Y^2$ is O; $R^2$ is Me; $R^4$ is H; $R^5$ is H; $Q^2$ is Ph(2-Me,3-Cl,4-F); and $Q^1$ is
| 899  $Y^1$ is O; $Y^2$ is O; $R^2$ is Me; $R^4$ is H; $R^5$ is H; $Q^2$ is Ph(2-Me,4-Cl); and $Q^1$ is
| 900  $Y^1$ is O; $Y^2$ is O; $R^2$ is Me; $R^4$ is H; $R^5$ is H; $Q^2$ is Ph(2-Me,4-F); and $Q^1$ is
| 901  $Y^1$ is O; $Y^2$ is O; $R^2$ is Me; $R^4$ is H; $R^5$ is H; $Q^2$ is Ph(2-Me,5-F); and $Q^1$ is
| 902  $Y^1$ is O; $Y^2$ is O; $R^2$ is Me; $R^4$ is H; $R^5$ is H; $Q^2$ is Ph(2-Me,3,4-di-F); and $Q^1$ is
| 903  $Y^1$ is O; $Y^2$ is O; $R^2$ is Me; $R^4$ is H; $R^5$ is H; $Q^2$ is Ph(2-Me,3,5-di-F); and $Q^1$ is
| 904  $Y^1$ is O; $Y^2$ is O; $R^2$ is Me; $R^4$ is H; $R^5$ is H; $Q^2$ is Ph(2-Et); and $Q^1$ is
| 905  $Y^1$ is O; $Y^2$ is O; $R^2$ is Me; $R^4$ is H; $R^5$ is H; $Q^2$ is Ph(2-Et,3-F); and $Q^1$ is
| 906  $Y^1$ is O; $Y^2$ is O; $R^2$ is Me; $R^4$ is H; $R^5$ is H; $Q^2$ is Ph(2-Et,3-Cl); and $Q^1$ is
| 907  $Y^1$ is O; $Y^2$ is O; $R^2$ is Me; $R^4$ is H; $R^5$ is H; $Q^2$ is Ph(2-Et,4-F); and $Q^1$ is
| 908  $Y^1$ is O; $Y^2$ is O; $R^2$ is Me; $R^4$ is H; $R^5$ is H; $Q^2$ is Ph(2-Et,3,4-di-F); and $Q^1$ is
| 909  $Y^1$ is O; $Y^2$ is O; $R^2$ is Me; $R^4$ is H; $R^5$ is H; $Q^2$ is Ph(2-i-Pr); and $Q^1$ is
| 910  $Y^1$ is O; $Y^2$ is O; $R^2$ is Me; $R^4$ is H; $R^5$ is H; $Q^2$ is Ph(2-i-Pr,3-F); and $Q^1$ is
| 911  $Y^1$ is O; $Y^2$ is O; $R^2$ is Me; $R^4$ is H; $R^5$ is H; $Q^2$ is Ph(2-i-Pr,3-Cl); and $Q^1$ is
| 912  $Y^1$ is O; $Y^2$ is O; $R^2$ is Me; $R^4$ is H; $R^5$ is H; $Q^2$ is Ph(2-i-Pr,4-F); and $Q^1$ is
| 913  $Y^1$ is O; $Y^2$ is O; $R^2$ is Me; $R^4$ is H; $R^5$ is H; $Q^2$ is Ph(2-i-Pr,3,4-di-F); and $Q^1$ is
| 914  $Y^1$ is O; $Y^2$ is O; $R^2$ is Me; $R^4$ is H; $R^5$ is H; $Q^2$ is Ph(2-c-Pr); and $Q^1$ is
| 915  $Y^1$ is O; $Y^2$ is O; $R^2$ is Me; $R^4$ is H; $R^5$ is H; $Q^2$ is Ph(2-c-Pr,3-F); and $Q^1$ is
| 916  $Y^1$ is O; $Y^2$ is O; $R^2$ is Me; $R^4$ is H; $R^5$ is H; $Q^2$ is Ph(2-c-Pr,3-Cl); and $Q^1$ is
| 917  $Y^1$ is O; $Y^2$ is O; $R^2$ is Me; $R^4$ is H; $R^5$ is H; $Q^2$ is Ph(2-c-Pr,4-F); and $Q^1$ is
| 918  $Y^1$ is O; $Y^2$ is O; $R^2$ is Me; $R^4$ is H; $R^5$ is H; $Q^2$ is Ph(2-c-Pr,3,4-di-F); and $Q^1$ is
| 919  $Y^1$ is O; $Y^2$ is O; $R^2$ is Me; $R^4$ is H; $R^5$ is H; $Q^2$ is Ph(2-NO$_2$); and $Q^1$ is
| 920  $Y^1$ is O; $Y^2$ is O; $R^2$ is Me; $R^4$ is H; $R^5$ is H; $Q^2$ is Ph(2-NO$_2$,3-F); and $Q^1$ is
| 921  $Y^1$ is O; $Y^2$ is O; $R^2$ is Me; $R^4$ is H; $R^5$ is H; $Q^2$ is Ph(2-NO$_2$,3-Cl); and $Q^1$ is
| 922  $Y^1$ is O; $Y^2$ is O; $R^2$ is Me; $R^4$ is H; $R^5$ is H; $Q^2$ is Ph(2-NO$_2$,4-F); and $Q^1$ is
| 923  $Y^1$ is O; $Y^2$ is O; $R^2$ is Me; $R^4$ is H; $R^5$ is H; $Q^2$ is Ph(2-NO$_2$,3,4-di-F); and $Q^1$ is
| 924  $Y^1$ is O; $Y^2$ is O; $R^2$ is Me; $R^4$ is H; $R^5$ is H; $Q^2$ is Ph(2-OCF$_3$); and $Q^1$ is
| 925  $Y^1$ is O; $Y^2$ is O; $R^2$ is Me; $R^4$ is H; $R^5$ is H; $Q^2$ is Ph(2-OCF$_3$,3-F); and $Q^1$ is
| 926  $Y^1$ is O; $Y^2$ is O; $R^2$ is Me; $R^4$ is H; $R^5$ is H; $Q^2$ is Ph(2-OCF$_3$,4-F); and $Q^1$ is
| 927  $Y^1$ is O; $Y^2$ is O; $R^2$ is Me; $R^4$ is H; $R^5$ is H; $Q^2$ is Ph(2-Cl); and $Q^1$ is
| 928  $Y^1$ is O; $Y^2$ is O; $R^2$ is Me; $R^4$ is H; $R^5$ is H; $Q^2$ is Ph(2-Cl,3-Me); and $Q^1$ is
| 929  $Y^1$ is O; $Y^2$ is O; $R^2$ is Me; $R^4$ is H; $R^5$ is H; $Q^2$ is Ph(2-Cl,3-Me,4-F); and $Q^1$ is
| 930  $Y^1$ is O; $Y^2$ is O; $R^2$ is Me; $R^4$ is H; $R^5$ is H; $Q^2$ is Ph(2,3-di-Cl); and $Q^1$ is
| 931  $Y^1$ is O; $Y^2$ is O; $R^2$ is Me; $R^4$ is H; $R^5$ is H; $Q^2$ is Ph(2,4-di-Cl); and $Q^1$ is
| 932  $Y^1$ is O; $Y^2$ is O; $R^2$ is Me; $R^4$ is H; $R^5$ is H; $Q^2$ is Ph(2-Cl,3-F); and $Q^1$ is
| 933  $Y^1$ is O; $Y^2$ is O; $R^2$ is Me; $R^4$ is H; $R^5$ is H; $Q^2$ is Ph(2-Cl,4-F); and $Q^1$ is
| 934  $Y^1$ is O; $Y^2$ is O; $R^2$ is Me; $R^4$ is H; $R^5$ is H; $Q^2$ is Ph(2-Cl,5-F); and $Q^1$ is
| 935  $Y^1$ is O; $Y^2$ is O; $R^2$ is Me; $R^4$ is H; $R^5$ is H; $Q^2$ is Ph(2-Cl,3,4-di-F); and $Q^1$ is
| 936  $Y^1$ is O; $Y^2$ is O; $R^2$ is Me; $R^4$ is H; $R^5$ is H; $Q^2$ is Ph(2-Cl,3,5-di-F); and $Q^1$ is
| 937  $Y^1$ is O; $Y^2$ is O; $R^2$ is Me; $R^4$ is H; $R^5$ is H; $Q^2$ is Ph(2-OCF$_2$H); and $Q^1$ is
| 938  $Y^1$ is O; $Y^2$ is O; $R^2$ is Me; $R^4$ is H; $R^5$ is H; $Q^2$ is Ph(2-OCF$_2$H,3-Me); and $Q^1$ is
| 939  $Y^1$ is O; $Y^2$ is O; $R^2$ is Me; $R^4$ is H; $R^5$ is H; $Q^2$ is Ph(2-OCF$_2$H,3-Cl); and $Q^1$ is
| 940  $Y^1$ is O; $Y^2$ is O; $R^2$ is Me; $R^4$ is H; $R^5$ is H; $Q^2$ is Ph(2-OCF$_2$H,3-F); and $Q^1$ is
| 941  $Y^1$ is O; $Y^2$ is O; $R^2$ is Me; $R^4$ is H; $R^5$ is H; $Q^2$ is Ph(2-OCF$_2$H,4-F); and $Q^1$ is
| 942  $Y^1$ is O; $Y^2$ is O; $R^2$ is Me; $R^4$ is H; $R^5$ is H; $Q^2$ is Ph(2-OCF$_2$CF$_2$H); and $Q^1$ is
| 943  $Y^1$ is O; $Y^2$ is O; $R^2$ is Me; $R^4$ is H; $R^5$ is H; $Q^2$ is Ph(2-OCF$_2$CF$_2$H,3-F); and $Q^1$ is
| 944  $Y^1$ is O; $Y^2$ is O; $R^2$ is Me; $R^4$ is H; $R^5$ is H; $Q^2$ is Ph(2-OCF$_2$CF$_2$H,4-F); and $Q^1$ is
| 945  $Y^1$ is O; $Y^2$ is O; $R^2$ is Me; $R^4$ is H; $R^5$ is H; $Q^2$ is Ph(2-Br); and $Q^1$ is
| 946  $Y^1$ is O; $Y^2$ is O; $R^2$ is Me; $R^4$ is H; $R^5$ is H; $Q^2$ is Ph(2-Br,3-F); and $Q^1$ is
| 947  $Y^1$ is O; $Y^2$ is O; $R^2$ is Me; $R^4$ is H; $R^5$ is H; $Q^2$ is Ph(2-Br,4-F); and $Q^1$ is
| 948  $Y^1$ is O; $Y^2$ is O; $R^2$ is Me; $R^4$ is H; $R^5$ is H; $Q^2$ is Ph(2-Br,3,4-di-F); and $Q^1$ is
| 949  $Y^1$ is O; $Y^2$ is O; $R^2$ is Me; $R^4$ is H; $R^5$ is H; $Q^2$ is Ph(2-I); and $Q^1$ is
| 950  $Y^1$ is O; $Y^2$ is O; $R^2$ is Me; $R^4$ is H; $R^5$ is H; $Q^2$ is Ph(2-I,3-F); and $Q^1$ is
| 951  $Y^1$ is O; $Y^2$ is O; $R^2$ is Me; $R^4$ is H; $R^5$ is H; $Q^2$ is Ph(2-I,4-F); and $Q^1$ is
| 952  $Y^1$ is O; $Y^2$ is O; $R^2$ is Me; $R^4$ is H; $R^5$ is H; $Q^2$ is Ph(2-I,3,4-di-F); and $Q^1$ is
| 953  $Y^1$ is O; $Y^2$ is O; $R^2$ is Me; $R^4$ is H; $R^5$ is H; $Q^2$ is Ph(2-CN); and $Q^1$ is
| 954  $Y^1$ is O; $Y^2$ is O; $R^2$ is Me; $R^4$ is H; $R^5$ is H; $Q^2$ is Ph(2-CN,3-Me); and $Q^1$ is
| 955  $Y^1$ is O; $Y^2$ is O; $R^2$ is Me; $R^4$ is H; $R^5$ is H; $Q^2$ is Ph(2-CN,3-F); and $Q^1$ is
| 956  $Y^1$ is O; $Y^2$ is O; $R^2$ is Me; $R^4$ is H; $R^5$ is H; $Q^2$ is Ph(2-CN,4-F); and $Q^1$ is
| 957  $Y^1$ is O; $Y^2$ is O; $R^2$ is Me; $R^4$ is H; $R^5$ is H; $Q^2$ is Ph(2-CN,3-Cl); and $Q^1$ is
| 958  $Y^1$ is O; $Y^2$ is O; $R^2$ is Me; $R^4$ is H; $R^5$ is H; $Q^2$ is Ph(2-CN,4-Cl); and $Q^1$ is
| 959  $Y^1$ is O; $Y^2$ is O; $R^2$ is Me; $R^4$ is H; $R^5$ is H; $Q^2$ is Ph(2-CN,3,4-di-F); and $Q^1$ is
| 960  $Y^1$ is O; $Y^2$ is O; $R^2$ is Me; $R^4$ is H; $R^5$ is H; $Q^2$ is 2-Pyridinyl; and $Q^1$ is
| 961  $Y^1$ is O; $Y^2$ is O; $R^2$ is Me; $R^4$ is H; $R^5$ is H; $Q^2$ is 2-Pyridinyl,3-F; and $Q^1$ is -continued

| Table Row Heading |
|---|
| 962 $Y^1$ is O; $Y^2$ is O; $R^2$ is Me; $R^4$ is H; $R^5$ is H; $Q^2$ is 2-Pyridinyl,4-F; and $Q^1$ is |
| 963 $Y^1$ is O; $Y^2$ is O; $R^2$ is Me; $R^4$ is H; $R^5$ is H; $Q^2$ is 2-Pyridinyl,3,4-di-F; and $Q^1$ is |
| 964 $Y^1$ is O; $Y^2$ is O; $R^2$ is Me; $R^4$ is H; $R^5$ is H; $Q^2$ is 2-Pyridinyl,3-Cl; and $Q^1$ is |
| 965 $Y^1$ is O; $Y^2$ is O; $R^2$ is Me; $R^4$ is H; $R^5$ is H; $Q^2$ is 2-Pyridinyl,4-Cl; and $Q^1$ is |
| 966 $Y^1$ is O; $Y^2$ is O; $R^2$ is Me; $R^4$ is H; $R^5$ is H; $Q^2$ is 2-Pyridinyl,3-Cl,4-F; and $Q^1$ is |
| 967 $Y^1$ is O; $Y^2$ is O; $R^2$ is Me; $R^4$ is H; $R^5$ is H; $Q^2$ is Ph(2-SO$_2$Me); and $Q^1$ is |
| 968 $Y^1$ is O; $Y^2$ is O; $R^2$ is Me; $R^4$ is H; $R^5$ is H; $Q^2$ is Ph(2-SO$_2$Me, 3-F); and $Q^1$ is |
| 969 $Y^1$ is O; $Y^2$ is O; $R^2$ is Me; $R^4$ is H; $R^5$ is H; $Q^2$ is Ph(2-SO$_2$Me, 3-Me); and $Q^1$ is |
| 970 $Y^1$ is O; $Y^2$ is O; $R^2$ is Me; $R^4$ is H; $R^5$ is H; $Q^2$ is Ph(2-SO$_2$Me, 4-F); and $Q^1$ is |
| 971 $Y^1$ is O; $Y^2$ is O; $R^2$ is Me; $R^4$ is H; $R^5$ is H; $Q^2$ is Ph(2-SO$_2$Me, 5-F); and $Q^1$ is |
| 972 $Y^1$ is O; $Y^2$ is O; $R^2$ is Me; $R^4$ is H; $R^5$ is H; $Q^2$ is Ph(2-SO$_2$Me,3,4-di-F); and $Q^1$ is |
| 973 $Y^1$ is O; $Y^2$ is O; $R^2$ is Me; $R^4$ is H; $R^5$ is H; $Q^2$ is Ph(2-SO$_2$Me, 3-Cl); and $Q^1$ is |
| 974 $Y^1$ is O; $Y^2$ is O; $R^2$ is Me; $R^4$ is H; $R^5$ is H; $Q^2$ is Ph(2-SO$_2$Me, 4-Cl); and $Q^1$ is |
| 975 $Y^1$ is O; $Y^2$ is O; $R^2$ is Me; $R^4$ is H; $R^5$ is H; $Q^2$ is Ph(2-SO$_2$Me,3-Cl,4-F); and $Q^1$ is |
| 976 $Y^1$ is O; $Y^2$ is O; $R^2$ is Me; $R^4$ is H; $R^5$ is H; $Q^2$ is Ph(2-SO$_2$NH$_2$); and $Q^1$ is |
| 977 $Y^1$ is O; $Y^2$ is O; $R^2$ is Me; $R^4$ is H; $R^5$ is H; $Q^2$ is Ph(2-SO$_2$NH$_2$, 3-F); and $Q^1$ is |
| 978 $Y^1$ is O; $Y^2$ is O; $R^2$ is Me; $R^4$ is H; $R^5$ is H; $Q^2$ is Ph(2-SO$_2$NH$_2$, 3-Cl); and $Q^1$ is |
| 979 $Y^1$ is O; $Y^2$ is O; $R^2$ is Me; $R^4$ is H; $R^5$ is H; $Q^2$ is Ph(2-SO$_2$NH$_2$, 4-F); and $Q^1$ is |
| 980 $Y^1$ is O; $Y^2$ is O; $R^2$ is Me; $R^4$ is H; $R^5$ is H; $Q^2$ is Ph(2-SO$_2$NH$_2$, 5-F); and $Q^1$ is |
| 981 $Y^1$ is O; $Y^2$ is O; $R^2$ is Me; $R^4$ is H; $R^5$ is H; $Q^2$ is Ph(2-SO$_2$NH$_2$,3,4-di-F); and $Q^1$ is |
| 982 $Y^1$ is O; $Y^2$ is O; $R^2$ is Me; $R^4$ is H; $R^5$ is H; $Q^2$ is Ph(3-F); and $Q^1$ is |
| 983 $Y^1$ is O; $Y^2$ is O; $R^2$ is Me; $R^4$ is H; $R^5$ is H; $Q^2$ is Ph(3,4-di-F); and $Q^1$ is |
| 984 $Y^1$ is O; $Y^2$ is O; $R^2$ is Me; $R^4$ is H; $R^5$ is H; $Q^2$ is Ph(3,5-di-F); and $Q^1$ is |
| 985 $Y^1$ is O; $Y^2$ is O; $R^2$ is Me; $R^4$ is H; $R^5$ is H; $Q^2$ is Ph(3,4,5-tri-F); and $Q^1$ is |
| 986 $Y^1$ is O; $Y^2$ is O; $R^2$ is Me; $R^4$ is H; $R^5$ is H; $Q^2$ is Ph(3-F,4-Cl); and $Q^1$ is |
| 987 $Y^1$ is O; $Y^2$ is O; $R^2$ is Me; $R^4$ is H; $R^5$ is H; $Q^2$ is Ph(3-CF$_3$); and $Q^1$ is |
| 988 $Y^1$ is O; $Y^2$ is O; $R^2$ is Me; $R^4$ is H; $R^5$ is H; $Q^2$ is Ph(3-CF$_3$,4-F); and $Q^1$ is |
| 989 $Y^1$ is O; $Y^2$ is O; $R^2$ is Me; $R^4$ is H; $R^5$ is H; $Q^2$ is Ph(3-CF$_3$,4-Cl); and $Q^1$ is |
| 990 $Y^1$ is O; $Y^2$ is O; $R^2$ is Me; $R^4$ is H; $R^5$ is H; $Q^2$ is Ph(3-CF$_3$,5-F); and $Q^1$ is |
| 991 $Y^1$ is O; $Y^2$ is O; $R^2$ is Me; $R^4$ is H; $R^5$ is H; $Q^2$ is Ph(3-CF$_3$,4,5-di-F); and $Q^1$ is |
| 992 $Y^1$ is O; $Y^2$ is O; $R^2$ is Me; $R^4$ is H; $R^5$ is H; $Q^2$ is Ph(3-SO$_2$Me); and $Q^1$ is |
| 993 $Y^1$ is O; $Y^2$ is O; $R^2$ is Me; $R^4$ is H; $R^5$ is H; $Q^2$ is Ph(3-SO$_2$Me,4-Cl); and $Q^1$ is |
| 994 $Y^1$ is O; $Y^2$ is O; $R^2$ is Me; $R^4$ is H; $R^5$ is H; $Q^2$ is Ph(3-SO$_2$Me,4-F); and $Q^1$ is |
| 995 $Y^1$ is O; $Y^2$ is O; $R^2$ is Me; $R^4$ is H; $R^5$ is H; $Q^2$ is Ph(3-SO$_2$Me,4,5-di-F); and $Q^1$ is |
| 996 $Y^1$ is O; $Y^2$ is O; $R^2$ is Me; $R^4$ is H; $R^5$ is H; $Q^2$ is Ph(3-SO$_2$Me,5-F); and $Q^1$ is |
| 997 $Y^1$ is O; $Y^2$ is O; $R^2$ is Me; $R^4$ is H; $R^5$ is H; $Q^2$ is Ph(3-SO$_2$NH$_2$); and $Q^1$ is |
| 998 $Y^1$ is O; $Y^2$ is O; $R^2$ is Me; $R^4$ is H; $R^5$ is H; $Q^2$ is Ph(3-SO$_2$NH$_2$,4-F); and $Q^1$ is |
| 999 $Y^1$ is O; $Y^2$ is O; $R^2$ is Me; $R^4$ is H; $R^5$ is H; $Q^2$ is Ph(3-SO$_2$NH$_2$,4,5-di-F); and $Q^1$ is |
| 1000 $Y^1$ is O; $Y^2$ is O; $R^2$ is Me; $R^4$ is H; $R^5$ is H; $Q^2$ is Ph(3-SO$_2$NH$_2$,4-Cl); and $Q^1$ is |
| 1001 $Y^1$ is O; $Y^2$ is O; $R^2$ is Me; $R^4$ is H; $R^5$ is H; $Q^2$ is Ph(3-SO$_2$NH$_2$,5-F); and $Q^1$ is |
| 1002 $Y^1$ is O; $Y^2$ is O; $R^2$ is Me; $R^4$ is H; $R^5$ is H; $Q^2$ is Ph(3-Me); and $Q^1$ is |
| 1003 $Y^1$ is O; $Y^2$ is O; $R^2$ is Me; $R^4$ is H; $R^5$ is H; $Q^2$ is Ph(3-Me,4-F); and $Q^1$ is |
| 1004 $Y^1$ is O; $Y^2$ is O; $R^2$ is Me; $R^4$ is H; $R^5$ is H; $Q^2$ is Ph(3-Me,4-Cl); and $Q^1$ is |
| 1005 $Y^1$ is O; $Y^2$ is O; $R^2$ is Me; $R^4$ is H; $R^5$ is H; $Q^2$ is Ph(3-Me,5-F); and $Q^1$ is |
| 1006 $Y^1$ is O; $Y^2$ is O; $R^2$ is Me; $R^4$ is H; $R^5$ is H; $Q^2$ is Ph(3-Me,4,5-di-F); and $Q^1$ is |
| 1007 $Y^1$ is O; $Y^2$ is O; $R^2$ is Me; $R^4$ is H; $R^5$ is H; $Q^2$ is Ph(3-Cl); and $Q^1$ is |
| 1008 $Y^1$ is O; $Y^2$ is O; $R^2$ is Me; $R^4$ is H; $R^5$ is H; $Q^2$ is Ph(3-Cl,4-F); and $Q^1$ is |
| 1009 $Y^1$ is O; $Y^2$ is O; $R^2$ is Me; $R^4$ is H; $R^5$ is H; $Q^2$ is Ph(3,4-di-Cl); and $Q^1$ is |
| 1010 $Y^1$ is O; $Y^2$ is O; $R^2$ is Me; $R^4$ is H; $R^5$ is H; $Q^2$ is Ph(3-Cl,5-F); and $Q^1$ is |
| 1011 $Y^1$ is O; $Y^2$ is O; $R^2$ is Me; $R^4$ is H; $R^5$ is H; $Q^2$ is Ph(3-Cl,4,5-di-F); and $Q^1$ is |
| 1012 $Y^1$ is O; $Y^2$ is O; $R^2$ is Me; $R^4$ is H; $R^5$ is H; $Q^2$ is Ph(3,5-di-Cl); and $Q^1$ is |
| 1013 $Y^1$ is O; $Y^2$ is O; $R^2$ is Me; $R^4$ is H; $R^5$ is H; $Q^2$ is Ph(4-F); and $Q^1$ is |
| 1014 $Y^1$ is O; $Y^2$ is O; $R^2$ is Me; $R^4$ is H; $R^5$ is H; $Q^2$ is Ph(4-Cl); and $Q^1$ is |
| 1015 $Y^1$ is O; $Y^2$ is O; $R^2$ is Me; $R^4$ is H; $R^5$ is H; $Q^2$ is 2,2-di-F-1,3-benzodioxol-4-yl; and $Q^1$ is |
| 1016 $Y^1$ is O; $Y^2$ is O; $R^2$ is Me; $R^4$ is H; $R^5$ is H; $Q^2$ is 2,2-di-F-1,3-benzodioxol-5-yl; and $Q^1$ is |
| 1017 $Y^1$ is O; $Y^2$ is O; $R^2$ is Me; $R^4$ is H; $R^5$ is H; $Q^2$ is 2,2-di-Me-1,3-benzodioxol-4-yl; and $Q^1$ is |
| 1018 $Y^1$ is O; $Y^2$ is O; $R^2$ is Me; $R^4$ is H; $R^5$ is H; $Q^2$ is 2,2-di-Me-1,3-benzodioxol-5-yl; and $Q^1$ is |
| 1019 $Y^1$ is O; $Y^2$ is O; $R^2$ is Me; $R^4$ is H; $R^5$ is H; $Q^2$ is 1,3-benzodioxol-4-yl; and $Q^1$ is |
| 1020 $Y^1$ is O; $Y^2$ is O; $R^2$ is Me; $R^4$ is H; $R^5$ is H; $Q^2$ is 1,3-benzodioxol-5-yl; and $Q^1$ is |
| 1021 $Y^1$ is O; $Y^2$ is O; $R^2$ is H; $R^4$ is Br; $R^5$ is H; $Q^2$ is Ph(2-F); and $Q^1$ is |
| 1022 $Y^1$ is O; $Y^2$ is O; $R^2$ is H; $R^4$ is Br; $R^5$ is H; $Q^2$ is Ph(2,3-di-F); and $Q^1$ is |
| 1023 $Y^1$ is O; $Y^2$ is O; $R^2$ is H; $R^4$ is Br; $R^5$ is H; $Q^2$ is Ph(2,4-di-F); and $Q^1$ is |
| 1024 $Y^1$ is O; $Y^2$ is O; $R^2$ is H; $R^4$ is Br; $R^5$ is H; $Q^2$ is Ph(2,5-di-F); and $Q^1$ is |
| 1025 $Y^1$ is O; $Y^2$ is O; $R^2$ is H; $R^4$ is Br; $R^5$ is H; $Q^2$ is Ph(2,3,4-tri-F); and $Q^1$ is |
| 1026 $Y^1$ is O; $Y^2$ is O; $R^2$ is H; $R^4$ is Br; $R^5$ is H; $Q^2$ is Ph(2,3,5-tri-F); and $Q^1$ is |
| 1027 $Y^1$ is O; $Y^2$ is O; $R^2$ is H; $R^4$ is Br; $R^5$ is H; $Q^2$ is Ph(2,3,4,5-tetra-F); and $Q^1$ is |
| 1028 $Y^1$ is O; $Y^2$ is O; $R^2$ is H; $R^4$ is Br; $R^5$ is H; $Q^2$ is Ph(2-F,3-Cl,4-Br); and $Q^1$ is |
| 1029 $Y^1$ is O; $Y^2$ is O; $R^2$ is H; $R^4$ is Br; $R^5$ is H; $Q^2$ is Ph(2-F,3-Cl,4-F); and $Q^1$ is |
| 1030 $Y^1$ is O; $Y^2$ is O; $R^2$ is H; $R^4$ is Br; $R^5$ is H; $Q^2$ is Ph(2-F,3-Br,4-F); and $Q^1$ is |
| 1031 $Y^1$ is O; $Y^2$ is O; $R^2$ is H; $R^4$ is Br; $R^5$ is H; $Q^2$ is Ph(2-F,3-Me); and $Q^1$ is |
| 1032 $Y^1$ is O; $Y^2$ is O; $R^2$ is H; $R^4$ is Br; $R^5$ is H; $Q^2$ is Ph(2-F,3-Me,4-F); and $Q^1$ is |
| 1033 $Y^1$ is O; $Y^2$ is O; $R^2$ is H; $R^4$ is Br; $R^5$ is H; $Q^2$ is Ph(2-F,3-Me,4-Cl); and $Q^1$ is |
| 1034 $Y^1$ is O; $Y^2$ is O; $R^2$ is H; $R^4$ is Br; $R^5$ is H; $Q^2$ is Ph(2-F,3-Cl); and $Q^1$ is |
| 1035 $Y^1$ is O; $Y^2$ is O; $R^2$ is H; $R^4$ is Br; $R^5$ is H; $Q^2$ is Ph(2-F,4-Cl); and $Q^1$ is |
| 1036 $Y^1$ is O; $Y^2$ is O; $R^2$ is H; $R^4$ is Br; $R^5$ is H; $Q^2$ is Ph(2-F,3,4-di-Cl); and $Q^1$ is |
| 1037 $Y^1$ is O; $Y^2$ is O; $R^2$ is H; $R^4$ is Br; $R^5$ is H; $Q^2$ is Ph(2-F,4-Br); and $Q^1$ is |
| 1038 $Y^1$ is O; $Y^2$ is O; $R^2$ is H; $R^4$ is Br; $R^5$ is H; $Q^2$ is Ph(2-F,3-OMe); and $Q^1$ is |

-continued

| Table Row Heading |
|---|
| 1039 Y$^1$ is O; Y$^2$ is O; R$^2$ is H; R$^4$ is Br; R$^5$ is H; Q$^2$ is Ph(2-F,3-OMe,4-F); and Q$^1$ is
| 1040 Y$^1$ is O; Y$^2$ is O; R$^2$ is H; R$^4$ is Br; R$^5$ is H; Q$^2$ is Ph(2-F,3-OMe,4-Cl); and Q$^1$ is
| 1041 Y$^1$ is O; Y$^2$ is O; R$^2$ is H; R$^4$ is Br; R$^5$ is H; Q$^2$ is Ph(2-F,3-CF$_2$H); and Q$^1$ is
| 1042 Y$^1$ is O; Y$^2$ is O; R$^2$ is H; R$^4$ is Br; R$^5$ is H; Q$^2$ is Ph(2-F,3-CF$_3$); and Q$^1$ is
| 1043 Y$^1$ is O; Y$^2$ is O; R$^2$ is H; R$^4$ is Br; R$^5$ is H; Q$^2$ is Ph(2-F,3-CF$_3$,4-F); and Q$^1$ is
| 1044 Y$^1$ is O; Y$^2$ is O; R$^2$ is H; R$^4$ is Br; R$^5$ is H; Q$^2$ is Ph(2-F,3-NO$_2$); and Q$^1$ is
| 1045 Y$^1$ is O; Y$^2$ is O; R$^2$ is H; R$^4$ is Br; R$^5$ is H; Q$^2$ is Ph(2-F,3-NO$_2$,4-F); and Q$^1$ is
| 1046 Y$^1$ is O; Y$^2$ is O; R$^2$ is H; R$^4$ is Br; R$^5$ is H; Q$^2$ is Ph(2-F,3-SO$_2$Me); and Q$^1$ is
| 1047 Y$^1$ is O; Y$^2$ is O; R$^2$ is H; R$^4$ is Br; R$^5$ is H; Q$^2$ is Ph(2-F,3-SO$_2$Me,4-F); and Q$^1$ is
| 1048 Y$^1$ is O; Y$^2$ is O; R$^2$ is H; R$^4$ is Br; R$^5$ is H; Q$^2$ is Ph(2-CF$_3$); and Q$^1$ is
| 1049 Y$^1$ is O; Y$^2$ is O; R$^2$ is H; R$^4$ is Br; R$^5$ is H; Q$^2$ is Ph(2-CF$_3$,3-F); and Q$^1$ is
| 1050 Y$^1$ is O; Y$^2$ is O; R$^2$ is H; R$^4$ is Br; R$^5$ is H; Q$^2$ is Ph(2-CF$_3$,3-Me); and Q$^1$ is
| 1051 Y$^1$ is O; Y$^2$ is O; R$^2$ is H; R$^4$ is Br; R$^5$ is H; Q$^2$ is Ph(2-CF$_3$,4-F); and Q$^1$ is
| 1052 Y$^1$ is O; Y$^2$ is O; R$^2$ is H; R$^4$ is Br; R$^5$ is H; Q$^2$ is Ph(2-CF$_3$,3-Cl); and Q$^1$ is
| 1053 Y$^1$ is O; Y$^2$ is O; R$^2$ is H; R$^4$ is Br; R$^5$ is H; Q$^2$ is Ph(2-CF$_3$,4-Cl); and Q$^1$ is
| 1054 Y$^1$ is O; Y$^2$ is O; R$^2$ is H; R$^4$ is Br; R$^5$ is H; Q$^2$ is Ph(2-CF$_3$,3,4-di-F); and Q$^1$ is
| 1055 Y$^1$ is O; Y$^2$ is O; R$^2$ is H; R$^4$ is Br; R$^5$ is H; Q$^2$ is Ph(2-CF$_2$H); and Q$^1$ is
| 1056 Y$^1$ is O; Y$^2$ is O; R$^2$ is H; R$^4$ is Br; R$^5$ is H; Q$^2$ is Ph(2-CF$_2$H,3-F); and Q$^1$ is
| 1057 Y$^1$ is O; Y$^2$ is O; R$^2$ is H; R$^4$ is Br; R$^5$ is H; Q$^2$ is Ph(2-CF$_2$H,3-Me); and Q$^1$ is
| 1058 Y$^1$ is O; Y$^2$ is O; R$^2$ is H; R$^4$ is Br; R$^5$ is H; Q$^2$ is Ph(2-CF$_2$H,4-F); and Q$^1$ is
| 1059 Y$^1$ is O; Y$^2$ is O; R$^2$ is H; R$^4$ is Br; R$^5$ is H; Q$^2$ is Ph(2-CF$_2$H,3-Cl); and Q$^1$ is
| 1060 Y$^1$ is O; Y$^2$ is O; R$^2$ is H; R$^4$ is Br; R$^5$ is H; Q$^2$ is Ph(2-CF$_2$H,4-Cl); and Q$^1$ is
| 1061 Y$^1$ is O; Y$^2$ is O; R$^2$ is H; R$^4$ is Br; R$^5$ is H; Q$^2$ is Ph(2-CF$_2$H,3,4-di-F); and Q$^1$ is
| 1062 Y$^1$ is O; Y$^2$ is O; R$^2$ is H; R$^4$ is Br; R$^5$ is H; Q$^2$ is Ph(2-Me); and Q$^1$ is
| 1063 Y$^1$ is O; Y$^2$ is O; R$^2$ is H; R$^4$ is Br; R$^5$ is H; Q$^2$ is Ph(2,3-di-Me); and Q$^1$ is
| 1064 Y$^1$ is O; Y$^2$ is O; R$^2$ is H; R$^4$ is Br; R$^5$ is H; Q$^2$ is Ph(2-Me,3-F); and Q$^1$ is
| 1065 Y$^1$ is O; Y$^2$ is O; R$^2$ is H; R$^4$ is Br; R$^5$ is H; Q$^2$ is Ph(2-Me,3-Cl); and Q$^1$ is
| 1066 Y$^1$ is O; Y$^2$ is O; R$^2$ is H; R$^4$ is Br; R$^5$ is H; Q$^2$ is Ph(2-Me,3-CF$_3$); and Q$^1$ is
| 1067 Y$^1$ is O; Y$^2$ is O; R$^2$ is H; R$^4$ is Br; R$^5$ is H; Q$^2$ is Ph(2-Me,3,4-di-Cl); and Q$^1$ is
| 1068 Y$^1$ is O; Y$^2$ is O; R$^2$ is H; R$^4$ is Br; R$^5$ is H; Q$^2$ is Ph(2-Me,3-Cl,4-F); and Q$^1$ is
| 1069 Y$^1$ is O; Y$^2$ is O; R$^2$ is H; R$^4$ is Br; R$^5$ is H; Q$^2$ is Ph(2-Me,4-Cl); and Q$^1$ is
| 1070 Y$^1$ is O; Y$^2$ is O; R$^2$ is H; R$^4$ is Br; R$^5$ is H; Q$^2$ is Ph(2-Me,4-F); and Q$^1$ is
| 1071 Y$^1$ is O; Y$^2$ is O; R$^2$ is H; R$^4$ is Br; R$^5$ is H; Q$^2$ is Ph(2-Me,5-F); and Q$^1$ is
| 1072 Y$^1$ is O; Y$^2$ is O; R$^2$ is H; R$^4$ is Br; R$^5$ is H; Q$^2$ is Ph(2-Me,3,4-di-F); and Q$^1$ is
| 1073 Y$^1$ is O; Y$^2$ is O; R$^2$ is H; R$^4$ is Br; R$^5$ is H; Q$^2$ is Ph(2-Me,3,5-di-F); and Q$^1$ is
| 1074 Y$^1$ is O; Y$^2$ is O; R$^2$ is H; R$^4$ is Br; R$^5$ is H; Q$^2$ is Ph(2-Et); and Q$^1$ is
| 1075 Y$^1$ is O; Y$^2$ is O; R$^2$ is H; R$^4$ is Br; R$^5$ is H; Q$^2$ is Ph(2-Et,3-F); and Q$^1$ is
| 1076 Y$^1$ is O; Y$^2$ is O; R$^2$ is H; R$^4$ is Br; R$^5$ is H; Q$^2$ is Ph(2-Et,3-Cl); and Q$^1$ is
| 1077 Y$^1$ is O; Y$^2$ is O; R$^2$ is H; R$^4$ is Br; R$^5$ is H; Q$^2$ is Ph(2-Et,4-F); and Q$^1$ is
| 1078 Y$^1$ is O; Y$^2$ is O; R$^2$ is H; R$^4$ is Br; R$^5$ is H; Q$^2$ is Ph(2-Et,3,4-di-F); and Q$^1$ is
| 1079 Y$^1$ is O; Y$^2$ is O; R$^2$ is H; R$^4$ is Br; R$^5$ is H; Q$^2$ is Ph(2-i-Pr); and Q$^1$ is
| 1080 Y$^1$ is O; Y$^2$ is O; R$^2$ is H; R$^4$ is Br; R$^5$ is H; Q$^2$ is Ph(2-i-Pr,3-F); and Q$^1$ is
| 1081 Y$^1$ is O; Y$^2$ is O; R$^2$ is H; R$^4$ is Br; R$^5$ is H; Q$^2$ is Ph(2-i-Pr,3-Cl); and Q$^1$ is
| 1082 Y$^1$ is O; Y$^2$ is O; R$^2$ is H; R$^4$ is Br; R$^5$ is H; Q$^2$ is Ph(2-i-Pr,4-F); and Q$^1$ is
| 1083 Y$^1$ is O; Y$^2$ is O; R$^2$ is H; R$^4$ is Br; R$^5$ is H; Q$^2$ is Ph(2-i-Pr,3,4-di-F); and Q$^1$ is
| 1084 Y$^1$ is O; Y$^2$ is O; R$^2$ is H; R$^4$ is Br; R$^5$ is H; Q$^2$ is Ph(2-c-Pr); and Q$^1$ is
| 1085 Y$^1$ is O; Y$^2$ is O; R$^2$ is H; R$^4$ is Br; R$^5$ is H; Q$^2$ is Ph(2-c-Pr,3-F); and Q$^1$ is
| 1086 Y$^1$ is O; Y$^2$ is O; R$^2$ is H; R$^4$ is Br; R$^5$ is H; Q$^2$ is Ph(2-c-Pr,3-Cl); and Q$^1$ is
| 1087 Y$^1$ is O; Y$^2$ is O; R$^2$ is H; R$^4$ is Br; R$^5$ is H; Q$^2$ is Ph(2-c-Pr,4-F); and Q$^1$ is
| 1088 Y$^1$ is O; Y$^2$ is O; R$^2$ is H; R$^4$ is Br; R$^5$ is H; Q$^2$ is Ph(2-c-Pr,3,4-di-F); and Q$^1$ is
| 1089 Y$^1$ is O; Y$^2$ is O; R$^2$ is H; R$^4$ is Br; R$^5$ is H; Q$^2$ is Ph(2-NO$_2$); and Q$^1$ is
| 1090 Y$^1$ is O; Y$^2$ is O; R$^2$ is H; R$^4$ is Br; R$^5$ is H; Q$^2$ is Ph(2-NO$_2$,3-F); and Q$^1$ is
| 1091 Y$^1$ is O; Y$^2$ is O; R$^2$ is H; R$^4$ is Br; R$^5$ is H; Q$^2$ is Ph(2-NO$_2$,3-Cl); and Q$^1$ is
| 1092 Y$^1$ is O; Y$^2$ is O; R$^2$ is H; R$^4$ is Br; R$^5$ is H; Q$^2$ is Ph(2-NO$_2$,4-F); and Q$^1$ is
| 1093 Y$^1$ is O; Y$^2$ is O; R$^2$ is H; R$^4$ is Br; R$^5$ is H; Q$^2$ is Ph(2-NO$_2$,3,4-di-F); and Q$^1$ is
| 1094 Y$^1$ is O; Y$^2$ is O; R$^2$ is H; R$^4$ is Br; R$^5$ is H; Q$^2$ is Ph(2-OCF$_3$); and Q$^1$ is
| 1095 Y$^1$ is O; Y$^2$ is O; R$^2$ is H; R$^4$ is Br; R$^5$ is H; Q$^2$ is Ph(2-OCF$_3$,3-F); and Q$^1$ is
| 1096 Y$^1$ is O; Y$^2$ is O; R$^2$ is H; R$^4$ is Br; R$^5$ is H; Q$^2$ is Ph(2-OCF$_3$,4-F); and Q$^1$ is
| 1097 Y$^1$ is O; Y$^2$ is O; R$^2$ is H; R$^4$ is Br; R$^5$ is H; Q$^2$ is Ph(2-Cl); and Q$^1$ is
| 1098 Y$^1$ is O; Y$^2$ is O; R$^2$ is H; R$^4$ is Br; R$^5$ is H; Q$^2$ is Ph(2-Cl,3-Me); and Q$^1$ is
| 1099 Y$^1$ is O; Y$^2$ is O; R$^2$ is H; R$^4$ is Br; R$^5$ is H; Q$^2$ is Ph(2-Cl,3-Me,4-F); and Q$^1$ is
| 1100 Y$^1$ is O; Y$^2$ is O; R$^2$ is H; R$^4$ is Br; R$^5$ is H; Q$^2$ is Ph(2,3-di-Cl); and Q$^1$ is
| 1101 Y$^1$ is O; Y$^2$ is O; R$^2$ is H; R$^4$ is Br; R$^5$ is H; Q$^2$ is Ph(2,4-di-Cl); and Q$^1$ is
| 1102 Y$^1$ is O; Y$^2$ is O; R$^2$ is H; R$^4$ is Br; R$^5$ is H; Q$^2$ is Ph(2-Cl,3-F); and Q$^1$ is
| 1103 Y$^1$ is O; Y$^2$ is O; R$^2$ is H; R$^4$ is Br; R$^5$ is H; Q$^2$ is Ph(2-Cl,4-F); and Q$^1$ is
| 1104 Y$^1$ is O; Y$^2$ is O; R$^2$ is H; R$^4$ is Br; R$^5$ is H; Q$^2$ is Ph(2-Cl,5-F); and Q$^1$ is
| 1105 Y$^1$ is O; Y$^2$ is O; R$^2$ is H; R$^4$ is Br; R$^5$ is H; Q$^2$ is Ph(2-Cl,3,4-di-F); and Q$^1$ is
| 1106 Y$^1$ is O; Y$^2$ is O; R$^2$ is H; R$^4$ is Br; R$^5$ is H; Q$^2$ is Ph(2-Cl,3,5-di-F); and Q$^1$ is
| 1107 Y$^1$ is O; Y$^2$ is O; R$^2$ is H; R$^4$ is Br; R$^5$ is H; Q$^2$ is Ph(2-OCF$_2$H); and Q$^1$ is
| 1108 Y$^1$ is O; Y$^2$ is O; R$^2$ is H; R$^4$ is Br; R$^5$ is H; Q$^2$ is Ph(2-OCF$_2$H,3-Me); and Q$^1$ is
| 1109 Y$^1$ is O; Y$^2$ is O; R$^2$ is H; R$^4$ is Br; R$^5$ is H; Q$^2$ is Ph(2-OCF$_2$H,3-Cl); and Q$^1$ is
| 1110 Y$^1$ is O; Y$^2$ is O; R$^2$ is H; R$^4$ is Br; R$^5$ is H; Q$^2$ is Ph(2-OCF$_2$H,3-F); and Q$^1$ is
| 1111 Y$^1$ is O; Y$^2$ is O; R$^2$ is H; R$^4$ is Br; R$^5$ is H; Q$^2$ is Ph(2-OCF$_2$H,4-F); and Q$^1$ is
| 1112 Y$^1$ is O; Y$^2$ is O; R$^2$ is H; R$^4$ is Br; R$^5$ is H; Q$^2$ is Ph(2-OCF$_2$CF$_2$H); and Q$^1$ is
| 1113 Y$^1$ is O; Y$^2$ is O; R$^2$ is H; R$^4$ is Br; R$^5$ is H; Q$^2$ is Ph(2-OCF$_2$CF$_2$H,3-F); and Q$^1$ is
| 1114 Y$^1$ is O; Y$^2$ is O; R$^2$ is H; R$^4$ is Br; R$^5$ is H; Q$^2$ is Ph(2-OCF$_2$CF$_2$H,4-F); and Q$^1$ is
| 1115 Y$^1$ is O; Y$^2$ is O; R$^2$ is H; R$^4$ is Br; R$^5$ is H; Q$^2$ is Ph(2-Br); and Q$^1$ is -continued

| Table Row Heading |
|---|
| 1116 $Y^1$ is O; $Y^2$ is O; $R^2$ is H; $R^4$ is Br; $R^5$ is H; $Q^2$ is Ph(2-Br,3-F); and $Q^1$ is |
| 1117 $Y^1$ is O; $Y^2$ is O; $R^2$ is H; $R^4$ is Br; $R^5$ is H; $Q^2$ is Ph(2-Br,4-F); and $Q^1$ is |
| 1118 $Y^1$ is O; $Y^2$ is O; $R^2$ is H; $R^4$ is Br; $R^5$ is H; $Q^2$ is Ph(2-Br,3,4-di-F); and $Q^1$ is |
| 1119 $Y^1$ is O; $Y^2$ is O; $R^2$ is H; $R^4$ is Br; $R^5$ is H; $Q^2$ is Ph(2-I); and $Q^1$ is |
| 1120 $Y^1$ is O; $Y^2$ is O; $R^2$ is H; $R^4$ is Br; $R^5$ is H; $Q^2$ is Ph(2-I,3-F); and $Q^1$ is |
| 1121 $Y^1$ is O; $Y^2$ is O; $R^2$ is H; $R^4$ is Br; $R^5$ is H; $Q^2$ is Ph(2-I,4-F); and $Q^1$ is |
| 1122 $Y^1$ is O; $Y^2$ is O; $R^2$ is H; $R^4$ is Br; $R^5$ is H; $Q^2$ is Ph(2-I,3,4-di-F); and $Q^1$ is |
| 1123 $Y^1$ is O; $Y^2$ is O; $R^2$ is H; $R^4$ is Br; $R^5$ is H; $Q^2$ is Ph(2-CN); and $Q^1$ is |
| 1124 $Y^1$ is O; $Y^2$ is O; $R^2$ is H; $R^4$ is Br; $R^5$ is H; $Q^2$ is Ph(2-CN,3-Me); and $Q^1$ is |
| 1125 $Y^1$ is O; $Y^2$ is O; $R^2$ is H; $R^4$ is Br; $R^5$ is H; $Q^2$ is Ph(2-CN,3-F); and $Q^1$ is |
| 1126 $Y^1$ is O; $Y^2$ is O; $R^2$ is H; $R^4$ is Br; $R^5$ is H; $Q^2$ is Ph(2-CN,4-F); and $Q^1$ is |
| 1127 $Y^1$ is O; $Y^2$ is O; $R^2$ is H; $R^4$ is Br; $R^5$ is H; $Q^2$ is Ph(2-CN,3-Cl); and $Q^1$ is |
| 1128 $Y^1$ is O; $Y^2$ is O; $R^2$ is H; $R^4$ is Br; $R^5$ is H; $Q^2$ is Ph(2-CN,4-Cl); and $Q^1$ is |
| 1129 $Y^1$ is O; $Y^2$ is O; $R^2$ is H; $R^4$ is Br; $R^5$ is H; $Q^2$ is Ph(2-CN,3,4-di-F); and $Q^1$ is |
| 1130 $Y^1$ is O; $Y^2$ is O; $R^2$ is H; $R^4$ is Br; $R^5$ is H; $Q^2$ is 2-Pyridinyl; and $Q^1$ is |
| 1131 $Y^1$ is O; $Y^2$ is O; $R^2$ is H; $R^4$ is Br; $R^5$ is H; $Q^2$ is 2-Pyridinyl,3-F; and $Q^1$ is |
| 1132 $Y^1$ is O; $Y^2$ is O; $R^2$ is H; $R^4$ is Br; $R^5$ is H; $Q^2$ is 2-Pyridinyl,4-F; and $Q^1$ is |
| 1133 $Y^1$ is O; $Y^2$ is O; $R^2$ is H; $R^4$ is Br; $R^5$ is H; $Q^2$ is 2-Pyridinyl,3,4-di-F; and $Q^1$ is |
| 1134 $Y^1$ is O; $Y^2$ is O; $R^2$ is H; $R^4$ is Br; $R^5$ is H; $Q^2$ is 2-Pyridinyl,3-Cl; and $Q^1$ is |
| 1135 $Y^1$ is O; $Y^2$ is O; $R^2$ is H; $R^4$ is Br; $R^5$ is H; $Q^2$ is 2-Pyridinyl,4-Cl; and $Q^1$ is |
| 1136 $Y^1$ is O; $Y^2$ is O; $R^2$ is H; $R^4$ is Br; $R^5$ is H; $Q^2$ is 2-Pyridinyl,3-Cl,4-F; and $Q^1$ is |
| 1137 $Y^1$ is O; $Y^2$ is O; $R^2$ is H; $R^4$ is Br; $R^5$ is H; $Q^2$ is Ph(2-$SO_2$Me); and $Q^1$ is |
| 1138 $Y^1$ is O; $Y^2$ is O; $R^2$ is H; $R^4$ is Br; $R^5$ is H; $Q^2$ is Ph(2-$SO_2$Me, 3-F); and $Q^1$ is |
| 1139 $Y^1$ is O; $Y^2$ is O; $R^2$ is H; $R^4$ is Br; $R^5$ is H; $Q^2$ is Ph(2-$SO_2$Me, 3-Me); and $Q^1$ is |
| 1140 $Y^1$ is O; $Y^2$ is O; $R^2$ is H; $R^4$ is Br; $R^5$ is H; $Q^2$ is Ph(2-$SO_2$Me, 4-F); and $Q^1$ is |
| 1141 $Y^1$ is O; $Y^2$ is O; $R^2$ is H; $R^4$ is Br; $R^5$ is H; $Q^2$ is Ph(2-$SO_2$Me, 5-F); and $Q^1$ is |
| 1142 $Y^1$ is O; $Y^2$ is O; $R^2$ is H; $R^4$ is Br; $R^5$ is H; $Q^2$ is Ph(2-$SO_2$Me,3,4-di-F); and $Q^1$ is |
| 1143 $Y^1$ is O; $Y^2$ is O; $R^2$ is H; $R^4$ is Br; $R^5$ is H; $Q^2$ is Ph(2-$SO_2$Me, 3-Cl); and $Q^1$ is |
| 1144 $Y^1$ is O; $Y^2$ is O; $R^2$ is H; $R^4$ is Br; $R^5$ is H; $Q^2$ is Ph(2-$SO_2$Me, 4-Cl); and $Q^1$ is |
| 1145 $Y^1$ is O; $Y^2$ is O; $R^2$ is H; $R^4$ is Br; $R^5$ is H; $Q^2$ is Ph(2-$SO_2$Me,3-Cl,4-F); and $Q^1$ is |
| 1146 $Y^1$ is O; $Y^2$ is O; $R^2$ is H; $R^4$ is Br; $R^5$ is H; $Q^2$ is Ph(2-$SO_2NH_2$); and $Q^1$ is |
| 1147 $Y^1$ is O; $Y^2$ is O; $R^2$ is H; $R^4$ is Br; $R^5$ is H; $Q^2$ is Ph(2-$SO_2NH_2$, 3-F); and $Q^1$ is |
| 1148 $Y^1$ is O; $Y^2$ is O; $R^2$ is H; $R^4$ is Br; $R^5$ is H; $Q^2$ is Ph(2-$SO_2NH_2$, 3-Cl); and $Q^1$ is |
| 1149 $Y^1$ is O; $Y^2$ is O; $R^2$ is H; $R^4$ is Br; $R^5$ is H; $Q^2$ is Ph(2-$SO_2NH_2$, 4-F); and $Q^1$ is |
| 1150 $Y^1$ is O; $Y^2$ is O; $R^2$ is H; $R^4$ is Br; $R^5$ is H; $Q^2$ is Ph(2-$SO_2NH_2$, 5-F); and $Q^1$ is |
| 1151 $Y^1$ is O; $Y^2$ is O; $R^2$ is H; $R^4$ is Br; $R^5$ is H; $Q^2$ is Ph(2-$SO_2NH_2$,3,4-di-F); and $Q^1$ is |
| 1152 $Y^1$ is O; $Y^2$ is O; $R^2$ is H; $R^4$ is Br; $R^5$ is H; $Q^2$ is Ph(3-F); and $Q^1$ is |
| 1153 $Y^1$ is O; $Y^2$ is O; $R^2$ is H; $R^4$ is Br; $R^5$ is H; $Q^2$ is Ph(3,4-di-F); and $Q^1$ is |
| 1154 $Y^1$ is O; $Y^2$ is O; $R^2$ is H; $R^4$ is Br; $R^5$ is H; $Q^2$ is Ph(3,5-di-F); and $Q^1$ is |
| 1155 $Y^1$ is O; $Y^2$ is O; $R^2$ is H; $R^4$ is Br; $R^5$ is H; $Q^2$ is Ph(3,4,5-tri-F); and $Q^1$ is |
| 1156 $Y^1$ is O; $Y^2$ is O; $R^2$ is H; $R^4$ is Br; $R^5$ is H; $Q^2$ is Ph(3-F,4-Cl); and $Q^1$ is |
| 1157 $Y^1$ is O; $Y^2$ is O; $R^2$ is H; $R^4$ is Br; $R^5$ is H; $Q^2$ is Ph(3-$CF_3$); and $Q^1$ is |
| 1158 $Y^1$ is O; $Y^2$ is O; $R^2$ is H; $R^4$ is Br; $R^5$ is H; $Q^2$ is Ph(3-$CF_3$,4-F); and $Q^1$ is |
| 1159 $Y^1$ is O; $Y^2$ is O; $R^2$ is H; $R^4$ is Br; $R^5$ is H; $Q^2$ is Ph(3-$CF_3$,4-Cl); and $Q^1$ is |
| 1160 $Y^1$ is O; $Y^2$ is O; $R^2$ is H; $R^4$ is Br; $R^5$ is H; $Q^2$ is Ph(3-$CF_3$,5-F); and $Q^1$ is |
| 1161 $Y^1$ is O; $Y^2$ is O; $R^2$ is H; $R^4$ is Br; $R^5$ is H; $Q^2$ is Ph(3-$CF_3$,4,5-di-F); and $Q^1$ is |
| 1162 $Y^1$ is O; $Y^2$ is O; $R^2$ is H; $R^4$ is Br; $R^5$ is H; $Q^2$ is Ph(3-$SO_2$Me); and $Q^1$ is |
| 1163 $Y^1$ is O; $Y^2$ is O; $R^2$ is H; $R^4$ is Br; $R^5$ is H; $Q^2$ is Ph(3-$SO_2$Me,4-Cl); and $Q^1$ is |
| 1164 $Y^1$ is O; $Y^2$ is O; $R^2$ is H; $R^4$ is Br; $R^5$ is H; $Q^2$ is Ph(3-$SO_2$Me,4-F); and $Q^1$ is |
| 1165 $Y^1$ is O; $Y^2$ is O; $R^2$ is H; $R^4$ is Br; $R^5$ is H; $Q^2$ is Ph(3-$SO_2$Me,4,5-di-F); and $Q^1$ is |
| 1166 $Y^1$ is O; $Y^2$ is O; $R^2$ is H; $R^4$ is Br; $R^5$ is H; $Q^2$ is Ph(3-$SO_2$Me,5-F); and $Q^1$ is |
| 1167 $Y^1$ is O; $Y^2$ is O; $R^2$ is H; $R^4$ is Br; $R^5$ is H; $Q^2$ is Ph(3-$SO_2NH_2$); and $Q^1$ is |
| 1168 $Y^1$ is O; $Y^2$ is O; $R^2$ is H; $R^4$ is Br; $R^5$ is H; $Q^2$ is Ph(3-$SO_2NH_2$,4-F); and $Q^1$ is |
| 1169 $Y^1$ is O; $Y^2$ is O; $R^2$ is H; $R^4$ is Br; $R^5$ is H; $Q^2$ is Ph(3-$SO_2NH_2$,4,5-di-F); and $Q^1$ is |
| 1170 $Y^1$ is O; $Y^2$ is O; $R^2$ is H; $R^4$ is Br; $R^5$ is H; $Q^2$ is Ph(3-$SO_2NH_2$,4-Cl); and $Q^1$ is |
| 1171 $Y^1$ is O; $Y^2$ is O; $R^2$ is H; $R^4$ is Br; $R^5$ is H; $Q^2$ is Ph(3-$SO_2NH_2$,5-F); and $Q^1$ is |
| 1172 $Y^1$ is O; $Y^2$ is O; $R^2$ is H; $R^4$ is Br; $R^5$ is H; $Q^2$ is Ph(3-Me); and $Q^1$ is |
| 1173 $Y^1$ is O; $Y^2$ is O; $R^2$ is H; $R^4$ is Br; $R^5$ is H; $Q^2$ is Ph(3-Me,4-F); and $Q^1$ is |
| 1174 $Y^1$ is O; $Y^2$ is O; $R^2$ is H; $R^4$ is Br; $R^5$ is H; $Q^2$ is Ph(3-Me,4-Cl); and $Q^1$ is |
| 1175 $Y^1$ is O; $Y^2$ is O; $R^2$ is H; $R^4$ is Br; $R^5$ is H; $Q^2$ is Ph(3-Me,5-F); and $Q^1$ is |
| 1176 $Y^1$ is O; $Y^2$ is O; $R^2$ is H; $R^4$ is Br; $R^5$ is H; $Q^2$ is Ph(3-Me,4,5-di-F); and $Q^1$ is |
| 1177 $Y^1$ is O; $Y^2$ is O; $R^2$ is H; $R^4$ is Br; $R^5$ is H; $Q^2$ is Ph(3-Cl); and $Q^1$ is |
| 1178 $Y^1$ is O; $Y^2$ is O; $R^2$ is H; $R^4$ is Br; $R^5$ is H; $Q^2$ is Ph(3-Cl,4-F); and $Q^1$ is |
| 1179 $Y^1$ is O; $Y^2$ is O; $R^2$ is H; $R^4$ is Br; $R^5$ is H; $Q^2$ is Ph(3,4-di-Cl); and $Q^1$ is |
| 1180 $Y^1$ is O; $Y^2$ is O; $R^2$ is H; $R^4$ is Br; $R^5$ is H; $Q^2$ is Ph(3-Cl,5-F); and $Q^1$ is |
| 1181 $Y^1$ is O; $Y^2$ is O; $R^2$ is H; $R^4$ is Br; $R^5$ is H; $Q^2$ is Ph(3-Cl,4,5-di-F); and $Q^1$ is |
| 1182 $Y^1$ is O; $Y^2$ is O; $R^2$ is H; $R^4$ is Br; $R^5$ is H; $Q^2$ is Ph(3,5-di-Cl); and $Q^1$ is |
| 1183 $Y^1$ is O; $Y^2$ is O; $R^2$ is H; $R^4$ is Br; $R^5$ is H; $Q^2$ is Ph(4-F); and $Q^1$ is |
| 1184 $Y^1$ is O; $Y^2$ is O; $R^2$ is H; $R^4$ is Br; $R^5$ is H; $Q^2$ is Ph(4-Cl); and $Q^1$ is |
| 1185 $Y^1$ is O; $Y^2$ is O; $R^2$ is H; $R^4$ is Br; $R^5$ is H; $Q^2$ is 2,2-di-F-1,3-benzodioxol-4-yl; and $Q^1$ is |
| 1186 $Y^1$ is O; $Y^2$ is O; $R^2$ is H; $R^4$ is Br; $R^5$ is H; $Q^2$ is 2,2-di-F-1,3-benzodioxol-5-yl; and $Q^1$ is |
| 1187 $Y^1$ is O; $Y^2$ is O; $R^2$ is H; $R^4$ is Br; $R^5$ is H; $Q^2$ is 2,2-di-Me-1,3-benzodioxol-4-yl; and $Q^1$ is |
| 1188 $Y^1$ is O; $Y^2$ is O; $R^2$ is H; $R^4$ is Br; $R^5$ is H; $Q^2$ is 2,2-di-Me-1,3-benzodioxol-5-yl; and $Q^1$ is |
| 1189 $Y^1$ is O; $Y^2$ is O; $R^2$ is H; $R^4$ is Br; $R^5$ is H; $Q^2$ is 1,3-benzodioxol-4-yl; and $Q^1$ is |
| 1190 $Y^1$ is O; $Y^2$ is O; $R^2$ is H; $R^4$ is Br; $R^5$ is H; $Q^2$ is 1,3-benzodioxol-5-yl; and $Q^1$ is |
| 1191 $Y^1$ is O; $Y^2$ is O; $R^2$ is H; $R^4$ is Cl; $R^5$ is H; $Q^2$ is Ph(2-F); and $Q^1$ is |
| 1192 $Y^1$ is O; $Y^2$ is O; $R^2$ is H; $R^4$ is Cl; $R^5$ is H; $Q^2$ is Ph(2,3-di-F); and $Q^1$ is |

-continued

| Table Row Heading |
|---|
| 1193 $Y^1$ is O; $Y^2$ is O; $R^2$ is H; $R^4$ is Cl; $R^5$ is H; $Q^2$ is Ph(2,4-di-F); and $Q^1$ is |
| 1194 $Y^1$ is O; $Y^2$ is O; $R^2$ is H; $R^4$ is Cl; $R^5$ is H; $Q^2$ is Ph(2,5-di-F); and $Q^1$ is |
| 1195 $Y^1$ is O; $Y^2$ is O; $R^2$ is H; $R^4$ is Cl; $R^5$ is H; $Q^2$ is Ph(2,3,4-tri-F); and $Q^1$ is |
| 1196 $Y^1$ is O; $Y^2$ is O; $R^2$ is H; $R^4$ is Cl; $R^5$ is H; $Q^2$ is Ph(2,3,5-tri-F); and $Q^1$ is |
| 1197 $Y^1$ is O; $Y^2$ is O; $R^2$ is H; $R^4$ is Cl; $R^5$ is H; $Q^2$ is Ph(2,3,4,5-tetra-F); and $Q^1$ is |
| 1198 $Y^1$ is O; $Y^2$ is O; $R^2$ is H; $R^4$ is Cl; $R^5$ is H; $Q^2$ is Ph(2-F,3-Cl,4-Br); and $Q^1$ is |
| 1199 $Y^1$ is O; $Y^2$ is O; $R^2$ is H; $R^4$ is Cl; $R^5$ is H; $Q^2$ is Ph(2-F,3-Cl,4-F); and $Q^1$ is |
| 1200 $Y^1$ is O; $Y^2$ is O; $R^2$ is H; $R^4$ is Cl; $R^5$ is H; $Q^2$ is Ph(2-F,3-Br,4-F); and $Q^1$ is |
| 1201 $Y^1$ is O; $Y^2$ is O; $R^2$ is H; $R^4$ is Cl; $R^5$ is H; $Q^2$ is Ph(2-F,3-Me); and $Q^1$ is |
| 1202 $Y^1$ is O; $Y^2$ is O; $R^2$ is H; $R^4$ is Cl; $R^5$ is H; $Q^2$ is Ph(2-F,3-Me,4-F); and $Q^1$ is |
| 1203 $Y^1$ is O; $Y^2$ is O; $R^2$ is H; $R^4$ is Cl; $R^5$ is H; $Q^2$ is Ph(2-F,3-Me,4-Cl); and $Q^1$ is |
| 1204 $Y^1$ is O; $Y^2$ is O; $R^2$ is H; $R^4$ is Cl; $R^5$ is H; $Q^2$ is Ph(2-F,3-Cl); and $Q^1$ is |
| 1205 $Y^1$ is O; $Y^2$ is O; $R^2$ is H; $R^4$ is Cl; $R^5$ is H; $Q^2$ is Ph(2-F,4-Cl); and $Q^1$ is |
| 1206 $Y^1$ is O; $Y^2$ is O; $R^2$ is H; $R^4$ is Cl; $R^5$ is H; $Q^2$ is Ph(2-F,3,4-di-Cl); and $Q^1$ is |
| 1207 $Y^1$ is O; $Y^2$ is O; $R^2$ is H; $R^4$ is Cl; $R^5$ is H; $Q^2$ is Ph(2-F,4-Br); and $Q^1$ is |
| 1208 $Y^1$ is O; $Y^2$ is O; $R^2$ is H; $R^4$ is Cl; $R^5$ is H; $Q^2$ is Ph(2-F,3-OMe); and $Q^1$ is |
| 1209 $Y^1$ is O; $Y^2$ is O; $R^2$ is H; $R^4$ is Cl; $R^5$ is H; $Q^2$ is Ph(2-F,3-OMe,4-F); and $Q^1$ is |
| 1210 $Y^1$ is O; $Y^2$ is O; $R^2$ is H; $R^4$ is Cl; $R^5$ is H; $Q^2$ is Ph(2-F,3-OMe,4-Cl); and $Q^1$ is |
| 1211 $Y^1$ is O; $Y^2$ is O; $R^2$ is H; $R^4$ is Cl; $R^5$ is H; $Q^2$ is Ph(2-F,3-CF$_2$H); and $Q^1$ is |
| 1212 $Y^1$ is O; $Y^2$ is O; $R^2$ is H; $R^4$ is Cl; $R^5$ is H; $Q^2$ is Ph(2-F,3-CF$_3$); and $Q^1$ is |
| 1213 $Y^1$ is O; $Y^2$ is O; $R^2$ is H; $R^4$ is Cl; $R^5$ is H; $Q^2$ is Ph(2-F,3-CF$_3$,4-F); and $Q^1$ is |
| 1214 $Y^1$ is O; $Y^2$ is O; $R^2$ is H; $R^4$ is Cl; $R^5$ is H; $Q^2$ is Ph(2-F,3-NO$_2$); and $Q^1$ is |
| 1215 $Y^1$ is O; $Y^2$ is O; $R^2$ is H; $R^4$ is Cl; $R^5$ is H; $Q^2$ is Ph(2-F,3-NO$_2$,4-F); and $Q^1$ is |
| 1216 $Y^1$ is O; $Y^2$ is O; $R^2$ is H; $R^4$ is Cl; $R^5$ is H; $Q^2$ is Ph(2-F,3-SO$_2$Me); and $Q^1$ is |
| 1217 $Y^1$ is O; $Y^2$ is O; $R^2$ is H; $R^4$ is Cl; $R^5$ is H; $Q^2$ is Ph(2-F,3-SO$_2$Me,4-F); and $Q^1$ is |
| 1218 $Y^1$ is O; $Y^2$ is O; $R^2$ is H; $R^4$ is Cl; $R^5$ is H; $Q^2$ is Ph(2-CF$_3$); and $Q^1$ is |
| 1219 $Y^1$ is O; $Y^2$ is O; $R^2$ is H; $R^4$ is Cl; $R^5$ is H; $Q^2$ is Ph(2-CF$_3$,3-F); and $Q^1$ is |
| 1220 $Y^1$ is O; $Y^2$ is O; $R^2$ is H; $R^4$ is Cl; $R^5$ is H; $Q^2$ is Ph(2-CF$_3$,3-Me); and $Q^1$ is |
| 1221 $Y^1$ is O; $Y^2$ is O; $R^2$ is H; $R^4$ is Cl; $R^5$ is H; $Q^2$ is Ph(2-CF$_3$,4-F); and $Q^1$ is |
| 1222 $Y^1$ is O; $Y^2$ is O; $R^2$ is H; $R^4$ is Cl; $R^5$ is H; $Q^2$ is Ph(2-CF$_3$,3-Cl); and $Q^1$ is |
| 1223 $Y^1$ is O; $Y^2$ is O; $R^2$ is H; $R^4$ is Cl; $R^5$ is H; $Q^2$ is Ph(2-CF$_3$,4-Cl); and $Q^1$ is |
| 1224 $Y^1$ is O; $Y^2$ is O; $R^2$ is H; $R^4$ is Cl; $R^5$ is H; $Q^2$ is Ph(2-CF$_3$,3,4-di-F); and $Q^1$ is |
| 1225 $Y^1$ is O; $Y^2$ is O; $R^2$ is H; $R^4$ is Cl; $R^5$ is H; $Q^2$ is Ph(2-CF$_2$H); and $Q^1$ is |
| 1226 $Y^1$ is O; $Y^2$ is O; $R^2$ is H; $R^4$ is Cl; $R^5$ is H; $Q^2$ is Ph(2-CF$_2$H,3-F); and $Q^1$ is |
| 1227 $Y^1$ is O; $Y^2$ is O; $R^2$ is H; $R^4$ is Cl; $R^5$ is H; $Q^2$ is Ph(2-CF$_2$H,3-Me); and $Q^1$ is |
| 1228 $Y^1$ is O; $Y^2$ is O; $R^2$ is H; $R^4$ is Cl; $R^5$ is H; $Q^2$ is Ph(2-CF$_2$H,4-F); and $Q^1$ is |
| 1229 $Y^1$ is O; $Y^2$ is O; $R^2$ is H; $R^4$ is Cl; $R^5$ is H; $Q^2$ is Ph(2-CF$_2$H,3-Cl); and $Q^1$ is |
| 1230 $Y^1$ is O; $Y^2$ is O; $R^2$ is H; $R^4$ is Cl; $R^5$ is H; $Q^2$ is Ph(2-CF$_2$H,4-Cl); and $Q^1$ is |
| 1231 $Y^1$ is O; $Y^2$ is O; $R^2$ is H; $R^4$ is Cl; $R^5$ is H; $Q^2$ is Ph(2-CF$_2$H,3,4-di-F); and $Q^1$ is |
| 1232 $Y^1$ is O; $Y^2$ is O; $R^2$ is H; $R^4$ is Cl; $R^5$ is H; $Q^2$ is Ph(2-Me); and $Q^1$ is |
| 1233 $Y^1$ is O; $Y^2$ is O; $R^2$ is H; $R^4$ is Cl; $R^5$ is H; $Q^2$ is Ph(2,3-di-Me); and $Q^1$ is |
| 1234 $Y^1$ is O; $Y^2$ is O; $R^2$ is H; $R^4$ is Cl; $R^5$ is H; $Q^2$ is Ph(2-Me,3-F); and $Q^1$ is |
| 1235 $Y^1$ is O; $Y^2$ is O; $R^2$ is H; $R^4$ is Cl; $R^5$ is H; $Q^2$ is Ph(2-Me,3-Cl); and $Q^1$ is |
| 1236 $Y^1$ is O; $Y^2$ is O; $R^2$ is H; $R^4$ is Cl; $R^5$ is H; $Q^2$ is Ph(2-Me,3-CF$_3$); and $Q^1$ is |
| 1237 $Y^1$ is O; $Y^2$ is O; $R^2$ is H; $R^4$ is Cl; $R^5$ is H; $Q^2$ is Ph(2-Me,3,4-di-Cl); and $Q^1$ is |
| 1238 $Y^1$ is O; $Y^2$ is O; $R^2$ is H; $R^4$ is Cl; $R^5$ is H; $Q^2$ is Ph(2-Me,3-Cl,4-F); and $Q^1$ is |
| 1239 $Y^1$ is O; $Y^2$ is O; $R^2$ is H; $R^4$ is Cl; $R^5$ is H; $Q^2$ is Ph(2-Me,4-Cl); and $Q^1$ is |
| 1240 $Y^1$ is O; $Y^2$ is O; $R^2$ is H; $R^4$ is Cl; $R^5$ is H; $Q^2$ is Ph(2-Me,4-F); and $Q^1$ is |
| 1241 $Y^1$ is O; $Y^2$ is O; $R^2$ is H; $R^4$ is Cl; $R^5$ is H; $Q^2$ is Ph(2-Me,5-F); and $Q^1$ is |
| 1242 $Y^1$ is O; $Y^2$ is O; $R^2$ is H; $R^4$ is Cl; $R^5$ is H; $Q^2$ is Ph(2-Me,3,4-di-F); and $Q^1$ is |
| 1243 $Y^1$ is O; $Y^2$ is O; $R^2$ is H; $R^4$ is Cl; $R^5$ is H; $Q^2$ is Ph(2-Me,3,5-di-F); and $Q^1$ is |
| 1244 $Y^1$ is O; $Y^2$ is O; $R^2$ is H; $R^4$ is Cl; $R^5$ is H; $Q^2$ is Ph(2-Et); and $Q^1$ is |
| 1245 $Y^1$ is O; $Y^2$ is O; $R^2$ is H; $R^4$ is Cl; $R^5$ is H; $Q^2$ is Ph(2-Et,3-F); and $Q^1$ is |
| 1246 $Y^1$ is O; $Y^2$ is O; $R^2$ is H; $R^4$ is Cl; $R^5$ is H; $Q^2$ is Ph(2-Et,3-Cl); and $Q^1$ is |
| 1247 $Y^1$ is O; $Y^2$ is O; $R^2$ is H; $R^4$ is Cl; $R^5$ is H; $Q^2$ is Ph(2-Et,4-F); and $Q^1$ is |
| 1248 $Y^1$ is O; $Y^2$ is O; $R^2$ is H; $R^4$ is Cl; $R^5$ is H; $Q^2$ is Ph(2-Et,3,4-di-F); and $Q^1$ is |
| 1249 $Y^1$ is O; $Y^2$ is O; $R^2$ is H; $R^4$ is Cl; $R^5$ is H; $Q^2$ is Ph(2-i-Pr); and $Q^1$ is |
| 1250 $Y^1$ is O; $Y^2$ is O; $R^2$ is H; $R^4$ is Cl; $R^5$ is H; $Q^2$ is Ph(2-i-Pr,3-F); and $Q^1$ is |
| 1251 $Y^1$ is O; $Y^2$ is O; $R^2$ is H; $R^4$ is Cl; $R^5$ is H; $Q^2$ is Ph(2-i-Pr,3-Cl); and $Q^1$ is |
| 1252 $Y^1$ is O; $Y^2$ is O; $R^2$ is H; $R^4$ is Cl; $R^5$ is H; $Q^2$ is Ph(2-i-Pr,4-F); and $Q^1$ is |
| 1253 $Y^1$ is O; $Y^2$ is O; $R^2$ is H; $R^4$ is Cl; $R^5$ is H; $Q^2$ is Ph(2-i-Pr,3,4-di-F); and $Q^1$ is |
| 1254 $Y^1$ is O; $Y^2$ is O; $R^2$ is H; $R^4$ is Cl; $R^5$ is H; $Q^2$ is Ph(2-c-Pr); and $Q^1$ is |
| 1255 $Y^1$ is O; $Y^2$ is O; $R^2$ is H; $R^4$ is Cl; $R^5$ is H; $Q^2$ is Ph(2-c-Pr,3-F); and $Q^1$ is |
| 1256 $Y^1$ is O; $Y^2$ is O; $R^2$ is H; $R^4$ is Cl; $R^5$ is H; $Q^2$ is Ph(2-c-Pr,3-Cl); and $Q^1$ is |
| 1257 $Y^1$ is O; $Y^2$ is O; $R^2$ is H; $R^4$ is Cl; $R^5$ is H; $Q^2$ is Ph(2-c-Pr,4-F); and $Q^1$ is |
| 1258 $Y^1$ is O; $Y^2$ is O; $R^2$ is H; $R^4$ is Cl; $R^5$ is H; $Q^2$ is Ph(2-c-Pr,3,4-di-F); and $Q^1$ is |
| 1259 $Y^1$ is O; $Y^2$ is O; $R^2$ is H; $R^4$ is Cl; $R^5$ is H; $Q^2$ is Ph(2-NO$_2$); and $Q^1$ is |
| 1260 $Y^1$ is O; $Y^2$ is O; $R^2$ is H; $R^4$ is Cl; $R^5$ is H; $Q^2$ is Ph(2-NO$_2$,3-F); and $Q^1$ is |
| 1261 $Y^1$ is O; $Y^2$ is O; $R^2$ is H; $R^4$ is Cl; $R^5$ is H; $Q^2$ is Ph(2-NO$_2$,3-Cl); and $Q^1$ is |
| 1262 $Y^1$ is O; $Y^2$ is O; $R^2$ is H; $R^4$ is Cl; $R^5$ is H; $Q^2$ is Ph(2-NO$_2$,4-F); and $Q^1$ is |
| 1263 $Y^1$ is O; $Y^2$ is O; $R^2$ is H; $R^4$ is Cl; $R^5$ is H; $Q^2$ is Ph(2-NO$_2$,3,4-di-F); and $Q^1$ is |
| 1264 $Y^1$ is O; $Y^2$ is O; $R^2$ is H; $R^4$ is Cl; $R^5$ is H; $Q^2$ is Ph(2-OCF$_3$); and $Q^1$ is |
| 1265 $Y^1$ is O; $Y^2$ is O; $R^2$ is H; $R^4$ is Cl; $R^5$ is H; $Q^2$ is Ph(2-OCF$_3$,3-F); and $Q^1$ is |
| 1266 $Y^1$ is O; $Y^2$ is O; $R^2$ is H; $R^4$ is Cl; $R^5$ is H; $Q^2$ is Ph(2-OCF$_3$,4-F); and $Q^1$ is |
| 1267 $Y^1$ is O; $Y^2$ is O; $R^2$ is H; $R^4$ is Cl; $R^5$ is H; $Q^2$ is Ph(2-Cl); and $Q^1$ is |
| 1268 $Y^1$ is O; $Y^2$ is O; $R^2$ is H; $R^4$ is Cl; $R^5$ is H; $Q^2$ is Ph(2-Cl,3-Me); and $Q^1$ is |
| 1269 $Y^1$ is O; $Y^2$ is O; $R^2$ is H; $R^4$ is Cl; $R^5$ is H; $Q^2$ is Ph(2-Cl,3-Me,4-F); and $Q^1$ is |

-continued

| Table Row Heading |
|---|
| 1270 $Y^1$ is O; $Y^2$ is O; $R^2$ is H; $R^4$ is Cl; $R^5$ is H; $Q^2$ is Ph(2,3-di-Cl); and $Q^1$ is |
| 1271 $Y^1$ is O; $Y^2$ is O; $R^2$ is H; $R^4$ is Cl; $R^5$ is H; $Q^2$ is Ph(2,4-di-Cl); and $Q^1$ is |
| 1272 $Y^1$ is O; $Y^2$ is O; $R^2$ is H; $R^4$ is Cl; $R^5$ is H; $Q^2$ is Ph(2-Cl,3-F); and $Q^1$ is |
| 1273 $Y^1$ is O; $Y^2$ is O; $R^2$ is H; $R^4$ is Cl; $R^5$ is H; $Q^2$ is Ph(2-Cl,4-F); and $Q^1$ is |
| 1274 $Y^1$ is O; $Y^2$ is O; $R^2$ is H; $R^4$ is Cl; $R^5$ is H; $Q^2$ is Ph(2-Cl,5-F); and $Q^1$ is |
| 1275 $Y^1$ is O; $Y^2$ is O; $R^2$ is H; $R^4$ is Cl; $R^5$ is H; $Q^2$ is Ph(2-Cl,3,4-di-F); and $Q^1$ is |
| 1276 $Y^1$ is O; $Y^2$ is O; $R^2$ is H; $R^4$ is Cl; $R^5$ is H; $Q^2$ is Ph(2-Cl,3,5-di-F); and $Q^1$ is |
| 1277 $Y^1$ is O; $Y^2$ is O; $R^2$ is H; $R^4$ is Cl; $R^5$ is H; $Q^2$ is Ph(2-OCF$_2$H); and $Q^1$ is |
| 1278 $Y^1$ is O; $Y^2$ is O; $R^2$ is H; $R^4$ is Cl; $R^5$ is H; $Q^2$ is Ph(2-OCF$_2$H,3-Me); and $Q^1$ is |
| 1279 $Y^1$ is O; $Y^2$ is O; $R^2$ is H; $R^4$ is Cl; $R^5$ is H; $Q^2$ is Ph(2-OCF$_2$H,3-Cl); and $Q^1$ is |
| 1280 $Y^1$ is O; $Y^2$ is O; $R^2$ is H; $R^4$ is Cl; $R^5$ is H; $Q^2$ is Ph(2-OCF$_2$H,3-F); and $Q^1$ is |
| 1281 $Y^1$ is O; $Y^2$ is O; $R^2$ is H; $R^4$ is Cl; $R^5$ is H; $Q^2$ is Ph(2-OCF$_2$H,4-F); and $Q^1$ is |
| 1282 $Y^1$ is O; $Y^2$ is O; $R^2$ is H; $R^4$ is Cl; $R^5$ is H; $Q^2$ is Ph(2-OCF$_2$CF$_2$H); and $Q^1$ is |
| 1283 $Y^1$ is O; $Y^2$ is O; $R^2$ is H; $R^4$ is Cl; $R^5$ is H; $Q^2$ is Ph(2-OCF$_2$CF$_2$H,3-F); and $Q^1$ is |
| 1284 $Y^1$ is O; $Y^2$ is O; $R^2$ is H; $R^4$ is Cl; $R^5$ is H; $Q^2$ is Ph(2-OCF$_2$CF$_2$H,4-F); and $Q^1$ is |
| 1285 $Y^1$ is O; $Y^2$ is O; $R^2$ is H; $R^4$ is Cl; $R^5$ is H; $Q^2$ is Ph(2-Br); and $Q^1$ is |
| 1286 $Y^1$ is O; $Y^2$ is O; $R^2$ is H; $R^4$ is Cl; $R^5$ is H; $Q^2$ is Ph(2-Br,3-F); and $Q^1$ is |
| 1287 $Y^1$ is O; $Y^2$ is O; $R^2$ is H; $R^4$ is Cl; $R^5$ is H; $Q^2$ is Ph(2-Br,4-F); and $Q^1$ is |
| 1288 $Y^1$ is O; $Y^2$ is O; $R^2$ is H; $R^4$ is Cl; $R^5$ is H; $Q^2$ is Ph(2-Br,3,4-di-F); and $Q^1$ is |
| 1289 $Y^1$ is O; $Y^2$ is O; $R^2$ is H; $R^4$ is Cl; $R^5$ is H; $Q^2$ is Ph(2-I); and $Q^1$ is |
| 1290 $Y^1$ is O; $Y^2$ is O; $R^2$ is H; $R^4$ is Cl; $R^5$ is H; $Q^2$ is Ph(2-I,3-F); and $Q^1$ is |
| 1291 $Y^1$ is O; $Y^2$ is O; $R^2$ is H; $R^4$ is Cl; $R^5$ is H; $Q^2$ is Ph(2-I,4-F); and $Q^1$ is |
| 1292 $Y^1$ is O; $Y^2$ is O; $R^2$ is H; $R^4$ is Cl; $R^5$ is H; $Q^2$ is Ph(2-I,3,4-di-F); and $Q^1$ is |
| 1293 $Y^1$ is O; $Y^2$ is O; $R^2$ is H; $R^4$ is Cl; $R^5$ is H; $Q^2$ is Ph(2-CN); and $Q^1$ is |
| 1294 $Y^1$ is O; $Y^2$ is O; $R^2$ is H; $R^4$ is Cl; $R^5$ is H; $Q^2$ is Ph(2-CN,3-Me); and $Q^1$ is |
| 1295 $Y^1$ is O; $Y^2$ is O; $R^2$ is H; $R^4$ is Cl; $R^5$ is H; $Q^2$ is Ph(2-CN,3-F); and $Q^1$ is |
| 1296 $Y^1$ is O; $Y^2$ is O; $R^2$ is H; $R^4$ is Cl; $R^5$ is H; $Q^2$ is Ph(2-CN,4-F); and $Q^1$ is |
| 1297 $Y^1$ is O; $Y^2$ is O; $R^2$ is H; $R^4$ is Cl; $R^5$ is H; $Q^2$ is Ph(2-CN,3-Cl); and $Q^1$ is |
| 1298 $Y^1$ is O; $Y^2$ is O; $R^2$ is H; $R^4$ is Cl; $R^5$ is H; $Q^2$ is Ph(2-CN,4-Cl); and $Q^1$ is |
| 1299 $Y^1$ is O; $Y^2$ is O; $R^2$ is H; $R^4$ is Cl; $R^5$ is H; $Q^2$ is Ph(2-CN,3,4-di-F); and $Q^1$ is |
| 1300 $Y^1$ is O; $Y^2$ is O; $R^2$ is H; $R^4$ is Cl; $R^5$ is H; $Q^2$ is 2-Pyridinyl; and $Q^1$ is |
| 1301 $Y^1$ is O; $Y^2$ is O; $R^2$ is H; $R^4$ is Cl; $R^5$ is H; $Q^2$ is 2-Pyridinyl,3-F; and $Q^1$ is |
| 1302 $Y^1$ is O; $Y^2$ is O; $R^2$ is H; $R^4$ is Cl; $R^5$ is H; $Q^2$ is 2-Pyridinyl,4-F; and $Q^1$ is |
| 1303 $Y^1$ is O; $Y^2$ is O; $R^2$ is H; $R^4$ is Cl; $R^5$ is H; $Q^2$ is 2-Pyridinyl,3,4-di-F; and $Q^1$ is |
| 1304 $Y^1$ is O; $Y^2$ is O; $R^2$ is H; $R^4$ is Cl; $R^5$ is H; $Q^2$ is 2-Pyridinyl,3-Cl; and $Q^1$ is |
| 1305 $Y^1$ is O; $Y^2$ is O; $R^2$ is H; $R^4$ is Cl; $R^5$ is H; $Q^2$ is 2-Pyridinyl,4-Cl; and $Q^1$ is |
| 1306 $Y^1$ is O; $Y^2$ is O; $R^2$ is H; $R^4$ is Cl; $R^5$ is H; $Q^2$ is 2-Pyridinyl,3-Cl,4-F; and $Q^1$ is |
| 1307 $Y^1$ is O; $Y^2$ is O; $R^2$ is H; $R^4$ is Cl; $R^5$ is H; $Q^2$ is Ph(2-SO$_2$Me); and $Q^1$ is |
| 1308 $Y^1$ is O; $Y^2$ is O; $R^2$ is H; $R^4$ is Cl; $R^5$ is H; $Q^2$ is Ph(2-SO$_2$Me, 3-F); and $Q^1$ is |
| 1309 $Y^1$ is O; $Y^2$ is O; $R^2$ is H; $R^4$ is Cl; $R^5$ is H; $Q^2$ is Ph(2-SO$_2$Me, 3-Me); and $Q^1$ is |
| 1310 $Y^1$ is O; $Y^2$ is O; $R^2$ is H; $R^4$ is Cl; $R^5$ is H; $Q^2$ is Ph(2-SO$_2$Me, 4-F); and $Q^1$ is |
| 1311 $Y^1$ is O; $Y^2$ is O; $R^2$ is H; $R^4$ is Cl; $R^5$ is H; $Q^2$ is Ph(2-SO$_2$Me, 5-F); and $Q^1$ is |
| 1312 $Y^1$ is O; $Y^2$ is O; $R^2$ is H; $R^4$ is Cl; $R^5$ is H; $Q^2$ is Ph(2-SO$_2$Me,3,4-di-F); and $Q^1$ is |
| 1313 $Y^1$ is O; $Y^2$ is O; $R^2$ is H; $R^4$ is Cl; $R^5$ is H; $Q^2$ is Ph(2-SO$_2$Me, 3-Cl); and $Q^1$ is |
| 1314 $Y^1$ is O; $Y^2$ is O; $R^2$ is H; $R^4$ is Cl; $R^5$ is H; $Q^2$ is Ph(2-SO$_2$Me, 4-Cl); and $Q^1$ is |
| 1315 $Y^1$ is O; $Y^2$ is O; $R^2$ is H; $R^4$ is Cl; $R^5$ is H; $Q^2$ is Ph(2-SO$_2$Me,3-Cl,4-F); and $Q^1$ is |
| 1316 $Y^1$ is O; $Y^2$ is O; $R^2$ is H; $R^4$ is Cl; $R^5$ is H; $Q^2$ is Ph(2-SO$_2$NH$_2$); and $Q^1$ is |
| 1317 $Y^1$ is O; $Y^2$ is O; $R^2$ is H; $R^4$ is Cl; $R^5$ is H; $Q^2$ is Ph(2-SO$_2$NH$_2$, 3-F); and $Q^1$ is |
| 1318 $Y^1$ is O; $Y^2$ is O; $R^2$ is H; $R^4$ is Cl; $R^5$ is H; $Q^2$ is Ph(2-SO$_2$NH$_2$, 3-Cl); and $Q^1$ is |
| 1319 $Y^1$ is O; $Y^2$ is O; $R^2$ is H; $R^4$ is Cl; $R^5$ is H; $Q^2$ is Ph(2-SO$_2$NH$_2$, 4-F); and $Q^1$ is |
| 1320 $Y^1$ is O; $Y^2$ is O; $R^2$ is H; $R^4$ is Cl; $R^5$ is H; $Q^2$ is Ph(2-SO$_2$NH$_2$, 5-F); and $Q^1$ is |
| 1321 $Y^1$ is O; $Y^2$ is O; $R^2$ is H; $R^4$ is Cl; $R^5$ is H; $Q^2$ is Ph(2-SO$_2$NH$_2$,3,4-di-F); and $Q^1$ is |
| 1322 $Y^1$ is O; $Y^2$ is O; $R^2$ is H; $R^4$ is Cl; $R^5$ is H; $Q^2$ is Ph(3-F); and $Q^1$ is |
| 1323 $Y^1$ is O; $Y^2$ is O; $R^2$ is H; $R^4$ is Cl; $R^5$ is H; $Q^2$ is Ph(3,4-di-F); and $Q^1$ is |
| 1324 $Y^1$ is O; $Y^2$ is O; $R^2$ is H; $R^4$ is Cl; $R^5$ is H; $Q^2$ is Ph(3,5-di-F); and $Q^1$ is |
| 1325 $Y^1$ is O; $Y^2$ is O; $R^2$ is H; $R^4$ is Cl; $R^5$ is H; $Q^2$ is Ph(3,4,5-tri-F); and $Q^1$ is |
| 1326 $Y^1$ is O; $Y^2$ is O; $R^2$ is H; $R^4$ is Cl; $R^5$ is H; $Q^2$ is Ph(3-F,4-Cl); and $Q^1$ is |
| 1327 $Y^1$ is O; $Y^2$ is O; $R^2$ is H; $R^4$ is Cl; $R^5$ is H; $Q^2$ is Ph(3-CF$_3$); and $Q^1$ is |
| 1328 $Y^1$ is O; $Y^2$ is O; $R^2$ is H; $R^4$ is Cl; $R^5$ is H; $Q^2$ is Ph(3-CF$_3$,4-F); and $Q^1$ is |
| 1329 $Y^1$ is O; $Y^2$ is O; $R^2$ is H; $R^4$ is Cl; $R^5$ is H; $Q^2$ is Ph(3-CF$_3$,4-Cl); and $Q^1$ is |
| 1330 $Y^1$ is O; $Y^2$ is O; $R^2$ is H; $R^4$ is Cl; $R^5$ is H; $Q^2$ is Ph(3-CF$_3$,5-F); and $Q^1$ is |
| 1331 $Y^1$ is O; $Y^2$ is O; $R^2$ is H; $R^4$ is Cl; $R^5$ is H; $Q^2$ is Ph(3-CF$_3$,4,5-di-F); and $Q^1$ is |
| 1332 $Y^1$ is O; $Y^2$ is O; $R^2$ is H; $R^4$ is Cl; $R^5$ is H; $Q^2$ is Ph(3-SO$_2$Me); and $Q^1$ is |
| 1333 $Y^1$ is O; $Y^2$ is O; $R^2$ is H; $R^4$ is Cl; $R^5$ is H; $Q^2$ is Ph(3-SO$_2$Me,4-Cl); and $Q^1$ is |
| 1334 $Y^1$ is O; $Y^2$ is O; $R^2$ is H; $R^4$ is Cl; $R^5$ is H; $Q^2$ is Ph(3-SO$_2$Me,4-F); and $Q^1$ is |
| 1335 $Y^1$ is O; $Y^2$ is O; $R^2$ is H; $R^4$ is Cl; $R^5$ is H; $Q^2$ is Ph(3-SO$_2$Me,4,5-di-F); and $Q^1$ is |
| 1336 $Y^1$ is O; $Y^2$ is O; $R^2$ is H; $R^4$ is Cl; $R^5$ is H; $Q^2$ is Ph(3-SO$_2$Me,5-F); and $Q^1$ is |
| 1337 $Y^1$ is O; $Y^2$ is O; $R^2$ is H; $R^4$ is Cl; $R^5$ is H; $Q^2$ is Ph(3-SO$_2$NH$_2$); and $Q^1$ is |
| 1338 $Y^1$ is O; $Y^2$ is O; $R^2$ is H; $R^4$ is Cl; $R^5$ is H; $Q^2$ is Ph(3-SO$_2$NH$_2$,4-F); and $Q^1$ is |
| 1339 $Y^1$ is O; $Y^2$ is O; $R^2$ is H; $R^4$ is Cl; $R^5$ is H; $Q^2$ is Ph(3-SO$_2$NH$_2$,4,5-di-F); and $Q^1$ is |
| 1340 $Y^1$ is O; $Y^2$ is O; $R^2$ is H; $R^4$ is Cl; $R^5$ is H; $Q^2$ is Ph(3-SO$_2$NH$_2$,4-Cl); and $Q^1$ is |
| 1341 $Y^1$ is O; $Y^2$ is O; $R^2$ is H; $R^4$ is Cl; $R^5$ is H; $Q^2$ is Ph(3-SO$_2$NH$_2$,5-F); and $Q^1$ is |
| 1342 $Y^1$ is O; $Y^2$ is O; $R^2$ is H; $R^4$ is Cl; $R^5$ is H; $Q^2$ is Ph(3-Me); and $Q^1$ is |
| 1343 $Y^1$ is O; $Y^2$ is O; $R^2$ is H; $R^4$ is Cl; $R^5$ is H; $Q^2$ is Ph(3-Me,4-F); and $Q^1$ is |
| 1344 $Y^1$ is O; $Y^2$ is O; $R^2$ is H; $R^4$ is Cl; $R^5$ is H; $Q^2$ is Ph(3-Me,4-Cl); and $Q^1$ is |
| 1345 $Y^1$ is O; $Y^2$ is O; $R^2$ is H; $R^4$ is Cl; $R^5$ is H; $Q^2$ is Ph(3-Me,5-F); and $Q^1$ is |
| 1346 $Y^1$ is O; $Y^2$ is O; $R^2$ is H; $R^4$ is Cl; $R^5$ is H; $Q^2$ is Ph(3-Me,4,5-di-F); and $Q^1$ is |

| Table Row Heading |
|---|
| 1347 $Y^1$ is O; $Y^2$ is O; $R^2$ is H; $R^4$ is Cl; $R^5$ is H; $Q^2$ is Ph(3-Cl); and $Q^1$ is |
| 1348 $Y^1$ is O; $Y^2$ is O; $R^2$ is H; $R^4$ is Cl; $R^5$ is H; $Q^2$ is Ph(3-Cl,4-F); and $Q^1$ is |
| 1349 $Y^1$ is O; $Y^2$ is O; $R^2$ is H; $R^4$ is Cl; $R^5$ is H; $Q^2$ is Ph(3,4-di-Cl); and $Q^1$ is |
| 1350 $Y^1$ is O; $Y^2$ is O; $R^2$ is H; $R^4$ is Cl; $R^5$ is H; $Q^2$ is Ph(3-Cl,5-F); and $Q^1$ is |
| 1351 $Y^1$ is O; $Y^2$ is O; $R^2$ is H; $R^4$ is Cl; $R^5$ is H; $Q^2$ is Ph(3-Cl,4,5-di-F); and $Q^1$ is |
| 1352 $Y^1$ is O; $Y^2$ is O; $R^2$ is H; $R^4$ is Cl; $R^5$ is H; $Q^2$ is Ph(3,5-di-Cl); and $Q^1$ is |
| 1353 $Y^1$ is O; $Y^2$ is O; $R^2$ is H; $R^4$ is Cl; $R^5$ is H; $Q^2$ is Ph(4-F); and $Q^1$ is |
| 1354 $Y^1$ is O; $Y^2$ is O; $R^2$ is H; $R^4$ is Cl; $R^5$ is H; $Q^2$ is Ph(4-Cl); and $Q^1$ is |
| 1355 $Y^1$ is O; $Y^2$ is O; $R^2$ is H; $R^4$ is Cl; $R^5$ is H; $Q^2$ is 2,2-di-F-1,3-benzodioxol-4-yl; and $Q^1$ is |
| 1356 $Y^1$ is O; $Y^2$ is O; $R^2$ is H; $R^4$ is Cl; $R^5$ is H; $Q^2$ is 2,2-di-F-1,3-benzodioxol-5-yl; and $Q^1$ is |
| 1357 $Y^1$ is O; $Y^2$ is O; $R^2$ is H; $R^4$ is Cl; $R^5$ is H; $Q^2$ is 2,2-di-Me-1,3-benzodioxol-4-yl; and $Q^1$ is |
| 1358 $Y^1$ is O; $Y^2$ is O; $R^2$ is H; $R^4$ is Cl; $R^5$ is H; $Q^2$ is 2,2-di-Me-1,3-benzodioxol-5-yl; and $Q^1$ is |
| 1359 $Y^1$ is O; $Y^2$ is O; $R^2$ is H; $R^4$ is Cl; $R^5$ is H; $Q^2$ is 1,3-benzodioxol-4-yl; and $Q^1$ is |
| 1360 $Y^1$ is O; $Y^2$ is O; $R^2$ is H; $R^4$ is Cl; $R^5$ is H; $Q^2$ is 1,3-benzodioxol-5-yl; and $Q^1$ is |
| 1361 $Y^1$ is O; $Y^2$ is O; $R^2$ is H; $R^4$ is H; $R^5$ is Br; $Q^2$ is Ph(2-F); and $Q^1$ is |
| 1362 $Y^1$ is O; $Y^2$ is O; $R^2$ is H; $R^4$ is H; $R^5$ is Br; $Q^2$ is Ph(2,3-di-F); and $Q^1$ is |
| 1363 $Y^1$ is O; $Y^2$ is O; $R^2$ is H; $R^4$ is H; $R^5$ is Br; $Q^2$ is Ph(2,4-di-F); and $Q^1$ is |
| 1364 $Y^1$ is O; $Y^2$ is O; $R^2$ is H; $R^4$ is H; $R^5$ is Br; $Q^2$ is Ph(2,5-di-F); and $Q^1$ is |
| 1365 $Y^1$ is O; $Y^2$ is O; $R^2$ is H; $R^4$ is H; $R^5$ is Br; $Q^2$ is Ph(2,3,4-tri-F); and $Q^1$ is |
| 1366 $Y^1$ is O; $Y^2$ is O; $R^2$ is H; $R^4$ is H; $R^5$ is Br; $Q^2$ is Ph(2,3,5-tri-F); and $Q^1$ is |
| 1367 $Y^1$ is O; $Y^2$ is O; $R^2$ is H; $R^4$ is H; $R^5$ is Br; $Q^2$ is Ph(2,3,4,5-tetra-F); and $Q^1$ is |
| 1368 $Y^1$ is O; $Y^2$ is O; $R^2$ is H; $R^4$ is H; $R^5$ is Br; $Q^2$ is Ph(2-F,3-Cl,4-Br); and $Q^1$ is |
| 1369 $Y^1$ is O; $Y^2$ is O; $R^2$ is H; $R^4$ is H; $R^5$ is Br; $Q^2$ is Ph(2-F,3-Cl,4-F); and $Q^1$ is |
| 1370 $Y^1$ is O; $Y^2$ is O; $R^2$ is H; $R^4$ is H; $R^5$ is Br; $Q^2$ is Ph(2-F,3-Br,4-F); and $Q^1$ is |
| 1371 $Y^1$ is O; $Y^2$ is O; $R^2$ is H; $R^4$ is H; $R^5$ is Br; $Q^2$ is Ph(2-F,3-Me); and $Q^1$ is |
| 1372 $Y^1$ is O; $Y^2$ is O; $R^2$ is H; $R^4$ is H; $R^5$ is Br; $Q^2$ is Ph(2-F,3-Me,4-F); and $Q^1$ is |
| 1373 $Y^1$ is O; $Y^2$ is O; $R^2$ is H; $R^4$ is H; $R^5$ is Br; $Q^2$ is Ph(2-F,3-Me,4-Cl); and $Q^1$ is |
| 1374 $Y^1$ is O; $Y^2$ is O; $R^2$ is H; $R^4$ is H; $R^5$ is Br; $Q^2$ is Ph(2-F,3-Cl); and $Q^1$ is |
| 1375 $Y^1$ is O; $Y^2$ is O; $R^2$ is H; $R^4$ is H; $R^5$ is Br; $Q^2$ is Ph(2-F,4-Cl); and $Q^1$ is |
| 1376 $Y^1$ is O; $Y^2$ is O; $R^2$ is H; $R^4$ is H; $R^5$ is Br; $Q^2$ is Ph(2-F,3,4-di-Cl); and $Q^1$ is |
| 1377 $Y^1$ is O; $Y^2$ is O; $R^2$ is H; $R^4$ is H; $R^5$ is Br; $Q^2$ is Ph(2-F,4-Br); and $Q^1$ is |
| 1378 $Y^1$ is O; $Y^2$ is O; $R^2$ is H; $R^4$ is H; $R^5$ is Br; $Q^2$ is Ph(2-F,3-OMe); and $Q^1$ is |
| 1379 $Y^1$ is O; $Y^2$ is O; $R^2$ is H; $R^4$ is H; $R^5$ is Br; $Q^2$ is Ph(2-F,3-OMe,4-F); and $Q^1$ is |
| 1380 $Y^1$ is O; $Y^2$ is O; $R^2$ is H; $R^4$ is H; $R^5$ is Br; $Q^2$ is Ph(2-F,3-OMe,4-Cl); and $Q^1$ is |
| 1381 $Y^1$ is O; $Y^2$ is O; $R^2$ is H; $R^4$ is H; $R^5$ is Br; $Q^2$ is Ph(2-F,3-CF$_2$H); and $Q^1$ is |
| 1382 $Y^1$ is O; $Y^2$ is O; $R^2$ is H; $R^4$ is H; $R^5$ is Br; $Q^2$ is Ph(2-F,3-CF$_3$); and $Q^1$ is |
| 1383 $Y^1$ is O; $Y^2$ is O; $R^2$ is H; $R^4$ is H; $R^5$ is Br; $Q^2$ is Ph(2-F,3-CF$_3$,4-F); and $Q^1$ is |
| 1384 $Y^1$ is O; $Y^2$ is O; $R^2$ is H; $R^4$ is H; $R^5$ is Br; $Q^2$ is Ph(2-F,3-NO$_2$); and $Q^1$ is |
| 1385 $Y^1$ is O; $Y^2$ is O; $R^2$ is H; $R^4$ is H; $R^5$ is Br; $Q^2$ is Ph(2-F,3-NO$_2$,4-F); and $Q^1$ is |
| 1386 $Y^1$ is O; $Y^2$ is O; $R^2$ is H; $R^4$ is H; $R^5$ is Br; $Q^2$ is Ph(2-F,3-SO$_2$Me); and $Q^1$ is |
| 1387 $Y^1$ is O; $Y^2$ is O; $R^2$ is H; $R^4$ is H; $R^5$ is Br; $Q^2$ is Ph(2-F,3-SO$_2$Me,4-F); and $Q^1$ is |
| 1388 $Y^1$ is O; $Y^2$ is O; $R^2$ is H; $R^4$ is H; $R^5$ is Br; $Q^2$ is Ph(2-CF$_3$); and $Q^1$ is |
| 1389 $Y^1$ is O; $Y^2$ is O; $R^2$ is H; $R^4$ is H; $R^5$ is Br; $Q^2$ is Ph(2-CF$_3$,3-F); and $Q^1$ is |
| 1390 $Y^1$ is O; $Y^2$ is O; $R^2$ is H; $R^4$ is H; $R^5$ is Br; $Q^2$ is Ph(2-CF$_3$,3-Me); and $Q^1$ is |
| 1391 $Y^1$ is O; $Y^2$ is O; $R^2$ is H; $R^4$ is H; $R^5$ is Br; $Q^2$ is Ph(2-CF$_3$,4-F); and $Q^1$ is |
| 1392 $Y^1$ is O; $Y^2$ is O; $R^2$ is H; $R^4$ is H; $R^5$ is Br; $Q^2$ is Ph(2-CF$_3$,3-Cl); and $Q^1$ is |
| 1393 $Y^1$ is O; $Y^2$ is O; $R^2$ is H; $R^4$ is H; $R^5$ is Br; $Q^2$ is Ph(2-CF$_3$,4-Cl); and $Q^1$ is |
| 1394 $Y^1$ is O; $Y^2$ is O; $R^2$ is H; $R^4$ is H; $R^5$ is Br; $Q^2$ is Ph(2-CF$_3$,3,4-di-F); and $Q^1$ is |
| 1395 $Y^1$ is O; $Y^2$ is O; $R^2$ is H; $R^4$ is H; $R^5$ is Br; $Q^2$ is Ph(2-CF$_2$H); and $Q^1$ is |
| 1396 $Y^1$ is O; $Y^2$ is O; $R^2$ is H; $R^4$ is H; $R^5$ is Br; $Q^2$ is Ph(2-CF$_2$H,3-F); and $Q^1$ is |
| 1397 $Y^1$ is O; $Y^2$ is O; $R^2$ is H; $R^4$ is H; $R^5$ is Br; $Q^2$ is Ph(2-CF$_2$H,3-Me); and $Q^1$ is |
| 1398 $Y^1$ is O; $Y^2$ is O; $R^2$ is H; $R^4$ is H; $R^5$ is Br; $Q^2$ is Ph(2-CF$_2$H,4-F); and $Q^1$ is |
| 1399 $Y^1$ is O; $Y^2$ is O; $R^2$ is H; $R^4$ is H; $R^5$ is Br; $Q^2$ is Ph(2-CF$_2$H,3-Cl); and $Q^1$ is |
| 1400 $Y^1$ is O; $Y^2$ is O; $R^2$ is H; $R^4$ is H; $R^5$ is Br; $Q^2$ is Ph(2-CF$_2$H,4-Cl); and $Q^1$ is |
| 1401 $Y^1$ is O; $Y^2$ is O; $R^2$ is H; $R^4$ is H; $R^5$ is Br; $Q^2$ is Ph(2-CF$_2$H,3,4-di-F); and $Q^1$ is |
| 1402 $Y^1$ is O; $Y^2$ is O; $R^2$ is H; $R^4$ is H; $R^5$ is Br; $Q^2$ is Ph(2-Me); and $Q^1$ is |
| 1403 $Y^1$ is O; $Y^2$ is O; $R^2$ is H; $R^4$ is H; $R^5$ is Br; $Q^2$ is Ph(2,3-di-Me); and $Q^1$ is |
| 1404 $Y^1$ is O; $Y^2$ is O; $R^2$ is H; $R^4$ is H; $R^5$ is Br; $Q^2$ is Ph(2-Me,3-F); and $Q^1$ is |
| 1405 $Y^1$ is O; $Y^2$ is O; $R^2$ is H; $R^4$ is H; $R^5$ is Br; $Q^2$ is Ph(2-Me,3-Cl); and $Q^1$ is |
| 1406 $Y^1$ is O; $Y^2$ is O; $R^2$ is H; $R^4$ is H; $R^5$ is Br; $Q^2$ is Ph(2-Me,3-CF$_3$); and $Q^1$ is |
| 1407 $Y^1$ is O; $Y^2$ is O; $R^2$ is H; $R^4$ is H; $R^5$ is Br; $Q^2$ is Ph(2-Me,3,4-di-Cl); and $Q^1$ is |
| 1408 $Y^1$ is O; $Y^2$ is O; $R^2$ is H; $R^4$ is H; $R^5$ is Br; $Q^2$ is Ph(2-Me,3-Cl,4-F); and $Q^1$ is |
| 1409 $Y^1$ is O; $Y^2$ is O; $R^2$ is H; $R^4$ is H; $R^5$ is Br; $Q^2$ is Ph(2-Me,4-Cl); and $Q^1$ is |
| 1410 $Y^1$ is O; $Y^2$ is O; $R^2$ is H; $R^4$ is H; $R^5$ is Br; $Q^2$ is Ph(2-Me,4-F); and $Q^1$ is |
| 1411 $Y^1$ is O; $Y^2$ is O; $R^2$ is H; $R^4$ is H; $R^5$ is Br; $Q^2$ is Ph(2-Me,5-F); and $Q^1$ is |
| 1412 $Y^1$ is O; $Y^2$ is O; $R^2$ is H; $R^4$ is H; $R^5$ is Br; $Q^2$ is Ph(2-Me,3,4-di-F); and $Q^1$ is |
| 1413 $Y^1$ is O; $Y^2$ is O; $R^2$ is H; $R^4$ is H; $R^5$ is Br; $Q^2$ is Ph(2-Me,3,5-di-F); and $Q^1$ is |
| 1414 $Y^1$ is O; $Y^2$ is O; $R^2$ is H; $R^4$ is H; $R^5$ is Br; $Q^2$ is Ph(2-Et); and $Q^1$ is |
| 1415 $Y^1$ is O; $Y^2$ is O; $R^2$ is H; $R^4$ is H; $R^5$ is Br; $Q^2$ is Ph(2-Et,3-F); and $Q^1$ is |
| 1416 $Y^1$ is O; $Y^2$ is O; $R^2$ is H; $R^4$ is H; $R^5$ is Br; $Q^2$ is Ph(2-Et,3-Cl); and $Q^1$ is |
| 1417 $Y^1$ is O; $Y^2$ is O; $R^2$ is H; $R^4$ is H; $R^5$ is Br; $Q^2$ is Ph(2-Et,4-F); and $Q^1$ is |
| 1418 $Y^1$ is O; $Y^2$ is O; $R^2$ is H; $R^4$ is H; $R^5$ is Br; $Q^2$ is Ph(2-Et,3,4-di-F); and $Q^1$ is |
| 1419 $Y^1$ is O; $Y^2$ is O; $R^2$ is H; $R^4$ is H; $R^5$ is Br; $Q^2$ is Ph(2-i-Pr); and $Q^1$ is |
| 1420 $Y^1$ is O; $Y^2$ is O; $R^2$ is H; $R^4$ is H; $R^5$ is Br; $Q^2$ is Ph(2-i-Pr,3-F); and $Q^1$ is |
| 1421 $Y^1$ is O; $Y^2$ is O; $R^2$ is H; $R^4$ is H; $R^5$ is Br; $Q^2$ is Ph(2-i-Pr,3-Cl); and $Q^1$ is |
| 1422 $Y^1$ is O; $Y^2$ is O; $R^2$ is H; $R^4$ is H; $R^5$ is Br; $Q^2$ is Ph(2-i-Pr,4-F); and $Q^1$ is |
| 1423 $Y^1$ is O; $Y^2$ is O; $R^2$ is H; $R^4$ is H; $R^5$ is Br; $Q^2$ is Ph(2-i-Pr,3,4-di-F); and $Q^1$ is |

-continued

| Table Row Heading |
|---|
| 1424 $Y^1$ is O; $Y^2$ is O; $R^2$ is H; $R^4$ is H; $R^5$ is Br; $Q^2$ is Ph(2-c-Pr); and $Q^1$ is
| 1425 $Y^1$ is O; $Y^2$ is O; $R^2$ is H; $R^4$ is H; $R^5$ is Br; $Q^2$ is Ph(2-c-Pr,3-F); and $Q^1$ is
| 1426 $Y^1$ is O; $Y^2$ is O; $R^2$ is H; $R^4$ is H; $R^5$ is Br; $Q^2$ is Ph(2-c-Pr,3-Cl); and $Q^1$ is
| 1427 $Y^1$ is O; $Y^2$ is O; $R^2$ is H; $R^4$ is H; $R^5$ is Br; $Q^2$ is Ph(2-c-Pr,4-F); and $Q^1$ is
| 1428 $Y^1$ is O; $Y^2$ is O; $R^2$ is H; $R^4$ is H; $R^5$ is Br; $Q^2$ is Ph(2-c-Pr,3,4-di-F); and $Q^1$ is
| 1429 $Y^1$ is O; $Y^2$ is O; $R^2$ is H; $R^4$ is H; $R^5$ is Br; $Q^2$ is Ph(2-NO$_2$); and $Q^1$ is
| 1430 $Y^1$ is O; $Y^2$ is O; $R^2$ is H; $R^4$ is H; $R^5$ is Br; $Q^2$ is Ph(2-NO$_2$,3-F); and $Q^1$ is
| 1431 $Y^1$ is O; $Y^2$ is O; $R^2$ is H; $R^4$ is H; $R^5$ is Br; $Q^2$ is Ph(2-NO$_2$,3-Cl); and $Q^1$ is
| 1432 $Y^1$ is O; $Y^2$ is O; $R^2$ is H; $R^4$ is H; $R^5$ is Br; $Q^2$ is Ph(2-NO$_2$,4-F); and $Q^1$ is
| 1433 $Y^1$ is O; $Y^2$ is O; $R^2$ is H; $R^4$ is H; $R^5$ is Br; $Q^2$ is Ph(2-NO$_2$,3,4-di-F); and $Q^1$ is
| 1434 $Y^1$ is O; $Y^2$ is O; $R^2$ is H; $R^4$ is H; $R^5$ is Br; $Q^2$ is Ph(2-OCF$_3$); and $Q^1$ is
| 1435 $Y^1$ is O; $Y^2$ is O; $R^2$ is H; $R^4$ is H; $R^5$ is Br; $Q^2$ is Ph(2-OCF$_3$,3-F); and $Q^1$ is
| 1436 $Y^1$ is O; $Y^2$ is O; $R^2$ is H; $R^4$ is H; $R^5$ is Br; $Q^2$ is Ph(2-OCF$_3$,4-F); and $Q^1$ is
| 1437 $Y^1$ is O; $Y^2$ is O; $R^2$ is H; $R^4$ is H; $R^5$ is Br; $Q^2$ is Ph(2-Cl); and $Q^1$ is
| 1438 $Y^1$ is O; $Y^2$ is O; $R^2$ is H; $R^4$ is H; $R^5$ is Br; $Q^2$ is Ph(2-Cl,3-Me); and $Q^1$ is
| 1439 $Y^1$ is O; $Y^2$ is O; $R^2$ is H; $R^4$ is H; $R^5$ is Br; $Q^2$ is Ph(2-Cl,3-Me,4-F); and $Q^1$ is
| 1440 $Y^1$ is O; $Y^2$ is O; $R^2$ is H; $R^4$ is H; $R^5$ is Br; $Q^2$ is Ph(2,3-di-Cl); and $Q^1$ is
| 1441 $Y^1$ is O; $Y^2$ is O; $R^2$ is H; $R^4$ is H; $R^5$ is Br; $Q^2$ is Ph(2,4-di-Cl); and $Q^1$ is
| 1442 $Y^1$ is O; $Y^2$ is O; $R^2$ is H; $R^4$ is H; $R^5$ is Br; $Q^2$ is Ph(2-Cl,3-F); and $Q^1$ is
| 1443 $Y^1$ is O; $Y^2$ is O; $R^2$ is H; $R^4$ is H; $R^5$ is Br; $Q^2$ is Ph(2-Cl,4-F); and $Q^1$ is
| 1444 $Y^1$ is O; $Y^2$ is O; $R^2$ is H; $R^4$ is H; $R^5$ is Br; $Q^2$ is Ph(2-Cl,5-F); and $Q^1$ is
| 1445 $Y^1$ is O; $Y^2$ is O; $R^2$ is H; $R^4$ is H; $R^5$ is Br; $Q^2$ is Ph(2-Cl,3,4-di-F); and $Q^1$ is
| 1446 $Y^1$ is O; $Y^2$ is O; $R^2$ is H; $R^4$ is H; $R^5$ is Br; $Q^2$ is Ph(2-Cl,3,5-di-F); and $Q^1$ is
| 1447 $Y^1$ is O; $Y^2$ is O; $R^2$ is H; $R^4$ is H; $R^5$ is Br; $Q^2$ is Ph(2-OCF$_2$H); and $Q^1$ is
| 1448 $Y^1$ is O; $Y^2$ is O; $R^2$ is H; $R^4$ is H; $R^5$ is Br; $Q^2$ is Ph(2-OCF$_2$H,3-Me); and $Q^1$ is
| 1449 $Y^1$ is O; $Y^2$ is O; $R^2$ is H; $R^4$ is H; $R^5$ is Br; $Q^2$ is Ph(2-OCF$_2$H,3-Cl); and $Q^1$ is
| 1450 $Y^1$ is O; $Y^2$ is O; $R^2$ is H; $R^4$ is H; $R^5$ is Br; $Q^2$ is Ph(2-OCF$_2$H,3-F); and $Q^1$ is
| 1451 $Y^1$ is O; $Y^2$ is O; $R^2$ is H; $R^4$ is H; $R^5$ is Br; $Q^2$ is Ph(2-OCF$_2$H,4-F); and $Q^1$ is
| 1452 $Y^1$ is O; $Y^2$ is O; $R^2$ is H; $R^4$ is H; $R^5$ is Br; $Q^2$ is Ph(2-OCF$_2$CF$_2$H); and $Q^1$ is
| 1453 $Y^1$ is O; $Y^2$ is O; $R^2$ is H; $R^4$ is H; $R^5$ is Br; $Q^2$ is Ph(2-OCF$_2$CF$_2$H,3-F); and $Q^1$ is
| 1454 $Y^1$ is O; $Y^2$ is O; $R^2$ is H; $R^4$ is H; $R^5$ is Br; $Q^2$ is Ph(2-OCF$_2$CF$_2$H,4-F); and $Q^1$ is
| 1455 $Y^1$ is O; $Y^2$ is O; $R^2$ is H; $R^4$ is H; $R^5$ is Br; $Q^2$ is Ph(2-Br); and $Q^1$ is
| 1456 $Y^1$ is O; $Y^2$ is O; $R^2$ is H; $R^4$ is H; $R^5$ is Br; $Q^2$ is Ph(2-Br,3-F); and $Q^1$ is
| 1457 $Y^1$ is O; $Y^2$ is O; $R^2$ is H; $R^4$ is H; $R^5$ is Br; $Q^2$ is Ph(2-Br,4-F); and $Q^1$ is
| 1458 $Y^1$ is O; $Y^2$ is O; $R^2$ is H; $R^4$ is H; $R^5$ is Br; $Q^2$ is Ph(2-Br,3,4-di-F); and $Q^1$ is
| 1459 $Y^1$ is O; $Y^2$ is O; $R^2$ is H; $R^4$ is H; $R^5$ is Br; $Q^2$ is Ph(2-I); and $Q^1$ is
| 1460 $Y^1$ is O; $Y^2$ is O; $R^2$ is H; $R^4$ is H; $R^5$ is Br; $Q^2$ is Ph(2-I,3-F); and $Q^1$ is
| 1461 $Y^1$ is O; $Y^2$ is O; $R^2$ is H; $R^4$ is H; $R^5$ is Br; $Q^2$ is Ph(2-I,4-F); and $Q^1$ is
| 1462 $Y^1$ is O; $Y^2$ is O; $R^2$ is H; $R^4$ is H; $R^5$ is Br; $Q^2$ is Ph(2-I,3,4-di-F); and $Q^1$ is
| 1463 $Y^1$ is O; $Y^2$ is O; $R^2$ is H; $R^4$ is H; $R^5$ is Br; $Q^2$ is Ph(2-CN); and $Q^1$ is
| 1464 $Y^1$ is O; $Y^2$ is O; $R^2$ is H; $R^4$ is H; $R^5$ is Br; $Q^2$ is Ph(2-CN,3-Me); and $Q^1$ is
| 1465 $Y^1$ is O; $Y^2$ is O; $R^2$ is H; $R^4$ is H; $R^5$ is Br; $Q^2$ is Ph(2-CN,3-F); and $Q^1$ is
| 1466 $Y^1$ is O; $Y^2$ is O; $R^2$ is H; $R^4$ is H; $R^5$ is Br; $Q^2$ is Ph(2-CN,4-F); and $Q^1$ is
| 1467 $Y^1$ is O; $Y^2$ is O; $R^2$ is H; $R^4$ is H; $R^5$ is Br; $Q^2$ is Ph(2-CN,3-Cl); and $Q^1$ is
| 1468 $Y^1$ is O; $Y^2$ is O; $R^2$ is H; $R^4$ is H; $R^5$ is Br; $Q^2$ is Ph(2-CN,4-Cl); and $Q^1$ is
| 1469 $Y^1$ is O; $Y^2$ is O; $R^2$ is H; $R^4$ is H; $R^5$ is Br; $Q^2$ is Ph(2-CN,3,4-di-F); and $Q^1$ is
| 1470 $Y^1$ is O; $Y^2$ is O; $R^2$ is H; $R^4$ is H; $R^5$ is Br; $Q^2$ is 2-Pyridinyl; and $Q^1$ is
| 1471 $Y^1$ is O; $Y^2$ is O; $R^2$ is H; $R^4$ is H; $R^5$ is Br; $Q^2$ is 2-Pyridinyl,3-F; and $Q^1$ is
| 1472 $Y^1$ is O; $Y^2$ is O; $R^2$ is H; $R^4$ is H; $R^5$ is Br; $Q^2$ is 2-Pyridinyl,4-F; and $Q^1$ is
| 1473 $Y^1$ is O; $Y^2$ is O; $R^2$ is H; $R^4$ is H; $R^5$ is Br; $Q^2$ is 2-Pyridinyl,3,4-di-F; and $Q^1$ is
| 1474 $Y^1$ is O; $Y^2$ is O; $R^2$ is H; $R^4$ is H; $R^5$ is Br; $Q^2$ is 2-Pyridinyl,3-Cl; and $Q^1$ is
| 1475 $Y^1$ is O; $Y^2$ is O; $R^2$ is H; $R^4$ is H; $R^5$ is Br; $Q^2$ is 2-Pyridinyl,4-Cl; and $Q^1$ is
| 1476 $Y^1$ is O; $Y^2$ is O; $R^2$ is H; $R^4$ is H; $R^5$ is Br; $Q^2$ is 2-Pyridinyl,3-Cl,4-F; and $Q^1$ is
| 1477 $Y^1$ is O; $Y^2$ is O; $R^2$ is H; $R^4$ is H; $R^5$ is Br; $Q^2$ is Ph(2-SO$_2$Me); and $Q^1$ is
| 1478 $Y^1$ is O; $Y^2$ is O; $R^2$ is H; $R^4$ is H; $R^5$ is Br; $Q^2$ is Ph(2-SO$_2$Me, 3-F); and $Q^1$ is
| 1479 $Y^1$ is O; $Y^2$ is O; $R^2$ is H; $R^4$ is H; $R^5$ is Br; $Q^2$ is Ph(2-SO$_2$Me, 3-Me); and $Q^1$ is
| 1480 $Y^1$ is O; $Y^2$ is O; $R^2$ is H; $R^4$ is H; $R^5$ is Br; $Q^2$ is Ph(2-SO$_2$Me, 4-F); and $Q^1$ is
| 1481 $Y^1$ is O; $Y^2$ is O; $R^2$ is H; $R^4$ is H; $R^5$ is Br; $Q^2$ is Ph(2-SO$_2$Me, 5-F); and $Q^1$ is
| 1482 $Y^1$ is O; $Y^2$ is O; $R^2$ is H; $R^4$ is H; $R^5$ is Br; $Q^2$ is Ph(2-SO$_2$Me,3,4-di-F); and $Q^1$ is
| 1483 $Y^1$ is O; $Y^2$ is O; $R^2$ is H; $R^4$ is H; $R^5$ is Br; $Q^2$ is Ph(2-SO$_2$Me, 3-Cl); and $Q^1$ is
| 1484 $Y^1$ is O; $Y^2$ is O; $R^2$ is H; $R^4$ is H; $R^5$ is Br; $Q^2$ is Ph(2-SO$_2$Me, 4-Cl); and $Q^1$ is
| 1485 $Y^1$ is O; $Y^2$ is O; $R^2$ is H; $R^4$ is H; $R^5$ is Br; $Q^2$ is Ph(2-SO$_2$Me,3-Cl,4-F); and $Q^1$ is
| 1486 $Y^1$ is O; $Y^2$ is O; $R^2$ is H; $R^4$ is H; $R^5$ is Br; $Q^2$ is Ph(2-SO$_2$NH$_2$); and $Q^1$ is
| 1487 $Y^1$ is O; $Y^2$ is O; $R^2$ is H; $R^4$ is H; $R^5$ is Br; $Q^2$ is Ph(2-SO$_2$NH$_2$, 3-F); and $Q^1$ is
| 1488 $Y^1$ is O; $Y^2$ is O; $R^2$ is H; $R^4$ is H; $R^5$ is Br; $Q^2$ is Ph(2-SO$_2$NH$_2$, 3-Cl); and $Q^1$ is
| 1489 $Y^1$ is O; $Y^2$ is O; $R^2$ is H; $R^4$ is H; $R^5$ is Br; $Q^2$ is Ph(2-SO$_2$NH$_2$, 4-F); and $Q^1$ is
| 1490 $Y^1$ is O; $Y^2$ is O; $R^2$ is H; $R^4$ is H; $R^5$ is Br; $Q^2$ is Ph(2-SO$_2$NH$_2$, 5-F); and $Q^1$ is
| 1491 $Y^1$ is O; $Y^2$ is O; $R^2$ is H; $R^4$ is H; $R^5$ is Br; $Q^2$ is Ph(2-SO$_2$NH$_2$,3,4-di-F); and $Q^1$ is
| 1492 $Y^1$ is O; $Y^2$ is O; $R^2$ is H; $R^4$ is H; $R^5$ is Br; $Q^2$ is Ph(3-F); and $Q^1$ is
| 1493 $Y^1$ is O; $Y^2$ is O; $R^2$ is H; $R^4$ is H; $R^5$ is Br; $Q^2$ is Ph(3,4-di-F); and $Q^1$ is
| 1494 $Y^1$ is O; $Y^2$ is O; $R^2$ is H; $R^4$ is H; $R^5$ is Br; $Q^2$ is Ph(3,5-di-F); and $Q^1$ is
| 1495 $Y^1$ is O; $Y^2$ is O; $R^2$ is H; $R^4$ is H; $R^5$ is Br; $Q^2$ is Ph(3,4,5-tri-F); and $Q^1$ is
| 1496 $Y^1$ is O; $Y^2$ is O; $R^2$ is H; $R^4$ is H; $R^5$ is Br; $Q^2$ is Ph(3-F,4-Cl); and $Q^1$ is
| 1497 $Y^1$ is O; $Y^2$ is O; $R^2$ is H; $R^4$ is H; $R^5$ is Br; $Q^2$ is Ph(3-CF$_3$); and $Q^1$ is
| 1498 $Y^1$ is O; $Y^2$ is O; $R^2$ is H; $R^4$ is H; $R^5$ is Br; $Q^2$ is Ph(3-CF$_3$,4-F); and $Q^1$ is
| 1499 $Y^1$ is O; $Y^2$ is O; $R^2$ is H; $R^4$ is H; $R^5$ is Br; $Q^2$ is Ph(3-CF$_3$,4-Cl); and $Q^1$ is
| 1500 $Y^1$ is O; $Y^2$ is O; $R^2$ is H; $R^4$ is H; $R^5$ is Br; $Q^2$ is Ph(3-CF$_3$,5-F); and $Q^1$ is -continued

| Table Row Heading |
|---|
| 1501 $Y^1$ is O; $Y^2$ is O; $R^2$ is H; $R^4$ is H; $R^5$ is Br; $Q^2$ is Ph(3-CF$_3$,4,5-di-F); and $Q^1$ is |
| 1502 $Y^1$ is O; $Y^2$ is O; $R^2$ is H; $R^4$ is H; $R^5$ is Br; $Q^2$ is Ph(3-SO$_2$Me); and $Q^1$ is |
| 1503 $Y^1$ is O; $Y^2$ is O; $R^2$ is H; $R^4$ is H; $R^5$ is Br; $Q^2$ is Ph(3-SO$_2$Me,4-Cl); and $Q^1$ is |
| 1504 $Y^1$ is O; $Y^2$ is O; $R^2$ is H; $R^4$ is H; $R^5$ is Br; $Q^2$ is Ph(3-SO$_2$Me,4-F); and $Q^1$ is |
| 1505 $Y^1$ is O; $Y^2$ is O; $R^2$ is H; $R^4$ is H; $R^5$ is Br; $Q^2$ is Ph(3-SO$_2$Me,4,5-di-F); and $Q^1$ is |
| 1506 $Y^1$ is O; $Y^2$ is O; $R^2$ is H; $R^4$ is H; $R^5$ is Br; $Q^2$ is Ph(3-SO$_2$Me,5-F); and $Q^1$ is |
| 1507 $Y^1$ is O; $Y^2$ is O; $R^2$ is H; $R^4$ is H; $R^5$ is Br; $Q^2$ is Ph(3-SO$_2$NH$_2$); and $Q^1$ is |
| 1508 $Y^1$ is O; $Y^2$ is O; $R^2$ is H; $R^4$ is H; $R^5$ is Br; $Q^2$ is Ph(3-SO$_2$NH$_2$,4-F); and $Q^1$ is |
| 1509 $Y^1$ is O; $Y^2$ is O; $R^2$ is H; $R^4$ is H; $R^5$ is Br; $Q^2$ is Ph(3-SO$_2$NH$_2$,4,5-di-F); and $Q^1$ is |
| 1510 $Y^1$ is O; $Y^2$ is O; $R^2$ is H; $R^4$ is H; $R^5$ is Br; $Q^2$ is Ph(3-SO$_2$NH$_2$,4-Cl); and $Q^1$ is |
| 1511 $Y^1$ is O; $Y^2$ is O; $R^2$ is H; $R^4$ is H; $R^5$ is Br; $Q^2$ is Ph(3-SO$_2$NH$_2$,5-F); and $Q^1$ is |
| 1512 $Y^1$ is O; $Y^2$ is O; $R^2$ is H; $R^4$ is H; $R^5$ is Br; $Q^2$ is Ph(3-Me); and $Q^1$ is |
| 1513 $Y^1$ is O; $Y^2$ is O; $R^2$ is H; $R^4$ is H; $R^5$ is Br; $Q^2$ is Ph(3-Me,4-F); and $Q^1$ is |
| 1514 $Y^1$ is O; $Y^2$ is O; $R^2$ is H; $R^4$ is H; $R^5$ is Br; $Q^2$ is Ph(3-Me,4-Cl); and $Q^1$ is |
| 1515 $Y^1$ is O; $Y^2$ is O; $R^2$ is H; $R^4$ is H; $R^5$ is Br; $Q^2$ is Ph(3-Me,5-F); and $Q^1$ is |
| 1516 $Y^1$ is O; $Y^2$ is O; $R^2$ is H; $R^4$ is H; $R^5$ is Br; $Q^2$ is Ph(3-Me,4,5-di-F); and $Q^1$ is |
| 1517 $Y^1$ is O; $Y^2$ is O; $R^2$ is H; $R^4$ is H; $R^5$ is Br; $Q^2$ is Ph(3-Cl); and $Q^1$ is |
| 1518 $Y^1$ is O; $Y^2$ is O; $R^2$ is H; $R^4$ is H; $R^5$ is Br; $Q^2$ is Ph(3-Cl,4-F); and $Q^1$ is |
| 1519 $Y^1$ is O; $Y^2$ is O; $R^2$ is H; $R^4$ is H; $R^5$ is Br; $Q^2$ is Ph(3,4-di-Cl); and $Q^1$ is |
| 1520 $Y^1$ is O; $Y^2$ is O; $R^2$ is H; $R^4$ is H; $R^5$ is Br; $Q^2$ is Ph(3-Cl,5-F); and $Q^1$ is |
| 1521 $Y^1$ is O; $Y^2$ is O; $R^2$ is H; $R^4$ is H; $R^5$ is Br; $Q^2$ is Ph(3-Cl,4,5-di-F); and $Q^1$ is |
| 1522 $Y^1$ is O; $Y^2$ is O; $R^2$ is H; $R^4$ is H; $R^5$ is Br; $Q^2$ is Ph(3,5-di-Cl); and $Q^1$ is |
| 1523 $Y^1$ is O; $Y^2$ is O; $R^2$ is H; $R^4$ is H; $R^5$ is Br; $Q^2$ is Ph(4-F); and $Q^1$ is |
| 1524 $Y^1$ is O; $Y^2$ is O; $R^2$ is H; $R^4$ is H; $R^5$ is Br; $Q^2$ is Ph(4-Cl); and $Q^1$ is |
| 1525 $Y^1$ is O; $Y^2$ is O; $R^2$ is H; $R^4$ is H; $R^5$ is Br; $Q^2$ is 2,2-di-F-1,3-benzodioxol-4-yl; and $Q^1$ is |
| 1526 $Y^1$ is O; $Y^2$ is O; $R^2$ is H; $R^4$ is H; $R^5$ is Br; $Q^2$ is 2,2-di-F-1,3-benzodioxol-5-yl; and $Q^1$ is |
| 1527 $Y^1$ is O; $Y^2$ is O; $R^2$ is H; $R^4$ is H; $R^5$ is Br; $Q^2$ is 2,2-di-Me-1,3-benzodioxol-4-yl; and $Q^1$ is |
| 1528 $Y^1$ is O; $Y^2$ is O; $R^2$ is H; $R^4$ is H; $R^5$ is Br; $Q^2$ is 2,2-di-Me-1,3-benzodioxol-5-yl; and $Q^1$ is |
| 1529 $Y^1$ is O; $Y^2$ is O; $R^2$ is H; $R^4$ is H; $R^5$ is Br; $Q^2$ is 1,3-benzodioxol-4-yl; and $Q^1$ is |
| 1530 $Y^1$ is O; $Y^2$ is O; $R^2$ is H; $R^4$ is H; $R^5$ is Br; $Q^2$ is 1,3-benzodioxol-5-yl; and $Q^1$ is |
| 1531 $Y^1$ is O; $Y^2$ is O; $R^2$ is H; $R^4$ is H; $R^5$ is Cl; $Q^2$ is Ph(2-F); and $Q^1$ is |
| 1532 $Y^1$ is O; $Y^2$ is O; $R^2$ is H; $R^4$ is H; $R^5$ is Cl; $Q^2$ is Ph(2,3-di-F); and $Q^1$ is |
| 1533 $Y^1$ is O; $Y^2$ is O; $R^2$ is H; $R^4$ is H; $R^5$ is Cl; $Q^2$ is Ph(2,4-di-F); and $Q^1$ is |
| 1534 $Y^1$ is O; $Y^2$ is O; $R^2$ is H; $R^4$ is H; $R^5$ is Cl; $Q^2$ is Ph(2,5-di-F); and $Q^1$ is |
| 1535 $Y^1$ is O; $Y^2$ is O; $R^2$ is H; $R^4$ is H; $R^5$ is Cl; $Q^2$ is Ph(2,3,4-tri-F); and $Q^1$ is |
| 1536 $Y^1$ is O; $Y^2$ is O; $R^2$ is H; $R^4$ is H; $R^5$ is Cl; $Q^2$ is Ph(2,3,5-tri-F); and $Q^1$ is |
| 1537 $Y^1$ is O; $Y^2$ is O; $R^2$ is H; $R^4$ is H; $R^5$ is Cl; $Q^2$ is Ph(2,3,4,5-tetra-F); and $Q^1$ is |
| 1538 $Y^1$ is O; $Y^2$ is O; $R^2$ is H; $R^4$ is H; $R^5$ is Cl; $Q^2$ is Ph(2-F,3-Cl,4-Br); and $Q^1$ is |
| 1539 $Y^1$ is O; $Y^2$ is O; $R^2$ is H; $R^4$ is H; $R^5$ is Cl; $Q^2$ is Ph(2-F,3-Cl,4-F); and $Q^1$ is |
| 1540 $Y^1$ is O; $Y^2$ is O; $R^2$ is H; $R^4$ is H; $R^5$ is Cl; $Q^2$ is Ph(2-F,3-Br,4-F); and $Q^1$ is |
| 1541 $Y^1$ is O; $Y^2$ is O; $R^2$ is H; $R^4$ is H; $R^5$ is Cl; $Q^2$ is Ph(2-F,3-Me); and $Q^1$ is |
| 1542 $Y^1$ is O; $Y^2$ is O; $R^2$ is H; $R^4$ is H; $R^5$ is Cl; $Q^2$ is Ph(2-F,3-Me,4-F); and $Q^1$ is |
| 1543 $Y^1$ is O; $Y^2$ is O; $R^2$ is H; $R^4$ is H; $R^5$ is Cl; $Q^2$ is Ph(2-F,3-Me,4-Cl); and $Q^1$ is |
| 1544 $Y^1$ is O; $Y^2$ is O; $R^2$ is H; $R^4$ is H; $R^5$ is Cl; $Q^2$ is Ph(2-F,3-Cl); and $Q^1$ is |
| 1545 $Y^1$ is O; $Y^2$ is O; $R^2$ is H; $R^4$ is H; $R^5$ is Cl; $Q^2$ is Ph(2-F,4-Cl); and $Q^1$ is |
| 1546 $Y^1$ is O; $Y^2$ is O; $R^2$ is H; $R^4$ is H; $R^5$ is Cl; $Q^2$ is Ph(2-F,3,4-di-Cl); and $Q^1$ is |
| 1547 $Y^1$ is O; $Y^2$ is O; $R^2$ is H; $R^4$ is H; $R^5$ is Cl; $Q^2$ is Ph(2-F,4-Br); and $Q^1$ is |
| 1548 $Y^1$ is O; $Y^2$ is O; $R^2$ is H; $R^4$ is H; $R^5$ is Cl; $Q^2$ is Ph(2-F,3-OMe); and $Q^1$ is |
| 1549 $Y^1$ is O; $Y^2$ is O; $R^2$ is H; $R^4$ is H; $R^5$ is Cl; $Q^2$ is Ph(2-F,3-OMe,4-F); and $Q^1$ is |
| 1550 $Y^1$ is O; $Y^2$ is O; $R^2$ is H; $R^4$ is H; $R^5$ is Cl; $Q^2$ is Ph(2-F,3-OMe,4-Cl); and $Q^1$ is |
| 1551 $Y^1$ is O; $Y^2$ is O; $R^2$ is H; $R^4$ is H; $R^5$ is Cl; $Q^2$ is Ph(2-F,3-CF$_2$H); and $Q^1$ is |
| 1552 $Y^1$ is O; $Y^2$ is O; $R^2$ is H; $R^4$ is H; $R^5$ is Cl; $Q^2$ is Ph(2-F,3-CF$_3$); and $Q^1$ is |
| 1553 $Y^1$ is O; $Y^2$ is O; $R^2$ is H; $R^4$ is H; $R^5$ is Cl; $Q^2$ is Ph(2-F,3-CF$_3$,4-F); and $Q^1$ is |
| 1554 $Y^1$ is O; $Y^2$ is O; $R^2$ is H; $R^4$ is H; $R^5$ is Cl; $Q^2$ is Ph(2-F,3-NO$_2$); and $Q^1$ is |
| 1555 $Y^1$ is O; $Y^2$ is O; $R^2$ is H; $R^4$ is H; $R^5$ is Cl; $Q^2$ is Ph(2-F,3-NO$_2$,4-F); and $Q^1$ is |
| 1556 $Y^1$ is O; $Y^2$ is O; $R^2$ is H; $R^4$ is H; $R^5$ is Cl; $Q^2$ is Ph(2-F,3-SO$_2$Me); and $Q^1$ is |
| 1557 $Y^1$ is O; $Y^2$ is O; $R^2$ is H; $R^4$ is H; $R^5$ is Cl; $Q^2$ is Ph(2-F,3-SO$_2$Me,4-F); and $Q^1$ is |
| 1558 $Y^1$ is O; $Y^2$ is O; $R^2$ is H; $R^4$ is H; $R^5$ is Cl; $Q^2$ is Ph(2-CF$_3$); and $Q^1$ is |
| 1559 $Y^1$ is O; $Y^2$ is O; $R^2$ is H; $R^4$ is H; $R^5$ is Cl; $Q^2$ is Ph(2-CF$_3$,3-F); and $Q^1$ is |
| 1560 $Y^1$ is O; $Y^2$ is O; $R^2$ is H; $R^4$ is H; $R^5$ is Cl; $Q^2$ is Ph(2-CF$_3$,3-Me); and $Q^1$ is |
| 1561 $Y^1$ is O; $Y^2$ is O; $R^2$ is H; $R^4$ is H; $R^5$ is Cl; $Q^2$ is Ph(2-CF$_3$,4-F); and $Q^1$ is |
| 1562 $Y^1$ is O; $Y^2$ is O; $R^2$ is H; $R^4$ is H; $R^5$ is Cl; $Q^2$ is Ph(2-CF$_3$,3-Cl); and $Q^1$ is |
| 1563 $Y^1$ is O; $Y^2$ is O; $R^2$ is H; $R^4$ is H; $R^5$ is Cl; $Q^2$ is Ph(2-CF$_3$,4-Cl); and $Q^1$ is |
| 1564 $Y^1$ is O; $Y^2$ is O; $R^2$ is H; $R^4$ is H; $R^5$ is Cl; $Q^2$ is Ph(2-CF$_3$,3,4-di-F); and $Q^1$ is |
| 1565 $Y^1$ is O; $Y^2$ is O; $R^2$ is H; $R^4$ is H; $R^5$ is Cl; $Q^2$ is Ph(2-CF$_2$H); and $Q^1$ is |
| 1566 $Y^1$ is O; $Y^2$ is O; $R^2$ is H; $R^4$ is H; $R^5$ is Cl; $Q^2$ is Ph(2-CF$_2$H,3-F); and $Q^1$ is |
| 1567 $Y^1$ is O; $Y^2$ is O; $R^2$ is H; $R^4$ is H; $R^5$ is Cl; $Q^2$ is Ph(2-CF$_2$H,3-Me); and $Q^1$ is |
| 1568 $Y^1$ is O; $Y^2$ is O; $R^2$ is H; $R^4$ is H; $R^5$ is Cl; $Q^2$ is Ph(2-CF$_2$H,4-F); and $Q^1$ is |
| 1569 $Y^1$ is O; $Y^2$ is O; $R^2$ is H; $R^4$ is H; $R^5$ is Cl; $Q^2$ is Ph(2-CF$_2$H,3-Cl); and $Q^1$ is |
| 1570 $Y^1$ is O; $Y^2$ is O; $R^2$ is H; $R^4$ is H; $R^5$ is Cl; $Q^2$ is Ph(2-CF$_2$H,4-Cl); and $Q^1$ is |
| 1571 $Y^1$ is O; $Y^2$ is O; $R^2$ is H; $R^4$ is H; $R^5$ is Cl; $Q^2$ is Ph(2-CF$_2$H,3,4-di-F); and $Q^1$ is |
| 1572 $Y^1$ is O; $Y^2$ is O; $R^2$ is H; $R^4$ is H; $R^5$ is Cl; $Q^2$ is Ph(2-Me); and $Q^1$ is |
| 1573 $Y^1$ is O; $Y^2$ is O; $R^2$ is H; $R^4$ is H; $R^5$ is Cl; $Q^2$ is Ph(2,3-di-Me); and $Q^1$ is |
| 1574 $Y^1$ is O; $Y^2$ is O; $R^2$ is H; $R^4$ is H; $R^5$ is Cl; $Q^2$ is Ph(2-Me,3-F); and $Q^1$ is |
| 1575 $Y^1$ is O; $Y^2$ is O; $R^2$ is H; $R^4$ is H; $R^5$ is Cl; $Q^2$ is Ph(2-Me,3-Cl); and $Q^1$ is |
| 1576 $Y^1$ is O; $Y^2$ is O; $R^2$ is H; $R^4$ is H; $R^5$ is Cl; $Q^2$ is Ph(2-Me,3-CF$_3$); and $Q^1$ is |
| 1577 $Y^1$ is O; $Y^2$ is O; $R^2$ is H; $R^4$ is H; $R^5$ is Cl; $Q^2$ is Ph(2-Me,3,4-di-Cl); and $Q^1$ is |

| Table Row Heading |
|---|
| 1578 $Y^1$ is O; $Y^2$ is O; $R^2$ is H; $R^4$ is H; $R^5$ is Cl; $Q^2$ is Ph(2-Me,3-Cl,4-F); and $Q^1$ is
| 1579 $Y^1$ is O; $Y^2$ is O; $R^2$ is H; $R^4$ is H; $R^5$ is Cl; $Q^2$ is Ph(2-Me,4-Cl); and $Q^1$ is
| 1580 $Y^1$ is O; $Y^2$ is O; $R^2$ is H; $R^4$ is H; $R^5$ is Cl; $Q^2$ is Ph(2-Me,4-F); and $Q^1$ is
| 1581 $Y^1$ is O; $Y^2$ is O; $R^2$ is H; $R^4$ is H; $R^5$ is Cl; $Q^2$ is Ph(2-Me,5-F); and $Q^1$ is
| 1582 $Y^1$ is O; $Y^2$ is O; $R^2$ is H; $R^4$ is H; $R^5$ is Cl; $Q^2$ is Ph(2-Me,3,4-di-F); and $Q^1$ is
| 1583 $Y^1$ is O; $Y^2$ is O; $R^2$ is H; $R^4$ is H; $R^5$ is Cl; $Q^2$ is Ph(2-Me,3,5-di-F); and $Q^1$ is
| 1584 $Y^1$ is O; $Y^2$ is O; $R^2$ is H; $R^4$ is H; $R^5$ is Cl; $Q^2$ is Ph(2-Et); and $Q^1$ is
| 1585 $Y^1$ is O; $Y^2$ is O; $R^2$ is H; $R^4$ is H; $R^5$ is Cl; $Q^2$ is Ph(2-Et,3-F); and $Q^1$ is
| 1586 $Y^1$ is O; $Y^2$ is O; $R^2$ is H; $R^4$ is H; $R^5$ is Cl; $Q^2$ is Ph(2-Et,3-Cl); and $Q^1$ is
| 1587 $Y^1$ is O; $Y^2$ is O; $R^2$ is H; $R^4$ is H; $R^5$ is Cl; $Q^2$ is Ph(2-Et,4-F); and $Q^1$ is
| 1588 $Y^1$ is O; $Y^2$ is O; $R^2$ is H; $R^4$ is H; $R^5$ is Cl; $Q^2$ is Ph(2-Et,3,4-di-F); and $Q^1$ is
| 1589 $Y^1$ is O; $Y^2$ is O; $R^2$ is H; $R^4$ is H; $R^5$ is Cl; $Q^2$ is Ph(2-i-Pr); and $Q^1$ is
| 1590 $Y^1$ is O; $Y^2$ is O; $R^2$ is H; $R^4$ is H; $R^5$ is Cl; $Q^2$ is Ph(2-i-Pr,3-F); and $Q^1$ is
| 1591 $Y^1$ is O; $Y^2$ is O; $R^2$ is H; $R^4$ is H; $R^5$ is Cl; $Q^2$ is Ph(2-i-Pr,3-Cl); and $Q^1$ is
| 1592 $Y^1$ is O; $Y^2$ is O; $R^2$ is H; $R^4$ is H; $R^5$ is Cl; $Q^2$ is Ph(2-i-Pr,4-F); and $Q^1$ is
| 1593 $Y^1$ is O; $Y^2$ is O; $R^2$ is H; $R^4$ is H; $R^5$ is Cl; $Q^2$ is Ph(2-i-Pr,3,4-di-F); and $Q^1$ is
| 1594 $Y^1$ is O; $Y^2$ is O; $R^2$ is H; $R^4$ is H; $R^5$ is Cl; $Q^2$ is Ph(2-c-Pr); and $Q^1$ is
| 1595 $Y^1$ is O; $Y^2$ is O; $R^2$ is H; $R^4$ is H; $R^5$ is Cl; $Q^2$ is Ph(2-c-Pr,3-F); and $Q^1$ is
| 1596 $Y^1$ is O; $Y^2$ is O; $R^2$ is H; $R^4$ is H; $R^5$ is Cl; $Q^2$ is Ph(2-c-Pr,3-Cl); and $Q^1$ is
| 1597 $Y^1$ is O; $Y^2$ is O; $R^2$ is H; $R^4$ is H; $R^5$ is Cl; $Q^2$ is Ph(2-c-Pr,4-F); and $Q^1$ is
| 1598 $Y^1$ is O; $Y^2$ is O; $R^2$ is H; $R^4$ is H; $R^5$ is Cl; $Q^2$ is Ph(2-c-Pr,3,4-di-F); and $Q^1$ is
| 1599 $Y^1$ is O; $Y^2$ is O; $R^2$ is H; $R^4$ is H; $R^5$ is Cl; $Q^2$ is Ph(2-NO$_2$); and $Q^1$ is
| 1600 $Y^1$ is O; $Y^2$ is O; $R^2$ is H; $R^4$ is H; $R^5$ is Cl; $Q^2$ is Ph(2-NO$_2$,3-F); and $Q^1$ is
| 1601 $Y^1$ is O; $Y^2$ is O; $R^2$ is H; $R^4$ is H; $R^5$ is Cl; $Q^2$ is Ph(2-NO$_2$,3-Cl); and $Q^1$ is
| 1602 $Y^1$ is O; $Y^2$ is O; $R^2$ is H; $R^4$ is H; $R^5$ is Cl; $Q^2$ is Ph(2-NO$_2$,4-F); and $Q^1$ is
| 1603 $Y^1$ is O; $Y^2$ is O; $R^2$ is H; $R^4$ is H; $R^5$ is Cl; $Q^2$ is Ph(2-NO$_2$,3,4-di-F); and $Q^1$ is
| 1604 $Y^1$ is O; $Y^2$ is O; $R^2$ is H; $R^4$ is H; $R^5$ is Cl; $Q^2$ is Ph(2-OCF$_3$); and $Q^1$ is
| 1605 $Y^1$ is O; $Y^2$ is O; $R^2$ is H; $R^4$ is H; $R^5$ is Cl; $Q^2$ is Ph(2-OCF$_3$,3-F); and $Q^1$ is
| 1606 $Y^1$ is O; $Y^2$ is O; $R^2$ is H; $R^4$ is H; $R^5$ is Cl; $Q^2$ is Ph(2-OCF$_3$,4-F); and $Q^1$ is
| 1607 $Y^1$ is O; $Y^2$ is O; $R^2$ is H; $R^4$ is H; $R^5$ is Cl; $Q^2$ is Ph(2-Cl); and $Q^1$ is
| 1608 $Y^1$ is O; $Y^2$ is O; $R^2$ is H; $R^4$ is H; $R^5$ is Cl; $Q^2$ is Ph(2-Cl,3-Me); and $Q^1$ is
| 1609 $Y^1$ is O; $Y^2$ is O; $R^2$ is H; $R^4$ is H; $R^5$ is Cl; $Q^2$ is Ph(2-Cl,3-Me,4-F); and $Q^1$ is
| 1610 $Y^1$ is O; $Y^2$ is O; $R^2$ is H; $R^4$ is H; $R^5$ is Cl; $Q^2$ is Ph(2,3-di-Cl); and $Q^1$ is
| 1611 $Y^1$ is O; $Y^2$ is O; $R^2$ is H; $R^4$ is H; $R^5$ is Cl; $Q^2$ is Ph(2,4-di-Cl); and $Q^1$ is
| 1612 $Y^1$ is O; $Y^2$ is O; $R^2$ is H; $R^4$ is H; $R^5$ is Cl; $Q^2$ is Ph(2-Cl,3-F); and $Q^1$ is
| 1613 $Y^1$ is O; $Y^2$ is O; $R^2$ is H; $R^4$ is H; $R^5$ is Cl; $Q^2$ is Ph(2-Cl,4-F); and $Q^1$ is
| 1614 $Y^1$ is O; $Y^2$ is O; $R^2$ is H; $R^4$ is H; $R^5$ is Cl; $Q^2$ is Ph(2-Cl,5-F); and $Q^1$ is
| 1615 $Y^1$ is O; $Y^2$ is O; $R^2$ is H; $R^4$ is H; $R^5$ is Cl; $Q^2$ is Ph(2-Cl,3,4-di-F); and $Q^1$ is
| 1616 $Y^1$ is O; $Y^2$ is O; $R^2$ is H; $R^4$ is H; $R^5$ is Cl; $Q^2$ is Ph(2-Cl,3,5-di-F); and $Q^1$ is
| 1617 $Y^1$ is O; $Y^2$ is O; $R^2$ is H; $R^4$ is H; $R^5$ is Cl; $Q^2$ is Ph(2-OCF$_2$H); and $Q^1$ is
| 1618 $Y^1$ is O; $Y^2$ is O; $R^2$ is H; $R^4$ is H; $R^5$ is Cl; $Q^2$ is Ph(2-OCF$_2$H,3-Me); and $Q^1$ is
| 1619 $Y^1$ is O; $Y^2$ is O; $R^2$ is H; $R^4$ is H; $R^5$ is Cl; $Q^2$ is Ph(2-OCF$_2$H,3-Cl); and $Q^1$ is
| 1620 $Y^1$ is O; $Y^2$ is O; $R^2$ is H; $R^4$ is H; $R^5$ is Cl; $Q^2$ is Ph(2-OCF$_2$H,3-F); and $Q^1$ is
| 1621 $Y^1$ is O; $Y^2$ is O; $R^2$ is H; $R^4$ is H; $R^5$ is Cl; $Q^2$ is Ph(2-OCF$_2$H,4-F); and $Q^1$ is
| 1622 $Y^1$ is O; $Y^2$ is O; $R^2$ is H; $R^4$ is H; $R^5$ is Cl; $Q^2$ is Ph(2-OCF$_2$CF$_2$H); and $Q^1$ is
| 1623 $Y^1$ is O; $Y^2$ is O; $R^2$ is H; $R^4$ is H; $R^5$ is Cl; $Q^2$ is Ph(2-OCF$_2$CF$_2$H,3-F); and $Q^1$ is
| 1624 $Y^1$ is O; $Y^2$ is O; $R^2$ is H; $R^4$ is H; $R^5$ is Cl; $Q^2$ is Ph(2-OCF$_2$CF$_2$H,4-F); and $Q^1$ is
| 1625 $Y^1$ is O; $Y^2$ is O; $R^2$ is H; $R^4$ is H; $R^5$ is Cl; $Q^2$ is Ph(2-Br); and $Q^1$ is
| 1626 $Y^1$ is O; $Y^2$ is O; $R^2$ is H; $R^4$ is H; $R^5$ is Cl; $Q^2$ is Ph(2-Br,3-F); and $Q^1$ is
| 1627 $Y^1$ is O; $Y^2$ is O; $R^2$ is H; $R^4$ is H; $R^5$ is Cl; $Q^2$ is Ph(2-Br,4-F); and $Q^1$ is
| 1628 $Y^1$ is O; $Y^2$ is O; $R^2$ is H; $R^4$ is H; $R^5$ is Cl; $Q^2$ is Ph(2-Br,3,4-di-F); and $Q^1$ is
| 1629 $Y^1$ is O; $Y^2$ is O; $R^2$ is H; $R^4$ is H; $R^5$ is Cl; $Q^2$ is Ph(2-I); and $Q^1$ is
| 1630 $Y^1$ is O; $Y^2$ is O; $R^2$ is H; $R^4$ is H; $R^5$ is Cl; $Q^2$ is Ph(2-I,3-F); and $Q^1$ is
| 1631 $Y^1$ is O; $Y^2$ is O; $R^2$ is H; $R^4$ is H; $R^5$ is Cl; $Q^2$ is Ph(2-I,4-F); and $Q^1$ is
| 1632 $Y^1$ is O; $Y^2$ is O; $R^2$ is H; $R^4$ is H; $R^5$ is Cl; $Q^2$ is Ph(2-I,3,4-di-F); and $Q^1$ is
| 1633 $Y^1$ is O; $Y^2$ is O; $R^2$ is H; $R^4$ is H; $R^5$ is Cl; $Q^2$ is Ph(2-CN); and $Q^1$ is
| 1634 $Y^1$ is O; $Y^2$ is O; $R^2$ is H; $R^4$ is H; $R^5$ is Cl; $Q^2$ is Ph(2-CN,3-Me); and $Q^1$ is
| 1635 $Y^1$ is O; $Y^2$ is O; $R^2$ is H; $R^4$ is H; $R^5$ is Cl; $Q^2$ is Ph(2-CN,3-F); and $Q^1$ is
| 1636 $Y^1$ is O; $Y^2$ is O; $R^2$ is H; $R^4$ is H; $R^5$ is Cl; $Q^2$ is Ph(2-CN,4-F); and $Q^1$ is
| 1637 $Y^1$ is O; $Y^2$ is O; $R^2$ is H; $R^4$ is H; $R^5$ is Cl; $Q^2$ is Ph(2-CN,3-Cl); and $Q^1$ is
| 1638 $Y^1$ is O; $Y^2$ is O; $R^2$ is H; $R^4$ is H; $R^5$ is Cl; $Q^2$ is Ph(2-CN,4-Cl); and $Q^1$ is
| 1639 $Y^1$ is O; $Y^2$ is O; $R^2$ is H; $R^4$ is H; $R^5$ is Cl; $Q^2$ is Ph(2-CN,3,4-di-F); and $Q^1$ is
| 1640 $Y^1$ is O; $Y^2$ is O; $R^2$ is H; $R^4$ is H; $R^5$ is Cl; $Q^2$ is 2-Pyridinyl; and $Q^1$ is
| 1641 $Y^1$ is O; $Y^2$ is O; $R^2$ is H; $R^4$ is H; $R^5$ is Cl; $Q^2$ is 2-Pyridinyl,3-F; and $Q^1$ is
| 1642 $Y^1$ is O; $Y^2$ is O; $R^2$ is H; $R^4$ is H; $R^5$ is Cl; $Q^2$ is 2-Pyridinyl,4-F; and $Q^1$ is
| 1643 $Y^1$ is O; $Y^2$ is O; $R^2$ is H; $R^4$ is H; $R^5$ is Cl; $Q^2$ is 2-Pyridinyl,3,4-di-F; and $Q^1$ is
| 1644 $Y^1$ is O; $Y^2$ is O; $R^2$ is H; $R^4$ is H; $R^5$ is Cl; $Q^2$ is 2-Pyridinyl,3-Cl; and $Q^1$ is
| 1645 $Y^1$ is O; $Y^2$ is O; $R^2$ is H; $R^4$ is H; $R^5$ is Cl; $Q^2$ is 2-Pyridinyl,4-Cl; and $Q^1$ is
| 1646 $Y^1$ is O; $Y^2$ is O; $R^2$ is H; $R^4$ is H; $R^5$ is Cl; $Q^2$ is 2-Pyridinyl,3-Cl,4-F; and $Q^1$ is
| 1647 $Y^1$ is O; $Y^2$ is O; $R^2$ is H; $R^4$ is H; $R^5$ is Cl; $Q^2$ is Ph(2-SO$_2$Me); and $Q^1$ is
| 1648 $Y^1$ is O; $Y^2$ is O; $R^2$ is H; $R^4$ is H; $R^5$ is Cl; $Q^2$ is Ph(2-SO$_2$Me, 3-F); and $Q^1$ is
| 1649 $Y^1$ is O; $Y^2$ is O; $R^2$ is H; $R^4$ is H; $R^5$ is Cl; $Q^2$ is Ph(2-SO$_2$Me, 3-Me); and $Q^1$ is
| 1650 $Y^1$ is O; $Y^2$ is O; $R^2$ is H; $R^4$ is H; $R^5$ is Cl; $Q^2$ is Ph(2-SO$_2$Me, 4-F); and $Q^1$ is
| 1651 $Y^1$ is O; $Y^2$ is O; $R^2$ is H; $R^4$ is H; $R^5$ is Cl; $Q^2$ is Ph(2-SO$_2$Me, 5-F); and $Q^1$ is
| 1652 $Y^1$ is O; $Y^2$ is O; $R^2$ is H; $R^4$ is H; $R^5$ is Cl; $Q^2$ is Ph(2-SO$_2$Me,3,4-di-F); and $Q^1$ is
| 1653 $Y^1$ is O; $Y^2$ is O; $R^2$ is H; $R^4$ is H; $R^5$ is Cl; $Q^2$ is Ph(2-SO$_2$Me, 3-Cl); and $Q^1$ is
| 1654 $Y^1$ is O; $Y^2$ is O; $R^2$ is H; $R^4$ is H; $R^5$ is Cl; $Q^2$ is Ph(2-SO$_2$Me, 4-Cl); and $Q^1$ is -continued

| Table Row Heading |
|---|
| 1655 $Y^1$ is O; $Y^2$ is O; $R^2$ is H; $R^4$ is H; $R^5$ is Cl; $Q^2$ is Ph(2-SO$_2$Me,3-Cl,4-F); and $Q^1$ is |
| 1656 $Y^1$ is O; $Y^2$ is O; $R^2$ is H; $R^4$ is H; $R^5$ is Cl; $Q^2$ is Ph(2-SO$_2$NH$_2$); and $Q^1$ is |
| 1657 $Y^1$ is O; $Y^2$ is O; $R^2$ is H; $R^4$ is H; $R^5$ is Cl; $Q^2$ is Ph(2-SO$_2$NH$_2$, 3-F); and $Q^1$ is |
| 1658 $Y^1$ is O; $Y^2$ is O; $R^2$ is H; $R^4$ is H; $R^5$ is Cl; $Q^2$ is Ph(2-SO$_2$NH$_2$, 3-Cl); and $Q^1$ is |
| 1659 $Y^1$ is O; $Y^2$ is O; $R^2$ is H; $R^4$ is H; $R^5$ is Cl; $Q^2$ is Ph(2-SO$_2$NH$_2$, 4-F); and $Q^1$ is |
| 1660 $Y^1$ is O; $Y^2$ is O; $R^2$ is H; $R^4$ is H; $R^5$ is Cl; $Q^2$ is Ph(2-SO$_2$NH$_2$, 5-F); and $Q^1$ is |
| 1661 $Y^1$ is O; $Y^2$ is O; $R^2$ is H; $R^4$ is H; $R^5$ is Cl; $Q^2$ is Ph(2-SO$_2$NH$_2$,3,4-di-F); and $Q^1$ is |
| 1662 $Y^1$ is O; $Y^2$ is O; $R^2$ is H; $R^4$ is H; $R^5$ is Cl; $Q^2$ is Ph(3-F); and $Q^1$ is |
| 1663 $Y^1$ is O; $Y^2$ is O; $R^2$ is H; $R^4$ is H; $R^5$ is Cl; $Q^2$ is Ph(3,4-di-F); and $Q^1$ is |
| 1664 $Y^1$ is O; $Y^2$ is O; $R^2$ is H; $R^4$ is H; $R^5$ is Cl; $Q^2$ is Ph(3,5-di-F); and $Q^1$ is |
| 1665 $Y^1$ is O; $Y^2$ is O; $R^2$ is H; $R^4$ is H; $R^5$ is Cl; $Q^2$ is Ph(3,4,5-tri-F); and $Q^1$ is |
| 1666 $Y^1$ is O; $Y^2$ is O; $R^2$ is H; $R^4$ is H; $R^5$ is Cl; $Q^2$ is Ph(3-F,4-Cl); and $Q^1$ is |
| 1667 $Y^1$ is O; $Y^2$ is O; $R^2$ is H; $R^4$ is H; $R^5$ is Cl; $Q^2$ is Ph(3-CF$_3$); and $Q^1$ is |
| 1668 $Y^1$ is O; $Y^2$ is O; $R^2$ is H; $R^4$ is H; $R^5$ is Cl; $Q^2$ is Ph(3-CF$_3$,4-F); and $Q^1$ is |
| 1669 $Y^1$ is O; $Y^2$ is O; $R^2$ is H; $R^4$ is H; $R^5$ is Cl; $Q^2$ is Ph(3-CF$_3$,4-Cl); and $Q^1$ is |
| 1670 $Y^1$ is O; $Y^2$ is O; $R^2$ is H; $R^4$ is H; $R^5$ is Cl; $Q^2$ is Ph(3-CF$_3$,5-F); and $Q^1$ is |
| 1671 $Y^1$ is O; $Y^2$ is O; $R^2$ is H; $R^4$ is H; $R^5$ is Cl; $Q^2$ is Ph(3-CF$_3$,4,5-di-F); and $Q^1$ is |
| 1672 $Y^1$ is O; $Y^2$ is O; $R^2$ is H; $R^4$ is H; $R^5$ is Cl; $Q^2$ is Ph(3-SO$_2$Me); and $Q^1$ is |
| 1673 $Y^1$ is O; $Y^2$ is O; $R^2$ is H; $R^4$ is H; $R^5$ is Cl; $Q^2$ is Ph(3-SO$_2$Me,4-Cl); and $Q^1$ is |
| 1674 $Y^1$ is O; $Y^2$ is O; $R^2$ is H; $R^4$ is H; $R^5$ is Cl; $Q^2$ is Ph(3-SO$_2$Me,4-F); and $Q^1$ is |
| 1675 $Y^1$ is O; $Y^2$ is O; $R^2$ is H; $R^4$ is H; $R^5$ is Cl; $Q^2$ is Ph(3-SO$_2$Me,4,5-di-F); and $Q^1$ is |
| 1676 $Y^1$ is O; $Y^2$ is O; $R^2$ is H; $R^4$ is H; $R^5$ is Cl; $Q^2$ is Ph(3-SO$_2$Me,5-F); and $Q^1$ is |
| 1677 $Y^1$ is O; $Y^2$ is O; $R^2$ is H; $R^4$ is H; $R^5$ is Cl; $Q^2$ is Ph(3-SO$_2$NH$_2$); and $Q^1$ is |
| 1678 $Y^1$ is O; $Y^2$ is O; $R^2$ is H; $R^4$ is H; $R^5$ is Cl; $Q^2$ is Ph(3-SO$_2$NH$_2$,4-F); and $Q^1$ is |
| 1679 $Y^1$ is O; $Y^2$ is O; $R^2$ is H; $R^4$ is H; $R^5$ is Cl; $Q^2$ is Ph(3-SO$_2$NH$_2$,4,5-di-F); and $Q^1$ is |
| 1680 $Y^1$ is O; $Y^2$ is O; $R^2$ is H; $R^4$ is H; $R^5$ is Cl; $Q^2$ is Ph(3-SO$_2$NH$_2$,4-Cl); and $Q^1$ is |
| 1681 $Y^1$ is O; $Y^2$ is O; $R^2$ is H; $R^4$ is H; $R^5$ is Cl; $Q^2$ is Ph(3-SO$_2$NH$_2$,5-F); and $Q^1$ is |
| 1682 $Y^1$ is O; $Y^2$ is O; $R^2$ is H; $R^4$ is H; $R^5$ is Cl; $Q^2$ is Ph(3-Me); and $Q^1$ is |
| 1683 $Y^1$ is O; $Y^2$ is O; $R^2$ is H; $R^4$ is H; $R^5$ is Cl; $Q^2$ is Ph(3-Me,4-F); and $Q^1$ is |
| 1684 $Y^1$ is O; $Y^2$ is O; $R^2$ is H; $R^4$ is H; $R^5$ is Cl; $Q^2$ is Ph(3-Me,4-Cl); and $Q^1$ is |
| 1685 $Y^1$ is O; $Y^2$ is O; $R^2$ is H; $R^4$ is H; $R^5$ is Cl; $Q^2$ is Ph(3-Me,5-F); and $Q^1$ is |
| 1686 $Y^1$ is O; $Y^2$ is O; $R^2$ is H; $R^4$ is H; $R^5$ is Cl; $Q^2$ is Ph(3-Me,4,5-di-F); and $Q^1$ is |
| 1687 $Y^1$ is O; $Y^2$ is O; $R^2$ is H; $R^4$ is H; $R^5$ is Cl; $Q^2$ is Ph(3-Cl); and $Q^1$ is |
| 1688 $Y^1$ is O; $Y^2$ is O; $R^2$ is H; $R^4$ is H; $R^5$ is Cl; $Q^2$ is Ph(3-Cl,4-F); and $Q^1$ is |
| 1689 $Y^1$ is O; $Y^2$ is O; $R^2$ is H; $R^4$ is H; $R^5$ is Cl; $Q^2$ is Ph(3,4-di-Cl); and $Q^1$ is |
| 1690 $Y^1$ is O; $Y^2$ is O; $R^2$ is H; $R^4$ is H; $R^5$ is Cl; $Q^2$ is Ph(3-Cl,5-F); and $Q^1$ is |
| 1691 $Y^1$ is O; $Y^2$ is O; $R^2$ is H; $R^4$ is H; $R^5$ is Cl; $Q^2$ is Ph(3-Cl,4,5-di-F); and $Q^1$ is |
| 1692 $Y^1$ is O; $Y^2$ is O; $R^2$ is H; $R^4$ is H; $R^5$ is Cl; $Q^2$ is Ph(3,5-di-Cl); and $Q^1$ is |
| 1693 $Y^1$ is O; $Y^2$ is O; $R^2$ is H; $R^4$ is H; $R^5$ is Cl; $Q^2$ is Ph(4-F); and $Q^1$ is |
| 1694 $Y^1$ is O; $Y^2$ is O; $R^2$ is H; $R^4$ is H; $R^5$ is Cl; $Q^2$ is Ph(4-Cl); and $Q^1$ is |
| 1695 $Y^1$ is O; $Y^2$ is O; $R^2$ is H; $R^4$ is H; $R^5$ is Cl; $Q^2$ is 2,2-di-F-1,3-benzodioxol-4-yl; and $Q^1$ is |
| 1696 $Y^1$ is O; $Y^2$ is O; $R^2$ is H; $R^4$ is H; $R^5$ is Cl; $Q^2$ is 2,2-di-F-1,3-benzodioxol-5-yl; and $Q^1$ is |
| 1697 $Y^1$ is O; $Y^2$ is O; $R^2$ is H; $R^4$ is H; $R^5$ is Cl; $Q^2$ is 2,2-di-Me-1,3-benzodioxol-4-yl; and $Q^1$ is |
| 1698 $Y^1$ is O; $Y^2$ is O; $R^2$ is H; $R^4$ is H; $R^5$ is Cl; $Q^2$ is 2,2-di-Me-1,3-benzodioxol-5-yl; and $Q^1$ is |
| 1699 $Y^1$ is O; $Y^2$ is O; $R^2$ is H; $R^4$ is H; $R^5$ is Cl; $Q^2$ is 1,3-benzodioxol-4-yl; and $Q^1$ is |

Table 1700

Table 1700 is constructed the same way as Table 1 above, except the structure is replaced with the following:

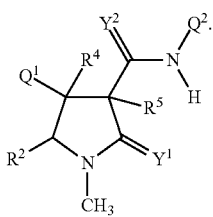

Tables 1701 Through 3399

This disclosure also includes Tables 1701 through 3399, each TabR1 is constructed in the same fashion as Tables 2 through 1699 above, except that the structure is replaced with the structure in Table 1700 above.

Table 3400

Table 3400 is constructed the same way as Table 1 above, except the structure is replaced with the following:

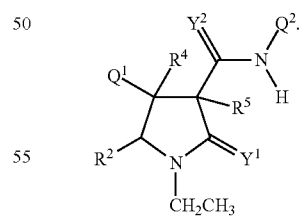

Tables 3401 Through 5099

This disclosure also includes Tables 3401 through 5099, each TabR1 is constructed in the same fashion as Tables 2 through 1699 above, except that the structure is replaced with the structure in Table 3400 above.

147

Table 5100

Table 5100 is constructed the same way as Table 1 above, except the structure is replaced with the following:

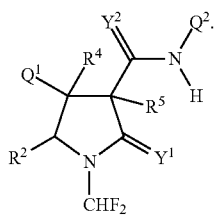

Tables 5101 Through 6799

This disclosure also includes Tables 5101 through 6799, each TabR1 is constructed in the same fashion as Tables 2 through 1699 above, except that the structure is replaced with the structure in Table 5100 above.

TABLE I

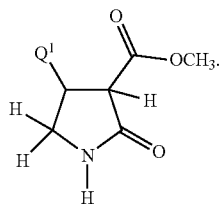

The present disclosure also includes the intermediate compounds listed in Table I. Table 1 is constructed using the above Table I structure, combined with the individual values listed for $Q^1$ from Table 1.

TABLE II

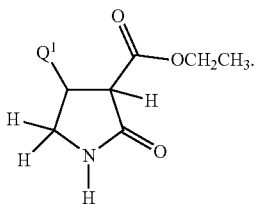

The present disclosure also includes the intermediate compounds listed in Table II. Table II is constructed using the above Table II structure, combined with the individual values listed for $Q^1$ from Table 1.

TABLE III

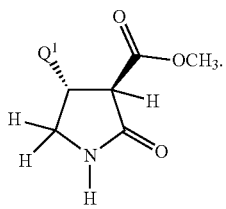

The present disclosure also includes the intermediate compounds listed in Table 111. Table III is constructed using the above Table III structure, combined with the individual values listed for $Q^1$ from Table 1.

TABLE IV

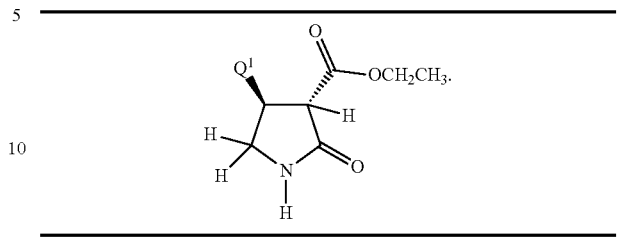

The present disclosure also includes the intermediate compounds listed in Table IV. Table IV is constructed using the above Table IV structure, combined with the individual values listed for $Q^1$ from Table 1.

Formulation/Utility

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide and/or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof): amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons. N.Y., 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*. 4th Ed., McGraw-Hill. N.Y., 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience. The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Tables A-C. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 17 | 98.5% |
| silica aerogel | 0.5% |
| synthetic amorphous fine silica | 1.0% |

Example B

| Wettable Powder | |
|---|---|
| Compound 79 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 80 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 5 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 17 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 79 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 80 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Emulsion in Water

| | |
|---|---|
| Compound 5 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 17 | 25% |
| polyoxyethylene sorbitol hexaoleate | 15% |
| organically modified bentonite clay | 2.5% |
| fatty acid methyl ester | 57.5% |

Example J

Suspoemulsion

| | |
|---|---|
| Compound 79 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Test results indicate that the compounds of the present invention are highly active preemergent and/or postemergent herbicides and/or plant growth regulators. The compounds of the invention generally show highest activity for early postemergence weed control (i.e. applied soon after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have (both preemergent and postemergent herbicidal) activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.005 to 20 kg/ha with a preferred range of about 0.01 to 1 kg/ha. One skilled in the art can easily determine the herbicidally effective amount necessary for the desired level of weed control.

Compounds of the invention are useful in treating all plants and plant parts. Plant varieties and cultivars can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of for example, herbicide tolerance, insect-resistance, modified oil profiles or drought tolerance. Useful genetically modified plants containing single gene transformation events or combinations of transformation events are listed in Table 3. Additional information for the genetic modifications listed in Table 3 can be obtained from publicly available databases maintained, for example, by the U.S. Department of Agriculture.

The following abbreviations, T1 through T37, are used in Table 3 for traits. A "–" means the entry is not available.

| Trait | Description |
| --- | --- |
| T1 | Glyphosate tolerance |
| T2 | High lauric acid oil |
| T3 | Glufosinate tolerance |
| T4 | Phytate breakdown |
| T5 | Oxynil tolerance |
| T6 | Disease resistance |
| T7 | Insect resistance |
| T9 | Modified flower color |
| T11 | ALS Herbicide Tol. |
| T12 | Dicamba Tolerance |
| T13 | Anti-allergy |
| T14 | Salt tolerance |
| T15 | Cold tolerance |
| T16 | Imidazolinone herb. tol. |
| T17 | Modified alpha-amylase |
| T18 | Pollination control |
| T19 | 2,4-D tolerance |
| T20 | Increased lysine |
| T21 | Drought tolerance |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tolerance |
| T31 | Modified oil/fatty acid |
| T32 | HPPD tolerance |
| T33 | High oil |
| T34 | Aryloxyalkanoate tol. |
| T35 | Mesotrione tolerance |
| T36 | Reduced nicotine |
| T37 | Modified product |

TABLE 3

| Crop | Event Name | Event Code | Trait(s) | Gene(s) |
| --- | --- | --- | --- | --- |
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |

TABLE 3-continued

| Crop | Event Name | Event Code | Trait(s) | Gene(s) |
|---|---|---|---|---|
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |

TABLE 3-continued

| Crop | Event Name | Event Code | Trait(s) | Gene(s) |
|---|---|---|---|---|
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |

TABLE 3-continued

| Crop | Event Name | Event Code | Trait(s) | Gene(s) |
|---|---|---|---|---|
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Treatment of genetically modified plants with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, cyclopyrimorate, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron. DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofenethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione, 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*. 13th Edition, C. D. S. Tomlin, Ed., British Crop Protection Council, Farnham. Surrey, U. K., 2003 and *The BioPesticide Manual*. 2nd Edition, L. G. Copping, Ed., British Crop Protection Council, Farnham, Surrey, U K., 2001.

For embodiments where one or more of these various mixing partners are used, the weight ratio of these various mixing partners (in total) to the compound of Formula 1 is typically between about 1:3000 and about 3000:1. Of note are weight ratios between about 1:3 (0 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide. N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with another herbicide. Table A1 lists particular combinations of Component (a) (i.e. a specific compound of the present invention) with another herbicide as Component (b) illustrative of the mixtures, compositions and methods of the present invention. Compound 17 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 17 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 17 | 2,4-D | 1:192-6:1 | 1:64-2:1 | 1:24-1:3 |
| 17 | Acetochlor | 1:768-2:1 | 1:256-1:2 | 1:96-1:11 |
| 17 | Acifluorfen | 1:96-12:1 | 1:32-4:1 | 1:12-1:2 |
| 17 | Aclonifen | 1:857-2:1 | 1:285-1:3 | 1:107-1:12 |
| 17 | Alachlor | 1:768-2:1 | 1:256-1:2 | 1:96-1:11 |
| 17 | Ametryn | 1:384-3:1 | 1:128-1:1 | 1:48-1:6 |
| 17 | Amicarbazone | 1:192-6:1 | 1:64-2:1 | 1:24-1:3 |
| 17 | Amidosulfuron | 1:6-168:1 | 1:2-56:1 | 1:1-11:1 |
| 17 | Aminocyclopyrachlor | 1:48-24:1 | 1:16-8:1 | 1:6-2:1 |
| 17 | Aminopyralid | 1:20-56:1 | 1:6-19:1 | 1:2-4:1 |
| 17 | Amitrole | 1:768-2:1 | 1:256-1:2 | 1:96-1:11 |
| 17 | Anilofos | 1:96-12:1 | 1:32-4:1 | 1:12-1:2 |
| 17 | Asulam | 1:960-2:1 | 1:320-1:3 | 1:120-1:14 |
| 17 | Atrazine | 1:192-6:1 | 1:64-2:1 | 1:24-1:3 |
| 17 | Azimsulfuron | 1:6-168:1 | 1:2-56:1 | 1:1-11:1 |
| 17 | Beflubutamid | 1:342-4:1 | 1:114-2:1 | 1:42-1:5 |
| 17 | Benfuresate | 1:617-2:1 | 1:205-1:2 | 1:77-1:9 |
| 17 | Bensulfuron-methyl | 1:25-45:1 | 1:8-15:1 | 1:3-3:1 |
| 17 | Bentazone | 1:192-6:1 | 1:64-2:1 | 1:24-1:3 |
| 17 | Benzobicyclon | 1:85-14:1 | 1:28-5:1 | 1:10-1:2 |

TABLE A1-continued

| Component (a) (Compound #) | Component (b) | Typical Weight Ratio | More Typical Weight Ratio | Most Typical Weight Ratio |
|---|---|---|---|---|
| 17 | Benzofenap | 1:257-5:1 | 1:85-2:1 | 1:32-1:4 |
| 17 | Bicyclopyrone | 1:42-27:1 | 1:14-9:1 | 1:5-2:1 |
| 17 | Bifenox | 1:257-5:1 | 1:85-2:1 | 1:32-1:4 |
| 17 | Bispyribac-sodium | 1:10-112:1 | 1:3-38:1 | 1:1-7:1 |
| 17 | Bromacil | 1:384-3:1 | 1:128-1:1 | 1:48-1:6 |
| 17 | Bromobutide | 1:384-3:1 | 1:128-1:1 | 1:48-1:6 |
| 17 | Bromoxynil | 1:96-12:1 | 1:32-4:1 | 1:12-1:2 |
| 17 | Butachlor | 1:768-2:1 | 1:256-1:2 | 1:96-1:11 |
| 17 | Butafenacil | 1:42-27:1 | 1:14-9:1 | 1:5-2:1 |
| 17 | Butylate | 1:1542-1:2 | 1:514-1:5 | 1:192-1:22 |
| 17 | Cafenstrole | 1:192-6:1 | 1:64-2:1 | 1:24-1:3 |
| 17 | Carfentrazone-ethyl | 1:128-9:1 | 1:42-3:1 | 1:16-1:2 |
| 17 | Chlorimuron-ethyl | 1:8-135:1 | 1:2-45:1 | 1:1-9:1 |
| 17 | Chlorotoluron | 1:768-2:1 | 1:256-1:2 | 1:96-1:11 |
| 17 | Chlorsulfuron | 1:6-168:1 | 1:2-56:1 | 1:1-11:1 |
| 17 | Cinosulfuron | 1:17-68:1 | 1:5-23:1 | 1:2-5:1 |
| 17 | Cinidon-ethyl | 1:384-3:1 | 1:128-1:1 | 1:48-1:6 |
| 17 | Cinmethylin | 1:34-34:1 | 1:11-12:1 | 1:4-3:1 |
| 17 | Clacyfos | 1:34-34:1 | 1:11-12:1 | 1:4-3:1 |
| 17 | Clethodim | 1:48-24:1 | 1:16-8:1 | 1:6-2:1 |
| 17 | Clodinafop-propargyl | 1:20-56:1 | 1:6-19:1 | 1:2-4:1 |
| 17 | Clomazone | 1:384-3:1 | 1:128-1:1 | 1:48-1:6 |
| 17 | Clomeprop | 1:171-7:1 | 1:57-3:1 | 1:21-1:3 |
| 17 | Clopyralid | 1:192-6:1 | 1:64-2:1 | 1:24-1:3 |
| 17 | Cloransulam-methyl | 1:12-96:1 | 1:4-32:1 | 1:1-6:1 |
| 17 | Cumyluron | 1:384-3:1 | 1:128-1:1 | 1:48-1:6 |
| 17 | Cyanazine | 1:384-3:1 | 1:128-1:1 | 1:48-1:6 |
| 17 | Cyclopyrimorate | 1:17-68:1 | 1:5-23:1 | 1:2-5:1 |
| 17 | Cyclosulfamuron | 1:17-68:1 | 1:5-23:1 | 1:2-5:1 |
| 17 | Cycloxydim | 1:96-12:1 | 1:32-4:1 | 1:12-1:2 |
| 17 | Cyhalofop | 1:25-45:1 | 1:8-15:1 | 1:3-3:1 |
| 17 | Daimuron | 1:192-6:1 | 1:64-2:1 | 1:24-1:3 |
| 17 | Desmedipham | 1:322-4:1 | 1:107-2:1 | 1:40-1:5 |
| 17 | Dicamba | 1:192-6:1 | 1:64-2:1 | 1:24-1:3 |
| 17 | Dichlobenil | 1:1371-1:2 | 1:457-1:4 | 1:171-1:20 |
| 17 | Dichlorprop | 1:925-2:1 | 1:308-1:3 | 1:115-1:13 |
| 17 | Diclofop-methyl | 1:384-3:1 | 1:128-1:1 | 1:48-1:6 |
| 17 | Diclosulam | 1:10-112:1 | 1:3-38:1 | 1:1-7:1 |
| 17 | Difenzoquat | 1:288-4:1 | 1:96-2:1 | 1:36-1:4 |
| 17 | Diflufenican | 1:857-2:1 | 1:285-1:3 | 1:107-1:12 |
| 17 | Diflufenzopyr | 1:12-96:1 | 1:4-32:1 | 1:1-6:1 |
| 17 | Dimethachlor | 1:768-2:1 | 1:256-1:2 | 1:96-1:11 |
| 17 | Dimethametryn | 1:192-6:1 | 1:64-2:1 | 1:24-1:3 |
| 17 | Dimethenamid-P | 1:384-3:1 | 1:128-1:1 | 1:48-1:6 |
| 17 | Dithiopyr | 1:192-6:1 | 1:64-2:1 | 1:24-1:3 |
| 17 | Diuron | 1:384-3:1 | 1:128-1:1 | 1:48-1:6 |
| 17 | EPTC | 1:768-2:1 | 1:256-1:2 | 1:96-1:11 |
| 17 | Esprocarb | 1:1371-1:2 | 1:457-1:4 | 1:171-1:20 |
| 17 | Ethalfluralin | 1:384-3:1 | 1:128-1:1 | 1:48-1:6 |
| 17 | Ethametsulfuron-methyl | 1:17-68:1 | 1:5-23:1 | 1:2-5:1 |
| 17 | Ethoxyfen | 1:8-135:1 | 1:2-45:1 | 1:1-9:1 |
| 17 | Ethoxysulfuron | 1:20-56:1 | 1:6-19:1 | 1:2-4:1 |
| 17 | Etobenzanid | 1:257-5:1 | 1:85-2:1 | 1:32-1:4 |
| 17 | Fenoxaprop-ethyl | 1:120-10:1 | 1:40-4:1 | 1:15-1:2 |
| 17 | Fenoxasulfone | 1:85-14:1 | 1:28-5:1 | 1:10-1:2 |
| 17 | Fenquinotrione | 1:17-68:1 | 1:5-23:1 | 1:2-5:1 |
| 17 | Fentrazamide | 1:17-68:1 | 1:5-23:1 | 1:2-5:1 |
| 17 | Flazasulfuron | 1:17-68:1 | 1:5-23:1 | 1:2-5:1 |
| 17 | Florasulam | 1:2-420:1 | 1:1-140:1 | 2:1-27:1 |
| 17 | Fluazifop-butyl | 1:192-6:1 | 1:64-2:1 | 1:24-1:3 |
| 17 | Flucarbazone | 1:8-135:1 | 1:2-45:1 | 1:1-9:1 |
| 17 | Flucetosulfuron | 1:8-135:1 | 1:2-45:1 | 1:1-9:1 |
| 17 | Flufenacet | 1:257-5:1 | 1:85-2:1 | 1:32-1:4 |
| 17 | Flumetsulam | 1:24-48:1 | 1:8-16:1 | 1:3-3:1 |
| 17 | Flumiclorac-pentyl | 1:10-112:1 | 1:3-38:1 | 1:1-7:1 |
| 17 | Flumioxazin | 1:25-45:1 | 1:8-15:1 | 1:3-3:1 |
| 17 | Fluometuron | 1:384-3:1 | 1:128-1:1 | 1:48-1:6 |
| 17 | Flupyrsulfuron-methyl | 1:3-336:1 | 1:1-112:1 | 2:1-21:1 |
| 17 | Fluridone | 1:384-3:1 | 1:128-1:1 | 1:48-1:6 |
| 17 | Fluroxypyr | 1:96-12:1 | 1:32-4:1 | 1:12-1:2 |
| 17 | Flurtamone | 1:857-2:1 | 1:285-1:3 | 1:107-1:12 |
| 17 | Fluthiacet-methyl | 1:48-42:1 | 1:16-14:1 | 1:3-3:1 |
| 17 | Fomesafen | 1:96-12:1 | 1:32-4:1 | 1:12-1:2 |
| 17 | Foramsulfuron | 1:13-84:1 | 1:4-28:1 | 1:1-6:1 |
| 17 | Glufosinate | 1:288-4:1 | 1:96-2:1 | 1:36-1:4 |
| 17 | Glyphosate | 1:288-4:1 | 1:96-2:1 | 1:36-1:4 |
| 17 | Halauxifen | 1:20-56:1 | 1:6-19:1 | 1:2-4:1 |

TABLE A1-continued

| Component (a) (Compound #) | Component (b) | Typical Weight Ratio | More Typical Weight Ratio | Most Typical Weight Ratio |
|---|---|---|---|---|
| 17 | Halauxifen-methyl | 1:20-56:1 | 1:6-19:1 | 1:2-4:1 |
| 17 | Halosulfuron-methyl | 1:17-68:1 | 1:5-23:1 | 1:2-5:1 |
| 17 | Haloxyfop-methyl | 1:34-34:1 | 1:11-12:1 | 1:4-3:1 |
| 17 | Hexazinone | 1:192-6:1 | 1:64-2:1 | 1:24-1:3 |
| 17 | Imazamox | 1:13-84:1 | 1:4-28:1 | 1:1-6:1 |
| 17 | Imazapic | 1:20-56:1 | 1:6-19:1 | 1:2-4:1 |
| 17 | Imazapyr | 1:85-14:1 | 1:28-5:1 | 1:10-1:2 |
| 17 | Imazaquin | 1:34-34:1 | 1:11-12:1 | 1:4-3:1 |
| 17 | Imazethabenz-methyl | 1:171-7:1 | 1:57-3:1 | 1:21-1:3 |
| 17 | Imazethapyr | 1:24-48:1 | 1:8-16:1 | 1:3-3:1 |
| 17 | Imazosulfuron | 1:27-42:1 | 1:9-14:1 | 1:3-3:1 |
| 17 | Indanofan | 1:342-4:1 | 1:114-2:1 | 1:42-1:5 |
| 17 | Indaziflam | 1:25-45:1 | 1:8-15:1 | 1:3-3:1 |
| 17 | Iodosulfuron-methyl | 1:3-336:1 | 1:1-112:1 | 2:1-21:1 |
| 17 | Ioxynil | 1:192-6:1 | 1:64-2:1 | 1:24-1:3 |
| 17 | Ipfencarbazone | 1:85-14:1 | 1:28-5:1 | 1:10-1:2 |
| 17 | Isoproturon | 1:384-3:1 | 1:128-1:1 | 1:48-1:6 |
| 17 | Isoxaben | 1:288-4:1 | 1:96-2:1 | 1:36-1:4 |
| 17 | Isoxaflutole | 1:60-20:1 | 1:20-7:1 | 1:7-2:1 |
| 17 | Lactofen | 1:42-27:1 | 1:14-9:1 | 1:5-2:1 |
| 17 | Lenacil | 1:384-3:1 | 1:128-1:1 | 1:48-1:6 |
| 17 | Linuron | 1:384-3:1 | 1:128-1:1 | 1:48-1:6 |
| 17 | MCPA | 1:192-6:1 | 1:64-2:1 | 1:24-1:3 |
| 17 | MCPB | 1:288-4:1 | 1:96-2:1 | 1:36-1:4 |
| 17 | Mecoprop | 1:768-2:1 | 1:256-1:2 | 1:96-1:11 |
| 17 | Mefenacet | 1:384-3:1 | 1:128-1:1 | 1:48-1:6 |
| 17 | Mefluidide | 1:192-6:1 | 1:64-2:1 | 1:24-1:3 |
| 17 | Mesosulfuron-methyl | 1:5-224:1 | 1:1-75:1 | 1:1-14:1 |
| 17 | Mesotrione | 1:42-27:1 | 1:14-9:1 | 1:5-2:1 |
| 17 | Metamifop | 1:42-27:1 | 1:14-9:1 | 1:5-2:1 |
| 17 | Metazachlor | 1:384-3:1 | 1:128-1:1 | 1:48-1:6 |
| 17 | Metazosulfuron | 1:25-45:1 | 1:8-15:1 | 1:3-3:1 |
| 17 | Methabenzthiazuron | 1:768-2:1 | 1:256-1:2 | 1:96-1:11 |
| 17 | Metolachlor | 1:768-2:1 | 1:256-1:2 | 1:96-1:11 |
| 17 | Metosulam | 1:8-135:1 | 1:2-45:1 | 1:1-9:1 |
| 17 | Metribuzin | 1:192-6:1 | 1:64-2:1 | 1:24-1:3 |
| 17 | Metsulfuron-methyl | 1:2-560:1 | 1:1-187:1 | 3:1-35:1 |
| 17 | Molinate | 1:1028-2:1 | 1:342-1:3 | 1:128-1:15 |
| 17 | Napropamide | 1:384-3:1 | 1:128-1:1 | 1:48-1:6 |
| 17 | Napropamide-M | 1:192-6:1 | 1:64-2:1 | 1:24-1:3 |
| 17 | Naptalam | 1:192-6:1 | 1:64-2:1 | 1:24-1:3 |
| 17 | Nicosulfuron | 1:12-96:1 | 1:4-32:1 | 1:1-6:1 |
| 17 | Norflurazon | 1:1152-1:1 | 1:384-1:3 | 1:144-1:16 |
| 17 | Orbencarb | 1:1371-1:2 | 1:457-1:4 | 1:171-1:20 |
| 17 | Orthosulfamuron | 1:20-56:1 | 1:6-19:1 | 1:2-4:1 |
| 17 | Oryzalin | 1:514-3:1 | 1:171-1:2 | 1:64-1:8 |
| 17 | Oxadiargyl | 1:384-3:1 | 1:128-1:1 | 1:48-1:6 |
| 17 | Oxadiazon | 1:548-3:1 | 1:182-1:2 | 1:68-1:8 |
| 17 | Oxasulfuron | 1:27-42:1 | 1:9-14:1 | 1:3-3:1 |
| 17 | Oxaziclomefone | 1:42-27:1 | 1:14-9:1 | 1:5-2:1 |
| 17 | Oxyfluorfen | 1:384-3:1 | 1:128-1:1 | 1:48-1:6 |
| 17 | Paraquat | 1:192-6:1 | 1:64-2:1 | 1:24-1:3 |
| 17 | Pendimethalin | 1:384-3:1 | 1:128-1:1 | 1:48-1:6 |
| 17 | Penoxsulam | 1:10-112:1 | 1:3-38:1 | 1:1-7:1 |
| 17 | Penthoxamid | 1:384-3:1 | 1:128-1:1 | 1:48-1:6 |
| 17 | Pentoxazone | 1:102-12:1 | 1:34-4:1 | 1:12-1:2 |
| 17 | Phenmedipham | 1:102-12:1 | 1:34-4:1 | 1:12-1:2 |
| 17 | Picloram | 1:96-12:1 | 1:32-4:1 | 1:12-1:2 |
| 17 | Picolinafen | 1:34-34:1 | 1:11-12:1 | 1:4-3:1 |
| 17 | Pinoxaden | 1:25-45:1 | 1:8-15:1 | 1:3-3:1 |
| 17 | Pretilachlor | 1:192-6:1 | 1:64-2:1 | 1:24-1:3 |
| 17 | Primisulfuron-methyl | 1:8-135:1 | 1:2-45:1 | 1:1-9:1 |
| 17 | Prodiamine | 1:384-3:1 | 1:128-1:1 | 1:48-1:6 |
| 17 | Profoxydim | 1:42-27:1 | 1:14-9:1 | 1:5-2:1 |
| 17 | Prometryn | 1:384-3:1 | 1:128-1:1 | 1:48-1:6 |
| 17 | Propachlor | 1:1152-1:1 | 1:384-1:3 | 1:144-1:16 |
| 17 | Propanil | 1:384-3:1 | 1:128-1:1 | 1:48-1:6 |
| 17 | Propaquizafop | 1:48-24:1 | 1:16-8:1 | 1:6-2:1 |
| 17 | Propoxycarbazone | 1:17-68:1 | 1:5-23:1 | 1:2-5:1 |
| 17 | Propyrisulfuron | 1:17-68:1 | 1:5-23:1 | 1:2-5:1 |
| 17 | Propyzamide | 1:384-3:1 | 1:128-1:1 | 1:48-1:6 |
| 17 | Prosulfocarb | 1:1200-1:2 | 1:400-1:4 | 1:150-1:17 |
| 17 | Prosulfuron | 1:6-168:1 | 1:2-56:1 | 1:1-11:1 |
| 17 | Pyraclonil | 1:42-27:1 | 1:14-9:1 | 1:5-2:1 |
| 17 | Pyraflufen-ethyl | 1:5-224:1 | 1:1-75:1 | 1:1-14:1 |
| 17 | Pyrasulfotole | 1:13-84:1 | 1:4-28:1 | 1:1-6:1 |
| 17 | Pyrazolynate | 1:857-2:1 | 1:285-1:3 | 1:107-1:12 |

TABLE A1-continued

| Component (a) (Compound #) | Component (b) | Typical Weight Ratio | More Typical Weight Ratio | Most Typical Weight Ratio |
|---|---|---|---|---|
| 17 | Pyrazosulfuron-ethyl | 1:10-112:1 | 1:3-38:1 | 1:1-7:1 |
| 17 | Pyrazoxyfen | 1:5-224:1 | 1:1-75:1 | 1:1-14:1 |
| 17 | Pyribenzoxim | 1:10-112:1 | 1:3-38:1 | 1:1-7:1 |
| 17 | Pyributicarb | 1:384-3:1 | 1:128-1:1 | 1:48-1:6 |
| 17 | Pyridate | 1:288-4:1 | 1:96-2:1 | 1:36-1:4 |
| 17 | Pyriftalid | 1:10-112:1 | 1:3-38:1 | 1:1-7:1 |
| 17 | Pyriminobac-methyl | 1:20-56:1 | 1:6-19:1 | 1:2-4:1 |
| 17 | Pyrimisulfan | 1:17-68:1 | 1:5-23:1 | 1:2-5:1 |
| 17 | Pyrithiobac | 1:24-48:1 | 1:8-16:1 | 1:3-3:1 |
| 17 | Pyroxasulfone | 1:85-14:1 | 1:28-5:1 | 1:10-1:2 |
| 17 | Pyroxsulam | 1:5-224:1 | 1:1-75:1 | 1:1-14:1 |
| 17 | Quinclorac | 1:192-6:1 | 1:64-2:1 | 1:24-1:3 |
| 17 | Quizalofop-ethyl | 1:42-27:1 | 1:14-9:1 | 1:5-2:1 |
| 17 | Rimsulfuron | 1:13-84:1 | 1:4-28:1 | 1:1-6:1 |
| 17 | Saflufenacil | 1:25-45:1 | 1:8-15:1 | 1:3-3:1 |
| 17 | Sethoxydim | 1:96-12:1 | 1:32-4:1 | 1:12-1:2 |
| 17 | Simazine | 1:384-3:1 | 1:128-1:1 | 1:48-1:6 |
| 17 | Sulcotrione | 1:120-10:1 | 1:40-4:1 | 1:15-1:2 |
| 17 | Sulfentrazone | 1:147-8:1 | 1:49-3:1 | 1:18-1:3 |
| 17 | Sulfometuron-methyl | 1:34-34:1 | 1:11-12:1 | 1:4-3:1 |
| 17 | Sulfosulfuron | 1:8-135:1 | 1:2-45:1 | 1:1-9:1 |
| 17 | Tebuthiuron | 1:384-3:1 | 1:128-1:1 | 1:48-1:6 |
| 17 | Tefuryltrione | 1:42-27:1 | 1:14-9:1 | 1:5-2:1 |
| 17 | Tembotrione | 1:31-37:1 | 1:10-13:1 | 1:3-3:1 |
| 17 | Tepraloxydim | 1:25-45:1 | 1:8-15:1 | 1:3-3:1 |
| 17 | Terbacil | 1:288-4:1 | 1:96-2:1 | 1:36-1:4 |
| 17 | Terbuthylazine | 1:857-2:1 | 1:285-1:3 | 1:107-1:12 |
| 17 | Terbutryn | 1:192-6:1 | 1:64-2:1 | 1:24-1:3 |
| 17 | Thenylchlor | 1:85-14:1 | 1:28-5:1 | 1:10-1:2 |
| 17 | Thiazopyr | 1:384-3:1 | 1:128-1:1 | 1:48-1:6 |
| 17 | Thiencarbazone | 1:3-336:1 | 1:1-112:1 | 2:1-21:1 |
| 17 | Thifensulfuron-methyl | 1:5-224:1 | 1:1-75:1 | 1:1-14:1 |
| 17 | Tiafenacil | 1:17-68:1 | 1:5-23:1 | 1:2-5:1 |
| 17 | Thiobencarb | 1:768-2:1 | 1:256-1:2 | 1:96-1:11 |
| 17 | Topramezone | 1:6-168:1 | 1:2-56:1 | 1:1-11:1 |
| 17 | Tralkoxydim | 1:68-17:1 | 1:22-6:1 | 1:8-2:1 |
| 17 | Triallate | 1:768-2:1 | 1:256-1:2 | 1:96-1:11 |
| 17 | Triasulfuron | 1:5-224:1 | 1:1-75:1 | 1:1-14:1 |
| 17 | Triaziflam | 1:171-7:1 | 1:57-3:1 | 1:21-1:3 |
| 17 | Tribenuron-methyl | 1:3-336:1 | 1:1-112:1 | 2:1-21:1 |
| 17 | Triclopyr | 1:192-6:1 | 1:64-2:1 | 1:24-1:3 |
| 17 | Trifloxysulfuron | 1:2-420:1 | 1:1-140:1 | 2:1-27:1 |
| 17 | Trifluralin | 1:288-4:1 | 1:96-2:1 | 1:36-1:4 |
| 17 | Triflusulfuron-methyl | 1:17-68:1 | 1:5-23:1 | 1:2-5:1 |
| 17 | Tritosulfuron | 1:13-84:1 | 1:4-28:1 | 1:1-6:1 |

Table 42 is constructed the same as Table A1 above except that entries below the "Component (a)" column heading are replaced with the respective Component (a) Column Entry shown below. Compound 79 in the Component (a) column is identified in Index Table A. Thus, for example, in Table A2 the entries below the "Component (a)" column heading all recite "Compound 79" (i.e. Compound 79 identified in Index Table A), and the first line below the column headings in Table A2 specifically discloses a mixture of Compound 79 with 2,4-D. Tables A3 and 44 are constructed similarly.

| Table Number | Component (a) Column Entries |
|---|---|
| A2 | Compound 79 |
| A3 | Compound 80 |
| A4 | Compound 5 |
| A5 | Compound 3 |
| A6 | Compound 5 |
| A7 | Compound 80 |
| A8 | Compound 101 |
| A9 | Compound 103 |
| A10 | Compound 156 |
| A11 | Compound 202 |
| A12 | Compound 204 |
| A13 | Compound 206 |
| A14 | Compound 232 |
| A15 | Compound 263 |
| A16 | Compound 271 |
| A17 | Compound 304 |
| A18 | Compound 306 |
| A19 | Compound 315 |
| A20 | Compound 319 |
| A21 | Compound 323 |
| A22 | Compound 351 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of compounds of this invention on specific pathogens. The pathogen control protection afforded by the compounds is not limited, however, to these species. See Index Tables A-C for compound descriptions. The following abbreviations are used in the Index Tables which follow: Me is methyl, Ph is phenyl, OMe is methoxy, —CN is cyano, —NO$_2$ is nitro, t-Boc is tertiary-butoxycarbonyl, and TMS is trimethylsilyl. The abbreviation "Ex." stands for "Example" and is followed by a number indicating in which example the compound is prepared. Mass spectra are reported as the molecular weight of the highest isotopic abundance parent ion (M+1) formed by addition of H+(molecular weight of 1) to the molecule, or (M-1) formed by the loss of H+(molecular weight of 1) from the molecule, observed by using liquid chromatography coupled to a mass spectrometer (LCMS) using either atmospheric pressure chemical ionization (AP$^+$) or electrospray ionization (ESI$^+$).

INDEX TABLE A[(1)]

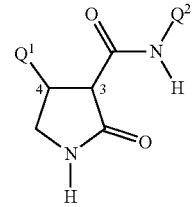

| Cmpd. No. | Q$^1$ | Q$^2$ | m.p. (° C.) | M − 1 | M + 1 |
|---|---|---|---|---|---|
| 1 | Ph(3-F) | Ph(2-F) | 317 | | |
| 2 | Ph(3-F) | Ph(2-CF$_3$) | 367 | | |
| 3 | Ph(3-CF$_3$) | Ph(2-F) | 367 | | |
| 4 | Ph(3-CF$_3$) | Ph(2-CF$_3$) | 417 | | |
| 5 | Ph(3,4-di-F) | Ph(2-F) | | | 335 |
| 6 | Ph(3,4-di-F) | Ph(2-CF$_3$) | | | 385 |
| 12 | Ph(3,4-di-F) | Ph(3-F) | | | 335 |
| 13 | Ph(3,4-di-F) | Ph(3-CF$_3$) | | | 385 |
| 14 | Ph(3,4-di-F) | Ph(2-F) | | 367 | |
| 15 | Ph(3,4-di-F) | Ph(2-CN) | | | 376 |
| 16 | Ph(4-F) | Ph(2-F) | | | 317 |
| 17 | Ph(3,4-di-F) | Ph(2,3-di-F) | 198-200 | | |
| 18 | Ph(3,4-di-F) | Ph(3-Cl) | 165-167 | | |
| 19 | Ph(3,4-di-F) | Ph(2-Me) | 158-160 | | |
| 20 | Ph(3,4-di-F) | Ph(2-NO$_2$) | 173-175 | | |
| 21 | Ph(3,4-di-F) | Ph(2-SO$_2$Me) | 203-205 | | |
| 22 | Ph(3,4-di-F) | 4-pyridinyl(2-F) | 210-212 | | |
| 23 | Ph(3,4-di-F) | Ph(2,4-di-F) | 188-190 | | |
| 25 | Ph(3,4-di-Cl) | Ph(2,3-di-F) | 171-173 | | |
| 26 | Ph(3,4-di-Cl) | Ph(2-CF$_3$) | 170-172 | | |
| 27 | Ph(3,4-di-Cl) | Ph(3-F) | 174-176 | | |
| 28 | 3-thienyl | Ph(2-CF$_3$) | 146-148 | | |
| 29 | 3-thienyl | Ph(2-F) | ** | | |
| 30 | Ph(3,4-di-F) | Ph | 184-186 | | |
| 31 | Ph(3,4-di-F) | 1H-pyrazol-3-yl(1-Me) | 181-183 | | |
| 32 | Ph(3,4-di-Cl) | Ph(2-OCF$_3$) | | 432 | |
| 33 | Ph(3,4,5-tri-F) | Ph(2-CF$_3$) | 160-162 | | |
| 34 | Ph(3,4,5-tri-F) | Ph(2-F) | 196-198 | | |
| 35 | Ph(3,4,5-tri-F) | Ph(2-Me) | 170-172 | | |
| 36 | Ph(3-OMe) | Ph(2-F) | | | 329 |
| 38 | Ph(3-Me) | Ph(2-F) | | | 313 |
| 39 | Ph(3,4-di-Cl) | Ph(2-NO$_2$) | 178-180 | | |
| 40 | Ph(3,4-di-Cl) | Ph(2-Me) | 194-196 | | |
| 41 | pyridin-3-yl(6-Cl) | Ph(2-F) | 200-204 | | |
| 42 | pyridin-3-yl(6-Cl) | Ph(2-CF$_3$) | | | |
| 43 | Ph(3,4-di-Cl) | Ph(2-SO$_2$Me) | 219-221 | | |
| 45 | Ph(3,4-di-F) | 2-pyridinyl | | 316 | 318 |
| 46 | Ph(3,4-di-F) | 3-pyridinyl(2-OMe) | | 346 | 348 |
| 47 | Ph(3,4-di-F) | 2-pyridinyl(1-oxido) | | | 334 |
| 48 | Ph(3,4,5-tri-F) | Ph(2,3-di-F) | | | 371 |
| 49 | Ph(3,4,5-tri-F) | Ph(3-NO$_2$) | | | 380 |
| 50 | Ph(2,4,5-tri-F) | Ph(2,3-di-F) | | | 371 |
| 51 | Ph(2,4,5-tri-F) | Ph(2-F) | | | 353 |
| 52 | Ph(3-F,4-Cl) | Ph(2,3-di-F) | | | 369 |
| 53 | Ph(3-F,4-Cl) | Ph(2-F) | | | 351 |
| 54 | Ph(3,4-di-F) | Ph(2-OCF$_3$) | | 399 | 401 |
| 55 | Ph(3,4-di-F) | Ph(2-Br) | | 393 | 395 |
| 56 | Ph(3,4-di-F) | Ph(3-Me) | | 329 | 331 |
| 57 | Ph(3,4-di-F) | 1,3-benzodioxol-4-yl(2,2-di-F) | | 395 | 397 |
| 58 | Ph(3,4-di-F) | 2-pyridinyl(6-OMe) | | 346 | 348 |
| 59 | Ph(3-Cl,4-F) | Ph(2,3-di-F) | | | 369 |
| 60 | Ph(3-Cl,4-F) | Ph(2-F) | | | 351 |
| 62 | 1,3-benzodioxol-5-yl(2,2-di-F) | Ph(2,3-di-F) | | | 397 |

-continued

INDEX TABLE A[(1)]

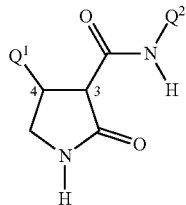

| Cmpd. No. | Q[1] | Q[2] | m.p. (° C.) | M − 1 | M + 1 |
|---|---|---|---|---|---|
| 63 | 1,3-benzodioxol-5-yl(2,2-di-F) | Ph(2-F) | | | 379 |
| 64 | Ph(3-Br) | Ph(2,3-di-F) | | | 395 |
| 65 | Ph | Ph(2,3-di-F) | | | 317 |
| 66 | Ph(3-Br) | Ph(2-F) | | | 377 |
| 67 | Ph(3,4-di-F) | Ph(2-CF$_3$,3-F) | | 401 | 403 |
| 68 | Ph(3-OCF$_3$) | Ph(2,3-di-F) | | | 401 |
| 69 | Ph(3-OCF$_3$) | Ph(2-F) | | | 383 |
| 70 | Ph(3-NH-t-Boc) | Ph(2,3-di-F) | | | 432 |
| 72 | Ph(3-CN) | Ph(2-F) | | | 324 |
| 73 | Ph(3-CN) | Ph(2,3-di-F) | | | 342 |
| 74 (Ex. 1) | Ph(3-Cl,4-F) | Ph(2-CF$_3$) | | | 401 |
| 75 | 1,3-benzodioxol-5-yl(2,2-di-F) | Ph(2-CF$_3$) | | | 429 |
| 76 | Ph(3-CF$_3$,4-F) | Ph(2-F) | | | 385 |
| 77 | Ph(3-CF$_3$,4-F) | Ph(2,3-di-F) | | | 403 |
| 78 | Ph(3-CF$_3$,4-F) | Ph(2-CF$_3$) | | | 435 |
| 79 | Ph(4-CF$_3$) | Ph(2-F) | | | 367 |
| 80 | Ph(4-CF$_3$) | Ph(2,3-di-F) | | | 385 |
| 81 | Ph | Ph(2-F) | 158-159 | | |
| 82 | Ph | Ph(2-CF$_3$) | 159-160 | | |
| 83 | Ph | Ph(2-Cl) | 154-155 | | |
| 84 | Ph | Ph(2-F,4-Br) | 184-186 | | |
| 85 | Ph(2-F) | Ph(2-F) | ** | | |
| 86 | Ph | Ph(2-CN) | ** | | |
| 87 | Ph(4-Cl) | Ph(2-F) | 189-192 | | |
| 88 | Ph(2-Cl) | Ph(2-F) | 163-165 | | |
| 89 | Ph(3-Cl) | Ph(2-F) | 164-166 | | |
| 90 | Ph(3,5-di-Cl) | Ph(2-F) | 199-203 | | |
| 91 | Ph(2,4-di-Cl) | Ph(2-F) | 192-194 | | |
| 96 | Ph(3,4-F) | 2-pyridin-6-one | | | 334 |
| 97 | Ph(3,4-F) | 3-pyridin-2-one | | | 334 |
| 98 | Ph(3,4-F) | 3-pyridinyl(2-CF$_3$) | 170-173 | | |
| 99 | Ph(3,4-F) | Ph(2-Cl) | 155-158 | | |
| 100 | Ph(3,4-F) | Ph(3-Cl,2-Me) | 198-201 | | |
| 101 | Ph(3,4-F) | Ph(2,3-di-F) | 170-172 | | |
| 102 (3S,4R) | Ph(3,4-F) | Ph(2-F) | 180-182 | | |
| 103 (3R,4S) | Ph(3,4-F) | Ph(2-F) | 179-181 | | |
| 104 | Ph(3,4-F) | Ph(3-Cl,2-F) | 196-198 | | |
| 105 | Ph(3,4-F) | 3-pyridinyl(2-F) | 171-174 | | |
| 106 | Ph(3,4-F) | Ph(3-F,2-Me) | 200-202 | | |
| 107 | Ph(3,4-F) | Ph(2,3-di-F) | 171-173 | | |
| 108 | Ph(3,4-F) | Ph(2-Cl,3-F) | 219-223 | | |
| 109 | Ph(3-CF$_3$) | Ph(2-Me) | 163-165 | | |
| 110 | Ph(3-CF$_3$) | 2-pyridinyl | 175-177 | | |
| 111 | Ph(3-CF$_3$) | 1,3,4-thiadiazol-2-yl | | | 357.3 |
| 112 | Ph(3-CF$_3$) | 1,3,4-thiadiazol-2-yl(5-CF$_3$) | | | 425.3 |
| 113 | Ph(3-CF$_3$) | 1,3-thiazol-2-yl(5-Cl) | | | 390.3 |
| 114 | Ph(3-CF$_3$) | oxazol-2-yl(5-Cl) | | | 408.4 |
| 115 | 2-naphthyl | Ph(2-F) | | | 349 |
| 116 | 2-naphthyl | Ph(2,3-di-F) | | | 367 |
| 117 | 2-naphthyl | Ph(2-CF$_3$) | | | 399 |
| 118 | Ph(4-F) | Ph(2-OCHF$_2$) | | 363.3 | |
| 119 | Ph(4-F) | Ph(2,3-di-F) | | | 335.3 |
| 120 | Ph(4-F) | Ph(2,3,4-tri-F) | | | 353.5 |

-continued

INDEX TABLE A[(1)]

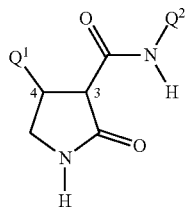

| Cmpd. No. | Q[1] | Q[2] | m.p. (° C.) | M − 1 | M + 1 |
|---|---|---|---|---|---|
| 121 | Ph(3-OCF$_2$CHF$_2$) | Ph(2-F) | | | 415 |
| 122 | Ph(3-OCF$_2$CHF$_2$) | Ph(2,4-di-F) | | | 433 |
| 123 | Ph(3-OCF$_2$CHF$_2$) | Ph(2,3-di-F) | | | 433 |
| 124 | Ph(3-OCF$_2$CHF$_2$) | Ph(2,3,4-tri-F) | | | 451 |
| 125 | Ph(3-OCF$_2$CHF$_2$) | Ph(2-Cl) | | | 431 |
| 126 | Ph(OCH$_2$CF$_3$) | Ph(2-F) | | | 397 |
| 127 | Ph(OCH$_2$CF$_3$) | Ph(2,4-di-F) | | | 415 |
| 128 | Ph(OCH$_2$CF$_3$) | Ph(2,3-di-F) | | | 415 |
| 129 | Ph(OCH$_2$CF$_3$) | Ph(2,3,4-tri-F) | | | 433 |
| 130 | Ph(OCH$_2$CF$_3$) | Ph(2-Cl) | | | 413 |
| 131 | Ph(3-OMe,4-F) | Ph(2,4-di-F) | | | 365 |
| 132 | Ph(3-OMe,4-F) | Ph(2,3,4-tri-F) | | | 383 |
| 133 | Ph(3-OMe,4-F) | Ph(2-Cl) | | | 363 |
| 134 | Ph(3-SO$_2$Me) | Ph(2-F) | | | 377 |
| 135 | Ph(3-SO$_2$Me) | Ph(2,3-di-F) | | | 395 |
| 136 | Ph(3-SO$_2$Me) | Ph(2,3-di-F) | | | 395 |
| 137 | Ph(3-SO$_2$Me) | Ph(2,3,4-tri-F) | | | 413 |
| 138 | Ph(3-SO$_2$Me) | Ph(2-Cl) | | | 393 |
| 139 | Ph(4-F,3-Me) | Ph(2-F) | | | 331 |
| 140 | Ph(4-F,3-Me) | Ph(2,4-di-F) | | | 349 |
| 141 | Ph(4-F,3-Me) | Ph(2,3-di-F) | | | 349 |
| 142 | Ph(4-F,3-Me) | Ph(2,3,4-tri-F) | | | 367 |
| 143 | Ph(4-F,3-Me) | Ph(2-Cl) | | | 347 |
| 144 | Ph(3-F,4-Me) | Ph(2-F) | | | 331 |
| 145 | Ph(3-F,4-Me) | Ph(2,4-di-F) | | | 349 |
| 146 | Ph(3-F,4-Me) | Ph(2,3-di-F) | | | 349 |
| 147 | Ph(3-F,4-Me) | Ph(2,3,4-tri-F) | | | 367 |
| 148 | Ph(3-F,4-Me) | Ph(2-Cl) | | | 347 |
| 149 | Ph(4-Me) | Ph(2-F) | | | 313 |
| 150 | Ph(4-Me) | Ph(2,4-di-F) | | | 331 |
| 151 | Ph(4-Me) | Ph(2,3-di-F) | | | 331 |
| 152 | Ph(4-Me) | Ph(2-Cl) | | | 329 |
| 153 | Ph(4-Me) | Ph(3-F) | | | 313 |
| 154 | Ph(3-CF$_3$) | Ph(2-Cl) | | | 397.5 |
| 155 | Ph(3,5-di-F) | Ph(2-F) | | | 335 |
| 156 | Ph(3,5-di-F) | Ph(2,4-di-F) | | | 353 |
| 157 | Ph(3,5-di-F) | Ph(2,3-di-F) | | | 353 |
| 158 | Ph(3,5-di-F) | Ph(2,3,4-tri-F) | | | 371 |
| 159 | Ph(3,5-di-F) | Ph(2-Cl) | | | 351 |
| 160 | Ph(3-CF$_3$) | Ph(2-SO$_2$Me) | | | 427 |
| 161 | 1,3-benzodioxol-5-yl(2,2-di-F) | Ph(2-F) | | | 379 |
| 162 | 1,3-benzodioxol-5-yl(2,2-di-F) | Ph(2,3,4-tri-F) | | | 415 |
| 163 | Ph(3-CHF$_2$) | Ph(2-F) | | | 349 |
| 164 | Ph(3-CHF$_2$) | Ph(2,3-di-F) | | | 367 |
| 165 | Ph(3-CHF$_2$) | Ph(2,3,4-tri-F) | | | 385 |
| 166 | Ph(3-c-Pr) | Ph(2-F) | | | 339 |
| 167 | Ph(3-c-Pr) | Ph(2,3-di-F) | | | 357 |
| 168 | Ph(3-c-Pr) | Ph(2,3,4-tri-F) | | | 375 |
| 169 | Ph(3-Et) | Ph(2-F) | | | 327 |
| 170 | Ph(3-Et) | Ph(2,3-di-F) | | | 345 |
| 171 | Ph(3-Et) | Ph(2,3,4-tri-F) | | | 363 |
| 172 | Ph(4-OCF$_2$CHF$_2$) | Ph(2,3-di-F) | | | 433 |
| 173 | Ph(4-OCF$_2$CHF$_2$) | Ph(2,4-di-F) | | | 433 |
| 174 | Ph(4-OCF$_2$CHF$_2$) | Ph(2,3,4-di-F) | | | 451 |
| 176 | Ph(4-Cl) | Ph(2,3-di-F) | | | 351 |
| 177 | Ph(4-Cl) | Ph(2,4-di-F) | | | 351 |
| 178 | Ph(4-Cl) | Ph(2-F) | | | 333 |
| 179 | Ph(4-Cl) | Ph(3-F) | | | 333 |
| 180 | Ph(4-Cl) | Ph(2-Cl) | | | 350 |

-continued

INDEX TABLE A[(1)]

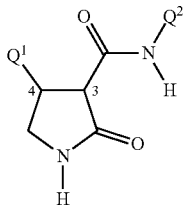

| Cmpd. No. | $Q^1$ | $Q^2$ | m.p. (° C.) | M − 1 | M + 1 |
|---|---|---|---|---|---|
| 183 | Ph(3-CF$_3$) | Ph(2-F,5-Me) | | | 381 |
| 184 | Ph(3-CF$_3$) | Ph(2-F,3-Me) | | | 381 |
| 185 | Ph(3-CF$_3$) | Ph(4-F,3-Me) | | | 381 |
| 186 | Ph(3-CF$_3$) | Ph(5-CF$_3$,4-Me) | | | 431 |
| 187 | Ph(3-CF$_3$) | Ph(4-OMe,2-F) | | | 397 |
| 188 | Ph(3-CF$_3$) | Ph(4-OMe,3-F) | | | 397 |
| 189 | Ph(3-CF$_3$) | Ph(2-Cl) | | | 383 |
| 190 | Ph(3-CF$_3$) | Ph(2-Br) | | | 428.9 |
| 191 | 1H-pyrazol-3-yl(1-Me) | Ph(2-CF$_3$) | 141-143 | | |
| 192 | 1H-pyrazol-3-yl(1-Me) | Ph(2,3-di-F) | 188-190 | | |
| 193 | Ph(3,4-di-F) | Ph(4-F) | 162-164 | | |
| 194 | Ph(3-OMe,4-F) | Ph(2-F) | | | 347 |
| 195 | Ph(3-OMe,4-F) | Ph(2,3-di-F) | | | 365 |
| 196 | Ph(3-OMe,4-F) | Ph(2-CF$_3$) | | | 397 |
| 197 | Ph(4-OMe,3-F) | Ph(2-F) | | | 347 |
| 198 | Ph(4-OMe,3-F) | Ph(2,3-di-F) | | | 365 |
| 199 | Ph(4-OMe,3-F) | Ph(2-CF$_3$) | | | 397 |
| 200 | Ph(3-t-Bu) | Ph(2,3-di-F) | | | 373 |
| 201 | Ph(3-t-Bu) | Ph(2-CF$_3$) | | | 405 |
| 202 | Ph(4-CF$_3$) | Ph(2,3-di-F) | | | 385.5 |
| 203 (3S,4R) | Ph(3-CF$_3$) | Ph(2-F) | 138-140 | | |
| 204 (3R,4S) | Ph(3-CF$_3$) | Ph(2-F) | 135-137 | | |
| 205 (3S,4R) | Ph(3-CF$_3$) | Ph(2,3-di-F) | 121-123 | | |
| 206 (3R,4S) | Ph(3-CF$_3$) | Ph(2,3-di-F) | 120-122 | | |
| 207 | Ph(3-CF$_3$) | Ph(2,4-di-F) | 164-166 | | |
| 208 | Ph(3-CF$_3$) | Ph(3-F) | 123-125 | | |
| 209 | Ph(3-CF$_3$,4-OCH$_3$) | Ph(2-F) | | | 397 |
| 210 | Ph(3-CHF$_2$) | Ph(2-F) | | | 349 |
| 211 | Ph(3-CHF$_2$) | Ph(2,3-di-F) | | | 367 |
| 212 | Ph(3-CHF$_2$) | Ph(2-CF$_3$) | | | 399 |
| 213 | Ph(3-SF$_5$) | Ph(2-F) | | | 425 |
| 214 | Ph(3-SF$_5$) | Ph(2,3-di-F) | | | 443 |
| 215 | Ph(3-SF$_5$) | Ph(2-CF$_3$) | | | 475 |
| 216 | naphthalen-1-yl | Ph(2-F) | | | 349 |
| 217 | Ph(4-Cl) | Ph(2-F) | | | 333 |
| 218 | Ph(4-Cl) | Ph(2,3-di-F) | | | 351 |
| 219 | Ph(4-Cl) | Ph(2-CF$_3$) | | | 383 |
| 220 | Ph(4-Cl) | Ph(2-Cl) | | | 349 |
| 221 | Ph(4-Cl) | Ph(2,3-di-Cl) | | | 383 |
| 222 | Ph(3-OCHF$_2$) | Ph(2-CF$_3$) | | | 415.1 |
| 223 | Ph(3-OCHF$_2$) | Ph(2-F) | | | 365.1 |
| 224 | Ph(3-OCHF$_2$) | Ph(2,3-di-F) | | | 383.1 |
| 225 | Ph(4-OCHF$_2$) | Ph(2-Br) | | | 427 |
| 226 | Ph(4-OCHF$_2$) | Ph(2-Cl) | | | 381 |
| 227 | Ph(4-OCHF$_2$) | Ph(2-Me) | | | 361.1 |
| 228 | Ph(3-OCHF$_2$) | Ph(2-Br) | | | 427 |
| 229 | Ph(3-OCHF$_2$) | Ph(2-Cl) | | | 381.1 |
| 230 | Ph(3-OCHF$_2$) | Ph(2-Me) | | | 361.1 |
| 231 (3R,4S) | Ph(4-CF$_3$) | Ph(2-F) | | | 367.5 |
| 232 | Ph(4-CF$_3$) | Ph(2,3,4-tri-F) | | | 403.5 |
| 233 | Ph(4-CF$_3$) | Ph(2-Cl) | | | 383.5 |
| 234 | Ph(3-CF$_3$,4-OMe) | Ph(2,3-di-F) | | | 415 |
| 235 | Ph(4-Ph(2-F)) | Ph(2,3-di-F) | 131.6-136.5 | | |
| 236 | Ph(4-Ph(2-CF$_3$)) | Ph(2,3-di-F) | 177.9-191.1 | | |
| 237 | Ph(3-Ph(2-CF$_3$)) | Ph(2-CF$_3$) | 57.1-66.2 | | |
| 238 | Ph(3-Ph(2-F)) | Ph(2-CF$_3$) | 152.7-157.5 | | |
| 239 | Ph(4-F) | Ph(2-F) | | | 317.4 |
| 240 | Ph(3-CF$_3$,4-OMe) | Ph(2-CF$_3$) | | | 447 |

-continued

INDEX TABLE A[(1)]

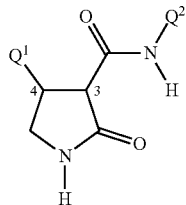

| Cmpd. No. | Q[1] | Q[2] | m.p. (° C.) | M − 1 | M + 1 |
|---|---|---|---|---|---|
| 241 | Ph(3-CF$_3$) | Ph(2,3-di-F) | | | 385 |
| 242 | Ph(3-CF$_3$) | Ph(2-CF$_3$,3-F) | | | 436 |
| 244 | Ph(3,4-di-F) | 2-pyridinyl(6-F) | | | 337.3 |
| 245 | Ph(3,4-di-F) | 2-pyridinyl(6-CF$_3$) | | | 386.4 |
| 246 | Ph(4-CF$_3$,3-F) | Ph(2-F) | | | 385 |
| 247 | Ph(4-CF$_3$,3-F) | Ph(2,3-di-F) | | | 403 |
| 248 | Ph(4-CF$_3$,3-F) | Ph(2-CF$_3$) | | | 435 |
| 249 | Ph(4-CF$_3$,3-Cl) | Ph(2-F) | | | 401 |
| 250 | Ph(4-CF$_3$,3-Cl) | Ph(2,3-di-F) | | | 419 |
| 251 | Ph(4-CF$_3$,3-Cl) | Ph(2-CF$_3$) | | | 451 |
| 252 | 1H-imidazol-2-yl(1-Me) | Ph(2,3-di-F) | 170-174 | | |
| 253 | 1H-pyrazol-4-yl(1-Me) | Ph(2,3-di-F) | 165-168 | | |
| 254 | 1H-pyrazol-4-yl(1-Me) | Ph(2-F) | 189-193 | | |
| 255 | 1H-imidazol-2-yl(1-Me) | Ph(2-F) | 167-170 | | |
| 256 | Ph(4-OCF$_3$) | Ph(2-F) | | | 383 |
| 257 | Ph(4-OCF$_3$) | Ph(2,3-di-F) | | | 401 |
| 258 | Ph(4-OCF$_3$) | Ph(2-CF$_3$) | | | 433 |
| 259 | Ph(4-CF$_3$,2-F) | Ph(2-F) | | | 385 |
| 260 | Ph(4-CF$_3$,2-F) | Ph(2,3-di-F) | | | 403 |
| 261 | Ph(4-CF$_3$,2-F) | Ph(2-CF$_3$) | | | 435 |
| 262 | 3-pyridinyl(6-CF$_3$) | Ph(2-F) | | | 368 |
| 263 | 3-pyridinyl(6-CF$_3$) | Ph(2,3-di-F) | | | 386 |
| 264 | 3-pyridinyl(6-CF$_3$) | Ph(2-CF$_3$) | | | 418 |
| 267 | Ph(3-CF$_3$,4-Cl) | Ph(2-F) | | | 401 |
| 268 | Ph(3-CF$_3$,4-Cl) | Ph(2,3-di-F) | | | 419 |
| 269 | Ph(3-CF$_3$,4-Cl) | Ph(2-CF$_3$) | | | 451 |
| 272 | Ph(3,4-di-Cl) | Ph(2,4-di-F) | | | 385 |
| 273 | Ph(3,4-di-Cl) | Ph(2-Cl) | | | 383 |
| 275 | Ph(3-Cl) | Ph(2,3-di-F) | | | 351.4 |
| 278 | Ph(3,5-di-F) | Ph(2,4-di-F) | | | 353 |
| 279 | Ph(3,5-di-F) | Ph(2,3-di-F) | | | 353 |
| 280 | Ph(3,5-di-F) | Ph(2-Cl) | | | 351 |
| 281 | 2-benzofuranyl | Ph(2-F) | | | 339 |
| 282 | 2-benzofuranyl | Ph(2,3-di-F) | | | 357 |
| 283 | 2-benzofuranyl | Ph(2-CF$_3$) | | | 389 |
| 284 | 2-furanyl(5-Cl) | Ph(2-F) | | | 323 |
| 285 | 2-furanyl(5-Cl) | Ph(2,3-di-F) | | | 341 |
| 286 | Ph(3,4-di-Cl) | Ph(2,3,4-tri-F) | | | 403 |
| 287 | Ph(3-SMe) | Ph(2-F) | | | 345 |
| 288 | Ph(3-SMe) | Ph(2,4-di-F) | | | 363 |
| 289 | Ph(3-SMe) | Ph(2,3-di-F) | | | 363 |
| 290 | Ph(3-SMe) | Ph(2,3,4-tri-F) | | | 381 |
| 291 | Ph(3-SMe) | Ph(2-Cl) | | | 361 |
| 292 | 2-thienyl(5-Cl) | Ph(2-F) | | | 339 |
| 293 | 2-thienyl(5-Cl) | Ph(2-CF$_3$) | | | 389 |
| 294 | 2-thienyl(5-Cl) | Ph(2,3-di-F) | | | 357 |
| 295 | 2-benzothiophenyl | Ph(2-F) | | | 355 |
| 296 | 2-benzothiophenyl | Ph(2,3-di-F) | | | 373 |
| 297 | 2-benzothiophenyl | Ph(2-CF$_3$) | | | 405 |
| 298 | 1H-pyrazol-4-yl(1-CH$_2$CF$_3$) | Ph(2-F) | | | 371 |
| 299 | 1H-pyrazol-4-yl(1-CH$_2$CF$_3$) | Ph(2,3-di-F) | | | 389 |
| 300 | 1H-pyrazol-4-yl(1-CH$_2$CF$_3$) | Ph(2-CF$_3$) | | | 421 |
| 307 | Ph(3-Br) | Ph(2-F) | | | 378 |
| 308 | Ph(3-Br) | Ph(2,4-di-F) | | 394 | |
| 309 | Ph(3-Br) | Ph(2,3-di-F) | | | 396 |
| 310 | Ph(3-Br) | Ph(2,3,4-tri-F) | | 412 | |
| 311 | Ph(3-Br) | Ph(2-Cl) | | | 394 |
| 312 | Ph(3-CF$_3$) | Ph(2-Cl) | | | 383 |
| 313 | Ph(3-CF$_3$) | Ph(3-CF$_3$) | | | 417 |

INDEX TABLE A[(1)]

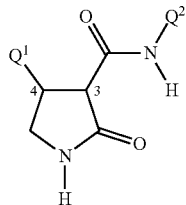

| Cmpd. No. | Q¹ | Q² | m.p. (° C.) | M − 1 | M + 1 |
|---|---|---|---|---|---|
| 314 | Ph(3-CF₃) | Ph(2,5-di-F) | | | 385 |
| 315 | Ph(3-CF₃) | Ph(2,3,4-tri-F) | | | 403 |
| 316 | Ph(3-CF₃) | Ph(3-Cl,2-F) | | | 401 |
| 317 | Ph(3-CF₃) | Ph(3-Me) | | | 363 |
| 318 | Ph(3-i-Pr) | Ph(2-F) | | | 341 |
| 319 | Ph(3-i-Pr) | Ph(2,3-di-F) | | | 359 |
| 320 | Ph(3-i-Pr) | Ph(2-CF₃) | | | 391 |
| 321 | Ph(4-SCF₃) | Ph(2-F) | | | 399 |
| 322 | Ph(4-SCF₃) | Ph(2,3,4-tri-F) | | | 435 |
| 323 | Ph(3-OCHF₂) | Ph(2-F) | | | 365 |
| 324 | Ph(3-OCHF₂) | Ph(2,3-di-F) | | | 383 |
| 325 | Ph(3-OCHF₂) | Ph(2,3,4-tri-F) | | | 401 |
| 326 | Ph(3-(1H-pyrazol-1-yl(3-CF₃))) | Ph(2,3-di-F) | 190.8-193.9 | | |
| 327 | Ph(3-I) | Ph(2,3-di-F) | 152.7-160.9 | | |
| 328 | Ph(3-I) | Ph(2-CF₃) | 106.8-110.4 | | |
| 329 | Ph(3-(1H-pyrazol-1-yl(3-CF₃))) | Ph(2-CF₃) | 174.8-179.8 | | |
| 330 | Ph(3-OPh) | Ph(2-F) | | | 391 |
| 331 | Ph(3-OPh) | Ph(2,4-di-F) | | | 409 |
| 332 | Ph(3-OPh) | Ph(2,3-di-F) | | | 409 |
| 333 | Ph(3-OPh) | Ph(2,3,4-tri-F) | | | 427 |
| 334 | Ph(3-OPh) | Ph(2-Cl) | | | 407 |
| 337 | Ph(3-(1H-pyrazol-1-yl)) | Ph(2,3-di-F) | | | 383.5 |
| 338 | Ph(3-(1H-pyrazol-1-yl)) | Ph(2-CF₃) | | | 415.5 |
| 339 | Ph(3,4-di-Br) | Ph(2-F) | | | 457 |
| 340 | Ph(3,4-di-Br) | Ph(2,4-di-F) | | | 475 |
| 341 | Ph(3,4-di-Br) | Ph(2,3-di-F) | | | 475 |
| 342 | Ph(3,4-di-Br) | Ph(2,3,4-tri-F) | | | 493 |
| 343 | Ph(3,4-di-Br) | Ph(2-Cl) | | | 473 |
| 344 | Ph(3-CF₃) | Ph(3-Cl,2-F) | 155-156 | | |
| 345 | Ph(3-CF₃) | Ph(2,3,4-tri-F) | 156158 | | |
| 346 | Ph(3,4-di-F) | Ph(2,3,4-tri-F) | 205-207 | | |
| 347 | Ph(3-t-Bu) | Ph(2-F) | | | 355 |
| 348 | Ph(4-OCHF₂) | Ph(2-CF₃) | 143-144 | | |
| 349 | Ph(4-OCHF₂) | Ph(2-F) | 161-162 | | |
| 350 | Ph(4-OCHF₂) | Ph(2,3-di-F) | 167-168 | | |

[(1)]Substituents in the 3 and 4 positions of the pyrrolidinone ring, i.e. C(O)N(Q²)(R⁶) and Q¹, respectively, are predominately in the trans configuration. In some instances the presence of minor amounts of the cis isomer can be detected by NMR.
*See synthesis example for ¹H NMR data.
**See Index Table D for ¹H NMR data.

INDEX TABLE B

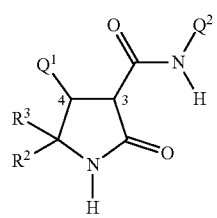

| Cmpd. No. | R² | R³ | Q¹ | Q² | M + 1 |
|---|---|---|---|---|---|
| 7 (Diastereomer Mixture A) | Me | H | Ph(3,4-di-F) | Ph(2-F) | 349 |
| 8 (Diastereomer Mixture B) | Me | H | Ph(3,4-di-F) | Ph(2-F) | 349 |
| 9 (Diastereomer Mixture A) | Me | H | Ph(3,4-di-F) | Ph(2-CF₃) | 399 |

INDEX TABLE B -continued

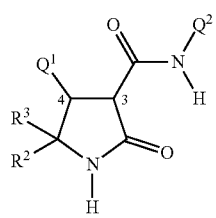

| Cmpd. No. | R² | R³ | Q¹ | Q² | M + 1 |
|---|---|---|---|---|---|
| 10 (Diastereomer Mixture B) | Me | H | Ph(3,4-di-F) | Ph(2-CF₃) | 399 |
| 11 | Me | Me | Ph(3,4-di-F) | Ph(2-F) | 363 |

INDEX TABLE C

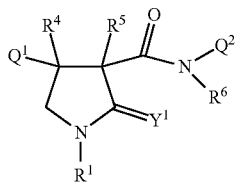

| Cmpd. No. | R¹ | Q¹ | R⁴ | R⁵ | R⁶ | Q² | Y¹ | m.p. (° C.) | M − 1 | M + 1 |
|---|---|---|---|---|---|---|---|---|---|---|
| 24 | H | Ph(3,4-di-F) | H | H | Me | Ph(2-F) | O | 171-172 | | |
| 37 | t-Boc | Ph(3-Me) | H | H | H | Ph(2-F) | O | 70.2-73.4 | | |
| 44 (Ex. 3) | OH | Ph(3,4-di-F) | H | H | H | Ph(2-F) | O | | 351 | |
| 61 | H | Ph(3-Cl,4-F) | H | Me | H | Ph(2,3-di-F) | O | | | 383 |
| 71 | H | Ph(3,4-di-F) | H | H | OH | Ph | O | | 331 | |
| 92 (Ex. 2) | H | Ph | H | Br | H | Ph(2-F) | O | * | | |
| 93 (Ex. 2) | H | Ph | Br | H | H | Ph(2-F) | O | * | | |
| 94 | H | Ph | H | Br | H | Ph(2-F,4-Br) | O | ** | | |
| 95 (Ex. 4) | H | Ph(3,4-di-F) | H | H | H | Ph(2-F) | NH | * | | |
| 175 | H | Ph(3,4-F) | H | H | OMe | Ph(2-F,5-NO₂) | O | 170-175 | | |
| 181 | n-Pr | Ph(4-CF₃) | H | H | H | Ph(2-F) | O | | 409.5 | |
| 182 | n-Pr | Ph(4-CF₃) | H | H | H | Ph(2,3-di-F) | O | | | 427.5 |
| 243 | H | Ph(3,4-di-F) | H | H | OMe | Ph(2-NO₂) | O | 155-159 | | |
| 265 | H | Ph(3,4-di-F) | H | H | propargyl | Ph(2-NO₂) | O | 226-230 | | |
| 266 | H | Ph(3,4-di-F) | H | H | allyl | Ph(2-NO₂) | O | 206-210 | | |
| 270 | Me | Ph(4-F) | H | H | H | Ph(2-F) | O | | | 331 |
| 271 | Me | Ph(4-F) | H | H | H | Ph(2,3-di-F) | O | | | 349 |
| 274 | H | Ph(3-CF₃) | H | H | H | Ph(2-F) | S | | | 383 |
| 276 | i-Pr | Ph(4-F) | H | H | H | Ph(2,3-di-F) | O | | | 377.5 |
| 277 | Me | Ph(3-CF₃) | H | H | H | Ph(2-F) | O | | | 381.5 |
| 301 | H | Ph | CH₃ | H | H | Ph(2-F) | O | | | 313.1 |
| 302 | Me | Ph(3,4-di-F) | H | H | H | Ph(2-F) | O | | | 349.3 |
| 303 | Me | Ph(3,4-di-F) | H | H | H | Ph(2,3-di-F) | O | | | 367.3 |
| 304 | Me | Ph(4-CF₃) | H | H | H | Ph(2-F) | O | | | 381.5 |
| 305 | Me | Ph(3-CF₃) | H | H | H | Ph(2,3-di-F) | O | | | 399.5 |
| 306 | Me | Ph(4-CF₃) | H | H | H | Ph(2,3-di-F) | O | | | 399.5 |
| 335 | Et | Ph(4-CF₃) | H | H | H | Ph(2-F) | O | | | 395 |
| 336 | Et | Ph(4-CF₃) | H | H | H | Ph(2,3-di-F) | O | | | 413 |
| 351 (3S,4S) (Ex. 6) | Me | Ph(3-CF₃) | H | H | H | Ph(2-F) | O | * | | |

*See synthesis example for ¹H NMR data.
**See Index Table D for ¹H NMR data.

INDEX TABLE D

| Cmpd. No. | ¹H NMR Data (CDCl₃ solution unless indicated otherwise)ᵃ |
|---|---|
| 29 | δ 9.65 (br s, 1H), 8.28 (m, 1H), 7.37 (m, 1H), 7.25 (m, 1H), 7.10 (m, 4H), 6.18 (br s, 1H), 4.36 (m, 1H), 3.84 (m, 1H), 3.53 (m, 2H). |
| 85 | δ 9.80 (brs, 1H), 8.25 (t, 1H), 7.40 (t, 1H), 7.25 (m, 1H), 7.15 (m, 1H), 7.05 (m, 4H), 6.35 (br s, 1H), 4.10 (q, 1H), 3.80 (m, 2H), 3.50 (t, 1H). |
| 86 | δ 10.3 (br s, 1H), 8.20 (br s, 1H), 7.80 (d, 1H), 7.70 (d, 1H), 7.65 (t, 1H), 7.40-7.20 (m, 6H), 4.00 (q, 1H), 3.85 (d, 1H), 3.70 (t, 1H), 3.30 (t, 1H) |
| 94 | δ 9.55 (br s, 1H), 8.25 (t, 1H), 7.48 (d, 2H), 7.38 (m, 3H), 7.11 (m, 3H), 6.85 (br s, 1H), 4.45 (m, 1H), 3.77 (m, 1H), 3.65 (m, 1H). |

ᵃ¹H NMR data are in ppm downfield from tetramethylsilane. Couplings are designated by (s)—singlet, (d)—doublet, (t)—triplet, (m)—multiplet, (br s)—broad singlet.

Biological Examples of the Invention

Test A

Seeds of plant species selected from barnyardgrass (*Echinochloa crus-galli*), kochia (*Kochia scoparia*), ragweed (common ragweed, *Ambrosia elatior*) ryegrass, Italian (Italian ryegrass, *Lolium multiflorum*), crabgrass, large (large crabgrass *Digitaria sanguinalis*), giant foxtail (*Setaria faberii*), morningglory (*Ipomoea* spp.), pigweed (*Amaranthus retrolexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in anon-phytotoxic solvent mixture which included a surfactant.

At the same time, plants selected from these crop and weed species and also blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| Postemergence |
| --- |

| | 1000 g ai/ha Compounds | | | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- | --- |
| | 17 | 18 | 19 | 20 | 21 | 22 | 23 | 24 | 25 | 26 | 27 | 30 | 31 | 33 | 34 | 35 | 39 | 40 | 43 | 44 | 71 | 96 | 98 | 99 | 100 | 104 |
| Barnyardgrass | 90 | 50 | 90 | 80 | 90 | 0 | 90 | 0 | 80 | 70 | 70 | 90 | 60 | 90 | 90 | 90 | 50 | 80 | 40 | 60 | 50 | 0 | 50 | 90 | 80 | 80 |
| Blackgrass | — | — | — | — | — | — | — | — | — | — | — | — | — | — | — | — | — | — | — | — | — | — | — | — | — | — |
| Corn | 60 | 0 | 0 | 0 | 0 | 0 | 0 | 0 | 0 | 0 | 0 | 0 | 30 | 40 | 50 | 20 | 0 | 20 | 0 | 0 | 0 | 0 | 0 | 20 | 40 | 0 |
| Crabgrass, Large | 90 | 70 | 90 | 90 | 80 | 0 | 80 | 30 | 80 | 60 | 70 | 80 | 20 | 90 | 90 | 90 | 80 | 90 | 20 | 50 | 80 | 0 | 90 | 90 | 90 | 80 |
| Foxtail, Giant | 90 | 70 | 80 | 80 | 80 | 0 | 80 | 0 | 90 | 70 | 60 | 80 | 20 | 90 | 90 | 90 | 70 | 90 | 50 | 30 | 60 | 0 | 60 | 90 | 80 | 70 |
| Galium | — | — | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 10 | 0 | 0 | 0 | 0 | 20 | 20 | 0 | 10 | 10 | 10 | 0 | — | 0 | 0 | 10 | 0 | 0 |
| Pigweed | 40 | 0 | 0 | 0 | — | 0 | 0 | 0 | 0 | 0 | 0 | 0 | 0 | 0 | 0 | 0 | 50 | 0 | 20 | 0 | 0 | 0 | 0 | 0 | 0 | 0 |
| Ragweed | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — |
| Velvetleaf | 50 | 0 | 10 | 0 | 60 | 0 | 40 | 0 | 10 | 0 | 0 | 0 | 0 | 20 | 20 | 0 | 10 | 0 | 30 | 0 | 0 | 0 | 10 | 10 | 0 | 10 |
| Wheat | 60 | 0 | 30 | 20 | 30 | 0 | 0 | 0 | 0 | 0 | 0 | 0 | 0 | 60 | 70 | 40 | 40 | 20 | 0 | 0 | 0 | 0 | 20 | 20 | 30 | 0 |

| | 1000 g ai/ha Compounds | | | | | | | | | | | | | | | 500 g ai/ha Compounds | | |
| --- | --- | --- | --- | --- | --- | --- | --- | --- | --- | --- | --- | --- | --- | --- | --- | --- | --- | --- |
| | 105 | 106 | 108 | 191 | 192 | 193 | 237 | 238 | 243 | 252 | 253 | 254 | 255 | 265 | 266 | 274 | 1 | 2 | 3 |
| Barnyardgrass | 90 | 90 | 90 | 0 | 0 | 90 | 20 | 30 | 60 | 0 | 0 | 0 | 0 | 0 | 0 | 90 | 80 | 60 | 80 |
| Blackgrass | — | — | — | — | — | — | 0 | 20 | — | — | — | — | — | — | — | 50 | — | — | — |
| Corn | 0 | 50 | 0 | 0 | 0 | 0 | 0 | 0 | 0 | 0 | 0 | 0 | 0 | 0 | 0 | 70 | 0 | 0 | 60 |
| Crabgrass, Large | 90 | 90 | 90 | 0 | 0 | 90 | — | — | 0 | 0 | 20 | 0 | 0 | 0 | 0 | — | 80 | 70 | 80 |
| Foxtail, Giant | 80 | 90 | 80 | 0 | 0 | 80 | 0 | 30 | 20 | 0 | 20 | 0 | 0 | 0 | 0 | 90 | 60 | 60 | 80 |
| Galium | — | — | — | — | — | — | 0 | 20 | — | — | — | — | — | — | — | 0 | — | — | — |
| Kochia | — | — | — | — | — | — | 0 | 0 | — | — | — | — | — | — | — | 40 | — | — | — |
| Morningglory | 10 | 20 | 10 | 0 | 0 | 0 | — | — | 0 | 0 | 10 | 0 | 0 | 0 | 0 | — | 0 | 0 | 30 |
| Pigweed | 0 | 0 | 0 | 0 | 0 | 0 | 0 | 0 | 0 | 0 | 0 | 0 | 0 | 0 | 0 | 20 | 0 | 0 | 50 |
| Ragweed | — | — | — | — | — | — | 0 | 0 | — | — | — | — | — | — | — | 30 | — | — | — |
| Ryegrass, Italian | — | — | — | — | — | — | 0 | 0 | — | — | — | — | — | — | — | 20 | — | — | — |
| Velvetleaf | 10 | 40 | 10 | 0 | 0 | 0 | — | — | 0 | 0 | 0 | 0 | 0 | 0 | 0 | — | 0 | 0 | 0 |
| Wheat | 0 | 30 | 0 | 0 | 0 | 0 | 0 | 0 | 0 | 0 | 0 | 0 | 0 | 0 | 0 | 40 | 0 | 0 | 50 |

| | 500 g ai/ha Compounds | | | | | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- | --- | --- |
| | 4 | 5 | 6 | 7 | 8 | 9 | 10 | 11 | 12 | 13 | 14 | 15 | 16 | 28 | 29 | 32 | 36 | 37 | 38 | 41 | 42 | 45 | 46 | 47 | 48 | 49 | 50 |
| Barnyardgrass | 70 | 90 | 80 | 70 | 60 | 50 | 40 | 50 | 90 | 30 | 80 | 0 | 90 | 0 | 0 | 0 | 80 | 50 | 30 | 50 | 40 | 80 | 0 | 0 | 90 | 20 | 80 |
| Blackgrass | — | — | — | — | — | — | — | — | — | — | — | — | — | — | — | — | — | — | — | — | — | — | — | — | — | — | — |
| Corn | 50 | 0 | 0 | 0 | 0 | 0 | 0 | 0 | 0 | 0 | 0 | 0 | 30 | 0 | 0 | 0 | 0 | 0 | 0 | 0 | 0 | — | — | — | 50 | 0 | 0 |
| Crabgrass, Large | 80 | 80 | 80 | 80 | 70 | 70 | 60 | 50 | 90 | 60 | 90 | 0 | 90 | 40 | 0 | 30 | 20 | 20 | 50 | 60 | 70 | 80 | 60 | 0 | 80 | 70 | 80 |
| Foxtail, Giant | 70 | 80 | 80 | 50 | 50 | 70 | 30 | — | 80 | 0 | 80 | 0 | 90 | 0 | 0 | 40 | 20 | 20 | 20 | 0 | 20 | 70 | 40 | 0 | 80 | 40 | 80 |
| Galium | — | — | — | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — | — | — | — |
| Morningglory | 30 | 10 | 0 | 0 | 0 | 0 | 0 | 0 | 0 | 0 | 0 | 0 | 10 | 0 | 0 | 0 | 0 | 0 | 0 | 0 | 0 | 50 | 0 | 20 | 20 | 0 | 0 |
| Pigweed | 50 | 0 | 10 | 0 | 0 | 0 | 0 | 0 | 0 | 0 | 0 | 0 | 0 | 0 | 0 | 0 | 0 | 0 | 0 | 30 | 0 | 0 | 0 | 0 | 0 | 0 | 0 |
| Ragweed | — | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — | — |
| Velvetleaf | 0 | 0 | 10 | 0 | 0 | 0 | 0 | 0 | 20 | 0 | 90 | 0 | 0 | 0 | 0 | 0 | 0 | 0 | 0 | 30 | 50 | 0 | 0 | 0 | 20 | 0 | 0 |
| Wheat | 50 | 0 | 0 | 0 | 0 | 0 | 0 | 0 | 20 | 0 | 0 | 0 | 50 | 0 | 0 | 0 | 0 | 0 | 0 | 0 | 0 | 0 | 0 | 0 | 40 | 0 | 0 |

| | 500 g ai/ha Compounds | | | | | | | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- | --- | --- | --- | --- |
| | 51 | 52 | 53 | 54 | 55 | 56 | 57 | 58 | 59 | 60 | 61 | 62 | 63 | 64 | 65 | 66 | 67 | 68 | 69 | 70 | 72 | 73 | 74 | 75 | 76 | 77 | 78 |
| Barnyardgrass | 20 | 80 | 80 | 0 | 90 | 50 | 80 | 0 | 90 | 90 | 20 | 80 | 80 | 80 | 70 | 80 | 60 | 80 | 80 | 60 | 60 | 80 | 80 | 70 | 90 | 80 | 70 |
| Blackgrass | — | — | — | — | — | — | — | — | — | — | — | — | — | — | — | — | — | — | — | — | — | — | — | — | — | — | — |
| Corn | 0 | 30 | 0 | 0 | 0 | 0 | 0 | 0 | 30 | 60 | 0 | 70 | 50 | 40 | 20 | 80 | 0 | 90 | 90 | 0 | 0 | 0 | 50 | 0 | 70 | 70 | 50 |
| Crabgrass, Large | 80 | 80 | 80 | 80 | 80 | 80 | 70 | 80 | 90 | 90 | 70 | 90 | 90 | 80 | 90 | 80 | 90 | 90 | 90 | 70 | 70 | 80 | 90 | 80 | 90 | 80 | 80 |
| Foxtail, Giant | 30 | 80 | 80 | 70 | 80 | 60 | 60 | 70 | 80 | 80 | 30 | 80 | 90 | 80 | 90 | 80 | 90 | 80 | 80 | 80 | 50 | 80 | 90 | 80 | 80 | 80 | 80 |
| Galium | — | — | — | — | — | — | — | — | — | — | — | — | — | — | — | — | — | — | — | — | — | — | — | — | — | — | — |
| Kochia | — | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 20 | 0 | 0 | 0 | 0 | 0 | 10 | 20 | 0 | 0 | 40 | 30 | 0 |
| Pigweed | 0 | 40 | 0 | 0 | 0 | 0 | 0 | 0 | 40 | 0 | 70 | 0 | 30 | 0 | 0 | 0 | 20 | 60 | 30 | 20 | 0 | 0 | 0 | 0 | 60 | 50 | 50 |
| Ragweed | — | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — | — |
| Velvetleaf | 0 | 0 | 0 | 0 | 0 | 0 | 0 | 0 | 0 | 0 | 0 | 0 | 30 | 30 | 0 | 0 | 20 | 30 | 20 | 0 | 0 | 30 | 50 | 20 | 60 | 40 | 60 |
| Wheat | 0 | 30 | 0 | 0 | 0 | 0 | 0 | 0 | 60 | 50 | 0 | 60 | 30 | 40 | 20 | 30 | 0 | 20 | 40 | 40 | 0 | 0 | 60 | 30 | 60 | 60 | 50 |

TABLE A-continued

| | 500 g ai/ha Compounds | | | | | | | | | | | | | | | | | | | | | | | |
|---|---|---|---|---|---|---|---|---|---|---|---|---|---|---|---|---|---|---|---|---|---|---|---|---|
| | 79 | 80 | 81 | 82 | 83 | 84 | 85 | 86 | 87 | 88 | 89 | 90 | 91 | 92 | 93 | 94 | 95 | 97 | 101 | 102 | 103 | 107 | 109 | 110 |
| Barnyardgrass | 90 | 80 | 80 | 50 | 60 | 0 | 20 | 20 | 80 | 40 | 80 | 70 | 20 | 70 | 60 | 0 | 90 | 0 | 90 | 0 | 90 | 80 | 90 | 90 |
| Blackgrass | — | — | — | — | — | — | — | — | — | — | — | — | — | — | — | — | — | — | — | — | — | — | 80 | 70 |
| Corn | 70 | 60 | 0 | 0 | 0 | 0 | 0 | 0 | 0 | 0 | 30 | 30 | 0 | 0 | 0 | 0 | 0 | 0 | 50 | 0 | 20 | 0 | 80 | 20 |
| Crabgrass, Large | 90 | 90 | 80 | 70 | 70 | 20 | 50 | 60 | 80 | 60 | 80 | 70 | 50 | 70 | 80 | 0 | 90 | 0 | 80 | 0 | 90 | 70 | — | — |
| Foxtail, Giant | 80 | 80 | 70 | 70 | 50 | 0 | 0 | 10 | 80 | 0 | 80 | 70 | 20 | 10 | 60 | 0 | 80 | 0 | 90 | 0 | 90 | 70 | 90 | 90 |
| *Galium* | — | — | — | — | — | — | — | — | — | — | — | — | — | — | — | — | — | — | — | — | — | — | 60 | 40 |
| *Kochia* | — | — | — | — | — | — | — | — | — | — | — | — | — | — | — | — | — | — | — | — | — | — | 0 | 0 |
| Morningglory | 10 | 0 | 0 | 10 | 0 | 0 | 0 | 0 | 10 | 0 | 10 | 0 | 0 | 0 | 0 | 0 | 0 | 0 | 60 | 0 | 0 | 40 | — | — |
| Pigweed | 70 | 70 | 0 | 0 | 0 | 0 | 0 | 0 | 20 | 0 | 20 | 20 | 0 | 0 | 0 | 0 | 0 | 0 | 70 | 0 | 20 | 30 | 0 | 0 |
| Ragweed | — | — | — | — | — | — | — | — | — | — | — | — | — | — | — | — | — | — | — | — | — | — | 0 | 0 |
| Ryegrass, Italian | — | — | — | — | — | — | — | — | — | — | — | — | — | — | — | — | — | — | — | — | — | — | 30 | 40 |
| Velvetleaf | 60 | 60 | 0 | 20 | 0 | 0 | 0 | 0 | 0 | 0 | 0 | 0 | 0 | 0 | 0 | 0 | 0 | 0 | 70 | 0 | 0 | 20 | — | — |
| Wheat | 50 | 50 | 0 | 10 | 0 | 0 | 0 | 0 | 20 | 0 | 20 | 0 | 0 | 0 | 0 | 0 | 0 | 0 | 60 | 0 | 20 | 0 | 60 | 20 |

| | 500 g ai/ha Compounds | | | | | | | | | | | | | | | | | |
|---|---|---|---|---|---|---|---|---|---|---|---|---|---|---|---|---|---|---|
| | 111 | 112 | 113 | 114 | 115 | 116 | 117 | 118 | 119 | 120 | 121 | 122 | 123 | 124 | 125 | 126 | 127 | 128 |
| Barnyardgrass | 0 | 0 | 0 | 60 | 50 | 40 | 30 | 60 | 90 | 90 | 80 | 80 | 80 | 70 | 70 | 80 | 70 | 60 |
| Blackgrass | 0 | 0 | 0 | 30 | — | — | — | 0 | 50 | 50 | 70 | 70 | 70 | 70 | 50 | 30 | 40 | 50 |
| Corn | 0 | 0 | 0 | 20 | 0 | 20 | 20 | 0 | 70 | 80 | 70 | 60 | 80 | 50 | 0 | 0 | 20 | 20 |
| Crabgrass, Large | — | — | — | — | 50 | 30 | 60 | — | — | — | — | — | — | — | — | — | — | — |
| Foxtail, Giant | 0 | 0 | 0 | 70 | 10 | 20 | 50 | 80 | 90 | 90 | 90 | 80 | 90 | 90 | 80 | 80 | 80 | 80 |
| *Galium* | 0 | 0 | 0 | 20 | — | — | — | 60 | 50 | 60 | 70 | 80 | 70 | 80 | 60 | 30 | 60 | 0 |
| *Kochia* | 0 | 0 | 0 | 20 | — | — | — | 50 | 50 | 70 | 60 | 70 | 70 | 80 | 60 | 0 | 60 | 0 |
| Morningglory | — | — | — | — | 0 | 0 | 0 | — | — | — | — | — | — | — | — | — | — | — |
| Pigweed | 0 | 0 | 0 | 0 | 0 | 0 | 0 | 0 | 30 | 50 | 0 | 80 | 90 | 70 | 20 | 0 | 0 | 50 |
| Ragweed | 0 | 0 | 0 | 0 | — | — | — | 0 | 30 | 50 | 30 | 70 | 70 | 70 | 0 | 0 | 0 | 0 |
| Ryegrass, Italian | 0 | 0 | 0 | 60 | — | — | — | 0 | 40 | 50 | 50 | 40 | 50 | 50 | 0 | 0 | 0 | 0 |
| Velvetleaf | — | — | — | — | 0 | 0 | 0 | — | — | — | — | — | — | — | — | — | — | — |
| Wheat | 0 | 0 | 0 | 20 | 0 | 0 | 0 | 0 | 70 | 60 | 60 | 60 | 60 | 50 | 0 | 0 | 0 | 40 |

| | 500 g ai/ha Compounds | | | | | | | | | | | | | | | | | |
|---|---|---|---|---|---|---|---|---|---|---|---|---|---|---|---|---|---|---|
| | 129 | 130 | 131 | 132 | 133 | 139 | 140 | 141 | 142 | 143 | 144 | 145 | 146 | 147 | 148 | 149 | 150 | 151 |
| Barnyardgrass | 70 | 70 | 60 | 80 | 80 | 90 | 80 | 90 | 90 | 90 | 90 | 90 | 90 | 90 | 90 | 80 | 80 | 90 |
| Blackgrass | 50 | 0 | 0 | 0 | 0 | 20 | 20 | 50 | 30 | 0 | 30 | 30 | 70 | 60 | 0 | 40 | 10 | 70 |
| Corn | 30 | 0 | 0 | 0 | 0 | 0 | 0 | 50 | 0 | 0 | 20 | 0 | 50 | 50 | 0 | 70 | 30 | 50 |
| Crabgrass, Large | — | — | — | — | — | — | — | — | — | — | — | — | — | — | — | — | — | — |
| Foxtail, Giant | 80 | 70 | 50 | 70 | 50 | 30 | 50 | 50 | 50 | 30 | 70 | 70 | 70 | 70 | 30 | 70 | 70 | 70 |
| *Galium* | 60 | 0 | 0 | 0 | 0 | 30 | 30 | 50 | 40 | 40 | 70 | 50 | 70 | 60 | 40 | 60 | 60 | 70 |
| *Kochia* | 0 | 0 | 0 | 10 | 0 | 0 | 0 | 20 | 0 | 0 | 0 | 20 | 70 | 60 | 0 | 60 | 60 | 80 |
| Morningglory | — | — | — | — | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 10 | 0 | 0 | 20 | 60 |
| Ragweed | 0 | 0 | 0 | 0 | 0 | 0 | 0 | 40 | 0 | 0 | 0 | 20 | 60 | 50 | 0 | 40 | 20 | 70 |
| Ryegrass, Italian | 50 | 0 | 0 | 0 | 0 | 0 | 0 | 40 | 20 | 0 | 40 | 0 | 60 | 50 | 0 | 50 | 0 | 50 |
| Velvetleaf | — | — | — | — | — | — | — | — | — | — | — | — | — | — | — | — | — | — |
| Wheat | 40 | 0 | 0 | 0 | 0 | 0 | 0 | 30 | 20 | 0 | 0 | 0 | 70 | 40 | 0 | 20 | 0 | 60 |

| | 500 g ai/ha Compounds | | | | | | | | | | | | | | | | | |
|---|---|---|---|---|---|---|---|---|---|---|---|---|---|---|---|---|---|---|
| | 152 | 153 | 154 | 156 | 157 | 160 | 161 | 162 | 163 | 164 | 165 | 166 | 167 | 168 | 169 | 170 | 171 | 172 |
| Barnyardgrass | 80 | 80 | 80 | 80 | 80 | 80 | 90 | 90 | 90 | 90 | 90 | 80 | 90 | 90 | 90 | 90 | 90 | 20 |
| Blackgrass | 50 | 30 | 70 | 20 | 30 | 70 | 50 | 50 | 60 | 70 | 70 | 60 | 60 | 60 | 60 | 60 | 60 | 0 |
| Corn | 0 | 0 | 70 | 30 | 80 | 70 | 60 | 60 | 40 | 80 | 80 | 80 | 70 | 70 | 50 | 70 | 70 | 0 |
| Crabgrass, Large | — | — | — | — | — | — | — | — | — | — | — | — | — | — | — | — | — | — |
| Foxtail, Giant | 60 | 60 | 80 | 80 | 80 | 90 | 90 | 90 | 80 | 90 | 90 | 90 | 90 | 90 | 90 | 90 | 80 | 30 |
| *Galium* | 70 | 60 | 60 | 30 | 40 | 70 | 60 | 70 | 60 | 60 | 50 | 60 | 60 | 70 | 50 | 60 | 70 | 0 |
| *Kochia* | 60 | 60 | 50 | 20 | 30 | 80 | 60 | 70 | 0 | 70 | 70 | 70 | 50 | 60 | 40 | 50 | 30 | 0 |
| Morningglory | — | — | — | — | — | — | — | — | — | — | — | — | — | — | — | — | — | — |
| Pigweed | 20 | 50 | 30 | 20 | 30 | 80 | 60 | 70 | 20 | 60 | 50 | 50 | 0 | 40 | 0 | 30 | 40 | 0 |
| Ragweed | 50 | 10 | 0 | 30 | 40 | 60 | 30 | 40 | 20 | 50 | 50 | 0 | 50 | 20 | 0 | 50 | 30 | 0 |
| Ryegrass, Italian | 50 | 0 | 50 | 30 | 30 | 10 | 50 | 50 | 30 | 50 | 50 | 50 | 40 | 50 | 40 | 60 | 30 | 0 |
| Velvetleaf | — | — | — | — | — | — | — | — | — | — | — | — | — | — | — | — | — | — |
| Wheat | 0 | 0 | 50 | 40 | 70 | 50 | 40 | 50 | 60 | 80 | 70 | 50 | 50 | 40 | 50 | 60 | 50 | 0 |

TABLE A-continued

| | 500 g ai/ha Compounds | | | | | | | | | | | | | | | | | |
|---|---|---|---|---|---|---|---|---|---|---|---|---|---|---|---|---|---|---|
| | 174 | 175 | 181 | 182 | 183 | 184 | 185 | 186 | 188 | 189 | 190 | 194 | 195 | 196 | 197 | 198 | 199 | 200 |
| Barnyardgrass | 20 | 0 | 0 | 0 | 0 | 80 | 80 | 0 | 0 | 90 | 90 | 80 | 90 | 80 | 70 | 80 | 70 | 90 |
| Blackgrass | 0 | 0 | 50 | 0 | 0 | 20 | 20 | 0 | 0 | — | — | — | — | — | — | — | — | 0 |
| Corn | 0 | 0 | 0 | 0 | 0 | 20 | 20 | 0 | 0 | 60 | 40 | 0 | 0 | 0 | 0 | 0 | 0 | 20 |
| Crabgrass, Large | — | — | — | — | — | — | — | — | — | 80 | 90 | 80 | 80 | 80 | 70 | 80 | 80 | — |
| Foxtail, Giant | 30 | 0 | 0 | 10 | 0 | 80 | 80 | 0 | 0 | 90 | 80 | 50 | 70 | 70 | 40 | 60 | 50 | 40 |
| *Galium* | 0 | 0 | 0 | 0 | 0 | 20 | 0 | 0 | 0 | — | — | — | — | — | — | — | — | 0 |
| *Kochia* | 0 | 0 | 70 | 0 | 0 | 0 | 0 | 0 | 0 | — | — | — | — | — | — | — | — | 0 |
| Morningglory | — | — | — | — | — | — | — | — | — | 0 | 10 | 0 | 0 | 0 | 10 | 0 | 0 | — |
| Pigweed | 0 | 0 | 50 | 0 | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | — | — | — | — | — | — | — | — | 0 |
| Ryegrass, Italian | 0 | 0 | 0 | 0 | 0 | 20 | 0 | 0 | 0 | — | — | — | — | — | — | — | — | 0 |
| Velvetleaf | — | — | — | — | — | — | — | — | — | 0 | 10 | 0 | 0 | 0 | 0 | 0 | 40 | — |
| Wheat | 0 | 0 | 0 | 0 | 0 | 40 | 20 | 0 | 0 | 0 | 0 | 0 | 30 | 0 | 0 | 0 | 0 | 20 |

| | 500 g ai/ha Compounds | | | | | | | | | | | | | | | | | |
|---|---|---|---|---|---|---|---|---|---|---|---|---|---|---|---|---|---|---|
| | 201 | 202 | 203 | 204 | 205 | 206 | 207 | 208 | 209 | 210 | 211 | 212 | 213 | 214 | 215 | 216 | 217 | 218 |
| Barnyardgrass | 30 | 90 | 80 | 90 | 70 | 90 | 90 | 80 | 80 | 90 | 90 | 90 | 70 | 70 | 60 | 0 | 90 | 90 |
| Blackgrass | 0 | 50 | 30 | 80 | 70 | 80 | 70 | 60 | 20 | 60 | 70 | 60 | 60 | 70 | 50 | 0 | 50 | 40 |
| Corn | 0 | 90 | 0 | 80 | 0 | 80 | 70 | 50 | 0 | 60 | 70 | 50 | 50 | 50 | 0 | 0 | 30 | 30 |
| Crabgrass, Large | — | — | — | — | — | — | — | — | — | — | — | — | — | — | — | — | — | — |
| Foxtail, Giant | 0 | 90 | 70 | 90 | 90 | 90 | 90 | 90 | 70 | 90 | 90 | 90 | 90 | 90 | 80 | 10 | 90 | 90 |
| *Galium* | 0 | 60 | 0 | 60 | 60 | 80 | 50 | 50 | 0 | 60 | 70 | 60 | 0 | 70 | 60 | 0 | 50 | 60 |
| *Kochia* | 0 | 90 | 0 | 60 | 40 | 70 | 0 | 60 | 0 | 60 | 60 | 20 | 0 | 40 | 0 | 0 | 70 | 60 |
| Morningglory | — | — | — | — | — | — | — | — | — | — | — | — | — | — | — | — | — | — |
| Pigweed | 0 | 80 | 0 | 20 | 30 | 70 | 0 | 0 | 0 | 20 | 50 | 0 | 0 | 50 | 60 | 0 | 0 | 40 |
| Ragweed | 0 | 50 | 20 | 0 | 0 | 50 | 0 | 20 | 0 | 0 | 30 | 20 | 30 | 0 | 10 | 0 | 30 | 50 |
| Ryegrass, Italian | 0 | 40 | 0 | 50 | 0 | 60 | 50 | 40 | 20 | 50 | 60 | 0 | 50 | 30 | 0 | 0 | 30 | 30 |
| Velvetleaf | — | — | — | — | — | — | — | — | — | — | — | — | — | — | — | — | — | — |
| Wheat | 0 | 50 | 20 | 80 | 40 | 80 | 60 | 40 | 0 | 50 | 80 | 70 | 50 | 50 | 0 | 0 | 30 | 50 |

| | 500 g ai/ha Compounds | | | | | | | | | | | | | | | | | |
|---|---|---|---|---|---|---|---|---|---|---|---|---|---|---|---|---|---|---|
| | 219 | 220 | 221 | 222 | 223 | 224 | 225 | 226 | 227 | 228 | 229 | 230 | 231 | 232 | 233 | 234 | 235 | 236 |
| Barnyardgrass | 50 | 80 | 0 | 90 | 80 | 90 | 60 | 80 | 80 | 80 | 80 | 90 | 90 | 90 | 90 | 90 | 20 | 0 |
| Blackgrass | 50 | 40 | 0 | 60 | 70 | 70 | 30 | 30 | 40 | 40 | 70 | 50 | 60 | 50 | 60 | 30 | 20 | 0 |
| Corn | 0 | 20 | 0 | 60 | 50 | 80 | 20 | 0 | 0 | 30 | 0 | 40 | 40 | 80 | 20 | 60 | 20 | 0 |
| Crabgrass, Large | — | — | — | — | — | — | — | — | — | — | — | — | — | — | — | — | — | — |
| Foxtail, Giant | 80 | 80 | 30 | 90 | 90 | 80 | 70 | 80 | 80 | 90 | 90 | 90 | 90 | 90 | 90 | 80 | 50 | 0 |
| *Galium* | 60 | 30 | 0 | 60 | 60 | 70 | 30 | 20 | 0 | 40 | 70 | 50 | 50 | 60 | 50 | 50 | 70 | 0 |
| *Kochia* | 10 | 40 | 0 | 40 | 70 | 90 | 0 | 50 | 40 | 30 | 60 | 40 | 90 | 90 | 80 | 30 | 20 | 0 |
| Morningglory | — | — | — | — | — | — | — | — | — | — | — | — | — | — | — | — | — | — |
| Pigweed | 0 | 0 | 0 | 20 | 60 | 80 | 0 | 0 | 0 | 0 | 0 | 0 | 40 | 90 | 20 | 0 | 50 | 0 |
| Ragweed | 0 | 0 | 0 | 40 | 30 | 60 | 0 | 0 | 0 | 20 | 60 | 30 | 50 | 50 | 50 | 0 | 0 | 0 |
| Ryegrass, Italian | 0 | 20 | 0 | 30 | 40 | 60 | 0 | 20 | 20 | 20 | 40 | 20 | 40 | 50 | 40 | 30 | 0 | 0 |
| Velvetleaf | — | — | — | — | — | — | — | — | — | — | — | — | — | — | — | — | — | — |
| Wheat | 0 | 20 | 0 | 30 | 50 | 60 | 20 | 0 | 0 | 20 | 0 | 20 | 30 | 50 | 20 | 40 | 0 | 0 |

| | 500 g ai/ha Compounds | | | | | | | | | | | | | | | | | |
|---|---|---|---|---|---|---|---|---|---|---|---|---|---|---|---|---|---|---|
| | 239 | 240 | 241 | 242 | 244 | 245 | 246 | 247 | 248 | 249 | 250 | 251 | 256 | 257 | 258 | 259 | 260 | 261 |
| Barnyardgrass | 90 | 90 | 90 | 80 | 90 | 50 | 70 | 80 | 50 | 50 | 50 | 30 | 20 | 80 | 80 | 70 | 80 | 50 |
| Blackgrass | 20 | 0 | — | — | — | — | — | — | — | — | — | — | — | — | — | — | — | — |
| Corn | 0 | 20 | 80 | 70 | 20 | 0 | 30 | 20 | 20 | 0 | 0 | 0 | 0 | 20 | 20 | 0 | 0 | 0 |
| Crabgrass, Large | — | — | 80 | 80 | 80 | 30 | 60 | 70 | 70 | 40 | 40 | 30 | 90 | 90 | 90 | 90 | 90 | 80 |
| Foxtail, Giant | 90 | 80 | 90 | 80 | 80 | 30 | 80 | 80 | 50 | 40 | 50 | 20 | 70 | 90 | 80 | 70 | 90 | 60 |
| *Galium* | 30 | 0 | — | — | — | — | — | — | — | — | — | — | — | — | — | — | — | — |
| *Kochia* | 20 | 0 | — | — | — | — | — | — | — | — | — | — | — | — | — | — | — | — |
| Morningglory | — | — | 30 | 30 | 0 | 0 | 0 | 0 | 0 | 0 | 0 | 0 | 0 | 0 | 0 | 0 | 50 | 0 |
| Pigweed | 0 | 0 | 20 | 20 | 40 | 40 | 0 | 0 | 0 | 0 | 0 | 20 | 0 | 0 | 0 | 0 | 70 | 40 |
| Ragweed | 0 | 0 | — | — | — | — | — | — | — | — | — | — | — | — | — | — | — | — |
| Ryegrass, Italian | 20 | 0 | — | — | — | — | — | — | — | — | — | — | — | — | — | — | — | — |
| Velvetleaf | — | — | 20 | 20 | 30 | 40 | 0 | 0 | 0 | 0 | 0 | 0 | 0 | 0 | 0 | 0 | — | 30 |
| Wheat | 20 | 20 | 70 | 20 | 20 | 40 | 30 | 30 | 0 | 0 | 0 | 0 | 20 | 30 | 30 | 0 | 0 | 0 |

TABLE A-continued

| | 500 g ai/ha Compounds | | | | | | | | | | | | | | | | | |
|---|---|---|---|---|---|---|---|---|---|---|---|---|---|---|---|---|---|---|
| | 262 | 263 | 264 | 267 | 268 | 269 | 270 | 271 | 272 | 273 | 275 | 276 | 277 | 278 | 279 | 280 | 281 | 282 |
| Barnyardgrass | 70 | 80 | 80 | 80 | 70 | 70 | 90 | 90 | 80 | 30 | 90 | 0 | 90 | 90 | 90 | 90 | 70 | 90 |
| Blackgrass | — | — | — | — | — | — | 20 | 60 | 30 | 0 | 60 | 0 | 50 | 60 | 70 | 0 | 0 | 20 |
| Corn | 0 | 60 | 0 | 70 | 40 | 20 | 30 | 60 | 10 | 0 | 90 | 0 | 90 | 0 | 70 | 0 | 0 | 0 |
| Crabgrass, Large | 80 | 90 | 90 | 90 | 80 | 80 | — | — | — | — | — | — | — | — | — | — | — | — |
| Foxtail, Giant | 70 | 90 | 80 | 80 | 90 | 80 | 90 | 90 | 80 | 70 | 90 | 0 | 90 | 80 | 90 | 80 | 0 | 30 |
| Galium | — | — | — | — | — | — | 50 | 70 | 50 | 50 | 70 | 0 | 70 | 50 | 50 | 0 | 0 | 40 |
| Kochia | — | — | — | — | — | — | 30 | 80 | 60 | 0 | 80 | 0 | 30 | 0 | 40 | 0 | 0 | 0 |
| Morningglory | 0 | 60 | 0 | 60 | 0 | 0 | — | — | — | — | — | — | — | — | — | — | — | — |
| Pigweed | 0 | 70 | 60 | 60 | 80 | 60 | 0 | 20 | 20 | 0 | 40 | 0 | 30 | 10 | 0 | 0 | 0 | 0 |
| Ragweed | — | — | — | — | — | — | 0 | 60 | 0 | 0 | 30 | 0 | 30 | 0 | 0 | 0 | 0 | 0 |
| Ryegrass, Italian | — | — | — | — | — | — | 20 | 40 | 0 | 0 | 50 | 0 | 40 | 0 | 0 | 0 | 0 | 0 |
| Velvetleaf | — | — | 30 | — | — | — | — | — | — | — | — | — | — | — | — | — | — | — |
| Wheat | 0 | 60 | 0 | 0 | 0 | 0 | 20 | 80 | 0 | 0 | 70 | 0 | 70 | 0 | 60 | 0 | 0 | 0 |

| | 500 g ai/ha Compounds | | | | | | | | | | | | | | | | | |
|---|---|---|---|---|---|---|---|---|---|---|---|---|---|---|---|---|---|---|
| | 283 | 284 | 285 | 286 | 287 | 288 | 289 | 290 | 291 | 292 | 293 | 294 | 295 | 296 | 297 | 298 | 299 | 300 |
| Barnyardgrass | 60 | 50 | 70 | 60 | 80 | 80 | 70 | 80 | 60 | 70 | 70 | 90 | 50 | 20 | 0 | 0 | 70 | 0 |
| Blackgrass | 0 | 0 | 0 | 0 | 0 | 0 | 0 | 0 | 0 | 0 | 10 | 30 | 0 | 0 | 10 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 |
| Crabgrass, Large | — | — | — | — | — | — | — | — | — | — | — | — | — | — | — | — | — | — |
| Foxtail, Giant | 10 | 10 | 0 | 70 | 0 | 30 | 60 | 60 | 50 | 60 | 70 | 80 | 0 | 0 | 0 | 0 | 50 | 0 |
| Galium | 0 | 60 | 0 | 0 | 0 | 0 | 0 | 0 | 0 | 20 | 60 | 30 | 10 | 0 | 0 | 0 | 0 | 0 |
| Kochia | 0 | 0 | 0 | 20 | 0 | 20 | 0 | 0 | 0 | 0 | 0 | 50 | 0 | 0 | 0 | 0 | 0 | 0 |
| Morningglory | — | — | — | — | — | — | — | — | — | — | — | — | — | — | — | — | — | — |
| Pigweed | 0 | 0 | 0 | 0 | 0 | 0 | 0 | 10 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 20 | 0 | 0 | 0 | 0 | 0 | 0 |
| Ryegrass, Italian | 0 | 0 | 0 | 20 | 0 | 0 | 0 | 0 | 0 | 0 | 0 | 20 | 0 | 0 | 0 | 0 | 0 | 0 |
| Velvetleaf | — | — | — | — | — | — | — | — | — | — | — | — | — | — | — | — | — | — |
| Wheat | 0 | 0 | 0 | 0 | 0 | 0 | 0 | 0 | 0 | 0 | 0 | 20 | 0 | 0 | 0 | 0 | 0 | 0 |

| | 500 g ai/ha Compounds | | | | | | | | | | | | | | | | | |
|---|---|---|---|---|---|---|---|---|---|---|---|---|---|---|---|---|---|---|
| | 301 | 302 | 303 | 304 | 305 | 306 | 307 | 308 | 309 | 310 | 311 | 312 | 313 | 314 | 315 | 316 | 317 | 318 |
| Barnyardgrass | 0 | 90 | 90 | 90 | 90 | 80 | 90 | 70 | 90 | 90 | 80 | 90 | 80 | 80 | 90 | 90 | 90 | 90 |
| Blackgrass | 0 | 60 | 70 | 70 | 70 | 60 | 70 | 70 | 70 | 50 | 30 | 50 | 0 | 0 | 50 | 40 | 20 | 40 |
| Corn | 0 | 40 | 70 | 70 | 70 | 70 | 60 | 10 | 80 | 50 | 0 | 80 | 0 | 0 | 80 | 80 | 20 | 50 |
| Crabgrass, Large | — | — | — | — | — | — | — | — | — | — | — | — | — | — | — | — | — | — |
| Foxtail, Giant | 0 | 80 | 80 | 80 | 80 | 80 | 80 | 80 | 90 | 90 | 70 | 90 | 70 | 80 | 90 | 90 | 90 | 70 |
| Galium | 0 | 60 | 70 | 60 | 70 | 70 | 0 | 0 | 70 | 20 | 0 | 50 | 0 | 0 | 50 | 40 | 0 | 40 |
| Kochia | 0 | 60 | 80 | 80 | 70 | 70 | 0 | 0 | 0 | 30 | 0 | 40 | 0 | 0 | 70 | 40 | 0 | 30 |
| Morningglory | — | — | — | — | — | — | — | — | — | — | — | — | — | — | — | — | — | — |
| Pigweed | 0 | 10 | 60 | 60 | 70 | 80 | 0 | 0 | 0 | 0 | 0 | 30 | 0 | 0 | 50 | 20 | 0 | 20 |
| Ragweed | 0 | 0 | 40 | 20 | 0 | 40 | 0 | 0 | 30 | 0 | 0 | 40 | 0 | 0 | 40 | 30 | 0 | 30 |
| Ryegrass, Italian | 0 | 60 | 60 | 50 | 70 | 60 | 0 | 0 | 30 | 30 | 0 | 40 | 0 | 0 | 50 | 30 | 0 | 40 |
| Velvetleaf | — | — | — | — | — | — | — | — | — | — | — | — | — | — | — | — | — | — |
| Wheat | 0 | 50 | 60 | 60 | 70 | 60 | 30 | 20 | 60 | 50 | 0 | 70 | 0 | 0 | 70 | 40 | 20 | 30 |

| | 500 g ai/ha Compounds | | | | | | | | | | | | | | | | | |
|---|---|---|---|---|---|---|---|---|---|---|---|---|---|---|---|---|---|---|
| | 319 | 320 | 321 | 322 | 323 | 324 | 325 | 326 | 327 | 328 | 329 | 330 | 331 | 332 | 333 | 334 | 335 | 336 |
| Barnyardgrass | 90 | 90 | 50 | 60 | 90 | 90 | 90 | 20 | 80 | 80 | 0 | 60 | 70 | 50 | 60 | 0 | 60 | 60 |
| Blackgrass | 50 | 20 | 0 | 0 | 60 | 70 | 50 | 0 | 40 | 40 | 0 | 0 | 30 | 0 | 30 | 0 | 20 | 0 |
| Corn | 80 | 0 | 0 | 20 | 90 | 90 | 80 | 0 | 30 | 0 | 0 | 0 | 0 | 20 | 0 | 0 | 0 | 0 |
| Crabgrass, Large | — | — | — | — | — | — | — | — | — | — | — | — | — | — | — | — | — | — |
| Foxtail, Giant | 90 | 70 | 50 | 60 | 90 | 90 | 90 | 50 | 80 | 80 | 30 | 80 | 80 | 80 | 80 | 10 | 90 | 70 |
| Galium | 50 | 0 | 0 | 0 | 60 | 60 | 60 | 0 | 60 | 50 | 0 | 30 | 30 | 20 | 40 | 0 | 0 | 0 |
| Kochia | 50 | 20 | 0 | 0 | 90 | 80 | 80 | 30 | 40 | 20 | 0 | 0 | 20 | 20 | 20 | 0 | 0 | 0 |
| Morningglory | — | — | — | — | — | — | — | — | — | — | — | — | — | — | — | — | — | — |
| Pigweed | 20 | 0 | 0 | 0 | 30 | 70 | 50 | 0 | 20 | 0 | 0 | 0 | 0 | 0 | 20 | 0 | 0 | 0 |
| Ragweed | 40 | 30 | 0 | 0 | 20 | 50 | 60 | 0 | 20 | 0 | 0 | 0 | 0 | 0 | 20 | 0 | 0 | 0 |
| Ryegrass, Italian | 50 | 30 | 0 | 0 | 30 | 50 | 50 | 0 | 20 | 20 | 0 | 0 | 0 | 20 | 30 | 0 | 0 | 0 |
| Velvetleaf | — | — | — | — | — | — | — | — | — | — | — | — | — | — | — | — | — | — |
| Wheat | 50 | 0 | 0 | 0 | 80 | 80 | 80 | 0 | 20 | 0 | 0 | 0 | 0 | 20 | 20 | 0 | 20 | 0 |

TABLE A-continued

| | 500 g ai/ha Compounds | | | | | | | | | | | | | | 125 g ai/ha Compounds | | | | | |
|---|---|---|---|---|---|---|---|---|---|---|---|---|---|---|---|---|---|---|---|---|
| | 337 | 338 | 339 | 340 | 341 | 342 | 343 | 344 | 345 | 346 | 347 | 348 | 349 | 350 | 1 | 2 | 3 | 4 | 5 | 6 |
| Barnyardgrass | 50 | 30 | 60 | 50 | 50 | 60 | 30 | 90 | 90 | 90 | 50 | 50 | 90 | 90 | 50 | 30 | 70 | 60 | 60 | 40 |
| Blackgrass | 0 | 0 | 0 | 20 | 0 | 0 | 0 | 0 | 60 | 50 | 0 | 30 | 40 | 50 | — | — | — | — | — | — |
| Corn | 0 | 0 | 0 | 0 | 30 | 40 | 0 | 0 | 90 | 40 | 0 | 0 | 20 | 40 | 0 | 0 | 0 | 0 | 0 | 0 |
| Crabgrass, Large | — | — | — | — | — | — | — | — | — | — | — | — | — | — | 30 | 50 | 70 | 60 | 70 | 60 |
| Foxtail, Giant | 40 | 60 | 60 | 90 | 70 | 50 | 60 | 90 | 90 | 90 | 20 | 90 | 90 | 90 | 20 | 30 | 60 | 60 | 80 | 70 |
| *Galium* | 0 | 0 | 0 | 30 | 30 | 20 | 0 | 0 | 70 | 50 | 0 | 40 | 50 | 70 | — | — | — | — | — | — |
| *Kochia* | 30 | 0 | 0 | 30 | 70 | 70 | 20 | 0 | 70 | 0 | 0 | 40 | 60 | 80 | — | — | — | — | — | — |
| Morningglory | — | — | — | — | — | — | — | — | — | — | — | — | — | — | 0 | 0 | 30 | 20 | 0 | 0 |
| Pigweed | 0 | 0 | 0 | 20 | 50 | 50 | 0 | 0 | 70 | 20 | 0 | 20 | 20 | 70 | 0 | 0 | 0 | 40 | 0 | 0 |
| Ragweed | 0 | 0 | 0 | 0 | 20 | 0 | 0 | 0 | 30 | 20 | 0 | 0 | 20 | 30 | — | — | — | — | — | — |
| Ryegrass, Italian | 0 | 0 | 0 | 20 | 20 | 0 | 0 | 0 | 70 | 30 | 0 | 0 | 0 | 30 | — | — | — | — | — | — |
| Velvetleaf | — | — | — | — | — | — | — | — | — | — | — | — | — | — | 0 | 0 | 0 | 0 | 0 | 0 |
| Wheat | 0 | 0 | 0 | 0 | 20 | 20 | 0 | 0 | 70 | 40 | 0 | 20 | 30 | 50 | 0 | 0 | 0 | 30 | 0 | 0 |

| | 125 g ai/ha Compounds | | | | | | | | | | | | | | | | | | | | | | | | |
|---|---|---|---|---|---|---|---|---|---|---|---|---|---|---|---|---|---|---|---|---|---|---|---|---|---|
| | 7 | 8 | 9 | 10 | 11 | 12 | 13 | 14 | 15 | 16 | 28 | 29 | 32 | 36 | 37 | 38 | 41 | 42 | 45 | 46 | 47 | 48 | 49 | 50 | 51 | 52 | 53 |
| Barnyardgrass | 20 | 20 | 30 | 0 | 0 | 60 | 0 | 60 | 0 | 70 | 0 | 0 | 0 | 0 | 0 | 0 | 0 | 0 | 50 | 0 | 0 | 80 | 0 | 80 | 0 | 80 | 30 |
| Blackgrass | — | — | — | — | — | — | — | — | — | — | — | — | — | — | — | — | — | — | — | — | — | — | — | — | — | — | — |
| Corn | 0 | 0 | 0 | 0 | 0 | 0 | 0 | 0 | 0 | 0 | 0 | 0 | 0 | 0 | 0 | 0 | 0 | 0 | — | — | — | 0 | 0 | 0 | 0 | 0 | 0 |
| Crabgrass, Large | 30 | 60 | 40 | 20 | 0 | 80 | 0 | 80 | 0 | 90 | 20 | 0 | 0 | 0 | 0 | 0 | 30 | 0 | 60 | 30 | 0 | 80 | 20 | 80 | 20 | 80 | 80 |
| Foxtail, Giant | 0 | 0 | 0 | 0 | 0 | 60 | 0 | 60 | 0 | 60 | 0 | 0 | 0 | 0 | 0 | 0 | 0 | 0 | 20 | 0 | 0 | 80 | 0 | 80 | 0 | 80 | 30 |
| *Galium* | — | — | — | — | — | — | — | — | — | — | — | — | — | — | — | — | — | — | — | — | — | — | — | — | — | — | — |
| *Kochia* | — | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 0 | 0 | 0 | 0 | 40 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ragweed | — | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — | — |
| Velvetleaf | 0 | 0 | 0 | 0 | 0 | 0 | 0 | 0 | 0 | — | 0 | 0 | 0 | 0 | 0 | 0 | 30 | 0 | 0 | 0 | 0 | 0 | 0 | 0 | 0 | 0 | 0 |
| Wheat | 0 | 0 | 0 | 0 | 0 | 0 | 0 | 0 | 0 | 20 | 0 | 0 | 0 | 0 | 0 | 0 | 0 | 0 | 0 | 0 | 0 | 20 | 0 | 0 | 0 | 0 | 0 |

| | 125 g ai/ha Compounds | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 54 | 55 | 56 | 57 | 58 | 59 | 60 | 61 | 62 | 63 | 64 | 65 | 66 | 67 | 68 | 69 | 70 | 72 | 73 | 74 | 75 | 76 | 77 | 78 | 79 | 80 | 81 |
| Barnyardgrass | 0 | 30 | 0 | 70 | 0 | 70 | 80 | 0 | 70 | 60 | 60 | 20 | 80 | 40 | 70 | 70 | 20 | 20 | 70 | 60 | 40 | 80 | 70 | 50 | 80 | 80 | 30 |
| Blackgrass | — | — | — | — | — | — | — | — | — | — | — | — | — | — | — | — | — | — | — | — | — | — | — | — | — | — | — |
| Corn | 0 | 0 | 0 | 0 | 0 | 0 | 0 | 0 | 40 | 0 | 30 | 0 | 20 | 0 | 20 | 20 | 0 | 0 | 0 | 0 | 0 | 40 | 50 | 20 | 20 | 30 | 0 |
| Crabgrass, Large | 70 | 80 | 50 | 50 | 40 | 70 | 80 | 0 | 80 | 80 | 80 | 90 | 80 | 50 | 90 | 70 | 20 | 30 | 50 | 80 | 60 | 90 | 80 | 70 | 80 | 80 | 50 |
| Foxtail, Giant | 60 | 70 | 20 | 50 | 20 | 80 | 80 | 0 | 80 | 70 | 70 | 50 | 70 | 80 | 80 | 80 | 20 | 10 | 30 | 80 | 70 | 80 | 80 | 80 | 80 | 80 | 20 |
| *Galium* | — | — | — | — | — | — | — | — | — | — | — | — | — | — | — | — | — | — | — | — | — | — | — | — | — | — | — |
| *Kochia* | — | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 20 | 0 | 0 | 0 | 0 | 0 |
| Pigweed | 0 | 0 | 0 | 0 | 0 | 0 | 0 | 0 | 30 | 0 | 0 | 0 | 0 | 0 | 40 | 20 | 0 | 0 | — | 0 | 0 | 50 | 40 | 50 | 70 | 60 | 0 |
| Ragweed | — | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — | — |
| Velvetleaf | 0 | 0 | 0 | 0 | 0 | 0 | 0 | 0 | 0 | 0 | 0 | 0 | 0 | 0 | 20 | 20 | 0 | 0 | 0 | 30 | 10 | 20 | 20 | 20 | 10 | 10 | 0 |
| Wheat | 0 | 0 | 0 | 0 | 0 | 0 | 0 | 0 | 20 | 0 | 0 | 0 | 0 | 0 | 0 | 0 | 0 | 0 | 0 | 0 | 0 | 50 | 50 | 40 | 30 | 40 | 0 |

| | 125 g ai/ha Compounds | | | | | | | | | | | | | | | | | | | | |
|---|---|---|---|---|---|---|---|---|---|---|---|---|---|---|---|---|---|---|---|---|---|
| | 82 | 83 | 84 | 85 | 86 | 87 | 88 | 89 | 90 | 91 | 92 | 93 | 94 | 95 | 97 | 101 | 102 | 103 | 107 | 109 | 110 | 111 |
| Barnyardgrass | 0 | — | 0 | 0 | 0 | 50 | 0 | 60 | 30 | 0 | 20 | 10 | 0 | 80 | 0 | 80 | 0 | 90 | 50 | 90 | 50 | 0 |
| Blackgrass | — | — | — | — | — | — | — | — | — | — | — | — | — | — | — | — | — | — | — | 50 | 0 | 0 |
| Corn | 0 | 0 | 0 | 0 | 0 | 0 | 0 | 0 | 0 | 0 | 0 | 0 | 0 | 0 | 0 | 0 | 0 | 20 | 0 | 50 | 0 | 0 |
| Crabgrass, Large | 50 | 20 | 0 | 0 | 0 | 60 | 0 | 60 | 50 | 30 | 20 | 50 | 0 | 80 | 0 | 80 | 0 | 90 | 60 | — | — | — |
| Foxtail, Giant | 0 | 0 | 0 | 0 | 0 | 50 | 0 | 60 | 40 | 0 | 0 | 10 | 0 | 70 | 0 | 80 | 0 | 90 | 10 | 90 | 80 | 0 |
| *Galium* | — | — | — | — | — | — | — | — | — | — | — | — | — | — | — | — | — | — | — | 30 | 20 | 0 |
| *Kochia* | — | — | — | — | — | — | — | — | — | — | — | — | — | — | — | — | — | — | — | 0 | 0 | 0 |
| Morningglory | 0 | 0 | 0 | 0 | 0 | 0 | 0 | 0 | 0 | 0 | 0 | 0 | 0 | 0 | 0 | 30 | 0 | 0 | 0 | — | — | — |
| Pigweed | 0 | 0 | 0 | 0 | 0 | 0 | 0 | 0 | 0 | 0 | 0 | 0 | 0 | 0 | 0 | 20 | 0 | 20 | 0 | 0 | 0 | 0 |
| Ragweed | — | — | — | — | — | — | — | — | — | — | — | — | — | — | — | — | — | — | — | 0 | 0 | 0 |
| Ryegrass, Italian | — | — | — | — | — | — | — | — | — | — | — | — | — | — | — | — | — | — | — | 20 | 20 | 0 |
| Velvetleaf | 0 | 0 | 0 | 0 | 0 | 0 | 0 | 0 | 0 | 0 | 0 | 0 | 0 | 50 | 0 | 0 | 0 | 0 | 0 | — | — | — |
| Wheat | 0 | 0 | 0 | 0 | 0 | 0 | 0 | 0 | 0 | 0 | 0 | 0 | 0 | 50 | 0 | 0 | 0 | 0 | 0 | 20 | 0 | 0 |

TABLE A-continued

| | 125 g ai/ha Compounds | | | | | | | | | | | | | | | | | |
|---|---|---|---|---|---|---|---|---|---|---|---|---|---|---|---|---|---|---|
| | 112 | 113 | 114 | 115 | 116 | 117 | 118 | 119 | 120 | 121 | 122 | 123 | 124 | 125 | 126 | 127 | 128 | 129 |
| Barnyardgrass | 0 | 0 | 20 | 10 | — | 0 | 0 | 90 | 80 | 70 | 70 | 70 | 60 | 60 | 60 | 60 | 50 | 60 |
| Blackgrass | 0 | 0 | 20 | — | — | — | 0 | 30 | 40 | 60 | 50 | 60 | 40 | 20 | 0 | 30 | 30 | 30 |
| Corn | 0 | 0 | 0 | 0 | 0 | 0 | 0 | 30 | 20 | 50 | 40 | 50 | 0 | 0 | 0 | 0 | 0 | 0 |
| Crabgrass, Large | — | — | — | 0 | 20 | 30 | — | — | — | — | — | — | — | — | — | — | — | — |
| Foxtail, Giant | 0 | 0 | 40 | 0 | 0 | 20 | 50 | 90 | 80 | 80 | 80 | 80 | 80 | 70 | 70 | 70 | 70 | 70 |
| *Galium* | 0 | 0 | 0 | — | — | — | 50 | 30 | 50 | 60 | 70 | 60 | 70 | 0 | 0 | 20 | 0 | 40 |
| *Kochia* | 0 | 0 | 0 | — | — | — | 10 | 40 | 60 | 50 | 70 | 60 | 70 | 20 | 0 | 20 | 0 | 0 |
| Morningglory | — | — | — | 0 | 0 | 0 | — | — | — | — | — | — | — | — | — | — | — | — |
| Pigweed | 0 | 0 | 0 | 0 | 0 | 0 | 0 | 30 | 20 | 0 | 60 | 80 | 60 | 0 | 0 | 0 | 30 | 0 |
| Ragweed | 0 | 0 | 0 | — | — | — | 0 | 20 | 30 | 0 | 30 | 50 | 40 | 0 | 0 | 0 | 0 | 0 |
| Ryegrass, Italian | 0 | 0 | 0 | — | — | — | 0 | 20 | 30 | 40 | 0 | 40 | 30 | 0 | 0 | 0 | 0 | 30 |
| Velvetleaf | — | — | — | 0 | 0 | 0 | — | — | — | — | — | — | — | — | — | — | — | — |
| Wheat | 0 | 0 | 0 | 0 | 0 | 0 | 0 | 20 | 20 | 50 | 50 | 50 | 30 | 0 | 0 | 0 | 0 | 0 |

| | 125 g ai/ha Compounds | | | | | | | | | | | | | | | | |
|---|---|---|---|---|---|---|---|---|---|---|---|---|---|---|---|---|---|
| | 130 | 131 | 132 | 133 | 139 | 140 | 141 | 142 | 143 | 144 | 145 | 146 | 147 | 148 | 149 | 150 | 151 | 152 |
| Barnyardgrass | 50 | 50 | 60 | 30 | 80 | 70 | 80 | 80 | 50 | 90 | 70 | 90 | 90 | 50 | 70 | 80 | 80 | 70 |
| Blackgrass | 0 | 0 | 0 | 0 | 0 | 0 | 0 | 0 | 0 | 0 | 0 | 30 | 40 | 0 | 30 | 0 | 40 | 0 |
| Corn | 0 | 0 | 0 | 0 | 0 | 0 | 0 | 0 | 0 | 0 | 0 | 0 | 0 | 0 | 10 | 0 | 0 | 0 |
| Crabgrass, Large | — | — | — | — | — | — | — | — | — | — | — | — | — | — | — | — | — | — |
| Foxtail, Giant | 60 | 50 | 50 | 20 | 30 | 0 | 0 | 0 | 20 | 40 | 40 | 0 | 40 | 20 | 40 | 30 | 60 | 50 |
| *Galium* | 0 | 0 | 0 | 0 | 0 | 0 | 20 | 0 | 0 | 10 | 20 | 40 | 50 | 0 | 50 | 50 | 60 | 60 |
| *Kochia* | 0 | 0 | 0 | 0 | 0 | 0 | 0 | 0 | 0 | 0 | 0 | 40 | 0 | 0 | 50 | 30 | 70 | 50 |
| Morningglory | — | — | — | — | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 | 0 | 0 | 50 | 0 |
| Ragweed | 0 | 0 | 0 | 0 | 0 | 0 | 0 | 0 | 0 | 0 | 0 | 0 | 0 | 0 | 30 | 0 | 60 | 40 |
| Ryegrass, Italian | 0 | 0 | 0 | 0 | 0 | 0 | 0 | 0 | 0 | 0 | 0 | 20 | 20 | 0 | 10 | 0 | 30 | 10 |
| Velvetleaf | — | — | — | — | — | — | — | — | — | — | — | — | — | — | — | — | — | — |
| Wheat | 0 | 0 | 0 | 0 | 0 | 0 | 0 | 0 | 0 | 0 | 0 | 0 | 0 | 0 | 0 | 0 | 0 | 0 |

| | 125 g ai/ha Compounds | | | | | | | | | | | | | | | | |
|---|---|---|---|---|---|---|---|---|---|---|---|---|---|---|---|---|---|
| | 153 | 154 | 156 | 157 | 160 | 161 | 162 | 163 | 164 | 165 | 166 | 167 | 168 | 169 | 170 | 171 | 172 | 174 |
| Barnyardgrass | 60 | 70 | 80 | 70 | 70 | 90 | 70 | 90 | 90 | 90 | 80 | 90 | 90 | 90 | 90 | 90 | 0 | 0 |
| Blackgrass | 40 | 60 | 0 | 30 | 60 | 50 | 50 | 50 | 50 | 60 | 50 | 50 | 40 | 30 | 50 | 50 | 0 | 0 |
| Corn | 0 | 60 | 20 | 50 | 40 | 10 | 30 | 10 | 50 | 60 | 30 | 0 | 30 | 0 | 20 | 20 | 0 | 0 |
| Crabgrass, Large | — | — | — | — | — | — | — | — | — | — | — | — | — | — | — | — | — | — |
| Foxtail, Giant | 50 | 80 | 80 | 80 | 80 | 90 | 90 | 70 | 70 | 70 | 80 | 90 | 90 | 60 | 60 | 60 | 0 | 20 |
| *Galium* | 0 | 0 | 20 | 40 | 60 | 50 | 30 | 20 | 50 | 40 | 20 | 50 | 60 | 20 | 60 | 50 | 0 | 0 |
| *Kochia* | 60 | 40 | 0 | 20 | 70 | 20 | 40 | 0 | 60 | 50 | 30 | 30 | 40 | 0 | 20 | 0 | 0 | 0 |
| Morningglory | — | — | — | — | — | — | — | — | — | — | — | — | — | — | — | — | — | — |
| Pigweed | 40 | 20 | 0 | 0 | 60 | 20 | 20 | 0 | 20 | 30 | 40 | 0 | 0 | 0 | 20 | 0 | 0 | 0 |
| Ragweed | 0 | 0 | 0 | 20 | 50 | 0 | 0 | 0 | 20 | 20 | 0 | 20 | 0 | 0 | 20 | 0 | 0 | 0 |
| Ryegrass, Italian | 0 | 30 | 20 | 30 | 0 | 20 | 0 | 0 | 40 | 40 | 0 | 20 | 20 | 20 | 20 | 20 | 0 | 0 |
| Velvetleaf | — | — | — | — | — | — | — | — | — | — | — | — | — | — | — | — | — | — |
| Wheat | 0 | 0 | 0 | 40 | 0 | 20 | 0 | 20 | 40 | 30 | 20 | 0 | 0 | 0 | 0 | 0 | 0 | 0 |

| | 125 g ai/ha Compounds | | | | | | | | | | | | | | | | |
|---|---|---|---|---|---|---|---|---|---|---|---|---|---|---|---|---|---|
| | 175 | 181 | 182 | 183 | 184 | 185 | 186 | 188 | 189 | 190 | 194 | 195 | 196 | 197 | 198 | 199 | 200 | 201 |
| Barnyardgrass | 0 | 0 | 0 | 0 | 70 | 40 | 0 | 0 | 90 | 70 | 50 | 80 | 30 | 30 | 50 | 50 | 70 | 0 |
| Blackgrass | 0 | 40 | 0 | 0 | 0 | 0 | 0 | 0 | — | — | — | — | — | — | — | — | 0 | 0 |
| Corn | 0 | 0 | 0 | 0 | 0 | 0 | 0 | 0 | 0 | 0 | 0 | 0 | 0 | 0 | 0 | 0 | 0 | 0 |
| Crabgrass, Large | — | — | — | — | — | — | — | — | 60 | 70 | 60 | 80 | 70 | 50 | 50 | 60 | — | — |
| Foxtail, Giant | 0 | 0 | 0 | 0 | 70 | 20 | 0 | 0 | 70 | 70 | 10 | 30 | 20 | 0 | 10 | 0 | 20 | 0 |
| *Galium* | 0 | 0 | 0 | 0 | 0 | 0 | 0 | 0 | — | — | — | — | — | — | — | — | 0 | 0 |
| *Kochia* | 0 | 10 | 0 | 0 | 0 | 0 | 0 | 0 | — | — | — | — | — | — | — | — | 0 | 0 |
| Morningglory | — | — | — | — | — | — | — | — | 0 | 0 | 0 | 0 | 0 | 0 | 0 | 0 | — | — |
| Pigweed | 0 | 0 | 0 | 0 | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | — | — | — | — | — | — | — | — | 0 | 0 |
| Ryegrass, Italian | 0 | 0 | 0 | 0 | 0 | 0 | 0 | 0 | — | — | — | — | — | — | — | — | 0 | 0 |
| Velvetleaf | — | — | — | — | — | — | — | — | 0 | 0 | 0 | 0 | 0 | 0 | 0 | 0 | — | — |
| Wheat | 0 | 0 | 0 | 0 | 0 | 0 | 0 | 0 | 0 | 0 | 0 | 0 | 0 | 0 | 0 | 0 | 0 | 0 |

TABLE A-continued

| | 125 g ai/ha Compounds | | | | | | | | | | | | | | | | | |
|---|---|---|---|---|---|---|---|---|---|---|---|---|---|---|---|---|---|---|
| | 202 | 203 | 204 | 205 | 206 | 207 | 208 | 209 | 210 | 211 | 212 | 213 | 214 | 215 | 216 | 217 | 218 | 219 |
| Barnyardgrass | 80 | 40 | 90 | 40 | 90 | 80 | 50 | 60 | 80 | 90 | 60 | 60 | 60 | 50 | 0 | 70 | 60 | 40 |
| Blackgrass | 50 | 0 | 70 | 0 | 70 | 70 | 20 | 0 | 30 | 50 | 40 | 50 | 40 | 30 | 0 | 20 | 20 | 40 |
| Corn | 80 | 0 | 60 | 0 | 60 | 50 | 0 | 0 | 0 | 30 | 0 | 0 | 30 | 0 | 0 | 20 | 20 | 0 |
| Crabgrass, Large | — | — | — | — | — | — | — | — | — | — | — | — | — | — | — | — | — | — |
| Foxtail, Giant | 90 | 50 | 90 | 70 | 90 | 90 | 90 | 40 | 50 | 70 | 60 | 80 | 80 | 80 | 0 | 80 | 60 | 60 |
| *Galium* | 60 | 0 | 50 | 30 | 70 | 0 | 0 | 0 | 30 | 60 | 50 | 0 | 40 | 40 | 0 | 30 | 40 | 30 |
| *Kochia* | 80 | 0 | 20 | 0 | 70 | 0 | 0 | 0 | 20 | 40 | 0 | 0 | 0 | 0 | 0 | 20 | 50 | 0 |
| Morningglory | — | — | — | — | — | — | — | — | — | — | — | — | — | — | — | — | — | — |
| Pigweed | 70 | 0 | 0 | 0 | 50 | 0 | 0 | 0 | 0 | 0 | 0 | 0 | 0 | 50 | 0 | 0 | 0 | 0 |
| Ragweed | 30 | 0 | 0 | 0 | 0 | 0 | 0 | 0 | 0 | 0 | 0 | 0 | 0 | 0 | 0 | 0 | 0 | 0 |
| Ryegrass, Italian | 30 | 0 | 30 | 0 | 50 | 0 | 0 | 0 | 0 | 30 | 0 | 40 | 10 | 0 | 0 | 0 | 0 | 0 |
| Velvetleaf | — | — | — | — | — | — | — | — | — | — | — | — | — | — | — | — | — | — |
| Wheat | 40 | 0 | 60 | 0 | 70 | 0 | 0 | 0 | 0 | 30 | 0 | 0 | 0 | 0 | 0 | 20 | 20 | 0 |

| | 125 g ai/ha Compounds | | | | | | | | | | | | | | | | | |
|---|---|---|---|---|---|---|---|---|---|---|---|---|---|---|---|---|---|---|
| | 220 | 221 | 222 | 223 | 224 | 225 | 226 | 227 | 228 | 229 | 230 | 231 | 232 | 233 | 234 | 235 | 236 | 239 |
| Barnyardgrass | 40 | 0 | 70 | 80 | 80 | 30 | 30 | 20 | 60 | 70 | 60 | 80 | 80 | 70 | 60 | 10 | 0 | 50 |
| Blackgrass | 0 | 0 | 30 | 60 | 60 | 0 | 20 | 0 | 20 | 40 | 20 | 40 | 50 | 60 | 0 | 0 | 0 | 20 |
| Corn | 0 | 0 | 20 | 0 | 60 | 0 | 0 | 0 | 20 | 0 | 20 | 30 | 80 | 20 | 0 | 0 | 0 | 0 |
| Crabgrass, Large | — | — | — | — | — | — | — | — | — | — | — | — | — | — | — | — | — | — |
| Foxtail, Giant | 50 | 0 | 80 | 80 | 80 | 40 | 70 | 30 | 70 | 80 | 70 | 70 | 90 | 90 | 40 | 10 | 0 | 50 |
| *Galium* | 0 | 0 | 30 | 50 | 70 | 20 | 20 | 0 | 30 | 60 | 20 | 40 | 60 | 20 | 30 | 50 | 0 | 0 |
| *Kochia* | 0 | 0 | 0 | 50 | 80 | 0 | 30 | 0 | 20 | 10 | 0 | 70 | 80 | 60 | 0 | 0 | 0 | 0 |
| Morningglory | — | — | — | — | — | — | — | — | — | — | — | — | — | — | — | — | — | — |
| Pigweed | 0 | 0 | 0 | 40 | 60 | 0 | 0 | 0 | 0 | 0 | 0 | 0 | 80 | 0 | 0 | 0 | 0 | 0 |
| Ragweed | 0 | 0 | 0 | 0 | 40 | 0 | 0 | 0 | 0 | 20 | 0 | 20 | 20 | 30 | 0 | 0 | 0 | 0 |
| Ryegrass, Italian | 0 | 0 | 20 | 0 | 50 | 0 | 0 | 0 | 0 | 30 | 0 | 20 | 40 | 20 | 20 | 0 | 0 | 0 |
| Velvetleaf | — | — | — | — | — | — | — | — | — | — | — | — | — | — | — | — | — | — |
| Wheat | 0 | 0 | 20 | 40 | 50 | 0 | 0 | 0 | 0 | 0 | 20 | 20 | 30 | 0 | 0 | 0 | 0 | 0 |

| | 125 g ai/ha Compounds | | | | | | | | | | | | | | | | | |
|---|---|---|---|---|---|---|---|---|---|---|---|---|---|---|---|---|---|---|
| | 240 | 241 | 242 | 244 | 245 | 246 | 247 | 248 | 249 | 250 | 251 | 256 | 257 | 258 | 259 | 260 | 261 | 262 |
| Barnyardgrass | 30 | 80 | 70 | 80 | 30 | 70 | 60 | 20 | 30 | 30 | 0 | 0 | 50 | 40 | 50 | 70 | 0 | 60 |
| Blackgrass | 0 | — | — | — | — | — | — | — | — | — | — | — | — | — | — | — | — | — |
| Corn | 0 | 50 | 0 | 0 | 0 | 20 | 0 | 0 | 0 | 0 | 0 | 0 | 0 | 0 | 0 | 0 | 0 | 0 |
| Crabgrass, Large | — | 70 | 70 | 80 | 20 | 50 | 50 | 50 | 0 | 0 | 0 | 70 | 90 | 80 | 80 | 90 | 70 | 70 |
| Foxtail, Giant | 40 | 80 | 80 | 80 | 20 | 40 | 50 | 30 | 20 | 30 | 0 | 40 | 80 | 60 | 50 | 80 | 0 | 60 |
| *Galium* | 0 | — | — | — | — | — | — | — | — | — | — | — | — | — | — | — | — | — |
| *Kochia* | 0 | — | — | — | — | — | — | — | — | — | — | — | — | — | — | — | — | — |
| Morningglory | — | 20 | 0 | 20 | 0 | 0 | 0 | 0 | 0 | 0 | 0 | 0 | 0 | 0 | 0 | 0 | 0 | 0 |
| Pigweed | 0 | 0 | 0 | 20 | 40 | 0 | 0 | 0 | 0 | 0 | 0 | 0 | 0 | 0 | 0 | 60 | 0 | 0 |
| Ragweed | 0 | — | — | — | — | — | — | — | — | — | — | — | — | — | — | — | — | — |
| Ryegrass, Italian | 0 | — | — | — | — | — | — | — | — | — | — | — | — | — | — | — | — | — |
| Velvetleaf | — | 0 | 0 | 30 | 20 | 0 | 0 | 0 | 0 | 0 | 0 | 0 | 0 | 0 | 0 | — | 0 | — |
| Wheat | 0 | 30 | 0 | 20 | 0 | 0 | 0 | 0 | 0 | 0 | 0 | 0 | 20 | 0 | 0 | 0 | 0 | 0 |

| | 125 g ai/ha Compounds | | | | | | | | | | | | | | | | | |
|---|---|---|---|---|---|---|---|---|---|---|---|---|---|---|---|---|---|---|
| | 263 | 264 | 267 | 268 | 269 | 270 | 271 | 272 | 273 | 275 | 276 | 277 | 278 | 279 | 280 | 281 | 282 | 283 |
| Barnyardgrass | 70 | 30 | 70 | 50 | 50 | 90 | 90 | 50 | 10 | 90 | 0 | 90 | 80 | 80 | 80 | 40 | 50 | 0 |
| Blackgrass | — | — | — | — | — | 0 | 50 | 0 | 0 | 50 | 0 | 50 | 30 | 60 | 0 | 0 | 0 | 0 |
| Corn | 40 | 0 | 40 | 0 | 0 | 0 | 20 | 0 | 0 | 40 | 0 | 90 | 0 | 40 | 0 | 0 | 0 | 0 |
| Crabgrass, Large | 80 | 80 | 80 | 70 | 60 | — | — | — | — | — | — | — | — | — | — | — | — | — |
| Foxtail, Giant | 80 | 60 | 70 | 80 | 70 | 60 | 90 | 60 | 20 | 90 | 0 | 90 | 80 | 80 | 70 | 0 | 0 | 0 |
| *Galium* | — | — | — | — | — | 20 | 40 | 30 | 0 | 60 | 0 | 70 | 40 | 40 | 0 | 0 | 0 | 0 |
| *Kochia* | — | — | — | — | — | 0 | 60 | 20 | 0 | 50 | 0 | 30 | 0 | 0 | 0 | 0 | 0 | 0 |
| Morningglory | 20 | 0 | 20 | 0 | 0 | — | — | — | — | — | — | — | — | — | — | — | — | — |
| Pigweed | 40 | 0 | 50 | 70 | 40 | 0 | 0 | 0 | 0 | 30 | 0 | 30 | 0 | 0 | 0 | 0 | 0 | 0 |
| Ragweed | — | — | — | — | — | 0 | 40 | 0 | 0 | 30 | 0 | 30 | 0 | 0 | 0 | 0 | 0 | 0 |
| Ryegrass, Italian | — | — | — | — | — | 0 | 0 | 0 | 0 | 30 | 0 | 30 | 0 | 0 | 0 | 0 | 0 | 0 |
| Velvetleaf | — | 30 | — | — | — | — | — | — | — | — | — | — | — | — | — | — | — | — |
| Wheat | 40 | 0 | 0 | 0 | 0 | 0 | 0 | 0 | 0 | 40 | 0 | 60 | 0 | 40 | 0 | 0 | 0 | 0 |

TABLE A-continued

| | 125 g ai/ha Compounds | | | | | | | | | | | | | | | | | |
|---|---|---|---|---|---|---|---|---|---|---|---|---|---|---|---|---|---|---|
| | 284 | 285 | 286 | 287 | 288 | 289 | 290 | 291 | 292 | 293 | 294 | 295 | 296 | 297 | 298 | 299 | 300 | 301 |
| Barnyardgrass | 0 | 20 | 60 | 50 | 20 | 50 | 50 | 40 | 50 | 50 | 60 | 0 | 0 | 0 | 0 | 30 | 0 | 0 |
| Blackgrass | 0 | 0 | 0 | 0 | 0 | 0 | 0 | 0 | 0 | 0 | 20 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 |
| Crabgrass, Large | — | — | — | — | — | — | — | — | — | — | — | — | — | — | — | — | — | — |
| Foxtail, Giant | 0 | 0 | 60 | 0 | 20 | 30 | 30 | 20 | 50 | 50 | 30 | 0 | 0 | 0 | 0 | 0 | 0 | 0 |
| Galium | 0 | 0 | 0 | 0 | 0 | 0 | 0 | 20 | 10 | 20 | 0 | 0 | 0 | 0 | 0 | 0 | 0 | 0 |
| Kochia | 0 | 0 | 0 | 0 | 0 | 0 | 0 | 0 | 0 | 0 | 30 | 0 | 0 | 0 | 0 | 0 | 0 | 0 |
| Morningglory | — | — | — | — | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 | 0 | 0 | 0 | 0 |
| Velvetleaf | — | — | — | — | — | — | — | — | — | — | — | — | — | — | — | — | — | — |
| Wheat | 0 | 0 | 0 | 0 | 0 | 0 | 0 | 0 | 0 | 0 | 20 | 0 | 0 | 0 | 0 | 0 | 0 | 0 |

| | 125 g ai/ha Compounds | | | | | | | | | | | | | | | | | |
|---|---|---|---|---|---|---|---|---|---|---|---|---|---|---|---|---|---|---|
| | 302 | 303 | 304 | 305 | 306 | 307 | 308 | 309 | 310 | 311 | 312 | 313 | 314 | 315 | 316 | 317 | 318 | 319 |
| Barnyardgrass | 90 | 80 | 80 | 80 | 80 | 70 | 70 | 80 | 90 | 60 | 80 | 20 | 30 | 90 | 80 | 80 | 90 | 90 |
| Blackgrass | 40 | 60 | 50 | 60 | 50 | 30 | 50 | 60 | 30 | 0 | 40 | 0 | 0 | 40 | 30 | 0 | 30 | 40 |
| Corn | 0 | 50 | 30 | 70 | 50 | 0 | 0 | 30 | 20 | 0 | 60 | 0 | 0 | 70 | 60 | 0 | 20 | 40 |
| Crabgrass, Large | — | — | — | — | — | — | — | — | — | — | — | — | — | — | — | — | — | — |
| Foxtail, Giant | 80 | 80 | 80 | 80 | 80 | 70 | 70 | 80 | 90 | 60 | 80 | 40 | 60 | 90 | 90 | 80 | 40 | 50 |
| Galium | 60 | 60 | 20 | 50 | 60 | 0 | 0 | 60 | 20 | 0 | 30 | 0 | 0 | 40 | 20 | 0 | 30 | 30 |
| Kochia | 10 | 50 | 10 | 30 | 30 | 0 | 0 | 0 | 30 | 0 | 20 | 0 | 0 | 50 | 30 | 0 | 20 | 30 |
| Morningglory | — | — | — | — | — | — | — | — | — | — | — | — | — | — | — | — | — | — |
| Pigweed | 0 | 40 | 40 | 60 | 70 | 0 | 0 | 0 | 0 | 0 | 20 | 0 | 0 | 30 | 0 | 0 | 20 | 0 |
| Ragweed | 0 | 20 | 0 | 0 | 20 | 0 | 0 | 0 | 20 | 0 | 20 | 0 | 0 | 20 | 20 | 0 | 0 | 20 |
| Ryegrass, Italian | 0 | 40 | 50 | 60 | 50 | 0 | 0 | 10 | 30 | 0 | 20 | 0 | 0 | 20 | 20 | 0 | 20 | 30 |
| Velvetleaf | — | — | — | — | — | — | — | — | — | — | — | — | — | — | — | — | — | — |
| Wheat | 0 | 50 | 40 | 60 | 50 | 0 | 0 | 40 | 30 | 0 | 40 | 0 | 0 | 60 | 20 | 0 | 20 | 20 |

| | 125 g ai/ha Compounds | | | | | | | | | | | | | | | | | |
|---|---|---|---|---|---|---|---|---|---|---|---|---|---|---|---|---|---|---|
| | 320 | 321 | 322 | 323 | 324 | 325 | 326 | 327 | 328 | 329 | 330 | 331 | 332 | 333 | 334 | 335 | 336 | 337 |
| Barnyardgrass | 50 | 0 | 0 | 90 | 90 | 90 | 0 | 40 | 30 | 0 | 60 | 20 | 40 | 20 | 0 | 20 | 30 | 0 |
| Blackgrass | 0 | 0 | 0 | 40 | 60 | 50 | 0 | 30 | 30 | 0 | 0 | 0 | 0 | 0 | 0 | 0 | 0 | 0 |
| Corn | 0 | 0 | 0 | 70 | 50 | 80 | 0 | 0 | 0 | 0 | 0 | 0 | 0 | 0 | 0 | 0 | 0 | 0 |
| Crabgrass, Large | — | — | — | — | — | — | — | — | — | — | — | — | — | — | — | — | — | — |
| Foxtail, Giant | 30 | 0 | 0 | 90 | 90 | 90 | 20 | 40 | 70 | 0 | 80 | 20 | 30 | 50 | 0 | 70 | 70 | 0 |
| Galium | 0 | 0 | 0 | 40 | 40 | 50 | 0 | 40 | 20 | 0 | 20 | 0 | 0 | 0 | 0 | 0 | 0 | 0 |
| Kochia | 20 | 0 | 0 | 40 | 50 | 60 | 0 | 30 | 0 | 0 | 0 | 0 | 0 | 0 | 0 | 0 | 0 | 0 |
| Morningglory | — | — | — | — | — | — | — | — | — | — | — | — | — | — | — | — | — | — |
| Pigweed | 0 | 0 | 0 | 20 | 40 | 40 | 0 | 0 | 0 | 0 | 0 | 0 | 0 | 0 | 0 | 0 | 0 | 0 |
| Ragweed | 0 | 0 | 0 | 0 | 20 | 20 | 0 | 0 | 0 | 0 | 0 | 0 | 0 | 0 | 0 | 0 | 0 | 0 |
| Ryegrass, Italian | 0 | 0 | 0 | 30 | 30 | 30 | 0 | 20 | 0 | 0 | 0 | 0 | 0 | 0 | 0 | 0 | 0 | 0 |
| Velvetleaf | — | — | — | — | — | — | — | — | — | — | — | — | — | — | — | — | — | — |
| Wheat | 0 | 0 | 0 | 40 | 30 | 60 | 0 | 0 | 0 | 0 | 0 | 0 | 0 | 0 | 0 | 0 | 0 | 0 |

| | 125 g ai/ha Compounds | | | | | | | | | | | | |
|---|---|---|---|---|---|---|---|---|---|---|---|---|---|
| | 338 | 339 | 340 | 341 | 342 | 343 | 344 | 345 | 346 | 347 | 348 | 349 | 350 |
| Barnyardgrass | 0 | 40 | 30 | 30 | 30 | 0 | 60 | 70 | 80 | 50 | 20 | 80 | 70 |
| Blackgrass | 0 | 0 | 0 | 0 | 0 | 0 | 0 | 50 | 20 | 0 | 20 | 20 | 50 |
| Corn | 0 | 0 | 0 | 0 | 0 | 0 | 0 | 80 | 20 | 0 | 0 | 0 | 20 |
| Crabgrass, Large | — | — | — | — | — | — | — | — | — | — | — | — | — |
| Foxtail, Giant | 20 | 60 | 30 | 50 | 40 | 30 | 80 | 90 | 80 | 20 | 70 | 60 | 80 |
| Galium | 0 | 0 | 0 | 0 | 0 | 0 | 0 | 60 | 30 | 0 | 0 | 20 | 60 |
| Kochia | 0 | 0 | 0 | 0 | 20 | 0 | 0 | 50 | 0 | 0 | 20 | 40 | 70 |
| Morningglory | — | — | — | — | — | — | — | — | — | — | — | — | — |
| Pigweed | 0 | 0 | 0 | 0 | 0 | 0 | 0 | 20 | 0 | 0 | 0 | 0 | 20 |
| Ragweed | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 50 | 20 | 0 | 0 | 0 | 0 |
| Velvetleaf | — | — | — | — | — | — | — | — | — | — | — | — | — |
| Wheat | 0 | 0 | 0 | 0 | 0 | 0 | 0 | 50 | 0 | 0 | 0 | 0 | 20 |

TABLE A-continued

Preemergence

| | 1000 g ai/ha Compounds | | | | | | | | | | | | | | | | | | | | | | | |
|---|---|---|---|---|---|---|---|---|---|---|---|---|---|---|---|---|---|---|---|---|---|---|---|---|
| | 17 | 18 | 19 | 20 | 21 | 22 | 23 | 24 | 25 | 26 | 27 | 30 | 31 | 33 | 34 | 35 | 39 | 40 | 43 | 44 | 71 | 96 | 98 | 99 | 100 | 104 |
| Barnyardgrass | 90 | 80 | 90 | 90 | 90 | 0 | 90 | 0 | 80 | 70 | 70 | 90 | 50 | 90 | 90 | 90 | 70 | 90 | 20 | 40 | 50 | 0 | 50 | 90 | 90 | 80 |
| Corn | 60 | 0 | 0 | 0 | 0 | 0 | 0 | 0 | 0 | 0 | 0 | 0 | 20 | 0 | 30 | 20 | 0 | 30 | 0 | 0 | 0 | 0 | 20 | 20 | 20 | 20 |
| Crabgrass, Large | 90 | 80 | 90 | 90 | 90 | 70 | 90 | 70 | 90 | 90 | 90 | 90 | 80 | 90 | 90 | 90 | 90 | 90 | 90 | 90 | 80 | 0 | 90 | 90 | 90 | 90 |
| Foxtail, Giant | 90 | 80 | 90 | 90 | 90 | 30 | 90 | 40 | 90 | 90 | 90 | 90 | 80 | 90 | 90 | 90 | 80 | 90 | 80 | 70 | 60 | 0 | 90 | 90 | 90 | 90 |
| Kochia | — | — | — | — | — | — | — | — | — | — | — | — | — | — | — | — | — | — | — | — | — | — | — | — | — | — |
| Morningglory | 30 | 0 | 0 | 0 | 40 | 0 | 0 | 0 | 0 | 0 | 0 | 0 | — | — | — | 0 | 0 | 0 | 0 | 0 | — | 0 | 0 | 0 | 0 | 0 |
| Pigweed | 50 | 0 | 0 | 0 | 40 | — | — | 0 | 0 | 0 | 0 | 0 | 0 | 0 | 0 | 0 | 0 | 0 | 0 | 0 | 0 | 0 | 0 | 0 | 0 | 0 |
| Ragweed | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — |
| Velvetleaf | 40 | 0 | 0 | 30 | 50 | 0 | 40 | 60 | 0 | 0 | 0 | 0 | 0 | 0 | 0 | 0 | 0 | 0 | 0 | 0 | 0 | 0 | 0 | 0 | 0 | 0 |
| Wheat | 70 | 0 | 0 | 0 | 20 | 0 | 0 | 0 | 0 | 0 | 0 | 0 | 50 | 50 | 60 | 0 | 0 | 20 | 0 | 0 | 0 | 0 | 0 | 20 | 20 | 20 |

| | 1000 g ai/ha Compounds | | | | | | | | | | | | | | | | 500 g ai/ha Compounds | | |
|---|---|---|---|---|---|---|---|---|---|---|---|---|---|---|---|---|---|---|---|
| | 105 | 106 | 108 | 191 | 192 | 193 | 237 | 238 | 243 | 252 | 253 | 254 | 255 | 265 | 266 | 274 | 1 | 2 | 3 |
| Barnyardgrass | 90 | 90 | 90 | 0 | 0 | 80 | 60 | 50 | 80 | 20 | 0 | 0 | 60 | 0 | 0 | 90 | 90 | 60 | 80 |
| Corn | 0 | 30 | 0 | 0 | 0 | 0 | — | — | 0 | 0 | 0 | 0 | 0 | 0 | 0 | — | 20 | 0 | 50 |
| Crabgrass, Large | 90 | 90 | 90 | 0 | 0 | 100 | — | — | 90 | 40 | 0 | 70 | 90 | 0 | 0 | — | 90 | 90 | 90 |
| Foxtail, Giant | 90 | 90 | 90 | 0 | 0 | 90 | 80 | 90 | 90 | 20 | 0 | 40 | 70 | 0 | 0 | 90 | 90 | 90 | 90 |
| Kochia | — | — | — | — | — | — | 0 | 0 | — | — | — | — | — | — | — | 40 | — | — | — |
| Morningglory | 0 | 0 | 0 | 0 | 0 | 0 | — | — | 0 | 0 | 0 | 0 | 0 | 0 | 0 | — | 0 | 0 | 0 |
| Pigweed | 0 | 0 | 0 | 0 | 0 | 0 | 0 | 0 | 0 | — | 0 | 0 | 0 | 0 | 0 | 0 | 0 | 0 | 0 |
| Ragweed | — | — | — | — | — | — | 0 | 0 | — | — | — | — | — | — | — | 20 | — | — | — |
| Ryegrass, Italian | — | — | — | — | — | — | 0 | 0 | — | — | — | — | — | — | — | 40 | — | — | — |
| Velvetleaf | 0 | 0 | 0 | 0 | 0 | 0 | — | — | 0 | 0 | 0 | 0 | 0 | 0 | 0 | — | 0 | 0 | 0 |
| Wheat | 0 | 50 | 0 | 0 | 0 | 0 | — | — | 0 | 0 | 0 | 0 | 0 | 0 | 0 | — | 0 | 0 | 60 |

| | 500 g ai/ha Compounds | | | | | | | | | | | | | | | | | | | | | | | | |
|---|---|---|---|---|---|---|---|---|---|---|---|---|---|---|---|---|---|---|---|---|---|---|---|---|---|
| | 4 | 5 | 6 | 7 | 8 | 9 | 10 | 11 | 12 | 13 | 14 | 15 | 16 | 28 | 29 | 32 | 36 | 37 | 38 | 41 | 42 | 45 | 46 | 47 | 48 | 49 | 50 |
| Barnyardgrass | 80 | 90 | 80 | 80 | 60 | 60 | 40 | 20 | 90 | 50 | 90 | 0 | 90 | 20 | 50 | 0 | 80 | 80 | 80 | 60 | 60 | 80 | 50 | 0 | 90 | 20 | 90 |
| Corn | 0 | 0 | 0 | 0 | 20 | 0 | 0 | 0 | 0 | 0 | 0 | 0 | 30 | 0 | 0 | 0 | 0 | 0 | 0 | 0 | 0 | 0 | 0 | 20 | 0 | 0 |
| Crabgrass, Large | 90 | 90 | 90 | 90 | 90 | 90 | 90 | 90 | 90 | 80 | 90 | 80 | 90 | 80 | 70 | 80 | 80 | 80 | 80 | 90 | 90 | 90 | 90 | 60 | 90 | 90 | 90 |
| Foxtail, Giant | 90 | 100 | 90 | 90 | 90 | 90 | 90 | 50 | 90 | 30 | 90 | 50 | 90 | 20 | 0 | 80 | 70 | 20 | 30 | 70 | 80 | 80 | 80 | 0 | 90 | 70 | 90 |
| Kochia | — | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 0 | 0 | 0 | 0 | 0 | — | — | 0 | 0 | 0 | 0 | 0 | 0 |
| Pigweed | 0 | 0 | 0 | 0 | 0 | 0 | 0 | 0 | 0 | 0 | 20 | 0 | 0 | 0 | 0 | 0 | 0 | 0 | 0 | 0 | 30 | 0 | 0 | 0 | 0 | 0 | 0 |
| Ragweed | — | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — | — |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 70 | 0 | 0 | 0 | 0 | 0 | 0 | 0 | 20 | 0 | 0 | 0 | 0 | 0 | 0 | 0 | 20 | 30 | 0 | 0 | 0 | 0 | 0 | 0 | 50 | 0 | 0 |

| | 500 g ai/ha Compounds | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | 51 | 52 | 53 | 54 | 55 | 56 | 57 | 58 | 59 | 60 | 61 | 62 | 63 | 64 | 65 | 66 | 67 | 68 | 69 | 70 | 72 | 73 | 74 | 75 | 76 | 77 | 78 |
| Barnyardgrass | 0 | 90 | 90 | 20 | 80 | 40 | 80 | 20 | 90 | 90 | 0 | 80 | 80 | 90 | 90 | 90 | 70 | 90 | 90 | 90 | 50 | 80 | 90 | 70 | 80 | 90 | 90 |
| Corn | 0 | 0 | 0 | 0 | 0 | 0 | 0 | 0 | 0 | 0 | 0 | 0 | 20 | 0 | 20 | 0 | 0 | 0 | 0 | 0 | 0 | 0 | 0 | 40 | 30 | 0 |
| Crabgrass, Large | 90 | 90 | 90 | 90 | 90 | 90 | 90 | 90 | 90 | 90 | 80 | 90 | 90 | 90 | 90 | 90 | 90 | 90 | 90 | 90 | 90 | 90 | 90 | 90 | 90 | 90 | 90 |
| Foxtail, Giant | 90 | 90 | 90 | 90 | 90 | 50 | 80 | 80 | 90 | 90 | 0 | 90 | 90 | 90 | 90 | 90 | 90 | 90 | 90 | 90 | 80 | 90 | 90 | 90 | 90 | 90 | 90 |
| Kochia | — | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 50 | 60 | 0 |
| Pigweed | 0 | 40 | 0 | 0 | 0 | 0 | 0 | 0 | 0 | 0 | 0 | 30 | 0 | 0 | 0 | 0 | 0 | 30 | 20 | 0 | 0 | 50 | 0 | 50 | 70 | 60 |
| Ragweed | — | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — | — |
| Velvetleaf | 0 | 20 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 30 |
| Wheat | 0 | 0 | 20 | 20 | 0 | 0 | 0 | 0 | 0 | 0 | 0 | 0 | 0 | 0 | 0 | 0 | 20 | 0 | 20 | 20 | 20 | 0 | 0 | 0 | 30 | 0 | 30 | 0 |

| | 500 g ai/ha Compounds | | | | | | | | | | | | | | | | | | | | | | |
|---|---|---|---|---|---|---|---|---|---|---|---|---|---|---|---|---|---|---|---|---|---|---|---|
| | 79 | 80 | 81 | 82 | 83 | 84 | 85 | 86 | 87 | 88 | 89 | 90 | 91 | 92 | 93 | 94 | 95 | 97 | 101 | 102 | 103 | 107 | 109 | 110 |
| Barnyardgrass | 90 | 80 | 80 | 50 | 50 | 0 | 30 | 40 | 80 | 50 | 80 | 70 | 20 | 90 | 90 | 0 | 90 | 0 | 90 | 0 | 90 | 70 | 90 | 90 |
| Corn | 0 | 0 | 0 | 0 | 0 | 0 | 0 | 20 | 0 | 0 | 0 | 0 | 0 | 0 | 0 | 0 | 0 | 0 | 0 | 0 | 0 | 0 | — | — |
| Crabgrass, Large | 90 | 90 | 90 | 90 | 90 | 50 | 80 | 80 | 90 | 80 | 90 | 80 | 60 | 90 | 90 | 50 | 90 | 0 | 100 | 0 | 100 | 90 | — | — |
| Foxtail, Giant | 90 | 90 | 90 | 70 | 70 | 0 | 50 | 60 | 90 | 30 | 90 | 70 | 40 | 90 | 90 | 0 | 90 | 0 | 90 | 0 | 90 | 80 | 90 | 90 |
| Kochia | — | — | — | — | — | — | — | — | — | — | — | — | — | — | — | — | — | — | — | — | — | — | 0 | 0 |

TABLE A-continued

| | | | | | | | | | | | | | | | | | | | | | | | |
|---|---|---|---|---|---|---|---|---|---|---|---|---|---|---|---|---|---|---|---|---|---|---|---|
| Morningglory | 0 | 0 | 20 | 0 | 0 | 0 | 0 | 0 | 0 | 0 | 0 | 0 | 0 | 0 | 0 | 0 | 0 | 0 | 50 | 0 | 0 | 0 | — | — |
| Pigweed | 80 | 80 | 0 | 0 | 0 | 0 | 0 | 0 | 0 | 30 | 0 | 0 | 0 | 0 | 0 | — | 0 | 0 | 70 | 0 | 20 | 20 | 0 | 0 |
| Ragweed | — | — | — | — | — | — | — | — | — | — | — | — | — | — | — | — | — | — | — | — | — | — | 0 | 0 |
| Ryegrass, Italian | — | — | — | — | — | — | — | — | — | — | — | — | — | — | — | — | — | — | — | — | — | — | 50 | 0 |
| Velvetleaf | 30 | 30 | 0 | 0 | 0 | 0 | 0 | 0 | 0 | 0 | 0 | 0 | 0 | 0 | 0 | — | 0 | 0 | 40 | 0 | 0 | 0 | — | — |
| Wheat | 20 | 20 | 20 | 0 | 0 | 0 | 0 | 0 | 10 | 0 | 10 | 0 | 0 | 0 | 0 | 0 | 0 | 0 | 70 | 0 | 0 | 0 | — | — |

| | 500 g ai/ha Compounds | | | | | | | | | | | | | | | | | |
|---|---|---|---|---|---|---|---|---|---|---|---|---|---|---|---|---|---|---|
| | 111 | 112 | 113 | 114 | 115 | 116 | 117 | 118 | 119 | 120 | 121 | 122 | 123 | 124 | 125 | 126 | 127 | 128 |
| Barnyardgrass | 0 | 0 | 0 | 50 | 50 | 50 | 20 | 70 | 90 | 90 | 90 | 90 | 90 | 80 | 90 | 90 | 90 | 80 |
| Corn | — | — | — | — | 0 | 0 | 0 | — | — | — | — | — | — | — | — | — | — | — |
| Crabgrass, Large | — | — | — | — | 80 | 80 | 80 | — | — | — | — | — | — | — | — | — | — | — |
| Foxtail, Giant | 0 | 0 | 0 | 70 | 20 | 30 | 70 | 90 | 90 | 90 | 90 | 90 | 90 | 90 | 90 | 90 | 90 | 90 |
| Kochia | 0 | 0 | 0 | 0 | — | — | — | 0 | 60 | 80 | 70 | 70 | 90 | 70 | 70 | 10 | 60 | 60 |
| Morningglory | — | — | — | — | 0 | 0 | 0 | — | — | — | — | — | — | — | — | — | — | — |
| Pigweed | 0 | 0 | 0 | 0 | 0 | 0 | 0 | 0 | 40 | 40 | 70 | 80 | 80 | 80 | 0 | 0 | 0 | 0 |
| Ragweed | 0 | 0 | 0 | 0 | — | — | — | 0 | 80 | 80 | 70 | 60 | 80 | 50 | 0 | 0 | 0 | — |
| Ryegrass, Italian | 0 | 0 | 0 | 30 | — | — | — | 0 | 60 | 50 | 0 | 0 | 60 | 40 | 20 | 0 | 0 | 0 |
| Velvetleaf | — | — | — | — | 0 | 0 | 0 | — | — | — | — | — | — | — | — | — | — | — |
| Wheat | — | — | — | — | 0 | 0 | 0 | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 129 | 130 | 131 | 132 | 133 | 139 | 140 | 141 | 142 | 143 | 144 | 145 | 146 | 147 | 148 | 149 | 150 | 151 |
| Barnyardgrass | 80 | 70 | 60 | 90 | 30 | 90 | 90 | 90 | 90 | 90 | 90 | 90 | 90 | 90 | 90 | 90 | 90 | 90 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 90 | 90 | 60 | 80 | 90 | 90 | 90 | 90 | 90 | 90 | 80 | 90 | 90 | 90 | 90 | 90 | 90 | 90 |
| Kochia | 70 | 0 | 0 | 0 | 0 | 30 | 0 | 20 | 0 | 30 | 0 | 0 | 30 | 80 | 30 | 70 | 90 | 90 |
| Morningglory | — | — | — | — | — | — | — | — | — | — | — | — | — | — | — | — | — | — |
| Pigweed | 0 | 0 | 0 | 0 | 0 | 20 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 30 | 50 | 0 | 80 | 50 | 90 |
| Ryegrass, Italian | 60 | 0 | 0 | 0 | 0 | 0 | 0 | 20 | 0 | 0 | 20 | 0 | 40 | 40 | 0 | 70 | 50 | 60 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 152 | 153 | 154 | 156 | 157 | 160 | 161 | 162 | 163 | 164 | 165 | 166 | 167 | 168 | 169 | 170 | 171 | 172 |
| Barnyardgrass | 90 | 90 | 80 | 90 | 90 | 90 | 90 | 90 | 90 | 90 | 90 | 90 | 90 | 90 | 90 | 90 | 90 | 20 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 90 | 80 | 90 | 90 | 90 | 90 | 90 | 90 | 90 | 90 | 90 | 90 | 90 | 90 | 90 | 90 | 90 | 30 |
| Kochia | 60 | 80 | 70 | 40 | 70 | 90 | 60 | 60 | 50 | 80 | 70 | 70 | 60 | 60 | 60 | 70 | 70 | 30 |
| Morningglory | — | — | — | — | — | — | — | — | — | — | — | — | — | — | — | — | — | — |
| Pigweed | 10 | 0 | 30 | 0 | 50 | 90 | 70 | 80 | 40 | 70 | 70 | 10 | 50 | 50 | 20 | 50 | 40 | 0 |
| Ragweed | 70 | 80 | 0 | 0 | 50 | 80 | 70 | 60 | 40 | 60 | 80 | 50 | 50 | 50 | 20 | 60 | 30 | 0 |
| Ryegrass, Italian | 30 | 0 | 50 | 30 | 60 | 70 | 50 | 50 | 0 | 50 | 20 | 60 | 70 | 40 | 20 | 50 | 30 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 174 | 175 | 181 | 182 | 183 | 184 | 185 | 186 | 188 | 189 | 190 | 194 | 195 | 196 | 197 | 198 | 199 | 200 |
| Barnyardgrass | 20 | 0 | 0 | 0 | 0 | 90 | 70 | 0 | 0 | 90 | 90 | 80 | 90 | 70 | 70 | 90 | 60 | 90 |
| Corn | — | — | — | — | — | — | — | — | — | 0 | 0 | 0 | 0 | 0 | 0 | 0 | 0 | — |
| Crabgrass, Large | — | — | — | — | — | — | — | — | — | 90 | 90 | 100 | 90 | 100 | 100 | 100 | 100 | — |
| Foxtail, Giant | 50 | 0 | 70 | 70 | 0 | 90 | 90 | 0 | 0 | 90 | 90 | 90 | 90 | 90 | 80 | 80 | 90 | 80 |
| Kochia | 20 | 0 | 80 | 0 | 0 | 20 | 40 | 0 | 0 | — | — | — | — | — | — | — | — | 0 |
| Morningglory | — | — | — | — | — | — | — | — | — | 0 | 0 | 0 | 0 | 0 | 0 | 0 | 0 | — |
| Pigweed | 0 | 0 | 0 | 0 | 0 | 0 | 20 | 0 | 0 | 0 | 0 | 0 | 0 | 0 | 0 | 0 | 0 | — |
| Ragweed | 0 | 0 | 0 | 0 | 0 | 0 | 0 | 0 | 0 | — | — | — | — | — | — | — | — | 0 |
| Ryegrass, Italian | 0 | 0 | 0 | 0 | 0 | 0 | 20 | 0 | 0 | — | — | — | — | — | — | — | — | 0 |
| Velvetleaf | — | — | — | — | — | — | — | — | — | 0 | 0 | 0 | 0 | 0 | 0 | 0 | 0 | — |
| Wheat | — | — | — | — | — | — | — | — | — | 20 | 30 | 0 | 0 | 0 | 0 | 0 | 0 | — |

TABLE A-continued

| | 500 g ai/ha Compounds | | | | | | | | | | | | | | | | | |
|---|---|---|---|---|---|---|---|---|---|---|---|---|---|---|---|---|---|---|
| | 201 | 202 | 203 | 204 | 205 | 206 | 207 | 208 | 209 | 210 | 211 | 212 | 213 | 214 | 215 | 216 | 217 | 218 |
| Barnyardgrass | 20 | 90 | 60 | 90 | 80 | 90 | 90 | 90 | 60 | 90 | 90 | 90 | 80 | 80 | 80 | 60 | 90 | 90 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 30 | 90 | 80 | 90 | 90 | 90 | 90 | 90 | 90 | 90 | 90 | 90 | 90 | 90 | 90 | 50 | 90 | 90 |
| Kochia | 0 | 80 | 0 | 80 | 50 | 80 | 30 | 20 | 20 | 30 | 70 | 20 | 0 | 80 | 0 | 0 | 70 | 70 |
| Morningglory | — | — | — | — | — | — | — | — | — | — | — | — | — | — | — | — | — | — |
| Pigweed | 0 | 70 | 0 | 50 | 20 | 80 | 20 | 0 | 20 | 50 | 70 | 0 | 0 | 70 | 50 | 0 | 40 | 70 |
| Ragweed | 0 | 90 | 0 | 80 | 30 | 70 | 20 | 0 | 0 | 30 | 80 | 50 | 0 | 0 | 0 | 0 | 50 | 50 |
| Ryegrass, Italian | 0 | 60 | 0 | 50 | 20 | 80 | 40 | 20 | 20 | 50 | 40 | 30 | 40 | 0 | 10 | 0 | 60 | 60 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 219 | 220 | 221 | 222 | 223 | 224 | 225 | 226 | 227 | 228 | 229 | 230 | 231 | 232 | 233 | 234 | 235 | 236 |
| Barnyardgrass | 60 | 80 | 0 | 90 | 90 | 90 | 30 | 90 | 50 | 80 | 90 | 90 | 90 | 90 | 90 | 90 | 60 | 0 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 90 | 90 | 80 | 90 | 90 | 90 | 90 | 90 | 90 | 90 | 90 | 90 | 90 | 90 | 90 | 90 | 80 | 0 |
| Kochia | 70 | 40 | 0 | 50 | 80 | 90 | 30 | 30 | 20 | 20 | 70 | 30 | 90 | 80 | 80 | 50 | 0 | 0 |
| Morningglory | — | — | — | — | — | — | — | — | — | — | — | — | — | — | — | — | — | — |
| Pigweed | 0 | 20 | 0 | 30 | 50 | 80 | 0 | 30 | 20 | 0 | 0 | 20 | 70 | 60 | 30 | 20 | 0 | 0 |
| Ragweed | 0 | 0 | 0 | 20 | 50 | 90 | 0 | 0 | 0 | 20 | — | 20 | 90 | 90 | 50 | 20 | 0 | 30 |
| Ryegrass, Italian | 0 | 30 | 0 | 50 | 60 | 70 | 40 | 20 | 30 | 40 | 20 | 30 | 60 | 80 | 60 | 30 | 0 | 50 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 239 | 240 | 241 | 242 | 244 | 245 | 246 | 247 | 248 | 249 | 250 | 251 | 256 | 257 | 258 | 259 | 260 | 261 |
| Barnyardgrass | 90 | 50 | 90 | 90 | 90 | 20 | 90 | 90 | 80 | 80 | 80 | 80 | 20 | 80 | 90 | 80 | 80 | 0 |
| Corn | — | — | 50 | 20 | 0 | 0 | 0 | 0 | 0 | 0 | 0 | 0 | 0 | 0 | 0 | 0 | 10 | 0 |
| Crabgrass, Large | — | — | 90 | 90 | 100 | 80 | 90 | 90 | 90 | 90 | 90 | 90 | 90 | 90 | 90 | 90 | 90 | 90 |
| Foxtail, Giant | 90 | 90 | 90 | 90 | 90 | 70 | 90 | 90 | 90 | 90 | 80 | 80 | 60 | 90 | 90 | 90 | 90 | 70 |
| Kochia | 70 | 0 | — | — | — | — | — | — | — | — | — | — | — | — | — | — | — | — |
| Morningglory | — | — | 0 | 0 | 0 | 0 | 0 | 0 | 0 | 0 | 0 | 0 | 0 | 0 | 0 | 0 | 50 | 0 |
| Pigweed | 0 | 0 | 30 | 20 | 50 | 30 | 0 | 0 | 0 | 0 | 0 | 30 | 0 | 0 | 0 | 0 | 80 | 0 |
| Ragweed | 90 | 0 | — | — | — | — | — | — | — | — | — | — | — | — | — | — | — | — |
| Ryegrass, Italian | 0 | 0 | — | — | — | — | — | — | — | — | — | — | — | — | — | — | — | — |
| Velvetleaf | — | — | 0 | 0 | 0 | 0 | 0 | 0 | 0 | 0 | 0 | 0 | 0 | 0 | 0 | 0 | 40 | 0 |
| Wheat | — | — | 30 | 30 | 0 | 0 | — | 0 | 0 | 0 | 0 | 0 | 0 | 0 | 0 | 0 | 0 | 0 |

| | 500 g ai/ha Compounds | | | | | | | | | | | | | | | | | |
|---|---|---|---|---|---|---|---|---|---|---|---|---|---|---|---|---|---|---|
| | 262 | 263 | 264 | 267 | 268 | 269 | 270 | 271 | 272 | 273 | 275 | 276 | 277 | 278 | 279 | 280 | 281 | 282 |
| Barnyardgrass | 90 | 90 | 90 | 80 | 80 | 80 | 90 | 90 | 90 | 80 | 90 | 0 | 90 | 90 | 90 | 80 | 70 | 90 |
| Corn | 0 | 70 | 0 | 0 | 80 | 0 | — | — | — | — | — | — | — | — | — | — | — | — |
| Crabgrass, Large | 90 | 100 | 100 | 90 | 90 | 90 | — | — | — | — | — | — | — | — | — | — | — | — |
| Foxtail, Giant | 90 | 100 | 90 | 90 | 80 | 80 | 90 | 90 | 90 | 90 | 90 | 0 | 90 | 90 | 90 | 90 | 70 | 70 |
| Kochia | — | — | — | — | — | — | 80 | 80 | 20 | 70 | 80 | 0 | 60 | 0 | 80 | 0 | 0 | 50 |
| Morningglory | 0 | 0 | 0 | 0 | 60 | 0 | — | — | — | — | — | — | — | — | — | — | — | — |
| Pigweed | 70 | 100 | 80 | 50 | 60 | 70 | 20 | 80 | 30 | 0 | 30 | 0 | 30 | 0 | 40 | 0 | 0 | 0 |
| Ragweed | — | — | — | — | — | — | 20 | 80 | 0 | 0 | 40 | 0 | 20 | 0 | 0 | 0 | 0 | 0 |
| Ryegrass, Italian | — | — | — | — | — | — | 0 | 30 | 0 | 0 | 60 | 0 | 30 | 0 | 60 | 0 | 0 | 0 |
| Velvetleaf | 0 | 50 | 0 | 0 | 0 | 0 | — | — | — | — | — | — | — | — | — | — | — | — |
| Wheat | 0 | 60 | 0 | 0 | 0 | 0 | — | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 283 | 284 | 285 | 286 | 287 | 288 | 289 | 290 | 291 | 292 | 293 | 294 | 295 | 296 | 297 | 298 | 299 | 300 |
| Barnyardgrass | 0 | 60 | 0 | 60 | 80 | 70 | 80 | 80 | 60 | 80 | 70 | 90 | 70 | 0 | 50 | 0 | 70 | 0 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 0 | 70 | 10 | 80 | 80 | 90 | 90 | 80 | 80 | 60 | 90 | 90 | 20 | 0 | 70 | 0 | 80 | 0 |
| Kochia | 0 | 30 | 0 | 40 | 0 | 50 | 0 | 0 | 20 | 80 | 0 | 90 | 0 | 0 | 0 | 0 | 0 | 0 |
| Morningglory | — | — | — | — | — | — | — | — | — | — | — | — | — | — | — | — | — | — |
| Pigweed | 0 | 40 | 0 | 30 | 0 | 0 | 0 | 0 | 0 | 0 | 0 | 20 | 0 | 0 | 0 | 0 | 0 | 0 |

TABLE A-continued

| | | | | | | | | | | | | | | | | | | |
|---|---|---|---|---|---|---|---|---|---|---|---|---|---|---|---|---|---|---|
| Ragweed | 0 | 0 | 0 | 0 | 0 | 0 | 0 | 0 | 0 | 0 | — | 0 | 0 | 0 | 0 | 0 | 0 | 0 |
| Ryegrass, Italian | 0 | 0 | 0 | 20 | 0 | 20 | 0 | 0 | 30 | 0 | 0 | 30 | 0 | 0 | 0 | 0 | 0 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 301 | 302 | 303 | 304 | 305 | 306 | 307 | 308 | 309 | 310 | 311 | 312 | 313 | 314 | 315 | 316 | 317 | 318 |
| Barnyardgrass | 0 | 90 | 90 | 90 | 90 | 90 | 90 | 80 | 80 | 90 | 80 | 90 | 80 | 80 | 90 | 90 | 90 | 90 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 0 | 90 | 90 | 90 | 90 | 90 | 90 | 90 | 90 | 90 | 90 | 90 | 80 | 90 | 90 | 90 | 90 | 90 |
| Kochia | 0 | 70 | 80 | 70 | 70 | 80 | 0 | 0 | 0 | 70 | 0 | 70 | 0 | 0 | 60 | 30 | 0 | 70 |
| Morningglory | — | — | — | — | — | — | — | — | — | — | — | — | — | — | — | — | — | — |
| Pigweed | 0 | 60 | 50 | 80 | 40 | 90 | 0 | 0 | 0 | 40 | 0 | 20 | 0 | 0 | 30 | 20 | 0 | 20 |
| Ragweed | 0 | 30 | — | — | 50 | 80 | 0 | 0 | — | 0 | 0 | 30 | 0 | 0 | 30 | 30 | 0 | 40 |
| Ryegrass, Italian | 0 | 60 | 40 | 0 | 90 | 80 | 0 | 0 | 20 | 40 | 0 | 60 | 0 | 0 | 70 | 50 | 0 | 60 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 500 g ai/ha Compounds | | | | | | | | | | | | | | | | | |
|---|---|---|---|---|---|---|---|---|---|---|---|---|---|---|---|---|---|---|
| | 319 | 320 | 321 | 322 | 323 | 324 | 325 | 326 | 327 | 328 | 329 | 330 | 331 | 332 | 333 | 334 | 335 | 336 |
| Barnyardgrass | 90 | 80 | 30 | 40 | 90 | 90 | 90 | 30 | 80 | 80 | 0 | 70 | 80 | 80 | 90 | 0 | 50 | 60 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 90 | 90 | 50 | 70 | 90 | 90 | 90 | 60 | 90 | 90 | 60 | 80 | 90 | 90 | 90 | 50 | 90 | 90 |
| Kochia | 80 | 20 | 0 | 0 | 80 | 80 | 80 | 50 | 70 | 20 | 0 | 20 | 0 | 0 | 0 | 0 | 60 | 60 |
| Morningglory | — | — | — | — | — | — | — | — | — | — | — | — | — | — | — | — | — | — |
| Pigweed | 20 | 0 | 0 | 0 | 30 | 60 | 60 | 0 | 20 | 0 | 0 | 20 | 20 | 0 | 0 | 0 | 30 | 20 |
| Ragweed | 40 | 30 | 0 | 0 | 80 | 60 | 50 | 0 | 30 | 0 | 0 | 0 | 20 | 0 | 0 | 0 | 0 | 0 |
| Ryegrass, Italian | 60 | 50 | 0 | 0 | 30 | 40 | 50 | 40 | 40 | 40 | 0 | 40 | 20 | 0 | 20 | 0 | 0 | 20 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 500 g ai/ha Compounds | | | | | | | | | | | | | | 125 g ai/ha Compounds | | | | | |
|---|---|---|---|---|---|---|---|---|---|---|---|---|---|---|---|---|---|---|---|---|
| | 337 | 338 | 339 | 340 | 341 | 342 | 343 | 344 | 345 | 346 | 347 | 348 | 349 | 350 | 1 | 2 | 3 | 4 | 5 | 6 |
| Barnyardgrass | 20 | 20 | 80 | 80 | 80 | 80 | 80 | 90 | 90 | 90 | 90 | 60 | 90 | 90 | 30 | 30 | 60 | 60 | 70 | 50 |
| Corn | — | — | — | — | — | — | — | — | — | — | — | — | — | — | 0 | 0 | 0 | 0 | 0 | 0 |
| Crabgrass, Large | — | — | — | — | — | — | — | — | — | — | — | — | — | — | 90 | 90 | 90 | 90 | 80 | 80 |
| Foxtail, Giant | 30 | 80 | 80 | 90 | 90 | 90 | 80 | 90 | 90 | 90 | 40 | 90 | 90 | 90 | 70 | 90 | 90 | 80 | 90 | 90 |
| Kochia | 0 | 20 | 0 | 0 | 0 | 0 | 0 | 0 | 80 | 80 | 0 | 70 | 80 | 80 | — | — | — | — | — | — |
| Morningglory | — | — | — | — | — | — | — | — | — | — | — | — | — | — | 0 | 0 | 0 | 0 | 0 | 0 |
| Pigweed | 0 | 0 | 0 | 0 | 0 | 50 | 0 | 0 | 70 | 30 | 0 | 50 | 40 | 80 | 0 | 0 | 0 | 0 | 0 | 0 |
| Ragweed | 0 | 0 | 0 | 0 | 0 | 0 | 0 | 0 | 0 | 0 | 0 | 30 | 40 | 30 | — | — | — | — | — | — |
| Ryegrass, Italian | 0 | 0 | 20 | 20 | 0 | 20 | 0 | 30 | 40 | 30 | 0 | 0 | 0 | 0 | — | — | — | — | — | — |
| Velvetleaf | — | — | — | — | — | — | — | — | — | — | — | — | — | — | 0 | 0 | 0 | 0 | 0 | 0 |
| Wheat | — | — | — | — | — | — | — | — | — | — | — | — | — | — | 0 | 0 | 40 | 60 | 0 | 0 |

| | 125 g ai/ha Compounds | | | | | | | | | | | | | | | | | | | | | | | |
|---|---|---|---|---|---|---|---|---|---|---|---|---|---|---|---|---|---|---|---|---|---|---|---|---|
| | 7 | 8 | 9 | 10 | 11 | 12 | 13 | 14 | 15 | 16 | 28 | 29 | 32 | 36 | 37 | 38 | 41 | 42 | 45 | 46 | 47 | 48 | 49 | 50 | 51 | 52 | 53 |
| Barnyardgrass | 20 | 20 | 20 | 0 | 0 | 60 | 0 | 80 | 0 | 80 | 0 | 0 | 0 | 40 | 0 | 0 | 30 | 0 | 10 | 0 | 0 | 80 | 0 | 30 | 0 | 80 | 80 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass, Large | 80 | 80 | 80 | 90 | 70 | 90 | 50 | 90 | 60 | 90 | 30 | 30 | 80 | 20 | 0 | 70 | 60 | 80 | 80 | 70 | 10 | 90 | 70 | 90 | 90 | 90 | 90 |
| Foxtail, Giant | 70 | 60 | 70 | 60 | 20 | 70 | 0 | 80 | 20 | 90 | 0 | 0 | 70 | 20 | 0 | 0 | 10 | 20 | 50 | 40 | 0 | 80 | 20 | 90 | 30 | 80 | 90 |
| Kochia | — | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 0 | 0 | — | — | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ragweed | — | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — | — |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | 125 g ai/ha Compounds | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 54 | 55 | 56 | 57 | 58 | 59 | 60 | 61 | 62 | 63 | 64 | 65 | 66 | 67 | 68 | 69 | 70 | 72 | 73 | 74 | 75 | 76 | 77 | 78 | 79 | 80 | 81 |
| Barnyardgrass | 0 | 20 | 0 | 40 | 0 | 80 | 80 | 0 | 80 | 50 | 80 | 40 | 80 | 30 | 80 | 80 | 20 | 0 | 50 | 60 | 50 | 80 | 80 | 80 | 80 | 80 | 40 |
| Corn | 0 | 0 | 0 | 0 | 0 | 0 | 0 | 0 | 0 | 0 | 20 | 0 | 20 | 0 | 0 | 0 | 0 | 0 | 0 | 0 | 0 | 0 | 0 | 0 | 0 | 0 | 0 |

TABLE A-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| Crabgrass, Large | 90 | 80 | 60 | 80 | 70 | 90 | 90 | 0 | 90 | 90 | 80 | 90 | 80 | 90 | 90 | 90 | 80 | 80 | 80 | 90 | 90 | 90 | 90 | 90 | 90 | 80 |
| Foxtail, Giant | 90 | 70 | 20 | 60 | 20 | 80 | 90 | 0 | 80 | 70 | 80 | 80 | 80 | 80 | 90 | 90 | 70 | 60 | 80 | 90 | 80 | 90 | 90 | 90 | 90 | 30 |
| *Kochia* | — | — | — | — | — | — | — | — | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 20 | 0 | 0 | 0 | 0 |
| Pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 40 | 10 | 80 | 60 | 0 |
| Ragweed | — | — | — | — | — | — | — | — | — | — | — | — | — | — | — | — | — | — | — | — | — | — | — | — | — | — |
| Ryegrass, Italian | — | — | — | — | — | — | — | — | — | — | — | — | — | — | — | — | — | — | — | — | — | — | — | — | — | — |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

125 g ai/ha Compounds

| | 82 | 83 | 84 | 85 | 86 | 87 | 88 | 89 | 90 | 91 | 92 | 93 | 94 | 95 | 97 | 101 | 102 | 103 | 107 | 109 | 110 | 111 | 112 |
|---|---|---|---|---|---|---|---|---|---|---|---|---|---|---|---|---|---|---|---|---|---|---|---|
| Barnyardgrass | 0 | 0 | 0 | 0 | 0 | 20 | 0 | 60 | 30 | 0 | 60 | 50 | 0 | 60 | 0 | 90 | 0 | 80 | 20 | 80 | 70 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | — | — | — | — |
| Crabgrass, Large | 80 | 70 | 0 | 30 | 60 | 80 | 40 | 80 | 70 | 40 | 80 | 90 | 0 | 90 | 0 | 90 | 0 | 90 | 80 | — | — | — | — |
| Foxtail, Giant | 20 | 0 | 0 | 0 | 20 | 60 | 0 | 80 | 60 | 0 | 0 | 80 | 0 | 80 | 0 | 90 | 0 | 90 | 70 | 90 | 60 | 0 | 0 |
| *Kochia* | — | — | — | — | — | — | — | — | — | — | — | — | — | — | — | — | — | — | — | 0 | 0 | 0 | 0 |
| Morningglory | — | 0 | 0 | 0 | 0 | 0 | 0 | 0 | 0 | 0 | 0 | 0 | 0 | 0 | 0 | 0 | 0 | 0 | 0 | — | — | — | — |
| Pigweed | 0 | 0 | 0 | 0 | 0 | 0 | 0 | 0 | 0 | 0 | 0 | 0 | 0 | 0 | 0 | 10 | 0 | 0 | 0 | 0 | 0 | 0 | 0 |
| Ragweed | — | — | — | — | — | — | — | — | — | — | — | — | — | — | — | — | — | — | — | 0 | 0 | 0 | 0 |
| Ryegrass, Italian | — | — | — | — | — | — | — | — | — | — | — | — | — | — | — | — | — | — | — | 0 | 0 | 0 | 0 |
| Velvetleaf | 0 | 0 | 0 | 0 | 0 | 0 | 0 | 0 | 0 | 0 | 0 | 0 | 0 | 0 | 0 | 30 | 0 | 0 | 0 | — | — | — | — |
| Wheat | 0 | 0 | 0 | 0 | 0 | 0 | 0 | 0 | 0 | 0 | 0 | 0 | 0 | 0 | 0 | 60 | 0 | 0 | 0 | — | — | — | — |

125 g ai/ha Compounds

| | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|
| Barnyardgrass | 0 | 20 | 0 | 0 | 0 | 50 | 90 | 90 | 80 | 80 | 80 | 70 | 80 | 70 | 70 | 60 | 80 | 60 |
| Corn | — | — | 0 | 0 | 0 | — | — | — | — | — | — | — | — | — | — | — | — | — |
| Crabgrass, Large | — | — | 70 | 70 | 60 | — | — | — | — | — | — | — | — | — | — | — | — | — |
| Foxtail, Giant | 0 | 20 | 20 | 0 | 20 | 90 | 90 | 90 | 90 | 90 | 90 | 80 | 80 | 90 | 90 | 80 | 80 | 80 |
| *Kochia* | 0 | 0 | — | — | — | 0 | 40 | 60 | 60 | 60 | 80 | 60 | 30 | 0 | 40 | 10 | 50 | 0 |
| Morningglory | — | — | 0 | 0 | 0 | — | — | — | — | — | — | — | — | — | — | — | — | — |
| Pigweed | 0 | 0 | 0 | 0 | 0 | 0 | 30 | 30 | 50 | 50 | 70 | 70 | 0 | 0 | 0 | 0 | 0 | 0 |
| Ragweed | 0 | 0 | — | — | — | 0 | 70 | 60 | 70 | 0 | 70 | 40 | 0 | 0 | 0 | 0 | 0 | 0 |
| Ryegrass, Italian | 0 | 0 | — | — | — | 0 | 20 | 30 | 0 | 0 | 40 | 0 | 0 | 0 | 0 | 0 | 0 | 0 |
| Velvetleaf | — | — | 0 | 0 | 0 | — | — | — | — | — | — | — | — | — | — | — | — | — |
| Wheat | — | — | 0 | 0 | 0 | — | — | — | — | — | — | — | — | — | — | — | — | — |

125 g ai/ha Compounds

| | 131 | 132 | 133 | 139 | 140 | 141 | 142 | 143 | 144 | 145 | 146 | 147 | 148 | 149 | 150 | 151 | 152 | 153 |
|---|---|---|---|---|---|---|---|---|---|---|---|---|---|---|---|---|---|---|
| Barnyardgrass | 50 | 70 | 20 | 70 | 80 | 90 | 90 | 60 | 90 | 80 | 90 | 90 | 30 | 90 | 80 | 90 | 90 | 80 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 50 | 70 | 30 | 50 | 50 | 50 | 70 | 30 | 60 | 70 | 80 | 80 | 40 | 70 | 70 | 80 | 70 | 60 |
| *Kochia* | 0 | 0 | 0 | 0 | 0 | 0 | 0 | 30 | 0 | 0 | 0 | 30 | 30 | 10 | 60 | 90 | 30 | 60 |
| Morningglory | — | — | — | — | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 60 | 0 | 90 | 50 | 0 |
| Ryegrass, Italian | 0 | 0 | 0 | 0 | 0 | 0 | 0 | 0 | 0 | 0 | 0 | 0 | 0 | 20 | 0 | 10 | 0 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

125 g ai/ha Compounds

| | 154 | 156 | 157 | 160 | 161 | 162 | 163 | 164 | 165 | 166 | 167 | 168 | 169 | 170 | 171 | 172 | 174 | 175 |
|---|---|---|---|---|---|---|---|---|---|---|---|---|---|---|---|---|---|---|
| Barnyardgrass | 80 | 90 | 90 | 80 | 90 | 90 | 80 | 90 | 90 | 80 | 90 | 90 | 90 | 90 | 90 | 0 | 0 | 0 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 90 | 90 | 90 | 80 | 90 | 80 | 90 | 90 | 90 | 90 | 90 | 90 | 80 | 80 | 90 | 20 | 30 | 0 |
| *Kochia* | 40 | 20 | 50 | 80 | 20 | 50 | 0 | 60 | 70 | 30 | 20 | 40 | 40 | 50 | 60 | 30 | 0 | 0 |
| Morningglory | — | — | — | — | — | — | — | — | — | — | — | — | — | — | — | — | — | — |
| Pigweed | 0 | 0 | 0 | 70 | 20 | 60 | 40 | 50 | 50 | 0 | 50 | 40 | 0 | 50 | 20 | 0 | 0 | 0 |
| Ragweed | 0 | 0 | 30 | 70 | 20 | 0 | 0 | 20 | 0 | 0 | 0 | 0 | 0 | 0 | 0 | 0 | 0 | 0 |
| Ryegrass, Italian | 40 | 0 | 30 | 60 | 0 | 0 | 0 | 20 | 0 | 20 | 20 | 0 | 0 | 0 | 0 | 0 | 0 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

TABLE A-continued

| | 125 g ai/ha Compounds | | | | | | | | | | | | | | | | | |
|---|---|---|---|---|---|---|---|---|---|---|---|---|---|---|---|---|---|---|
| | 181 | 182 | 183 | 184 | 185 | 186 | 188 | 189 | 190 | 194 | 195 | 196 | 197 | 198 | 199 | 200 | 201 | 202 |
| Barnyardgrass | 0 | 0 | 0 | 70 | 40 | 0 | 0 | 80 | 60 | 0 | 30 | 0 | 0 | 50 | 0 | 60 | 0 | 90 |
| Corn | — | — | — | — | — | — | — | 0 | 0 | 0 | 0 | 0 | 0 | 0 | 0 | — | — | — |
| Crabgrass, Large | — | — | — | — | — | — | — | 90 | 90 | 90 | 90 | 90 | 80 | 90 | 90 | — | — | — |
| Foxtail, Giant | 10 | 50 | 0 | 90 | 70 | 0 | 0 | 90 | 80 | 50 | 80 | 80 | 30 | 50 | 50 | 30 | 20 | 90 |
| Kochia | 50 | 0 | 0 | 0 | 0 | 0 | 0 | — | — | — | — | — | — | — | — | 0 | 0 | 70 |
| Morningglory | — | — | — | — | — | — | — | 0 | 0 | 0 | 0 | 0 | 0 | 0 | 0 | — | — | — |
| Pigweed | 0 | 0 | 0 | 0 | 0 | 0 | 0 | 0 | 0 | 0 | 0 | 0 | 0 | 0 | 0 | 0 | 0 | 60 |
| Ragweed | 0 | 0 | 0 | 0 | 0 | 0 | 0 | — | — | — | — | — | — | — | — | 0 | 0 | 50 |
| Ryegrass, Italian | 0 | 0 | 0 | 0 | 0 | 0 | 0 | — | — | — | — | — | — | — | — | 0 | 0 | 60 |
| Velvetleaf | — | — | — | — | — | — | — | 0 | 0 | 0 | 0 | 0 | 0 | 0 | 0 | — | — | — |
| Wheat | — | — | — | — | — | — | — | 0 | 0 | 0 | 0 | 0 | 0 | 0 | 0 | — | — | — |

| | 125 g ai/ha Compounds | | | | | | | | | | | | | | | | | |
|---|---|---|---|---|---|---|---|---|---|---|---|---|---|---|---|---|---|---|
| | 203 | 204 | 205 | 206 | 207 | 208 | 209 | 210 | 211 | 212 | 213 | 214 | 215 | 216 | 217 | 218 | 219 | 220 |
| Barnyardgrass | 20 | 90 | 30 | 90 | 90 | 40 | 30 | 60 | 80 | 60 | 50 | 70 | 60 | 20 | 70 | 80 | 30 | 30 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 30 | 90 | 60 | 90 | 90 | 80 | 50 | 80 | 80 | 70 | 80 | 80 | 80 | 40 | 90 | 90 | 90 | 80 |
| Kochia | 0 | 0 | 20 | 70 | 20 | 0 | 0 | 0 | 40 | 0 | 0 | 0 | 0 | 0 | 30 | 30 | 10 | 0 |
| Morningglory | — | — | — | — | — | — | — | — | — | — | — | — | — | — | — | — | — | — |
| Pigweed | 0 | 0 | 0 | 30 | 0 | 0 | 0 | 0 | 20 | 0 | 0 | 0 | 0 | 0 | 20 | 30 | 0 | 0 |
| Ragweed | 0 | 0 | 0 | 60 | 0 | 0 | 0 | 0 | 30 | 0 | 0 | 0 | 0 | 0 | 0 | 0 | 0 | 0 |
| Ryegrass, Italian | 0 | 20 | 0 | 40 | 20 | 0 | 0 | 0 | 0 | 0 | 0 | 0 | 0 | 0 | 40 | 40 | 0 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 125 g ai/ha Compounds | | | | | | | | | | | | | | | | | |
|---|---|---|---|---|---|---|---|---|---|---|---|---|---|---|---|---|---|---|
| | 221 | 222 | 223 | 224 | 225 | 226 | 227 | 228 | 229 | 230 | 231 | 232 | 233 | 234 | 235 | 236 | 239 | 240 |
| Barnyardgrass | 0 | 70 | 90 | 90 | 20 | 50 | 20 | 50 | 70 | 30 | 90 | 90 | 80 | 60 | 0 | 0 | 50 | 20 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 60 | 90 | 90 | 90 | 80 | 70 | 80 | 80 | 90 | 90 | 90 | 90 | 90 | 70 | 40 | 0 | 80 | 70 |
| Kochia | 0 | 0 | 30 | 80 | 0 | 0 | 20 | 0 | 0 | 0 | 70 | 70 | 50 | 20 | 0 | 0 | 0 | 0 |
| Morningglory | — | — | — | — | — | — | — | — | — | — | — | — | — | — | — | — | — | — |
| Pigweed | 0 | 0 | 20 | 80 | 0 | 0 | 0 | 0 | 0 | 0 | 70 | 50 | 30 | 0 | 0 | 0 | 0 | 0 |
| Ragweed | 0 | 0 | 30 | 90 | 0 | 0 | 0 | 0 | 0 | 0 | 70 | 30 | 40 | 0 | 0 | 0 | 0 | 0 |
| Ryegrass, Italian | 0 | 20 | 30 | 60 | 0 | 0 | 0 | 30 | 10 | 0 | 40 | 40 | 30 | 30 | 0 | 0 | 0 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 125 g ai/ha Compounds | | | | | | | | | | | | | | | | | |
|---|---|---|---|---|---|---|---|---|---|---|---|---|---|---|---|---|---|---|
| | 241 | 242 | 244 | 245 | 246 | 247 | 248 | 249 | 250 | 251 | 256 | 257 | 258 | 259 | 260 | 261 | 262 | 263 |
| Barnyardgrass | 80 | 60 | 40 | 20 | 80 | 90 | 30 | 50 | 20 | 20 | 0 | 40 | 20 | 10 | 70 | 0 | 80 | 80 |
| Corn | 20 | 0 | 0 | 0 | 0 | 0 | 0 | 0 | 0 | 0 | 0 | 0 | 0 | 0 | 0 | 0 | 0 | 0 |
| Crabgrass, Large | 90 | 90 | 90 | 60 | 90 | 90 | 90 | 80 | 80 | 80 | 80 | 90 | 90 | — | 90 | 80 | 90 | 90 |
| Foxtail, Giant | 90 | 90 | 90 | 60 | 80 | 80 | 80 | 50 | 50 | 40 | 20 | 80 | 50 | 60 | 80 | 10 | 80 | 90 |
| Kochia | — | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 20 | 0 | 0 | 0 |
| Pigweed | 0 | 0 | 30 | 0 | 0 | 0 | 0 | 0 | 0 | 0 | 0 | 0 | 0 | 0 | 60 | 0 | 50 | 60 |
| Ragweed | — | — | — | — | — | — | — | — | — | — | — | — | — | — | — | — | — | — |
| Ryegrass, Italian | — | — | — | — | — | — | — | — | — | — | — | — | — | — | — | — | — | — |
| Velvetleaf | 0 | 0 | 0 | 0 | 0 | 0 | 0 | 0 | 0 | 0 | 0 | 0 | 0 | — | 0 | 0 | 0 | 50 |
| Wheat | 20 | 20 | 0 | 0 | 0 | 0 | 0 | 0 | 0 | 0 | 0 | 0 | 0 | 0 | 0 | 0 | 0 | 0 |

| | 125 g ai/ha Compounds | | | | | | | | | | | | | | | | | |
|---|---|---|---|---|---|---|---|---|---|---|---|---|---|---|---|---|---|---|
| | 264 | 267 | 268 | 269 | 270 | 271 | 272 | 273 | 275 | 276 | 277 | 278 | 279 | 280 | 281 | 282 | 283 | 284 |
| Barnyardgrass | 50 | 70 | 70 | 70 | 60 | 90 | 70 | 50 | 90 | 0 | 90 | 80 | 80 | 80 | 50 | 60 | 0 | 0 |
| Corn | 0 | 0 | 0 | 0 | — | — | — | — | — | — | — | — | — | — | — | — | — | — |
| Crabgrass, Large | 100 | 90 | 80 | 80 | — | — | — | — | — | — | — | — | — | — | — | — | — | — |
| Foxtail, Giant | 80 | 80 | 70 | 80 | 80 | 90 | 90 | 90 | 90 | 0 | 90 | 90 | 90 | 90 | 10 | 20 | 0 | 40 |
| Kochia | — | — | — | — | 0 | 50 | 0 | 0 | 60 | 0 | 30 | 0 | 40 | 0 | 0 | 0 | 0 | 0 |
| Morningglory | 0 | 0 | 0 | 0 | — | — | — | — | — | — | — | — | — | — | — | — | — | — |
| Pigweed | 50 | 0 | 30 | 50 | 0 | 40 | 0 | 0 | 20 | 0 | 20 | 0 | 0 | 0 | 0 | 0 | 0 | 0 |

TABLE A-continued

| | | | | | | | | | | | | | | | | | | |
|---|---|---|---|---|---|---|---|---|---|---|---|---|---|---|---|---|---|---|
| Ragweed | — | — | — | — | 0 | 20 | 0 | 0 | 20 | 0 | 20 | 0 | 0 | 0 | 0 | 0 | 0 | 0 |
| Ryegrass, Italian | — | — | — | — | 0 | 0 | 0 | 0 | 30 | 0 | 30 | 0 | 0 | 0 | 0 | 0 | 0 | 0 |
| Velvetleaf | 0 | 0 | 0 | 0 | — | — | — | — | — | — | — | — | — | — | — | — | — | — |
| Wheat | 0 | 0 | 0 | 0 | — | — | — | — | — | — | — | — | — | — | — | — | — | — |

| | 125 g ai/ha Compounds | | | | | | | | | | | | | | | | | |
|---|---|---|---|---|---|---|---|---|---|---|---|---|---|---|---|---|---|---|
| | 285 | 286 | 287 | 288 | 289 | 290 | 291 | 292 | 293 | 294 | 295 | 296 | 297 | 298 | 299 | 300 | 301 | 302 |
| Barnyardgrass | 0 | 60 | 50 | 30 | 50 | 60 | 20 | 70 | 20 | 70 | 0 | 0 | 0 | 0 | 10 | 0 | 0 | 90 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 0 | 80 | 50 | 30 | 60 | 60 | 20 | 50 | 80 | 70 | 0 | 0 | 30 | 0 | 50 | 0 | 0 | 90 |
| Kochia | 0 | 30 | 0 | 30 | 0 | 0 | 20 | 30 | 0 | 40 | 0 | 0 | 0 | 0 | 0 | 0 | 0 | 50 |
| Morningglory | — | — | — | — | — | — | — | — | — | — | — | — | — | — | — | — | — | — |
| Pigweed | 0 | 20 | 0 | 0 | — | 0 | 0 | 0 | 0 | 0 | 0 | 0 | 0 | 0 | 0 | 0 | 0 | 10 |
| Ragweed | 0 | 0 | 0 | 0 | 0 | 0 | 0 | 0 | — | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 | 0 | 0 | 0 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 125 g ai/ha Compounds | | | | | | | | | | | | | | | | | |
|---|---|---|---|---|---|---|---|---|---|---|---|---|---|---|---|---|---|---|
| | 303 | 304 | 305 | 306 | 307 | 308 | 309 | 310 | 311 | 312 | 313 | 314 | 315 | 316 | 317 | 318 | 319 | 320 |
| Barnyardgrass | 90 | 90 | 80 | 90 | 80 | 70 | 80 | 90 | 70 | 80 | 50 | 20 | 90 | 80 | 90 | 90 | 90 | 20 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 90 | 90 | 90 | 90 | 80 | 80 | 90 | 90 | 80 | 90 | 30 | 30 | 90 | 90 | 90 | 90 | 90 | 30 |
| Kochia | 70 | — | 70 | 70 | 0 | 0 | 0 | 30 | 0 | 20 | 0 | 0 | 40 | 0 | 0 | 20 | 60 | 0 |
| Morningglory | — | — | — | — | — | — | — | — | — | — | — | — | — | — | — | — | — | — |
| Pigweed | 20 | 70 | 0 | 80 | 0 | 0 | 0 | 40 | 0 | 0 | 0 | 0 | 30 | 20 | 0 | 0 | 0 | 0 |
| Ragweed | 0 | 0 | 30 | — | 0 | 0 | 0 | 0 | 0 | 0 | 0 | 0 | 20 | 20 | 0 | 20 | 30 | 0 |
| Ryegrass, Italian | 30 | 0 | 70 | 40 | 0 | 0 | 0 | 30 | 0 | 20 | 0 | 0 | 40 | 20 | 0 | 20 | 30 | 20 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 125 g ai/ha Compounds | | | | | | | | | | | | | | | | | |
|---|---|---|---|---|---|---|---|---|---|---|---|---|---|---|---|---|---|---|
| | 321 | 322 | 323 | 324 | 325 | 326 | 327 | 328 | 329 | 330 | 331 | 332 | 333 | 334 | 335 | 336 | 337 | 338 |
| Barnyardgrass | 0 | 0 | 90 | 90 | 90 | 0 | 70 | 40 | 0 | 60 | 20 | 70 | 50 | 0 | 0 | 50 | 0 | 0 |
| Corn | — | — | — | — | — | — | — | — | — | — | — | — | — | — | — | — | — | — |
| Crabgrass, Large | — | — | — | — | — | — | — | — | — | — | — | — | — | — | — | — | — | — |
| Foxtail, Giant | 0 | 0 | 90 | 90 | 90 | 50 | 80 | 80 | 0 | 50 | 50 | 80 | 80 | 0 | 70 | 80 | 0 | 30 |
| Kochia | 0 | 0 | 50 | 70 | 70 | 40 | 30 | 0 | 0 | 20 | 0 | 0 | 0 | 0 | 40 | 0 | 0 | 0 |
| Morningglory | — | — | — | — | — | — | — | — | — | — | — | — | — | — | — | — | — | — |
| Pigweed | 0 | 0 | 20 | 30 | 30 | 0 | 0 | 0 | 0 | 0 | 0 | 0 | 0 | 0 | 0 | 0 | 0 | 0 |
| Ragweed | 0 | 0 | 20 | 30 | 30 | 0 | 20 | 0 | 0 | 0 | 0 | 0 | 0 | 0 | 0 | 0 | 0 | 0 |
| Ryegrass, Italian | 0 | 0 | 20 | 30 | 30 | 0 | 40 | 0 | 0 | 30 | 0 | 0 | 0 | 0 | 0 | 0 | 0 | 0 |
| Velvetleaf | — | — | — | — | — | — | — | — | — | — | — | — | — | — | — | — | — | — |
| Wheat | — | — | — | — | — | — | — | — | — | — | — | — | — | — | — | — | — | — |

| | 125 g ai/ha Compounds | | | | | | | | | | | |
|---|---|---|---|---|---|---|---|---|---|---|---|---|
| | 339 | 340 | 341 | 342 | 343 | 344 | 345 | 346 | 347 | 348 | 349 | 350 |
| Barnyardgrass | 60 | 60 | 50 | 50 | 20 | 50 | 80 | 80 | 50 | 30 | 70 | 90 |
| Corn | — | — | — | — | — | — | — | — | — | — | — | — |
| Crabgrass, Large | — | — | — | — | — | — | — | — | — | — | — | — |
| Foxtail, Giant | 70 | 80 | 80 | 70 | 60 | 80 | 90 | 90 | 20 | 90 | 80 | 90 |
| Kochia | 0 | 0 | 0 | 0 | 0 | 0 | 10 | 0 | 0 | 0 | 50 | 80 |
| Morningglory | — | — | — | — | — | — | — | — | — | — | — | — |
| Pigweed | 0 | 0 | 0 | 0 | 0 | 0 | 0 | 20 | 0 | 20 | 0 | 50 |
| Ragweed | 0 | 0 | 0 | 0 | 0 | 0 | 0 | 0 | — | 0 | 0 | 30 |
| Ryegrass, Italian | 0 | 0 | 0 | 0 | 0 | 0 | 0 | 0 | 0 | 0 | 0 | 0 |
| Velvetleaf | — | — | — | — | — | — | — | — | — | — | — | — |
| Wheat | — | — | — | — | — | — | — | — | — | — | — | — |

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| Flood |
| --- |

| 1000 g ai/ha Compounds | | | | | | | | | | | | | | | | | | |
| --- | --- | --- | --- | --- | --- | --- | --- | --- | --- | --- | --- | --- | --- | --- | --- | --- | --- |
| | 98 | 99 | 100 | 104 | 105 | 106 | 108 | 109 | 110 | 115 | 116 | 117 | 193 | 194 | 195 | 196 | 197 | 198 |
| Barnyardgrass | 0 | 80 | 25 | 70 | 25 | 60 | 50 | 0 | 0 | 20 | 20 | 40 | 0 | 65 | 70 | 20 | 30 | 65 |
| Ducksalad | 90 | 95 | 75 | 95 | 90 | 90 | 95 | 95 | 95 | 90 | 80 | 90 | 60 | 80 | 100 | 90 | 75 | 95 |
| Rice | 0 | 10 | 0 | 0 | 10 | 15 | 0 | 0 | 0 | 0 | 15 | 0 | 20 | 20 | 15 | 0 | 10 | 15 |
| Sedge, Umbrella | 0 | 0 | 0 | 0 | 0 | 0 | 0 | 80 | 50 | 0 | 0 | 0 | 20 | 0 | 0 | 0 | 0 | 0 |

| 1000 g ai/ha Compounds | | | | | | | | | | | | | | | | | | |
| --- | --- | --- | --- | --- | --- | --- | --- | --- | --- | --- | --- | --- | --- | --- | --- | --- | --- |
| | 199 | 200 | 201 | 209 | 213 | 214 | 215 | 234 | 235 | 236 | 240 | 241 | 242 | 244 | 245 | 246 | 247 | 248 |
| Barnyardgrass | 20 | 85 | 20 | 45 | 60 | 75 | 60 | 75 | 45 | 40 | 70 | 75 | 55 | 30 | 20 | 60 | 85 | 55 |
| Ducksalad | 80 | 95 | 70 | 95 | 85 | 90 | 80 | 85 | 50 | 70 | 85 | 100 | 100 | 100 | 90 | 95 | 95 | 95 |
| Rice | 0 | 15 | 0 | 0 | 0 | 20 | 0 | 0 | 0 | 0 | 0 | 10 | 0 | 0 | 0 | 20 | 0 | 0 |
| Sedge, Umbrella | 0 | 0 | 0 | 0 | 0 | 0 | 0 | 0 | 0 | 0 | 0 | 20 | 0 | 0 | 0 | 20 | 0 | 0 |

| 1000 g ai/ha Compounds | | | | | | | | | | | | | | | 500 g ai/ha Compounds | | |
| --- | --- | --- | --- | --- | --- | --- | --- | --- | --- | --- | --- | --- | --- | --- | --- | --- | --- |
| | 249 | 250 | 251 | 259 | 260 | 261 | 262 | 263 | 264 | 267 | 268 | 269 | 344 | 345 | 346 | 103 | 118 | 119 |
| Barnyardgrass | 55 | 0 | 45 | 20 | 0 | 0 | 20 | 0 | 0 | 20 | 0 | 0 | 85 | 0 | 85 | 85 | 20 | 80 |
| Ducksalad | 85 | 80 | 90 | 90 | 95 | 90 | 100 | 90 | 100 | 100 | 100 | 100 | 90 | 30 | 100 | 100 | 100 | 100 |
| Rice | 15 | 0 | 0 | 10 | 0 | 0 | 0 | 0 | 0 | 15 | 20 | 0 | 10 | 0 | 0 | 0 | 0 | 10 |
| Sedge, Umbrella | 40 | 0 | 0 | 10 | 0 | 0 | 0 | 0 | 0 | 0 | 0 | 0 | 0 | 0 | 0 | 0 | 0 | 0 |

| 500 g ai/ha Compounds | | | | | | | | | | | | | | | | | | |
| --- | --- | --- | --- | --- | --- | --- | --- | --- | --- | --- | --- | --- | --- | --- | --- | --- | --- |
| | 120 | 121 | 122 | 123 | 124 | 125 | 126 | 127 | 128 | 129 | 130 | 131 | 132 | 133 | 139 | 140 | 141 | 142 |
| Barnyardgrass | 80 | 70 | 65 | 60 | 40 | 30 | 60 | 40 | 60 | 60 | 40 | 40 | 40 | 30 | 60 | 70 | 50 | 75 |
| Ducksalad | 100 | 100 | 100 | 100 | 100 | 85 | 80 | 40 | 95 | 100 | 40 | 70 | 85 | 60 | 100 | 100 | 100 | 100 |
| Rice | 20 | 35 | 15 | 0 | 0 | 0 | 0 | 20 | 20 | 15 | 20 | 0 | 0 | 0 | 0 | 0 | 0 | 0 |
| Sedge, Umbrella | 0 | 0 | 0 | 0 | 0 | 0 | 0 | 30 | 0 | 0 | 0 | 30 | 0 | 0 | 0 | 0 | 0 | 0 |

| 500 g ai/ha Compounds | | | | | | | | | | | | | | | | | | |
| --- | --- | --- | --- | --- | --- | --- | --- | --- | --- | --- | --- | --- | --- | --- | --- | --- | --- |
| | 143 | 144 | 146 | 147 | 148 | 149 | 150 | 151 | 152 | 153 | 154 | 160 | 161 | 162 | 163 | 164 | 165 | 166 |
| Barnyardgrass | 35 | 65 | 80 | 70 | 40 | 70 | 80 | 90 | 60 | 60 | 70 | 60 | 65 | 75 | 90 | 80 | 75 | 75 |
| Ducksalad | 100 | 100 | 100 | 100 | 100 | 100 | 100 | 100 | 100 | 100 | 90 | 100 | 100 | 100 | 100 | 100 | 100 | 100 |
| Rice | 0 | 0 | 0 | 0 | 0 | 0 | 0 | 0 | 15 | 10 | 0 | 10 | 10 | 0 | 15 | 20 | 10 | 0 |
| Sedge, Umbrella | 0 | 0 | 0 | 0 | 0 | 0 | 0 | 0 | 0 | 0 | 0 | 0 | 0 | 0 | 0 | 0 | 0 | 0 |

| 500 g ai/ha Compounds | | | | | | | | | | | | | | | | | | |
| --- | --- | --- | --- | --- | --- | --- | --- | --- | --- | --- | --- | --- | --- | --- | --- | --- | --- |
| | 167 | 168 | 169 | 170 | 171 | 175 | 181 | 182 | 202 | 216 | 217 | 218 | 219 | 220 | 221 | 222 | 223 | 224 |
| Barnyardgrass | 75 | 65 | 80 | 85 | 70 | 0 | 0 | 0 | 65 | 0 | 40 | 70 | 40 | 0 | 0 | 60 | 75 | 70 |
| Ducksalad | 100 | 100 | 100 | 100 | 100 | 30 | 0 | 30 | 100 | 0 | 100 | 100 | 100 | 100 | 0 | 100 | 100 | 100 |
| Rice | 10 | 0 | 0 | 15 | 0 | 0 | 0 | 0 | 15 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 20 | 0 | 0 | 0 | 0 |

| 500 g ai/ha Compounds | | | | | | | | | | | | | | | | | | |
| --- | --- | --- | --- | --- | --- | --- | --- | --- | --- | --- | --- | --- | --- | --- | --- | --- | --- |
| | 225 | 226 | 227 | 228 | 229 | 230 | 231 | 232 | 233 | 239 | 272 | 273 | 274 | 275 | 276 | 277 | 278 | 279 |
| Barnyardgrass | 0 | 0 | 0 | 0 | 50 | 60 | 0 | 85 | 60 | 50 | 20 | 0 | 0 | 85 | 0 | 90 | 60 | 75 |
| Ducksalad | 90 | 100 | 90 | 90 | 100 | 75 | 0 | 100 | 100 | 100 | 100 | 70 | 35 | 100 | 30 | 100 | 100 | 100 |
| Rice | 0 | 0 | 0 | 0 | 0 | 0 | 0 | 20 | 0 | 0 | 0 | 0 | 0 | 0 | 0 | 0 | 0 | 10 |
| Sedge, Umbrella | 0 | 0 | 0 | 0 | 0 | 0 | 0 | 0 | 0 | 0 | 0 | 0 | 30 | 0 | 0 | 0 | 0 | 0 |

TABLE B-continued

| | 500 g ai/ha Compounds | | | | | | | | | | | | | | | | | |
|---|---|---|---|---|---|---|---|---|---|---|---|---|---|---|---|---|---|---|
| | 280 | 281 | 282 | 283 | 284 | 285 | 286 | 287 | 288 | 289 | 290 | 291 | 292 | 293 | 294 | 295 | 296 | 297 |
| Barnyardgrass | 65 | 20 | 30 | 20 | 0 | 20 | 15 | 30 | 20 | 30 | 40 | 0 | 50 | 35 | 20 | 30 | 30 | 0 |
| Ducksalad | 100 | 75 | 95 | 85 | 80 | 100 | 75 | 75 | 65 | 90 | 75 | 0 | 100 | 95 | 98 | 40 | 60 | 0 |
| Rice | 0 | 0 | 0 | 0 | 10 | 0 | 10 | 0 | 0 | 20 | 0 | 20 | 0 | 0 | 0 | 0 | 0 | 0 |
| Sedge, Umbrella | 0 | 0 | 30 | 0 | 0 | 0 | 0 | 0 | 0 | 0 | 0 | 0 | 0 | 0 | 0 | 0 | 0 | 0 |

| | 500 g ai/ha Compounds | | | | | | | | | | | | | | | | | |
|---|---|---|---|---|---|---|---|---|---|---|---|---|---|---|---|---|---|---|
| | 298 | 299 | 300 | 301 | 302 | 303 | 304 | 305 | 306 | 307 | 308 | 309 | 310 | 311 | 312 | 313 | 314 | 315 |
| Barnyardgrass | 0 | 30 | 0 | 0 | 80 | 80 | 80 | 75 | 75 | 65 | 70 | 65 | 60 | 50 | 75 | 60 | 25 | 70 |
| Ducksalad | 0 | 50 | 0 | 0 | 98 | 100 | 100 | 100 | 100 | 98 | 90 | 100 | 100 | 98 | 100 | 0 | 40 | 100 |
| Rice | 0 | 0 | 0 | 0 | 0 | 30 | 35 | 15 | 50 | 0 | 0 | 0 | 0 | 0 | 20 | 0 | 15 | 15 |
| Sedge, Umbrella | 0 | 0 | 0 | 0 | 0 | 0 | 0 | 0 | 0 | 0 | 0 | 0 | 0 | 0 | 0 | 0 | 0 | 0 |

| | 500 g ai/ha Compounds | | | | | | | | | | | | | | | | | |
|---|---|---|---|---|---|---|---|---|---|---|---|---|---|---|---|---|---|---|
| | 316 | 317 | 318 | 319 | 320 | 321 | 322 | 323 | 324 | 325 | 326 | 327 | 328 | 329 | 330 | 331 | 332 | 333 |
| Barnyardgrass | 60 | 75 | 75 | 70 | 45 | 20 | 0 | 80 | 80 | 70 | 0 | 0 | 0 | 0 | 0 | 40 | 40 | 0 |
| Ducksalad | 100 | 80 | 100 | 100 | 100 | 40 | 100 | 100 | 100 | 100 | 0 | 60 | 35 | 0 | 100 | 65 | 75 | 20 |
| Rice | 0 | 0 | 15 | 0 | 0 | 15 | 0 | 20 | 30 | 20 | 0 | 0 | 0 | 0 | 0 | 0 | 0 | 0 |
| Sedge, Umbrella | 0 | 0 | 0 | 0 | 0 | 0 | 0 | 0 | 0 | 40 | 0 | 0 | 0 | 0 | 0 | 0 | 0 | 0 |

| | 500 g ai/ha Compounds | | | | | | | | | | | | 250 g ai/ha Compounds | | | | | |
|---|---|---|---|---|---|---|---|---|---|---|---|---|---|---|---|---|---|---|
| | 334 | 335 | 336 | 337 | 338 | 339 | 340 | 341 | 342 | 343 | 348 | 349 | 350 | 30 | 31 | 32 | 33 | 34 |
| Barnyardgrass | 30 | 0 | 50 | 0 | 0 | 40 | 0 | 0 | 0 | 0 | 40 | 40 | 60 | 0 | 0 | 0 | 0 | 0 |
| Ducksalad | 40 | 65 | 60 | 0 | 0 | 65 | 50 | 0 | 0 | 0 | 100 | 90 | 100 | 0 | 0 | 50 | 100 | 5 |
| Rice | 0 | 0 | 0 | 0 | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 | 0 | 0 | 0 | 0 |

| | 250 g ai/ha Compounds | | | | | | | | | | | | | | | | | |
|---|---|---|---|---|---|---|---|---|---|---|---|---|---|---|---|---|---|---|
| | 35 | 36 | 37 | 38 | 39 | 40 | 41 | 42 | 43 | 45 | 46 | 47 | 48 | 49 | 50 | 51 | 52 | 53 |
| Barnyardgrass | 0 | 0 | 0 | 0 | 0 | 0 | 0 | 0 | 0 | 0 | 0 | 0 | 40 | 0 | 0 | 20 | 55 | 0 |
| Ducksalad | 80 | 60 | 0 | 0 | 0 | 0 | 70 | 60 | 0 | 80 | 0 | 0 | 100 | 70 | 90 | 80 | 90 | 100 |
| Rice | 0 | 0 | 0 | 0 | 0 | 0 | 0 | 0 | 0 | 20 | 0 | 0 | 20 | 0 | 0 | 15 | 25 | 0 |
| Sedge, Umbrella | 0 | 40 | 20 | 0 | 0 | 0 | 20 | 0 | 0 | 40 | 0 | 0 | 60 | 40 | 55 | 45 | 85 | 20 |

| | 250 g ai/ha Compounds | | | | | | | | | | | | | | | | |
|---|---|---|---|---|---|---|---|---|---|---|---|---|---|---|---|---|---|
| | 54 | 55 | 56 | 57 | 58 | 59 | 60 | 61 | 62 | 63 | 64 | 65 | 66 | 67 | 68 | 69 | 70 | 72 |
| Barnyardgrass | 0 | 50 | 0 | 0 | 0 | 40 | 30 | 0 | 20 | 20 | 0 | 0 | 0 | 0 | 40 | 40 | 40 | 0 |
| Ducksalad | 70 | 75 | 0 | 0 | 0 | 75 | 90 | 0 | 75 | 60 | 80 | 80 | 75 | 70 | 90 | 85 | 85 | 60 |
| Rice | 20 | 50 | 0 | 0 | 0 | 20 | 0 | 0 | 0 | 0 | 15 | 0 | 0 | 0 | 25 | 30 | 35 | 0 |
| Sedge, Umbrella | 0 | 70 | 0 | 0 | 0 | 60 | 60 | 30 | 80 | 0 | 40 | 40 | 50 | 50 | 70 | 65 | 70 | 0 |

| | 250 g ai/ha Compounds | | | | | | | | | | | | | | | | | |
|---|---|---|---|---|---|---|---|---|---|---|---|---|---|---|---|---|---|---|
| | 73 | 74 | 75 | 76 | 77 | 78 | 79 | 80 | 81 | 82 | 83 | 84 | 87 | 89 | 95 | 97 | 194 | 195 |
| Barnyardgrass | 0 | 0 | 0 | 0 | 20 | 0 | 0 | 30 | 20 | 0 | 30 | 0 | 60 | 60 | 0 | 50 | 0 | 30 |
| Ducksalad | 60 | 90 | 0 | 90 | 100 | 85 | 90 | 75 | 70 | 70 | 50 | 0 | 80 | 70 | 90 | 70 | 45 | 35 |
| Rice | 0 | 0 | 0 | 0 | 10 | 0 | 0 | 0 | 0 | — | — | 0 | 0 | 0 | 20 | 0 | 50 | 0 |
| Sedge, Umbrella | 0 | 0 | 0 | 0 | 0 | 0 | 0 | 0 | 0 | 80 | 0 | 0 | 0 | 0 | 0 | 75 | 0 | 0 |

| | 250 g ai/ha Compounds | | | | | | | | | |
|---|---|---|---|---|---|---|---|---|---|---|
| | 196 | 197 | 198 | 199 | 235 | 241 | 242 | 243 | 256 | 257 | 258 |
| Barnyardgrass | 0 | 0 | 0 | 20 | 0 | 55 | 40 | 0 | 0 | 0 | 0 |
| Ducksalad | 0 | 0 | 70 | 90 | 0 | 100 | 90 | 0 | 60 | 70 | 60 |
| Rice | 0 | 0 | 0 | 0 | 0 | 0 | 20 | 0 | 0 | 15 | 0 |
| Sedge, Umbrella | 0 | 0 | 0 | 0 | 0 | 0 | 0 | 0 | 50 | 0 | 40 |

Test C

Seeds of plant species selected from blackgrass (*Alopecurus myosuroides*), ryegrass, Italian (Italian ryegrass, *Lolium multiflorum*), wheat (winter wheat, *Triticum aestivum*), galium (catchweed bedstraw, *Galium aparine*), corn (*Zea mays*), crabgrass, large (large crabgrass, *Digitaria sanguinalis*), foxtail, giant (giant foxtail, *Setaria faberii*), johnsongrass (*Sorghum halepense*), lambsquarters (*Chenopodium album*), morningglory (*Ipomoea coccinea*), nutsedge, yellow (yellow nutsedge, *Cyperus esculentus*), pigweed (*Amaranthus retroflexus*), ragweed (common ragweed, *Ambrosia elatior*), soybean (Gycine max), barnyardgrass (*Echinochloa crus-galli*), oilseed rape (*Brassica napus*), waterhemp (common waterhemp, *Amaranthus rudis*), kochia (*Kochia scoparia*), oat, wild (wild oat, *Avena fatua*), surinam grass (*Brachiaria decumbens*), foxtail, green (green foxtail, *Setaria viridis*), goosegrass (*Eleusine indica*), bromegrass, downy (downy bromegrass, *Bromus tectorum*), nightshade (eastern black nightshade, *Solanum ptycanthum*), cocklebur (common cocklebur, *Xanthium strumarium*), cupgrass, woolly (woolly cupgrass, *Eriochloa villosa*), bermudagrass (*Cynodon dactylon*), sunflower, (common oilseed sunflower, *Helianthus annuus*), Russian thistle (*Salsola kali*) and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also barley (winter barley, *Hordeum vulgare*), windgrass (*Apera spica-venti*), chickweed (common chickweed, *Stellaria media*), deadnettle (henbit deadnettle, *Lamium amplexicaule*), and canarygrass (littleseed canarygrass, *Phalaris minor*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

Plant species in the flooded paddy test consisted of rice (*Oryza sativa*), sedge, umbrella (small-flower umbrella sedge, *Cyperus difformis*), ducksalad (*Heteranthera limosa*), and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

TABLE C

| | Postemergence | | | | | | | | | | | |
|---|---|---|---|---|---|---|---|---|---|---|---|---|
| | 250 g ai/ha Compounds | | | | | | | | | | | |
| | 17 | 34 | 50 | 52 | 76 | 79 | 80 | 81 | 101 | 103 | 106 | 109 |
| Barley | 0 | 0 | 0 | 15 | — | — | — | 0 | — | — | — | — |
| Barnyardgrass | — | — | — | — | 90 | 60 | 70 | — | 90 | 65 | 30 | 45 |
| Bermudagrass | 0 | 0 | 0 | 10 | — | — | — | 0 | — | — | — | — |
| Blackgrass | 0 | 0 | 0 | 0 | 10 | 5 | 5 | 0 | 5 | 0 | 0 | 0 |
| Bromegrass, Downy | 0 | 0 | 0 | 10 | — | — | — | 7 | — | — | — | — |
| Canarygrass | 0 | 0 | 0 | 0 | — | — | — | 0 | — | — | — | — |
| Chickweed | 10 | 5 | 5 | 60 | 80 | 90 | 90 | 0 | 80 | 5 | 30 | 0 |
| Cocklebur | 0 | 25 | 5 | 5 | — | — | — | 0 | — | — | — | — |
| Corn | 0 | 0 | 5 | 5 | 0 | 0 | 10 | 0 | 0 | 0 | 0 | 5 |
| Crabgrass, Large | 70 | 60 | 75 | 75 | 75 | 75 | 75 | 7 | 85 | 85 | 60 | 70 |
| Cupgrass, Woolly | 0 | 30 | 10 | 10 | — | — | — | 0 | — | — | — | — |
| Deadnettle | 0 | 0 | — | — | — | — | — | — | — | — | — | — |
| Foxtail, Giant | 10 | 35 | 10 | 25 | 70 | 15 | 45 | 7 | 90 | 80 | 50 | 70 |
| Foxtail, Green | 0 | 60 | 30 | 80 | — | — | — | 48 | — | — | — | — |
| *Galium* | 0 | 10 | — | — | 65 | — | 65 | — | 70 | 50 | — | 30 |
| Goosegrass | 0 | 25 | 25 | 20 | — | — | — | 0 | — | — | — | — |
| Johnsongrass | 0 | 0 | 10 | 0 | 0 | 5 | 10 | 0 | 0 | 0 | 0 | 0 |
| *Kochia* | 5 | 5 | 0 | 50 | 65 | — | 65 | 0 | 50 | 40 | 35 | 0 |
| Lambsquarters | 0 | 55 | 15 | 40 | 50 | 85 | 70 | 3 | 70 | 30 | 0 | 5 |
| Morningglory | 0 | 10 | 10 | 30 | 40 | 5 | 5 | 0 | 55 | 40 | 5 | 15 |
| Nutsedge, Yellow | 0 | 10 | 5 | 10 | 0 | 0 | 0 | 0 | 5 | 0 | 0 | 0 |
| Oat, Wild | 0 | 0 | 0 | 0 | 0 | 0 | 0 | 0 | 0 | 0 | 0 | 0 |
| Oilseed Rape | — | — | — | — | 10 | 0 | 60 | — | 35 | 5 | 0 | 5 |
| Pigweed | 0 | 10 | 20 | 60 | 30 | 35 | 75 | 0 | 45 | 10 | 30 | 10 |
| Ragweed | 0 | 5 | 10 | 55 | 55 | 45 | 30 | 0 | 45 | 10 | 5 | 5 |
| Ryegrass, Italian | 5 | 0 | 0 | 0 | 5 | 0 | 0 | 0 | 0 | 0 | 5 | 0 |
| Soybean | 0 | 10 | 20 | 5 | 10 | 10 | 25 | 8 | 5 | 0 | 5 | 5 |
| Surinam Grass | 60 | 60 | 15 | 30 | — | — | — | 0 | — | — | — | — |
| Velvetleaf | 0 | 5 | 45 | 35 | 0 | 0 | 25 | 0 | 30 | 0 | 5 | 5 |
| Waterhemp | — | — | — | — | 10 | 30 | 65 | — | 35 | 10 | 20 | 0 |
| Wheat | 0 | 0 | 0 | 0 | 5 | 0 | 0 | 0 | 0 | 0 | 0 | 0 |
| Windgrass | 0 | 5 | 0 | 20 | — | — | — | 20 | — | — | — | — |

TABLE C-continued

| | 250 g ai/ha Compounds | | | | | | | | | | | |
|---|---|---|---|---|---|---|---|---|---|---|---|---|
| | 119 | 120 | 202 | 204 | 206 | 207 | 223 | 224 | 232 | 244 | 275 | 278 |
| Barley | — | — | — | — | — | — | — | — | — | — | — | — |
| Barnyardgrass | 80 | 65 | 85 | 90 | 80 | 65 | 60 | 75 | 75 | 5 | 85 | 75 |
| Bermudagrass | — | — | — | — | — | — | — | — | — | — | — | — |
| Blackgrass | 0 | 0 | 10 | 50 | 60 | 0 | 0 | 0 | 0 | 0 | 40 | 0 |
| Bromegrass, Downy | — | — | — | — | — | — | — | — | — | — | — | — |
| Canarygrass | — | — | — | — | — | — | — | — | — | — | — | — |
| Chickweed | — | — | 85 | 65 | 85 | 90 | 80 | 85 | 85 | 65 | 85 | 0 |
| Cocklebur | — | — | — | — | — | — | — | — | — | — | — | — |
| Corn | 5 | 0 | 35 | 40 | 50 | 5 | 5 | 10 | 0 | 0 | 55 | 0 |
| Crabgrass, Large | 90 | 75 | 75 | 80 | 80 | 65 | 80 | 75 | 75 | 40 | 85 | 75 |
| Cupgrass, Woolly | — | — | — | — | — | — | — | — | — | — | — | — |
| Deadnettle | — | — | — | — | — | — | — | — | — | — | — | — |
| Foxtail, Giant | 90 | 85 | 85 | 90 | 85 | 75 | 35 | 35 | 70 | 5 | 90 | 75 |
| Foxtail, Green | — | — | — | — | — | — | — | — | — | — | — | — |
| *Galium* | — | — | 80 | 60 | 75 | 50 | 70 | 85 | 80 | 65 | 80 | 20 |
| Goosegrass | — | — | — | — | — | — | — | — | — | — | — | — |
| Johnsongrass | 5 | 0 | 25 | 0 | 35 | 0 | 0 | 25 | 25 | 5 | 25 | 0 |
| *Kochia* | — | — | 80 | 40 | 70 | 30 | 60 | 70 | 75 | 50 | 85 | 5 |
| Lambsquarters | 70 | 70 | 85 | 30 | 20 | 15 | 60 | 60 | 85 | 35 | 75 | 20 |
| Morningglory | 5 | 5 | 10 | 35 | 45 | 20 | 35 | 35 | 60 | 5 | 20 | 0 |
| Nutsedge, Yellow | 0 | 0 | 0 | 0 | 0 | 0 | 0 | 0 | 5 | 5 | 20 | 15 |
| Oat, Wild | 0 | 0 | 10 | 5 | 50 | 0 | 0 | 15 | 30 | 0 | 5 | 0 |
| Oilseed Rape | 5 | 0 | 50 | 45 | 55 | 30 | 10 | 5 | 40 | 10 | 45 | 0 |
| Pigweed | 25 | 60 | 85 | 10 | 30 | 20 | 60 | 65 | 85 | 10 | 35 | 15 |
| Ragweed | 25 | 45 | 85 | 0 | 5 | 15 | 35 | 80 | 75 | 0 | 70 | 0 |
| Ryegrass, Italian | 5 | 10 | 35 | 15 | 35 | 0 | 0 | 5 | 40 | 0 | 25 | 0 |
| Soybean | 5 | 0 | 10 | 5 | 5 | 5 | 30 | 5 | 20 | 5 | 10 | 15 |
| Surinam Grass | — | — | — | — | — | — | — | — | — | — | — | — |
| Velvetleaf | 20 | 25 | 55 | 10 | 15 | 0 | 20 | 35 | 60 | 5 | 50 | 20 |
| Waterhemp | 40 | 20 | 85 | 5 | 30 | 10 | 10 | 30 | 80 | 5 | 20 | 5 |
| Wheat | 0 | 0 | 5 | 0 | 45 | 0 | 0 | 5 | 5 | 0 | 0 | 0 |
| Windgrass | — | — | — | — | — | — | — | — | — | — | — | — |

| | 250 g ai/ha Compounds | | | | | | | | | | | |
|---|---|---|---|---|---|---|---|---|---|---|---|---|
| | 279 | 302 | 303 | 305 | 306 | 309 | 310 | 312 | 315 | 316 | 317 | 323 |
| Barley | — | — | — | — | — | — | — | — | — | — | — | — |
| Barnyardgrass | 85 | 90 | 70 | 80 | 85 | 60 | 7 | 75 | 85 | 70 | 70 | 70 |
| Bermudagrass | — | — | — | — | — | — | — | — | — | — | — | — |
| Blackgrass | 0 | 5 | 0 | 10 | 5 | 5 | 5 | 0 | 25 | 0 | 0 | 15 |
| Bromegrass, Downy | — | — | — | — | — | — | — | — | — | — | — | — |
| Canarygrass | — | — | — | — | — | — | — | — | — | — | — | — |
| Chickweed | 5 | 70 | — | — | — | 70 | 85 | — | — | — | — | — |
| Cocklebur | — | — | — | — | — | — | — | — | — | — | — | — |
| Corn | 0 | 0 | 15 | 45 | 20 | 20 | 30 | 10 | 60 | 0 | 0 | 10 |
| Crabgrass, Large | 80 | 85 | 90 | 80 | 85 | 65 | 70 | 90 | 75 | 70 | 50 | 80 |
| Cupgrass, Woolly | — | — | — | — | — | — | — | — | — | — | — | — |
| Deadnettle | — | — | — | — | — | — | — | — | — | — | — | — |
| Foxtail, Giant | 90 | 80 | 90 | 90 | 85 | 80 | 70 | 80 | 85 | 85 | 50 | 70 |
| Foxtail, Green | — | — | — | — | — | — | — | — | — | — | — | — |
| *Galium* | 30 | 45 | — | — | — | 60 | 65 | — | — | — | — | — |
| Goosegrass | — | — | — | — | — | — | — | — | — | — | — | — |
| Johnsongrass | 0 | 10 | 5 | 20 | 0 | 15 | 5 | 0 | 35 | 0 | 5 | 10 |
| *Kochia* | 35 | 60 | — | — | — | 75 | 80 | — | — | — | — | — |
| Lambsquarters | 45 | 70 | 80 | 65 | 75 | 70 | 70 | 55 | 80 | 65 | 25 | 65 |
| Morningglory | 25 | 25 | 0 | 20 | 5 | 10 | 70 | 20 | 10 | 10 | 10 | 25 |
| Nutsedge, Yellow | 0 | 20 | 0 | 0 | 0 | 0 | 25 | 0 | 0 | 0 | 0 | 0 |
| Oat, Wild | 0 | 0 | 0 | 30 | 5 | 0 | 0 | 0 | 0 | 30 | 0 | 0 |
| Oilseed Rape | 0 | 0 | 30 | 0 | 70 | 5 | 40 | 0 | 10 | 0 | 0 | 0 |
| Pigweed | 20 | 30 | 25 | 65 | 90 | 60 | 70 | 45 | 80 | 75 | 5 | 25 |
| Ragweed | 35 | 55 | 55 | 45 | 85 | 40 | 60 | 55 | 70 | 65 | 40 | 20 |
| Ryegrass, Italian | 0 | 0 | 5 | 45 | 20 | 5 | 5 | 10 | 45 | 5 | 0 | 5 |
| Soybean | 10 | 65 | 0 | 0 | 5 | 0 | 0 | 0 | 15 | 0 | 0 | 0 |
| Surinam Grass | — | — | — | — | — | — | — | — | — | — | — | — |
| Velvetleaf | 10 | 20 | 35 | 65 | 65 | 15 | 40 | 35 | 55 | 35 | 0 | 0 |
| Waterhemp | 15 | 25 | 25 | 40 | 80 | 10 | 10 | 20 | 65 | 55 | 0 | 20 |
| Wheat | 0 | 0 | 0 | 5 | 0 | 0 | 0 | 0 | 5 | 0 | 0 | 0 |
| Windgrass | — | — | — | — | — | — | — | — | — | — | — | — |

TABLE C-continued

|  | 250 g ai/ha Compounds | | | | 125 g ai/ha Compounds | | | | | | | |
| --- | --- | --- | --- | --- | --- | --- | --- | --- | --- | --- | --- | --- |
|  | 324 | 325 | 345 | 346 | 17 | 34 | 48 | 50 | 52 | 60 | 76 | 79 |
| Barley | — | — | — | — | 0 | 0 | 0 | 0 | 0 | 20 | — | — |
| Barnyardgrass | 65 | 80 | — | 60 | — | — | — | — | — | — | 85 | 35 |
| Bermudagrass | — | — | — | — | 0 | 0 | 10 | 0 | 0 | 0 | — | — |
| Blackgrass | 0 | 35 | — | 5 | 0 | 0 | 0 | 0 | 0 | 0 | 0 | 0 |
| Bromegrass, Downy | — | — | — | — | 0 | 0 | 0 | 0 | 0 | 5 | — | — |
| Canarygrass | — | — | — | — | 0 | 0 | 0 | 0 | 0 | 0 | — | — |
| Chickweed | — | — | 30 | 85 | 0 | 5 | 30 | 0 | 45 | 30 | 65 | 90 |
| Cocklebur | — | — | — | — | 0 | 5 | 10 | 5 | 5 | 0 | — | — |
| Corn | 0 | 35 | — | 0 | 0 | 0 | 5 | 5 | 5 | 0 | 0 | 0 |
| Crabgrass, Large | 75 | 85 | — | 75 | 45 | 40 | 7 | 40 | 55 | 75 | 70 | 65 |
| Cupgrass, Woolly | — | — | — | — | 0 | 0 | 5 | 0 | 5 | 5 | — | — |
| Deadnettle | — | — | — | — | 0 | 0 | — | — | — | — | — | — |
| Foxtail, Giant | 60 | 75 | — | 85 | 0 | 5 | 40 | 5 | 0 | 30 | 20 | 15 |
| Foxtail, Green | — | — | — | — | 0 | 60 | 65 | 0 | 30 | 45 | — | — |
| *Galium* | — | — | — | 70 | 0 | 0 | — | — | — | — | 50 | 60 |
| Goosegrass | — | — | — | — | 0 | 15 | 10 | 25 | 20 | 0 | — | — |
| Johnsongrass | 10 | 0 | — | 0 | 0 | 0 | 0 | 0 | 0 | 5 | 0 | 0 |
| *Kochia* | — | — | — | 40 | 0 | 5 | 20 | 0 | 40 | 45 | 50 | 55 |
| Lambsquarters | 65 | 65 | — | 65 | 0 | 10 | 10 | 10 | 40 | 20 | 40 | 85 |
| Morningglory | 15 | 50 | — | 5 | 0 | 5 | 10 | 10 | 10 | 10 | 40 | 5 |
| Nutsedge, Yellow | 0 | 0 | — | 5 | 0 | 10 | 0 | 0 | 10 | 5 | 0 | 0 |
| Oat, Wild | 5 | 15 | — | 0 | 0 | 0 | 0 | 0 | 0 | 0 | 0 | 0 |
| Oilseed Rape | 0 | 60 | — | 0 | — | — | — | — | — | — | 0 | 0 |
| Pigweed | 55 | 65 | — | 40 | 0 | 0 | 40 | 20 | 50 | 20 | 10 | 35 |
| Ragweed | 40 | 35 | — | 20 | 0 | 5 | 35 | 0 | 50 | 35 | 40 | 20 |
| Ryegrass, Italian | 0 | 30 | — | 0 | 0 | 0 | 0 | 0 | 0 | 0 | 0 | 0 |
| Soybean | 0 | 0 | — | 5 | 0 | 5 | 10 | 15 | 5 | 5 | 5 | 10 |
| Surinam Grass | — | — | — | — | 45 | 55 | 25 | 5 | — | 0 | — | — |
| Velvetleaf | 55 | 40 | — | 20 | 0 | 5 | 35 | 25 | 20 | 5 | 0 | 0 |
| Waterhemp | 40 | 35 | — | 40 | — | — | — | — | — | — | 5 | 10 |
| Wheat | 0 | 5 | — | 0 | 0 | 0 | 5 | 0 | 0 | 5 | 0 | 0 |
| Windgrass | — | — | — | — | 0 | 0 | 0 | 0 | 20 | 0 | — | — |

|  | 125 g ai/ha Compounds | | | | | | | | | | | |
| --- | --- | --- | --- | --- | --- | --- | --- | --- | --- | --- | --- | --- |
|  | 80 | 81 | 101 | 103 | 106 | 109 | 119 | 120 | 202 | 204 | 206 | 207 |
| Barley | — | 0 | — | — | — | — | — | — | — | — | — | — |
| Barnyardgrass | 35 | — | 65 | 35 | 0 | 0 | 65 | 40 | 65 | 80 | 80 | 35 |
| Bermudagrass | — | 0 | — | — | — | — | — | — | — | — | — | — |
| Blackgrass | 0 | 0 | 10 | 0 | 0 | 0 | 0 | 0 | 5 | 0 | 40 | 0 |
| Bromegrass, Downy | — | 0 | — | — | — | — | — | — | — | — | — | — |
| Canarygrass | — | 0 | — | — | — | — | — | — | — | — | — | — |
| Chickweed | 90 | 0 | 70 | 5 | 5 | 0 | — | — | 85 | 55 | 85 | 60 |
| Cocklebur | — | 0 | — | — | — | — | — | — | — | — | — | — |
| Corn | 5 | 0 | 0 | 0 | 0 | 0 | 0 | 0 | 10 | 0 | 30 | 0 |
| Crabgrass, Large | 65 | 3 | 80 | 75 | 25 | 40 | 80 | 70 | 60 | 70 | 70 | 40 |
| Cupgrass, Woolly | — | 0 | — | — | — | — | — | — | — | — | — | — |
| Deadnettle | — | — | — | — | — | — | — | — | — | — | — | — |
| Foxtail, Giant | 45 | 0 | 75 | 45 | 45 | 50 | 85 | 75 | 70 | 90 | 50 | 65 |
| Foxtail, Green | — | 20 | — | — | — | — | — | — | — | — | — | — |
| *Galium* | 6.5 | — | 30 | 40 | 50 | 30 | — | — | 80 | 60 | 75 | 0 |
| Goosegrass | — | 0 | — | — | — | — | — | — | — | — | — | — |
| Johnsongrass | 5 | 0 | 0 | 0 | 0 | 0 | 0 | 0 | 25 | 0 | 0 | 0 |
| *Kochia* | 65 | 0 | 50 | 35 | 30 | 0 | — | — | 80 | 40 | 30 | 0 |
| Lambsquarters | 60 | 0 | 35 | 40 | 0 | 0 | 75 | 60 | 80 | 75 | 10 | 35 |
| Morningglory | 5 | 0 | 25 | 10 | 10 | 5 | 5 | 0 | 70 | 15 | 35 | 5 |
| Nutsedge, Yellow | 0 | 0 | 0 | 0 | 0 | 0 | 0 | 0 | 0 | 0 | 0 | 0 |
| Oat, Wild | 0 | 0 | 0 | 0 | 0 | 0 | 0 | 0 | 30 | 0 | 45 | 0 |
| Oilseed Rape | 20 | — | 50 | 0 | 0 | 5 | 0 | 0 | 50 | 0 | 50 | 10 |
| Pigweed | 60 | 0 | 15 | 5 | 5 | 5 | 15 | 40 | 85 | 10 | 50 | 10 |
| Ragweed | 30 | 0 | 5 | 10 | 0 | 0 | 45 | 40 | 80 | 0 | 25 | 0 |
| Ryegrass, Italian | 0 | 0 | 0 | 0 | 0 | 0 | 0 | 0 | 5 | 0 | 10 | 0 |
| Soybean | 5 | 3 | 5 | 0 | 5 | 5 | 0 | 0 | 5 | 0 | 5 | 5 |
| Surinam Grass | — | 0 | — | — | — | — | — | — | — | — | — | — |
| Velvetleaf | — | 0 | 10 | 0 | 5 | 0 | 15 | 5 | 30 | 0 | 15 | 0 |
| Waterhemp | 45 | — | 20 | 5 | 10 | 0 | 0 | 15 | 75 | 0 | 35 | 0 |
| Wheat | 0 | 0 | 0 | 0 | 0 | 0 | 0 | 0 | 0 | 0 | 30 | 0 |
| Windgrass | — | 20 | — | — | — | — | — | — | — | — | — | — |

TABLE C-continued

| | 125 g ai/ha Compounds | | | | | | | | | | | |
|---|---|---|---|---|---|---|---|---|---|---|---|---|
| | 223 | 224 | 232 | 244 | 275 | 277 | 278 | 279 | 302 | 303 | 304 | 305 |
| Barley | — | — | — | — | — | — | — | — | — | — | — | — |
| Barnyardgrass | 45 | 50 | 70 | 5 | 75 | 80 | 55 | 85 | 40 | 70 | 40 | 70 |
| Bermudagrass | — | — | — | — | — | — | — | — | — | — | — | — |
| Blackgrass | 0 | 0 | 0 | 0 | 5 | 0 | 0 | 0 | 0 | 0 | 0 | 30 |
| Bromegrass, Downy | — | — | — | — | — | — | — | — | — | — | — | — |
| Canarygrass | — | — | — | — | — | — | — | — | — | — | — | — |
| Chickweed | 50 | 70 | 85 | 20 | 85 | 40 | 0 | 30 | 5 | — | — | — |
| Cocklebur | — | — | — | — | — | — | — | — | — | — | — | — |
| Corn | 0 | 10 | 0 | 0 | 0 | 10 | 0 | 0 | 0 | 0 | 5 | 40 |
| Crabgrass, Large | 55 | 55 | 60 | 5 | 65 | 70 | 65 | 70 | 70 | 65 | 80 | 75 |
| Cupgrass, Woolly | — | — | — | — | — | — | — | — | — | — | — | — |
| Deadnettle | — | — | — | — | — | — | — | — | — | — | — | — |
| Foxtail, Giant | 30 | 60 | 15 | 5 | 35 | 85 | 40 | 90 | 80 | 85 | 45 | 85 |
| Foxtail, Green | — | — | — | — | — | — | — | — | — | — | — | — |
| Galium | 45 | 60 | 80 | 55 | 75 | 75 | 5 | 30 | 10 | — | — | — |
| Goosegrass | — | — | — | — | — | — | — | — | — | — | — | — |
| Johnsongrass | 0 | 15 | 20 | 0 | 0 | 10 | 0 | 0 | 0 | 0 | 0 | 20 |
| Kochia | 30 | 50 | 70 | 40 | 85 | 60 | 0 | 85 | 0 | — | — | — |
| Lambsquarters | 35 | 70 | 85 | 10 | 75 | 40 | 20 | 45 | 60 | 65 | 70 | 50 |
| Morningglory | 0 | 35 | 25 | 5 | 20 | 40 | 45 | 30 | 50 | 0 | 45 | 75 |
| Nutsedge, Yellow | 0 | 0 | 5 | 5 | 0 | 0 | 0 | 0 | 0 | 0 | 0 | 0 |
| Oat, Wild | 0 | 5 | 0 | 0 | 0 | 5 | 0 | 0 | 0 | 0 | 0 | 0 |
| Oilseed Rape | 0 | 20 | 65 | 5 | 35 | 0 | 5 | 0 | 40 | 0 | 0 | 0 |
| Pigweed | 10 | 60 | 85 | 5 | 30 | 30 | 15 | 30 | 20 | 10 | 55 | 65 |
| Ragweed | 35 | 45 | 85 | 0 | 70 | 40 | 10 | 35 | 20 | 40 | 35 | 40 |
| Ryegrass, Italian | 0 | 5 | 0 | 0 | 5 | 35 | 0 | 0 | 0 | 0 | 0 | 0 |
| Soybean | 0 | 5 | 10 | 5 | 0 | 0 | 40 | 0 | 0 | 0 | 10 | 0 |
| Surinam Grass | — | — | — | — | — | — | — | — | — | — | — | — |
| Velvetleaf | 0 | 25 | 30 | 5 | 10 | 15 | 10 | 10 | 0 | 25 | 15 | 40 |
| Waterhemp | 10 | 30 | 80 | 5 | 0 | 5 | 5 | 15 | 20 | 0 | 80 | 35 |
| Wheat | 0 | 5 | 5 | 0 | 0 | 0 | 0 | 0 | 0 | 0 | 0 | 0 |
| Windgrass | — | — | — | — | — | — | — | — | — | — | — | — |

| | 125 g ai/ha Compounds | | | | | | | | | | | 62 g ai/ha Compounds |
|---|---|---|---|---|---|---|---|---|---|---|---|---|
| | 306 | 309 | 310 | 312 | 315 | 316 | 317 | 323 | 324 | 325 | 346 | 17 |
| Barley | — | — | — | — | — | — | — | — | — | — | — | 0 |
| Barnyardgrass | 85 | 55 | 50 | 70 | 70 | 60 | 25 | 35 | 55 | 70 | 30 | — |
| Bermudagrass | — | — | — | — | — | — | — | — | — | — | — | 0 |
| Blackgrass | 5 | 5 | 5 | 0 | 30 | 0 | 0 | 0 | 0 | 0 | 0 | 0 |
| Bromegrass, Downy | — | — | — | — | — | — | — | — | — | — | — | 0 |
| Canarygrass | — | — | — | — | — | — | — | — | — | — | — | 0 |
| Chickweed | — | 65 | 90 | — | — | — | — | — | — | — | 40 | 0 |
| Cocklebur | — | — | — | — | — | — | — | — | — | — | — | 0 |
| Corn | 0 | 0 | 60 | 10 | 10 | 0 | 0 | 5 | 55 | 10 | 0 | 0 |
| Crabgrass, Large | 75 | 60 | 70 | 80 | 70 | 60 | 45 | 70 | 70 | 65 | 60 | 0 |
| Cupgrass, Woolly | — | — | — | — | — | — | — | — | — | — | — | 0 |
| Deadnettle | — | — | — | — | — | — | — | — | — | — | — | 0 |
| Foxtail, Giant | 60 | 40 | 30 | 75 | 85 | 85 | 0 | 35 | 75 | 65 | 40 | 0 |
| Foxtail, Green | — | — | — | — | — | — | — | — | — | — | — | 0 |
| Galium | — | 55 | 50 | — | — | — | — | — | — | — | 40 | 0 |
| Goosegrass | — | — | — | — | — | — | — | — | — | — | — | 0 |
| Johnsongrass | 0 | 0 | 0 | 25 | 0 | 0 | 0 | 0 | 0 | 0 | 0 | 0 |
| Kochia | — | 75 | 90 | — | — | — | — | — | — | — | 45 | 0 |
| Lambsquarters | 90 | 65 | 65 | 95 | 65 | 40 | 25 | 65 | 70 | 70 | 5 | 0 |
| Morningglory | 65 | 25 | 10 | 10 | 35 | 10 | 0 | 5 | 10 | 35 | 15 | 0 |
| Nutsedge, Yellow | — | 30 | 0 | 0 | 0 | 0 | 0 | 0 | 0 | 0 | 0 | 0 |
| Oat, Wild | 0 | 0 | 0 | 0 | 0 | 5 | 0 | 0 | 0 | 5 | 0 | 0 |
| Oilseed Rape | 40 | 40 | 0 | 0 | 0 | 0 | 0 | 0 | 0 | 50 | 0 | — |
| Pigweed | 85 | 50 | 60 | 25 | 65 | 60 | 5 | 25 | 65 | 50 | 20 | 0 |
| Ragweed | 80 | 35 | 20 | 45 | 65 | 35 | 25 | 15 | 25 | 25 | 0 | 0 |
| Ryegrass, Italian | 5 | 0 | 0 | 35 | 15 | 0 | 0 | 0 | 0 | 0 | 0 | 0 |
| Soybean | 5 | 15 | 0 | 0 | 0 | 0 | 0 | 0 | 0 | 0 | 0 | 0 |
| Surinam Grass | — | — | — | — | — | — | — | — | — | — | — | 0 |
| Velvetleaf | 50 | 0 | 0 | 0 | 30 | 45 | 0 | 0 | 50 | 20 | 5 | 0 |
| Waterhemp | 80 | 10 | 10 | 20 | 60 | 10 | 20 | 0 | 20 | 25 | 15 | — |
| Wheat | 0 | 0 | 0 | 0 | 0 | 0 | 0 | 0 | 0 | 0 | 0 | 0 |
| Windgrass | — | — | — | — | — | — | — | — | — | — | — | 0 |

TABLE C-continued

| | 62 g ai/ha Compounds | | | | | | | | | | | |
|---|---|---|---|---|---|---|---|---|---|---|---|---|
| | 34 | 48 | 50 | 52 | 60 | 76 | 79 | 80 | 81 | 101 | 103 | 106 |
| Barley | 0 | 0 | 0 | 0 | 0 | — | — | — | 0 | — | — | — |
| Barnyardgrass | — | — | — | — | — | 35 | 0 | 20 | — | 35 | 10 | 0 |
| Bermudagrass | 0 | 0 | 0 | 0 | 0 | — | — | — | 0 | — | — | — |
| Blackgrass | 0 | 0 | 0 | 0 | 0 | 0 | 0 | 0 | 0 | 0 | 0 | 0 |
| Bromegrass, Downy | 0 | 0 | 0 | 0 | 0 | — | — | — | 0 | — | — | — |
| Canarygrass | 0 | 0 | 0 | 0 | 0 | — | — | — | 0 | — | — | — |
| Chickweed | 0 | 30 | 0 | 25 | 10 | 40 | 80 | 85 | 0 | 60 | 5 | 0 |
| Cocklebur | 5 | 10 | 5 | 5 | 0 | — | — | — | 0 | — | — | — |
| Corn | 0 | 5 | 0 | 0 | 0 | 0 | 0 | 5 | 0 | 0 | 0 | 0 |
| Crabgrass, Large | 30 | 65 | 25 | 55 | 50 | 50 | 5 | 40 | 0 | 50 | 15 | 10 |
| Cupgrass, Woolly | 0 | 5 | 0 | 5 | 0 | — | — | — | 0 | — | — | — |
| Deadnettle | 0 | — | — | — | — | — | — | — | — | — | — | — |
| Foxtail, Giant | 5 | 20 | 5 | 0 | 15 | 5 | 15 | 0 | 0 | 20 | 0 | 35 |
| Foxtail, Green | 60 | 0 | 0 | 10 | 35 | — | — | — | 5 | — | — | — |
| Galium | 0 | — | — | — | — | 50 | 60 | 55 | — | 50 | 0 | 0 |
| Goosegrass | 15 | 10 | 25 | 0 | 0 | — | — | — | 0 | — | — | — |
| Johnsongrass | 0 | 0 | 0 | 0 | 5 | 0 | 0 | 5 | 0 | 0 | 0 | 0 |
| Kochia | 5 | 10 | 0 | 35 | 10 | 50 | 55 | 55 | 0 | 30 | 30 | 40 |
| Lambsquarters | 0 | — | 10 | 10 | 20 | 40 | 50 | 55 | 0 | 25 | 0 | 25 |
| Morningglory | 5 | 10 | 0 | 10 | 10 | 10 | 0 | 5 | 0 | 15 | 0 | 5 |
| Nutsedge, Yellow | 5 | 0 | 0 | 10 | 0 | 0 | 0 | 0 | 0 | 0 | 0 | 0 |
| Oat, Wild | 0 | 0 | 0 | 0 | 0 | 0 | 0 | 0 | 0 | 0 | 0 | 0 |
| Oilseed Rape | — | — | — | — | — | 0 | 0 | 0 | — | 10 | 0 | 0 |
| Pigweed | 0 | 30 | 10 | 40 | 20 | 10 | 35 | 40 | 0 | 10 | 0 | 0 |
| Ragweed | 5 | 5 | 0 | 10 | 25 | 40 | 20 | 30 | 0 | 0 | 0 | 0 |
| Ryegrass, Italian | 0 | 0 | 0 | 0 | 0 | 0 | 0 | 0 | 0 | 0 | 0 | 0 |
| Soybean | 0 | 10 | 15 | 0 | 0 | 0 | 0 | 5 | 3 | 0 | 0 | 0 |
| Surinam Grass | 0 | 25 | 5 | 5 | 0 | — | — | — | 0 | — | — | — |
| Velvetleaf | 5 | 15 | 15 | 20 | 0 | 0 | 0 | 15 | 0 | 0 | 0 | 0 |
| Waterhemp | — | — | — | — | — | 5 | 10 | 45 | — | 5 | 5 | 0 |
| Wheat | 0 | 0 | 0 | 0 | 0 | 0 | 0 | 0 | 0 | 0 | 0 | 0 |
| Windgrass | 0 | 0 | 0 | 0 | 0 | — | — | — | 0 | — | — | — |

| | 62 g ai/ha Compounds | | | | | | | | | | | |
|---|---|---|---|---|---|---|---|---|---|---|---|---|
| | 109 | 119 | 120 | 202 | 204 | 206 | 207 | 223 | 224 | 232 | 244 | 271 |
| Barley | — | — | — | — | — | — | — | — | — | — | — | — |
| Barnyardgrass | 0 | 40 | 30 | 65 | 55 | 40 | 10 | 0 | 30 | 55 | 0 | 0 |
| Bermudagrass | — | — | — | — | — | — | — | — | — | — | — | — |
| Blackgrass | 0 | 0 | 0 | 0 | 0 | 0 | 0 | 0 | 0 | 0 | 0 | 0 |
| Bromegrass, Downy | — | — | — | — | — | — | — | — | — | — | — | — |
| Canarygrass | — | — | — | — | — | — | — | — | — | — | — | — |
| Chickweed | 0 | — | — | 80 | 30 | 60 | 50 | 45 | 70 | 85 | 50 | 50 |
| Cocklebur | — | — | — | — | — | — | — | — | — | — | — | — |
| Corn | 0 | 0 | 0 | 0 | 0 | 0 | 0 | 0 | 0 | 0 | 0 | 0 |
| Crabgrass, Large | 10 | 65 | 70 | 50 | 50 | 50 | 15 | 10 | 35 | 35 | 5 | 5 |
| Cupgrass, Woolly | — | — | — | — | — | — | — | — | — | — | — | — |
| Deadnettle | — | — | — | — | — | — | — | — | — | — | — | — |
| Foxtail, Giant | 15 | 25 | 65 | 25 | 10 | 50 | 0 | 35 | 0 | 5 | 0 | 0 |
| Foxtail, Green | — | — | — | — | — | — | — | — | — | — | — | — |
| Galium | 0 | — | — | 80 | 45 | 75 | 0 | 5 | 45 | 80 | 30 | 30 |
| Goosegrass | — | — | — | — | — | — | — | — | — | — | — | — |
| Johnsongrass | 0 | 0 | 0 | 20 | 0 | 0 | 0 | 0 | 0 | 20 | 0 | 10 |
| Kochia | 0 | — | — | 75 | 30 | 70 | 0 | 5 | 40 | 70 | 10 | 10 |
| Lambsquarters | 0 | 50 | 55 | 80 | 65 | 75 | 10 | 5 | 50 | 85 | 20 | 55 |
| Morningglory | 0 | 0 | 5 | 10 | 5 | 20 | 5 | 0 | 5 | 0 | 0 | 45 |
| Nutsedge, Yellow | 0 | 0 | 0 | 0 | 0 | 20 | 0 | 0 | 0 | 0 | 10 | 0 |
| Oat, Wild | 0 | 0 | 0 | 0 | 0 | 5 | 0 | 0 | 0 | 0 | 0 | 0 |
| Oilseed Rape | 0 | 0 | 0 | 0 | 0 | 30 | 0 | 0 | 15 | 50 | 0 | 20 |
| Pigweed | 5 | 10 | 20 | 80 | 10 | 40 | 10 | 10 | 55 | 85 | 5 | 30 |
| Ragweed | 0 | 0 | 45 | 75 | 0 | 0 | 0 | 0 | 65 | 80 | 0 | 40 |
| Ryegrass, Italian | 0 | 0 | 0 | 0 | 0 | 0 | 0 | 0 | 0 | 0 | 0 | 0 |
| Soybean | 0 | 5 | 0 | 0 | 0 | 5 | 5 | 0 | 10 | 10 | 5 | 60 |
| Surinam Grass | — | — | — | — | — | — | — | — | — | — | — | — |
| Velvetleaf | 0 | 0 | 0 | 20 | 0 | 0 | 0 | 0 | 15 | 5 | 5 | 5 |
| Waterhemp | 0 | 0 | 0 | 65 | 0 | 0 | 0 | 0 | 35 | 75 | 5 | 5 |
| Wheat | 0 | 0 | 0 | 0 | 0 | 0 | 0 | 0 | 0 | 0 | 0 | 0 |
| Windgrass | — | — | — | — | — | — | — | — | — | — | — | — |

TABLE C-continued

| | 62 g ai/ha Compounds | | | | | | | | | | | |
|---|---|---|---|---|---|---|---|---|---|---|---|---|
| | 275 | 277 | 278 | 279 | 302 | 303 | 304 | 305 | 306 | 309 | 310 | 312 |
| Barley | — | — | — | — | — | — | — | — | — | — | — | — |
| Barnyardgrass | 60 | 70 | 10 | 55 | 20 | 60 | 0 | 55 | 45 | 15 | 25 | 70 |
| Bermudagrass | — | — | — | — | — | — | — | — | — | — | — | — |
| Blackgrass | 0 | 0 | 0 | 0 | 0 | 0 | 0 | 0 | 0 | 0 | 0 | 0 |
| Bromegrass, Downy | — | — | — | — | — | — | — | — | — | — | — | — |
| Canarygrass | — | — | — | — | — | — | — | — | — | — | — | — |
| Chickweed | 60 | 0 | 0 | 75 | 0 | — | — | — | — | 50 | 45 | — |
| Cocklebur | — | — | — | — | — | — | — | — | — | — | — | — |
| Corn | 0 | 20 | 0 | 0 | 0 | 0 | 0 | 5 | 0 | 0 | 0 | 15 |
| Crabgrass, Large | 40 | 65 | 30 | 65 | 50 | 40 | 60 | 55 | 45 | 30 | 10 | 50 |
| Cupgrass, Woolly | — | — | — | — | — | — | — | — | — | — | — | — |
| Deadnettle | — | — | — | — | — | — | — | — | — | — | — | — |
| Foxtail, Giant | 75 | 85 | 10 | 30 | 45 | 80 | 10 | 65 | 75 | 0 | 5 | 75 |
| Foxtail, Green | — | — | — | — | — | — | — | — | — | — | — | — |
| Galium | 55 | 60 | 0 | 15 | 15 | — | — | — | — | 40 | 50 | — |
| Goosegrass | — | — | — | — | — | — | — | — | — | — | — | — |
| Johnsongrass | 0 | 0 | 0 | 0 | 0 | 0 | 0 | 0 | 0 | 0 | 0 | 0 |
| Kochia | 85 | 5 | 0 | 30 | 0 | — | — | — | — | 5 | 50 | — |
| Lambsquarters | 60 | 40 | 0 | 0 | 20 | 85 | 75 | 35 | 70 | 65 | 65 | 75 |
| Morningglory | 10 | 30 | 0 | 60 | 15 | 60 | 20 | 20 | 35 | 10 | 0 | 0 |
| Nutsedge, Yellow | 0 | 0 | 0 | 0 | 0 | 0 | 0 | 0 | 0 | 5 | 0 | 0 |
| Oat, Wild | 0 | 0 | 0 | 0 | 0 | 0 | 0 | 0 | 0 | 0 | 0 | 0 |
| Oilseed Rape | 5 | 0 | 0 | 30 | 0 | 0 | 0 | 0 | 50 | 30 | 0 | 0 |
| Pigweed | 5 | 10 | 5 | 10 | 20 | 0 | 55 | 60 | 85 | 50 | 40 | 20 |
| Ragweed | 65 | 35 | 0 | 20 | 20 | 0 | 0 | 0 | 55 | 0 | 10 | 35 |
| Ryegrass, Italian | 0 | 5 | 0 | 0 | 0 | 0 | 5 | 0 | 0 | 0 | 0 | 0 |
| Soybean | 0 | 0 | 55 | 10 | 0 | 0 | 5 | 0 | 5 | 0 | 10 | 0 |
| Surinam Grass | — | — | — | — | — | — | — | — | — | — | — | — |
| Velvetleaf | 10 | 0 | 0 | 10 | 0 | 0 | 15 | 40 | 10 | 5 | 0 | 0 |
| Waterhemp | 0 | 5 | 0 | 20 | 20 | 35 | 65 | 10 | 65 | 5 | 10 | 45 |
| Wheat | 0 | 0 | 0 | 0 | 0 | 0 | 0 | 0 | 0 | 0 | 0 | 0 |
| Windgrass | — | — | — | — | — | — | — | — | — | — | — | — |

| | 62 g ai/ha Compounds | | | | | | | 31 g ai/ha Compounds | | | | |
|---|---|---|---|---|---|---|---|---|---|---|---|---|
| | 315 | 316 | 317 | 323 | 324 | 325 | 346 | 17 | 34 | 48 | 50 | 52 |
| Barley | — | — | — | — | — | — | — | 0 | 0 | 0 | 0 | 0 |
| Barnyardgrass | 65 | 35 | 0 | 10 | 35 | 25 | 0 | — | — | — | — | — |
| Bermudagrass | — | — | — | — | — | — | — | 0 | 0 | 0 | 0 | 0 |
| Blackgrass | 0 | 0 | 0 | 0 | 0 | 0 | 0 | 0 | 0 | 0 | 0 | 0 |
| Bromegrass, Downy | — | — | — | — | — | — | — | 0 | 0 | 0 | 0 | 0 |
| Canarygrass | | | | | | | — | 0 | 0 | 0 | 0 | 0 |
| Chickweed | — | — | — | — | — | — | 65 | 0 | 0 | 0 | 0 | 0 |
| Cocklebur | — | — | — | — | — | — | — | 0 | 0 | 5 | 5 | 5 |
| Corn | 0 | 0 | 0 | 0 | 0 | 0 | 0 | 0 | 0 | 5 | 0 | 0 |
| Crabgrass, Large | 65 | 50 | 25 | 40 | 60 | 65 | 25 | 0 | 0 | 40 | 10 | 50 |
| Cupgrass, Woolly | — | — | — | — | — | — | — | 0 | 0 | 0 | 0 | 0 |
| Deadnettle | — | — | — | — | — | — | — | 0 | 0 | — | — | — |
| Foxtail, Giant | 40 | 5 | 0 | 0 | 10 | 35 | 0 | 0 | 0 | 5 | 0 | 0 |
| Foxtail, Green | — | — | — | — | — | — | — | 0 | 0 | 0 | 0 | 0 |
| Galium | — | — | — | — | — | — | 25 | 0 | 0 | — | — | — |
| Goosegrass | — | — | — | — | — | — | — | 0 | 10 | 10 | 25 | 0 |
| Johnsongrass | 0 | 0 | 0 | 0 | 0 | 0 | 0 | 0 | 0 | 0 | 0 | 0 |
| Kochia | — | — | — | — | — | — | 50 | 0 | 5 | 10 | 0 | 30 |
| Lambsquarters | 60 | 65 | 0 | 10 | 55 | 45 | 5 | 0 | 0 | 10 | 5 | — |
| Morningglory | 65 | 0 | 0 | 25 | 5 | 5 | 5 | 0 | 0 | 10 | 0 | 5 |
| Nutsedge, Yellow | 0 | 0 | 0 | 0 | 0 | 0 | 0 | 0 | 5 | 0 | 0 | 10 |
| Oat, Wild | 0 | 0 | 0 | 0 | 0 | 0 | 0 | 0 | 0 | 0 | 0 | 0 |
| Oilseed Rape | 0 | 0 | 0 | 0 | 0 | 0 | 0 | | | | | |
| Pigweed | 65 | 50 | 5 | 5 | 35 | 55 | 5 | 0 | 0 | 25 | 10 | 25 |
| Ragweed | 20 | 0 | 0 | 0 | 20 | 10 | 0 | 0 | 5 | 5 | 0 | 10 |
| Ryegrass, Italian | 5 | 0 | 0 | 0 | 0 | 0 | 0 | 0 | 0 | 0 | 0 | 0 |
| Soybean | 0 | 0 | 0 | 0 | 5 | 0 | 5 | 0 | 0 | 10 | 10 | 0 |
| Surinam Grass | — | — | — | — | — | — | — | 0 | 0 | 5 | 5 | 0 |
| Velvetleaf | 25 | 0 | 0 | 20 | 55 | 15 | 0 | 0 | 5 | 0 | 0 | 10 |
| Waterhemp | 60 | 10 | 0 | 0 | 10 | 0 | 0 | — | — | — | — | — |
| Wheat | 0 | 0 | 0 | 0 | 0 | 0 | 0 | 0 | 0 | 0 | 0 | 0 |
| Windgrass | — | — | — | — | — | — | — | 0 | 0 | 0 | 0 | 0 |

TABLE C-continued

| | 31 g ai/ha Compounds | | | | | | | | | | | |
|---|---|---|---|---|---|---|---|---|---|---|---|---|
| | 60 | 76 | 79 | 80 | 81 | 101 | 103 | 106 | 109 | 119 | 120 | 202 |
| Barley | 0 | — | — | — | 0 | — | — | — | — | — | — | — |
| Barnyardgrass | — | 0 | 0 | 0 | — | 0 | 0 | 0 | 0 | 25 | 0 | 25 |
| Bermudagrass | 0 | — | — | — | 0 | — | — | — | — | — | — | — |
| Blackgrass | 0 | 0 | 0 | 0 | 0 | 0 | 0 | 0 | 0 | 0 | 0 | 0 |
| Bromegrass, Downy | 0 | — | — | — | 0 | — | — | — | — | — | — | — |
| Canarygrass | 0 | — | — | — | 0 | — | — | — | — | — | — | — |
| Chickweed | 0 | 40 | 60 | 70 | 0 | 35 | 0 | 0 | 0 | — | — | 80 |
| Cocklebur | 0 | — | — | — | 0 | — | — | — | — | — | — | — |
| Corn | 0 | 0 | 0 | 0 | 0 | 0 | 0 | 0 | 0 | 0 | 0 | 0 |
| Crabgrass, Large | 20 | 0 | 5 | 5 | 0 | 25 | 0 | 10 | 10 | 55 | 55 | 30 |
| Cupgrass, Woolly | 0 | — | — | — | 0 | — | — | — | — | — | — | — |
| Deadnettle | — | — | — | — | — | — | — | — | — | — | — | — |
| Foxtail, Giant | 0 | 0 | 15 | 0 | 0 | 0 | 0 | 50 | 60 | 10 | 25 | 5 |
| Foxtail, Green | 20 | — | — | — | 5 | — | — | — | — | — | — | — |
| Galium | — | 30 | 30 | 5 | — | 50 | 0 | 0 | 0 | — | — | 80 |
| Goosegrass | 0 | — | — | — | 0 | — | — | — | — | — | — | — |
| Johnsongrass | 5 | 0 | 0 | 5 | 0 | 0 | 0 | 0 | 0 | 0 | 0 | 0 |
| Kochia | 0 | 40 | 5 | 30 | 0 | 45 | 30 | 0 | 0 | — | — | 70 |
| Lambsquarters | 5 | 40 | 25 | 55 | 0 | 10 | 0 | 0 | 0 | 5 | 55 | 70 |
| Morningglory | 5 | 10 | 0 | 0 | 0 | 15 | 20 | 0 | 20 | 0 | 0 | 5 |
| Nutsedge, Yellow | 0 | 0 | 0 | 0 | 0 | 0 | 0 | 0 | 0 | 0 | 0 | 0 |
| Oat, Wild | 0 | 0 | 0 | 0 | 0 | 0 | 0 | 0 | 0 | 0 | 0 | 0 |
| Oilseed Rape | — | 0 | 0 | 0 | — | 5 | 0 | 0 | 0 | 0 | 0 | 0 |
| Pigweed | — | 5 | 35 | 40 | 0 | 0 | 0 | 0 | 5 | 10 | 5 | 80 |
| Ragweed | 10 | 25 | 20 | 30 | 0 | 0 | 0 | 25 | 0 | 20 | 20 | 70 |
| Ryegrass, Italian | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 5 | 0 | 0 |
| Surinam Grass | 0 | — | — | — | 0 | — | — | — | — | — | — | — |
| Velvetleaf | 0 | 0 | 0 | 15 | 0 | 0 | 0 | 0 | 0 | 0 | 25 | 10 |
| Waterhemp | — | 0 | 10 | 30 | — | 0 | 0 | 0 | 0 | 0 | 0 | 60 |
| Wheat | 0 | 0 | 0 | 0 | 0 | 0 | 0 | 0 | 0 | 0 | 0 | 0 |
| Windgrass | 0 | — | — | — | 0 | — | — | — | — | — | — | — |

| | 31 g ai/ha Compounds | | | | | | | | | | | |
|---|---|---|---|---|---|---|---|---|---|---|---|---|
| | 204 | 206 | 207 | 223 | 224 | 232 | 244 | 271 | 275 | 277 | 278 | 279 |
| Barley | — | — | — | — | — | — | — | — | — | — | — | — |
| Barnyardgrass | 5 | 25 | 0 | 0 | 0 | 5 | 0 | 0 | 30 | 15 | 0 | 15 |
| Bermudagrass | — | — | — | — | — | — | — | — | — | — | — | — |
| Blackgrass | 0 | 0 | 0 | 0 | 0 | 0 | 0 | 0 | 0 | 0 | 0 | 0 |
| Bromegrass, Downy | — | — | — | — | — | — | — | — | — | — | — | — |
| Canarygrass | — | — | — | — | — | — | — | — | — | — | — | — |
| Chickweed | 0 | 85 | 30 | 40 | 70 | 70 | 45 | 5 | 50 | 40 | 0 | 5 |
| Cocklebur | — | — | — | — | — | — | — | — | — | — | — | — |
| Corn | 0 | 0 | 0 | 0 | 0 | 0 | 0 | 0 | 0 | 0 | 0 | 0 |
| Crabgrass, Large | 0 | 45 | 10 | 0 | 0 | 25 | 5 | 5 | 15 | 15 | 0 | 25 |
| Cupgrass, Woolly | — | — | — | — | — | — | — | — | — | — | — | — |
| Deadnettle | — | — | — | — | — | — | — | — | — | — | — | — |
| Foxtail, Giant | 0 | 0 | 20 | 0 | 0 | 0 | 0 | 0 | 10 | 10 | 10 | 0 |
| Foxtail, Green | — | — | — | — | — | — | — | — | — | — | — | — |
| Galium | 10 | 60 | 0 | 5 | 5 | 75 | 30 | 30 | 50 | 45 | 0 | 0 |
| Goosegrass | — | — | — | — | — | — | — | — | — | — | — | — |
| Johnsongrass | 0 | 0 | 0 | 0 | 0 | 0 | 0 | 10 | 0 | 0 | 0 | 0 |
| Kochia | 10 | 50 | 0 | 0 | 0 | 60 | 0 | 0 | 70 | 0 | 0 | 0 |
| Lambsquarters | 35 | 50 | 0 | 0 | 5 | 80 | 10 | 50 | 10 | 30 | 0 | 0 |
| Morningglory | 5 | 20 | 5 | 0 | 5 | 15 | 0 | 10 | 10 | 30 | 0 | 5 |
| Nutsedge, Yellow | 0 | 0 | 10 | 0 | 0 | 0 | 0 | 0 | 0 | 10 | 0 | 0 |
| Oat, Wild | 0 | 0 | 0 | 0 | 0 | 0 | 0 | 0 | 0 | 0 | 0 | 0 |
| Oilseed Rape | 0 | 0 | 0 | 0 | 0 | 0 | 0 | 0 | 5 | 0 | 0 | 0 |
| Pigweed | 20 | 30 | 0 | 5 | 40 | 80 | 5 | 10 | 5 | 10 | 0 | 30 |
| Ragweed | 0 | 5 | 0 | 0 | 20 | 75 | 0 | 25 | 20 | 40 | 0 | 15 |
| Ryegrass, Italian | 0 | 0 | 0 | 0 | 0 | 0 | 0 | 0 | 0 | 0 | 0 | 0 |
| Soybean | 0 | 5 | 0 | 10 | 0 | 0 | 5 | 15 | 0 | 0 | 50 | 40 |
| Surinam Grass | — | — | — | — | — | — | — | — | — | — | — | — |
| Velvetleaf | 0 | 0 | 0 | 0 | 0 | 5 | 5 | 5 | 5 | 0 | 0 | 0 |
| Waterhemp | 0 | 0 | 0 | 0 | 25 | 75 | 5 | 0 | 0 | 5 | 0 | 5 |
| Wheat | 0 | 0 | 0 | 0 | 0 | 0 | 0 | 0 | 0 | 0 | 0 | 0 |
| Windgrass | — | — | — | — | — | — | — | — | — | — | — | — |

TABLE C-continued

| | 31 g ai/ha Compounds | | | | | | | | | | | |
|---|---|---|---|---|---|---|---|---|---|---|---|---|
| | 302 | 303 | 304 | 305 | 306 | 309 | 310 | 312 | 315 | 316 | 317 | 323 |
| Barley | — | — | — | — | — | — | — | — | — | — | — | — |
| Barnyardgrass | 0 | 10 | 0 | 20 | 0 | 0 | 5 | 40 | 25 | 10 | 0 | 0 |
| Bermudagrass | — | — | — | — | — | — | — | — | — | — | — | — |
| Blackgrass | 0 | 0 | 0 | 0 | 0 | 0 | 0 | 0 | 0 | 0 | 0 | 0 |
| Bromegrass, Downy | — | — | — | — | — | — | — | — | — | — | — | — |
| Canarygrass | — | — | — | — | — | — | — | — | — | — | — | — |
| Chickweed | 0 | — | — | — | — | 30 | 20 | — | — | — | — | — |
| Cocklebur | — | — | — | — | — | — | — | — | — | — | — | — |
| Corn | 0 | 0 | 0 | 0 | 0 | 0 | 0 | 0 | 0 | 0 | 0 | 0 |
| Crabgrass, Large | 0 | 0 | 10 | 40 | 10 | 0 | 0 | 25 | 55 | 0 | 0 | 0 |
| Cupgrass, Woolly | — | — | — | — | — | — | — | — | — | — | — | — |
| Deadnettle | — | — | — | — | — | — | — | — | — | — | — | — |
| Foxtail, Giant | 0 | — | 0 | 0 | 5 | 10 | 0 | 55 | 0 | 5 | 0 | 0 |
| Foxtail, Green | — | — | — | — | — | — | — | — | — | — | — | — |
| *Galium* | 10 | — | — | — | — | 30 | 35 | — | — | — | — | — |
| Goosegrass | — | — | — | — | — | — | — | — | — | — | — | — |
| Johnsongrass | 0 | 0 | 0 | 0 | 0 | 0 | 0 | 0 | 0 | 0 | 0 | 0 |
| *Kochia* | 0 | — | — | — | — | 5 | 40 | — | — | — | — | — |
| Lambsquarters | 10 | 35 | 35 | 60 | 60 | 10 | 25 | 65 | 60 | 55 | 0 | 10 |
| Morningglory | 10 | 10 | 50 | 25 | 0 | 60 | 10 | 0 | 25 | 55 | 0 | 0 |
| Nutsedge, Yellow | 0 | 0 | 0 | 0 | 0 | 0 | 0 | 0 | 0 | 0 | 0 | 0 |
| Oat, Wild | 0 | 0 | 0 | 0 | 0 | 0 | 0 | 0 | 0 | 0 | 0 | 0 |
| Oilseed Rape | 0 | 0 | 0 | 0 | 0 | 35 | 0 | 0 | 0 | 0 | 0 | 0 |
| Pigweed | 15 | 0 | 35 | 55 | 75 | 30 | 35 | 10 | 25 | 15 | 5 | 0 |
| Ragweed | 10 | 0 | 0 | 0 | 60 | 0 | 10 | 40 | 0 | 45 | 0 | 0 |
| Ryegrass, Italian | 0 | 0 | 0 | 0 | 0 | 0 | 0 | 0 | 0 | 0 | 0 | 0 |
| Soybean | 0 | 0 | 0 | 10 | 0 | 0 | 10 | 0 | 0 | 0 | 0 | 0 |
| Surinam Grass | — | — | — | — | — | — | — | — | — | — | — | — |
| Velvetleaf | 0 | 35 | 5 | 10 | 0 | 5 | 35 | 30 | 10 | 0 | 0 | 0 |
| Waterhemp | 10 | 0 | 50 | 10 | 65 | 0 | 5 | 0 | 50 | 10 | 0 | 0 |
| Wheat | 0 | 0 | 0 | 0 | 0 | 0 | 0 | 0 | 0 | 0 | 0 | 0 |
| Windgrass | — | — | — | — | — | — | — | — | — | — | — | — |

| | 31 g ai/ha Compounds | | | 16 g ai/ha Compounds | | | | 8 g ai/ha Compound |
|---|---|---|---|---|---|---|---|---|
| | 324 | 325 | 346 | 48 | 271 | 277 | 304 | 271 |
| Barley | — | — | — | 0 | — | — | — | |
| Barnyardgrass | 0 | 10 | 0 | — | 0 | 5 | 0 | 0 |
| Bermudagrass | — | — | — | 0 | — | — | — | |
| Blackgrass | 0 | 0 | 0 | 0 | 0 | 0 | 0 | 0 |
| Bromegrass, Downy | — | — | — | 0 | — | — | — | |
| Canarygrass | — | — | — | 0 | — | — | — | |
| Chickweed | — | — | 40 | 0 | 5 | 0 | — | 0 |
| Cocklebur | — | — | — | 0 | — | — | — | |
| Corn | 0 | 0 | 0 | 0 | 0 | 0 | 0 | 0 |
| Crabgrass, Large | 25 | 55 | 0 | 20 | 0 | 5 | 10 | 0 |
| Cupgrass, Woolly | — | — | — | 0 | — | — | — | |
| Deadnettle | — | — | — | 0 | 0 | 0 | 0 | |
| Foxtail, Giant | 0 | 0 | 20 | 0 | — | — | — | 0 |
| Foxtail, Green | — | — | — | 0 | — | — | — | |
| *Galium* | — | — | 30 | — | 5 | 40 | — | 0 |
| Goosegrass | — | — | — | 10 | — | — | — | |
| Johnsongrass | 0 | 0 | 100 | 0 | 10 | 0 | 0 | 10 |
| *Kochia* | — | — | 45 | 0 | 0 | 0 | — | 0 |
| Lambsquarters | 0 | 20 | 45 | — | 45 | 25 | 65 | 10 |
| Morningglory | 10 | 5 | 0 | 10 | 0 | 15 | 20 | 0 |
| Nutsedge, Yellow | 0 | 0 | 0 | 0 | 0 | 0 | 0 | 0 |
| Oat, Wild | 0 | 0 | 0 | 0 | 0 | 0 | 0 | 0 |
| Oilseed Rape | 0 | 0 | 0 | — | 0 | 0 | 0 | 0 |
| Pigweed | 0 | 40 | 5 | 10 | 5 | 5 | 25 | 5 |
| Ragweed | 5 | 10 | 0 | 0 | 15 | 10 | 0 | 0 |
| Ryegrass, Italian | 0 | 0 | 0 | 0 | 0 | 0 | 0 | 0 |
| Soybean | 0 | 0 | 0 | 5 | 45 | 0 | 0 | 5 |
| Surinam Grass | — | — | — | 0 | — | — | — | |
| Velvetleaf | 0 | 0 | 0 | 0 | 0 | 0 | 0 | 0 |
| Waterhemp | 0 | 0 | 0 | — | 0 | 5 | 40 | 0 |
| Wheat | 0 | 0 | 0 | 0 | 0 | 0 | 0 | 0 |
| Windgrass | — | — | — | 0 | — | — | — | |

TABLE C-continued

| Preemergence | | | | | | | | | | | | |
|---|---|---|---|---|---|---|---|---|---|---|---|---|
| | 250 g ai/ha Compounds | | | | | | | | | | | |
| | 5 | 14 | 16 | 17 | 33 | 34 | 35 | 52 | 53 | 59 | 62 | 64 |
| Barnyardgrass | — | — | — | — | — | — | — | — | — | — | — | — |
| Bermudagrass | 45 | 95 | 95 | 90 | 98 | 45 | 75 | 65 | 50 | 50 | 60 | 55 |
| Blackgrass | 30 | 0 | — | 95 | 5 | 45 | 50 | 0 | 0 | 60 | 80 | 30 |
| Bromegrass, Downy | 0 | 0 | 35 | 65 | 55 | 30 | 40 | 0 | 0 | 20 | 0 | 50 |
| Cocklebur | 0 | 0 | 0 | 5 | 10 | 0 | 0 | — | 5 | — | 5 | — |
| Corn | 0 | 0 | 10 | 70 | 30 | 10 | 5 | 10 | 20 | 45 | 55 | 60 |
| Crabgrass, Large | 100 | 100 | 100 | 100 | 100 | 100 | 100 | 95 | 90 | 100 | 98 | 95 |
| Cupgrass, Woolly | 95 | 80 | 95 | 95 | 90 | 95 | 90 | 85 | 80 | 80 | 85 | 90 |
| Foxtail, Giant | 100 | 95 | 95 | 100 | 98 | 98 | 98 | 85 | 85 | 90 | 85 | 98 |
| Foxtail, Green | 95 | 95 | 90 | 98 | 100 | 100 | 98 | 90 | 90 | 98 | 90 | 98 |
| *Galium* | 40 | 85 | — | 90 | 90 | 60 | 30 | 90 | 70 | 85 | 90 | 0 |
| Goosegrass | 80 | 55 | 80 | 95 | 85 | 45 | 25 | 80 | 40 | 80 | 80 | 50 |
| Johnsongrass | 0 | 40 | 25 | 75 | 15 | 20 | 45 | 15 | 10 | 5 | 40 | 75 |
| *Kochia* | 0 | 0 | 0 | 80 | 0 | 0 | 10 | 20 | 20 | 40 | 25 | 35 |
| Lambsquarters | 95 | — | — | 100 | 25 | 80 | 20 | 75 | 65 | 35 | 85 | 35 |
| Morningglory | 0 | 0 | 0 | 0 | 0 | 5 | 20 | 0 | 0 | 25 | 20 | 30 |
| Nightshade | 98 | 0 | 0 | 40 | 15 | 0 | 0 | 40 | 70 | 30 | 70 | 5 |
| Nutsedge, Yellow | 0 | 0 | 45 | 0 | 40 | 0 | 0 | 25 | 20 | 35 | 20 | 40 |
| Oat, Wild | 20 | 0 | 15 | 80 | 90 | 85 | 75 | 10 | 0 | 80 | 50 | 70 |
| Oilseed Rape | — | — | — | — | — | — | — | — | — | — | — | — |
| Pigweed | 0 | 0 | 0 | 60 | 20 | 40 | 5 | 70 | 25 | 55 | 95 | 30 |
| Ragweed | 0 | 0 | 0 | 50 | 20 | 15 | 0 | 10 | 15 | 35 | 45 | 30 |
| Russian Thistle | — | 0 | 0 | — | — | 95 | — | — | — | 0 | 85 | 0 |
| Ryegrass, Italian | 0 | 10 | — | 70 | 30 | 45 | 30 | 5 | 0 | 0 | 50 | 0 |
| Soybean | 0 | 0 | 0 | 0 | 5 | 5 | 0 | 15 | 20 | 20 | 35 | 40 |
| Sunflower | 0 | 0 | 0 | 50 | 10 | 0 | 10 | 20 | 20 | 40 | 60 | 25 |
| Surinam Grass | 95 | 95 | 100 | 95 | 95 | 100 | 100 | 80 | 75 | 80 | 85 | 80 |
| Velvetleaf | 0 | 0 | 0 | 10 | 10 | 0 | 20 | 5 | 10 | 25 | 30 | 25 |
| Waterhemp | — | — | — | — | — | — | — | — | — | — | — | — |
| Wheat | 60 | 10 | 45 | 85 | 40 | 80 | 65 | 25 | 0 | 0 | 10 | 15 |

| | 250 g ai/ha Compounds | | | | | | | | | | | |
|---|---|---|---|---|---|---|---|---|---|---|---|---|
| | 66 | 68 | 69 | 76 | 77 | 78 | 79 | 80 | 81 | 101 | 103 | 109 |
| Barnyardgrass | — | — | — | 98 | 95 | 95 | 98 | 95 | — | 95 | 95 | 98 |
| Bermudagrass | 0 | 85 | 55 | — | — | — | — | — | 0 | — | — | — |
| Blackgrass | 20 | 80 | 35 | 80 | 95 | 85 | 85 | 90 | 0 | 90 | 0 | 95 |
| Bromegrass, Downy | 5 | 0 | 0 | — | — | — | — | — | 0 | — | — | — |
| Cocklebur | — | — | 0 | — | — | — | — | — | 0 | — | — | — |
| Corn | 20 | 50 | 30 | 65 | 70 | 60 | 30 | 65 | 0 | 65 | 10 | 75 |
| Crabgrass, Large | 98 | 95 | 95 | 100 | 98 | 98 | 100 | 100 | 95 | 100 | 100 | 100 |
| Cupgrass, Woolly | 85 | 90 | 90 | — | — | — | — | — | 82 | — | — | — |
| Foxtail, Giant | 95 | 95 | 90 | 98 | 100 | 98 | 98 | 98 | 73 | 98 | 98 | 100 |
| Foxtail, Green | 98 | 95 | 95 | — | — | — | — | — | 90 | — | — | — |
| *Galium* | 0 | 90 | 75 | 85 | 90 | 85 | 90 | 90 | 0 | 85 | 80 | 100 |
| Goosegrass | 10 | 85 | 75 | — | — | — | — | — | 0 | — | — | — |
| Johnsongrass | 40 | 75 | 0 | 80 | 90 | 60 | 10 | 55 | 0 | 75 | 40 | 70 |
| *Kochia* | 10 | 35 | 25 | — | — | — | — | — | — | — | — | — |
| Lambsquarters | 0 | 75 | 85 | 35 | 98 | 85 | 90 | 90 | 27 | 90 | 65 | 0 |
| Morningglory | 40 | 15 | 25 | 40 | 0 | 0 | 0 | 20 | 0 | 25 | 0 | 30 |
| Nightshade | 0 | 55 | 0 | — | — | — | — | — | 0 | — | — | — |
| Nutsedge, Yellow | 10 | 10 | 10 | 55 | 0 | 0 | 0 | 10 | 0 | 0 | 0 | 5 |
| Oat, Wild | 5 | 30 | 5 | — | — | — | — | — | 0 | — | — | — |
| Oilseed Rape | — | — | — | 75 | 85 | 75 | 80 | 90 | — | 80 | 5 | 40 |
| Pigweed | 0 | 85 | 25 | 40 | 85 | 40 | 65 | 90 | 0 | 85 | 5 | 20 |
| Ragweed | 25 | 0 | 20 | — | — | — | — | — | 0 | 5 | 0 | 10 |
| Russian Thistle | 0 | — | — | — | — | — | — | — | 0 | — | — | — |
| Ryegrass, Italian | 0 | 5 | 10 | 40 | 45 | 45 | 30 | 45 | 0 | 50 | 0 | 70 |
| Soybean | 20 | 15 | 0 | 0 | 0 | 0 | 0 | 0 | 0 | 10 | 0 | 0 |
| Sunflower | 5 | 15 | 15 | — | — | — | — | — | 0 | — | — | — |
| Surinam Grass | 75 | 85 | 85 | — | — | — | — | — | 90 | — | — | — |
| Velvetleaf | 25 | 25 | 30 | 35 | 40 | 20 | 35 | 50 | 0 | 70 | 0 | 10 |
| Waterhemp | — | — | — | 60 | 85 | 85 | 85 | 90 | — | 85 | 40 | 20 |
| Wheat | 25 | 50 | 5 | 80 | 90 | 90 | 75 | 80 | 0 | 55 | 10 | 85 |

TABLE C-continued

| | 250 g ai/ha Compounds | | | | | | | | | | | |
|---|---|---|---|---|---|---|---|---|---|---|---|---|
| | 119 | 120 | 202 | 204 | 206 | 207 | 211 | 218 | 223 | 224 | 231 | 232 |
| Barnyardgrass | 98 | 98 | 95 | 95 | 95 | 95 | 90 | 95 | 95 | 95 | 95 | 95 |
| Bermudagrass | — | — | — | — | — | — | — | — | — | — | — | — |
| Blackgrass | 85 | 70 | 90 | 90 | 90 | 90 | 90 | 80 | 85 | 85 | 90 | 85 |
| Bromegrass, Downy | — | — | — | — | — | — | — | — | — | — | — | — |
| Cocklebur | — | — | — | — | — | — | — | — | — | — | — | — |
| Corn | 45 | 65 | 85 | 75 | 60 | 30 | 80 | 0 | 45 | 85 | 85 | 75 |
| Crabgrass, Large | 100 | 100 | 98 | 95 | 95 | 95 | 5 | 100 | 100 | 100 | 100 | 90 |
| Cupgrass, Woolly | — | — | — | — | — | — | — | — | — | — | — | — |
| Foxtail, Giant | 98 | 98 | 98 | 95 | 95 | 98 | 95 | 95 | 98 | 98 | 95 | 95 |
| Foxtail, Green | — | — | — | — | — | — | — | — | — | — | — | — |
| *Galium* | 90 | 90 | 90 | 90 | 85 | 90 | 100 | 90 | 90 | 85 | 90 | 90 |
| Goosegrass | — | — | — | — | — | — | — | — | — | — | — | — |
| Johnsongrass | 70 | 65 | 85 | 85 | 85 | 60 | 65 | 40 | 55 | 85 | 60 | 70 |
| *Kochia* | — | — | — | — | — | — | — | — | — | — | — | — |
| Lambsquarters | 85 | 90 | 100 | 100 | 100 | 70 | 100 | 85 | 90 | 95 | 100 | 90 |
| Morningglory | 35 | 40 | 40 | 40 | 10 | 0 | 0 | 20 | 20 | 30 | 20 | 20 |
| Nightshade | — | — | — | — | — | — | — | — | — | — | — | — |
| Nutsedge, Yellow | 0 | 0 | 0 | 0 | 0 | 0 | 10 | 0 | 0 | 0 | 0 | 100 |
| Oat, Wild | — | — | — | — | — | — | — | — | — | — | — | — |
| Oilseed Rape | 80 | 90 | 90 | 60 | 90 | 80 | 90 | 70 | 5 | 85 | 90 | 85 |
| Pigweed | 85 | 80 | 100 | 75 | 85 | 0 | 70 | 85 | 30 | 85 | 90 | 95 |
| Ragweed | 80 | 80 | 100 | 65 | 98 | 5 | 100 | 85 | 25 | 100 | 85 | 90 |
| Russian Thistle | — | — | — | — | — | — | — | — | — | — | — | — |
| Ryegrass, Italian | 40 | 30 | 5 | 30 | 20 | 0 | 50 | 50 | 15 | 15 | 15 | 40 |
| Soybean | 0 | 0 | 10 | 10 | 0 | 0 | 0 | 20 | 15 | 5 | 5 | 5 |
| Sunflower | — | — | — | — | — | — | — | — | — | — | — | — |
| Surinam Grass | — | — | — | — | — | — | — | — | — | — | — | — |
| Velvetleaf | 50 | 40 | 65 | 30 | 60 | 0 | 35 | 40 | 35 | 40 | 60 | 75 |
| Waterhemp | 80 | 85 | 100 | 90 | 100 | 75 | 90 | 90 | 25 | 80 | 95 | 95 |
| Wheat | 90 | 85 | 60 | 90 | 70 | 45 | 45 | 10 | 35 | 45 | 80 | 5 |

| | 250 g ai/ha Compounds | | | | | | | | | | | |
|---|---|---|---|---|---|---|---|---|---|---|---|---|
| | 233 | 241 | 246 | 247 | 262 | 263 | 274 | 275 | 278 | 279 | 280 | 302 |
| Barnyardgrass | 90 | 95 | 90 | 90 | 95 | 98 | 90 | 98 | 100 | 98 | 95 | 100 |
| Bermudagrass | — | — | — | — | — | — | — | — | — | — | — | — |
| Blackgrass | 90 | 85 | 70 | 70 | 0 | 70 | 90 | 80 | 0 | 85 | 0 | 85 |
| Bromegrass, Downy | — | — | — | — | — | — | — | — | — | — | — | — |
| Cocklebur | — | — | — | — | — | — | — | — | — | — | — | — |
| Corn | 35 | 90 | 0 | 60 | 10 | 10 | 45 | 75 | 5 | 65 | 5 | 50 |
| Crabgrass, Large | 90 | 100 | 98 | 100 | 100 | 100 | 100 | 100 | 100 | 100 | 100 | 100 |
| Cupgrass, Woolly | — | — | — | — | — | — | — | — | — | — | — | — |
| Foxtail, Giant | 95 | 95 | 95 | 100 | 95 | 98 | 95 | 100 | 100 | 98 | 95 | 100 |
| Foxtail, Green | — | — | — | — | — | — | — | — | — | — | — | — |
| *Galium* | 90 | 85 | 90 | 90 | 85 | 90 | — | 85 | 5 | 85 | 85 | 85 |
| Goosegrass | — | — | — | — | — | — | — | — | — | — | — | — |
| Johnsongrass | 45 | 90 | 5 | 5 | 0 | 0 | 30 | 85 | 0 | 80 | 10 | 65 |
| *Kochia* | — | — | — | — | — | — | — | — | — | — | — | — |
| Lambsquarters | 90 | 100 | 90 | 80 | 100 | 80 | 0 | 98 | 0 | 90 | 10 | 65 |
| Morningglory | 20 | 30 | 5 | 20 | 10 | 10 | 0 | 50 | 0 | 10 | 30 | 0 |
| Nightshade | — | — | — | — | — | — | — | — | — | — | — | — |
| Nutsedge, Yellow | 0 | 0 | 0 | 0 | 0 | 0 | 0 | 100 | 5 | 55 | 100 | 10 |
| Oat, Wild | — | — | — | — | — | — | — | — | — | — | — | — |
| Oilseed Rape | 85 | 85 | 30 | 80 | 70 | 90 | 30 | 90 | 5 | 60 | 0 | 10 |
| Pigweed | 70 | 70 | 100 | 90 | 5 | 95 | 0 | 40 | 0 | 75 | 20 | 0 |
| Ragweed | 85 | 70 | 40 | 98 | 75 | 100 | 0 | 85 | 0 | 65 | 60 | 10 |
| Russian Thistle | — | — | — | — | — | — | — | — | — | — | — | — |
| Ryegrass, Italian | 40 | 55 | 10 | 50 | 0 | 35 | 30 | 60 | 0 | 60 | 5 | 40 |
| Soybean | 0 | 0 | 10 | 0 | 0 | 0 | 0 | 15 | 10 | 10 | 0 | 0 |
| Sunflower | — | — | — | — | — | — | — | — | — | — | — | — |
| Surinam Grass | — | — | — | — | — | — | — | — | — | — | — | — |
| Velvetleaf | 45 | 40 | 0 | 25 | 0 | 5 | 20 | 30 | 0 | 30 | 10 | 0 |
| Waterhemp | 95 | 60 | 90 | 85 | 50 | 100 | 0 | 60 | 0 | 80 | 35 | 55 |
| Wheat | 0 | 80 | 30 | 0 | 0 | 50 | 40 | 90 | 0 | 30 | 0 | 30 |

| | 250 g ai/ha Compounds | | | | | | | | | | | |
|---|---|---|---|---|---|---|---|---|---|---|---|---|
| | 303 | 305 | 306 | 307 | 309 | 310 | 312 | 315 | 316 | 317 | 318 | 319 |
| Barnyardgrass | 98 | 98 | 95 | 95 | 95 | 95 | 95 | 95 | 90 | 95 | 95 | 98 |
| Bermudagrass | — | — | — | — | — | — | — | — | — | — | — | — |
| Blackgrass | 90 | 90 | 90 | 5 | 45 | 45 | 75 | 85 | 60 | 50 | 45 | 80 |

TABLE C-continued

| | | | | | | | | | | | | |
|---|---|---|---|---|---|---|---|---|---|---|---|---|
| Bromegrass, Downy | — | — | — | — | — | — | — | — | — | — | — | — |
| Cocklebur | — | — | — | — | — | — | — | — | — | — | — | — |
| Corn | 45 | 80 | 75 | 40 | 70 | 55 | 70 | 85 | 75 | 30 | 60 | 65 |
| Crabgrass, Large | 100 | 95 | 98 | 100 | 98 | 95 | 95 | 98 | 98 | 98 | 100 | 98 |
| Cupgrass, Woolly | — | — | — | — | — | — | — | — | — | — | — | — |
| Foxtail, Giant | 100 | 95 | 100 | 95 | 95 | 90 | 95 | 98 | 95 | 95 | 90 | 95 |
| Foxtail, Green | — | — | — | — | — | — | — | — | — | — | — | — |
| *Galium* | 85 | 90 | 90 | 85 | 85 | 70 | 80 | 90 | 90 | 0 | 100 | 85 |
| Goosegrass | — | — | — | — | — | — | — | — | — | — | — | — |
| Johnsongrass | 80 | 90 | 85 | 45 | 80 | 75 | 85 | 90 | 85 | 30 | 60 | 75 |
| *Kochia* | — | — | — | — | — | — | — | — | — | — | — | — |
| Lambsquarters | 80 | 75 | 80 | 85 | 50 | 80 | 60 | 80 | 65 | 10 | 60 | 75 |
| Morningglory | 45 | 65 | 35 | 0 | 10 | 5 | 55 | 45 | 35 | 0 | 40 | 40 |
| Nightshade | — | — | — | — | — | — | — | — | — | — | — | — |
| Nutsedge, Yellow | 25 | 100 | 10 | 0 | 0 | 0 | 0 | 20 | 70 | 70 | 0 | 30 |
| Oat, Wild | — | — | — | — | — | — | — | — | — | — | — | — |
| Oilseed Rape | 85 | 90 | 75 | 5 | 70 | 85 | 30 | 80 | 60 | 0 | 5 | 65 |
| Pigweed | 80 | 85 | 90 | 35 | 40 | 20 | 55 | 85 | 65 | 0 | 50 | 40 |
| Ragweed | 80 | 75 | 80 | 35 | 65 | 35 | 10 | 80 | 35 | 0 | 20 | 85 |
| Russian Thistle | — | — | — | — | — | — | — | — | — | — | — | — |
| Ryegrass, Italian | 75 | 80 | 70 | 10 | 10 | 25 | 30 | 50 | 0 | 10 | 50 | 50 |
| Soybean | 20 | 0 | 0 | 0 | 0 | 0 | 0 | 0 | 0 | 10 | 0 | 0 |
| Sunflower | — | — | — | — | — | — | — | — | — | — | — | — |
| Surinam Grass | — | — | — | — | — | — | — | — | — | — | — | — |
| Velvetleaf | 55 | 55 | 65 | 0 | 15 | 35 | 40 | 50 | 30 | 5 | 35 | 65 |
| Waterhemp | 75 | 80 | 90 | 0 | 40 | 25 | 80 | 85 | 45 | 30 | 70 | 40 |
| Wheat | 90 | 90 | 85 | 15 | 0 | 10 | 65 | 90 | 45 | 35 | 5 | 35 |

| | 250 g ai/ha Compounds | | | | | | 125 g ai/ha Compounds | | | | | |
|---|---|---|---|---|---|---|---|---|---|---|---|---|
| | 323 | 324 | 325 | 345 | 346 | 350 | 5 | 14 | 16 | 17 | 33 | 34 |
| Barnyardgrass | 98 | 98 | 95 | 95 | 98 | 90 | — | — | — | — | — | — |
| Bermudagrass | — | — | — | — | — | — | 20 | 95 | 90 | 85 | 70 | 0 |
| Blackgrass | 85 | 95 | 85 | 90 | 85 | 55 | 0 | 0 | 10 | 80 | 0 | 10 |
| Bromegrass, Downy | — | — | — | — | — | — | 0 | 0 | 30 | 45 | 0 | 10 |
| Cocklebur | — | — | — | — | — | — | 0 | 0 | 0 | 5 | 10 | 0 |
| Corn | 75 | 85 | 85 | 85 | 5 | 40 | 0 | 0 | 5 | 30 | 20 | 0 |
| Crabgrass, Large | 100 | 98 | 100 | 98 | 100 | 90 | 100 | 98 | 100 | 100 | 100 | 100 |
| Cupgrass, Woolly | — | — | — | — | — | — | 90 | 0 | 95 | 90 | 90 | 95 |
| Foxtail, Giant | 98 | 95 | 95 | 98 | 98 | 90 | 100 | 90 | 90 | 100 | 98 | 98 |
| Foxtail, Green | — | — | — | — | — | — | 90 | 90 | 80 | 98 | 100 | 98 |
| *Galium* | 85 | 85 | 80 | 85 | 90 | 90 | — | 70 | — | 70 | 60 | 5 |
| Goosegrass | — | — | — | — | — | — | 0 | 0 | 0 | 85 | 40 | 10 |
| Johnsongrass | 60 | 85 | 75 | 90 | 60 | 30 | 0 | 0 | 0 | 65 | 0 | 10 |
| *Kochia* | — | — | — | — | — | — | 0 | 0 | 0 | 60 | 0 | 0 |
| Lambsquarters | 95 | 85 | 80 | 85 | 100 | 90 | 95 | — | — | 60 | 25 | 80 |
| Morningglory | 30 | 55 | 40 | 35 | 0 | 100 | 0 | 0 | 0 | — | 0 | 5 |
| Nightshade | — | — | — | — | — | — | 45 | 0 | 0 | 40 | 0 | 0 |
| Nutsedge, Yellow | 75 | 35 | 0 | 0 | 0 | 0 | 0 | 0 | 0 | 0 | — | 0 |
| Oat, Wild | — | — | — | — | — | — | 0 | 0 | 15 | 0 | 20 | 60 |
| Oilseed Rape | 85 | 90 | 90 | 85 | 60 | 85 | — | — | — | — | — | — |
| Pigweed | 65 | 85 | 85 | 60 | 70 | 90 | 0 | 0 | 0 | 50 | 0 | 0 |
| Ragweed | 80 | 85 | 85 | 70 | 70 | 80 | 0 | 0 | 0 | 30 | 0 | 0 |
| Russian Thistle | — | — | — | — | — | — | — | 0 | 0 | — | — | 0 |
| Ryegrass, Italian | 70 | 60 | 50 | 55 | 70 | 35 | 0 | 0 | — | 35 | 0 | 20 |
| Soybean | 0 | 0 | 0 | 0 | 10 | 0 | 0 | 0 | 0 | 0 | 0 | 5 |
| Sunflower | — | — | — | — | — | — | 0 | 0 | 0 | 20 | — | 0 |
| Surinam Grass | — | — | — | — | — | — | 95 | 95 | 98 | 90 | 95 | 100 |
| Velvetleaf | 45 | 50 | 65 | 40 | 25 | 5 | 0 | 0 | 0 | 0 | 10 | 0 |
| Waterhemp | 75 | 90 | 85 | 45 | 40 | 90 | — | — | — | — | — | — |
| Wheat | 80 | 85 | 70 | 80 | 40 | 15 | 5 | 10 | 0 | 0 | 35 | 35 |

| | 125 g ai/ha Compounds | | | | | | | | | | | |
|---|---|---|---|---|---|---|---|---|---|---|---|---|
| | 35 | 48 | 52 | 53 | 59 | 60 | 62 | 64 | 66 | 68 | 69 | 76 |
| Barnyardgrass | — | — | — | — | — | — | — | — | — | — | — | 95 |
| Bermudagrass | 0 | 0 | 40 | 50 | 40 | 0 | 50 | 25 | 0 | 85 | 50 | — |
| Blackgrass | 5 | 50 | 0 | 0 | 30 | 40 | 80 | 5 | 0 | 60 | 30 | 80 |
| Bromegrass, Downy | 5 | 0 | 0 | 0 | 0 | 0 | 0 | 0 | 0 | 0 | 0 | — |
| Cocklebur | 0 | 5 | 0 | 5 | — | 0 | 0 | — | — | — | — | — |
| Corn | 5 | 20 | 10 | 20 | 10 | 20 | 30 | 55 | 10 | 25 | 25 | 40 |
| Crabgrass, Large | 100 | 95 | 90 | 90 | 90 | 95 | 95 | 95 | 98 | 95 | 95 | 100 |
| Cupgrass, Woolly | 85 | 85 | 75 | 80 | 80 | 75 | 80 | 85 | 80 | 85 | 85 | — |
| Foxtail, Giant | 98 | 95 | 80 | 65 | 85 | 90 | 85 | 90 | 85 | 90 | 85 | 95 |
| Foxtail, Green | 98 | 90 | 90 | 90 | 90 | 90 | 90 | 90 | 90 | 95 | 95 | — |
| *Galium* | 5 | 60 | 90 | 0 | 30 | 5 | 85 | 0 | 0 | 90 | 5 | — |

TABLE C-continued

| | | | | | | | | | | | | |
|---|---|---|---|---|---|---|---|---|---|---|---|---|
| Goosegrass | 5 | 15 | 60 | 30 | 35 | 0 | 70 | 25 | 10 | 80 | 40 | — |
| Johnsongrass | 0 | 20 | 10 | 0 | 0 | 20 | 30 | 75 | — | 40 | 0 | 45 |
| Kochia | 5 | 10 | 15 | 0 | 10 | 0 | 15 | 20 | 10 | 0 | 0 | — |
| Lambsquarters | 0 | 65 | 70 | 40 | 0 | 10 | 70 | 30 | 0 | 65 | 65 | 0 |
| Morningglory | 10 | 15 | 0 | 0 | 15 | 10 | 15 | 20 | 35 | 15 | 25 | 40 |
| Nightshade | 0 | 0 | 0 | 40 | 25 | 0 | — | 0 | 0 | 55 | 0 | — |
| Nutsedge, Yellow | 0 | 20 | 25 | — | 0 | 15 | 20 | 20 | 0 | 10 | 0 | 20 |
| Oat, Wild | 0 | 10 | 0 | 0 | 0 | 5 | 50 | 10 | 0 | 0 | 5 | — |
| Oilseed Rape | — | — | — | — | — | — | — | — | — | — | — | 30 |
| Pigweed | 0 | 0 | 55 | 25 | — | 20 | 70 | 30 | 0 | 85 | 25 | 0 |
| Ragweed | 0 | 10 | 0 | 10 | 0 | 25 | 45 | 30 | 25 | 0 | 0 | — |
| Russian Thistle | — | — | — | — | 0 | 60 | 85 | 0 | 0 | — | — | — |
| Ryegrass, Italian | 5 | 0 | 0 | 0 | 0 | 0 | 30 | 0 | 0 | 0 | 0 | 40 |
| Soybean | 0 | 15 | 15 | 15 | 20 | 25 | 35 | 40 | 20 | 10 | 0 | 0 |
| Sunflower | 10 | 0 | 0 | 20 | 15 | 0 | 25 | 0 | 0 | 10 | 10 | — |
| Surinam Grass | 100 | 85 | 45 | 75 | 60 | 70 | 80 | 65 | 75 | 75 | 85 | — |
| Velvetleaf | 20 | 0 | 5 | 0 | 0 | 0 | 25 | 10 | 25 | 10 | 30 | 25 |
| Waterhemp | — | — | — | — | — | — | — | — | — | — | — | 50 |
| Wheat | 10 | 45 | 10 | 0 | 0 | 0 | 0 | 15 | 5 | 30 | 5 | 70 |

| | 125 g ai/ha Compounds | | | | | | | | | | | |
|---|---|---|---|---|---|---|---|---|---|---|---|---|
| | 77 | 78 | 79 | 80 | 81 | 101 | 103 | 109 | 119 | 120 | 189 | 202 |
| Barnyardgrass | 95 | 85 | 95 | 95 | — | 95 | 95 | 95 | 95 | 95 | 90 | 95 |
| Bermudagrass | — | — | — | — | 0 | — | — | — | — | — | — | — |
| Blackgrass | 85 | 75 | 85 | 85 | 0 | 70 | 30 | 90 | 80 | 50 | 55 | 90 |
| Bromegrass, Downy | — | — | — | — | 0 | — | — | — | — | — | — | — |
| Cocklebur | — | — | — | — | 0 | — | — | — | — | — | — | — |
| Corn | 55 | 40 | 10 | 0 | 0 | 5 | 0 | 60 | 15 | 20 | 40 | 75 |
| Crabgrass, Large | 98 | 98 | 100 | 98 | 90 | 98 | 100 | 100 | 100 | 100 | 98 | 98 |
| Cupgrass, Woolly | — | — | — | — | 67 | — | — | — | — | — | — | — |
| Foxtail, Giant | 95 | 95 | 95 | 98 | 37 | 98 | 95 | 98 | 98 | 98 | 95 | 95 |
| Foxtail, Green | — | — | — | — | 80 | — | — | — | — | — | — | — |
| Galium | 80 | 60 | 85 | 90 | 0 | 90 | 40 | 50 | 85 | 50 | 80 | 90 |
| Goosegrass | — | — | — | — | 0 | — | — | — | — | — | — | — |
| Johnsongrass | 75 | 15 | 10 | 30 | 0 | 55 | 15 | 40 | 30 | 25 | 15 | 70 |
| Kochia | — | — | — | — | — | — | — | — | — | — | — | — |
| Lambsquarters | 85 | 85 | 90 | 90 | 0 | 90 | 55 | 5 | 85 | 85 | 5 | 90 |
| Morningglory | 0 | 0 | 0 | 20 | 0 | 30 | 0 | 5 | 35 | 35 | 0 | 25 |
| Nightshade | — | — | — | — | 0 | — | — | — | — | — | — | — |
| Nutsedge, Yellow | 0 | 0 | 0 | 0 | 0 | 0 | 0 | 0 | 0 | 0 | 0 | 0 |
| Oat, Wild | — | — | — | — | 0 | — | — | — | — | — | — | — |
| Oilseed Rape | 60 | 10 | 70 | 90 | — | 80 | 0 | 5 | 80 | 70 | 20 | 85 |
| Pigweed | 60 | 40 | 50 | 90 | 0 | 55 | 0 | 0 | 75 | 65 | 0 | 90 |
| Ragweed | — | — | — | — | 0 | 5 | 40 | 0 | 75 | 55 | 0 | 85 |
| Russian Thistle | — | — | — | — | 0 | — | — | — | — | — | — | — |
| Ryegrass, Italian | 40 | 40 | 30 | 40 | 0 | 30 | 0 | 20 | 30 | 10 | 45 | 30 |
| Soybean | 0 | 0 | 0 | 0 | 0 | 0 | 0 | 55 | 0 | 0 | 0 | 0 |
| Sunflower | — | — | — | — | 0 | — | — | — | — | — | — | — |
| Surinam Grass | — | — | — | — | 77 | — | — | — | — | — | — | — |
| Velvetleaf | 30 | 20 | 20 | 35 | 0 | 5 | 0 | 0 | 40 | 35 | 0 | 50 |
| Waterhemp | 70 | 85 | 80 | 90 | — | 50 | 65 | 0 | 70 | 75 | 0 | 100 |
| Wheat | 80 | 60 | 60 | 80 | 0 | 50 | 0 | 50 | 60 | 30 | 0 | 55 |

| | 125 g ai/ha Compounds | | | | | | | | | | | |
|---|---|---|---|---|---|---|---|---|---|---|---|---|
| | 204 | 206 | 207 | 211 | 218 | 223 | 224 | 231 | 232 | 233 | 241 | 246 |
| Barnyardgrass | 95 | 95 | 85 | 85 | 95 | 90 | 90 | 95 | 95 | 85 | 95 | 75 |
| Bermudagrass | — | — | — | — | — | — | — | — | — | — | — | — |
| Blackgrass | 90 | 90 | 85 | 85 | 50 | 85 | 70 | 85 | 70 | 60 | 80 | 5 |
| Bromegrass, Downy | — | — | — | — | — | — | — | — | — | — | — | — |
| Cocklebur | — | — | — | — | — | — | — | — | — | — | — | — |
| Corn | 55 | 65 | 55 | 0 | 0 | 0 | 85 | 70 | 70 | 10 | 80 | 5 |
| Crabgrass, Large | 100 | 95 | 95 | 95 | 100 | 95 | 90 | 100 | 90 | 90 | 98 | 95 |
| Cupgrass, Woolly | — | — | — | — | — | — | — | — | — | — | — | — |
| Foxtail, Giant | 95 | 95 | 90 | 90 | 90 | 90 | 95 | 98 | 90 | 90 | 95 | 95 |
| Foxtail, Green | — | — | — | — | — | — | — | — | — | — | — | — |
| Galium | 90 | 70 | 85 | 85 | 85 | 90 | 85 | 90 | 90 | 90 | 85 | 90 |
| Goosegrass | — | — | — | — | — | — | — | — | — | — | — | — |
| Johnsongrass | 75 | 85 | 30 | 30 | 15 | 35 | 75 | 45 | 60 | 20 | 85 | 0 |
| Kochia | — | — | — | — | — | — | — | — | — | — | — | — |
| Lambsquarters | 75 | 100 | 60 | 100 | 75 | 85 | 95 | 85 | 90 | 95 | 10 | 80 |
| Morningglory | 20 | 0 | 0 | 0 | 25 | 10 | 5 | 0 | 15 | 20 | 10 | 10 |
| Nightshade | — | — | — | — | — | — | — | — | — | — | — | — |
| Nutsedge, Yellow | 0 | 0 | 0 | 0 | 0 | 0 | 0 | 0 | 0 | 0 | 0 | 100 |
| Oat, Wild | — | — | — | — | — | — | — | — | — | — | — | — |

TABLE C-continued

| | | | | | | | | | | | | |
|---|---|---|---|---|---|---|---|---|---|---|---|---|
| Oilseed Rape | 0 | 75 | 0 | 90 | 20 | 0 | 70 | 85 | 50 | 80 | 70 | 0 |
| Pigweed | 0 | 100 | 0 | 0 | 75 | 20 | 60 | 85 | 85 | 60 | 25 | 75 |
| Ragweed | 100 | 70 | 0 | 85 | 50 | 10 | 100 | 80 | 85 | 40 | 30 | 0 |
| Russian Thistle | — | — | — | — | — | — | — | — | — | — | — | — |
| Ryegrass, Italian | 50 | 45 | 0 | 40 | 0 | 10 | 0 | 15 | 20 | 30 | 30 | 10 |
| Soybean | 5 | 0 | 0 | 5 | 40 | 5 | 0 | 0 | 0 | 5 | 0 | 0 |
| Sunflower | — | — | — | — | — | — | — | — | — | — | — | — |
| Surinam Grass | — | — | — | — | — | — | — | — | — | — | — | — |
| Velvetleaf | 0 | 40 | 0 | 30 | 15 | 25 | 45 | 35 | 65 | 45 | 5 | 0 |
| Waterhemp | 80 | 100 | 85 | 100 | 90 | 0 | 70 | 100 | 90 | 85 | 45 | 90 |
| Wheat | 80 | 70 | 5 | 30 | 0 | 10 | 0 | 20 | 0 | 0 | 90 | 10 |

| | 125 g ai/ha Compounds | | | | | | | | | | | |
|---|---|---|---|---|---|---|---|---|---|---|---|---|
| | 247 | 262 | 263 | 274 | 275 | 277 | 278 | 279 | 280 | 302 | 303 | 304 |
| Barnyardgrass | 90 | 90 | 95 | 85 | 95 | 98 | 95 | 95 | 85 | 100 | 95 | 95 |
| Bermudagrass | — | — | — | — | — | — | — | — | — | — | — | — |
| Blackgrass | 60 | 0 | 40 | 75 | 70 | 90 | 0 | 30 | 0 | 60 | 80 | 70 |
| Bromegrass, Downy | — | — | — | — | — | — | — | — | — | — | — | — |
| Cocklebur | — | — | — | — | — | — | — | — | — | — | — | — |
| Corn | 60 | 10 | 0 | 10 | 75 | 90 | 0 | 5 | 0 | 0 | 35 | 65 |
| Crabgrass, Large | 98 | 100 | 100 | 98 | 100 | 100 | 98 | 98 | 95 | 100 | 98 | 98 |
| Cupgrass, Woolly | — | — | — | — | — | — | — | — | — | — | — | — |
| Foxtail, Giant | 98 | 95 | 98 | 90 | 98 | 98 | 95 | 98 | 90 | 100 | 98 | 95 |
| Foxtail, Green | — | — | — | — | — | — | — | — | — | — | — | — |
| *Galium* | 90 | 60 | 85 | 80 | 30 | 100 | 0 | 85 | 0 | 85 | 85 | 85 |
| Goosegrass | — | — | — | — | — | — | — | — | — | — | — | — |
| Johnsongrass | 10 | 0 | 0 | 0 | 75 | 85 | 0 | 70 | 10 | 45 | 65 | 35 |
| *Kochia* | — | — | — | — | — | — | — | — | — | — | — | — |
| Lambsquarters | 70 | 80 | 70 | — | 85 | 80 | 0 | 65 | 10 | 60 | 65 | 80 |
| Morningglory | 5 | 10 | 20 | 0 | 0 | 45 | 0 | 10 | 0 | 0 | 15 | 40 |
| Nightshade | — | — | — | — | — | — | — | — | — | — | — | — |
| Nutsedge, Yellow | 20 | 0 | 100 | 0 | 35 | 20 | 5 | 0 | 0 | 0 | 0 | 0 |
| Oat, Wild | — | — | — | — | — | — | — | — | — | — | — | — |
| Oilseed Rape | 30 | 35 | 60 | 5 | 90 | 80 | 0 | 30 | 0 | 0 | 80 | 55 |
| Pigweed | 85 | 0 | 98 | 0 | 10 | 40 | 0 | 0 | 20 | 25 | 65 | 85 |
| Ragweed | 70 | 10 | 80 | 0 | 60 | 40 | 0 | 10 | 0 | 5 | 75 | 80 |
| Russian Thistle | — | — | — | — | — | — | — | — | — | — | — | — |
| Ryegrass, Italian | 40 | 0 | 0 | 5 | 50 | 40 | 0 | 30 | 0 | 5 | 70 | 40 |
| Soybean | 0 | 0 | 100 | 5 | 0 | 5 | 10 | 0 | 0 | 0 | 0 | 0 |
| Sunflower | — | — | — | — | — | — | — | — | — | — | — | — |
| Surinam Grass | — | — | — | — | — | — | — | — | — | — | — | — |
| Velvetleaf | 30 | 0 | 20 | 20 | 25 | 35 | 0 | 0 | 0 | 0 | 50 | 50 |
| Waterhemp | 100 | 60 | 90 | — | 15 | 55 | 0 | 55 | 75 | 65 | 65 | 85 |
| Wheat | 5 | 0 | 15 | 0 | 50 | 80 | 0 | 30 | 0 | 15 | 80 | 85 |

| | 125 g ai/ha Compounds | | | | | | | | | | | |
|---|---|---|---|---|---|---|---|---|---|---|---|---|
| | 305 | 306 | 307 | 309 | 310 | 312 | 315 | 316 | 317 | 318 | 319 | 323 |
| Barnyardgrass | 95 | 90 | 85 | 90 | 90 | 90 | 90 | 90 | 95 | 95 | 95 | 98 |
| Bermudagrass | — | — | — | — | — | — | — | — | — | — | — | — |
| Blackgrass | 70 | 60 | 10 | 50 | 50 | 70 | 65 | 30 | 50 | 30 | 30 | 45 |
| Bromegrass, Downy | — | — | — | — | — | — | — | — | — | — | — | — |
| Cocklebur | — | — | — | — | — | — | — | — | — | — | — | — |
| Corn | 75 | 80 | 40 | 65 | 55 | 55 | 80 | 65 | 25 | 10 | 60 | 10 |
| Crabgrass, Large | 90 | 95 | 95 | 95 | 95 | 95 | 95 | 95 | 95 | 98 | 95 | 98 |
| Cupgrass, Woolly | — | — | — | — | — | — | — | — | — | — | — | — |
| Foxtail, Giant | 95 | 95 | 85 | 90 | 90 | 90 | 95 | 90 | 90 | 75 | 95 | 95 |
| Foxtail, Green | — | — | — | — | — | — | — | — | — | — | — | — |
| *Galium* | 90 | 90 | 100 | 75 | 0 | 5 | 80 | 0 | 0 | 40 | 80 | 85 |
| Goosegrass | — | — | — | — | — | — | — | — | — | — | — | — |
| Johnsongrass | 90 | 80 | 0 | 60 | 45 | 80 | 85 | 75 | 0 | 45 | 65 | 45 |
| *Kochia* | — | — | — | — | — | — | — | — | — | — | — | — |
| Lambsquarters | 70 | 75 | 10 | 30 | 55 | 50 | 70 | 65 | 0 | 50 | 65 | 75 |
| Morningglory | 40 | 35 | 0 | 10 | 5 | 40 | 35 | 25 | 0 | 30 | 45 | 0 |
| Nightshade | — | — | — | — | — | — | — | — | — | — | — | — |
| Nutsedge, Yellow | 0 | 0 | 0 | 0 | 0 | 0 | 20 | 0 | 20 | 0 | 0 | 25 |
| Oat, Wild | — | — | — | — | — | — | — | — | — | — | — | — |
| Oilseed Rape | 80 | 75 | 0 | 50 | 40 | 15 | 85 | 20 | 0 | 5 | 60 | 70 |
| Pigweed | 80 | 85 | 40 | 0 | 20 | 45 | 7 | 45 | 0 | 20 | 40 | 55 |
| Ragweed | 35 | 75 | 0 | 25 | 5 | 50 | 50 | 10 | 0 | 0 | 40 | 40 |
| Russian Thistle | — | — | — | — | — | — | — | — | — | — | — | — |
| Ryegrass, Italian | 50 | 55 | 5 | 0 | 20 | 35 | 50 | 10 | 0 | 0 | 20 | 0 |
| Soybean | 0 | 0 | 0 | 0 | 0 | 0 | 0 | 0 | 0 | 0 | 0 | 0 |
| Sunflower | — | — | — | — | — | — | — | — | — | — | — | — |
| Surinam Grass | — | — | — | — | — | — | — | — | — | — | — | — |

TABLE C-continued

| | | | | | | | | | | | | |
|---|---|---|---|---|---|---|---|---|---|---|---|---|
| Velvetleaf | 55 | 60 | 0 | 0 | 5 | 20 | 40 | 10 | 0 | 25 | 45 | 40 |
| Waterhemp | 80 | 85 | 0 | 30 | 25 | 65 | 85 | 35 | 10 | 10 | 35 | 60 |
| Wheat | 90 | 90 | 5 | 0 | 0 | 60 | 90 | 40 | 0 | 5 | 10 | 40 |

| | 125 g ai/ha Compounds | | | | | 62 g ai/ha Compounds | | | | | | |
|---|---|---|---|---|---|---|---|---|---|---|---|---|
| | 324 | 325 | 345 | 346 | 350 | 5 | 14 | 16 | 17 | 33 | 34 | 35 |
| Barnyardgrass | 95 | 95 | 95 | 95 | 90 | — | — | — | — | — | — | — |
| Bermudagrass | — | — | — | — | — | 0 | 90 | 0 | 45 | 0 | 0 | 0 |
| Blackgrass | 70 | 70 | 90 | 75 | 50 | 0 | 0 | 5 | 50 | 0 | 0 | 0 |
| Bromegrass, Downy | — | — | — | — | — | 0 | 0 | 5 | 30 | 0 | 0 | 0 |
| Cocklebur | — | — | — | — | — | 0 | 0 | 0 | 5 | — | 0 | 0 |
| Corn | 75 | 70 | 65 | 0 | 5 | 0 | 0 | 0 | 0 | 10 | 0 | 0 |
| Crabgrass, Large | 98 | 95 | 95 | 98 | 90 | 100 | 98 | 95 | 98 | 98 | 98 | 98 |
| Cupgrass, Woolly | — | — | — | — | — | 85 | 0 | 95 | 85 | 85 | 85 | 80 |
| Foxtail, Giant | 95 | 98 | 95 | 98 | 90 | 100 | 85 | 70 | 95 | 95 | 95 | 90 |
| Foxtail, Green | — | — | — | — | — | 90 | 90 | 35 | 95 | 98 | 98 | 98 |
| *Galium* | 85 | 50 | 90 | 90 | 90 | 5 | 0 | 0 | 70 | 0 | 0 | 0 |
| Goosegrass | — | — | — | — | — | 0 | 0 | 0 | 50 | 5 | 5 | 0 |
| Johnsongrass | 80 | 75 | 85 | 20 | 0 | 0 | 0 | 0 | 5 | 0 | 10 | 0 |
| *Kochia* | — | — | — | — | — | 0 | 0 | 0 | 50 | 0 | 0 | 0 |
| Lambsquarters | 80 | 80 | 85 | 100 | 90 | 95 | — | — | 60 | 0 | 40 | 0 |
| Morningglory | 35 | 30 | 0 | 30 | 100 | 0 | 0 | 0 | 0 | 0 | 0 | 10 |
| Nightshade | — | — | — | — | — | 45 | 0 | 0 | 20 | 0 | 0 | 0 |
| Nutsedge, Yellow | 0 | 0 | 0 | 0 | 0 | 0 | 0 | 0 | 0 | 10 | 0 | 0 |
| Oat, Wild | — | — | — | — | — | 0 | 0 | 5 | 0 | 0 | 0 | 0 |
| Oilseed Rape | 85 | 85 | 85 | 50 | 80 | — | — | — | — | — | — | — |
| Pigweed | 80 | 75 | 65 | 60 | 80 | 0 | 0 | 0 | 0 | 0 | 0 | 0 |
| Ragweed | 75 | 80 | 15 | 35 | 5 | 0 | 0 | 0 | 0 | 0 | 0 | 0 |
| Russian Thistle | — | — | — | — | — | 0 | 0 | 0 | — | — | 0 | 0 |
| Ryegrass, Italian | 35 | 50 | 10 | 5 | 5 | 0 | 0 | 0 | 5 | 0 | 0 | 5 |
| Soybean | 0 | 0 | 5 | 0 | 0 | 0 | 0 | 0 | 0 | — | 0 | 0 |
| Sunflower | — | — | — | — | — | 0 | 0 | 0 | 10 | 10 | 0 | 0 |
| Surinam Grass | — | — | — | — | — | 85 | 80 | 95 | 90 | 80 | 95 | 90 |
| Velvetleaf | 40 | 55 | 25 | 10 | 0 | 0 | 0 | 0 | 0 | 10 | 0 | 20 |
| Waterhemp | 80 | 80 | 40 | 10 | 90 | — | — | — | — | — | — | — |
| Wheat | 65 | 65 | 70 | 0 | 0 | 0 | 10 | 0 | 0 | 0 | 0 | 0 |

| | 62 g ai/ha Compounds | | | | | | | | | | | |
|---|---|---|---|---|---|---|---|---|---|---|---|---|
| | 48 | 52 | 53 | 59 | 60 | 62 | 64 | 66 | 68 | 69 | 76 | 77 |
| Barnyardgrass | — | — | — | — | — | — | — | — | — | — | 85 | 95 |
| Bermudagrass | 0 | 40 | 40 | 20 | 0 | 30 | 0 | 0 | 50 | 35 | — | — |
| Blackgrass | 20 | 0 | 0 | 0 | 10 | 45 | 5 | 0 | 60 | 5 | 50 | 85 |
| Bromegrass, Downy | 0 | 0 | 0 | 0 | 0 | 0 | 0 | 0 | 0 | 0 | — | — |
| Cocklebur | 0 | 0 | — | 0 | 0 | — | 0 | — | — | — | — | — |
| Corn | 20 | 10 | 20 | 10 | 10 | 20 | 0 | 0 | 25 | 15 | 10 | 20 |
| Crabgrass, Large | 90 | 90 | 85 | 85 | 95 | 90 | 90 | 95 | 90 | 90 | 98 | 95 |
| Cupgrass, Woolly | 70 | 70 | 65 | 70 | 75 | 75 | 70 | 75 | 75 | 85 | — | — |
| Foxtail, Giant | 85 | 80 | 65 | 85 | 85 | 80 | 80 | 75 | 90 | 85 | 95 | 90 |
| Foxtail, Green | 90 | 90 | 90 | 90 | 90 | 90 | 85 | 80 | 90 | 90 | — | — |
| *Galium* | 30 | 0 | 0 | 5 | 0 | 0 | 0 | 0 | 5 | 0 | — | 5 |
| Goosegrass | 10 | 20 | 10 | 25 | 0 | 25 | 20 | 5 | 75 | 40 | — | — |
| Johnsongrass | 10 | 0 | 0 | 0 | 20 | 10 | 40 | — | 35 | 0 | 45 | 55 |
| *Kochia* | 10 | 10 | 0 | 0 | 0 | 0 | 0 | 0 | 0 | 0 | — | — |
| Lambsquarters | 65 | 40 | 0 | 0 | — | 65 | 10 | 0 | 55 | 35 | 0 | 85 |
| Morningglory | 0 | 0 | 0 | 0 | 10 | 10 | 20 | 25 | 0 | — | 0 | 0 |
| Nightshade | 0 | 0 | 0 | — | 0 | 15 | 0 | 0 | 50 | 0 | — | — |
| Nutsedge, Yellow | 0 | 25 | 20 | 0 | 0 | 10 | 20 | 0 | 10 | — | 0 | 0 |
| Oat, Wild | 0 | 0 | 0 | 0 | 0 | 40 | 10 | 0 | — | 0 | — | — |
| Oilseed Rape | — | — | — | — | — | — | — | — | — | — | 0 | 30 |
| Pigweed | 0 | 20 | 25 | 35 | 10 | 40 | 0 | 0 | 75 | 25 | 0 | 60 |
| Ragweed | 10 | 0 | 10 | 0 | 10 | 15 | 0 | 20 | 0 | 0 | — | — |
| Russian Thistle | — | — | — | 0 | 50 | 30 | 0 | 0 | — | — | — | — |
| Ryegrass, Italian | 0 | 0 | 0 | 0 | 0 | 0 | 0 | 0 | 0 | 0 | 25 | 40 |
| Soybean | 10 | 10 | 15 | 15 | 25 | 30 | 35 | 20 | 0 | 0 | 0 | 0 |
| Sunflower | 0 | 0 | 15 | 5 | 0 | 20 | 0 | 0 | 0 | 10 | — | — |
| Surinam Grass | 75 | 35 | 25 | 35 | 70 | 60 | 50 | 0 | 75 | 75 | — | — |
| Velvetleaf | 0 | 5 | 0 | 0 | 0 | 20 | 10 | 20 | 10 | 30 | 0 | 25 |
| Waterhemp | — | — | — | — | — | — | — | — | — | — | 50 | 40 |
| Wheat | 20 | 0 | 0 | 0 | 0 | 0 | 5 | 0 | 5 | 0 | 45 | 55 |

TABLE C-continued

| | 62 g ai/ha Compounds | | | | | | | | | | | |
|---|---|---|---|---|---|---|---|---|---|---|---|---|
| | 78 | 79 | 80 | 81 | 101 | 103 | 109 | 119 | 120 | 189 | 202 | 204 |
| Barnyardgrass | 75 | 95 | 95 | — | 95 | 90 | 85 | 90 | 90 | 90 | 90 | 90 |
| Bermudagrass | — | — | — | 0 | — | — | — | — | — | — | — | — |
| Blackgrass | 75 | 65 | 80 | 0 | 50 | 0 | 60 | 70 | 50 | 50 | 80 | 90 |
| Bromegrass, Downy | — | — | — | 0 | — | — | — | — | — | — | — | — |
| Cocklebur | — | — | — | 0 | — | — | — | — | — | — | — | — |
| Corn | 0 | 0 | 0 | 0 | 0 | 0 | 5 | 0 | 0 | 0 | 85 | 25 |
| Crabgrass, Large | 98 | 98 | 98 | 75 | 98 | 98 | 100 | 98 | 100 | 95 | 95 | 90 |
| Cupgrass, Woolly | — | — | — | 32 | — | — | — | — | — | — | — | — |
| Foxtail, Giant | 95 | 90 | 95 | 17 | 95 | 95 | 95 | 90 | 95 | 90 | 90 | 90 |
| Foxtail, Green | — | — | — | 67 | — | — | — | — | — | — | — | — |
| *Galium* | 50 | 5 | 90 | 0 | 40 | 80 | 100 | 80 | 95 | 0 | 90 | 90 |
| Goosegrass | — | — | — | 0 | — | — | — | — | — | — | — | — |
| Johnsongrass | 0 | 0 | 0 | 0 | 15 | 10 | 10 | 0 | 0 | 0 | 60 | 40 |
| *Kochia* | — | — | — | — | — | — | — | — | — | — | — | — |
| Lambsquarters | 40 | 90 | 85 | 0 | 85 | 0 | 0 | 60 | 70 | 0 | 90 | 100 |
| Morningglory | 0 | 0 | 0 | 0 | 0 | 0 | 0 | 0 | 0 | 0 | 25 | 0 |
| Nightshade | — | — | — | 0 | — | — | — | — | — | — | — | — |
| Nutsedge, Yellow | 0 | 0 | 0 | 0 | 0 | 0 | 5 | 0 | 0 | 0 | 0 | 0 |
| Oat, Wild | — | — | — | 0 | — | — | — | — | — | — | — | — |
| Oilseed Rape | 10 | 5 | 85 | — | 35 | 0 | 0 | 5 | 0 | 0 | 80 | 0 |
| Pigweed | 40 | 40 | 90 | 0 | 0 | 0 | 0 | 60 | 45 | 0 | 85 | 0 |
| Ragweed | — | — | — | 0 | 0 | 0 | 0 | 35 | 20 | 0 | 85 | 30 |
| Russian Thistle | — | — | — | 0 | — | — | — | — | — | — | — | — |
| Ryegrass, Italian | 40 | 5 | 40 | 0 | 15 | 0 | 40 | 15 | 5 | 30 | 30 | 0 |
| Soybean | 0 | 0 | 0 | 0 | 0 | 10 | 0 | 20 | 0 | 10 | 25 | — |
| Sunflower | — | — | — | 0 | — | — | — | — | — | — | — | — |
| Surinam Grass | — | — | — | 53 | — | — | — | — | — | — | — | — |
| Velvetleaf | 15 | 0 | 30 | 0 | 0 | 0 | 0 | 15 | 20 | 0 | 30 | 0 |
| Waterhemp | 75 | 40 | 80 | — | 70 | 0 | 50 | 65 | 60 | 5 | 95 | 7 |
| Wheat | 30 | 40 | 5 | 0 | 20 | 0 | 10 | 5 | 35 | 0 | 30 | 70 |

| | 62 g ai/ha Compounds | | | | | | | | | | | |
|---|---|---|---|---|---|---|---|---|---|---|---|---|
| | 206 | 207 | 211 | 218 | 223 | 224 | 231 | 232 | 233 | 241 | 246 | 247 |
| Barnyardgrass | 90 | 85 | 65 | 90 | 85 | 85 | 90 | 85 | 75 | 95 | 75 | 85 |
| Bermudagrass | — | — | — | — | — | — | — | — | — | — | — | — |
| Blackgrass | 90 | 80 | 20 | 10 | 35 | 65 | 85 | 70 | 45 | 70 | 0 | 50 |
| Bromegrass, Downy | — | — | — | — | — | — | — | — | — | — | — | — |
| Cocklebur | — | — | — | — | — | — | — | — | — | — | — | — |
| Corn | 60 | 0 | 25 | 0 | 0 | 0 | 5 | 35 | 0 | 65 | 0 | 15 |
| Crabgrass, Large | 90 | 90 | 95 | 90 | 90 | 90 | 95 | 90 | 90 | 95 | 95 | 95 |
| Cupgrass, Woolly | — | — | — | — | — | — | — | — | — | — | — | — |
| Foxtail, Giant | 90 | 90 | 70 | 90 | 85 | 90 | 90 | 90 | 90 | 95 | 90 | 95 |
| Foxtail, Green | — | — | — | — | — | — | — | — | — | — | — | — |
| *Galium* | 70 | 0 | 5 | 0 | 0 | 40 | 85 | 85 | 80 | 80 | 90 | 90 |
| Goosegrass | — | — | — | — | — | — | — | — | — | — | — | — |
| Johnsongrass | 65 | 0 | 0 | 10 | 0 | 35 | 10 | 20 | 0 | 80 | 20 | 0 |
| *Kochia* | — | — | — | — | — | — | — | — | — | — | — | — |
| Lambsquarters | 100 | 0 | 85 | 40 | 70 | 65 | 85 | 85 | 85 | 0 | 65 | 90 |
| Morningglory | 0 | 0 | 0 | 0 | 0 | 75 | 0 | 15 | 0 | 0 | 5 | 0 |
| Nightshade | — | — | — | — | — | — | — | — | — | — | — | — |
| Nutsedge, Yellow | 0 | 0 | 0 | 0 | 0 | 10 | 0 | 0 | 0 | 0 | 100 | 20 |
| Oat, Wild | — | — | — | — | — | — | — | — | — | — | — | — |
| Oilseed Rape | 70 | 0 | 35 | 60 | 0 | 5 | 55 | 30 | 40 | 0 | 30 | 30 |
| Pigweed | 100 | 0 | 0 | 50 | 5 | 75 | 70 | 85 | 50 | 0 | 75 | 55 |
| Ragweed | 10 | 0 | 10 | 35 | 0 | 40 | 100 | 85 | 40 | 25 | 0 | 85 |
| Russian Thistle | — | — | — | — | — | — | — | — | — | — | — | — |
| Ryegrass, Italian | 40 | 0 | 35 | 0 | 0 | 0 | 10 | 0 | 0 | 20 | 0 | 35 |
| Soybean | 0 | 0 | 0 | 5 | 5 | 100 | 0 | 0 | 0 | 0 | 0 | 0 |
| Sunflower | — | — | — | — | — | — | — | — | — | — | — | — |
| Surinam Grass | — | — | — | — | — | — | — | — | — | — | — | — |
| Velvetleaf | 50 | 0 | 10 | 0 | 0 | 5 | 25 | 40 | 25 | 0 | 0 | 20 |
| Waterhemp | 100 | 0 | 75 | 7 | 0 | 5 | 85 | 90 | 80 | 40 | 98 | 100 |
| Wheat | 40 | 0 | 0 | 0 | 5 | 0 | 15 | 0 | 0 | 45 | 0 | 0 |

| | 62 g ai/ha Compounds | | | | | | | | | | | |
|---|---|---|---|---|---|---|---|---|---|---|---|---|
| | 262 | 263 | 271 | 274 | 275 | 277 | 278 | 279 | 280 | 302 | 303 | 304 |
| Barnyardgrass | 70 | 90 | 95 | 65 | 95 | 98 | 90 | 95 | 65 | 85 | 95 | 90 |
| Bermudagrass | — | — | — | — | — | — | — | — | — | — | — | — |
| Blackgrass | 0 | 0 | 50 | 70 | 60 | 70 | 0 | 0 | 0 | 30 | 40 | 60 |

TABLE C-continued

| | | | | | | | | | | | | |
|---|---|---|---|---|---|---|---|---|---|---|---|---|
| Bromegrass, Downy | — | — | — | — | — | — | — | — | — | — | — | — |
| Cocklebur | — | — | — | — | — | — | — | — | — | — | — | — |
| Corn | 0 | 0 | 0 | 5 | 10 | 85 | 0 | 0 | 0 | 0 | 20 | 40 |
| Crabgrass, Large | 98 | 100 | 100 | 90 | 95 | 100 | 95 | 95 | 90 | 98 | 98 | 95 |
| Cupgrass, Woolly | — | — | — | — | — | — | — | — | — | — | — | — |
| Foxtail, Giant | 70 | 95 | 98 | 85 | 95 | 98 | 90 | 95 | 80 | 95 | 95 | 95 |
| Foxtail, Green | — | — | — | — | — | — | — | — | — | — | — | — |
| *Galium* | 40 | 85 | — | 0 | 90 | 90 | 0 | 0 | 0 | 5 | 0 | 95 |
| Goosegrass | — | — | — | — | — | — | — | — | — | — | — | — |
| Johnsongrass | 0 | 0 | 10 | 0 | 50 | 65 | 0 | 25 | 0 | 15 | 55 | 35 |
| *Kochia* | — | — | — | — | — | — | — | — | — | — | — | — |
| Lambsquarters | 70 | 100 | 20 | 0 | 75 | 75 | 0 | 0 | 0 | 0 | 60 | 70 |
| Morningglory | 0 | 0 | 10 | 0 | 0 | 0 | 0 | 0 | 25 | 0 | 0 | 9 |
| Nightshade | — | — | — | — | — | — | — | — | — | — | — | — |
| Nutsedge, Yellow | 0 | 0 | 0 | 0 | 25 | 20 | 0 | 0 | 0 | 0 | 0 | 25 |
| Oat, Wild | — | — | — | — | — | — | — | — | — | — | — | — |
| Oilseed Rape | 35 | 60 | 20 | 0 | 50 | 0 | 0 | 0 | 30 | 0 | 35 | 55 |
| Pigweed | 0 | 70 | 25 | 0 | 0 | 35 | 0 | 5 | 0 | 20 | 55 | 75 |
| Ragweed | 20 | 90 | 10 | 0 | 5 | 0 | 0 | 0 | 0 | 5 | 70 | 60 |
| Russian Thistle | — | — | — | — | — | — | — | — | — | — | — | — |
| Ryegrass, Italian | 0 | 0 | 10 | 0 | 40 | 35 | 0 | 10 | 0 | 0 | 35 | 75 |
| Soybean | 0 | 0 | 0 | 0 | 0 | 0 | 0 | 0 | 5 | 30 | 0 | 0 |
| Sunflower | — | — | — | — | — | — | — | — | — | — | — | — |
| Surinam Grass | — | — | — | — | — | — | — | — | — | — | — | — |
| Velvetleaf | 0 | 5 | 10 | 20 | 0 | 0 | 0 | 0 | 0 | 0 | 25 | 35 |
| Waterhemp | 50 | 80 | 35 | 0 | 0 | 50 | 0 | 15 | 65 | 35 | 65 | 80 |
| Wheat | 0 | 10 | 0 | 0 | 45 | 70 | 0 | 15 | 0 | 5 | 75 | 50 |

| | 62 g ai/ha Compounds | | | | | | | | | | | |
|---|---|---|---|---|---|---|---|---|---|---|---|---|
| | 305 | 306 | 307 | 309 | 310 | 312 | 315 | 316 | 317 | 318 | 319 | 323 |
| Barnyardgrass | 95 | 90 | 70 | 90 | 90 | 90 | 90 | 85 | 90 | 95 | 95 | 85 |
| Bermudagrass | — | — | — | — | — | — | — | — | — | — | — | — |
| Blackgrass | 75 | 30 | 0 | 0 | 5 | 45 | 60 | 0 | 40 | 0 | 0 | 0 |
| Bromegrass, Downy | — | — | — | — | — | — | — | — | — | — | — | — |
| Cocklebur | — | — | — | — | — | — | — | — | — | — | — | — |
| Corn | 75 | 60 | 0 | 0 | 0 | 60 | 80 | 75 | 0 | 0 | 30 | 0 |
| Crabgrass, Large | 95 | 95 | 95 | 90 | 90 | 95 | 95 | 95 | 95 | 98 | 98 | 98 |
| Cupgrass, Woolly | — | — | — | — | — | — | — | — | — | — | — | — |
| Foxtail, Giant | 95 | 95 | 85 | 90 | 85 | 90 | 90 | 90 | 90 | 70 | 85 | 95 |
| Foxtail, Green | — | — | — | — | — | — | — | — | — | — | — | — |
| *Galium* | 80 | 60 | 0 | 0 | 0 | 0 | 80 | 0 | 0 | 0 | 70 | 0 |
| Goosegrass | — | — | — | — | — | — | — | — | — | — | — | — |
| Johnsongrass | 85 | 55 | 0 | 10 | 0 | 50 | 85 | 75 | 0 | 0 | 55 | 0 |
| *Kochia* | — | — | — | — | — | — | — | — | — | — | — | — |
| Lambsquarters | 70 | 65 | 0 | 0 | 5 | 0 | 40 | 20 | 0 | 55 | 65 | 50 |
| Morningglory | 30 | 35 | 0 | 0 | 0 | 35 | 25 | 0 | 0 | 40 | 40 | 0 |
| Nightshade | — | — | — | — | — | — | — | — | — | — | — | — |
| Nutsedge, Yellow | 0 | 0 | 0 | 0 | 0 | 35 | 0 | 0 | 0 | 0 | 0 | 25 |
| Oat, Wild | — | — | — | — | — | — | — | — | — | — | — | — |
| Oilseed Rape | 60 | 70 | 0 | 0 | 5 | 0 | 30 | 0 | 0 | 0 | 5 | 10 |
| Pigweed | 70 | 85 | 0 | 0 | 5 | 40 | 60 | 25 | 0 | 20 | 25 | 35 |
| Ragweed | 15 | 75 | 0 | 10 | 0 | 0 | 20 | 0 | 0 | 0 | 15 | 10 |
| Russian Thistle | — | — | — | — | — | — | — | — | — | — | — | — |
| Ryegrass, Italian | 50 | 40 | 0 | 0 | 0 | 30 | 50 | 0 | 0 | 0 | 10 | 10 |
| Soybean | 0 | 0 | 0 | 0 | 0 | 0 | 0 | 0 | 0 | 0 | 0 | 0 |
| Sunflower | — | — | — | — | — | — | — | — | — | — | — | — |
| Surinam Grass | — | — | — | — | — | — | — | — | — | — | — | — |
| Velvetleaf | 30 | 60 | 0 | 0 | 0 | 15 | 30 | 10 | 0 | 10 | 20 | 15 |
| Waterhemp | 65 | 85 | 0 | 0 | 0 | 45 | 75 | 35 | 0 | 30 | 35 | 50 |
| Wheat | 90 | 50 | 0 | 0 | 0 | 30 | 50 | 5 | 0 | 0 | 0 | 30 |

| | 62 g ai/ha Compounds | | | | | 31 g ai/ha Compounds | | | | | |
|---|---|---|---|---|---|---|---|---|---|---|---|
| | 324 | 325 | 345 | 346 | 350 | 5 | 14 | 16 | 17 | 33 | 34 | 35 |
| Barnyardgrass | 95 | 90 | 95 | 70 | 90 | — | — | — | — | — | — | — |
| Bermudagrass | — | — | — | — | — | 0 | 75 | 0 | 0 | 0 | 0 | 0 |
| Blackgrass | 30 | 50 | 50 | 60 | 0 | 0 | 0 | 0 | 5 | 0 | 0 | 0 |
| Bromegrass, Downy | — | — | — | — | — | 0 | 0 | 0 | 0 | 0 | 0 | 0 |
| Cocklebur | — | — | — | — | — | 0 | 0 | 0 | 0 | 0 | 0 | 0 |
| Corn | 70 | 60 | 35 | 0 | 0 | 0 | 0 | 0 | 0 | 0 | 0 | 0 |
| Crabgrass, Large | 95 | 95 | 98 | 95 | 90 | 100 | 90 | 95 | 95 | 95 | 95 | 95 |
| Cupgrass, Woolly | — | — | — | — | — | 30 | 0 | 55 | 80 | 60 | 50 | 55 |
| Foxtail, Giant | 90 | 95 | 90 | 90 | 90 | 95 | 85 | 0 | 90 | 75 | 90 | 80 |
| Foxtail, Green | — | — | — | — | — | 85 | 25 | 5 | 95 | 95 | 98 | 90 |
| *Galium* | 60 | 20 | 90 | 20 | 85 | 0 | 0 | 0 | 0 | 0 | 0 | 0 |

TABLE C-continued

| | | | | | | | | | | | | |
|---|---|---|---|---|---|---|---|---|---|---|---|---|
| Goosegrass | — | — | — | — | — | 0 | 0 | 0 | 0 | 5 | 0 | 0 |
| Johnsongrass | 65 | 35 | 75 | 0 | 0 | 0 | 0 | 0 | 0 | 0 | 10 | 0 |
| *Kochia* | — | — | — | — | — | 0 | 0 | 0 | 0 | 0 | 0 | 0 |
| Lambsquarters | 70 | 70 | 75 | 35 | 90 | 5 | — | 0 | 60 | 0 | 0 | 0 |
| Morningglory | 0 | 30 | 0 | 0 | 100 | 0 | 0 | 0 | 0 | 0 | 0 | 5 |
| Nightshade | — | — | — | — | — | 0 | 0 | 0 | 20 | 0 | 0 | 0 |
| Nutsedge, Yellow | 0 | 0 | 0 | 0 | 0 | 0 | 0 | 0 | 0 | 0 | 0 | 0 |
| Oat, Wild | — | — | — | — | — | 0 | 0 | 0 | 0 | 0 | 0 | 0 |
| Oilseed Rape | 70 | 65 | 55 | 0 | 70 | — | — | — | — | — | — | — |
| Pigweed | 75 | 65 | 30 | 55 | 10 | 0 | 0 | 0 | 0 | 0 | 0 | 0 |
| Ragweed | 60 | 60 | 40 | 35 | 0 | 0 | 0 | 0 | 0 | 0 | 0 | 0 |
| Russian Thistle | — | — | — | — | — | 0 | 0 | — | — | 0 | 0 | 0 |
| Ryegrass, Italian | 10 | 40 | 45 | 10 | 0 | 0 | 0 | 0 | 0 | 0 | 0 | 0 |
| Soybean | 0 | 0 | 0 | 0 | 0 | 0 | 0 | 0 | 0 | 0 | 0 | 0 |
| Sunflower | — | — | — | — | — | 0 | 0 | 0 | 0 | 0 | 0 | 0 |
| Surinam Grass | — | — | — | — | — | 65 | 55 | 80 | 85 | 80 | 95 | 85 |
| Velvetleaf | 35 | 35 | 0 | 0 | 0 | 0 | 0 | 0 | 0 | 0 | 0 | 0 |
| Waterhemp | 70 | 75 | 5 | 25 | 50 | — | — | — | — | — | — | — |
| Wheat | 25 | 40 | 10 | 0 | 0 | 0 | 5 | 0 | 0 | 0 | 0 | 0 |

| | 31 g ai/ha Compounds | | | | | | | | | | | |
|---|---|---|---|---|---|---|---|---|---|---|---|---|
| | 48 | 52 | 53 | 59 | 60 | 62 | 64 | 66 | 68 | 69 | 76 | 77 |
| Barnyardgrass | — | — | — | — | — | — | — | — | — | — | 80 | 90 |
| Bermudagrass | 0 | 0 | 40 | 20 | 0 | 0 | 0 | 0 | 30 | 35 | — | — |
| Blackgrass | 0 | 0 | 0 | 0 | 0 | 0 | 0 | 0 | 0 | 0 | 50 | 85 |
| Bromegrass, Downy | 0 | 0 | 0 | 0 | 0 | 0 | 0 | 0 | 0 | 0 | — | — |
| Cocklebur | 0 | 0 | — | — | — | 0 | — | 0 | 15 | 0 | — | — |
| Corn | 0 | 10 | 10 | 0 | 0 | 20 | 0 | 0 | 15 | 15 | 0 | 0 |
| Crabgrass, Large | 85 | 80 | 80 | 85 | 85 | 85 | 85 | 90 | 90 | 90 | 98 | 95 |
| Cupgrass, Woolly | 70 | 40 | 35 | 40 | 55 | 65 | 30 | 10 | 75 | 75 | — | — |
| Foxtail, Giant | 80 | 55 | 40 | 50 | 70 | 65 | 50 | 20 | 85 | 75 | 90 | 90 |
| Foxtail, Green | 80 | 80 | 30 | 85 | 90 | 75 | 70 | 50 | 90 | 90 | — | — |
| *Galium* | 0 | 0 | 0 | 0 | 0 | 0 | 0 | 0 | 0 | 0 | 5 | — |
| Goosegrass | 0 | 10 | 0 | 15 | 0 | 10 | 20 | 5 | 55 | 20 | — | — |
| Johnsongrass | 0 | 0 | 0 | 0 | 0 | 0 | — | 30 | 0 | 0 | 20 | 20 |
| *Kochia* | 0 | 10 | 0 | 0 | 0 | 0 | 0 | 0 | 0 | 0 | — | — |
| Lambsquarters | 0 | 0 | 0 | — | 0 | 40 | 0 | 0 | 55 | 35 | — | 75 |
| Morningglory | 0 | 0 | 0 | 0 | 0 | 0 | 15 | 15 | 0 | 20 | 0 | 0 |
| Nightshade | 0 | 0 | 0 | 0 | 0 | — | 0 | 0 | 10 | 0 | — | — |
| Nutsedge, Yellow | 0 | 25 | 15 | 0 | 0 | 10 | 0 | 0 | 10 | 0 | 0 | 0 |
| Oat, Wild | 0 | 0 | 0 | 0 | 0 | 20 | 0 | 0 | — | — | — | — |
| Oilseed Rape | — | — | — | — | — | — | — | — | — | — | 0 | 0 |
| Pigweed | 0 | 20 | 25 | 35 | 0 | 40 | 0 | 0 | 45 | 15 | — | 0 |
| Ragweed | 0 | 0 | 0 | 0 | 10 | 15 | 0 | 10 | 0 | 0 | — | — |
| Russian Thistle | — | — | — | 0 | 0 | 0 | 0 | 0 | — | — | — | — |
| Ryegrass, Italian | 0 | 0 | 0 | 0 | 0 | 0 | 0 | 0 | 0 | 0 | 0 | 40 |
| Soybean | 10 | — | 15 | 15 | 10 | 20 | 35 | 15 | 0 | 0 | 0 | 0 |
| Sunflower | 0 | 0 | 0 | 5 | 0 | 10 | 0 | 0 | 0 | 10 | — | — |
| Surinam Grass | 75 | 10 | 20 | 0 | 10 | 0 | 20 | 0 | 40 | 60 | — | — |
| Velvetleaf | 0 | 5 | 0 | 0 | 0 | 10 | 10 | 10 | 10 | 30 | 0 | 0 |
| Waterhemp | — | — | — | — | — | — | — | — | — | — | 50 | 40 |
| Wheat | 0 | 0 | 0 | 0 | 0 | 0 | 0 | 0 | 0 | 0 | 35 | 0 |

| | 31 g ai/ha Compounds | | | | | | | | | | | |
|---|---|---|---|---|---|---|---|---|---|---|---|---|
| | 78 | 79 | 80 | 81 | 101 | 103 | 109 | 119 | 120 | 189 | 202 | 204 |
| Barnyardgrass | 60 | 40 | 85 | — | 90 | 50 | 70 | 80 | 85 | 85 | 90 | 80 |
| Bermudagrass | — | — | — | 0 | — | — | — | — | — | — | — | — |
| Blackgrass | 30 | 0 | 30 | 0 | 0 | 0 | 0 | 0 | 35 | 10 | 70 | 90 |
| Bromegrass, Downy | — | — | — | 0 | — | — | — | — | — | — | — | — |
| Cocklebur | — | — | — | 0 | — | — | — | — | — | — | — | — |
| Corn | 0 | 0 | 0 | 0 | 0 | 0 | 0 | 0 | 0 | 0 | 20 | 45 |
| Crabgrass, Large | 95 | 95 | 95 | 50 | 95 | 95 | 98 | 98 | 98 | 95 | 90 | 90 |
| Cupgrass, Woolly | — | — | — | 0 | — | — | — | — | — | — | — | — |
| Foxtail, Giant | 85 | 80 | 90 | 0 | 95 | 85 | 90 | 90 | 90 | 80 | 90 | 90 |
| Foxtail, Green | — | — | — | 20 | — | — | — | — | — | — | — | — |
| *Galium* | 50 | 0 | 5 | 0 | 0 | 0 | 60 | 80 | 5 | 0 | 85 | — |
| Goosegrass | — | — | — | 0 | — | — | — | — | — | — | — | — |
| Johnsongrass | 0 | 0 | 0 | 0 | 0 | 0 | 0 | 0 | 0 | 0 | 10 | 10 |
| *Kochia* | — | — | — | 0 | — | — | — | — | — | — | — | — |
| Lambsquarters | — | 90 | 40 | 0 | 30 | 0 | 0 | 25 | 35 | 0 | 80 | 100 |
| Morningglory | 0 | 0 | 0 | 0 | 0 | 0 | 0 | 0 | 0 | 0 | 15 | 0 |
| Nightshade | — | — | — | 0 | — | — | — | — | — | — | — | — |
| Nutsedge, Yellow | 0 | 0 | 0 | 0 | 9 | 0 | 0 | 0 | 0 | 0 | 0 | 0 |
| Oat, Wild | — | — | — | 0 | — | — | — | — | — | — | — | — |

TABLE C-continued

| | | | | | | | | | | | | |
|---|---|---|---|---|---|---|---|---|---|---|---|---|
| Oilseed Rape | 0 | 0 | 5 | — | 0 | 0 | 0 | 0 | 0 | 0 | 25 | 0 |
| Pigweed | 0 | 10 | 75 | 0 | 0 | 0 | 30 | 30 | 50 | 0 | 85 | 0 |
| Ragweed | — | — | — | 0 | 15 | 40 | 0 | 60 | 0 | 0 | 65 | 30 |
| Russian Thistle | — | — | — | 0 | — | — | — | — | — | — | — | — |
| Ryegrass, Italian | 0 | 0 | 0 | 0 | 30 | 0 | 0 | 0 | 10 | 0 | 0 | 0 |
| Soybean | 0 | 0 | 0 | 0 | 0 | 10 | 100 | 0 | 0 | 5 | 0 | 5 |
| Sunflower | — | — | — | 0 | — | — | — | — | — | — | — | — |
| Surinam Grass | — | — | — | 0 | — | — | — | — | — | — | — | — |
| Velvetleaf | 15 | 0 | 0 | 0 | 15 | 0 | 0 | 0 | 0 | 0 | 10 | 0 |
| Waterhemp | 50 | 25 | 15 | — | 50 | 0 | 0 | 20 | 0 | 0 | 85 | 100 |
| Wheat | 10 | 10 | 0 | 0 | 0 | 0 | 0 | 5 | 10 | 0 | 0 | 0 |

| | 31 g ai/ha Compounds | | | | | | | | | | | |
|---|---|---|---|---|---|---|---|---|---|---|---|---|
| | 206 | 207 | 211 | 218 | 223 | 224 | 231 | 232 | 233 | 241 | 246 | 247 |
| Barnyardgrass | 90 | 75 | 30 | 80 | 65 | 75 | 85 | 85 | 80 | 90 | 20 | 15 |
| Bermudagrass | — | — | — | — | — | — | — | — | — | — | — | — |
| Blackgrass | 85 | 0 | 0 | 0 | 35 | 0 | 50 | 60 | 30 | 50 | 0 | 0 |
| Bromegrass, Downy | — | — | — | — | — | — | — | — | — | — | — | — |
| Cocklebur | — | — | — | — | — | — | — | — | — | — | — | — |
| Corn | 30 | 0 | 0 | 0 | 0 | 10 | 0 | 0 | 0 | 85 | 0 | 5 |
| Crabgrass, Large | 90 | 90 | 100 | 90 | 85 | 90 | 90 | 85 | 90 | 9 | 95 | 95 |
| Cupgrass, Woolly | — | — | — | — | — | — | — | — | — | — | — | — |
| Foxtail, Giant | 90 | 85 | 0 | 85 | 70 | 80 | 90 | 85 | 85 | 90 | 85 | 95 |
| Foxtail, Green | — | — | — | — | — | — | — | — | — | — | — | — |
| *Galium* | 20 | 0 | — | 0 | 0 | 0 | 0 | 85 | 0 | 20 | 10 | 90 |
| Goosegrass | — | — | — | — | — | — | — | — | — | — | — | — |
| Johnsongrass | 25 | 0 | 0 | 0 | 0 | 0 | 0 | 0 | 0 | 85 | 0 | 0 |
| *Kochia* | — | — | — | — | — | — | — | — | — | — | — | — |
| Lambsquarters | 75 | 0 | 100 | 10 | 70 | 55 | 40 | 75 | 85 | 0 | 65 | 0 |
| Morningglory | 0 | 0 | 0 | 0 | 0 | 5 | 0 | 0 | 0 | 0 | 5 | 0 |
| Nightshade | — | — | — | — | — | — | — | — | — | — | — | — |
| Nutsedge, Yellow | 0 | 0 | 0 | 0 | 100 | 0 | 0 | 0 | 0 | 0 | 85 | 0 |
| Oat, Wild | — | — | — | — | — | — | — | — | — | — | — | — |
| Oilseed Rape | 5 | 0 | 0 | 0 | 0 | 0 | 0 | 30 | 0 | 0 | 0 | 5 |
| Pigweed | 70 | 0 | — | 5 | 20 | 0 | 35 | 85 | 50 | 0 | 30 | 0 |
| Ragweed | 80 | 0 | 0 | 40 | 0 | 10 | 80 | 65 | 10 | 0 | 0 | 100 |
| Russian Thistle | — | — | — | — | — | — | — | — | — | — | — | — |
| Ryegrass, Italian | 30 | 0 | 0 | 0 | 0 | 0 | 0 | 0 | 0 | 20 | 0 | 0 |
| Soybean | 0 | 0 | 0 | 0 | 0 | 0 | 0 | 0 | 0 | 0 | 0 | 0 |
| Sunflower | — | — | — | — | — | — | — | — | — | — | — | — |
| Surinam Grass | — | — | — | — | — | — | — | — | — | — | — | — |
| Velvetleaf | 0 | 0 | 0 | 0 | 0 | 0 | 10 | 25 | 15 | 0 | 0 | 0 |
| Waterhemp | 70 | 0 | 85 | 30 | 90 | 75 | 75 | 85 | 95 | 25 | 100 | 70 |
| Wheat | 35 | 0 | 0 | 0 | 0 | 0 | 0 | 0 | 0 | 0 | 0 | 0 |

| | 31 g ai/ha Compounds | | | | | | | | | | | |
|---|---|---|---|---|---|---|---|---|---|---|---|---|
| | 262 | 263 | 271 | 274 | 275 | 277 | 278 | 279 | 280 | 302 | 303 | 304 |
| Barnyardgrass | 45 | 75 | 90 | 55 | 80 | 95 | 65 | 80 | 55 | 90 | 90 | 85 |
| Bermudagrass | — | — | — | — | — | — | — | — | — | — | — | — |
| Blackgrass | 0 | 0 | 0 | 0 | 45 | 70 | 0 | 0 | 0 | 0 | 0 | 35 |
| Bromegrass, Downy | — | — | — | — | — | — | — | — | — | — | — | — |
| Cocklebur | — | — | — | — | — | — | — | — | — | — | — | — |
| Corn | 0 | 0 | 0 | 0 | 0 | 25 | 0 | 0 | 0 | 0 | 10 | 0 |
| Crabgrass, Large | 95 | 100 | 95 | 85 | 90 | 98 | 90 | 95 | 85 | 95 | 95 | 95 |
| Cupgrass, Woolly | — | — | — | — | — | — | — | — | — | — | — | — |
| Foxtail, Giant | 20 | 65 | 90 | 30 | 90 | 98 | 80 | 90 | 70 | 90 | 90 | 90 |
| Foxtail, Green | — | — | — | — | — | — | — | — | — | — | — | — |
| *Galium* | 0 | 70 | — | 0 | 0 | 100 | 0 | 0 | 0 | 0 | 90 | 85 |
| Goosegrass | — | — | — | — | — | — | — | — | — | — | — | — |
| Johnsongrass | 0 | 5 | 0 | 0 | 10 | 40 | 0 | 0 | 0 | 0 | 0 | 0 |
| *Kochia* | — | — | — | — | — | — | — | — | — | — | — | — |
| Lambsquarters | 100 | 50 | 0 | — | 70 | 20 | 0 | 0 | 0 | 0 | 55 | 65 |
| Morningglory | 0 | 0 | 0 | 0 | 0 | 0 | 0 | 0 | 10 | 0 | 0 | 5 |
| Nightshade | — | — | — | — | — | — | — | — | — | — | — | — |
| Nutsedge, Yellow | 75 | 0 | 0 | 0 | 45 | 0 | 0 | 0 | 0 | 0 | 0 | 0 |
| Oat, Wild | — | — | — | — | — | — | — | — | — | — | — | — |
| Oilseed Rape | 0 | 40 | 0 | 0 | 0 | 0 | 0 | 0 | 0 | 0 | 0 | 50 |
| Pigweed | 0 | 70 | 0 | 0 | 0 | 10 | 5 | 0 | 10 | 0 | 35 | 55 |
| Ragweed | 0 | 0 | 0 | — | 5 | 0 | 0 | 0 | 0 | 35 | 5 | 60 |
| Russian Thistle | — | — | — | — | — | — | — | — | — | — | — | — |
| Ryegrass, Italian | 0 | 0 | 0 | 0 | 15 | 40 | 0 | 0 | 0 | 0 | 30 | 30 |
| Soybean | 0 | 0 | 0 | 0 | 0 | 0 | 0 | 0 | 0 | 0 | 0 | 0 |
| Sunflower | — | — | — | — | — | — | — | — | — | — | — | — |
| Surinam Grass | — | — | — | — | — | — | — | — | — | — | — | — |

TABLE C-continued

| | | | | | | | | | | | | |
|---|---|---|---|---|---|---|---|---|---|---|---|---|
| Velvetleaf | 0 | 5 | 0 | 0 | 0 | 0 | 0 | 0 | 0 | 0 | 10 | 20 |
| Waterhemp | 0 | 7 | 0 | 0 | 0 | 35 | 0 | 0 | 0 | 30 | 40 | 75 |
| Wheat | 0 | 0 | 0 | 0 | 5 | 60 | 0 | 0 | 0 | 0 | 0 | 40 |

| | 31 g ai/ha Compounds | | | | | | | | | | | |
|---|---|---|---|---|---|---|---|---|---|---|---|---|
| | 305 | 306 | 307 | 309 | 310 | 312 | 315 | 316 | 317 | 318 | 319 | 323 |
| Barnyardgrass | 90 | 90 | 40 | 60 | 50 | 85 | 90 | 35 | 90 | 80 | 90 | 80 |
| Bermudagrass | — | — | — | — | — | — | — | — | — | — | — | — |
| Blackgrass | 60 | 0 | 0 | 0 | 0 | 40 | 60 | 0 | 0 | 0 | 40 | 0 |
| Bromegrass, Downy | — | — | — | — | — | — | — | — | — | — | — | — |
| Cocklebur | — | — | — | — | — | — | — | — | — | — | — | — |
| Corn | 65 | 40 | 0 | 0 | 0 | 10 | 50 | 15 | 0 | 0 | 0 | 0 |
| Crabgrass, Large | 95 | 90 | 90 | 90 | 90 | 90 | 90 | 90 | 95 | 95 | 95 | 95 |
| Cupgrass, Woolly | — | — | — | — | — | — | — | — | — | — | — | — |
| Foxtail, Giant | 95 | 90 | 65 | 90 | 80 | 90 | 90 | 85 | 80 | 10 | 70 | 90 |
| Foxtail, Green | — | — | — | — | — | — | — | — | — | — | — | — |
| *Galium* | 80 | 90 | 0 | 0 | 0 | 90 | 90 | 0 | 0 | 0 | 95 | 0 |
| Goosegrass | — | — | — | — | — | — | — | — | — | — | — | — |
| Johnsongrass | 80 | 33 | 0 | 10 | 0 | 30 | 75 | 50 | 0 | 0 | 40 | 0 |
| *Kochia* | — | — | — | — | — | — | — | — | — | — | — | — |
| Lambsquarters | 60 | 55 | 0 | 0 | 0 | 0 | 40 | 0 | 0 | 10 | 60 | 40 |
| Morningglory | 0 | 0 | 0 | 0 | 0 | 0 | 20 | 0 | 25 | 30 | 55 | 0 |
| Nightshade | — | — | — | — | — | — | — | — | — | — | — | — |
| Nutsedge, Yellow | 0 | 0 | 0 | 0 | 0 | 0 | 0 | 0 | 0 | 0 | 0 | 20 |
| Oat, Wild | — | — | — | — | — | — | — | — | — | — | — | — |
| Oilseed Rape | 20 | 50 | 0 | 0 | 0 | 0 | 5 | 0 | 0 | 0 | 0 | 0 |
| Pigweed | 10 | 80 | 0 | 0 | 0 | 25 | 45 | 25 | 0 | 0 | 30 | 35 |
| Ragweed | 0 | 50 | 50 | 10 | 0 | 0 | 0 | 0 | 0 | 0 | 0 | 0 |
| Russian Thistle | — | — | — | — | — | — | — | — | — | — | — | — |
| Ryegrass, Italian | 15 | 15 | 0 | 0 | 0 | 10 | 40 | 0 | 0 | 10 | 0 | 0 |
| Soybean | 0 | 0 | 0 | 0 | 0 | 0 | 0 | 0 | 0 | 0 | 0 | 0 |
| Sunflower | — | — | — | — | — | — | — | — | — | — | — | — |
| Surinam Grass | — | — | — | — | — | — | — | — | — | — | — | — |
| Velvetleaf | 25 | 25 | 0 | 0 | 5 | 10 | 30 | 0 | 0 | 0 | 30 | 15 |
| Waterhemp | 40 | 85 | 0 | 0 | 0 | 10 | 65 | 0 | 0 | 0 | 35 | 50 |
| Wheat | 45 | 5 | 0 | 0 | 0 | 30 | 50 | 0 | 0 | 0 | 0 | 5 |

| | 31 g ai/ha Compounds | | | | | 16 g ai/ha Compounds | | | | | 8 g ai/ha Compound |
|---|---|---|---|---|---|---|---|---|---|---|---|
| | 324 | 325 | 345 | 346 | 350 | 48 | 189 | 271 | 277 | 304 | 271 |
| Barnyardgrass | 90 | 85 | 80 | 50 | 75 | — | 45 | 75 | 95 | 85 | 0 |
| Bermudagrass | — | — | — | — | — | 0 | — | — | — | — | |
| Blackgrass | 100 | 5 | 50 | 20 | 0 | 0 | 0 | — | 40 | 30 | 0 |
| Bromegrass, Downy | — | — | — | — | — | 0 | — | — | — | — | |
| Cocklebur | — | — | — | — | — | 0 | — | — | — | — | |
| Corn | 25 | 10 | 40 | 0 | 0 | 0 | 0 | 0 | 0 | 0 | 0 |
| Crabgrass, Large | 95 | 95 | 95 | 95 | 90 | 75 | 90 | 90 | 95 | 90 | 50 |
| Cupgrass, Woolly | — | — | — | — | — | 25 | — | — | — | — | |
| Foxtail, Giant | 90 | 90 | 85 | 90 | 85 | 40 | 85 | 75 | 95 | 90 | 55 |
| Foxtail, Green | — | — | — | — | — | 70 | — | — | — | — | |
| *Galium* | 0 | 0 | 20 | 10 | 30 | 0 | 0 | — | 0 | 100 | |
| Goosegrass | — | — | — | — | — | 0 | — | — | — | — | |
| Johnsongrass | 40 | 20 | 35 | 0 | 0 | 0 | 0 | 0 | 0 | 0 | 0 |
| *Kochia* | — | — | — | — | — | 0 | — | — | — | — | |
| Lambsquarters | 50 | 45 | 100 | 35 | — | 0 | 0 | 0 | 0 | 30 | 0 |
| Morningglory | 0 | 0 | 25 | 0 | 100 | 0 | 0 | 0 | 0 | 0 | 0 |
| Nightshade | — | — | — | — | — | 0 | — | — | — | — | |
| Nutsedge, Yellow | 0 | 0 | 0 | 0 | 0 | 0 | 0 | 0 | 0 | 0 | 0 |
| Oat, Wild | — | — | — | — | — | 0 | — | — | — | — | |
| Oilseed Rape | 0 | 0 | 50 | 0 | 5 | — | 0 | 0 | 0 | 30 | 0 |
| Pigweed | 55 | 65 | 30 | 40 | 0 | 0 | 0 | 0 | 0 | 40 | |
| Ragweed | 60 | 5 | 10 | 50 | 0 | 0 | 0 | 0 | 0 | 25 | 0 |
| Russian Thistle | — | — | — | — | — | 0 | 0 | 0 | 30 | 10 | |
| Ryegrass, Italian | 0 | 10 | 0 | 0 | 0 | 10 | 0 | 0 | 0 | 0 | 0 |
| Soybean | 0 | 0 | 0 | 0 | 0 | 0 | — | — | — | — | 0 |
| Sunflower | — | — | — | — | — | 10 | — | — | — | — | |
| Surinam Grass | — | — | — | — | — | 0 | 0 | 0 | 0 | 0 | |
| Velvetleaf | 0 | 0 | 0 | 0 | 0 | — | 0 | 0 | 0 | 70 | 0 |
| Waterhemp | 55 | 70 | 0 | 7 | 0 | 0 | 0 | 0 | 40 | 5 | 0 |
| Wheat | 0 | 10 | 0 | 0 | 0 | | | | | | 0 |

TABLE C-continued

| | Flood | | | | | | | | | | | |
|---|---|---|---|---|---|---|---|---|---|---|---|---|
| | 2000 g ai/ha Compound | | 1000 ai/ha Compounds | | | | | | | | | |
| | 77 | 247 | 77 | 87 | 89 | 101 | 102 | 103 | 107 | 111 | 112 | 113 |
| Barnyardgrass | 70 | 80 | 40 | 40 | 75 | 75 | 0 | 85 | 20 | 0 | 0 | 0 |
| Ducksalad | 100 | 100 | 100 | 100 | 100 | 100 | 0 | 100 | 70 | 40 | 0 | 70 |
| Rice | 60 | 15 | 20 | 30 | 0 | 10 | 0 | 10 | 0 | 0 | 0 | 0 |
| Sedge, Umbrella | 40 | 0 | 20 | 0 | 0 | 0 | 0 | 0 | 0 | 0 | 0 | 0 |

| | 1000 ai/ha Compounds | | | | | | | | | | | |
|---|---|---|---|---|---|---|---|---|---|---|---|---|
| | 114 | 189 | 190 | 200 | 203 | 204 | 205 | 206 | 207 | 208 | 210 | 211 |
| Barnyardgrass | 0 | 75 | 65 | 55 | 40 | 80 | 45 | 85 | 7 | 65 | 75 | 80 |
| Ducksalad | 80 | 100 | 100 | 100 | 50 | 100 | 65 | 100 | 80 | 100 | 100 | 100 |
| Rice | 0 | 0 | 15 | 0 | 0 | 10 | 0 | 15 | 15 | 15 | 0 | 15 |
| Sedge, Umbrella | 0 | 0 | 0 | 0 | 0 | 0 | 0 | 0 | 0 | 0 | 0 | 30 |

| | 1000 ai/ha Compounds | | | | | | 500 g ai/ha Compounds | | | | | |
|---|---|---|---|---|---|---|---|---|---|---|---|---|
| | 212 | 247 | 270 | 271 | 344 | 346 | 77 | 87 | 89 | 101 | 102 | 103 |
| Barnyardgrass | 65 | 70 | 80 | 80 | 55 | 70 | 30 | 25 | 40 | 60 | 0 | 60 |
| Ducksalad | 100 | 100 | 100 | 100 | 85 | 100 | 100 | 100 | 100 | 100 | 0 | 95 |
| Rice | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

| | 500 g ai/ha Compounds | | | | | | | | | | | |
|---|---|---|---|---|---|---|---|---|---|---|---|---|
| | 107 | 111 | 112 | 113 | 114 | 120 | 189 | 190 | 200 | 203 | 204 | 205 |
| Barnyardgrass | 0 | 0 | 0 | 0 | 0 | 75 | 50 | 50 | 40 | 0 | 75 | 30 |
| Ducksalad | 60 | 30 | 0 | 50 | 70 | 100 | 95 | 85 | 100 | 20 | 100 | 50 |
| Rice | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

| | 500 g ai/ha Compounds | | | | | | | | | | | |
|---|---|---|---|---|---|---|---|---|---|---|---|---|
| | 206 | 207 | 208 | 210 | 211 | 212 | 247 | 270 | 271 | 275 | 277 | 344 |
| Barnyardgrass | 75 | 70 | 45 | 70 | 55 | 40 | 35 | 60 | 75 | 70 | 70 | 40 |
| Ducksalad | 100 | 100 | 45 | 100 | 75 | 75 | 85 | 100 | 100 | 100 | 05 | 65 |
| Rice | 15 | 15 | 0 | 0 | 15 | 0 | 0 | 0 | 0 | 10 | 0 | 0 |
| Sedge, Umbrella | 0 | 0 | 0 | 0 | 0 | 0 | 0 | 0 | 0 | 0 | 0 | 0 |

| | 500 g ai/ha Compounds | 250 g ai/ha Compounds | | | | | | | | | | |
|---|---|---|---|---|---|---|---|---|---|---|---|---|
| | 346 | 1 | 2 | 3 | 4 | 5 | 7 | 8 | 10 | 11 | 12 | 14 |
| Barnyardgrass | 65 | 0 | 0 | 55 | 40 | 55 | 0 | 0 | 0 | 0 | 65 | 0 |
| Ducksalad | 100 | 0 | 0 | 90 | 85 | 80 | 0 | 0 | 0 | 0 | 0 | 85 |
| Rice | 0 | 0 | 0 | 0 | 0 | 0 | 0 | 0 | 0 | 0 | 0 | 0 |
| Sedge, Umbrella | 0 | 0 | 0 | 50 | 0 | 0 | 0 | 0 | 0 | 0 | 0 | 20 |

| | 250 g ai/ha Compounds | | | | | | | | | | | |
|---|---|---|---|---|---|---|---|---|---|---|---|---|
| | 15 | 16 | 17 | 18 | 19 | 20 | 21 | 23 | 25 | 26 | 27 | 28 |
| Barnyardgrass | 0 | 15 | 25 | 0 | 0 | 0 | 0 | 0 | 0 | 0 | 0 | 0 |
| Ducksalad | 0 | 100 | 100 | 0 | 0 | 0 | 85 | 100 | 60 | 80 | 30 | 85 |
| Rice | 0 | 0 | 0 | 0 | 0 | 0 | 0 | 0 | 0 | 0 | 0 | 0 |
| Sedge, Umbrella | 0 | 0 | 40 | 0 | 0 | 0 | 0 | 30 | 0 | 0 | 0 | 0 |

| | 250 g ai/ha Compounds | | | | | | | | | | | |
|---|---|---|---|---|---|---|---|---|---|---|---|---|
| | 29 | 52 | 77 | 80 | 87 | 89 | 92 | 93 | 101 | 102 | 103 | 107 |
| Barnyardgrass | 0 | 0 | 20 | 20 | 0 | 20 | 10 | 40 | 55 | 0 | 40 | 0 |
| Ducksalad | 40 | 95 | 95 | 100 | 95 | 85 | 70 | 85 | 95 | 0 | 90 | 30 |

TABLE C-continued

| | | | | | | | | | | | | |
|---|---|---|---|---|---|---|---|---|---|---|---|---|
| Rice | 0 | 15 | 0 | 0 | 0 | 0 | 20 | 30 | 0 | 0 | 0 | 0 |
| Sedge, Umbrella | 0 | 75 | 0 | 65 | 0 | 0 | 0 | 100 | 0 | 0 | 0 | 0 |

250 g ai/ha Compounds

| | 111 | 112 | 113 | 114 | 119 | 120 | 189 | 190 | 200 | 203 | 204 | 205 |
|---|---|---|---|---|---|---|---|---|---|---|---|---|
| Barnyardgrass | 0 | 0 | 0 | 0 | 75 | 60 | 30 | 25 | 25 | 0 | 70 | 20 |
| Ducksalad | 0 | 0 | 30 | 30 | 100 | 100 | 80 | 75 | 70 | 0 | 95 | 0 |
| Rice | 0 | 0 | 0 | 0 | 20 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

250 g ai/ha Compounds

| | 206 | 207 | 208 | 210 | 211 | 212 | 223 | 224 | 232 | 247 | 263 | 270 |
|---|---|---|---|---|---|---|---|---|---|---|---|---|
| Barnyardgrass | 60 | 60 | 20 | 45 | 50 | 15 | 0 | 60 | 60 | 25 | 80 | 30 |
| Ducksalad | 100 | 75 | 45 | 80 | 100 | 70 | 95 | 100 | 95 | 75 | 100 | 85 |
| Rice | 0 | 15 | 0 | 0 | 0 | 0 | 0 | 20 | 15 | 0 | 15 | 0 |
| Sedge, Umbrella | 0 | 0 | 0 | 0 | 0 | 0 | 0 | 0 | 0 | 0 | 0 | 0 |

| 250 g ai/ha Compounds | | | | | | | | | | | 125 g ai/ha Compounds |
|---|---|---|---|---|---|---|---|---|---|---|---|

| | 271 | 275 | 277 | 303 | 312 | 317 | 318 | 323 | 324 | 344 | 346 | 1 |
|---|---|---|---|---|---|---|---|---|---|---|---|---|
| Barnyardgrass | 45 | 60 | 70 | 70 | 60 | 30 | 70 | 65 | 70 | 35 | 45 | 0 |
| Ducksalad | 100 | 100 | 85 | 100 | 95 | 0 | 100 | 100 | 100 | 60 | 100 | 0 |
| Rice | 0 | 10 | 0 | 0 | 0 | 0 | 15 | 30 | 0 | 0 | 0 | 0 |
| Sedge, Umbrella | 0 | 0 | 0 | 0 | 0 | 0 | 0 | 0 | 0 | 0 | 0 | 0 |

125 g ai/ha Compounds

| | 2 | 3 | 4 | 5 | 7 | 8 | 10 | 11 | 12 | 16 | 17 | 18 |
|---|---|---|---|---|---|---|---|---|---|---|---|---|
| Barnyardgrass | 0 | 40 | 30 | 20 | 0 | 0 | 0 | 0 | 0 | 0 | 20 | 0 |
| Ducksalad | 0 | 85 | 80 | 70 | 0 | 0 | 0 | 0 | 0 | 85 | 100 | 0 |
| Rice | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

125 g ai/ha Compounds

| | 19 | 20 | 21 | 28 | 29 | 52 | 80 | 87 | 89 | 92 | 93 | 101 |
|---|---|---|---|---|---|---|---|---|---|---|---|---|
| Barnyardgrass | 0 | 0 | 0 | 0 | 0 | 0 | 0 | 0 | 20 | 10 | 0 | 20 |
| Ducksalad | 0 | 0 | 50 | 40 | 0 | 75 | 100 | 75 | 70 | 20 | 0 | 90 |
| Rice | 0 | 0 | 0 | 0 | 0 | 10 | 0 | 0 | 0 | 20 | 20 | 0 |
| Sedge, Umbrella | 0 | 0 | 0 | 0 | 0 | 50 | 55 | 0 | 0 | 0 | 0 | 0 |

125 g ai/ha Compounds

| | 102 | 103 | 107 | 111 | 112 | 113 | 114 | 119 | 120 | 189 | 190 | 200 |
|---|---|---|---|---|---|---|---|---|---|---|---|---|
| Barnyardgrass | 0 | 10 | 0 | 0 | 0 | 0 | 0 | 60 | 50 | 10 | 10 | 15 |
| Ducksalad | 0 | 85 | 0 | 0 | 0 | 20 | 20 | 100 | 100 | 75 | 50 | 70 |
| Rice | 0 | 0 | 9 | 0 | 0 | 0 | 0 | 10 | 0 | 0 | 0 | 0 |
| Sedge, Umbrella | 0 | 0 | 0 | 0 | 0 | 0 | 0 | 0 | 0 | 0 | 0 | 0 |

125 g ai/ha Compounds

| | 203 | 204 | 205 | 206 | 207 | 208 | 210 | 211 | 212 | 223 | 224 | 232 |
|---|---|---|---|---|---|---|---|---|---|---|---|---|
| Barnyardgrass | 0 | 50 | 0 | 35 | 40 | 0 | 0 | 0 | 0 | 0 | 40 | 40 |
| Ducksalad | 0 | 50 | 0 | 90 | 60 | 0 | 0 | 60 | 0 | 65 | 80 | 75 |
| Rice | 0 | 0 | 0 | 0 | 15 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

125 g ai/ha Compounds

| | 263 | 270 | 271 | 275 | 277 | 303 | 312 | 317 | 318 | 323 | 324 | 344 |
|---|---|---|---|---|---|---|---|---|---|---|---|---|
| Barnyardgrass | 45 | 10 | 40 | 45 | 65 | 60 | 30 | 30 | 60 | 50 | 60 | 0 |
| Ducksalad | 100 | 75 | 70 | 100 | 80 | 70 | 65 | 0 | 100 | 90 | 95 | 50 |

TABLE C-continued

|  | | | | | | | | | | | | |
|---|---|---|---|---|---|---|---|---|---|---|---|---|
| Rice | 0 | 0 | 0 | 0 | 0 | 0 | 0 | 0 | 10 | 0 | 0 | 0 |
| Sedge, Umbrella | 0 | 0 | 0 | 0 | 0 | 0 | 0 | 0 | 0 | 0 | 0 | 0 |

| | 125 g ai/ha Compounds | 62 g ai/ha Compounds | | | | | | | | | | |
|---|---|---|---|---|---|---|---|---|---|---|---|---|
| | 346 | 1 | 2 | 3 | 4 | 5 | 7 | 8 | 10 | 11 | 12 | 14 |
| Barnyardgrass | 30 | 0 | 0 | 20 | 0 | 0 | 0 | 0 | 0 | 0 | 0 | 0 |
| Ducksalad | 95 | 0 | 0 | 60 | 30 | 30 | 0 | 0 | 0 | 0 | 0 | 40 |
| Rice | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

| | 62 g ai/ha Compounds | | | | | | | | | | | |
|---|---|---|---|---|---|---|---|---|---|---|---|---|
| | 15 | 16 | 17 | 18 | 19 | 20 | 21 | 23 | 25 | 26 | 27 | 28 |
| Barnyardgrass | 0 | 0 | 0 | 0 | 0 | 0 | 0 | 0 | 0 | 0 | 0 | 0 |
| Ducksalad | 0 | 40 | 80 | 0 | 0 | 0 | 0 | 30 | 0 | 0 | 0 | 30 |
| Rice | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

| | 62 g ai/ha Compounds | | | | | | | | | | | |
|---|---|---|---|---|---|---|---|---|---|---|---|---|
| | 29 | 52 | 80 | 92 | 93 | 119 | 120 | 223 | 224 | 232 | 263 | 275 |
| Barnyardgrass | 0 | 0 | 0 | 10 | 0 | 50 | 40 | 0 | 20 | 30 | 35 | 35 |
| Ducksalad | 0 | 40 | 70 | 20 | 0 | 100 | 100 | 50 | 40 | 7 | 90 | 85 |
| Rice | 0 | 10 | 0 | 10 | 20 | 0 | 0 | 0 | 0 | 0 | 0 | 0 |
| Sedge, Umbrella | 0 | 40 | 35 | 0 | 0 | 0 | 0 | 0 | 0 | 0 | 0 | 0 |

| | 62 g ai/ha Compounds | | | | | | | 31 g ai/ha Compounds | | | | |
|---|---|---|---|---|---|---|---|---|---|---|---|---|
| | 277 | 303 | 312 | 317 | 318 | 323 | 324 | 1 | 2 | 3 | 4 | 7 |
| Barnyardgrass | 50 | 20 | 0 | 0 | 30 | 45 | 0 | 0 | 0 | 0 | 0 | 0 |
| Ducksalad | 65 | 60 | 60 | 0 | 60 | 75 | 70 | 0 | 0 | 40 | 20 | 0 |
| Rice | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

| | 31 g ai/ha Compounds | | | | | | | | | | | |
|---|---|---|---|---|---|---|---|---|---|---|---|---|
| | 8 | 10 | 11 | 12 | 16 | 17 | 18 | 19 | 20 | 21 | 28 | 29 |
| Barnyardgrass | 0 | 0 | 0 | 0 | 0 | 0 | 0 | 0 | 0 | 0 | 0 | 0 |
| Ducksalad | 0 | 0 | 0 | 0 | 0 | 40 | 0 | 0 | 0 | 0 | 20 | 0 |
| Rice | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 |

| | 31 g ai/ha Compounds | | | | | | | | | | | |
|---|---|---|---|---|---|---|---|---|---|---|---|---|
| | 52 | 80 | 92 | 93 | 119 | 223 | 224 | 232 | 263 | 303 | 312 | 317 |
| Barnyardgrass | 0 | 0 | 10 | 0 | 30 | 0 | 0 | 0 | 20 | 0 | 0 | 0 |
| Ducksalad | 40 | 70 | 0 | 0 | 100 | 30 | 0 | 50 | 70 | 50 | 50 | 0 |
| Rice | 10 | 0 | 10 | 10 | 0 | 0 | 0 | 0 | 0 | 0 | 0 | 0 |
| Sedge, Umbrella | 0 | 35 | 0 | 0 | 0 | 0 | 0 | 0 | 0 | 0 | 0 | 0 |

| | 31 g ai/ha Compounds | | |
|---|---|---|---|
| | 318 | 323 | 324 |
| Barnyardgrass | 20 | 25 | 0 |
| Ducksalad | 50 | 50 | 40 |
| Rice | 0 | 0 | 0 |
| Sedge, Umbrella | 0 | 0 | 0 |

Test D

Seeds of plant species selected from bluegrass (annual bluegrass, *Poa annua*), blackgrass (*Alopecurus myosuroides*), canarygrass (littleseed canarygrass. *Phalaris minor*), chickweed (common chickweed, *Stellaria media*), galium (catchweed bedstraw, *Galium aparine*), bromegrass, downy (downy bromegrass, *Bromus tectorum*), field poppy (*Papaver rhoeas*), field violet (*Viola arvensis*), foxtail, green (green foxtail, *Setaria viridis*), deadnettle (henbit deadnettle, *Lamium amplexicaule*), ryegrass, Italian (Italian ryegrass,

*Lolium multilorum*), kochia (*Kochia scoparia*), lambsquarters (*Chenopodium album*), oilseed rape (*Brassica napus*), pigweed (*Amaranthus retrolexus*), chamomile (scentless chamomile, *Matricaria inodora*), Russian thistle (*Salsola kali*), speedwell (bird's-eye speedwell, *Veronica persica*), barley, spring (spring barley, *Hordeum vulgare*), wheat, spring (spring wheat, *Triticum aestivum*), buckwheat, wild (wild buckwheat, *Polygonum convolvulus*), mustard, wild (wild mustard, *Sinapis arvensis*), oat, wild (wild oat, *Avena fatua*), radish, wild (wild radish, *Raphanus raphanistrum*), windgrass (*Apera spica-venti*), barley, winter (winter barley, *Hordeum vulgare*), and wheat, winter (winter wheat, *Triticum aestivum*) were planted into a silt loam soil and treated preemergence with test chemicals formulated in a non-phytotoxic solvent mixture which included a surfactant.

At the same time, these species were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of the test chemicals formulated in the same manner. Plants ranged in height from 2 to 18 cm (1- to 4-leaf stage). Treated plants and controls were maintained in a controlled growth environment for 7 to 21 days after which time all species were compared to controls and visually evaluated. Plant response ratings, summarized in Table D, are based on a scale of 0 to 100 where 0 is no effect and 100 is complete control. A dash (-) response means no test result.

TABLE D

Postemergence

| | 250 g ai/ha Compounds | | | | | | | | | 125 g ai/ha Compounds | | | | | | | | | | 62 g ai/ha Compounds | | | | |
|---|---|---|---|---|---|---|---|---|---|---|---|---|---|---|---|---|---|---|---|---|---|---|---|---|
| | 6 | 12 | 17 | 33 | 34 | 52 | 80 | 202 | 231 | 6 | 12 | 17 | 33 | 34 | 50 | 52 | 80 | 202 | 231 | 6 | 12 | 17 | 33 | 34 |
| Barley, Spring | 0 | 5 | 0 | 0 | 0 | 0 | 0 | 5 | 0 | 0 | 5 | 0 | 0 | 0 | 0 | 0 | 0 | 0 | 0 | 0 | 5 | 0 | 0 | 0 |
| Barley, Winter | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 10 | 20 | 0 | 0 | 0 | 0 | 5 | 40 | 20 | 5 | 15 | 0 | 0 | 0 | 0 | 0 | 5 | 10 | 10 | 5 | 10 | 0 | 0 | 0 |
| Bluegrass | 0 | 10 | 0 | 0 | 0 | 0 | 10 | 15 | 10 | 0 | 10 | 0 | 0 | 0 | 0 | 0 | 15 | 10 | 10 | 0 | 0 | 0 | 0 | 0 |
| Bromegrass, Downy | 0 | 5 | 0 | 0 | 0 | 0 | 20 | 15 | 25 | 0 | 0 | 0 | 0 | 0 | 0 | 0 | 20 | 5 | 25 | 0 | 0 | 0 | 0 | 0 |
| Buckwheat, Wild | 10 | 10 | 20 | 10 | 0 | 0 | 0 | 10 | 0 | 0 | 10 | 10 | 0 | 0 | 10 | 0 | 0 | 0 | 0 | 0 | 10 | 0 | 0 | 0 |
| Canarygrass | 0 | 30 | 0 | 0 | 0 | 0 | 0 | 0 | 0 | 0 | 15 | 0 | 0 | 0 | 0 | 0 | 0 | 0 | 0 | 0 | 15 | 0 | 0 | 0 |
| Chamomile | 0 | 0 | 0 | 0 | 0 | 20 | 50 | 60 | 50 | 0 | 0 | 0 | 0 | 0 | 0 | 20 | 35 | 65 | 50 | 0 | 0 | 0 | 0 | 0 |
| Chickweed | 30 | 30 | 30 | 10 | 20 | 25 | 85 | 80 | 80 | 10 | 20 | 25 | 10 | 10 | 15 | 15 | 85 | 80 | 80 | 0 | 0 | 0 | 0 | 0 |
| Deadnettle | 10 | 20 | 10 | 10 | 0 | 25 | 40 | 70 | 70 | 10 | 15 | 10 | 0 | 0 | 0 | 20 | 70 | 60 | 35 | 0 | 10 | 0 | 0 | 0 |
| Field Poppy | 30 | 80 | 0 | 0 | 20 | 0 | 50 | 100 | 50 | 20 | 60 | 0 | 0 | 0 | 0 | 0 | 20 | 100 | 0 | 20 | 50 | 0 | 0 | 0 |
| Field Violet | 25 | 40 | 10 | 0 | 20 | 0 | 25 | 30 | 25 | 20 | 35 | 0 | 0 | 0 | 0 | 0 | 15 | 30 | 10 | 20 | 30 | 0 | 0 | 0 |
| Foxtail, Green | 20 | 25 | 0 | 0 | 0 | 0 | 65 | 70 | 70 | 0 | 20 | 0 | 0 | 0 | 0 | 0 | 65 | 70 | 70 | 0 | 10 | 0 | 0 | 0 |
| *Galium* | 0 | 25 | 30 | 0 | 0 | 35 | 60 | 70 | 55 | 0 | 20 | 10 | 0 | 0 | 0 | 25 | 55 | 70 | 55 | 0 | 15 | 0 | 0 | 0 |
| *Kochia* | 10 | 35 | 40 | 10 | 25 | 35 | 75 | 75 | 65 | 5 | 20 | 20 | 0 | 10 | 0 | 25 | 70 | 75 | 60 | 5 | 20 | 20 | 0 | 0 |
| Lambsquarters | 30 | 25 | 40 | 20 | 20 | 30 | 35 | 75 | 75 | 20 | 10 | 20 | 0 | 0 | 20 | 30 | 40 | 70 | 70 | 20 | 10 | 0 | 0 | 0 |
| Mustard, Wild | 0 | — | 30 | 0 | 20 | 25 | 85 | 85 | 75 | 0 | 100 | 30 | 0 | 10 | 40 | 20 | 85 | 80 | 65 | — | 40 | 10 | 0 | 0 |
| Oat, Wild | 5 | 20 | 0 | 0 | 0 | 0 | 10 | 15 | 10 | 0 | 15 | 0 | 0 | 0 | 0 | 0 | 5 | 10 | 10 | 0 | 10 | 0 | 0 | 0 |
| Oilseed Rape | 20 | 25 | 40 | 30 | 20 | 25 | 60 | 55 | 40 | 15 | 20 | 20 | 20 | 0 | 5 | 10 | 45 | 60 | 20 | 10 | 10 | 10 | 10 | 0 |
| Pigweed | 20 | 50 | 50 | 10 | 10 | 40 | 75 | 80 | 45 | 20 | 30 | 50 | 10 | 0 | 10 | 30 | 70 | 75 | 35 | 10 | 25 | 40 | 0 | 0 |
| Radish, Wild | 10 | 25 | 15 | 0 | 0 | — | 60 | 70 | 70 | 0 | 25 | 15 | 0 | 0 | 0 | — | 35 | 75 | 75 | 0 | 20 | 0 | 0 | 0 |
| Russian Thistle | 100 | 80 | 40 | 0 | 0 | 0 | 35 | 35 | 35 | 0 | 30 | 20 | 0 | 0 | 5 | 0 | 25 | 30 | 35 | 0 | 20 | 0 | 0 | 0 |
| Ryegrass, Italian | 0 | 15 | 0 | 0 | 0 | 0 | 0 | 15 | 0 | 0 | 10 | 0 | 0 | 0 | 0 | 0 | 0 | 10 | 0 | 0 | 0 | 0 | 0 | 0 |
| Speedwell | 15 | 25 | 0 | 10 | 30 | 70 | 65 | 90 | 75 | 0 | 10 | 0 | 0 | 0 | — | 40 | 70 | 85 | 75 | 0 | 10 | 0 | 0 | 0 |
| Wheat, Spring | 5 | 0 | 0 | 0 | 0 | 0 | 0 | 5 | 0 | 5 | 0 | 0 | 0 | 0 | 0 | 0 | 0 | 0 | 0 | 5 | 0 | 0 | 0 | 0 |
| Wheat, Winter | 0 | 0 | 0 | 0 | 0 | 0 | 5 | 0 | 0 | 0 | 0 | 0 | 0 | 0 | 0 | 0 | 0 | 10 | 0 | 0 | 0 | 0 | 0 | 0 |
| Windgrass | 0 | 5 | 0 | 0 | 0 | 0 | 25 | 45 | 15 | 0 | 0 | 0 | 0 | 0 | 0 | 0 | 0 | 10 | 35 | 0 | 0 | 0 | 0 | 0 |

| | 62 g ai/ha Compounds | | | | | 31 g ai/ha Compounds | | | | | | | | | | 16 g ai/ha Compounds | | | | | | |
|---|---|---|---|---|---|---|---|---|---|---|---|---|---|---|---|---|---|---|---|---|---|---|
| | 50 | 52 | 80 | 202 | 231 | 6 | 12 | 17 | 33 | 34 | 50 | 52 | 80 | 202 | 231 | 6 | 12 | 17 | 33 | 34 | 50 | 52 |
| Barley, Spring | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barley, Winter | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 0 | 5 | 5 | 10 | 0 | 10 | 0 | 0 | 0 | 0 | 0 | 5 | 0 | 0 | 0 | 5 | 0 | 0 | 0 | 0 | 0 |
| Bluegrass | 0 | 0 | 10 | 10 | 10 | 0 | 0 | 0 | 0 | 0 | 0 | 0 | 5 | 0 | 5 | 0 | 0 | 0 | 0 | 0 | 0 | 0 |
| Bromegrass, Downy | 0 | 0 | 15 | 0 | 20 | 0 | 0 | 0 | 0 | 0 | 0 | 0 | 15 | 0 | 15 | 0 | 0 | 0 | 0 | 0 | 0 | 0 |
| Buckwheat, Wild | 10 | 0 | 10 | 0 | 0 | 0 | 0 | 0 | 0 | 0 | 10 | 0 | 0 | 0 | 0 | 0 | 0 | 0 | 0 | 0 | 10 | 0 |
| Canarygrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chamomile | 0 | 0 | 30 | 60 | 25 | 0 | 0 | 0 | 0 | 0 | 0 | 0 | 20 | 5 | 20 | 0 | 0 | 0 | 0 | 0 | 0 | 0 |
| Chickweed | 20 | 10 | 45 | 75 | 80 | 0 | 0 | 0 | 0 | 0 | 15 | 0 | 35 | 75 | 25 | 0 | 0 | 0 | 0 | 0 | 10 | 0 |
| Deadnettle | 0 | 0 | 60 | 35 | 70 | 0 | 0 | 0 | 0 | 0 | 0 | 0 | 70 | 5 | 35 | 0 | 0 | 0 | 0 | 0 | 0 | 0 |
| Field Poppy | 0 | 0 | 55 | 75 | 20 | 0 | 0 | 0 | 0 | 0 | 0 | 0 | 25 | 0 | 0 | 0 | 0 | 0 | 0 | 0 | 0 | 0 |
| Field Violet | 0 | 0 | 20 | 30 | 20 | 0 | 0 | 0 | 0 | 0 | 0 | 0 | 15 | 40 | 20 | 0 | 0 | 0 | 0 | 0 | 0 | 0 |
| Foxtail, Green | 0 | 0 | 45 | 65 | 65 | 0 | 0 | 0 | 0 | 0 | 0 | 0 | 45 | 60 | 10 | 0 | 0 | 0 | 0 | 0 | 0 | 0 |
| *Galium* | 0 | 0 | 45 | 70 | 45 | 0 | 0 | 0 | 0 | 0 | 0 | 0 | 20 | 60 | 40 | 0 | 0 | 0 | 0 | 0 | 0 | 0 |
| *Kochia* | 15 | 20 | 75 | 70 | 60 | 5 | 5 | 0 | 0 | — | 15 | 0 | 65 | 70 | 55 | 0 | 5 | 0 | 0 | 0 | 10 | 0 |
| Lambsquarters | 5 | 0 | 45 | 60 | 50 | 10 | 0 | 0 | 0 | 0 | 5 | 0 | 45 | 65 | 55 | 0 | 0 | 0 | 0 | 0 | 5 | 0 |
| Mustard, Wild | — | 20 | 80 | 80 | 65 | 0 | 10 | 0 | 0 | 0 | 60 | 10 | 70 | 85 | 35 | 0 | 0 | 0 | 0 | 0 | 40 | 0 |
| Oat, Wild | 0 | 0 | 10 | 10 | 10 | 0 | 0 | 0 | 0 | 0 | 0 | 0 | 10 | 5 | 5 | 0 | 0 | 0 | 0 | 0 | 0 | 0 |
| Oilseed Rape | 5 | 0 | 50 | 70 | 10 | 10 | 10 | 0 | 0 | 0 | 5 | 0 | 30 | 60 | 15 | 10 | 10 | 0 | 0 | 0 | 5 | 0 |
| Pigweed | 0 | 0 | 70 | 75 | 35 | 10 | 10 | 0 | 0 | 0 | 0 | 0 | 40 | 75 | 20 | 0 | 0 | 0 | 0 | 0 | 5 | 0 |
| Radish, Wild | 0 | — | 70 | 70 | 70 | 0 | 0 | 0 | 0 | 0 | 0 | — | 50 | 50 | 30 | 0 | 0 | 0 | 0 | 0 | 0 | — |

TABLE D-continued

| | | | | | | | | | | | | | | | | | | | | | | |
|---|---|---|---|---|---|---|---|---|---|---|---|---|---|---|---|---|---|---|---|---|---|---|
| Russian Thistle | 10 | 0 | 30 | 30 | 35 | 0 | 0 | 0 | 0 | 0 | 0 | 0 | 20 | 30 | 20 | 0 | 0 | 0 | 0 | 0 | 5 | 0 |
| Ryegrass, Italian | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Speedwell | — | 25 | 70 | 75 | 70 | 0 | 0 | 0 | 0 | 0 | — | 20 | 60 | 60 | 60 | 0 | 0 | 0 | 0 | 0 | 0 | 20 |
| Wheat, Spring | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat, Winter | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Windgrass | 0 | 0 | 10 | 10 | 5 | 0 | 0 | 0 | 0 | 0 | 0 | 0 | 0 | 0 | 0 | 0 | 0 | 0 | 0 | 0 | 0 | 0 |

Preemergence

| | 250 g ai/ha Compounds | | | | | | | | | | | 125 g ai/ha Compounds | | | | | | |
|---|---|---|---|---|---|---|---|---|---|---|---|---|---|---|---|---|---|---|
| | 6 | 12 | 52 | 77 | 80 | 202 | 204 | 206 | 207 | 231 | 241 | 6 | 12 | 50 | 52 | 77 | 80 | 202 |
| Barley, Spring | 10 | 0 | 5 | 25 | 30 | 30 | 45 | 55 | 25 | 35 | 35 | 0 | 0 | 0 | 0 | 25 | 15 | 25 |
| Barley, Winter | 20 | 0 | 25 | 55 | 25 | 25 | 35 | 65 | 45 | 20 | 65 | 0 | 0 | 0 | 0 | 45 | 15 | 20 |
| Blackgrass | 0 | 0 | 0 | 65 | 25 | 75 | 65 | 90 | 75 | 55 | 75 | 0 | 0 | 0 | 0 | 40 | 20 | 65 |
| Bluegrass | 0 | 40 | 20 | 55 | 45 | 70 | 35 | 70 | 30 | 25 | 70 | 0 | 20 | 0 | 0 | 45 | 20 | 65 |
| Bromegrass, Downy | 10 | 10 | 0 | 25 | 10 | 20 | 45 | 70 | 15 | 15 | 60 | 0 | 0 | 0 | 0 | 10 | 5 | 0 |
| Buckwheat, Wild | 0 | 100 | 10 | 55 | 15 | 15 | 25 | 55 | 35 | 10 | 80 | 0 | 0 | — | 10 | 55 | 5 | 10 |
| Canarygrass | 20 | 40 | 0 | 85 | 20 | 75 | 75 | 85 | 75 | 35 | 75 | 20 | 20 | 0 | 0 | 65 | 10 | 60 |
| Chamomile | 90 | 20 | 80 | — | 85 | 100 | — | — | 85 | 100 | — | 70 | 0 | 5 | 75 | — | 80 | 75 |
| Chickweed | — | 0 | — | 100 | 100 | 95 | 100 | 95 | 100 | 90 | 100 | — | 0 | 0 | — | 100 | 100 | 90 |
| Deadnettle | 40 | 50 | 30 | 75 | 70 | 85 | 35 | 75 | 20 | 85 | 45 | 40 | 0 | 100 | 0 | 60 | 65 | 80 |
| Field Poppy | 100 | 0 | 80 | 100 | 100 | 100 | 95 | 95 | 100 | 95 | 100 | 0 | 0 | 65 | — | 95 | 100 | 90 |
| Field Violet | 0 | 0 | — | 55 | 25 | 15 | 25 | 25 | 35 | 0 | 30 | 0 | 0 | 0 | — | 20 | 20 | 10 |
| Foxtail, Green | 10 | 0 | 60 | 85 | 80 | 95 | 100 | 98 | 90 | 98 | 90 | 0 | 0 | 40 | 0 | 70 | 75 | 98 |
| Galium | 100 | 10 | 20 | 85 | 75 | 85 | 25 | 80 | 20 | 40 | 80 | 100 | 0 | 0 | 0 | 85 | 65 | 80 |
| Kochia | 50 | 0 | 40 | 85 | 75 | 85 | 70 | 80 | 60 | 85 | 70 | 40 | 0 | 0 | 20 | 80 | 70 | 85 |
| Lambsquarters | 0 | 30 | 20 | 90 | 90 | 85 | 90 | 90 | 90 | 90 | 90 | 0 | 30 | 0 | 20 | 90 | 90 | 85 |
| Mustard, Wild | 20 | 70 | 10 | 45 | 70 | 75 | 20 | 75 | 30 | 15 | 25 | 10 | 20 | 80 | 0 | 25 | 65 | 20 |
| Oat, Wild | 0 | 0 | 0 | 45 | 20 | 40 | 40 | 55 | 20 | 30 | 55 | 0 | 0 | 0 | 0 | 20 | 10 | 35 |
| Oilseed Rape | 20 | 20 | 10 | 5 | 30 | 75 | 0 | 5 | 0 | 55 | 10 | 10 | 10 | 0 | 10 | 5 | 10 | 45 |
| Pigweed | 0 | 0 | 15 | 80 | 45 | 90 | 35 | 50 | 5 | 80 | 80 | 0 | 0 | 5 | 10 | 80 | 20 | 90 |
| Radish, Wild | — | — | — | 30 | 70 | 80 | 0 | 30 | 15 | 0 | 0 | — | — | — | — | 25 | 30 | 0 |
| Russian Thistle | 30 | 0 | 30 | — | — | 40 | — | — | — | 30 | — | 10 | 0 | 0 | 20 | — | — | 35 |
| Ryegrass, Italian | 0 | 0 | 0 | 35 | 15 | 10 | 60 | 75 | 15 | 0 | 50 | 0 | 0 | 0 | 0 | 25 | 5 | 5 |
| Speedwell | 50 | 100 | 100 | 100 | 100 | 100 | 70 | 90 | 30 | 100 | 85 | 30 | 0 | 0 | 100 | 35 | 85 | 90 |
| Wheat, Spring | 0 | 0 | 0 | 25 | 20 | 35 | 30 | 65 | 10 | 20 | 40 | 0 | 0 | 0 | 0 | 20 | 10 | 25 |
| Wheat, Winter | 0 | 0 | 10 | 55 | 10 | 25 | 20 | 30 | 20 | 25 | 25 | 0 | 0 | 0 | 0 | 25 | 10 | 25 |
| Windgrass | 100 | 0 | 60 | 95 | 90 | 90 | 95 | 90 | 65 | 85 | 98 | 100 | 0 | 0 | 40 | 90 | 75 | 90 |

| | 125 g ai/ha Compounds | | | | | 62 g ai/ha Compounds | | | | | | | | | | | |
|---|---|---|---|---|---|---|---|---|---|---|---|---|---|---|---|---|---|
| | 204 | 206 | 207 | 231 | 241 | 6 | 12 | 50 | 52 | 77 | 80 | 202 | 204 | 206 | 207 | 231 | 241 |
| Barley, Spring | 20 | 40 | 20 | 5 | 20 | 0 | 0 | 0 | 0 | 5 | 10 | 25 | 15 | 35 | 5 | 5 | 10 |
| Barley, Winter | 25 | 40 | 25 | 0 | 30 | 0 | 0 | 0 | 0 | 0 | 5 | 20 | 20 | 30 | 10 | 0 | 10 |
| Blackgrass | 40 | 85 | 20 | 15 | 50 | 0 | 0 | 0 | 0 | 25 | 10 | 35 | 10 | 70 | 5 | 0 | 55 |
| Bluegrass | 15 | 35 | 15 | 15 | 45 | 0 | 0 | 0 | 0 | 5 | 10 | 25 | 0 | 30 | 15 | 0 | 15 |
| Bromegrass, Downy | 35 | 55 | 15 | 0 | 15 | 0 | 0 | 0 | 0 | 0 | 5 | 0 | 20 | 25 | 15 | 0 | 15 |
| Buckwheat, Wild | 25 | 50 | 25 | 0 | 20 | 0 | 0 | 0 | 0 | 75 | 0 | 10 | 25 | 65 | 15 | 0 | 15 |
| Canarygrass | 10 | 85 | 0 | 20 | 65 | 10 | 0 | 0 | 0 | 45 | 0 | 10 | 10 | 75 | 5 | 15 | 45 |
| Chamomile | — | — | 85 | 80 | — | 30 | 0 | 0 | 75 | — | 80 | 65 | — | — | 80 | 75 | — |
| Chickweed | 100 | 70 | 70 | 95 | 95 | — | 0 | 0 | — | 90 | 100 | 80 | 100 | 100 | 60 | 85 | 80 |
| Deadnettle | 25 | 40 | 20 | 60 | 35 | 0 | 0 | 100 | 0 | 65 | 0 | 65 | 25 | 35 | 0 | 75 | 30 |
| Field Poppy | 80 | 90 | 80 | 100 | 95 | 0 | 0 | 0 | 50 | 90 | 100 | 85 | 85 | 90 | 75 | 80 | 95 |
| Field Violet | 25 | 35 | 35 | 10 | 20 | 0 | 0 | 0 | — | 20 | 20 | 0 | 15 | 35 | 15 | 0 | 15 |
| Foxtail, Green | 98 | 98 | 75 | 95 | 90 | 0 | 0 | 50 | 0 | 80 | 65 | 90 | 98 | 95 | 60 | 80 | 90 |
| Galium | 10 | 50 | 45 | 35 | 35 | 50 | 0 | 0 | 0 | 55 | 45 | 70 | 10 | 40 | 60 | 40 | 25 |
| Kochia | 15 | 70 | 10 | 80 | 80 | 30 | 0 | 10 | 20 | 75 | 35 | 85 | 45 | 60 | 10 | 20 | 30 |
| Lambsquarters | 65 | 85 | 65 | 90 | 90 | 0 | 0 | 0 | 0 | 85 | 80 | 85 | 30 | 80 | 30 | 80 | 90 |
| Mustard, Wild | 20 | 0 | 25 | 0 | 15 | 0 | 0 | 0 | 0 | 20 | 25 | 0 | 20 | 0 | 25 | 10 | 15 |
| Oat, Wild | 60 | 40 | 5 | 25 | 20 | 0 | 0 | 0 | 0 | 15 | 5 | 20 | 25 | 35 | 0 | 20 | 15 |
| Oilseed Rape | 0 | 0 | 0 | 45 | 5 | 0 | 10 | 0 | 0 | 5 | 10 | 35 | 0 | 0 | 0 | 0 | 0 |
| Pigweed | 35 | 40 | 0 | 60 | 85 | 0 | 0 | 25 | 10 | 70 | 10 | 80 | 5 | 20 | 0 | 50 | 15 |
| Radish, Wild | 0 | 30 | 15 | 0 | 0 | — | — | 0 | — | 10 | 30 | 0 | 0 | 25 | 10 | 0 | 0 |
| Russian Thistle | — | — | — | 15 | — | 0 | 0 | 0 | 0 | — | — | 20 | — | — | 0 | 5 | — |
| Ryegrass, Italian | 45 | 55 | 5 | 0 | 20 | 0 | 0 | 0 | 0 | 15 | 5 | 5 | 15 | 30 | 5 | 0 | 20 |
| Speedwell | 10 | 65 | 25 | 100 | 70 | 10 | 0 | 0 | 90 | 25 | 85 | 90 | 10 | 25 | 20 | 80 | 35 |
| Wheat, Spring | 25 | 45 | 10 | 0 | 25 | 0 | 0 | 0 | 0 | 10 | 10 | 5 | 0 | 25 | 10 | 5 | 0 |
| Wheat, Winter | 15 | 25 | 10 | 15 | 10 | 0 | 0 | 0 | 0 | 0 | 5 | 10 | 15 | 0 | 15 | 10 | 5 |
| Windgrass | 85 | 90 | 20 | 75 | 95 | 0 | 0 | 5 | 0 | 85 | 20 | 85 | 65 | 75 | 20 | 70 | 90 |

TABLE D-continued

|  | | 31 g ai/ha Compounds | | | | | | | | | | | 16 g ai/ha Compounds | | | |
|---|---|---|---|---|---|---|---|---|---|---|---|---|---|---|---|---|
|  | | 6 | 12 | 50 | 52 | 77 | 80 | 202 | 204 | 206 | 207 | 231 | 241 | 6 | 12 | 50 | 52 |
| Barley, Spring | | 0 | 0 | 0 | 0 | 5 | 0 | 0 | 0 | 5 | 0 | 0 | 0 | 0 | 0 | 0 | 0 |
| Barley, Winter | | 0 | 0 | 0 | 0 | 0 | 0 | 20 | 0 | 15 | 5 | 0 | 10 | 0 | 0 | 0 | 0 |
| Blackgrass | | 0 | 0 | 0 | 0 | 10 | 5 | 30 | 5 | 30 | 0 | 0 | 20 | 0 | 0 | 0 | 0 |
| Bluegrass | | 0 | 0 | 0 | 0 | 0 | 0 | 10 | 0 | 0 | 0 | 5 | 15 | 0 | 0 | 0 | 0 |
| Bromegrass, Downy | | 0 | 0 | 0 | 0 | 0 | 0 | 0 | 0 | 10 | 0 | 0 | 0 | 0 | 0 | 0 | 0 |
| Buckwheat, Wild | | 0 | 0 | 0 | 0 | 0 | 0 | 0 | 20 | 45 | 0 | 0 | 15 | 0 | 0 | 0 | 0 |
| Canarygrass | | 0 | 0 | 0 | 0 | 25 | 0 | 5 | 0 | 55 | 0 | 0 | 20 | 0 | 0 | 0 | 0 |
| Chamomile | | 0 | 0 | 0 | 20 | — | 80 | 60 | — | — | 75 | 75 | — | 0 | 0 | 0 | 20 |
| Chickweed | | — | — | 0 | — | 75 | 85 | 45 | 100 | 30 | 60 | 75 | 90 | — | — | 0 | — |
| Deadnettle | | 0 | 0 | 50 | 0 | 15 | 0 | 40 | 25 | 20 | 0 | 35 | 35 | 0 | 0 | 50 | 0 |
| Field Poppy | | 0 | 0 | 50 | 50 | 75 | 90 | 85 | 75 | 80 | 55 | 80 | 90 | — | 0 | 0 | 30 |
| Field Violet | | 0 | 0 | 0 | — | 15 | 0 | 0 | 10 | 15 | 10 | 0 | 15 | 0 | 0 | 0 | — |
| Foxtail, Green | | 0 | 0 | 0 | 0 | 15 | 20 | 90 | 90 | 85 | 15 | 45 | 35 | 0 | 0 | 0 | 0 |
| *Galium* | | 0 | 0 | 0 | 0 | 35 | 0 | 75 | 0 | 10 | 55 | 20 | 20 | 0 | 0 | 0 | 0 |
| *Kochia* | | 0 | 0 | 10 | 20 | 35 | 15 | 85 | 20 | 45 | 10 | 0 | 20 | 0 | 0 | 5 | 0 |
| Lambsquarters | | 0 | 0 | 0 | 0 | 85 | 85 | 80 | 35 | 50 | 0 | 45 | 85 | 0 | 0 | 0 | 0 |
| Mustard, Wild | | 0 | 0 | — | 0 | 0 | 0 | 0 | 0 | 0 | 10 | 0 | 10 | 0 | 0 | 50 | 0 |
| Oat, Wild | | 0 | 0 | 0 | 0 | 10 | 0 | 5 | 0 | 25 | 0 | 20 | 15 | 0 | 0 | 0 | 0 |
| Oilseed Rape | | 0 | 0 | 0 | 0 | 5 | 0 | 0 | 0 | 0 | 0 | 0 | 0 | 0 | 0 | 0 | 0 |
| Pigweed | | 0 | 0 | 10 | 10 | 25 | 5 | 75 | 0 | 5 | 0 | 50 | 15 | 0 | 0 | 10 | 0 |
| Radish, Wild | | — | — | — | — | 0 | 15 | 0 | 0 | 25 | 15 | 0 | 0 | 0 | 0 | 0 | 0 |
| Russian Thistle | | 0 | 0 | 0 | 0 | — | — | 15 | — | — | — | 0 | — | 0 | 0 | 0 | 0 |
| Ryegrass, Italian | | 0 | 0 | 0 | 0 | 15 | 0 | 0 | 5 | 35 | 0 | 0 | 15 | 0 | 0 | 0 | 40 |
| Speedwell | | 10 | 0 | 0 | 90 | 20 | 10 | 90 | 0 | 0 | 20 | 75 | 10 | 0 | 0 | 0 | 0 |
| Wheat, Spring | | 0 | 0 | 0 | 0 | 10 | 0 | 0 | 0 | 10 | 5 | 0 | 0 | 0 | 0 | 0 | 0 |
| Wheat, Winter | | 0 | 0 | 0 | 0 | 0 | 5 | 5 | 5 | 0 | 0 | 5 | 0 | 0 | 0 | 0 | 0 |
| Windgrass | | 0 | 0 | 0 | 0 | 45 | 5 | 65 | 50 | 75 | 5 | 55 | 65 | 0 | 0 | 0 | 0 |

Test E

Seeds of plant species selected from corn (*Zea mays*), soybean (*Glycine max*), velvetleaf (*Abutilon theophrasti*), lambsquarters (*Chenopodium album*), wild poinsettia (*Euphorbia heterophylla*), pigweed, palmer (palmer pigweed, *Amaranthus palmeri*), waterhemp (common waterhemp, *Amaranthus rudis*), surinam grass (*Brachiaria decumbens*), crabgrass, large (large crabgrass, *Digitaria sanguinalis*), crabgrass, Brazil (Brazilian crabgrass, *Digitaria horizontalis*), panicum, fall (fall panicum, *Panicum dichotomiflorum*), foxtail, giant (giant foxtail, *Setaria faberii*), foxtail, green (green foxtail, *Setaria viridis*), goosegrass (*Eleusine indica*), johnsongrass (*Sorghum halepense*), ragweed (common ragweed, *Ambrosia elatior*), barnyardgrass (*Echinochloa crusgalli*), sandbur (southern sandbur, *Cenchrus echinatus*), arrowleaf sida (*Sida rhombifolia*), ryegrass, Italian (Italian ryegrass, *Lolium multiflorum*), dayflower, VA (Virginia dayflower, *Commelina virginica*), field bindweed (*Convolvulus arvensis*), morningglory (*Ipomoea coccinea*), nightshade (eastern black nightshade, *Solanum ptycanthum*), kochia (*Kochia scoparia*), nutsedge, yellow (yellow nutsedge, *Cyperus esculentus*) cocklebur (common cocklebur *Xanthium strumarium*), smartweed (ladysthumb smartweed, *Polygonum Persicaria*) and beggarticks (hairy beggarticks. *Bidens pilosa*), were planted into a silt loam soil and treated preemergence with test chemicals formulated in a nonphytotoxic solvent mixture which included a surfactant. Treated plants and controls were maintained in a greenhouse for 21 days, after which time all species were compared to controls and visually evaluated. Plant response ratings, summarized in Table E, are based on a scale of 0 to 100 where 0 is no effect and 100 is complete control. A dash (-) response means no test result.

TABLE E

| | Preemergence | | | | | | | | | | | | | | | | | | | |
|---|---|---|---|---|---|---|---|---|---|---|---|---|---|---|---|---|---|---|---|---|
| | 250 g ai/ha Compounds | | | | | | | | | | 125 g ai/ha Compounds | | | | | | | | | |
| | 14 | 16 | 17 | 66 | 80 | 103 | 202 | 204 | 206 | 232 | 350 | 14 | 16 | 17 | 66 | 80 | 103 | 202 | 204 | 206 | 232 |
| Arrowleaf Sida | 0 | 0 | 0 | 0 | 10 | 65 | 80 | 0 | 50 | 90 | 50 | 0 | 0 | 0 | 0 | 0 | 0 | 70 | 0 | 10 | 65 |
| Barnyardgrass | 75 | 70 | 98 | 50 | 80 | 90 | 98 | 98 | 98 | 95 | 98 | 40 | 10 | 95 | 50 | 75 | 50 | 85 | 98 | 95 | 98 |
| Beggarticks | 0 | 0 | — | 0 | 60 | 15 | 80 | 0 | 0 | 60 | 20 | 0 | 0 | — | 0 | 20 | 0 | 35 | 0 | 0 | 20 |
| Cocklebur | 0 | 0 | — | — | 0 | — | — | — | 0 | — | — | 0 | 0 | 0 | — | 0 | — | — | — | 0 | — |
| Corn | 0 | 0 | 0 | 0 | 30 | 0 | 60 | 40 | 70 | 0 | 0 | 0 | 0 | 0 | 0 | 0 | 0 | 40 | 0 | 40 | 0 |
| Crabgrass, Brazil | 95 | 98 | 98 | 98 | 95 | 98 | 98 | 98 | 98 | 98 | 98 | 95 | 80 | 95 | 98 | 70 | 95 | 98 | 98 | 98 | 98 |
| Crabgrass, Large | 90 | 98 | 95 | 98 | 95 | 98 | 98 | 98 | 100 | 98 | 98 | 90 | 75 | 75 | 90 | 95 | 98 | 98 | 98 | 98 | 98 |
| Dayflower, VA | 0 | — | 0 | 0 | 0 | 0 | 40 | 30 | 20 | 10 | 40 | 0 | 0 | 0 | 0 | 0 | 0 | 0 | 20 | 0 | 0 |
| Field Bindweed | 0 | 0 | 0 | 0 | 0 | 35 | 70 | 30 | 50 | 40 | 60 | 0 | 0 | 0 | 0 | 0 | 40 | 50 | 0 | 30 | 40 |
| Foxtail, Giant | 90 | 95 | 98 | — | 90 | 98 | 98 | 98 | 98 | 98 | 80 | 10 | 25 | 95 | 98 | 80 | 95 | 95 | 95 | 98 | 95 |
| Foxtail, Green | 70 | 95 | 95 | 60 | 90 | 98 | 98 | 98 | 98 | 98 | 85 | 10 | 25 | 70 | 35 | 80 | 95 | 98 | 95 | 98 | 98 |
| Goosegrass | 0 | 0 | 35 | 0 | 80 | 0 | 98 | 0 | 90 | 95 | 25 | 0 | 0 | 0 | 0 | 70 | 0 | 90 | 0 | 70 | 85 |
| Johnsongrass | 0 | 0 | 0 | 0 | 30 | 20 | 25 | 40 | 90 | 25 | 0 | 0 | 0 | 0 | 0 | 10 | 0 | 20 | 35 | 75 | 0 |
| *Kochia* | 0 | 0 | 50 | 0 | 90 | 0 | 98 | 40 | 80 | 98 | 90 | 0 | 0 | 25 | 0 | 80 | 0 | 95 | 90 | 50 | 98 |

TABLE E-continued

Preemergence

| | | | | | | | | | | | | | | | | | | | | | |
|---|---|---|---|---|---|---|---|---|---|---|---|---|---|---|---|---|---|---|---|---|---|
| Lambsquarters | 70 | 0 | 0 | 0 | 90 | 98 | 98 | 65 | 98 | 98 | 95 | 50 | — | 0 | 0 | 90 | 65 | 98 | 90 | 95 | 100 |
| Morningglory | 0 | 0 | — | 0 | 40 | 10 | 30 | 30 | 0 | 35 | 0 | 0 | 0 | — | 0 | 20 | 0 | 0 | 20 | 0 | 0 |
| Nightshade | 70 | 0 | 0 | 0 | 70 | 0 | 80 | 100 | 10 | — | 80 | 50 | 0 | 0 | — | 70 | 0 | 90 | 100 | 5 | 98 |
| Nutsedge, Yellow | 0 | 0 | 15 | 0 | 0 | 15 | 0 | 0 | 75 | 0 | 15 | 0 | 0 | 0 | 0 | 0 | 0 | 0 | 0 | 20 | 0 |
| *Panicum*, Fall | 40 | — | 0 | 0 | 0 | 0 | 85 | 75 | 98 | 60 | 0 | — | 0 | 0 | 0 | 0 | 0 | 50 | 75 | 98 | 50 |
| Pigweed, Palmer | 0 | 0 | 0 | — | 90 | 25 | 80 | 0 | 0 | 65 | 35 | 0 | 0 | 0 | — | 65 | 0 | 85 | 0 | 0 | 80 |
| Poinsettia, Wild | 25 | 0 | 20 | 20 | 0 | 0 | 65 | 20 | 25 | 40 | 30 | 20 | 0 | 0 | 0 | 0 | 0 | 25 | 20 | 0 | 35 |
| Ragweed | 0 | 0 | 0 | 20 | 20 | 0 | 90 | 0 | 75 | 95 | 65 | 0 | 0 | 0 | 0 | 0 | 0 | 85 | 0 | 0 | 95 |
| Ryegrass, Italian | 0 | 30 | 0 | 0 | 60 | 0 | 50 | 30 | 65 | 40 | 35 | 0 | 0 | 0 | 0 | 45 | 0 | 25 | 25 | 80 | 20 |
| Sandbur | 30 | 95 | 95 | 35 | 70 | 95 | 80 | 80 | 98 | 90 | 85 | 0 | 70 | 65 | 0 | 65 | 75 | 85 | 75 | 95 | 90 |
| Smartweed | — | — | — | — | 40 | — | — | — | — | — | — | 0 | — | — | — | — | — | — | — | — | — |
| Soybean | 0 | 0 | 0 | 0 | 40 | 0 | 0 | — | 0 | 0 | 0 | 0 | 0 | 0 | 0 | 0 | 0 | 0 | 0 | 0 | 0 |
| Surinam Grass | 60 | 60 | 75 | 35 | 70 | 95 | 95 | 95 | 98 | 98 | 65 | 20 | 35 | 70 | 0 | 60 | 65 | 65 | 98 | 85 | 70 |
| Velvetleaf | 0 | 0 | 0 | 0 | 0 | 0 | 40 | 0 | 50 | 80 | 0 | 0 | 0 | 0 | 0 | 0 | 0 | 0 | 0 | 30 | 20 |
| Waterhemp | 0 | 0 | 0 | 0 | 60 | 0 | 95 | 0 | 50 | 95 | 35 | 0 | 0 | 0 | 0 | 50 | 0 | 95 | 0 | 50 | 85 |

| | 125 g ai/ha Compounds | 62 g ai/ha Compounds | | | | | | | | | | | 31 g ai/ha Compounds | | | | | | | |
|---|---|---|---|---|---|---|---|---|---|---|---|---|---|---|---|---|---|---|---|---|
| | 350 | 14 | 16 | 17 | 66 | 80 | 103 | 202 | 204 | 206 | 232 | 350 | 14 | 16 | 17 | 66 | 80 | 103 | 202 | 204 |
| Arrowleaf Sida | 20 | 0 | 0 | 0 | 0 | 0 | 0 | 30 | 0 | 0 | 20 | 0 | 0 | 0 | 0 | 0 | 0 | 0 | 0 | 0 |
| Barnyardgrass | 60 | 0 | 0 | 80 | 20 | 50 | 30 | 80 | 75 | 75 | 70 | 40 | 0 | 0 | 0 | 0 | 20 | 0 | 40 | 20 |
| Beggarticks | 20 | 0 | — | — | 0 | 0 | 0 | 0 | 0 | 0 | 0 | 0 | 0 | — | — | 0 | 0 | 0 | 0 | 0 |
| Cocklebur | — | 0 | 0 | 0 | 0 | 0 | — | — | — | 0 | — | — | — | 0 | 0 | 0 | — | — | — | — |
| Corn | 0 | 0 | 0 | 0 | 0 | 0 | 0 | 0 | 0 | 50 | 0 | 0 | 0 | 0 | 0 | 0 | 0 | 0 | 0 | 0 |
| Crabgrass, Brazil | 95 | 80 | 65 | 95 | 95 | — | 95 | 98 | 95 | 98 | 98 | 75 | 65 | 25 | 65 | 85 | — | 70 | 80 | 95 |
| Crabgrass, Large | 98 | 25 | 30 | 70 | 75 | 95 | 98 | 98 | 98 | 98 | 98 | 70 | — | 20 | 20 | 10 | 90 | 65 | 98 | 95 |
| Dayflower, VA | 0 | 0 | 0 | 0 | 0 | 0 | 0 | 0 | 0 | 0 | 0 | 0 | 0 | — | 0 | 0 | 0 | 0 | 0 | 0 |
| Field Bindweed | 65 | 0 | 0 | 0 | 0 | 0 | 0 | 40 | 0 | 20 | 0 | 60 | 0 | 0 | 0 | 0 | 0 | 0 | 60 | 0 |
| Foxtail, Giant | 50 | 0 | 15 | 35 | 0 | 75 | 90 | 50 | 95 | 98 | 90 | 20 | 0 | 0 | 35 | 0 | 65 | 60 | 35 | 50 |
| Foxtail, Green | 80 | 0 | 10 | 40 | 0 | 70 | 60 | 75 | 98 | 98 | 95 | 35 | 0 | 0 | 25 | 0 | 60 | 20 | 10 | 40 |
| Goosegrass | 0 | 0 | 0 | 0 | 0 | 60 | 0 | 70 | 0 | 0 | 80 | 0 | 0 | 0 | 0 | 0 | 30 | 0 | 35 | 0 |
| Johnsongrass | 0 | 0 | 0 | 0 | 0 | 0 | 0 | 0 | 0 | 50 | 0 | 0 | 0 | 0 | 0 | 0 | 0 | 0 | 0 | 0 |
| *Kochia* | 75 | 0 | — | 0 | 0 | 60 | 0 | 95 | 0 | 0 | 95 | 40 | 0 | 0 | 0 | 0 | 60 | 0 | 95 | 0 |
| Lambsquarters | 98 | 0 | 0 | 0 | 0 | 85 | 0 | 98 | 98 | 65 | 98 | 60 | 0 | 0 | 0 | 0 | 80 | 0 | 0 | 98 |
| Morningglory | 0 | — | 0 | — | 0 | 0 | 0 | 0 | 0 | 0 | 0 | 0 | 0 | 0 | — | 0 | 0 | 0 | 0 | 0 |
| Nightshade | 50 | 30 | 0 | 0 | 0 | 60 | 0 | 50 | 20 | 0 | 75 | 0 | 0 | 0 | — | 0 | — | 0 | 0 | 0 |
| Nutsedge, Yellow | 0 | 0 | 0 | 0 | 0 | 0 | 0 | 0 | 0 | 15 | 0 | 0 | 0 | 0 | 0 | 0 | 0 | 0 | 0 | 0 |
| *Panicum*, Fall | 0 | 0 | 0 | 0 | 0 | 0 | 0 | 0 | 0 | 98 | 50 | 0 | 0 | 0 | 0 | 0 | 0 | 0 | 0 | 0 |
| Pigweed, Palmer | 35 | 0 | 0 | 0 | — | — | 0 | 70 | 0 | 0 | 0 | 0 | 0 | 0 | 0 | — | 0 | 0 | 0 | 0 |
| Poinsettia, Wild | 0 | 15 | 0 | 0 | 0 | 0 | 0 | 0 | 0 | 10 | 0 | 0 | 0 | 0 | 0 | 0 | 0 | 0 | 0 | 0 |
| Ragweed | 60 | 0 | 0 | 0 | 0 | 0 | 0 | 80 | 0 | 0 | 75 | 0 | 0 | — | 0 | 0 | 0 | 0 | 20 | 0 |
| Ryegrass, Italian | 20 | 0 | 0 | 0 | 0 | 0 | 0 | 0 | 0 | 35 | 10 | 25 | 0 | 0 | 0 | 0 | 0 | 0 | 0 | 0 |
| Sandbur | 65 | 0 | 35 | 50 | 0 | 50 | 35 | 70 | 50 | 80 | 65 | 35 | 0 | 0 | 0 | 0 | 30 | 10 | 35 | 20 |
| Smartweed | — | — | — | — | — | 20 | — | — | — | — | — | — | — | — | — | — | 0 | — | — | — |
| Soybean | 0 | 0 | 0 | 0 | 0 | 0 | 0 | 0 | 0 | 0 | 0 | 0 | 0 | 0 | 0 | 0 | 0 | 0 | 0 | 0 |
| Surinam Grass | 50 | 0 | 20 | 50 | 0 | 50 | 50 | — | 60 | 95 | 50 | 0 | 0 | 0 | 0 | 0 | 40 | 20 | 20 | 35 |
| Velvetleaf | 0 | 0 | 0 | 0 | 0 | 0 | 0 | 0 | 0 | 35 | 0 | 0 | 0 | 0 | 0 | 0 | 0 | 0 | 0 | 0 |
| Waterhemp | 0 | 0 | 0 | 0 | 0 | 30 | 0 | 60 | 0 | — | 80 | 0 | 0 | 0 | 0 | 0 | 20 | 0 | 50 | 0 |

| | 31 g ai/ha Compounds | | | 16 g ai/ha Compounds | | | | |
|---|---|---|---|---|---|---|---|---|
| | 206 | 232 | 350 | 14 | 16 | 17 | 66 | 80 |
| Arrowleaf Sida | 0 | 0 | 0 | 0 | 0 | 0 | 0 | 0 |
| Barnyardgrass | 70 | 60 | 15 | 0 | 0 | 0 | 0 | 0 |
| Beggarticks | 0 | 0 | 0 | 0 | 0 | — | 0 | 0 |
| Cocklebur | 0 | — | — | — | 0 | 0 | 0 | 0 |
| Corn | 0 | 0 | 0 | 0 | 0 | 0 | 0 | 0 |
| Crabgrass, Brazil | 80 | 95 | 0 | 0 | 25 | 40 | 85 | — |
| Crabgrass, Large | 98 | 95 | 50 | 0 | 10 | 15 | 0 | 50 |
| Dayflower, VA | 0 | 0 | 0 | 0 | 0 | 0 | 0 | 0 |
| Field Bindweed | 20 | 0 | 40 | 0 | 0 | 0 | 0 | 0 |
| Foxtail, Giant | 90 | 35 | 0 | 0 | 0 | 0 | 0 | 0 |
| Foxtail, Green | 80 | 80 | 20 | 0 | 0 | 0 | 0 | 50 |
| Goosegrass | 0 | 35 | 0 | 0 | 0 | 0 | 0 | 10 |
| Johnsongrass | 30 | 0 | 0 | 0 | 0 | 0 | 0 | 0 |
| *Kochia* | 0 | 90 | 0 | 0 | — | 0 | 0 | — |
| Lambsquarters | 35 | 95 | 80 | 0 | 0 | 0 | 0 | 50 |
| Morningglory | 0 | 0 | 0 | 0 | 0 | — | 0 | 0 |
| Nightshade | 0 | 25 | 0 | 0 | 0 | 0 | 0 | 50 |
| Nutsedge, Yellow | 15 | 0 | 0 | 0 | 0 | 0 | 0 | 0 |
| *Panicum*, Fall | 75 | 35 | 0 | 0 | 0 | 0 | 0 | 0 |
| Pigweed, Palmer | 0 | 0 | 0 | 0 | 0 | 0 | — | 0 |
| Poinsettia, Wild | 0 | 0 | 0 | 0 | 0 | 0 | 0 | 0 |
| Ragweed | 0 | 35 | 0 | 0 | — | 0 | 0 | 0 |

TABLE E-continued

| | Preemergence | | | | | | | | |
|---|---|---|---|---|---|---|---|---|---|
| Ryegrass, Italian | 0 | 0 | 0 | 0 | 0 | 0 | 0 | 0 |
| Sandbur | 65 | 35 | 15 | 0 | 0 | 0 | 0 | 20 |
| Smartweed | — | — | — | — | — | — | — | 0 |
| Soybean | 0 | 0 | 0 | 0 | 0 | 0 | 0 | 0 |
| Surinam Grass | 50 | 40 | 0 | 0 | 0 | 0 | 0 | 30 |
| Velvetleaf | 0 | 0 | 0 | 0 | 0 | 0 | 0 | 0 |
| Waterhemp | 50 | 35 | 0 | 0 | 0 | 0 | 0 | 0 |

Test F

Three plastic pots (ca. 16-cm diameter) per rate were partially filled with sterilized Tama silt loam soil comprising a 35:50:15 ratio of sand, silt and clay and 2.6% organic matter. Separate plantings for each of the three pots were as follows. Seeds from the U.S. of monochoria (*Monochora vaginalis*), sedge, umbrella (small-flower umbrella sedge, *Cyperus difformis*), bulrush, hardstem (hardstem bulrush, *Scirpus juncoides*), and redstem (purple redstem, *Ammannia coccinea*), were planted into one 16-cm pot for each rate. Seeds from the U.S. of flatsedge, rice (rice flatsedge, *Cyperus iria*), sprangletop, Brdd. (bearded sprangletop, *Leptochloa fascicularis*), one stand of 9 or 10 water seeded rice seedlings (Rice, W. S. Jap. *Oryza sativa* cv. 'Japonica—M202' or Rice, W. S. Ind, 'Indica'), and two stands of 3 or 4 seedlings of rice, transplanted (transplanted rice, *Oryza sativa* cv. 'Japonica—M202') were planted into one 16-cm pot for each rate. Seeds from the U.S. of barnyardgrass (*Echinochloa crus-galli*), waterplantain (common waterplantain, *Alisma plantago-aquatica*), and watergrass, late (late watergrass, *Echinochloa oryzicola*) were planted into one 16-cm pot for each rate. Plantings were sequential so that crop and weed species were at the 2.0 to 2.5-leaf stage at time of treatment.

Potted plants were grown in a greenhouse with day/night temperature settings of 30/27° C., and supplemental balanced lighting was provided to maintain a 16-h photoperiod. Test pots were maintained in the greenhouse until test completion.

At time of treatment, test pots were flooded to 3 cm above the soil surface, treated by application of test compounds directly to the paddy water, and then maintained at that water depth for the duration of the test. Effects of treatments on rice and weeds were visually evaluated by comparison to untreated controls after 21 d. Plant response ratings, summarized in Table F, are based on a scale of 0 to 100 where 0 is no effect and 100 is complete control. A dash (-) response means no test result.

TABLE F

| | Flood | | | | | | |
|---|---|---|---|---|---|---|---|
| | 2000 g ai/ha Compounds | | | 1000 g ai/ha Compounds | | | |
| | 5 | 17 | 247 | 5 | 17 | 103 | 247 |
| Barnyardgrass | 90 | 100 | 75 | 90 | 95 | 100 | 70 |
| Bulrush, Hardstem | — | 40 | — | — | 0 | — | — |
| Flatsedge, Rice | 0 | 40 | 35 | 0 | 35 | — | 0 |
| *Monochoria* | 75 | 95 | 75 | 75 | 95 | 100 | 75 |
| Redstem | 45 | 40 | 55 | 45 | 35 | — | 50 |
| Rice, Transplanted | 0 | 10 | 15 | 0 | 10 | 0 | 10 |
| Rice, W.S. Jap | — | 85 | — | — | — | 15 | — |
| Sedge, Umbrella | 0 | 20 | 0 | — | 60 | — | — |
| Sprangletop, Brdd. | 90 | 100 | 98 | 0 | 0 | — | 0 |
| Watergrass, Late | 100 | 95 | 90 | 85 | 85 | 100 | 98 |
| Waterplantain | 90 | — | 90 | 100 | 90 | 100 | 85 |

| | 500 g ai/ha Compounds | | | | | | | | | | | |
|---|---|---|---|---|---|---|---|---|---|---|---|---|
| | 3 | 5 | 17 | 99 | 101 | 103 | 204 | 206 | 207 | 210 | 247 | 271 | 303 |
| Barnyardgrass | 90 | 75 | 90 | 80 | 90 | 100 | 100 | 100 | 100 | 100 | 70 | 100 | 100 |
| Bulrush, Hardstem | 30 | — | 0 | — | — | — | — | — | — | — | — | — | 80 |
| Flatsedge, Rice | 20 | 0 | 20 | — | — | — | — | — | — | — | 0 | — | 0 |
| *Monochoria* | 100 | 75 | 95 | 95 | 100 | 100 | 100 | 100 | 100 | 100 | 75 | 100 | 100 |
| Redstem | 20 | 40 | 0 | — | — | — | — | — | — | — | 0 | — | 30 |
| Rice, Transplanted | 0 | 0 | 10 | 0 | 0 | 0 | 0 | 40 | 0 | 0 | 0 | 15 | 30 |
| Rice, W.S. Ind | — | — | — | 0 | 60 | 0 | 20 | 65 | 10 | 0 | — | 60 | 70 |
| Rice, W.S. Jap | 10 | — | 15 | — | — | — | — | — | — | — | — | — | — |
| Sedge, Umbrella | 0 | 0 | 0 | — | — | — | — | — | — | — | 0 | — | 0 |
| Sprangletop, Brdd. | 85 | 85 | 85 | 85 | 95 | 100 | 100 | 100 | 100 | 100 | 98 | 95 | 90 |
| Watergrass, Late | 85 | 75 | 90 | 50 | 85 | 98 | 98 | 100 | 90 | 90 | 70 | 100 | 100 |
| Waterplantain | — | 80 | — | — | — | — | — | — | — | — | 90 | — | — |

TABLE F-continued

Flood 250 g ai/ha Compounds

| | 3 | 5 | 17 | 99 | 101 | 103 | 204 | 206 | 207 | 210 | 247 | 271 | 303 |
|---|---|---|---|---|---|---|---|---|---|---|---|---|---|
| Barnyardgrass | 90 | 65 | 90 | 50 | 85 | 100 | 100 | 100 | 100 | 100 | 65 | 100 | 100 |
| Bulrush, Hardstem | 0 | — | 0 | — | — | — | — | — | — | — | — | — | 70 |
| Flatsedge, Rice | 0 | 0 | 20 | — | — | — | — | — | — | — | 0 | — | 0 |
| Monochoria | 90 | 75 | 90 | 85 | 100 | 100 | 100 | 100 | 100 | 85 | 70 | 100 | 100 |
| Redstem | 0 | 0 | 0 | — | — | — | — | — | — | — | 0 | — | 0 |
| Rice, Transplanted | 0 | 0 | 10 | 0 | 0 | 0 | 0 | 10 | 0 | 0 | 0 | 0 | 15 |
| Rice, W.S. Ind | — | — | — | 0 | 35 | 0 | 10 | 45 | 0 | 0 | — | 30 | 40 |
| Rice, W.S. Jap | 0 | — | 15 | — | — | — | — | — | — | — | — | — | — |
| Sedge, Umbrella | 0 | 0 | 0 | — | — | — | — | — | — | — | 0 | — | 0 |
| Sprangletop, Brdd. | 80 | 85 | 85 | 75 | 95 | 100 | 100 | 100 | 100 | 100 | 95 | 80 | 85 |
| Watergrass, Late | 80 | 70 | 85 | 40 | 85 | 98 | 98 | 100 | 85 | 75 | 65 | 100 | 100 |
| Waterplantain | — | 70 | — | — | — | — | — | — | — | — | 85 | — | — |

125 g ai/ha Compounds

| | 5 | 17 | 99 | 101 | 103 | 204 | 206 | 207 | 210 | 247 | 271 | 303 |
|---|---|---|---|---|---|---|---|---|---|---|---|---|
| Barnyardgrass | 55 | 90 | 25 | 85 | 60 | 100 | 100 | 60 | 75 | 60 | 75 | 100 |
| Bulrush, Hardstem | — | 0 | — | — | — | — | — | — | — | — | — | 0 |
| Flatsedge, Rice | 0 | 20 | — | — | — | — | — | — | — | 0 | — | 0 |
| Monochoria | 75 | 90 | 50 | 100 | 100 | 95 | 90 | 65 | 65 | 70 | 100 | 100 |
| Redstem | 0 | 0 | — | — | — | — | — | — | — | 0 | — | 0 |
| Rice, Transplanted | 0 | 10 | 0 | 0 | 0 | 0 | 0 | 0 | 0 | 0 | 0 | 0 |
| Rice, W.S. Ind | — | — | 0 | 20 | 0 | 0 | 25 | 0 | 0 | — | 15 | 25 |
| Rice, W.S. Jap | — | 0 | — | — | — | — | — | — | — | — | — | — |
| Sedge, Umbrella | 0 | 0 | — | — | — | — | — | — | — | 0 | — | 0 |
| Sprangletop, Brdd. | 85 | 85 | 0 | 85 | 80 | 98 | 95 | 100 | 100 | 90 | 30 | 80 |
| Watergrass, Late | 55 | 80 | 30 | 75 | 60 | 70 | 100 | 65 | 55 | 65 | 75 | 95 |
| Waterplantain | 55 | — | — | — | — | — | — | — | — | 80 | — | — |

| | 64 g ai/ha Compounds | | | | | 62 g ai/ha Compound |
|---|---|---|---|---|---|---|
| | 101 | 103 | 206 | 271 | | 303 |
| Barnyardgrass | 60 | 60 | 90 | 55 | Barnyardgrass | 100 |
| Monochoria | 75 | 85 | 80 | 85 | Bulrush, Hardstem | 0 |
| Rice, Transplanted | 0 | 0 | 0 | 0 | Flatsedge, Rice | 0 |
| Rice, W.S. Ind | 0 | 0 | 15 | 0 | Monochoria | 100 |
| Sprangletop, Brdd. | 75 | 80 | 90 | 20 | Redstem | 0 |
| Watergrass, Late | 65 | 40 | 90 | 45 | Rice, Transplanted | 0 |
| | | | | | Rice, Water Seeded | 0 |
| | | | | | Sedge, Umbrella | 0 |
| | | | | | Sprangletop, Brdd. | 70 |
| | | | | | Watergrass, Late | 95 |

Test G

Seeds of small-flower umbrella sedge (CYPDI, *Cyperus difformis*) and ducksalad (HETLI, *Heteranthera limosa*) were sown on the soil surface in two separate quadrants of 11-cm (4-inch) tubs filled with steam pasteurized Tama soil. Simultaneously, plantings of barnyardgrass (ECHCG, *Echinochloa crus-galli*) and transplanted *japonica* rice (ORYSA. *Oryza sativa*) were established in separate "plug" flats. Plants were grown in a greenhouse using supplemental lighting to maintain a photoperiod of approximately 16 h; daytime and nighttime temperatures were approximately 27-30° C. and 24-27° C., respectively. After 8 d, barnyardgrass plants were transplanted to one of the remaining quadrants of the tub, and the water level was adjusted to a final depth of 3-cm. Herbicide application timing was targeted at the 2.0 to 2.5 leaf stage and the plants were treated with test chemicals formulated in a non-phytotoxic solvent. Treated plants and controls were maintained in a greenhouse for 14 d, after which time all species were compared to controls and visually evaluated. Plant response ratings are summarized in Tables G1 through G12, and are based on a scale of 0 to 100 where 0 is no effect and 100 is complete control. A dash (-) response means no test result.

Colby's Equation was used to determine the herbicidal effects expected from the mixtures. Colby's Equation (Colby, S. R. "Calculating Synergistic and Antagonistic Responses of Herbicide Combinations," *Weeds,* 15(1), pp 20-22 (1967)) calculates the expected additive effect of herbicidal mixtures and for two active ingredients is of the form:

$$P_{a+b} = P_a + P_b - (P_a P_b / 100)$$

where $P_{a+b}$ is the percentage effect of the mixture expected from additive contribution of the individual components;

$P_a$ is the observed percentage effect of the first active ingredient at the same use rate as in the mixture, and $P_b$ is the observed percentage effect of the second active ingredient at the same use rate as in the mixture.

In the following Tables, rates are shown in grams of active ingredient per hectare (g a./ha); "Obsd." is the observed effect. "Exp." is the expected effect calculated from Colby's Equation.

TABLE G1

Observed and Expected Results from Compound 204
Alone and in Combination with Fentrazamide

| Application Rate (g a.i./ha) | | CYPDI | | HETLI | | ECHCG | | ORYSA | |
|---|---|---|---|---|---|---|---|---|---|
| Cmpd. 204 | Fentrazamide | Obsd. | Exp. | Obsd. | Exp. | Obsd. | Exp. | Obsd. | Exp. |
| 125 | — | 0 | — | 100 | — | 65 | — | 0 | — |
| 500 | — | 0 | — | 100 | — | 90 | — | 0 | — |
| — | 100 | 90 | — | 85 | — | 50 | — | 0 | — |
| — | 200 | 100 | — | 100 | — | 95 | — | 15 | — |
| 125 | 100 | 95 | 90 | 100 | 100 | 80 | 83 | 0 | 0 |
| 125 | 200 | 95 | 90 | 100 | 100 | 95 | 95 | 0 | 0 |
| 500 | 100 | 100 | 100 | 100 | 100 | 95 | 98 | 0 | 15 |
| 500 | 200 | 100 | 100 | 100 | 100 | 95 | 100 | 0 | 15 |

TABLE G2

Observed and Expected Results from Compound 103
Alone and in Combination with Fentrazamide

| Application Rate (g a.i./ha) | | CYPDI | | HETLI | | ECHCG | | ORYSA | |
|---|---|---|---|---|---|---|---|---|---|
| Cmpd. 103 | Fentrazamide | Obsd. | Exp. | Obsd. | Exp. | Obsd. | Exp. | Obsd. | Exp. |
| 125 | — | 0 | — | 100 | — | 60 | — | 0 | — |
| 500 | — | 0 | — | 100 | — | 80 | — | 15 | — |
| — | 100 | 100 | — | 100 | — | 85 | — | 0 | — |
| — | 200 | 100 | — | 100 | — | 85 | — | 0 | — |
| 125 | 100 | 70 | 100 | 100 | 100 | 50 | 94 | 0 | 0 |
| 125 | 200 | 100 | 100 | 100 | 100 | 75 | 97 | 0 | 15 |
| 500 | 100 | 100 | 100 | 100 | 100 | 80 | 94 | 10 | 0 |
| 500 | 200 | 100 | 100 | 100 | 100 | 80 | 97 | 10 | 15 |

TABLE G3

Observed and Expected Results from Compound 204
Alone and in Combination with Tefuryltrione

| Application Rate (g a.i./ha) | | CYPDI | | HETLI | | ECHCG | | ORYSA | |
|---|---|---|---|---|---|---|---|---|---|
| Cmpd. 204 | Tefuryltrione | Obsd. | Exp. | Obsd. | Exp. | Obsd. | Exp. | Obsd. | Exp. |
| 125 | — | 0 | — | 100 | — | 65 | — | 0 | — |
| 500 | — | 0 | — | 100 | — | 90 | — | 0 | — |
| — | 100 | 100 | — | 100 | — | 40 | — | 0 | — |
| 125 | 100 | 100 | 100 | 100 | 100 | 95 | 79 | 0 | 0 |
| 500 | 100 | 100 | 100 | 100 | 100 | 95 | 94 | 0 | 0 |

TABLE G4

Observed and Expected Results from Compound 103
Alone and in Combination with Tefuryltrione

| Application Rate (g a.i./ha) | | CYPDI | | HETLI | | ECHCG | | ORYSA | |
|---|---|---|---|---|---|---|---|---|---|
| Cmpd. 103 | Tefuryltrione | Obsd. | Exp. | Obsd. | Exp. | Obsd. | Exp. | Obsd. | Exp. |
| 125 | — | 0 | — | 100 | — | 60 | — | 0 | — |
| 500 | — | 0 | — | 100 | — | 80 | — | 15 | — |
| — | 100 | 90 | — | 90 | — | 0 | — | 0 | — |
| 125 | 100 | 98 | 90 | 100 | 100 | 55 | 60 | 0 | 0 |
| 500 | 100 | 98 | 90 | 100 | 100 | 90 | 80 | 0 | 15 |

TABLE G5

Observed and Expected Results from Compound 204 Alone and in Combination with Triafamone

| Application Rate (g a.i./ha) | | CYPDI | | HETLI | | ECHCG | | ORYSA | |
|---|---|---|---|---|---|---|---|---|---|
| Cmpd. 204 | Triafamone | Obsd. | Exp. | Obsd. | Exp. | Obsd. | Exp. | Obsd. | Exp. |
| 125 | — | 0 | — | 100 | — | 65 | — | 0 | — |
| 500 | — | 0 | — | 100 | — | 90 | — | 0 | — |
| — | 20 | 0 | — | 0 | — | 90 | — | 0 | — |
| 125 | 20 | 0 | 0 | 98 | 100 | 85 | 97 | 0 | 0 |
| 500 | 20 | 45 | 0 | 100 | 100 | 90 | 99 | 0 | 0 |

TABLE G6

Observed and Expected Results from Compound 103 Alone and in Combination with Triafamone

| Application Rate (g a.i./ha) | | CYPDI | | HETLI | | ECHCG | | ORYSA | |
|---|---|---|---|---|---|---|---|---|---|
| Cmpd. 103 | Triafamone | Obsd. | Exp. | Obsd. | Exp. | Obsd. | Exp. | Obsd. | Exp. |
| 125 | — | 0 | — | 100 | — | 60 | — | 0 | — |
| 500 | — | 0 | — | 100 | — | 80 | — | 15 | — |
| — | 20 | 0 | — | 0 | — | 85 | — | 0 | — |
| 125 | 20 | 0 | 0 | 100 | 100 | 85 | 94 | 0 | 0 |
| 500 | 20 | 0 | 0 | 100 | 100 | 90 | 97 | 0 | 15 |

TABLE G7

Observed and Expected Results from Compound 204 Alone and in Combination with Pyrimisulfan

| Application Rate (g a.i./ha) | | CYPDI | | HETLI | | ECHCG | | ORYSA | |
|---|---|---|---|---|---|---|---|---|---|
| Cmpd. 204 | Pyrimisulfan | Obsd. | Exp. | Obsd. | Exp. | Obsd. | Exp. | Obsd. | Exp. |
| 125 | — | 0 | — | 100 | — | 65 | — | 0 | — |
| 500 | — | 0 | — | 100 | — | 90 | — | 0 | — |
| — | 20 | 98 | — | 100 | — | 75 | — | 25 | — |
| 125 | 20 | 100 | 98 | 100 | 100 | 85 | 91 | 25 | 25 |
| 500 | 20 | 100 | 98 | 100 | 100 | 95 | 98 | 25 | 25 |

TABLE G8

Observed and Expected Results from Compound 103 Alone and in Combination with Pyrimisulfan

| Application Rate (g a.i./ha) | | CYPDI | | HETLI | | ECHCG | | ORYSA | |
|---|---|---|---|---|---|---|---|---|---|
| Cmpd. 103 | Pyrimisulfan | Obsd. | Exp. | Obsd. | Exp. | Obsd. | Exp. | Obsd. | Exp. |
| 125 | — | 0 | — | 100 | — | 60 | — | 0 | — |
| 500 | — | 0 | — | 100 | — | 80 | — | 15 | — |
| — | 20 | 100 | — | 100 | — | 80 | — | 20 | — |
| 125 | 20 | 100 | 100 | 100 | 100 | 85 | 92 | 20 | 20 |
| 500 | 20 | 100 | 100 | 100 | 100 | 85 | 96 | 0 | 32 |

TABLE G9

Observed and Expected Results from Compound 204 Alone and in Combination with Mefenecet

| Application Rate (g a.i./ha) | | CYPDI | | HETLI | | ECHCG | | ORYSA | |
|---|---|---|---|---|---|---|---|---|---|
| Cmpd. 204 | Mefenecet | Obsd. | Exp. | Obsd. | Exp. | Obsd. | Exp. | Obsd. | Exp. |
| 125 | — | 0 | — | 100 | — | 65 | — | 0 | — |
| 500 | — | 0 | — | 100 | — | 90 | — | 0 | — |
| — | 300 | 100 | — | 100 | — | 30 | — | 0 | — |

TABLE G9-continued

Observed and Expected Results from Compound 204 Alone and in Combination with Mefenecet

| Application Rate (g a.i./ha) | | CYPDI | | HETLI | | ECHCG | | ORYSA | |
|---|---|---|---|---|---|---|---|---|---|
| Cmpd. 204 | Mefenecet | Obsd. | Exp. | Obsd. | Exp. | Obsd. | Exp. | Obsd. | Exp. |
| 125 | 300 | 100 | 98 | 100 | 100 | 60 | 76 | 0 | 0 |
| 500 | 300 | 100 | 98 | 100 | 100 | 90 | 93 | 0 | 0 |

TABLE G10

Observed and Expected Results from Compound 103 Alone and in Combination with Mefenecet

| Application Rate (g a.i./ha) | | CYPDI | | HETLI | | ECHCG | | ORYSA | |
|---|---|---|---|---|---|---|---|---|---|
| Cmpd. 103 | Mefenecet | Obsd. | Exp. | Obsd. | Exp. | Obsd. | Exp. | Obsd. | Exp. |
| 125 | — | 0 | — | 100 | — | 60 | — | 0 | — |
| 500 | — | 0 | — | 100 | — | 80 | — | 15 | — |
| — | 300 | 100 | — | 100 | — | 65 | — | 10 | — |
| 125 | 300 | 100 | 98 | 100 | 100 | 70 | 86 | 10 | 10 |
| 500 | 300 | 100 | 98 | 100 | 100 | 80 | 93 | 20 | 24 |

TABLE G11

Observed and Expected Results from Compound 204 Alone and in Combination with Bensulfuron-methyl

| Application Rate (g a.i./ha) | | CYPDI | | HETLI | | ECHCG | | ORYSA | |
|---|---|---|---|---|---|---|---|---|---|
| Cmpd. 204 | Bensulfuron-methyl | Obsd. | Exp. | Obsd. | Exp. | Obsd. | Exp. | Obsd. | Exp. |
| 125 | — | 0 | — | 100 | — | 65 | — | 0 | — |
| 500 | — | 0 | — | 100 | — | 90 | — | 0 | — |
| — | 20 | 100 | — | 100 | — | 65 | — | 10 | — |
| 125 | 20 | 100 | 100 | 100 | 100 | 70 | 88 | 0 | 10 |
| 500 | 20 | 100 | 100 | 100 | 100 | 90 | 97 | 0 | 10 |

TABLE G12

Observed and Expected Results from Compound 103 Alone and in Combination with Bensulfuron-methyl

| Application Rate (g a.i./ha) | | CYPDI | | HETLI | | ECHCG | | ORYSA | |
|---|---|---|---|---|---|---|---|---|---|
| Cmpd. 103 | Bensulfuron-methyl | Obsd. | Exp. | Obsd. | Exp. | Obsd. | Exp. | Obsd. | Exp. |
| 125 | — | 0 | — | 100 | — | 60 | — | 0 | — |
| 500 | — | 0 | — | 100 | — | 80 | — | 15 | — |
| — | 20 | 98 | — | 100 | — | 65 | — | 0 | — |
| 125 | 20 | 98 | 98 | 100 | 100 | 65 | 86 | 0 | 0 |
| 500 | 20 | 100 | 98 | 100 | 100 | 85 | 93 | 10 | 15 |

Test H

This test evaluated the effect of mixtures of compound 80 with several commercial herbicides on four plant species. Seeds of plant species selected from corn (ZEAMD, *Zea mays*), soybean (GLXMA, *Glycine max*), waterhemp (common waterhemp, AMATA, *Amaranthus rudis*), and giant foxtail (SETFA, *Setaria* faberii) were planted into a silt loam soil and treated preemergence with test chemicals formulated in anon-phytotoxic solvent mixture which included a surfactant and applied using a volume of 281 L/ha. Each treatment was replicated three times. Treated plants and controls were maintained in a greenhouse using supplemental lighting to maintain a photoperiod of about 16 h; daytime and nighttime temperatures were about 24-30° C. and 19-21° C., respectively. Nutrients were applied using a balanced fertilizer applied through the watering system. At 21 d after treatment, all species were compared to controls and visually evaluated. Plant response ratings were calculated as the means of the three replicates, are summarized in Tables H1 through H5, and are based on a scale of 0 to 100) where 0 is no effect and 100 is complete control. A dash (-) response means no test result. The Expected (Exp.) results were calculated using Colby's Equation as described for Test G above.

TABLE H1

Observed and Expected Results from Compound 80 Alone and in Combination with Chlorimuron-ethyl

| Application Rate (g a.i./ha) | | ZEAMD | | GLXMA | | AMATA | | SETFA | |
|---|---|---|---|---|---|---|---|---|---|
| Cmpd 80 | Chlorimuron-ethyl | Obsd. | Exp. | Obsd. | Exp. | Obsd. | Exp. | Obsd. | Exp. |
| 62 | — | 17 | — | 12 | — | 0 | — | 52 | — |
| 125 | — | 13 | — | 0 | — | 33 | — | 78 | — |
| — | 1 | 22 | — | 0 | — | 47 | — | 0 | — |
| — | 31 | 73 | — | 22 | — | 89 | — | 47 | — |
| 62 | 1 | 22 | 35 | 18 | 12 | 73 | 47 | 25 | 52 |
| 125 | 1 | 15 | 32 | 5 | 0 | 73 | 64 | 67 | 78 |
| 62 | 31 | 96 | 78 | 35 | 31 | 69 | 89 | 58 | 75 |
| 125 | 31 | 75 | 77 | 0 | 22 | 94 | 93 | 78 | 88 |

TABLE H2

Observed and Expected Results from Compound 80 Alone and in Combination with S-metolachlor

| Application Rate (g a.i./ha) | | ZEAMD | | GLXMA | | AMATA | | SETFA | |
|---|---|---|---|---|---|---|---|---|---|
| Cmpd 80 | S-metolachlor | Obsd. | Exp. | Obsd. | Exp. | Obsd. | Exp. | Obsd. | Exp. |
| 62 | — | 17 | — | 12 | — | 0 | — | 52 | — |
| 125 | — | 13 | — | 0 | — | 33 | — | 78 | — |
| — | 31 | 13 | — | 18 | — | 0 | — | 73 | — |
| — | 125 | 20 | — | 15 | — | 85 | — | 99 | — |
| 62 | 31 | 10 | 28 | 8 | 28 | 33 | 0 | 93 | 87 |
| 125 | 31 | 30 | 24 | 25 | 18 | 75 | 33 | 96 | 94 |
| 62 | 125 | 25 | 34 | 28 | 25 | 85 | 85 | 98 | 100 |
| 125 | 125 | 37 | 30 | 12 | 15 | 98 | 90 | 93 | 100 |

TABLE H3

Observed and Expected Results from Compound 80 Alone and in Combination with Saflufenacil

| Application Rate (g a.i./ha) | | ZEAMD | | GLXMA | | AMATA | | SETFA | |
|---|---|---|---|---|---|---|---|---|---|
| Cmpd 80 | Saflufenacil | Obsd. | Exp. | Obsd. | Exp. | Obsd. | Exp. | Obsd. | Exp. |
| 62 | — | 17 | — | 12 | — | 0 | — | 52 | — |
| 125 | — | 13 | — | 0 | — | 33 | — | 78 | — |
| — | 1 | 20 | — | 0 | — | 0 | — | 0 | — |
| — | 31 | 0 | — | 13 | — | 83 | — | 23 | — |
| 62 | 1 | 22 | 34 | 40 | 12 | 38 | 0 | 57 | 52 |
| 125 | 1 | 15 | 30 | 15 | 0 | 33 | 33 | 80 | 78 |
| 62 | 31 | 30 | 17 | 25 | 23 | 73 | 83 | 40 | 63 |
| 125 | 31 | 25 | 13 | 0 | 13 | 97 | 89 | 80 | 83 |

TABLE H4

Observed and Expected Results from Compound 80 Alone and in Combination with Atrazine

| Application Rate (g a.i./ha) | | ZEAMD | | GLXMA | | AMATA | | SETFA | |
|---|---|---|---|---|---|---|---|---|---|
| Cmpd 80 | Atrazine | Obsd. | Exp. | Obsd. | Exp. | Obsd. | Exp. | Obsd. | Exp. |
| 62 | — | 17 | — | 12 | — | 0 | — | 52 | — |
| 125 | — | 13 | — | 0 | — | 33 | — | 78 | — |
| — | 62 | 0 | — | 13 | — | 33 | — | 0 | — |
| — | 125 | 0 | — | 48 | — | 90 | — | 8 | — |
| 62 | 62 | 18 | 17 | 20 | 23 | 83 | 33 | 63 | 52 |
| 125 | 62 | 10 | 13 | 0 | 13 | 87 | 55 | 78 | 78 |
| 62 | 125 | 20 | 17 | 5 | 54 | 100 | 90 | 58 | 56 |
| 125 | 125 | 23 | 13 | 30 | 48 | 98 | 93 | 70 | 80 |

TABLE H5

Observed and Expected Results from Compound 80 Alone and in Combination with Mesotrione

| Application Rate (g a.i./ha) | | ZEAMD | | GLXMA | | AMATA | | SETFA | |
|---|---|---|---|---|---|---|---|---|---|
| Cmpd 80 | Mesotrione | Obsd. | Exp. | Obsd. | Exp. | Obsd. | Exp. | Obsd. | Exp. |
| 62 | — | 17 | — | 12 | — | 0 | — | 52 | — |
| 125 | — | 13 | — | 0 | — | 33 | — | 78 | — |
| — | 16 | 12 | — | 25 | — | 96 | — | 0 | — |
| 62 | 16 | 20 | 27 | 28 | 34 | 93 | 96 | 25 | 52 |
| 125 | 16 | 32 | 23 | 83 | 25 | 93 | 97 | 48 | 78 |

What is claimed is:

1. A herbicidal composition comprising a compound selected from Formula 1 N-oxides and salts thereof:

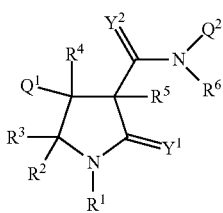

wherein
Q$^1$ is a phenyl ring substituted with 1 to 3 substituents independently selected from R$^7$;
Q$^2$ is a phenyl ring substituted with 1 to 3 substituents independently selected from R$^{10}$;
Y$^1$ and Y$^2$ are each O;
R$^1$ is H, C$_1$-C$_6$ alkyl, or C$_1$-C$_6$ haloalkyl;
R$^2$, R$^3$, R$^4$, R$^5$ and R$^6$ are each H;
each R$^7$ and R$^{10}$ is independently halogen, cyano, nitro, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl, C$_1$-C$_4$ nitroalkyl, C$_2$-C$_4$ nitroalkenyl, C$_2$-C$_4$ alkoxyalkyl, C$_2$-C$_4$ haloalkoxyalkyl, C$_3$-C$_4$ cycloalkyl, C$_3$-C$_4$ halocycloalkyl, cyclopropylmethyl, methylcyclopropyl, C$_1$-C$_4$alkoxy, C$_1$-C$_4$haloalkoxy, C$_2$-C$_4$ alkenyloxy, C$_2$-C$_4$ haloalkenyloxy, C$_3$-C$_4$ alkynyloxy, C$_3$-C$_4$ haloalkynyloxy, C$_3$-C$_4$ cycloalkoxy, C$_1$-C$_4$ alkylthio, C$_1$-C$_4$ haloalkylthio, C$_1$-C$_4$ alkylsulfinyl, C$_1$-C$_4$ haloalkylsulfinyl, C$_1$-C$_4$alkylsulfonyl, C$_1$-C$_4$haloalkylsulfonyl, hydroxy, formyl, C$_2$-C$_4$alkylcarbonyl, C$_2$-C$_4$ alkylcarbonyloxy, C$_1$-C$_4$ alkylsulfonyloxy, C$_1$-C$_4$ haloalkylsulfonyloxy, formylamino, C$_2$-C$_4$ alkylcarbonylamino, —SF5, —SCN, C$_3$-C$_4$ trialkylsilyl, trimethylsilylmethyl or trimethylsilylmethoxy;
provided that when Q$^1$ is a phenyl ring and said ring is substituted with IC at both ortho positions relative to the bond to the remainder of Formula 1, then said ring is also independently substituted with IC on at least one additional position; and
at least one component selected from the group consisting of surfactants, solid diluents and liquid diluents.

2. The herbicidal composition of claim 1 further comprising at least one additional active ingredient selected from the group consisting of other herbicides and herbicide safeners.

3. A herbicidal mixture comprising (a) a compound selected from Formula 1, N-oxides and salts thereof:

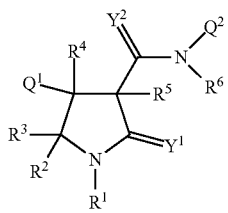

wherein
Q$^1$ is a phenyl ring substituted with 1 to 3 substituents independently selected from R$^7$;
Q$^2$ is a phenyl ring substituted with 1 to 3 substituents independently selected from R$^{10}$;
Y$^1$ and Y$^2$ are each O;
R$^1$ is H, C$_1$-C$_6$ alkyl, or C$_1$-C$_6$ haloalkyl;
R$^2$, R$^3$, R$^4$, R$^5$ and R$^6$ are each H;
each R$^7$ and R$^{10}$ is independently halogen, cyano, nitro, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl, C$_1$-C$_4$ nitroalkyl, C$_2$-C$_4$ nitroalkenyl, C$_2$-C$_4$ alkoxyalkyl, C$_2$-C$_4$ haloalkoxyalkyl, C$_3$-C$_4$ cycloalkyl, C$_3$-C$_4$ halocycloalkyl, cyclopropylmethyl, methylcyclopropyl, C$_1$-C$_4$alkoxy, C$_1$-C$_4$haloalkoxy, C$_2$-C$_4$ alkenyloxy, C$_2$-C$_4$ haloalkenyloxy, C$_3$-C$_4$ alkynyloxy, C$_3$-C$_4$ haloalkynyloxy, C$_3$-C$_4$ cycloalkoxy, C$_1$-C$_4$ alkylthio, C$_1$-C$_4$ haloalkylthio, C$_1$-C$_4$ alkylsulfinyl, C$_1$-C$_4$ haloalkylsulfinyl, C$_1$-C$_4$alkylsulfonyl, C$_1$-C$_4$haloalkylsulfonyl, hydroxy, formyl, C$_2$-C$_4$alkylcarbonyl, C$_2$-C$_4$ alkylcarbonyloxy, C$_1$-C$_4$ alkylsulfonyloxy, C$_1$-C$_4$ haloalkylsulfonyloxy, formylamino, C$_2$-C$_4$ alkylcarbonylamino, —SF5, —SCN, C$_3$-C$_4$ trialkylsilyl, trimethylsilylmethyl or trimethylsilylmethoxy;
provided that when Q$^1$ is a phenyl ring and said ring is substituted with R$^7$ at both ortho positions relative to the bond to the remainder of Formula 1, then said ring is also independently substituted with R$^7$ on at least one additional position; and (b) at least one additional active ingredient selected from the group consisting of photosystem II inhibitors, acetohydroxy acid synthase (AHAS) inhibitors, acetyl-CoA carboxylase (ACCase) inhibitors, auxin mimics, 5-enol-pyruvylshikimate-3-phosphate (EPSP) synthase inhibitors, photosystem I electron diverters, protoporphyrinogen oxidase (PPO) inhibitors, glutamine synthetase (GS) inhibitors, very long chain fatty acid (VLCFA) elongase inhibitors, auxin transport inhibitors, phytoene desaturase (PDS) inhibitors, 4-hydroxyphenyl-pyruvate dioxygenase (HPPD) inhibitors, homogentisate solanesyltransferase (HST) inhibitors, cellulose biosynthesis inhibitors, other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, herbicide safeners, and salts thereof.

4. The herbicidal mixture of claim 3, wherein the at least one additional active ingredient is selected from the group consisting of acetohydroxy acid synthase (AHAS) inhibitors, very long chain fatty acid (VLCFA) elongase inhibitors, 4-hydroxyphenyl-pyruvate dioxygenase (HPPD) inhibitors, and salts of compounds of, hydroxyphenyl-pyruvate dioxygenase (HPPD) inhibitors, and salts thereof.

5. A method for controlling the growth of undesired vegetation comprising contacting the vegetation or its environment with a herbicidally effective amount of a compound selected from Formula 1, N-oxides and salts thereof:

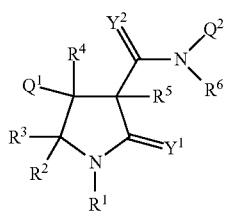

1 wherein
$Q^1$ is a phenyl ring substituted with 1 to 3 substituents independently selected from $R^7$;
$Q^2$ is a phenyl ring substituted with 1 to 3 substituents independently selected from $R^{10}$;
$Y^1$ and $Y^2$ are each O;
$R^1$ is H, $C_1$-$C_6$ alkyl, or $C_1$-$C_6$ haloalkyl;
$R^2$, $R^3$, $R^4$, $R^5$ and $R^6$ are each H;
each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$alkoxy, $C_1$-$C_4$haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$alkylcarbonyl, $C_2$-$C_4$ alkylcarbonyloxy, $C_1$-$C_4$ alkylsulfonyloxy, $C_1$-$C_4$ haloalkylsulfonyloxy, formylamino, $C_2$-$C_4$ alkylcarbonylamino, —SF5, —SCN, $C_3$-$C_4$ tri alkyl silyl, trimethylsilylmethyl or trimethylsilylmethoxy;
provided that when $Q^1$ is a phenyl ring and said ring is substituted with IC at both ortho positions relative to the bond to the remainder of Formula 1, then said ring is also independently substituted with IC on at least one additional position.

6. A mixture comprising a compound selected from Formula 1, N-oxides and salts thereof:

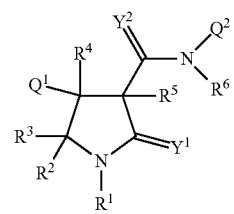

1 wherein
$Q^1$ is a phenyl ring substituted with 1 to 3 substituents independently selected from $R^7$;
$Q^2$ is a phenyl ring substituted with 1 to 3 substituents independently selected from $R^{10}$;
$Y^1$ and $Y^2$ are each O;
$R^1$ is H, $C_1$-$C_6$ alkyl, or $C_1$-$C_6$ haloalkyl;
$R^2$, $R^3$, $R^4$, $R^5$ and $R^6$ are each H;
each $R^7$ and $R^{10}$ is independently halogen, cyano, nitro, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$alkylcarbonyl, $C_2$-$C_4$ alkylcarbonyloxy, C i-$C_4$ alkylsulfonyloxy, $C_1$-$C_4$ haloalkylsulfonyloxy, formylamino, $C_2$-$C_4$ alkylcarbonylamino, —SF5, —SCN, $C_3$-$C_4$ trialkylsilyl, trimethylsilylmethyl or trimethylsilylmethoxy;
provided that when $Q^1$ is a phenyl ring and said ring is substituted with IC at both ortho positions relative to the bond to the remainder of Formula 1, then said ring is also independently substituted with $R^7$ on at least one additional position; and
a compound selected from the group consisting of benzobicyclon, bromobutide, fenquinotrione, metazosulfuron, pethoxamid, pretilachlor, pyrazolynate, pyrazosulfuron-ethyl, pyrimisulfan and triafamone.

* * * * *